United States Patent
Kaneko et al.

(10) Patent No.: US 8,299,055 B2
(45) Date of Patent: Oct. 30, 2012

(54) 8-SUBSTITUTED ISOQUINOLINE DERIVATIVE AND THE USE THEREOF

(75) Inventors: Shunsuke Kaneko, Tokyo (JP); Kenichiro Sato, Tokyo (JP); Daisuke Shikanai, Tokyo (JP); Rintaro Yamada, Tokyo (JP); Katsuhiko Sakurada, Tokyo (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 222 days.

(21) Appl. No.: 12/571,601

(22) Filed: Oct. 1, 2009

(65) Prior Publication Data

US 2010/0261701 A1    Oct. 14, 2010

Related U.S. Application Data

(60) Provisional application No. 61/102,086, filed on Oct. 2, 2008.

(51) Int. Cl.
    *C07D 401/12* (2006.01)
    *A61K 31/47* (2006.01)

(52) U.S. Cl. ........... 514/210.18; 514/210.21; 514/235.2; 514/252.04; 514/253.05; 514/256; 514/309; 514/310; 544/128; 544/238; 544/333; 544/363; 546/141; 546/143

(58) Field of Classification Search ................. None
    See application file for complete search history.

(56) References Cited

U.S. PATENT DOCUMENTS

| 6,960,585 B2 | 11/2005 | Beaulieu et al. |
| 7,094,789 B2 | 8/2006 | Yamada et al. |
| 7,122,544 B2 | 10/2006 | Kois et al. |
| 7,125,896 B2 | 10/2006 | Faull et al. |
| 7,342,029 B2 | 3/2008 | Ritzeler et al. |
| 7,410,986 B2 | 8/2008 | Murata et al. |
| 7,442,699 B2 | 10/2008 | Kois et al. |
| 2002/0072523 A1 | 6/2002 | Beaulieu et al. |
| 2002/0161004 A1 | 10/2002 | Browner et al. |
| 2003/0119820 A1 | 6/2003 | Ritzeler et al. |
| 2003/0187026 A1 | 10/2003 | Li et al. |
| 2003/0203926 A1 | 10/2003 | Kois et al. |
| 2004/0006118 A1 | 1/2004 | Callahan et al. |
| 2004/0097563 A1 | 5/2004 | Murata et al. |
| 2004/0209868 A1 | 10/2004 | Ritzeler et al. |
| 2004/0235839 A1 | 11/2004 | Hepperle et al. |
| 2004/0242573 A1 | 12/2004 | Faull et al. |
| 2005/0020623 A1 | 1/2005 | Yamada et al. |
| 2005/0282866 A1 | 12/2005 | Ritzeler et al. |
| 2006/0030576 A1 | 2/2006 | Kois et al. |
| 2007/0015819 A1 | 1/2007 | Faull et al. |
| 2007/0281933 A1 | 12/2007 | Kerns et al. |
| 2009/0088429 A1 | 4/2009 | Plettenburg et al. |

FOREIGN PATENT DOCUMENTS

| JP | 10-087491 | 4/1998 |
| WO | 01/30774 | 5/2001 |
| WO | 02/30423 | 4/2002 |
| WO | 02/44153 | 6/2002 |
| WO | 02/46171 | 6/2002 |
| WO | 02/060386 | 8/2002 |
| WO | 03/010158 | 2/2003 |
| WO | 2003/051366 | 6/2003 |
| WO | 2004/009555 | 1/2004 |
| WO | 2004/092167 | 10/2004 |
| WO | 2006/002434 | 1/2006 |
| WO | 2007/000240 | 1/2007 |

OTHER PUBLICATIONS

Australian Office Action that issued with respect to patent family member Australian Patent Application No. 2009298981, dated Aug. 18, 2011.
White et al., "The Gattermann Reaction of 3,5-Dimethoxyphenylacetonitrile. A Synthesis of 6,8-Dioxyisoquinolines" *The Journal of Organic Chemistry*, vol. 32, No. 9, Sep. 1, 1967, pp. 2689-2692.
Extended European Search Report issued with respect to patent family member European Patent App. No. 09817505.2, dated Feb. 10, 2012.
International Search Report that issued with respect to PCT/JP2009/005072, mailed Nov. 2, 2009.
Feldmann, "Pathogenesis of arthritis: recent research progress," Nature Immunol., vol. 2, No. 9, pp. 771-773, 2001.
Koch et al., "Angiogenesis mediated by soluble forms of E-selectin and vascular cell adhesion molecule-1," Nature, vol. 376, pp. 517-519, 1995.
Brand et al., "Activated Transcription Factor Nuclear Factor-Kappa B Is Present in the Atherosclerotic Lesion," J. Clin. Invest., vol. 97, No. 7, pp. 1715-1722, 1996.
Bohrer et al., "Role of NFκB in the Mortality of Sepsis," J. Clin. Invest., vol. 100, No. 5, pp. 972-985, 1997.

(Continued)

*Primary Examiner* — Zinna Northington Davis
(74) *Attorney, Agent, or Firm* — Greenblum & Bernstein, P.L.C.

(57) ABSTRACT

The present invention relates to a compound represented by the following formula (1):

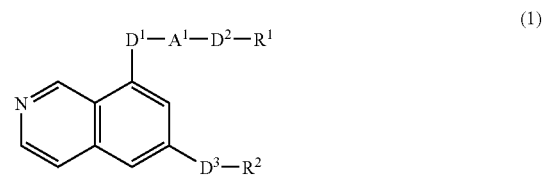

wherein $D^1$, $A^1$, $D^2$, $R^1$, $D^3$, and $R^2$ each have the same meaning as defined in the present specification or a salt thereof. The compound represented by the formula (1) or a salt thereof has an IKKβ inhibiting activity and the like and is useful for the prevention and/or treatment of IKKβ-associated diseases or symptoms and the like.

53 Claims, 3 Drawing Sheets

OTHER PUBLICATIONS

De Vry et al., Non-viral delivery of nuclear factor-κB decoy ameliorates murine inflammatory bowel disease and restores tissue homeostasis, Gut, vol. 56, pp. 524-533, published online Sep. 1, 2006.

Zwacka et al, "Redox gene therapy for ischemia/reperfusion injury of the liver reduces API and NF-κB activation," Nature Medicine, vol. 4, No. 6, pp. 698-704, 1998.

Barnes and Adcock, "NF-κB: a pivotal role in asthma and a new target for therapy," Trends Pharmacol. Sci., vol. 18, pp. 46-50, 1997.

Karin et al., "NF-κB in Cancer: From Innocent Bystander to Major Culprit", Nature Rev. Cancer, vol. 2, pp. 301-310, 2002.

Verma et al, "Rel/ NF-κB/IκB family: intimate tales of association and dissociation," Genes & Development, vol. 9, pp. 2723-2735, 1995.

DiDonato et al., "A cytokine-responsive IκB kinase that activates the transcription factor NF-κB," Nature, vol. 388, pp. 548-554, 1997.

Regnier et al., "Identification and Characterization of an IκB Kinase," Cell, vol. 90, No. 2, pp. 373-383, 1997.

Bondeson et al., "Defining therapeutic targets by using adenovirus: Blocking NF-κB inhibits both inflammatory and destructive mechanisms in rheumatoid synovium but spares anti-inflammatory mediators," Proc. Natl. Acad. Sci., U.S.A., vol. 96, pp. 5668-5673, 1999.

Seetharaman et al., "Essential Role of T Cell NF-κB Activation in Collagen-Induced Arthritis," J. Immunol., vol. 163, pp. 1577-1583, 1999.

Aupperle et al., "NF-{{kappa}}B Regulation by I{{kappa}}B Kinase-2 in Rheumatoid Arthritis Synoviocytes," J. Immunol., vol. 166, pp. 2705-2711, 2001.

Christopher et al., "Discovery of 6-Aryl-7-alkoxyisoquinoline Inhibitors of IκB Kinase-β (IKK-β)," Journal of Medicinal Chemistry, vol. 52, No. 9, pp. 3098-3102, 2009.

[Fig.1]
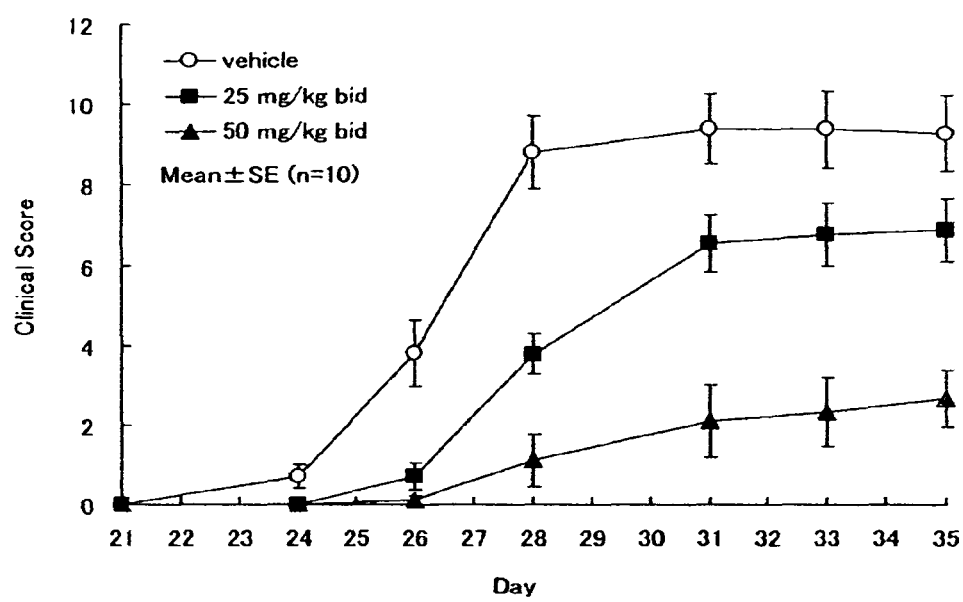

[Fig.2]
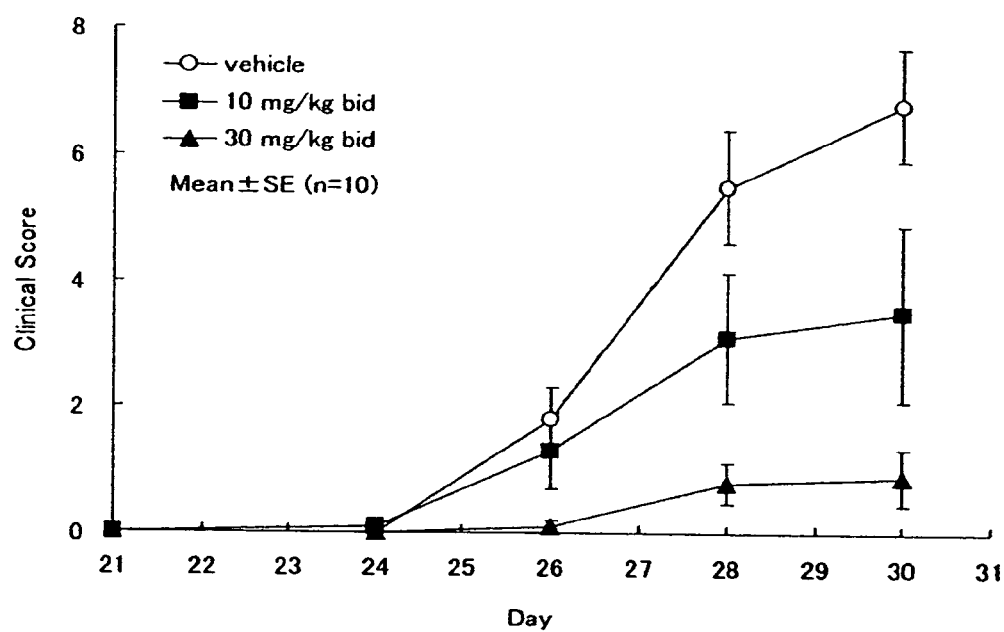

[Fig.3]
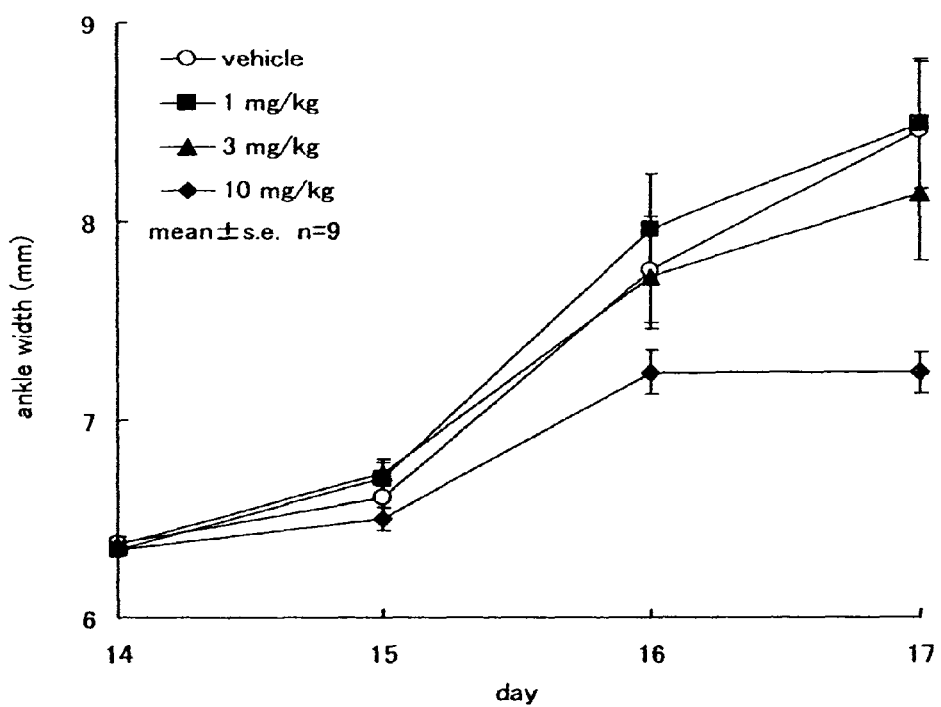

8-SUBSTITUTED ISOQUINOLINE DERIVATIVE AND THE USE THEREOF

TECHNICAL FIELD

The present invention relates to a novel isoquinoline derivative having a 8-substitution and a pharmaceutical composition comprising the same as an active ingredient thereof.

BACKGROUND ART

A nuclear factor κB (NF-κB) is a transcription factor that regulates the expression of genes responsible for reactions involved in the survival of an organism. Examples of known genes whose expression is regulated by this NF-κB include genes of many inflammatory factors including inflammatory cytokines such as tumor necrosis factor (TNF)-α, interleukin (IL)-1, and IL-6, cyclooxygenase-2 (COX-2), inducible NO synthetase (iNOS), and cell adhesion molecules such as ICAM and VCAM.

Meanwhile, many stimuli that induce the activation of NF-κB are also known and examples thereof include stimuli such as inflammatory cytokines such as IL-1 and TNF-α, bacterial cell products such as bacterial lipopolysaccharides (LPS), viruses, various stresses such as ultraviolet light and γ-ray irradiation, and T-cell mitogens.

NF-κB is thought to be involved in many conditions associated with inflammation, including rheumatoid arthritis (Non-patent Document 1), angiogenesis (Non-patent Document 2), arteriosclerosis (Non-patent Document 3), endotoxin shock and sepsis (Non-patent Document 4), inflammatory bowel disease (Non-patent Document 5), ischemic reperfusion injury (Non-patent Document 6), and pneumonia (Non-patent Document 7). Furthermore, previous studies have shown that NF-κB plays an important role in etiology and development of cancer (Non-patent Document 8).

In a cell with no stimulus, NF-κB binds to IκB, an inhibitory protein, to form a complex and exists in cytoplasm. This complex formation confines NF-κB in cytoplasm, inhibiting transfer thereof to the nucleus. When the cell is stimulated, specific amino acid residues of IκB (serine residues 32 and 36 in the case of IκBα) is phosphorylated, further polyubiquitinated, and degraded by proteasomes (Non-patent Document 9). NF-κB released from IκB rapidly transfers into the nucleus and activates the transcription of a target gene.

IκB is phosphorylated by IκB kinase (IKK). IKK is a kinase complex having catalytic subunits known as IKKα (also referred to as IKK1) and IKKβ (also referred to as IKK2) (Non-patent Documents 10 and 11). IKK is activated by phosphorylation, and MEKK1, MEKK3, NF-κB inducing kinase (NIK), and the like are known as phosphorylases thereof.

The view is advocated that inhibition of NF-κB activation by allowing IκB to exist stably is effective measure for the treatment of autoimmune diseases and other diseases. For example, when IκB is overexpressed in Synovial membrane cells collected from a patient with rheumatoid arthritis, the expression of TNF-α, IL-6, and IL-8 decreased (Non-patent Document 12). Furthermore, a transgenic mouse that expresses proteolysis-resistant IκB in T cells showed resistance to collagen-induced arthritis (Non-patent Document 13).

It has been reported that inhibition of phosphorylation of IκB by IKK is effective for the stabilization of IκB (Non-patent Document 14). NF-κB is activated by inflammatory cytokines in synovial membrane cells derived from a patient with rheumatoid arthritis. However, when NF-κB is expressed in synovial membrane cells deficient in the IKKβ kinase activity, IκB stably exists even with stimuli of inflammatory cytokines and then activation of NF-κB is suppressed. This suggests that the kinase activity of IKKβ plays a central role in activation of NF-κB (Non-patent Document 14).

Therefore, suppression of NF-κB activation by inhibiting the IKK activity may be effective for the treatment of autoimmune diseases, inflammatory diseases, cardiovascular diseases, and cancer.

β-carboline derivatives (Patent Document 1), aminothiophene derivatives (Patent Document 2), imidazole derivatives (Patent Document 3), indole derivatives (Patent Document 4), aminopyridine derivatives (Patent Document 5), anilinophenylpyrimidine derivatives (Patent Document 6), pyrazolaquinazoline derivatives (Patent Document 7), and indazole derivatives (Patent Document 8) are disclosed as examples of compounds inhibiting the IKK activity.

CITATION LIST

Patent Document

Patent Document 1: WO 2004/092167
Patent Document 2: WO 2003/010158
Patent Document 3: WO 2002/030423
Patent Document 4: WO 2001/030774
Patent Document 5: WO 2002/044153
Patent Document 6: WO 2002/046171
Patent Document 7: WO 2002/060386
Patent Document 8: WO 2006/002434

Non-Patent Document

Non-Patent Document 1: Nature Immunol., 2001, 2, p. 771-773
Non-Patent Document 2: Nature, 1995, 376, p. 517-519
Non-Patent Document 3: J. Clin. Inv., 1996, 97, p. 1715-1722
Non-Patent Document 4: J. Clin. Inv., 1997, 100, p. 972-985
Non-Patent Document 5: Gut, 2007, 56, p. 524-533
Non-Patent Document 6: Nature Medicine, 1998, 4, p. 698-704
Non-Patent Document 7: Trends Pharmacol. Sci., 1997, 18, p. 46-50
Non-Patent Document 8: Nature Rev. Cancer, 2002, 2, p. 301-310
Non-Patent Document 9: Genes & Development, 1995, 9(22), P. 2723-2735
Non-Patent Document 10: Nature, 1997, 388, p. 548-554
Non-Patent Document 11: Cell, 1997, 90(2), p. 373-383
Non-Patent Document 12: Proc. Natl. Acad. Sci. U.S.A., 1999, 96, p. 5668-5673
Non-Patent Document 13: J. Immunol., 1999, 163, p. 1577-1583
Non-Patent Document 14: J. Immunol., 2001, 166, p. 2705-2711

SUMMARY OF THE INVENTION

Problems to be Solved by the Invention

An object of the present invention is to provide a compound that has an excellent inhititing effect of IKK activity, in particular, an excellent inhititing effect of IKK activity and is useful for the prevention or treatment of diseases or symptoms associated with NF-κB. Another object of the present invention is to provide a pharmaceutical composition comprising the compound.

Means for Solving the Problems

The present inventors conducted various researches to achieve the foregoing objects. As a result, they found that a compound represented by the following formula (1) has an excellent IKK inhibiting activity and thus accomplished the present invention.

Specifically, the present invention relates to the following.

<1> A compound represented by the following general formula (1) or a salt thereof:

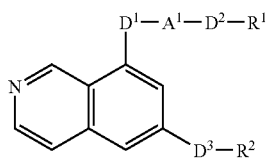
(1)

wherein
$D^1$ represents a single bond, —N($R^{11}$)—, —O—, —S—, —S(O)—, or —S(O)$_2$—, wherein $R^{11}$ represents a hydrogen atom or an alkyl group that may be substituted;

$A^1$ represents a single bond, an alkylene that may be substituted, or any of divalent groups selected from the following formulas (1a-1) to (1a-6):

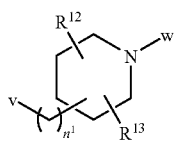
(1a-1)

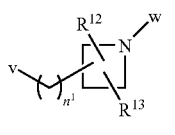
(1a-2)

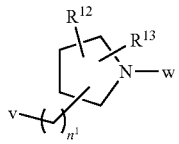
(1a-3)

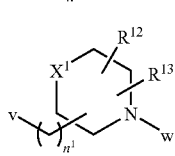
(1a-4)

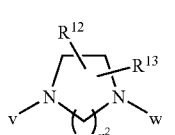
(1a-5)

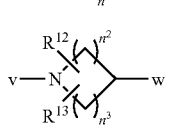
(1a-6)

wherein
$n^1$ is an integer of 0, 1, or 2;
$n^2$ is an integer of 2 or 3;
$n^3$ is an integer of 1 or 2;

$R^{12}$ and $R^{13}$ may be identical to or different from each other and each independently represents a hydrogen atom, a hydroxyl group, or an alkyl group that may be substituted;

$X^1$ represents —N($R^{14}$)—, —O—, or —S—, wherein $R^{14}$ represents a hydrogen atom or an alkyl group that may be substituted;

v represents a bond with $D^1$; and
w represents a bond with $D^2$;

$D^2$ represents a single bond, an alkylene that may be substituted, —C(O)—, —C(S)—, —S(O)$_2$—, —C(O)—N($R^{14}$)—, —C(S)—N($R^{15}$)—, or -E-C(O)—,
wherein
E represents an alkylene that may be substituted and
$R^{15}$ represents a hydrogen atom or an alkyl group;

$R^1$ represents a hydrogen atom, an alkyl group that may be substituted, an amino group that may be substituted, a saturated heterocyclic group that may be substituted, an aryl group that may be substituted, an aralkyl group that may be substituted, a carbamimidoyl group, or any of groups selected from the following formulas (1b-1) to (1b-4):

(1b-1)

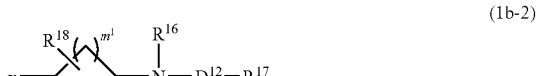
(1b-2)

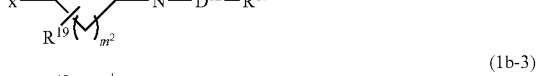
(1b-3)

(1b-4)

wherein
$m^1$ is an integer of 0, 1, or 2;
$m^2$ is an integer of 1 or 2;
$m^3$ is an integer of 0, 1, or 2;
$X^2$ represents —N($R^{14}$)—, —O—, or —S—, wherein $R^{14}$ represents a hydrogen atom or an alkyl group that may be substituted;

$D^{11}$ represents an alkylene that may be substituted;
$D^{12}$ represents a single bond, an alkylene that may be substituted, —C(O)—, —S(O)$_2$—, or —C(O)—N($R^{15}$)—, wherein
$R^{15}$ represents a hydrogen atom or an alkyl group;

$R^{16}$, $R^{18}$, and $R^{19}$ may be identical to or different from one another and each independently represents a hydrogen atom or an alkyl group that may be substituted;

$R^{17}$ represents a hydrogen atom, an alkyl group that may be substituted, an aryl group that may be substituted, or an aralkyl group that may be substituted; and x represents a bond with $D^2$;
with the proviso that, when $R^{17}$ represents a hydrogen atom, $D^{12}$ represents a single bond;
with the proviso that,
when $D^1$ represents a single bond, $A^1$ represents a divalent group represented by the above-mentioned formula (1a-5) or (1a-6);

when $D^1$ represents —N(R$^{14}$)—, —O—, —S—, —S(O)—, or —S(O)$_2$—, $A^1$ represents a single bond, an alkylene that may be substituted, or any of divalent groups selected from the formulas (1a-1) to (1a-4), wherein, when $A^1$ represents a single bond, $D^2$ represents an alkylene that may be substituted or -E-C(O)—;

when $R^1$ represents an amino group that may be substituted, $D^2$ represents an alkylene that may be substituted or -E-C(O)—; and $D^3$ represents a single bond, —N(R$^{21}$)—, —O—, —N(R$^{21}$)—C(O)—, or —S—, wherein R$^{21}$ represents a hydrogen atom or an alkyl group that may be substituted; and R$^2$ represents an alkyl group that may be substituted or the following formula (2a-1):

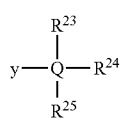

(2a-1)

wherein

Q represents an aryl group that may be substituted;

y represents a bond with $D^3$; and

R$^{23}$, R$^{24}$, and R$^{25}$ may be identical to or different from one another and each independently represents a hydrogen atom, a halogen atom, a cyano group, an alkyl group that may be substituted, an alkoxy group that may be substituted, an amino group that may be substituted, an aryl group that may be substituted, an aryloxy group that may be substituted, an aralkyl group that may be substituted, or the following formula (2b-1):

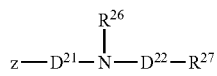

(2b-1)

wherein $D^{21}$ represents a single bond or an alkylene that may be substituted;

$D^{22}$ represents a single bond, an alkylene that may be substituted, —C(O)—, —S(O)$_2$—, or —C(O)—N(R$^{28}$)—;

R$^{26}$, R$^{27}$, and R$^{28}$ may be identical to or different from one another and each independently represents a hydrogen atom or an alkyl group that may be substituted; and z represents a bond with Q;

with the proviso that, when $D^{22}$ represents a single bond, R$^{27}$ represents a hydrogen atom;

<2> The compound according to the above <1> or a salt thereof, wherein $D^1$ represents a single bond, —N(R$^{11}$)—, —O—, or —S—, wherein R$^{11}$ has the same meaning as defined above;

<2-2> The compound according to the above <1> or a salt thereof, wherein $D^1$ represents —N(R$^{11}$)—, wherein R$^{11}$ has the same meaning as defined above;

<3> The compound according to the above <1> or <2> or a salt thereof, wherein $A^1$ represents an alkylene that may be substituted or any of divalent groups selected from the formulas (1a-1) to (1a-5), wherein n$^1$, n$^2$, X$^1$, R$^{12}$, R$^{13}$, R$^{14}$, v, and w have the same meanings as defined above;

<4> The compound according to the above <1> or <2> or a salt thereof, wherein $A^1$ represents any of divalent groups selected from the formulas (1a-1) to (1a-3) and (1a-5), wherein n$^1$, n$^2$, R$^{12}$, R$^{13}$, v, and w have the same meanings as defined above;

<4-2> The compound according to the above <1> or <2> or a salt thereof, wherein $A^1$ represents the formula (1a-1), wherein n$^1$, R$^{12}$, R$^{13}$, v, and w have the same meanings as defined above;

<4-3> The compound according to the above <1> or <2> or a salt thereof, wherein $A^1$ represents the formula (1a-2), wherein n$^1$, R$^{12}$, R$^{13}$, v, and w have the same meanings as defined above;

<4-4> The compound according to the above <1> or <2> or a salt thereof, wherein $A^1$ represents the formula (1a-5), wherein n$^2$, R$^{12}$, R$^{13}$, v, and w have the same meanings as defined above;

<4-5> The compound according to the above <1> or <2> or a salt thereof, wherein $A^1$ represents the following formula (1a-1-1):

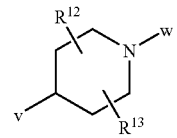

(1a-1-1)

wherein R$^{12}$, R$^{13}$, v, and w have the same meanings as defined above;

<4-6> The compound according to the above <1> or <2> or a salt thereof, wherein $A^1$ represents the following formula (1a-2-1):

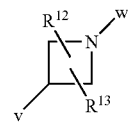

(1a-2-1)

wherein R$^{12}$, R$^{13}$, v, and w have the same meanings as defined above;

<4-7> The compound according to the above <1> or <2> or a salt thereof, wherein $A^1$ represents the following formula (1a-5-1):

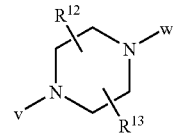

(1a-5-1)

wherein R$^{12}$, R$^{13}$, v, and w have the same meanings as defined above;

<5> The compound according to any one of the above <1> to <4-3> or a salt thereof, wherein n$^1$ is an integer of 0 or 1;

(It should be noted that when a range of item numbers referred to like "the above <1> to <4-3>" or "the above <1> to <5>" is provided and such a range includes an item number having a branch number such as <4-2>, the range means referring to the item number having a branch number such as <4-2> as well. It is same in the following.)

<6> The compound according to any one of the above <1> to <5> or a salt thereof, wherein $D^2$ represents an alkylene that may be substituted, —C(O)—, or —S(O)$_2$—;

<7> The compound according to any one of the above <1> to <5> or a salt thereof, wherein $D^2$ represents —C(O)— or —S(O)$_2$—;

<8> The compound according to any one of the above <1> to <7> or a salt thereof, wherein $R^1$ represents a hydrogen atom, an alkyl group that may be substituted, an aralkyl group that may be substituted, or an aryl group that may be substituted;

<8-2> The compound according to any one of the above <1> to <7> or a salt thereof, wherein $R^1$ represents an aryl group that may be substituted;

<8-3> The compound according to any one of the above <1> to <7> or a salt thereof, wherein $R^1$ represents an alkyl group that may be substituted;

<9> The compound according to any one of the above <1> to <7> or a salt thereof, wherein $R^1$ represents any of divalent groups selected from the formulas (1b-1) to (1b-4), wherein $m^1, m^2, m^3, X^2, D^{11}, D^{12}, R^{14}, R^{15}, R^{16}, R^{17}, R^{18}, R^{19}$, and x have the same meanings as defined above;

<10> The compound according to any one of the above <1> to <9> or a salt thereof, wherein $D^3$ represents a single bond, —O—, or —N($R^{21}$)—C(O)—, wherein $R^{21}$ have the same meaning as defined above;

<11> The compound according to any one of the above <1> to <10> or a salt thereof, wherein $D^3$ represents a single bond;

<12> The compound according to any one of the above <1> to <11> or a salt thereof, wherein $R^2$ represents the formula (2a-1), wherein Q, y, $R^{23}, R^{24}, R^{25}, D^{21}, D^{22}, R^{26}, R^{27}, R^{28}$, and z have the same meanings as defined above;

<13> The compound according to any one of the above <1> to <12> or a salt thereof, wherein Q in the formula (2a-1) represents a monocyclic aromatic group;

<13-2> The compound according to any one of the above <1> to <12> or a salt thereof, wherein Q in the formula (2a-1) represents a phenyl group that may be substituted, a pyridyl group that may be substituted, or a thiophenyl group that may be substituted;

<13-3> The compound according to any one of the above <1> to <12> or a salt thereof, wherein Q in the formula (2a-1) represents a phenyl group that may be substituted;

<13-4> The compound according to any one of the above <1> to <12> or a salt thereof, wherein Q in the formula (2a-1) represents a pyridyl group that may be substituted;

<14> A compound selected from the following groups or a salt thereof:

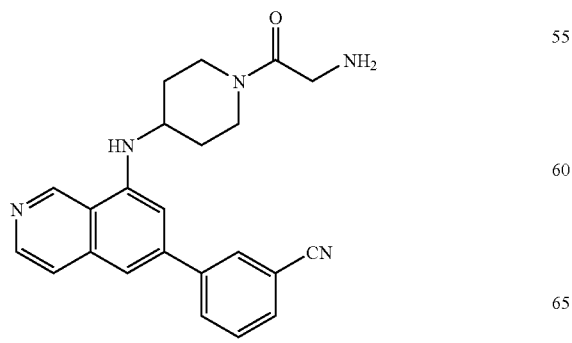

-continued

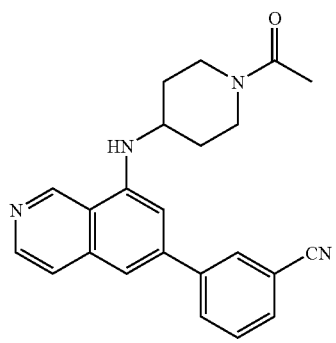

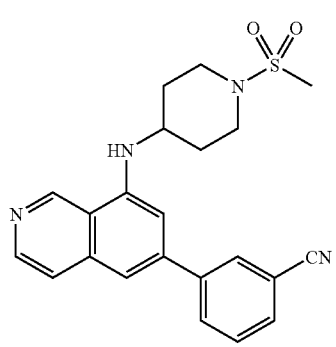

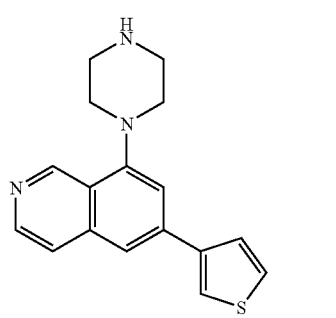

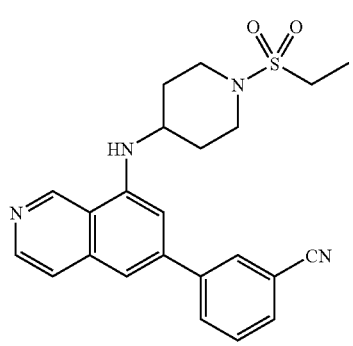

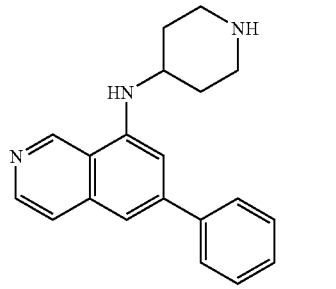

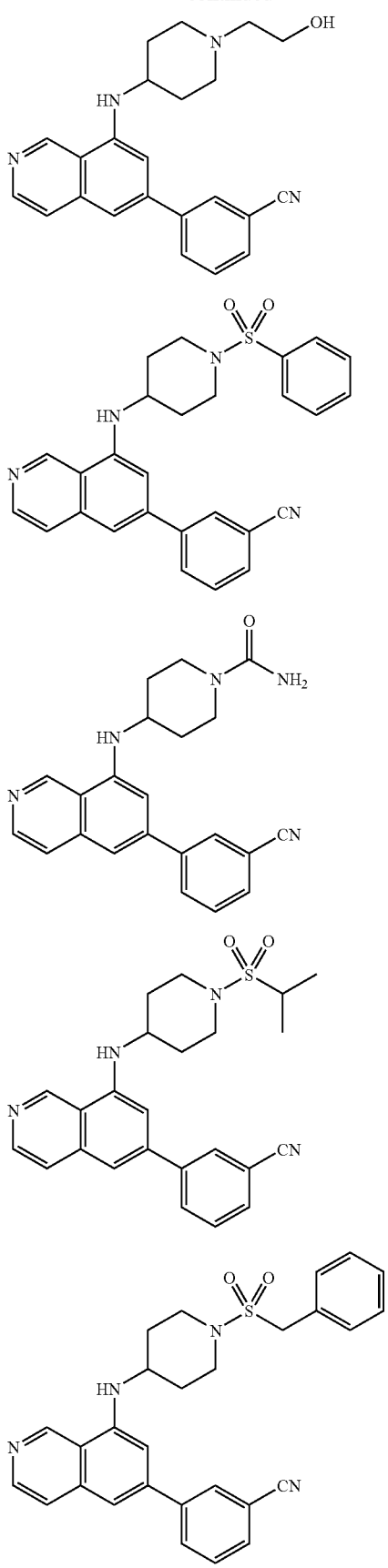
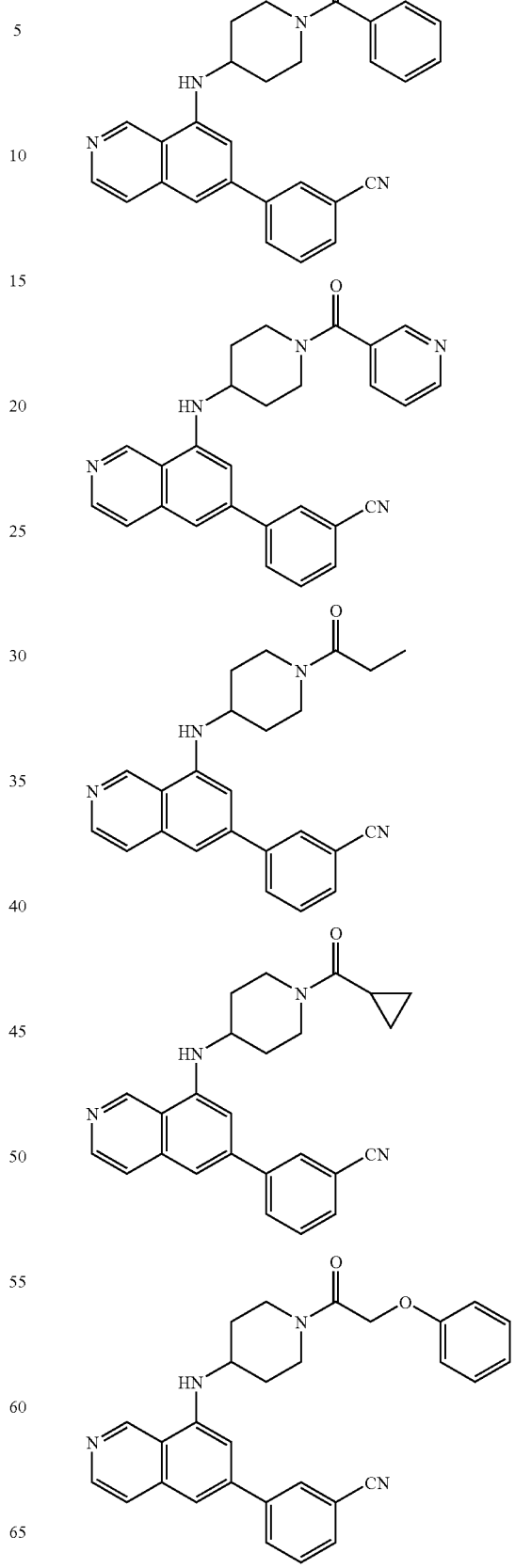

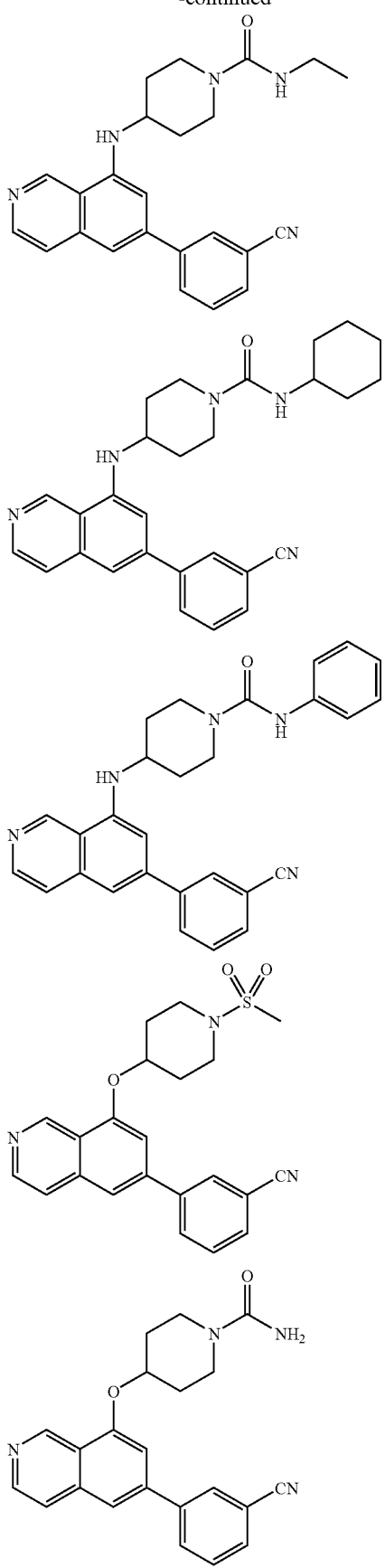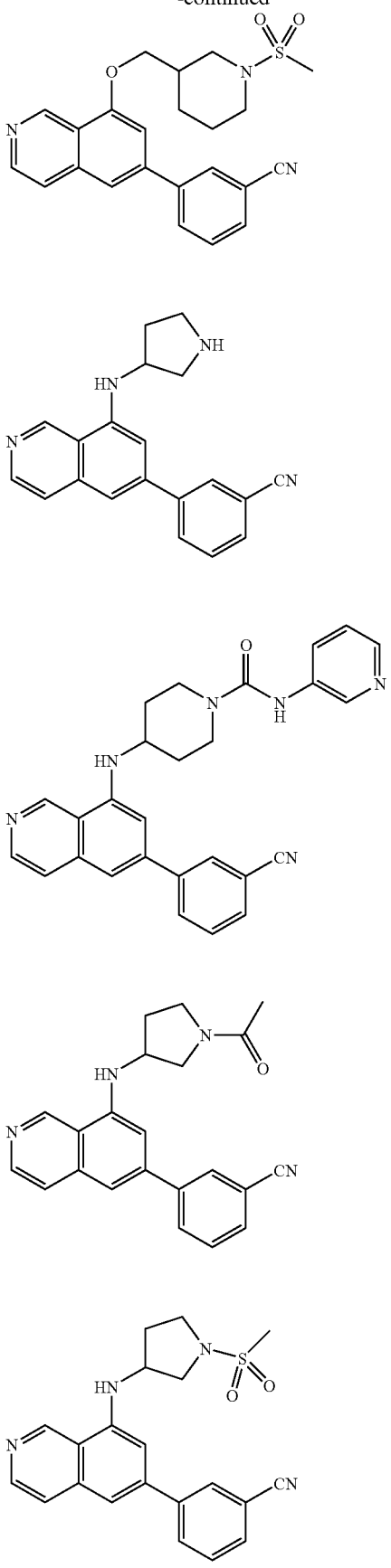

13
-continued
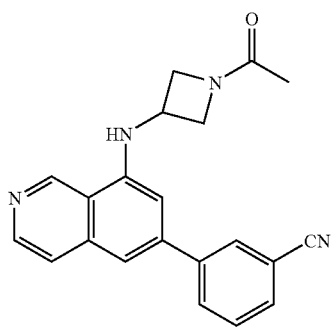
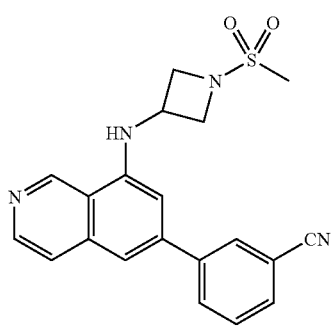
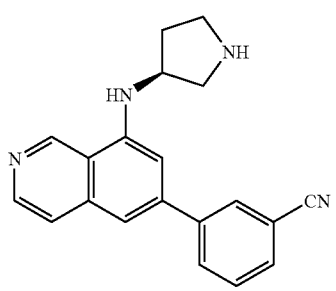
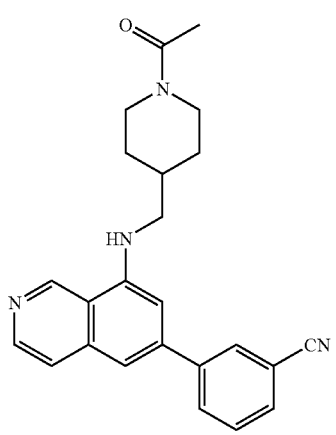
14
-continued
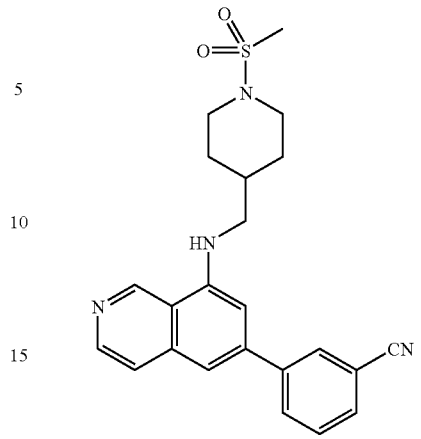
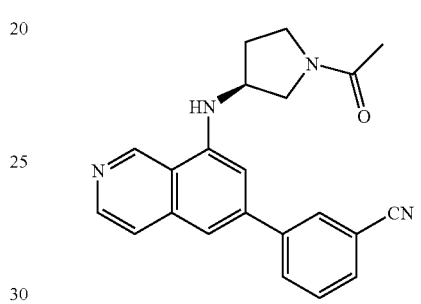
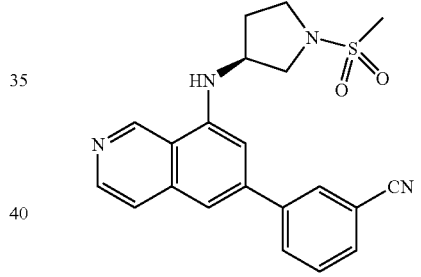
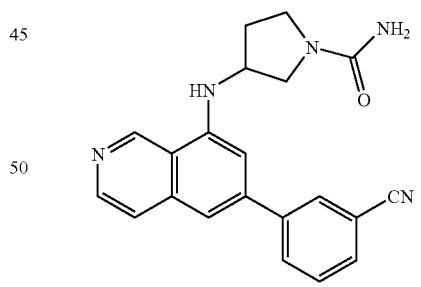
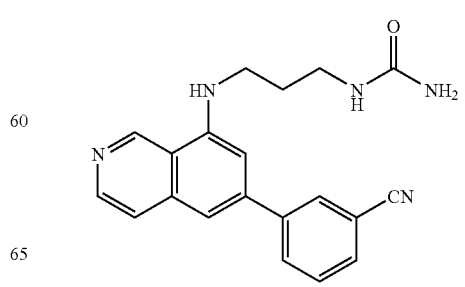

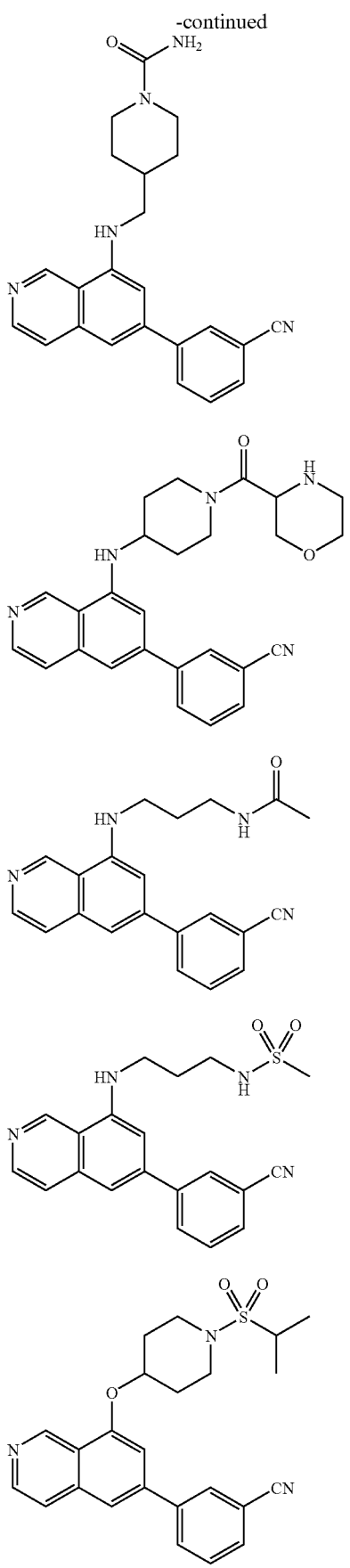
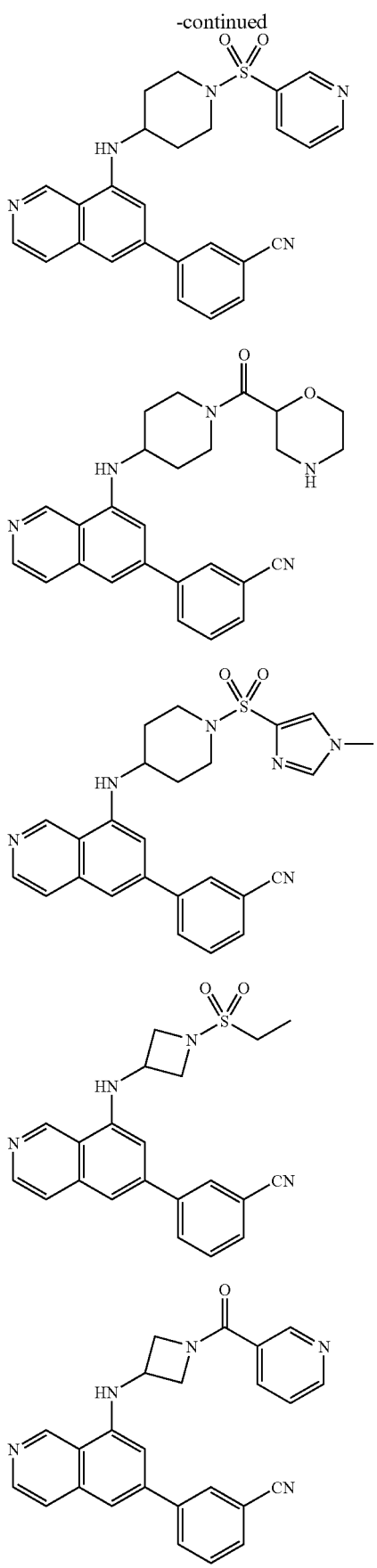

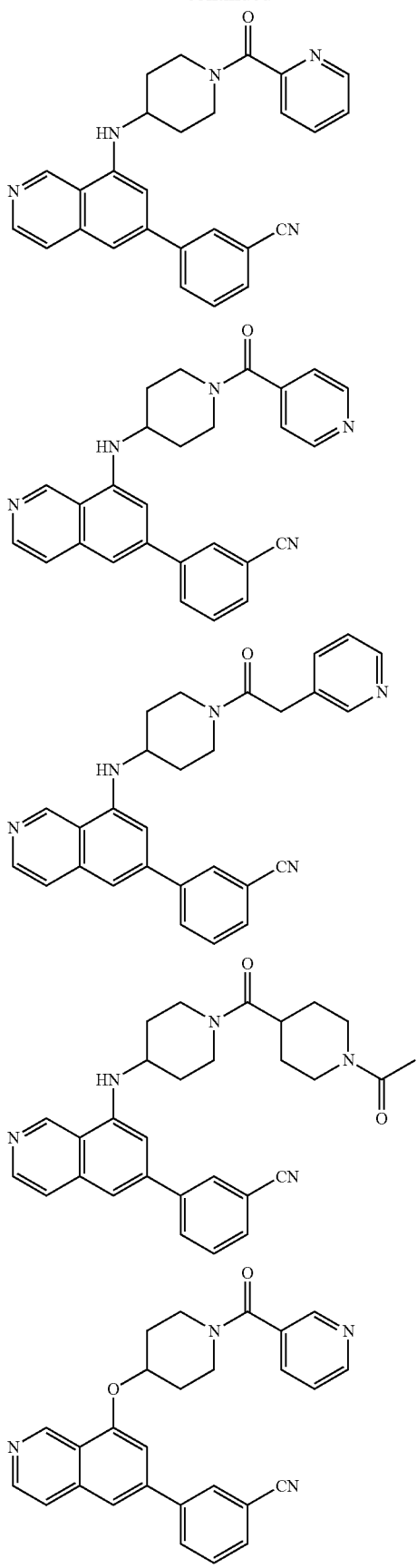
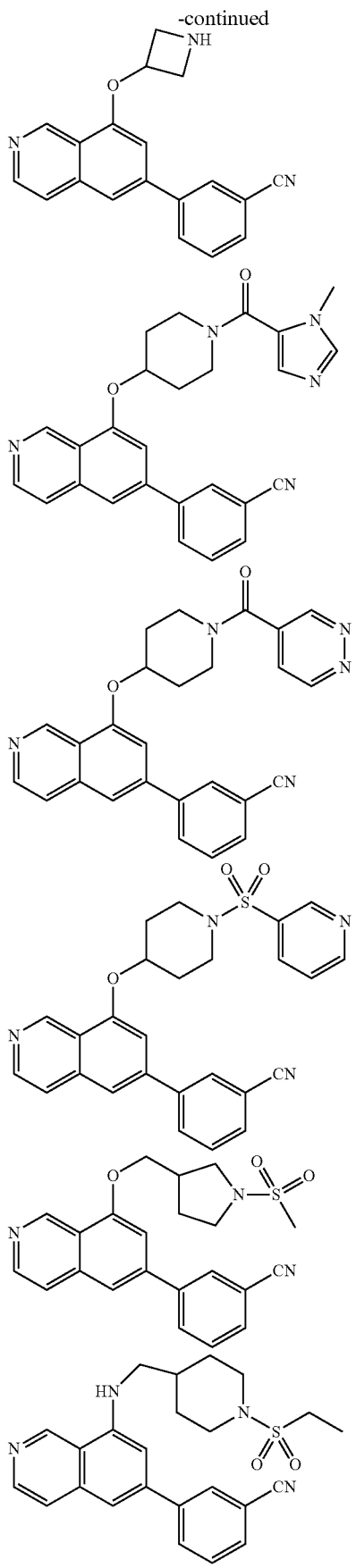

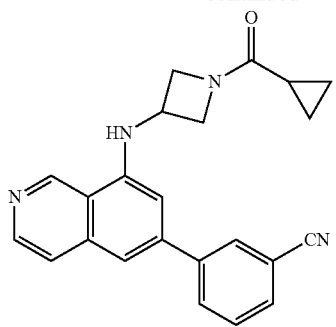
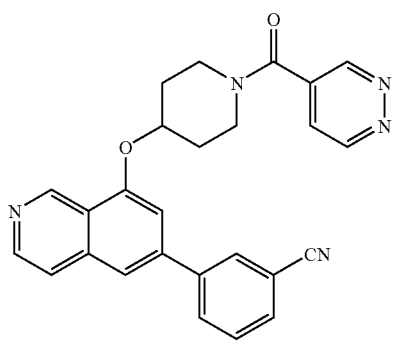
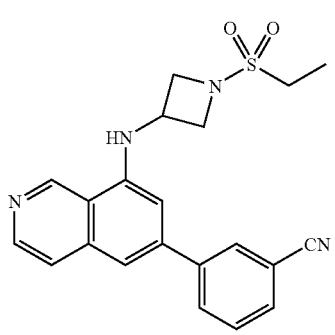
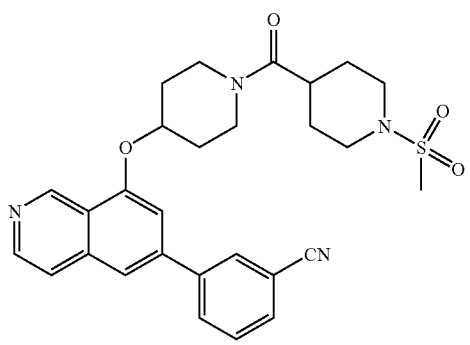
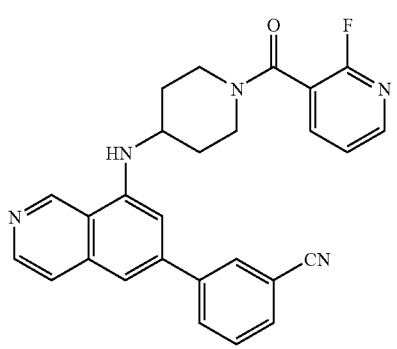
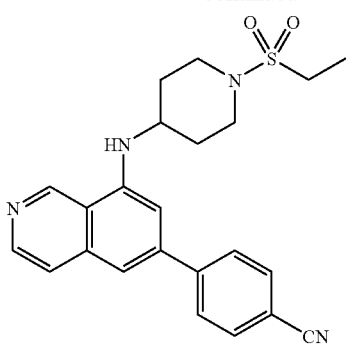
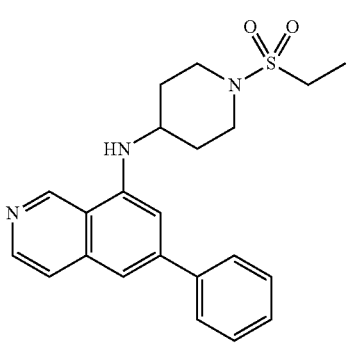
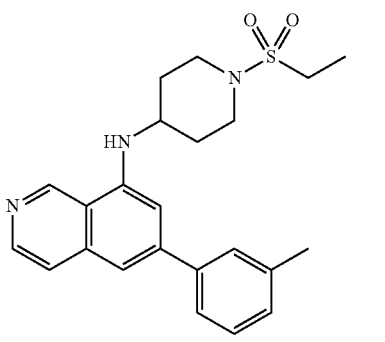
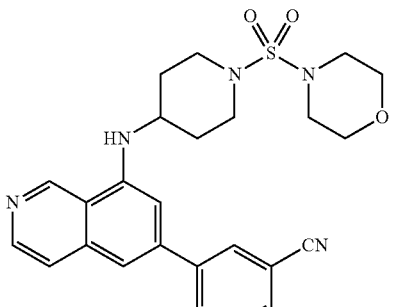
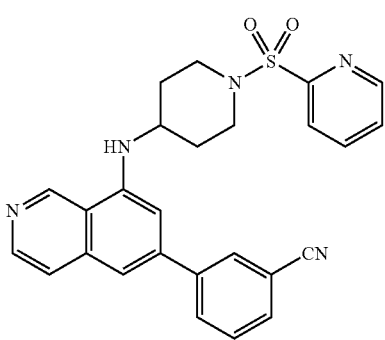

-continued
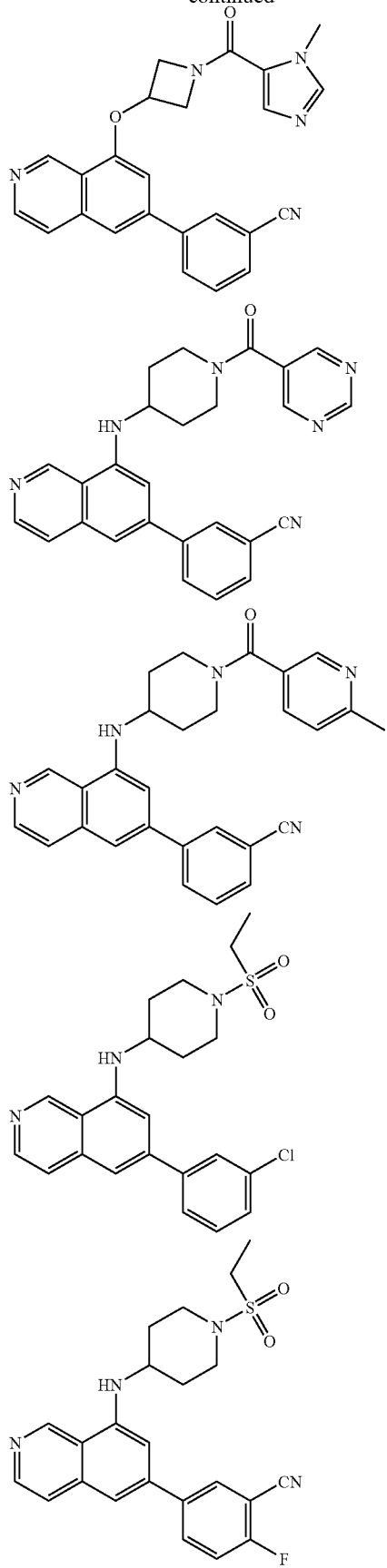
-continued
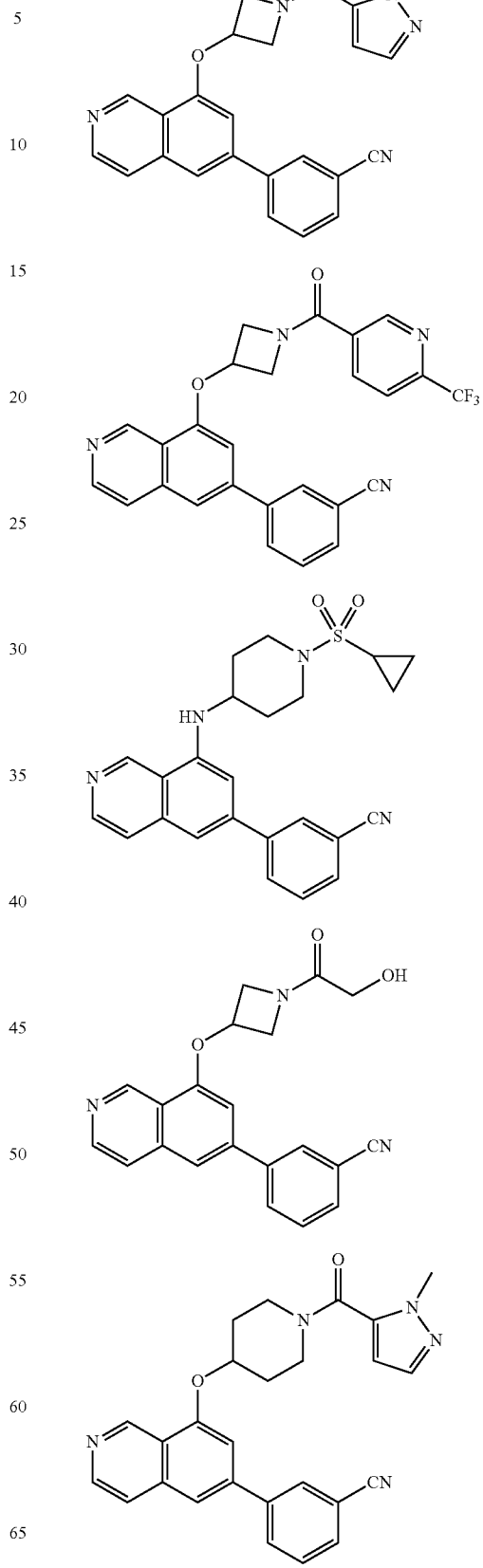

23
-continued
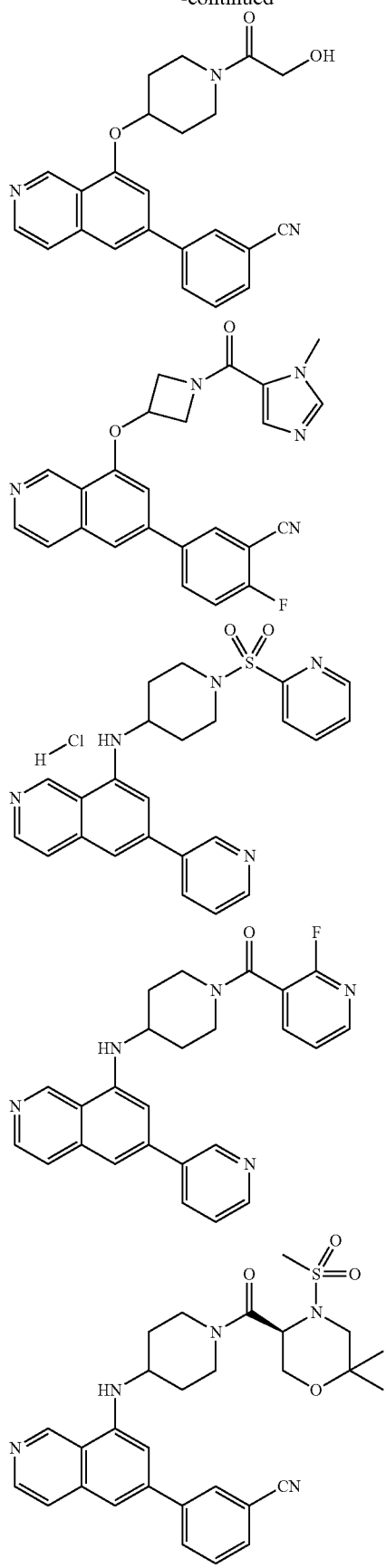
24
-continued
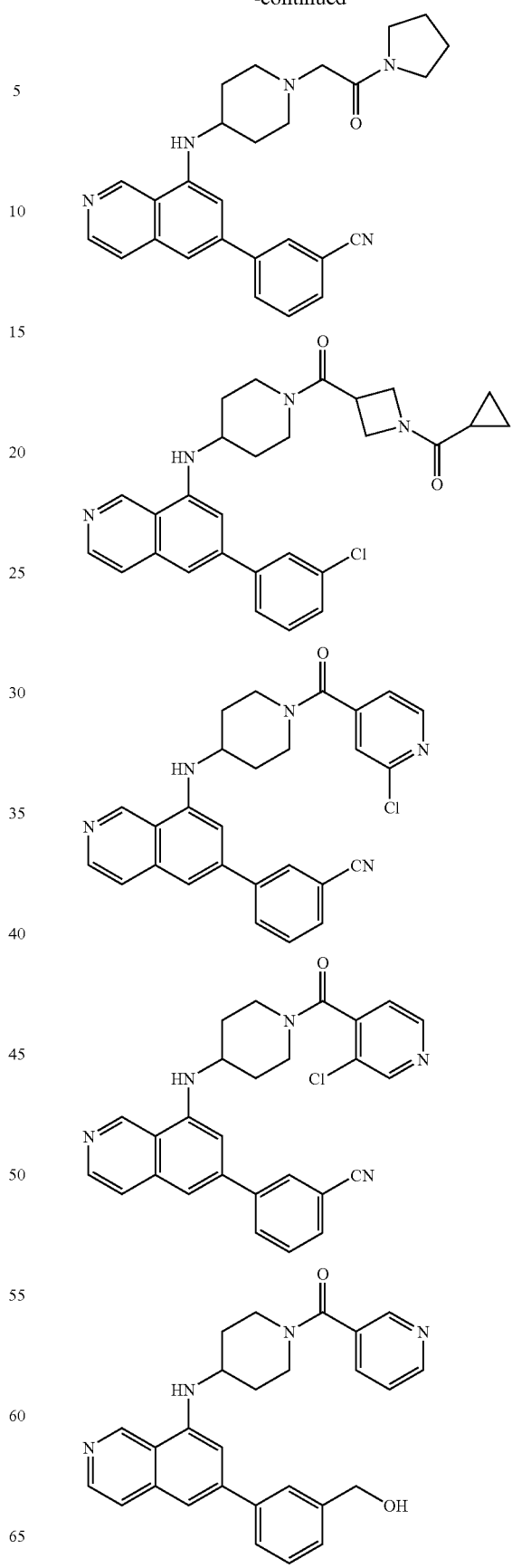

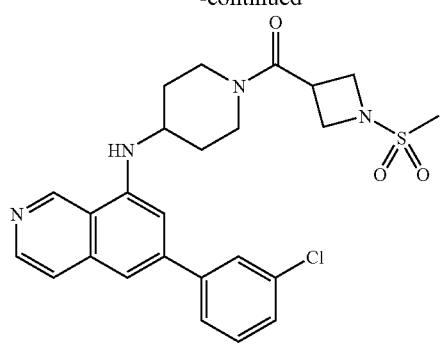
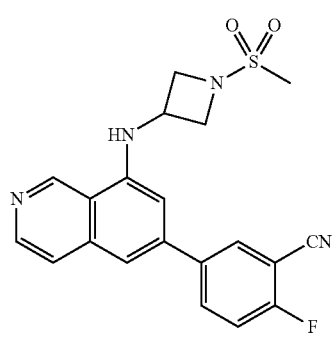
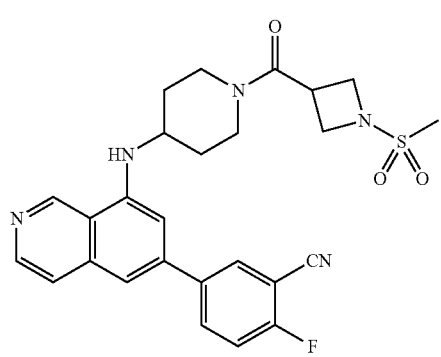
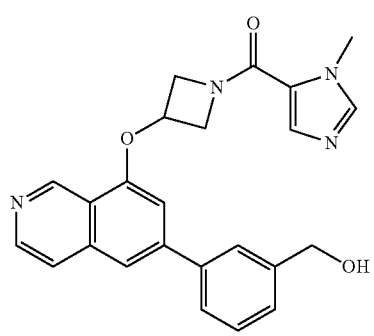
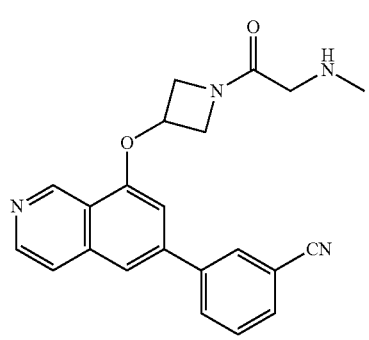
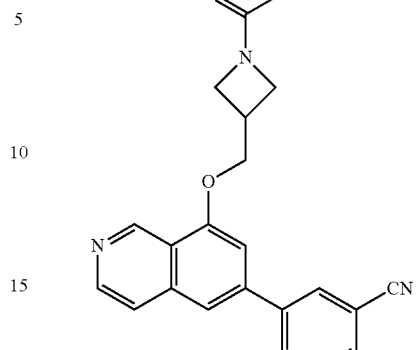
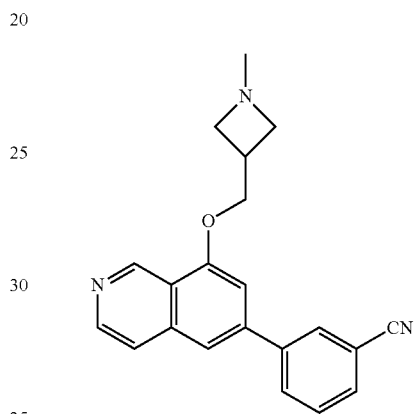
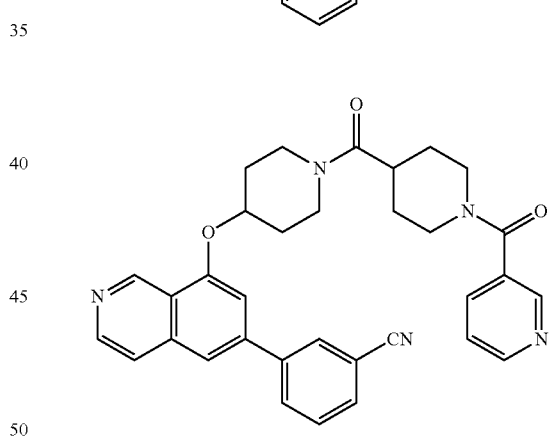
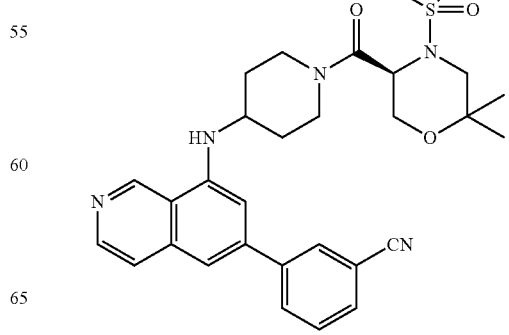

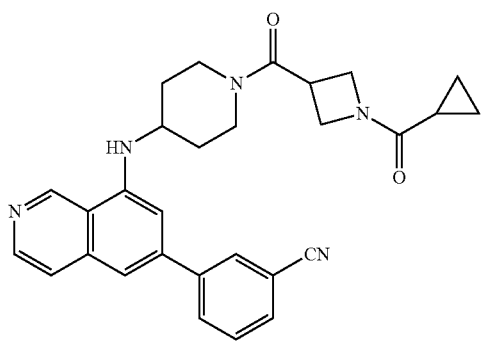
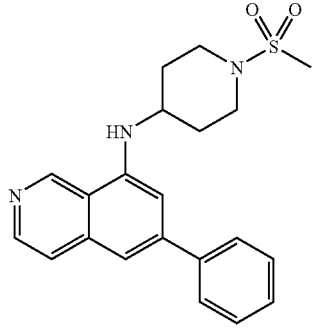
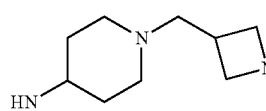

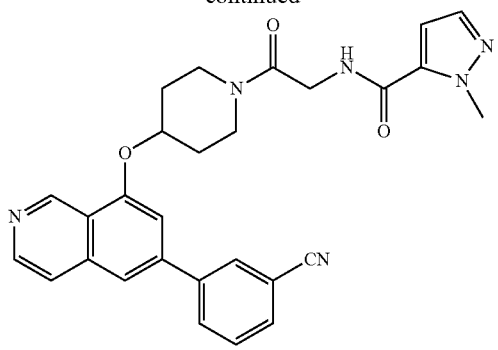
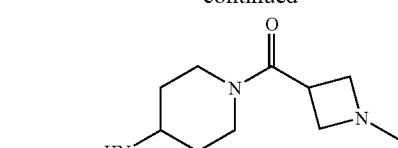
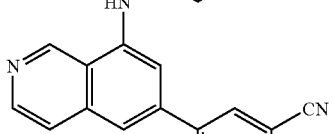
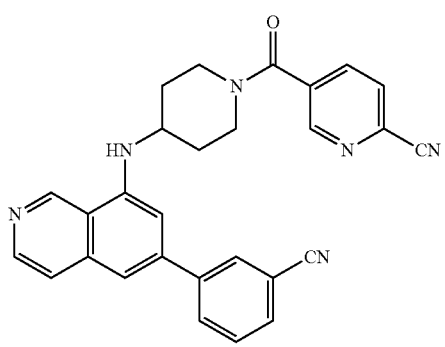
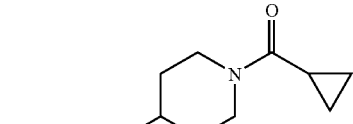
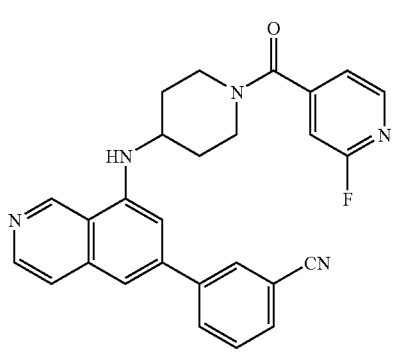
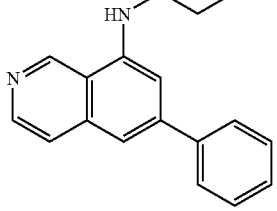
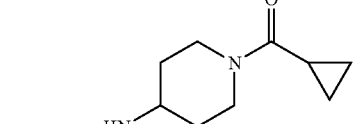
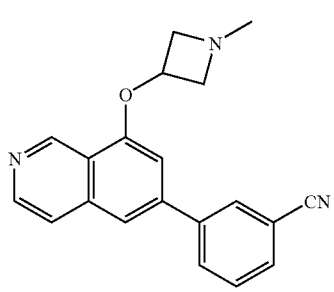
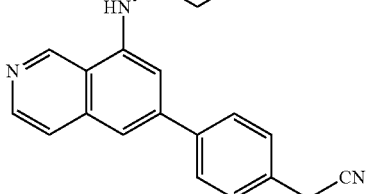
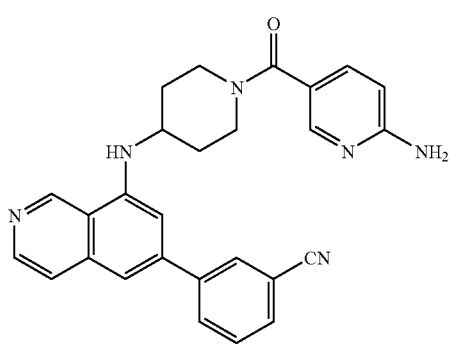
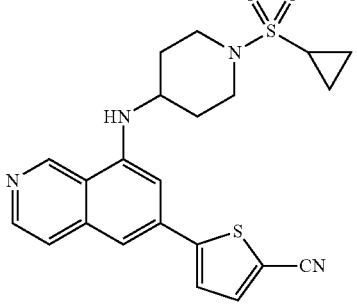
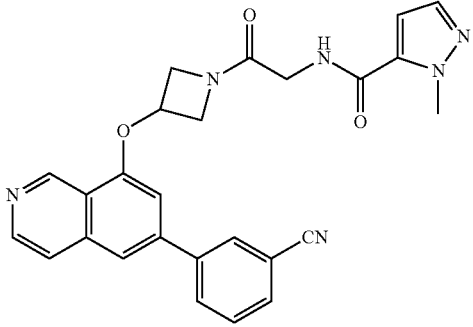

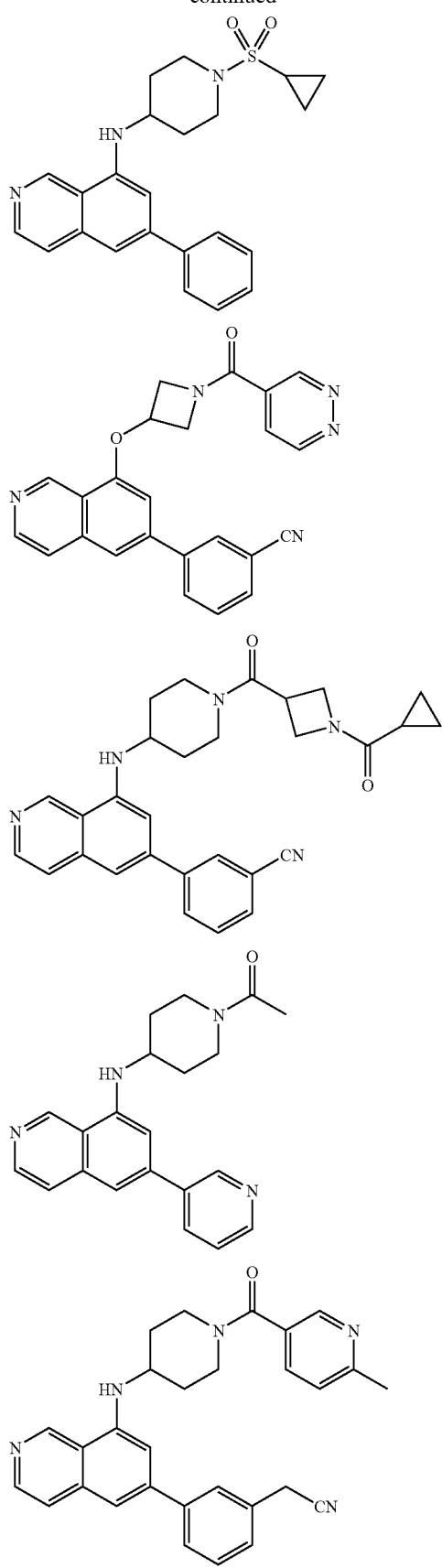
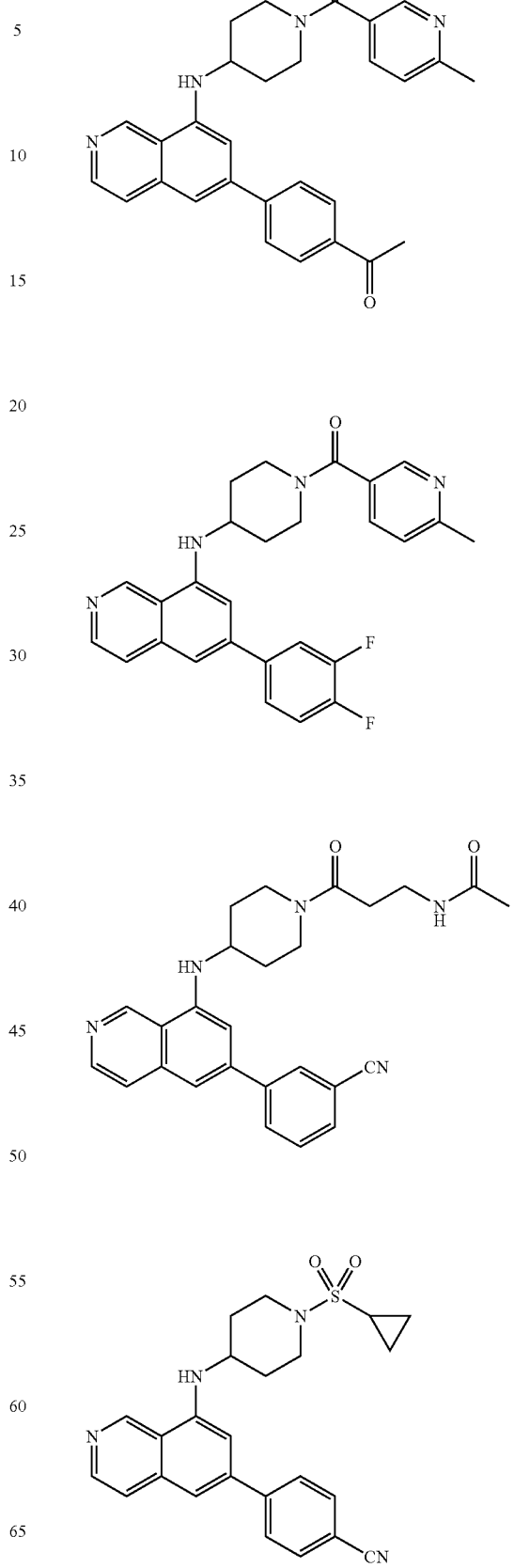

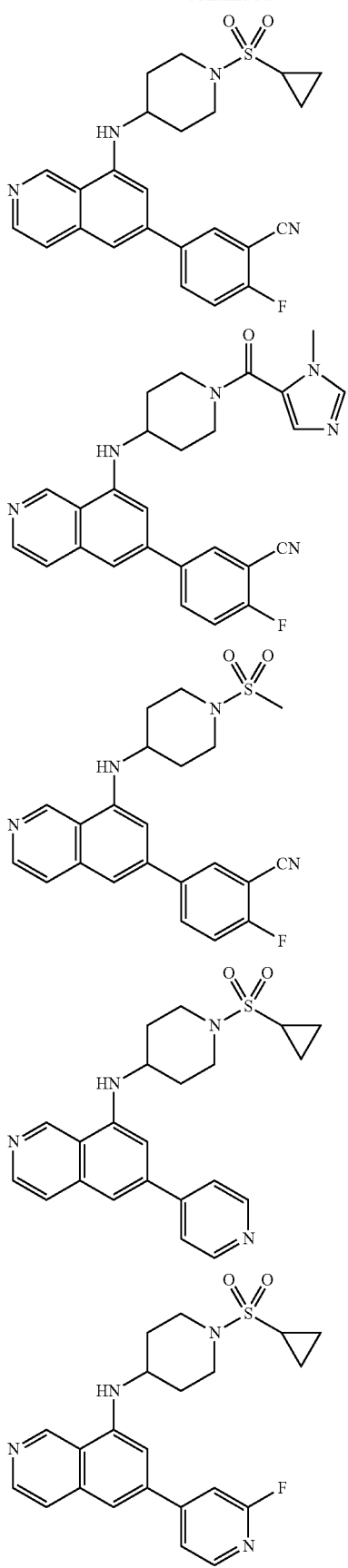
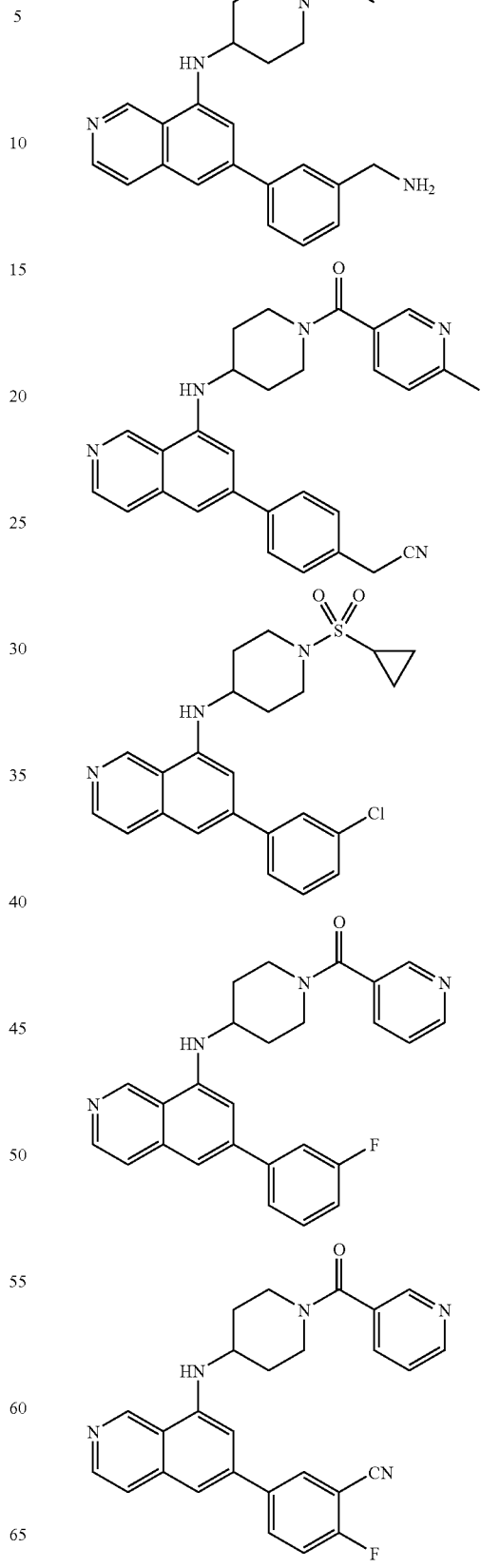

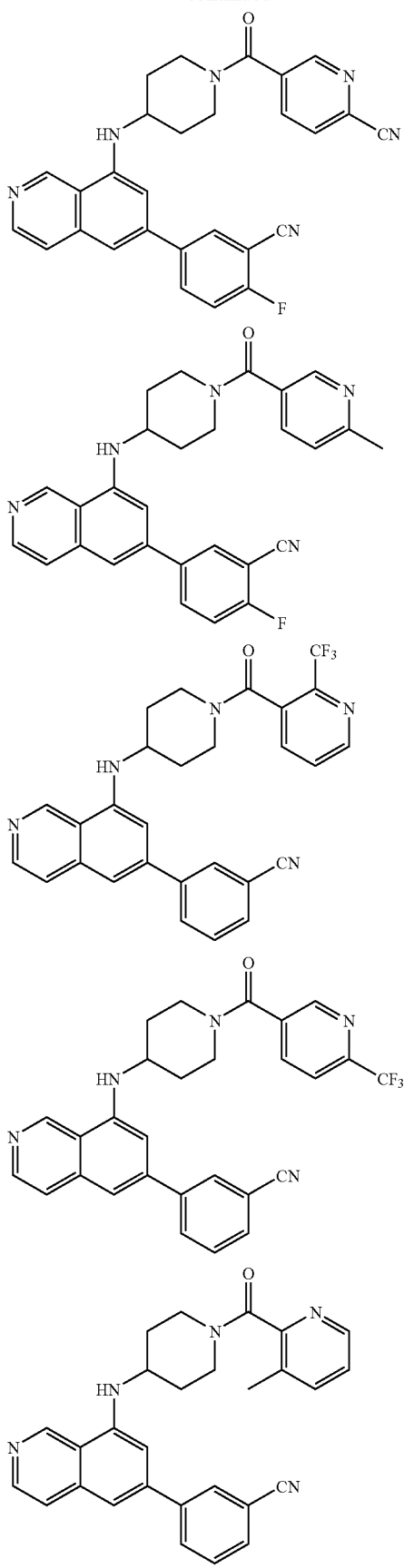
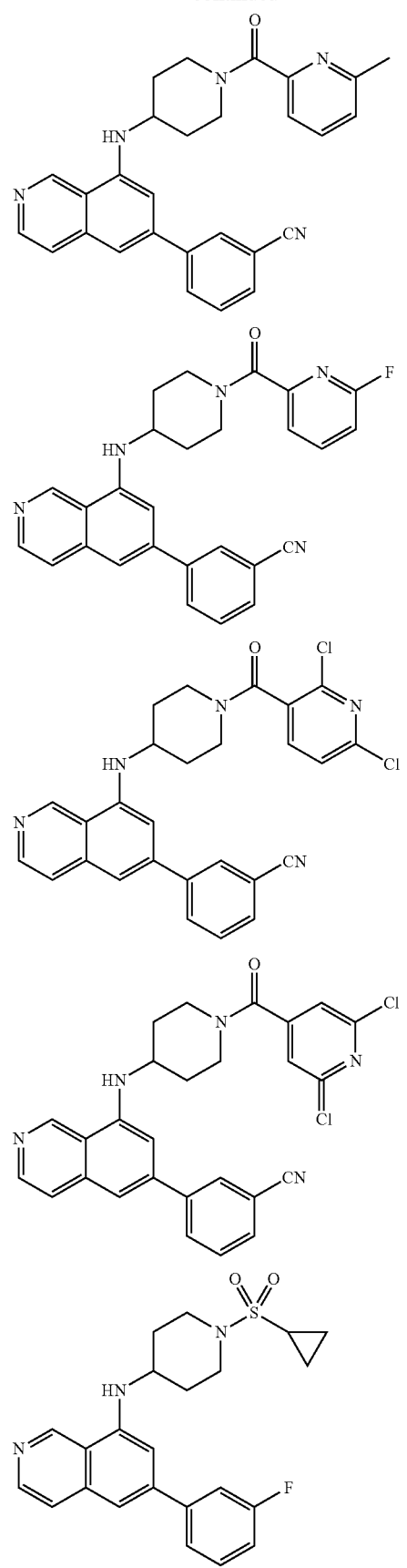

-continued
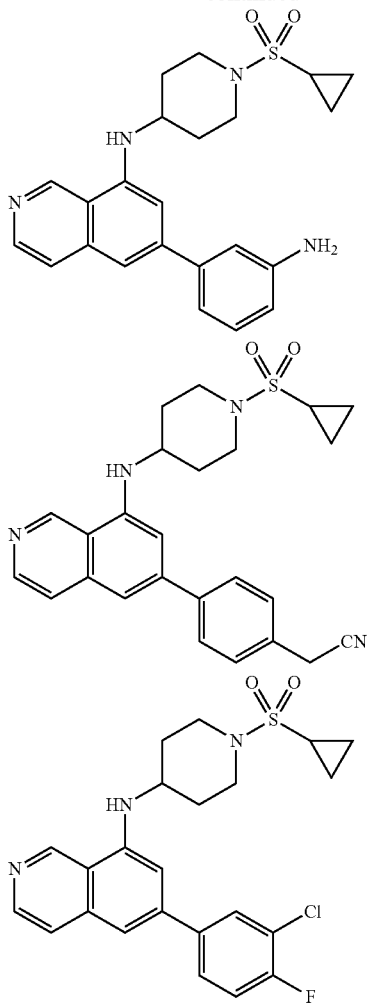
⑦ indicates text missing or illegible when filed
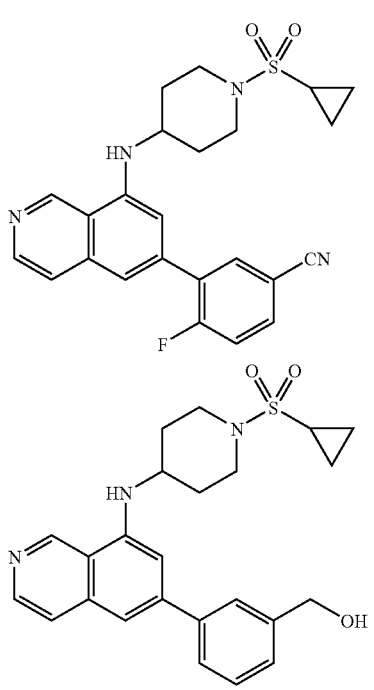
-continued
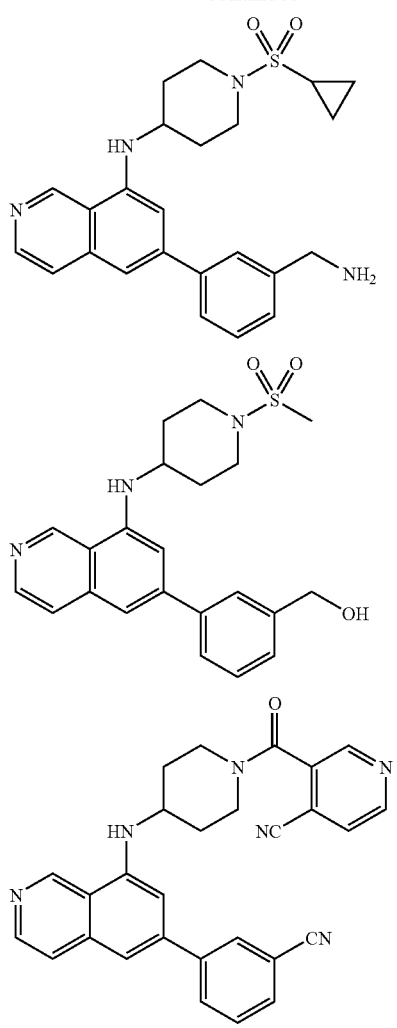

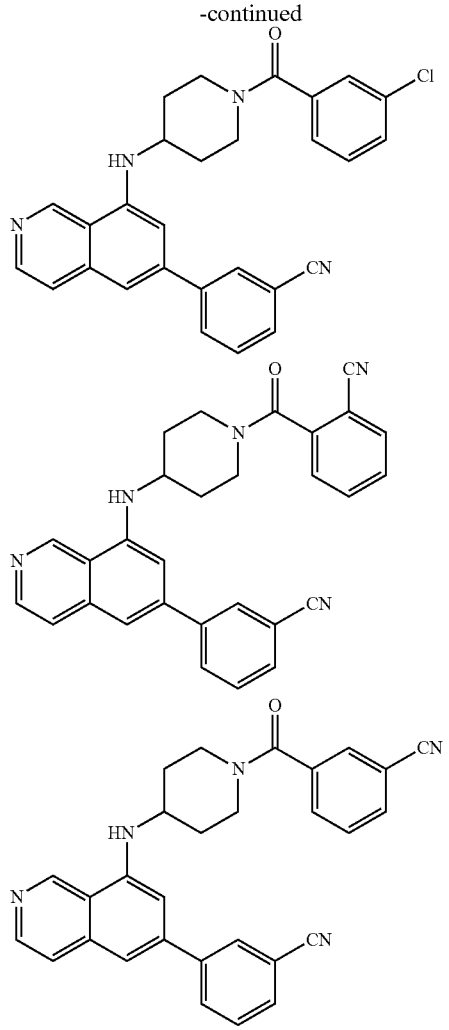
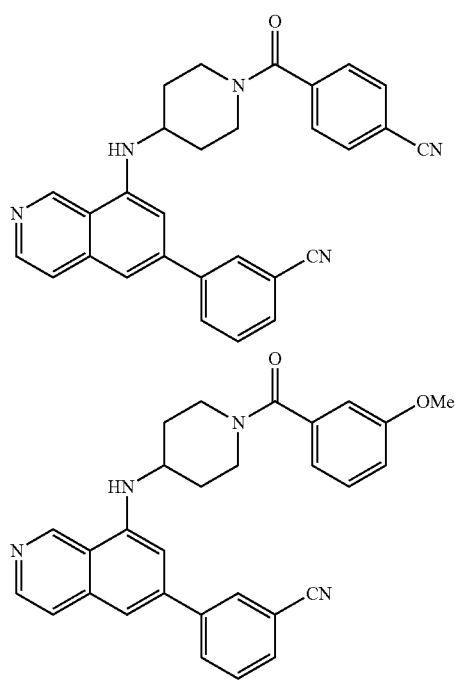
ⓘ indicates text missing or illegible when filed
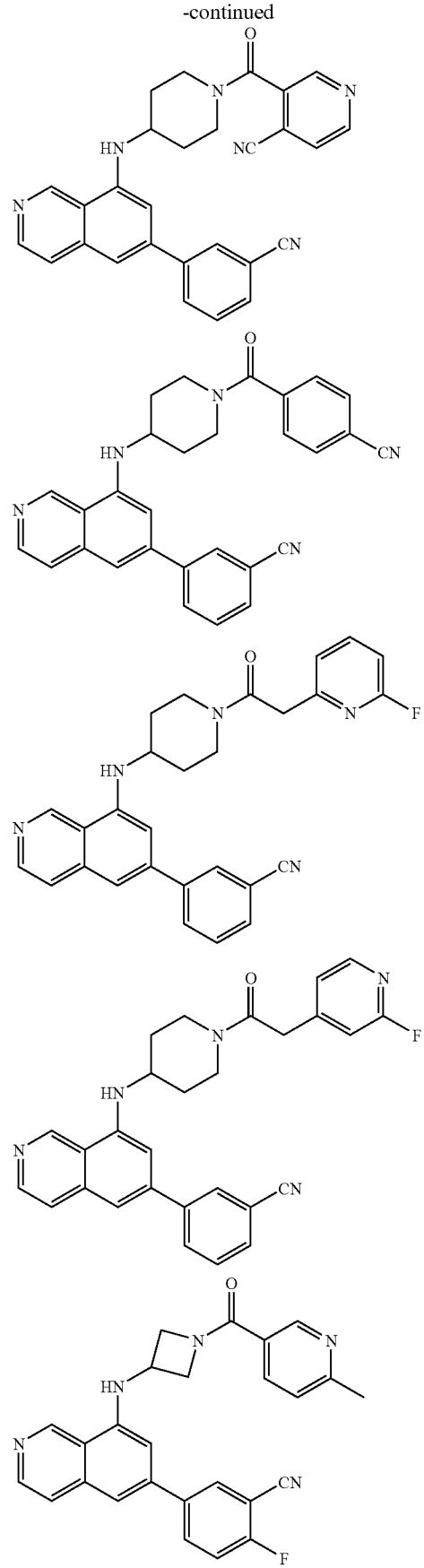

-continued
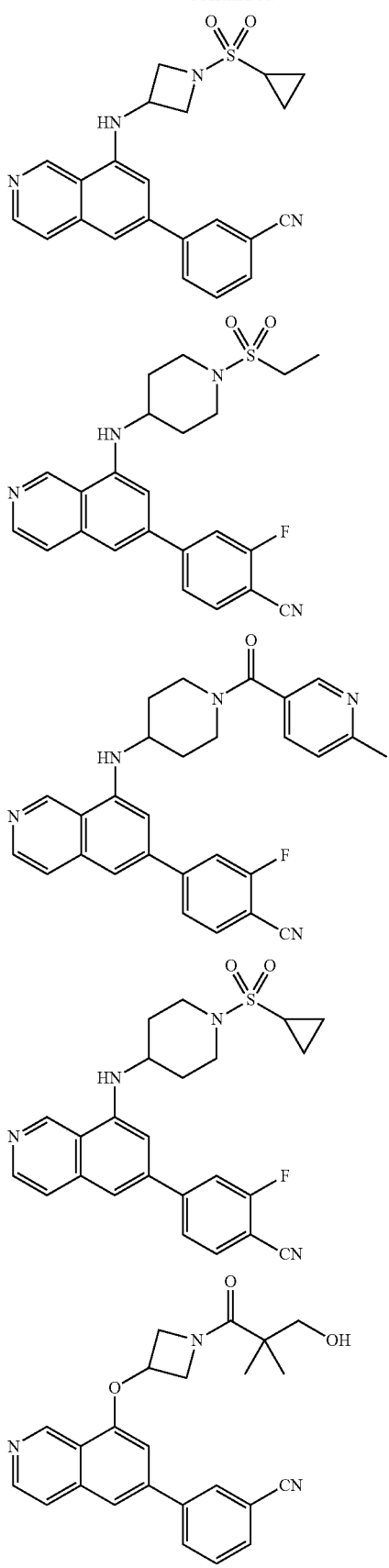
-continued
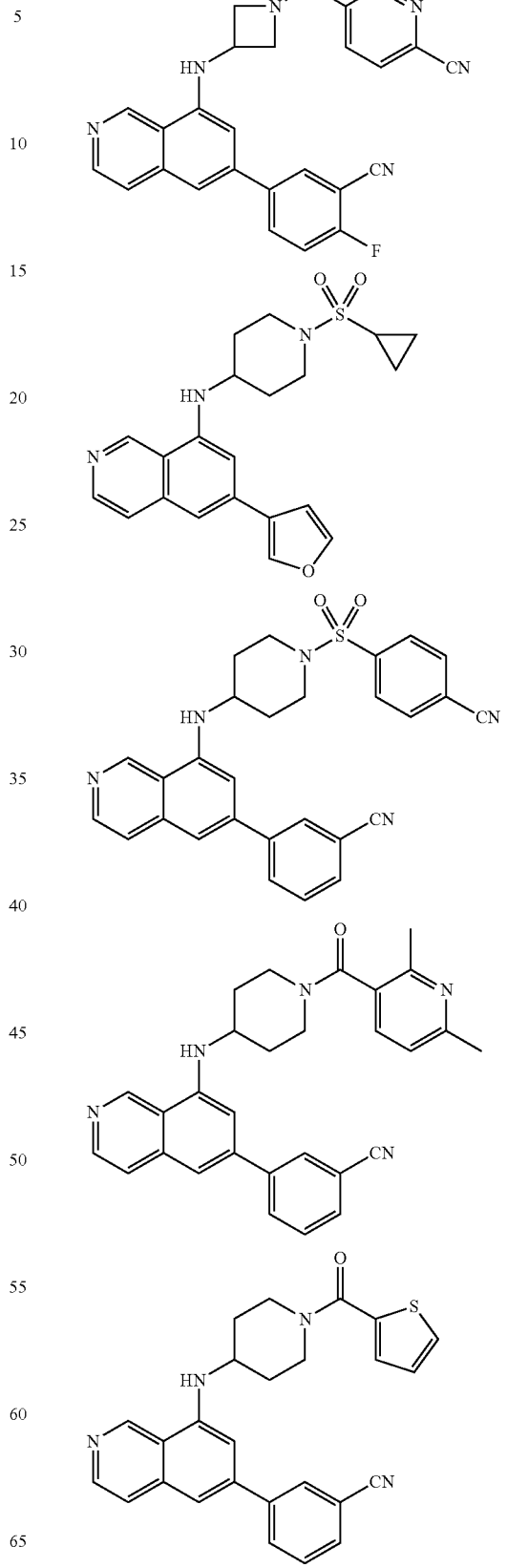

-continued
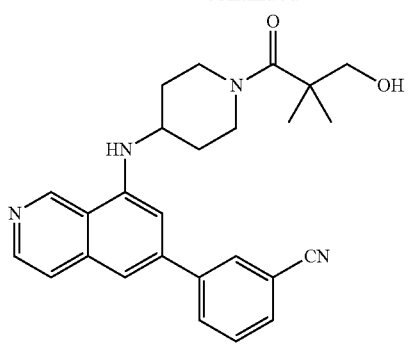
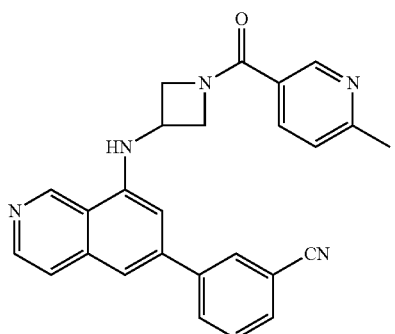
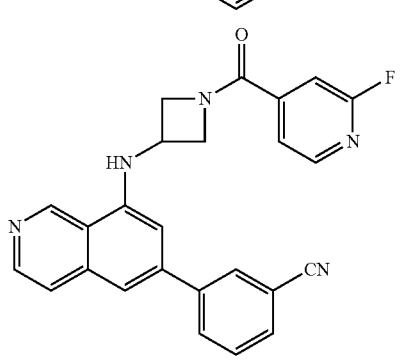
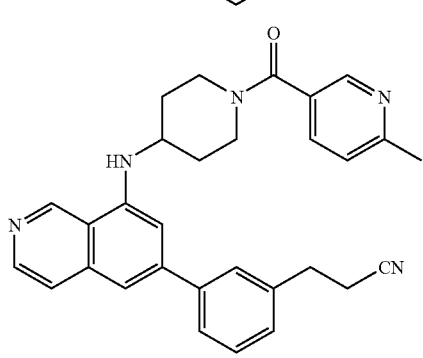
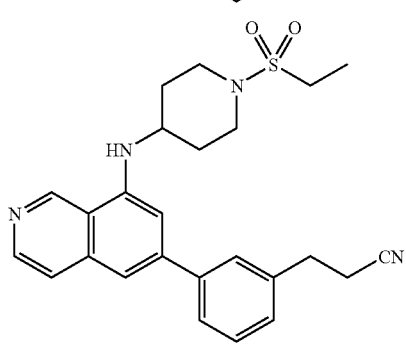
-continued
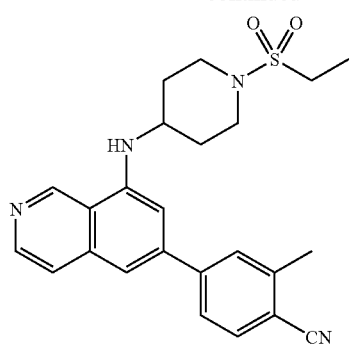
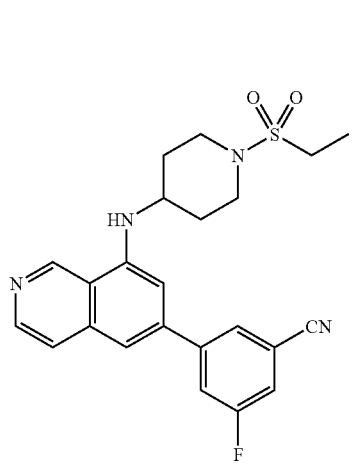
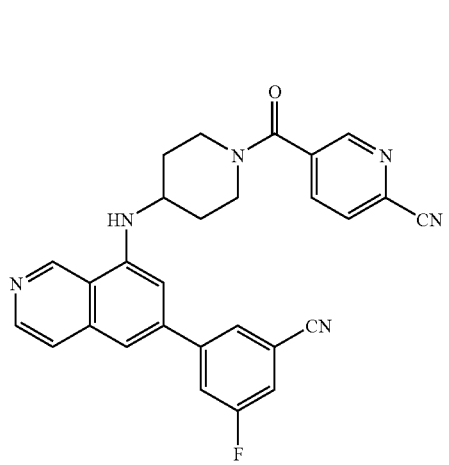
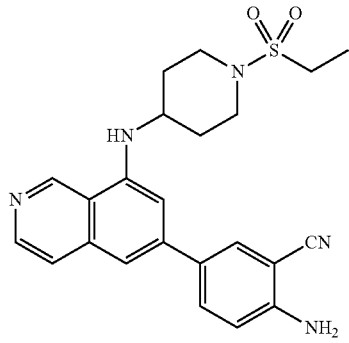

-continued
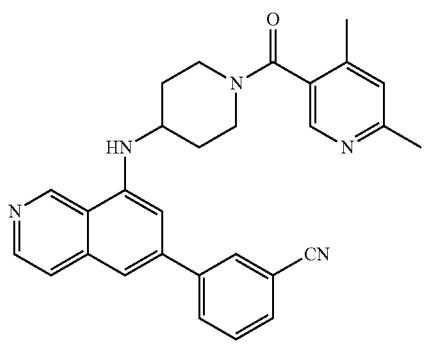
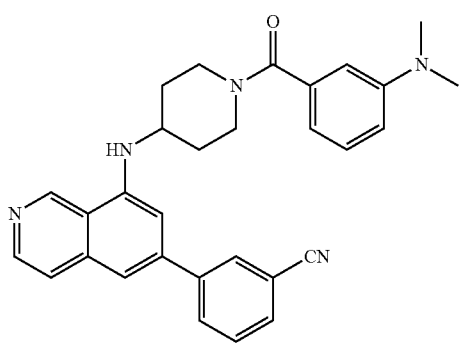
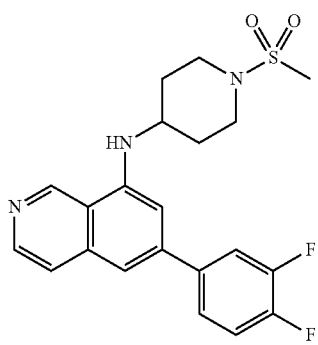
-continued
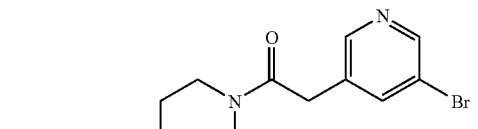
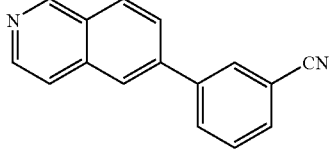
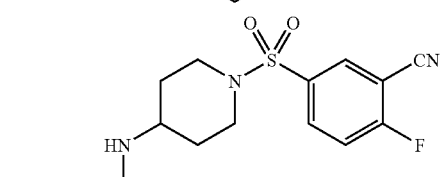
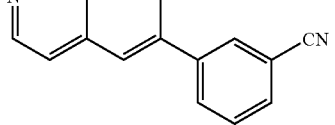
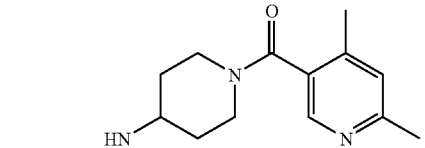
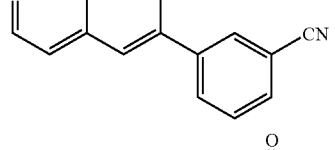
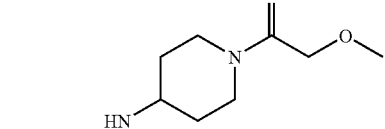
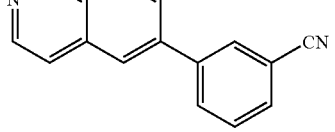
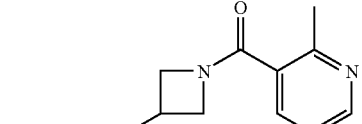

47
-continued
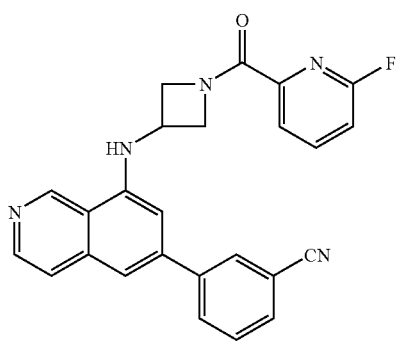
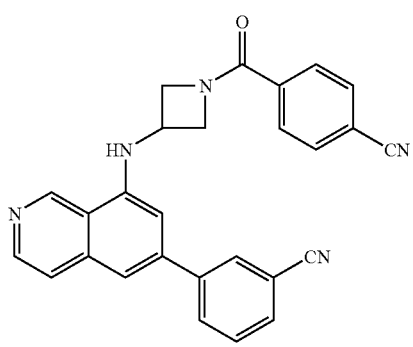
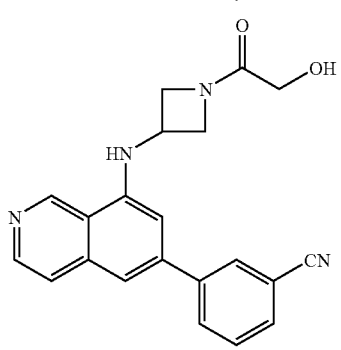
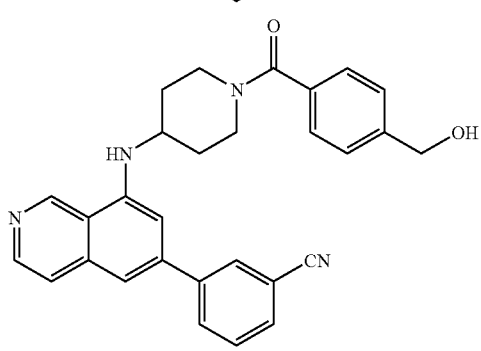
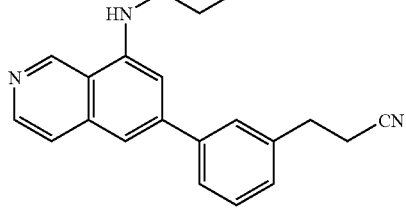
48
-continued
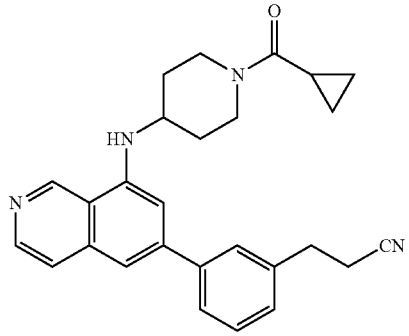
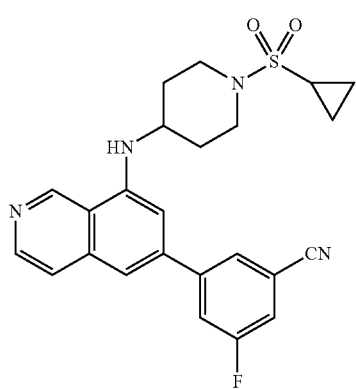
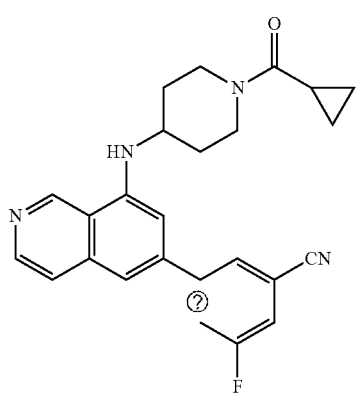
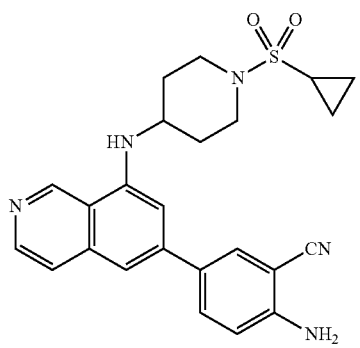

49
-continued
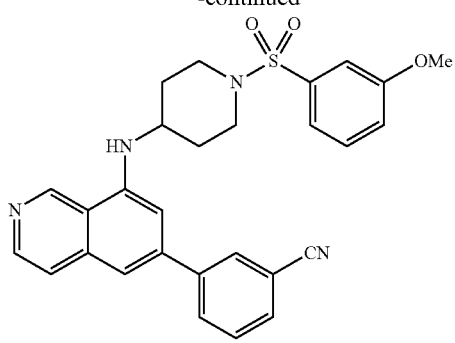
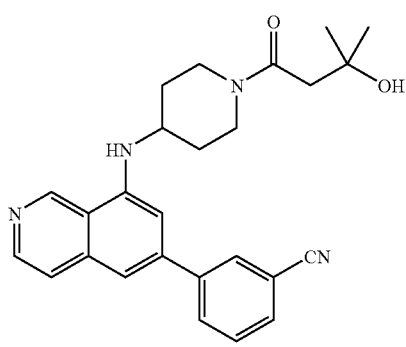
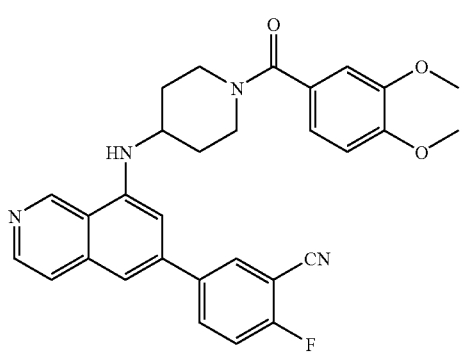
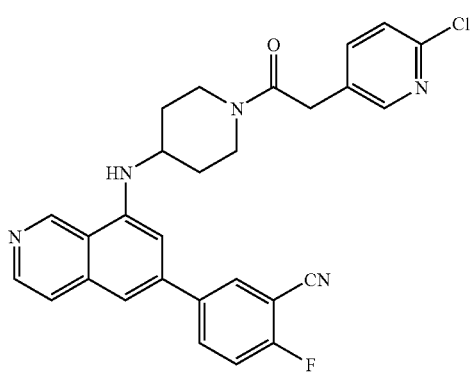
50
-continued
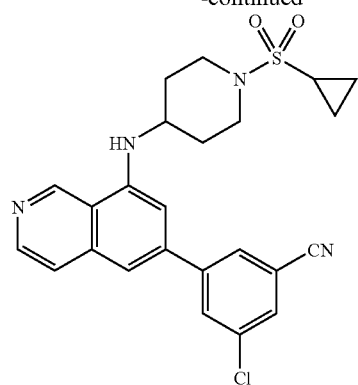
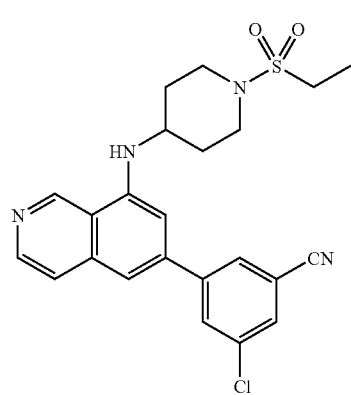
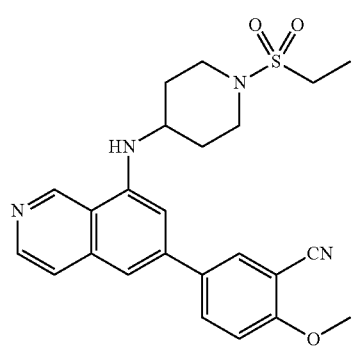
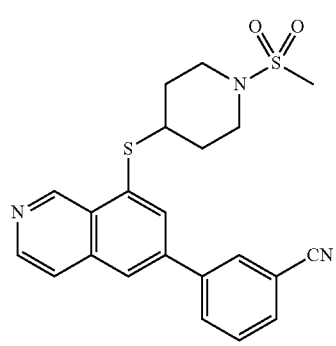

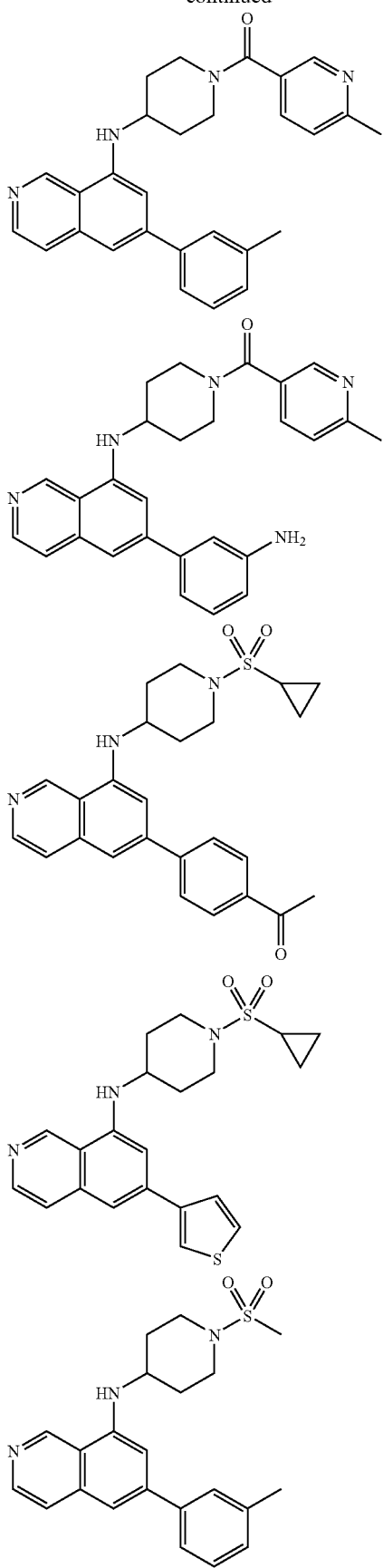
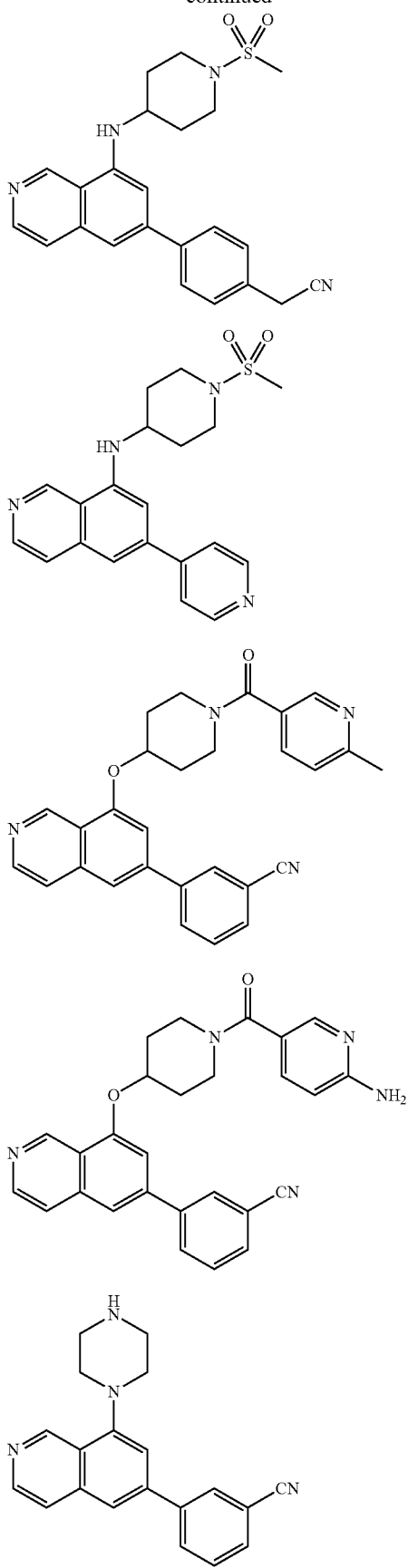

53
-continued
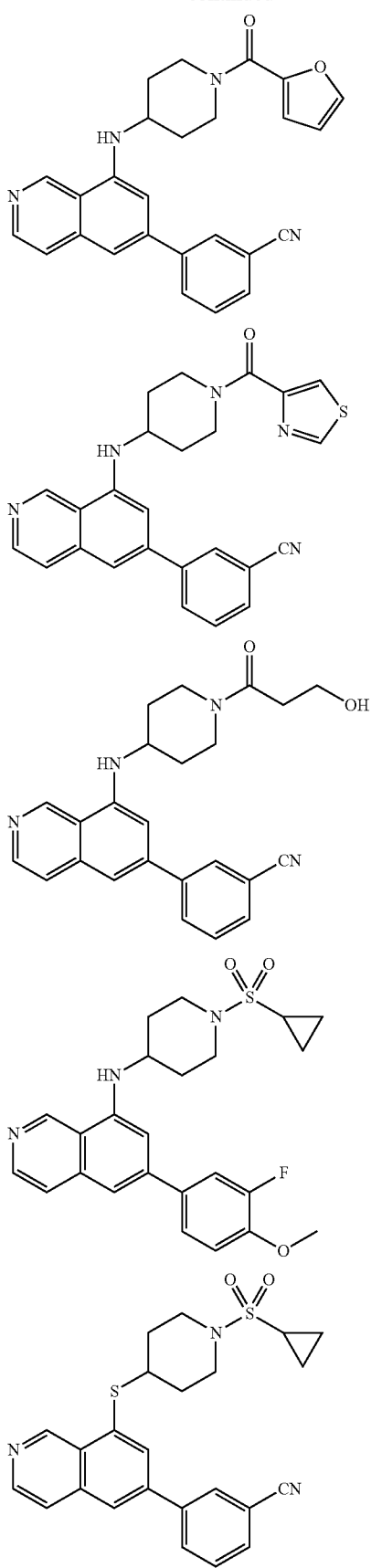
54
-continued
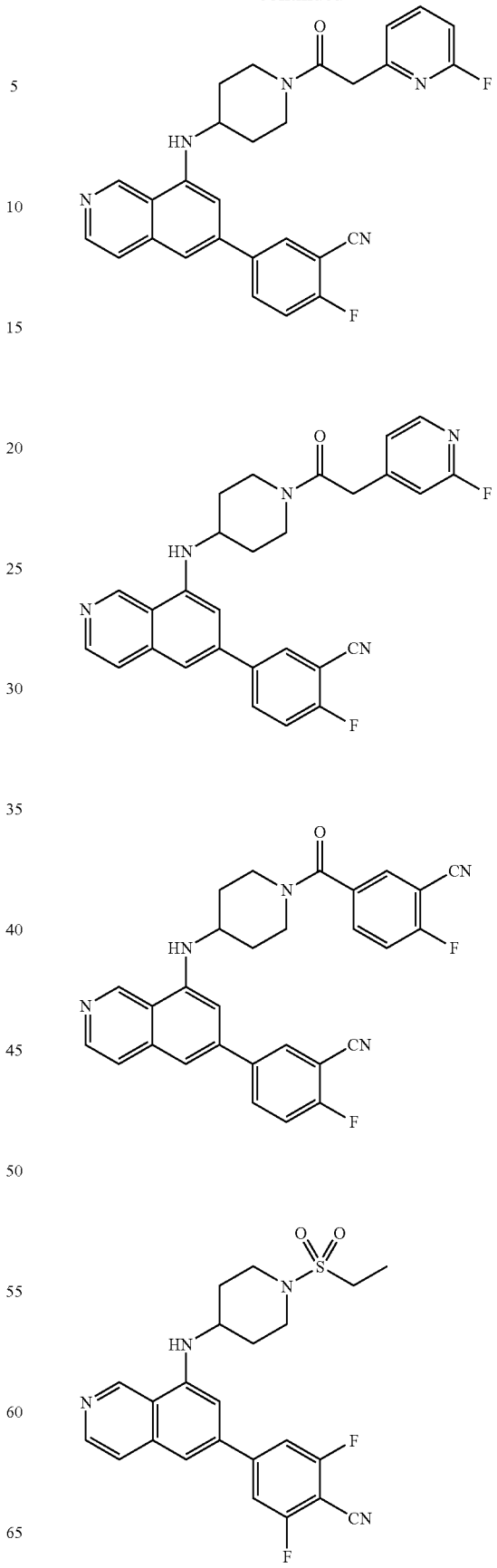

55
-continued
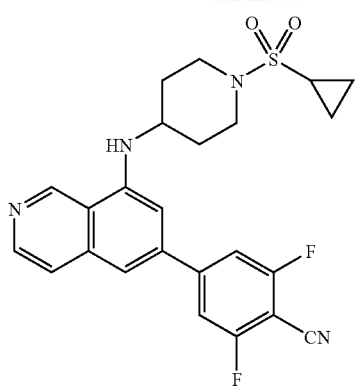
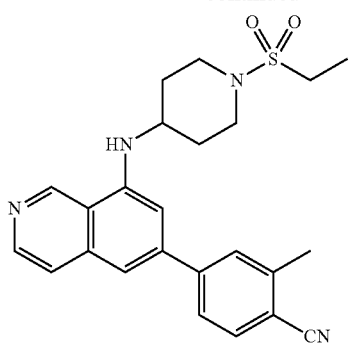
56
-continued
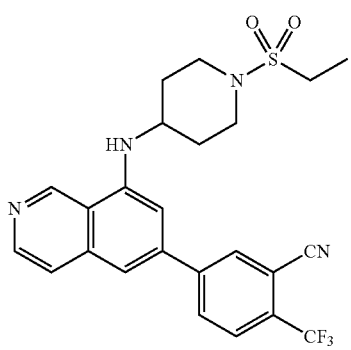
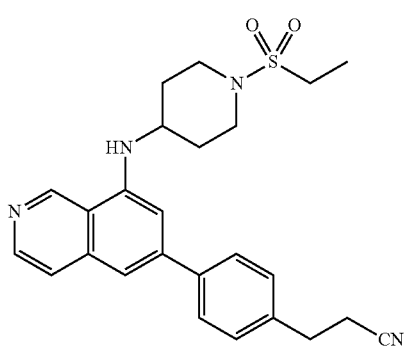
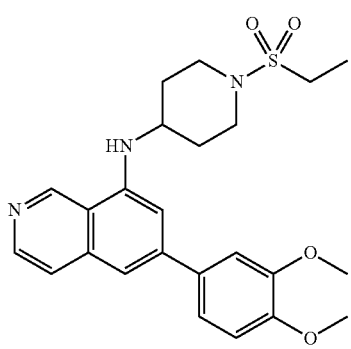
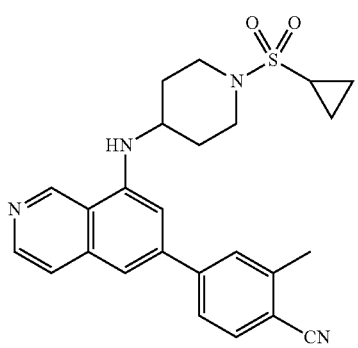

57
-continued
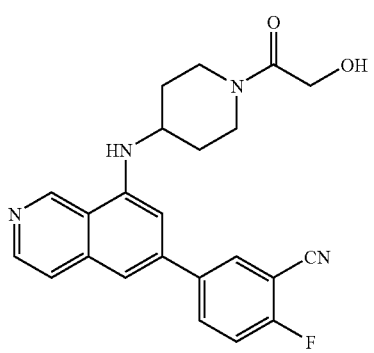
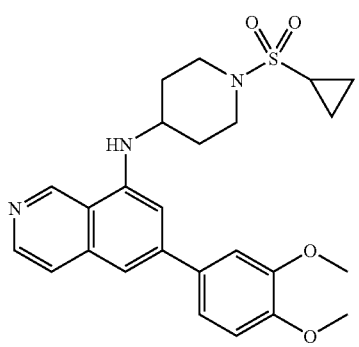
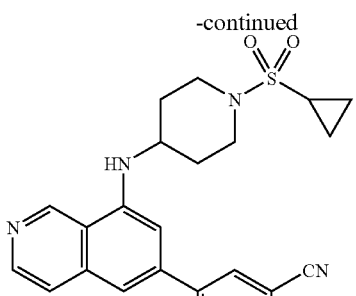
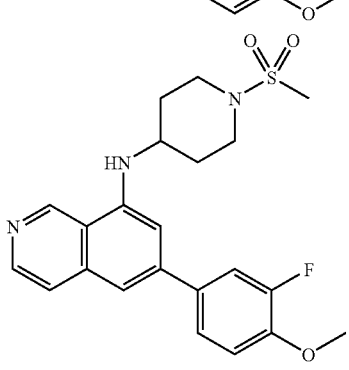
58
-continued
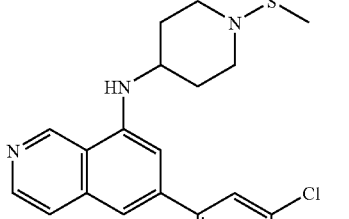
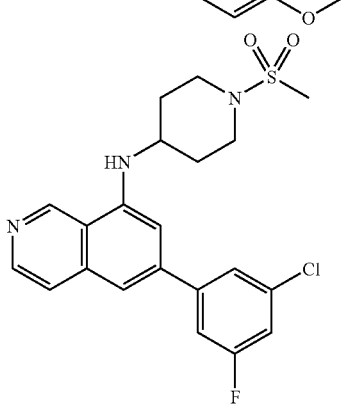
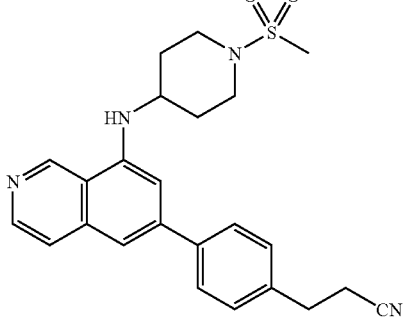

-continued
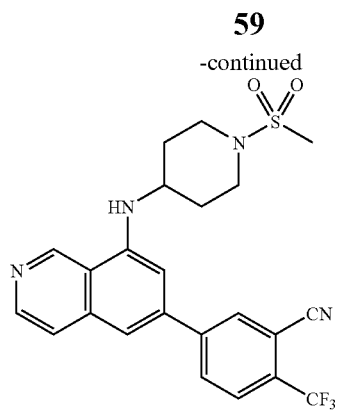
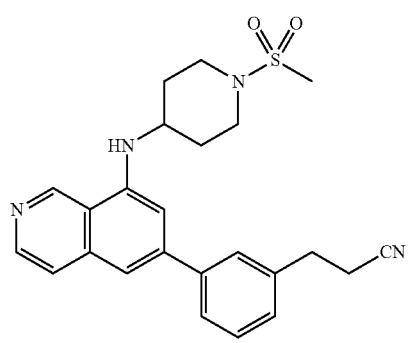
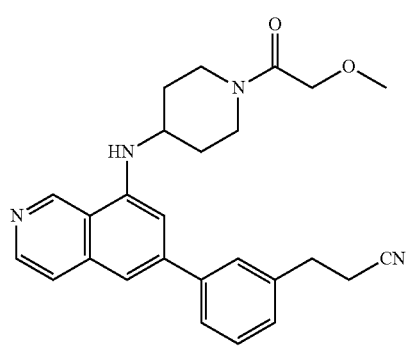
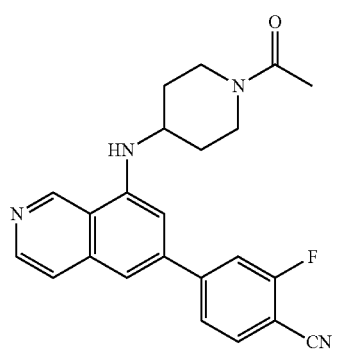
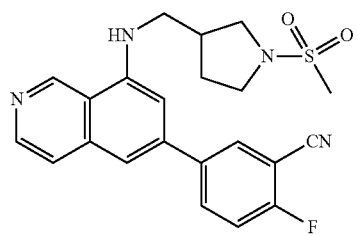
-continued
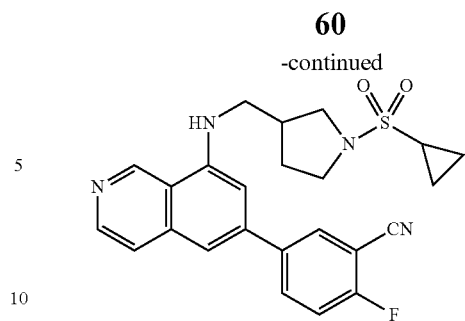
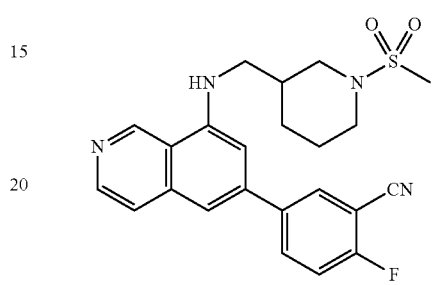
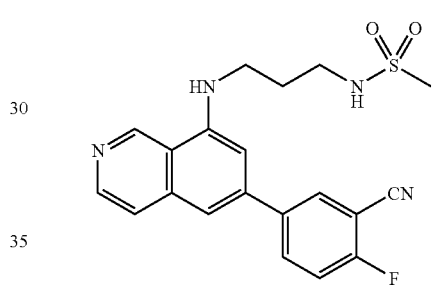
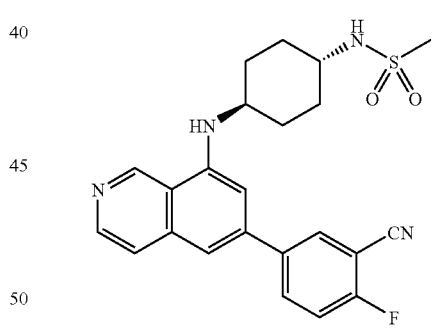
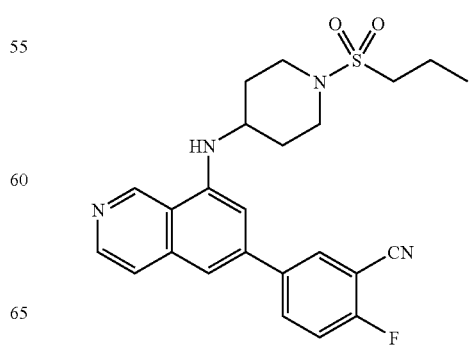

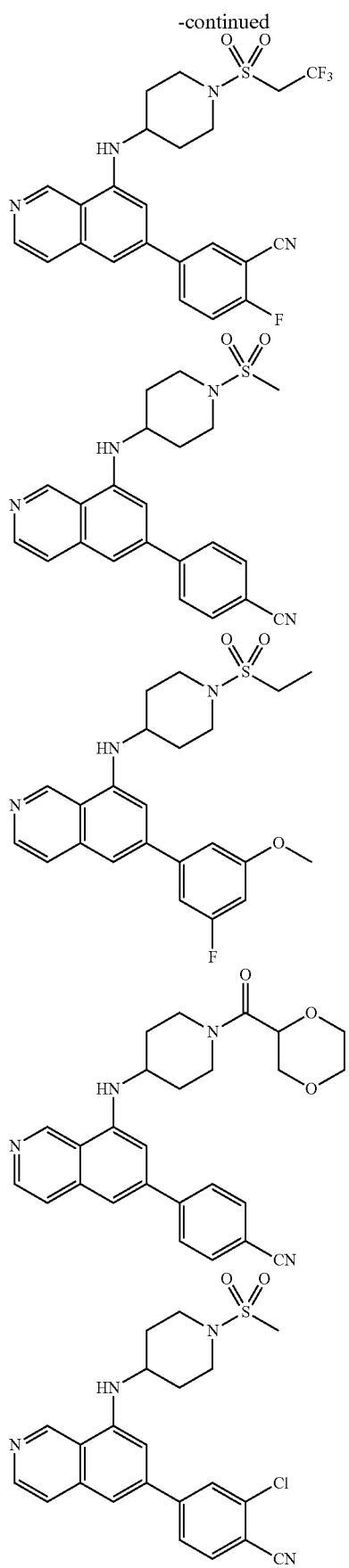
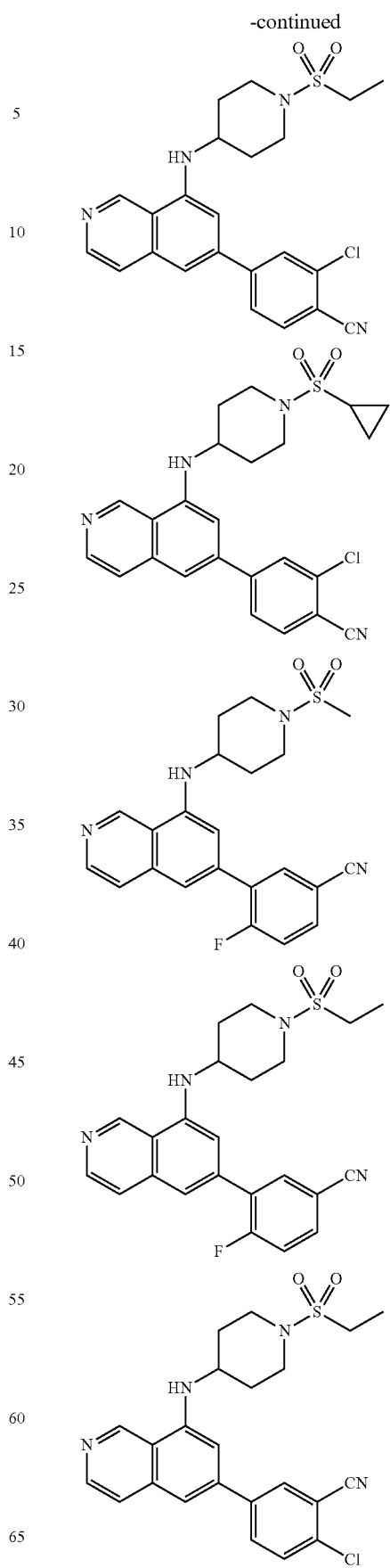

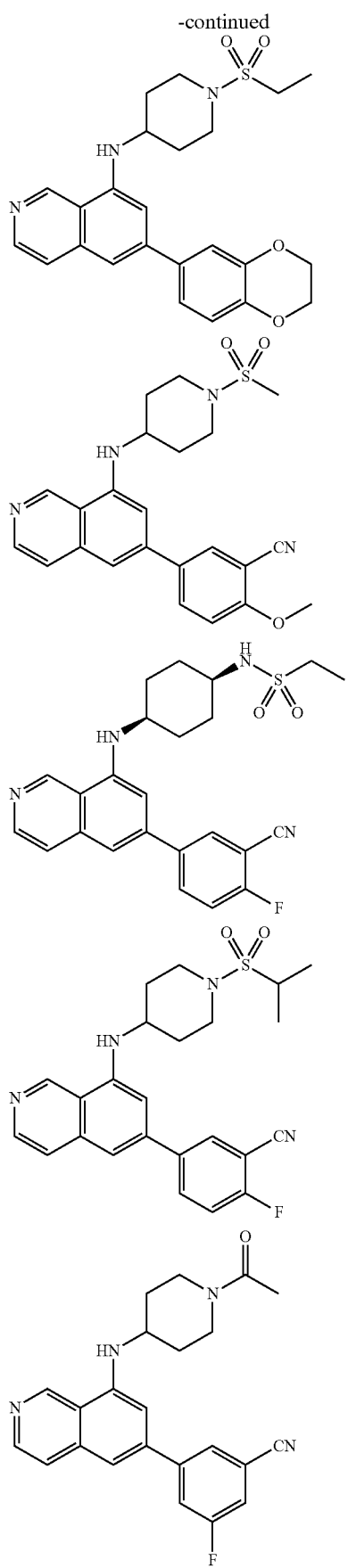
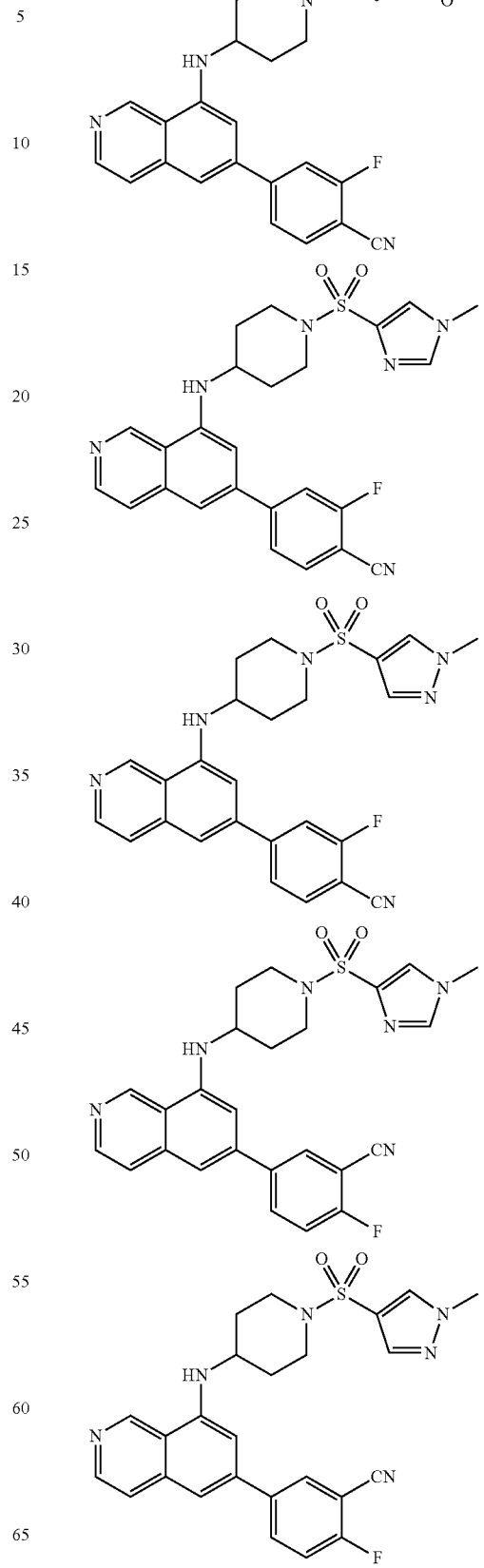

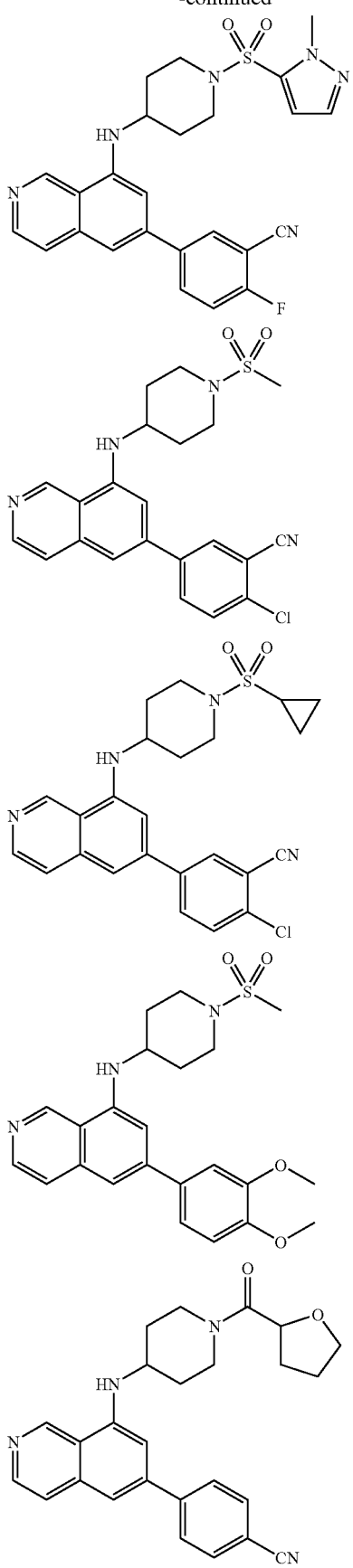
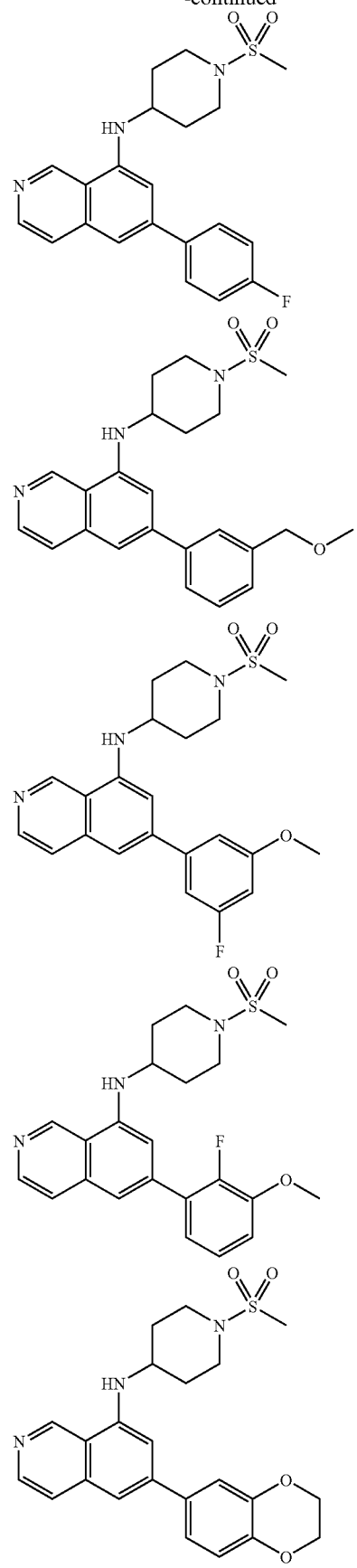

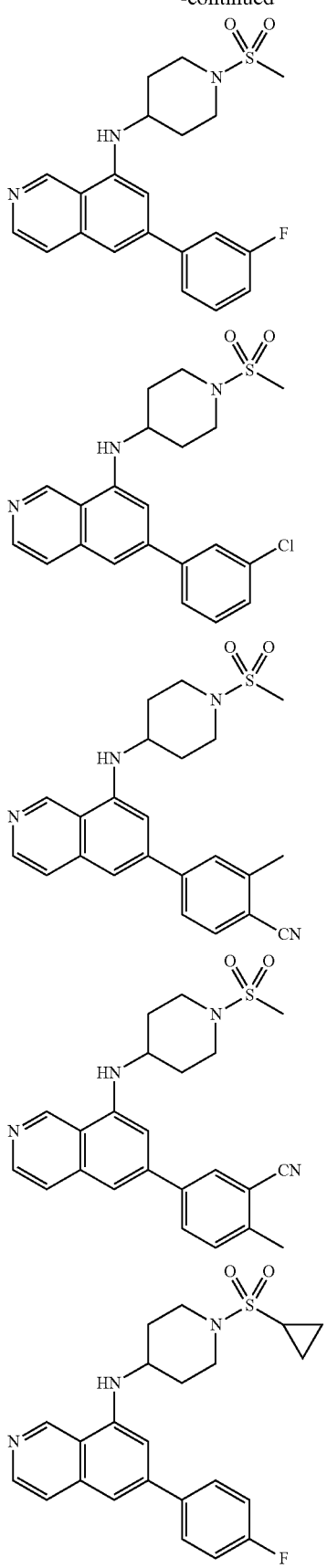
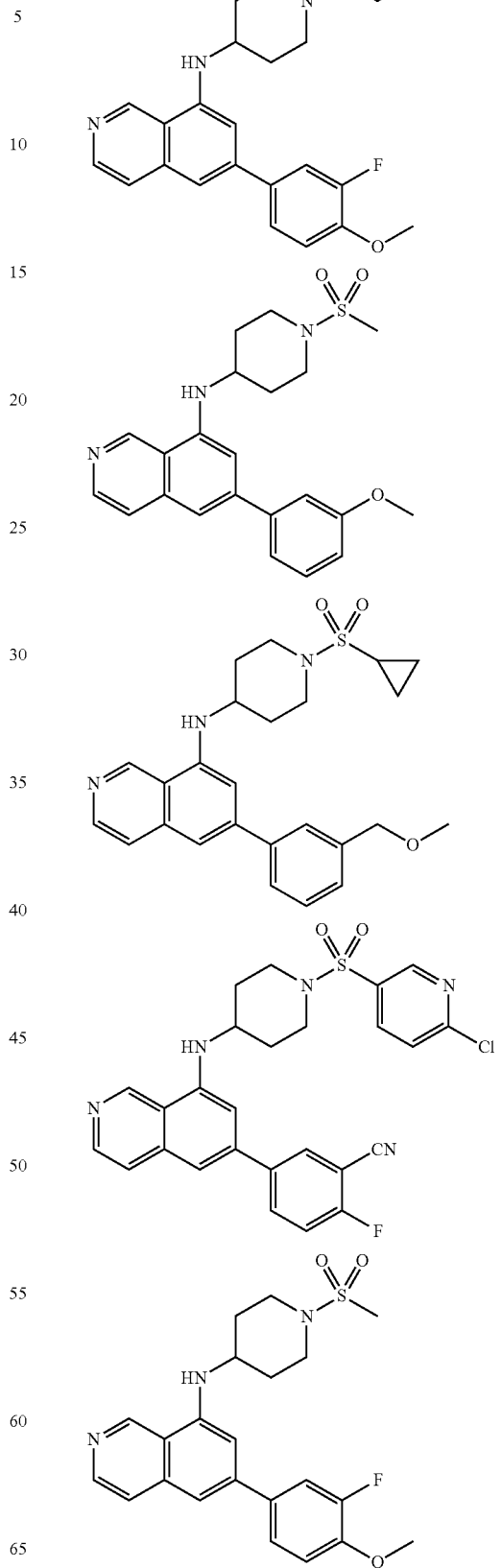

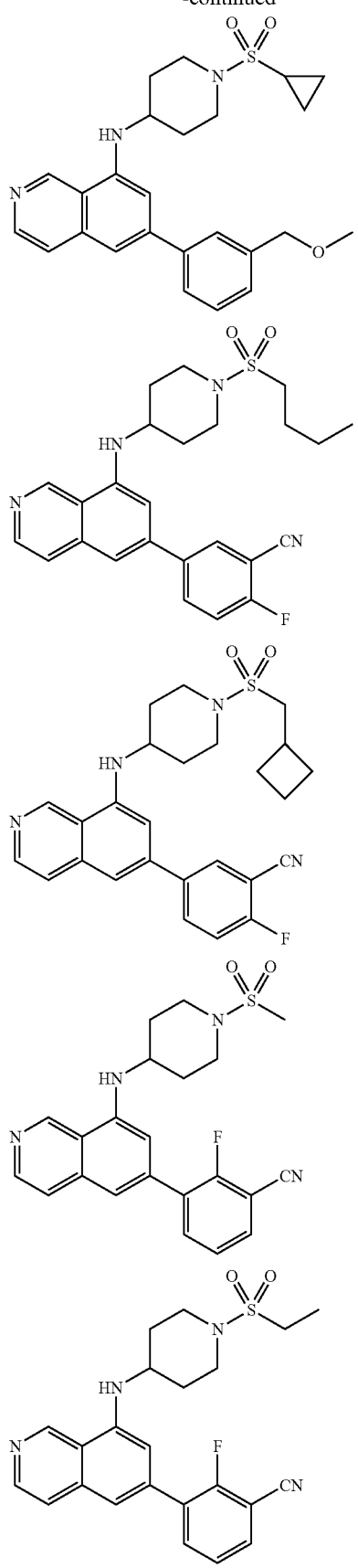
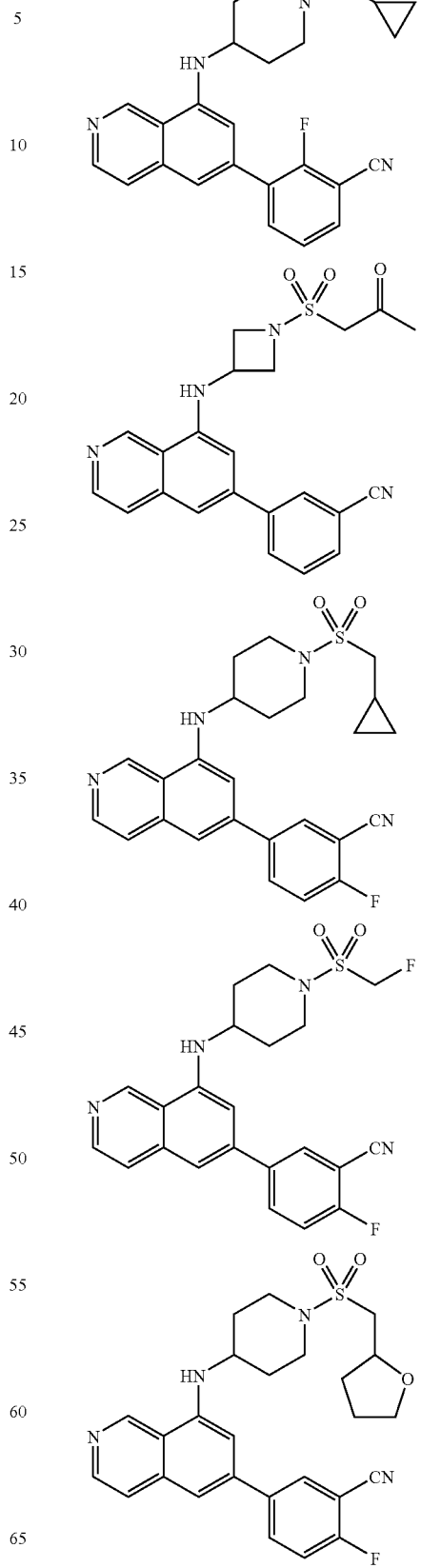

71
-continued
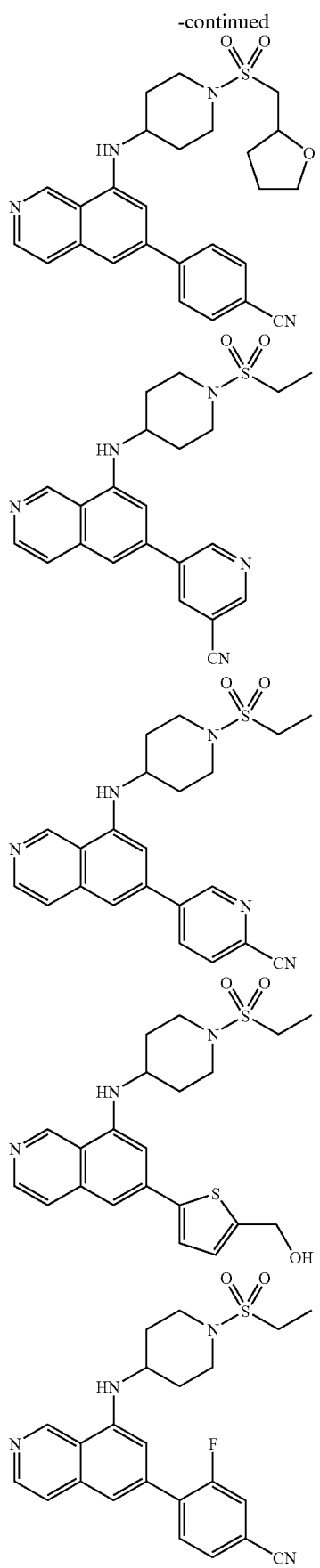
72
-continued
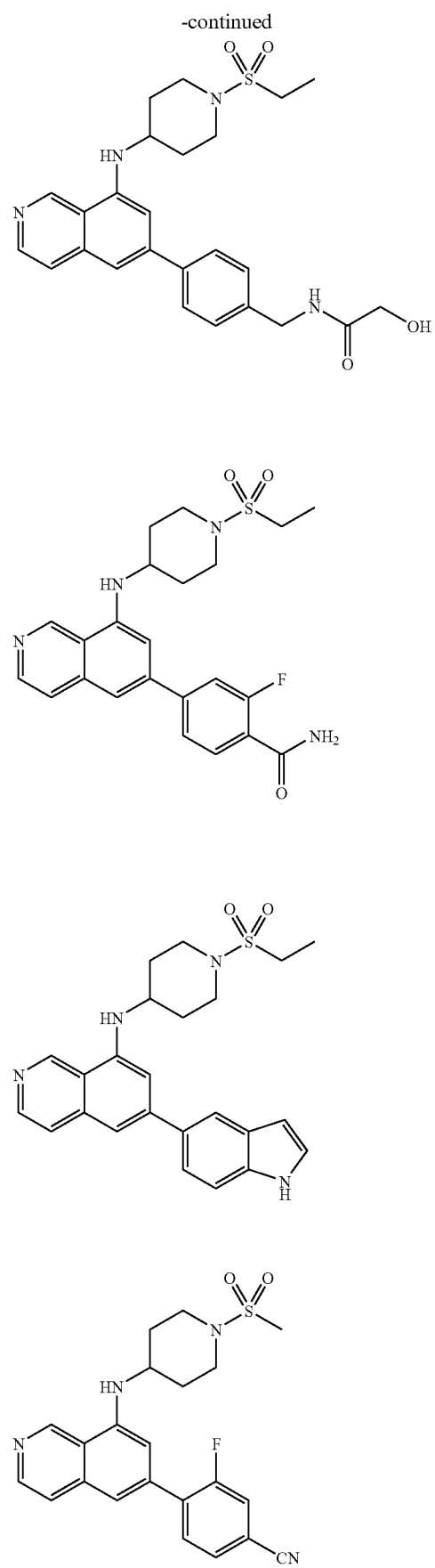

73
-continued
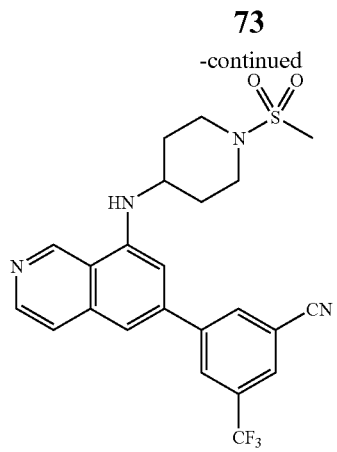
74
-continued
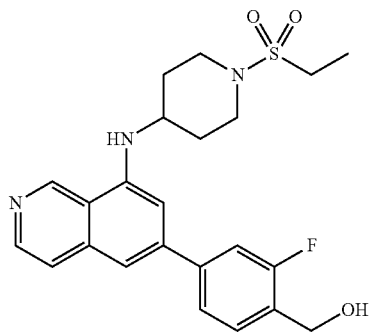
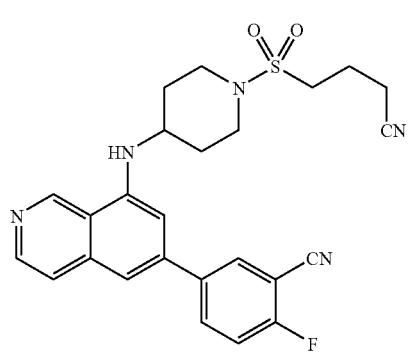
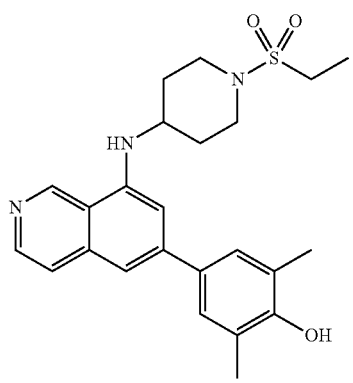
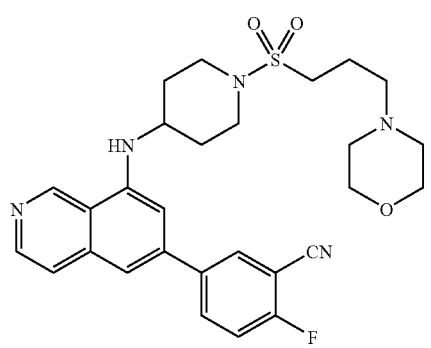
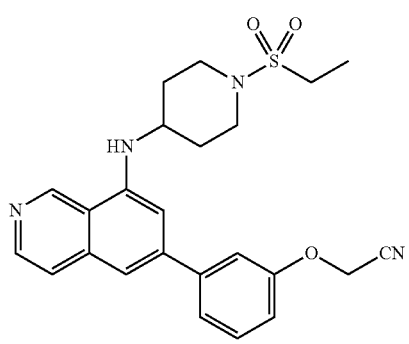
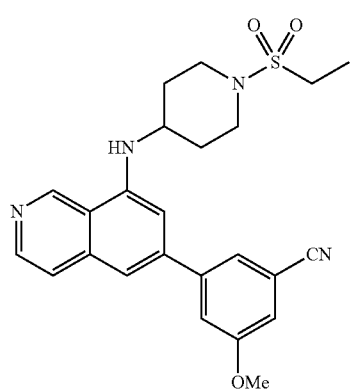
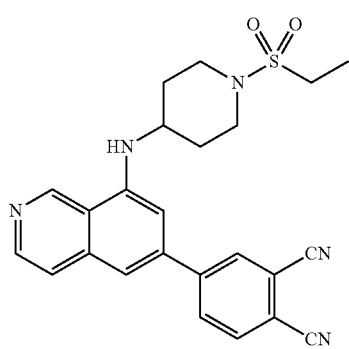

75
-continued
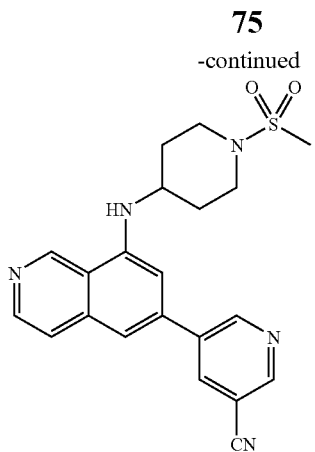
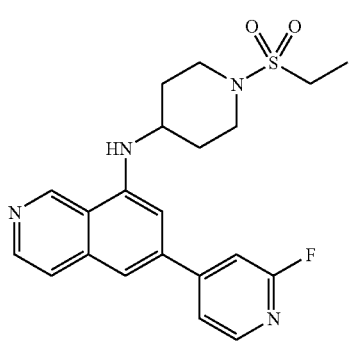
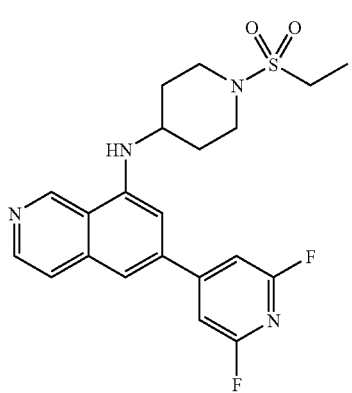
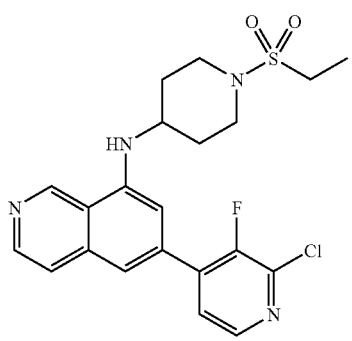
76
-continued
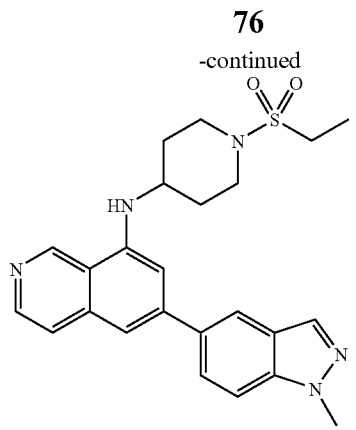
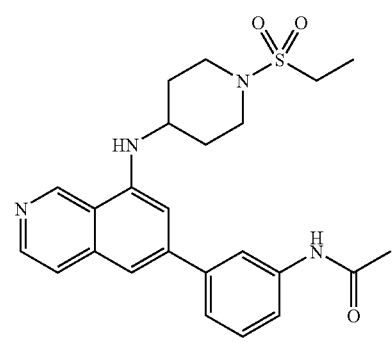
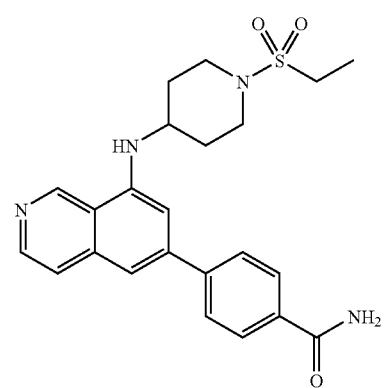
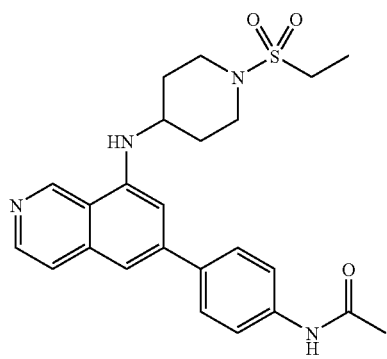

77
-continued
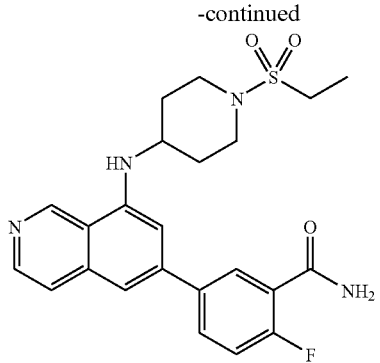
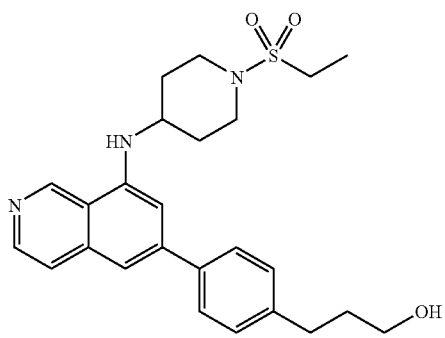
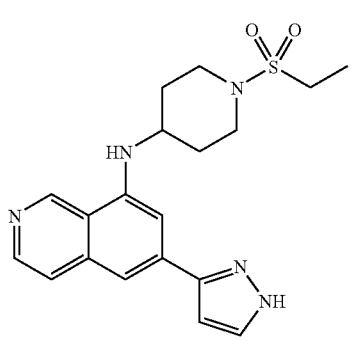
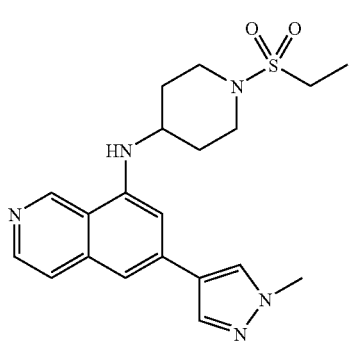
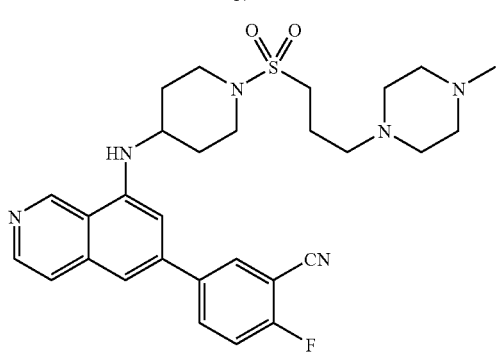
78
-continued
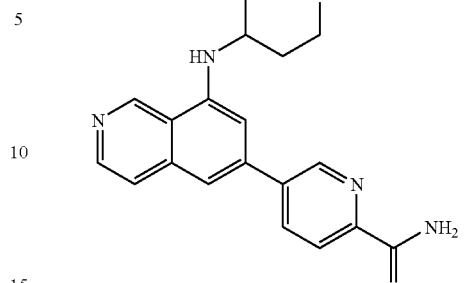
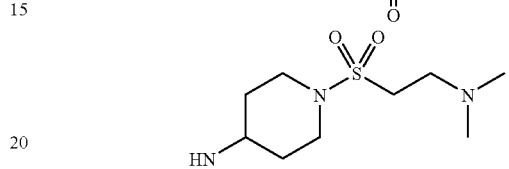
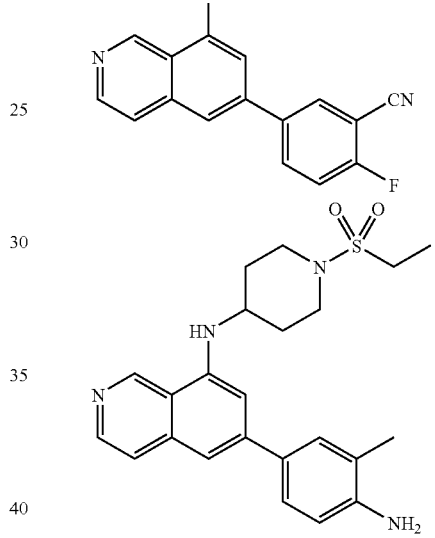
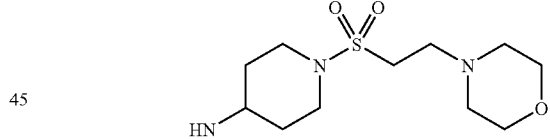
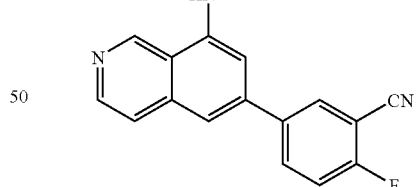
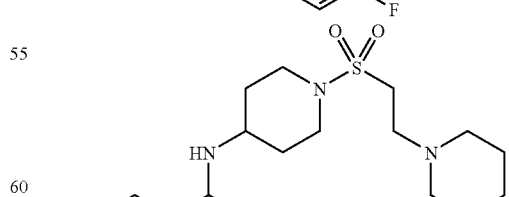
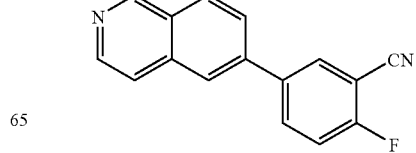

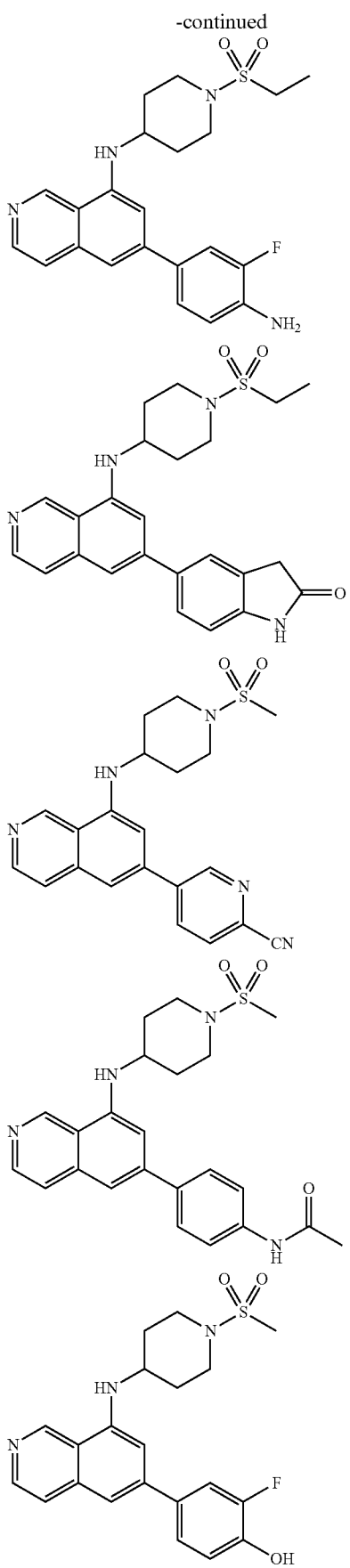
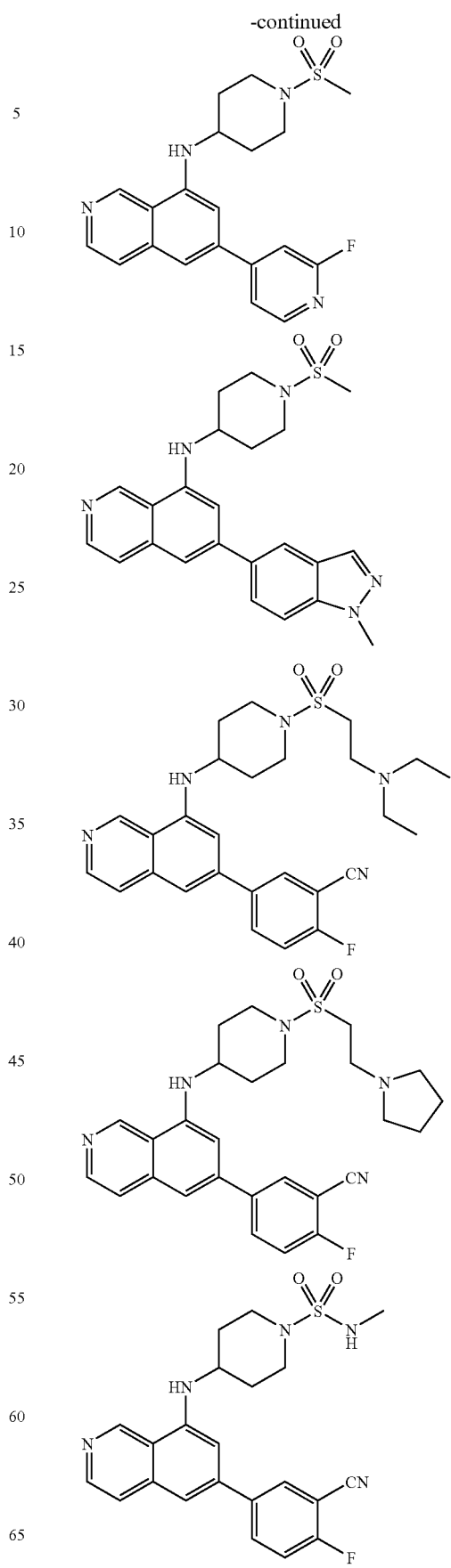

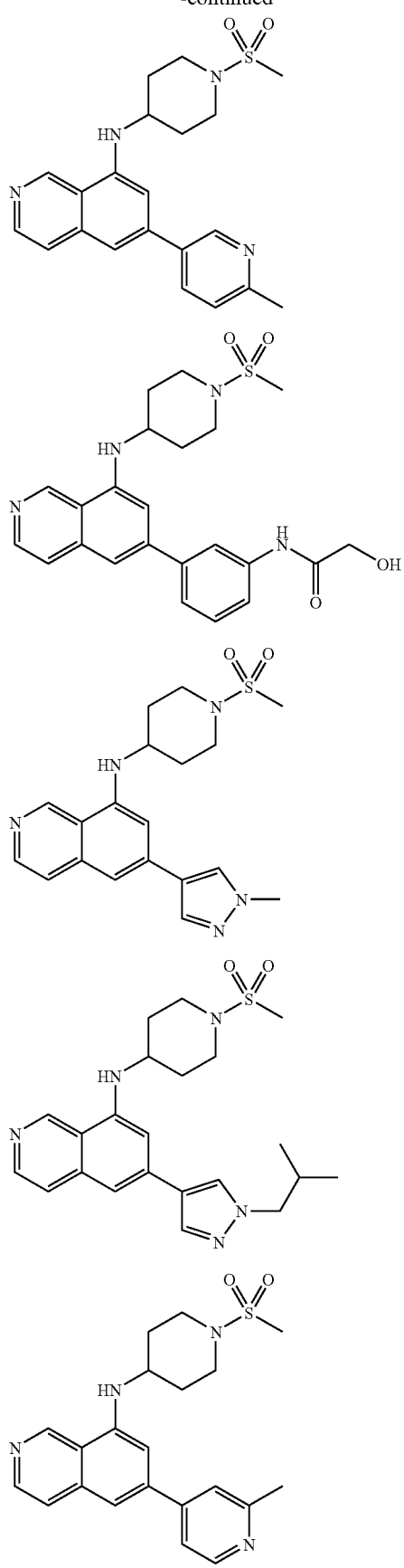
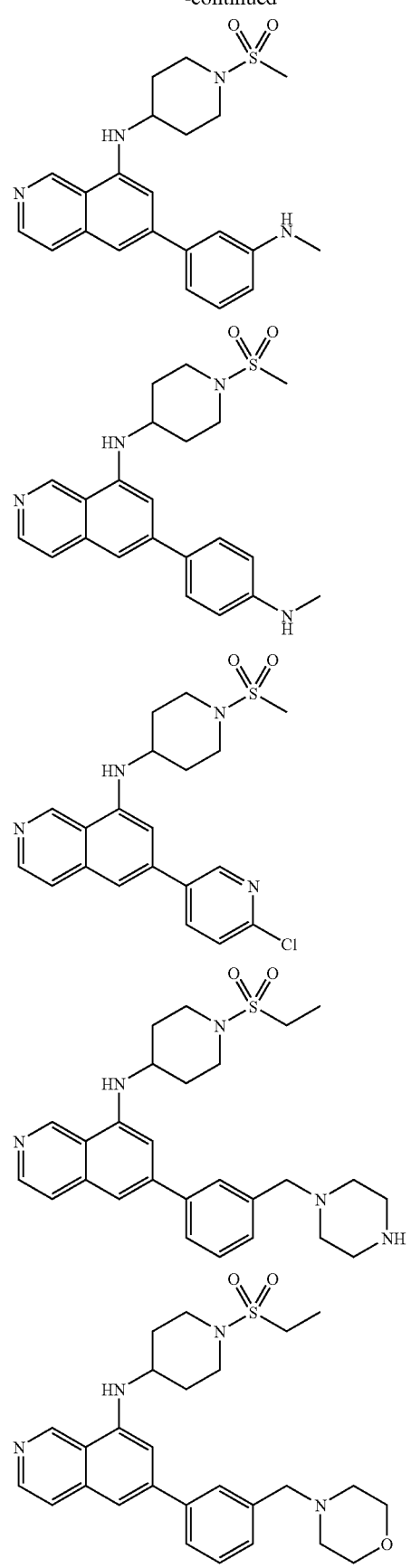

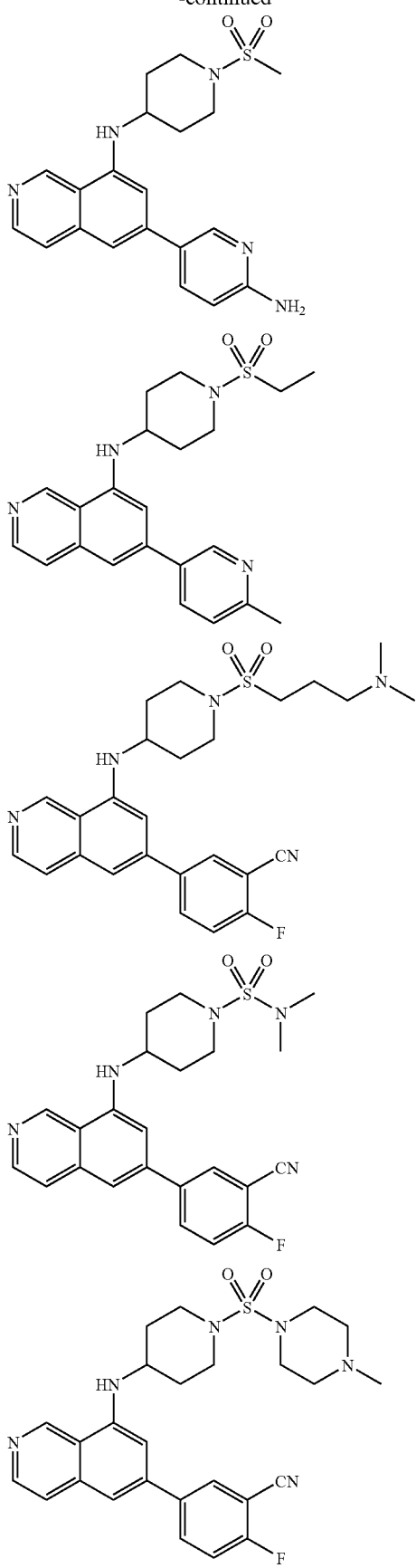
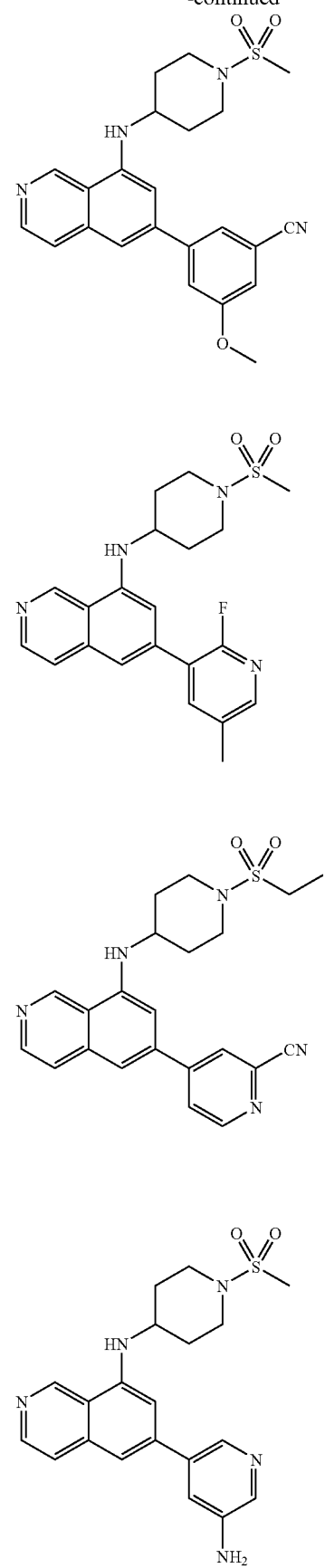

85
-continued
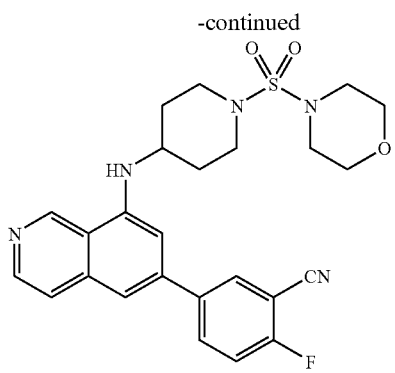
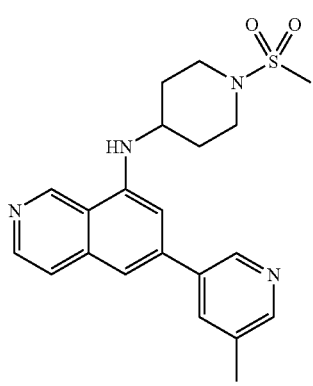
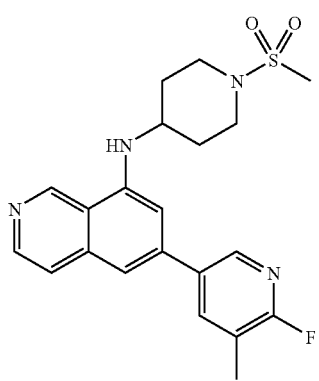
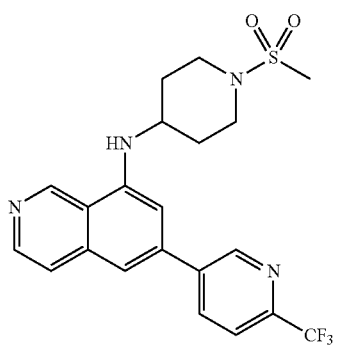
86
-continued
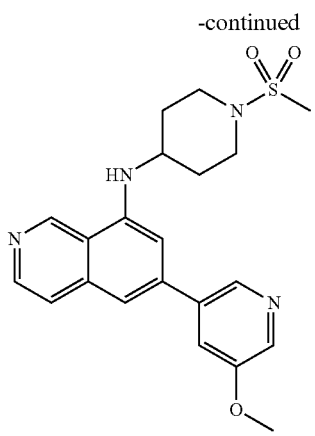
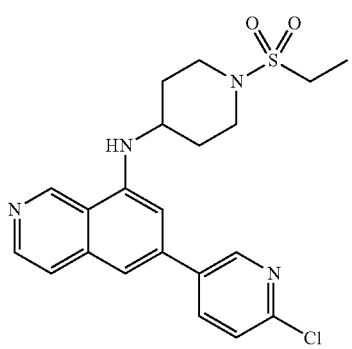
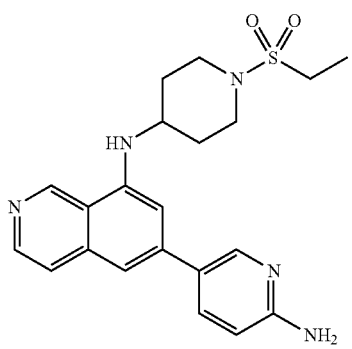
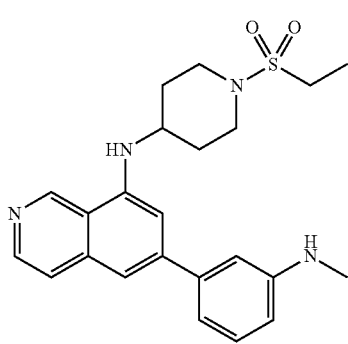

87
-continued
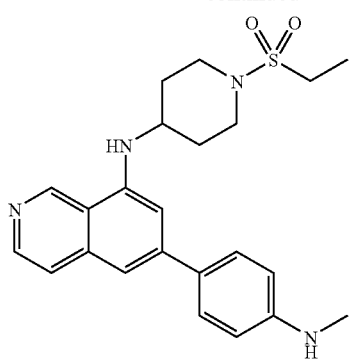
88
-continued
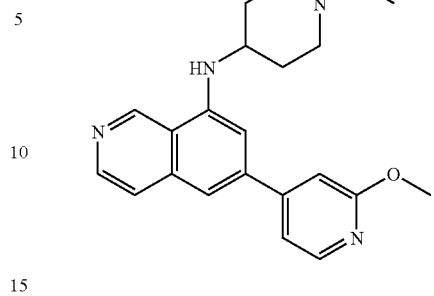
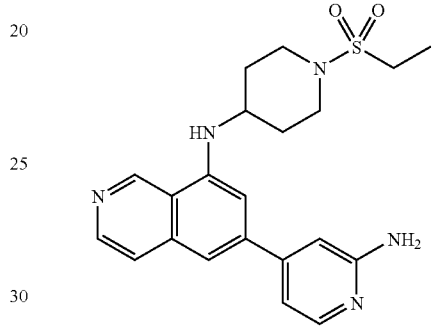
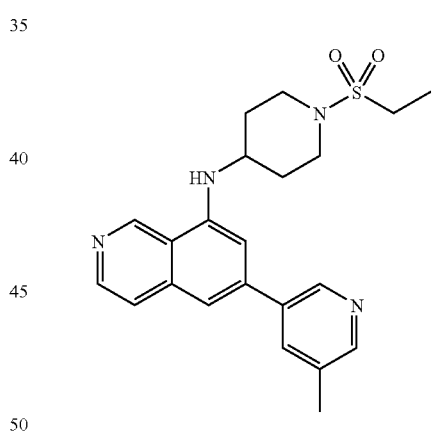
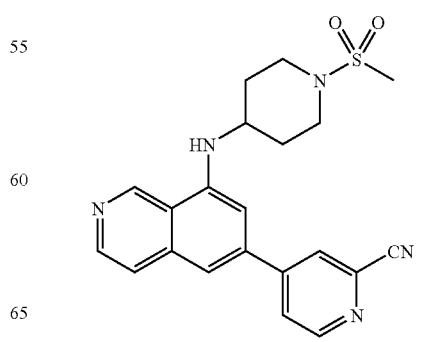

89
-continued
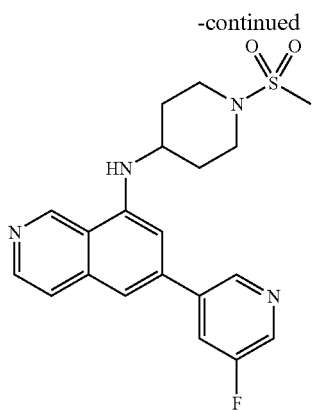
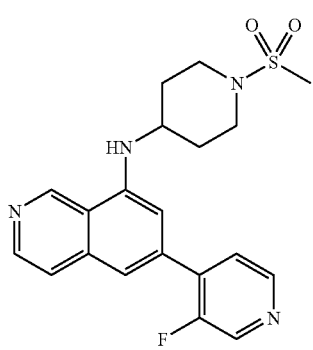
90
-continued
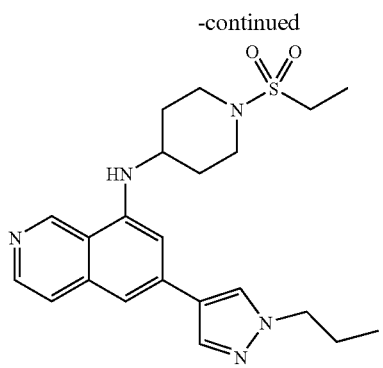
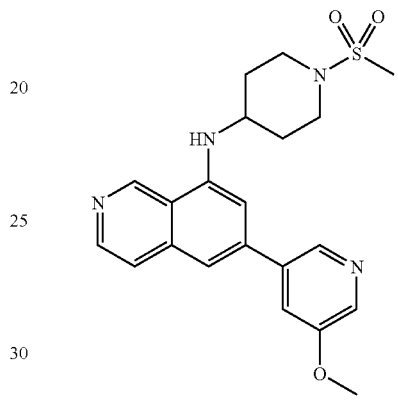
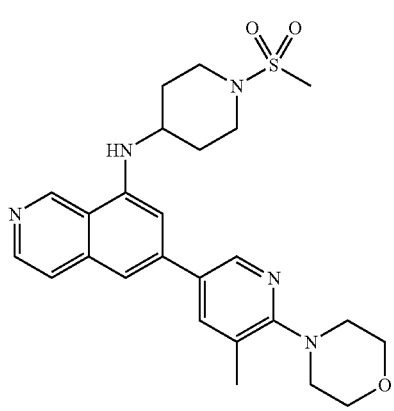
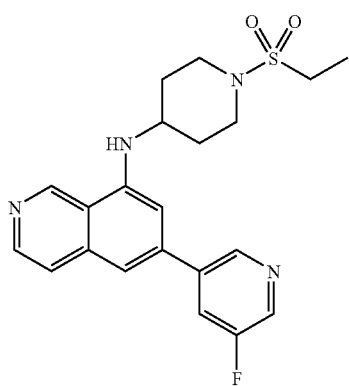

91
-continued
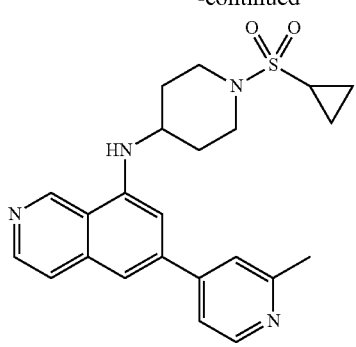
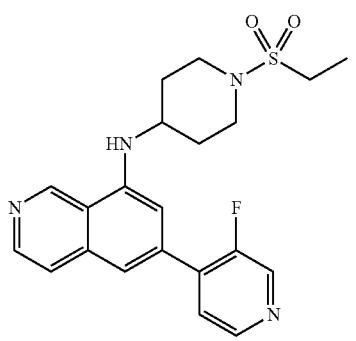
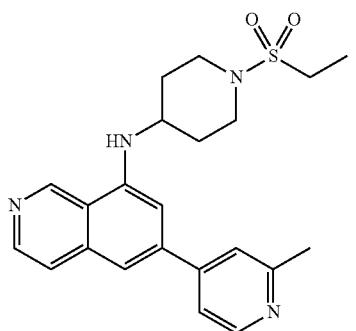
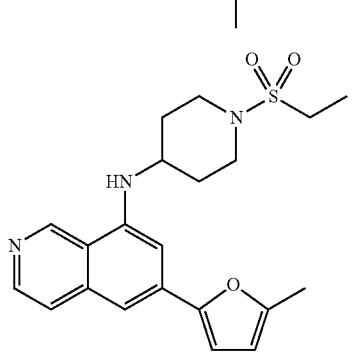
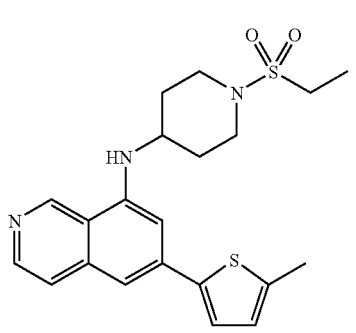
92
-continued
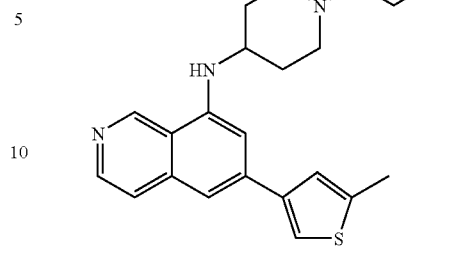
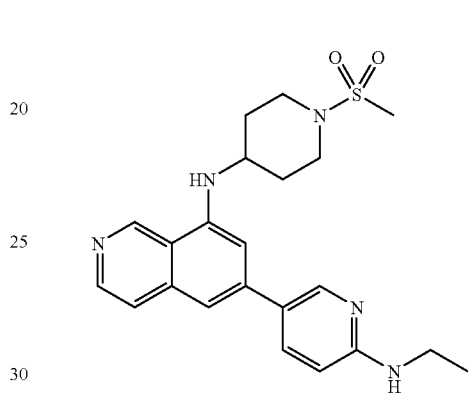
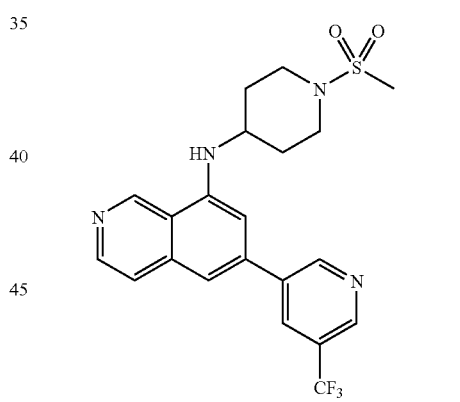
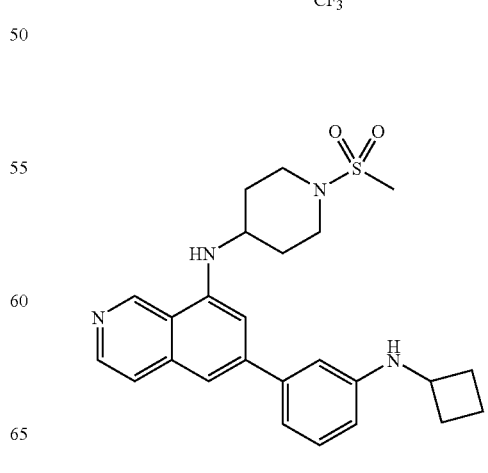

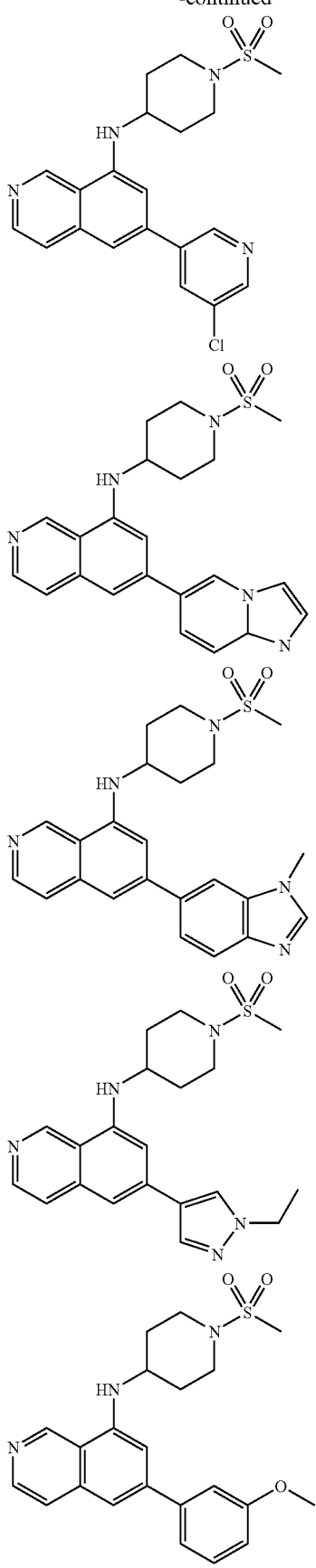
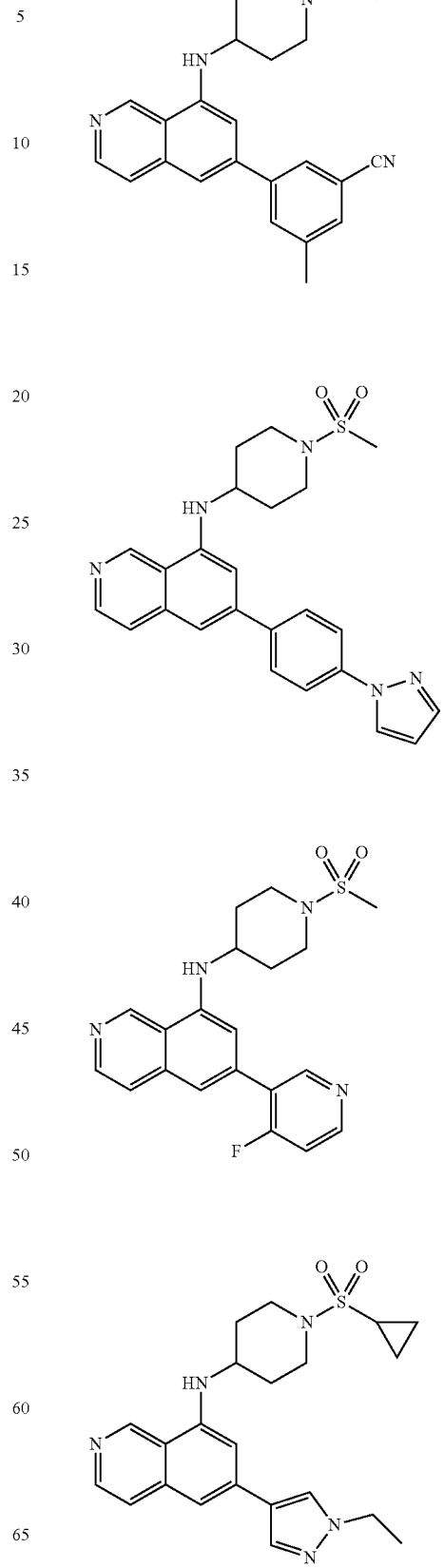

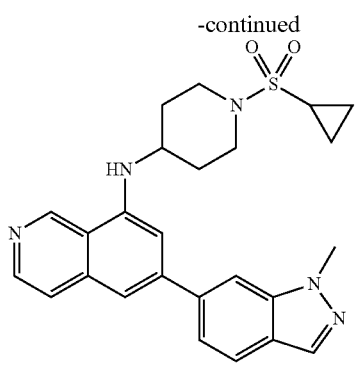
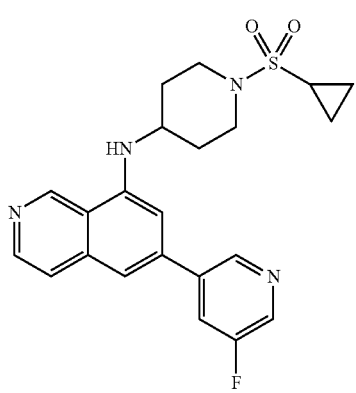
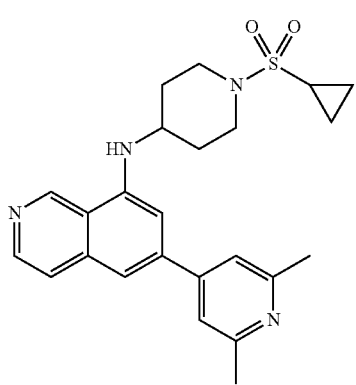
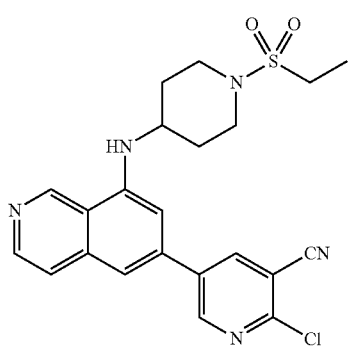
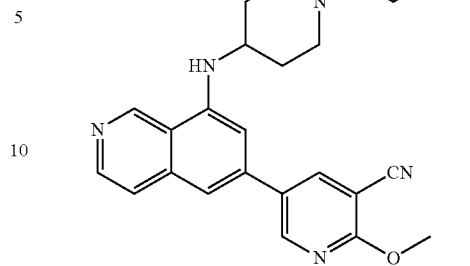
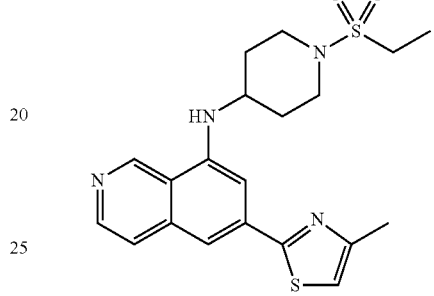
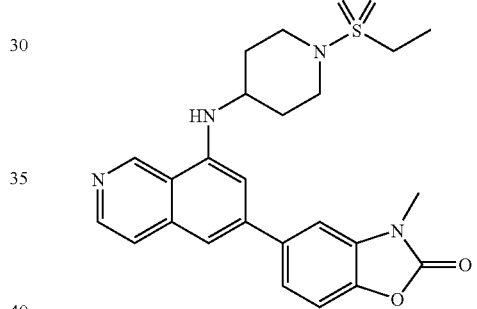
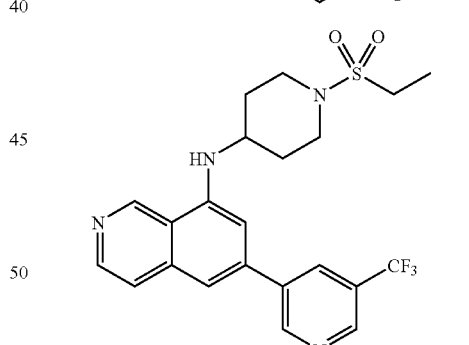
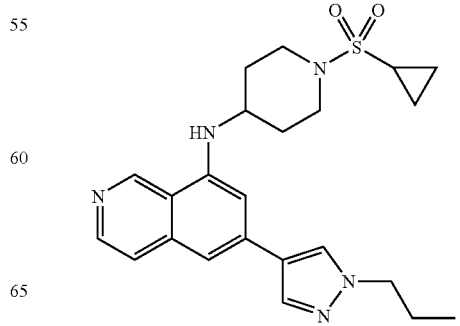

97
-continued
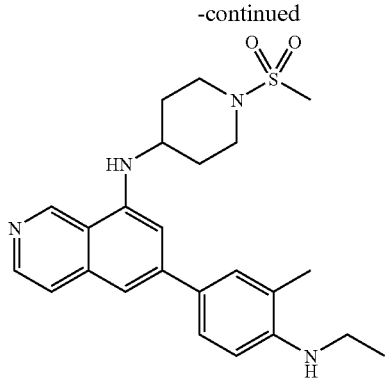
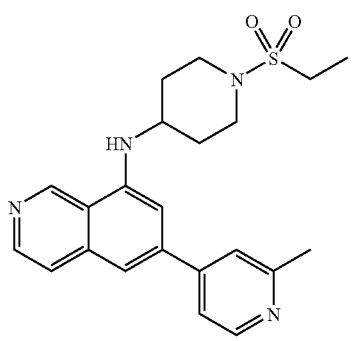
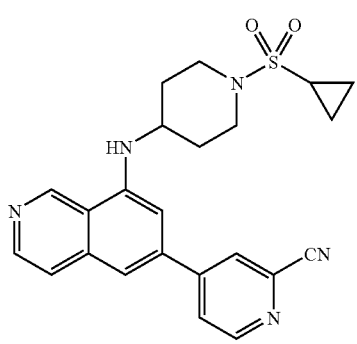
98
-continued
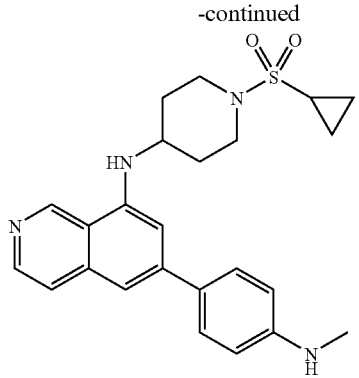
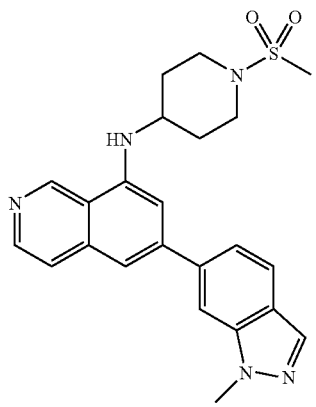
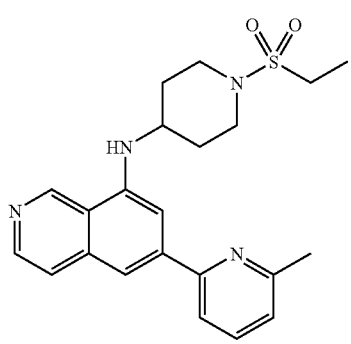

99
-continued
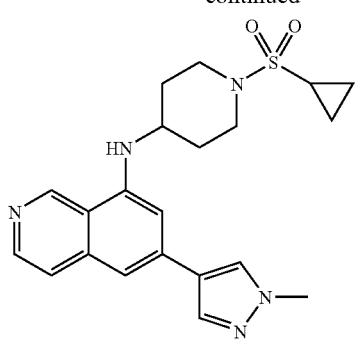
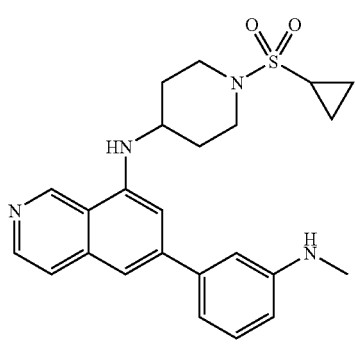
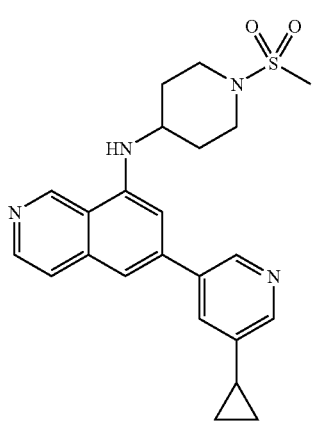
100
-continued

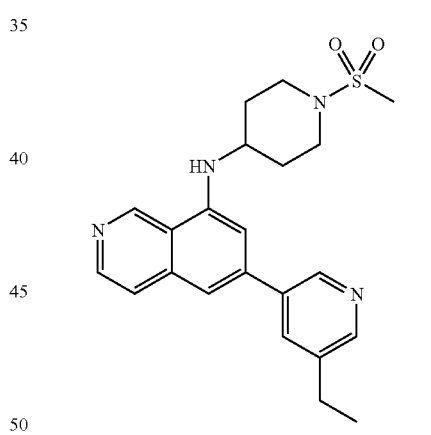
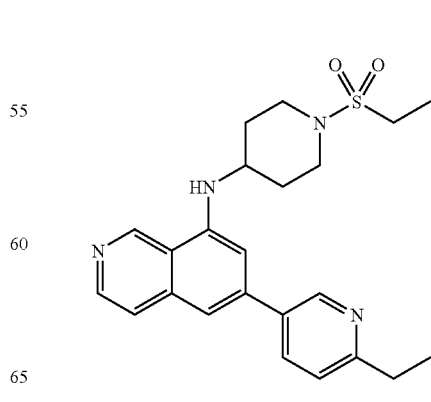

101
-continued
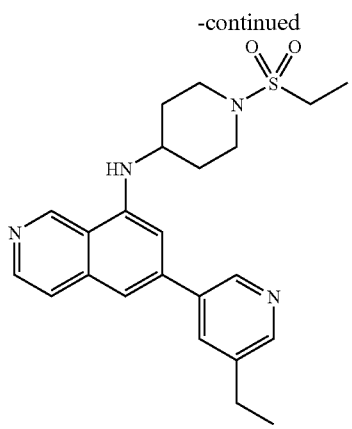
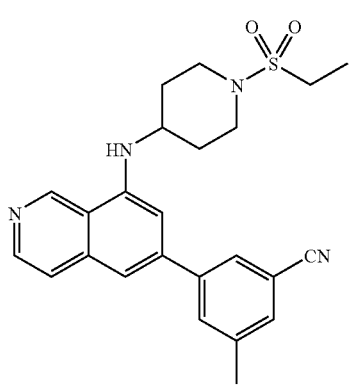
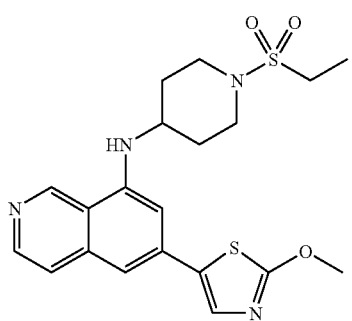
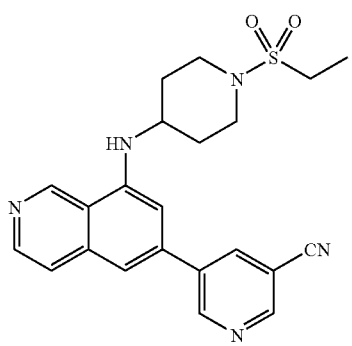
102
-continued
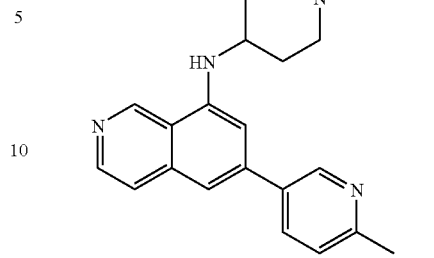
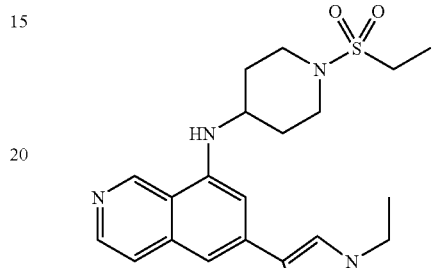
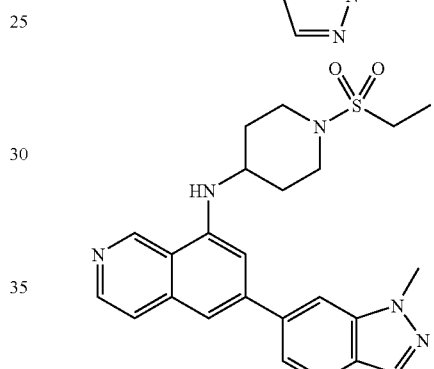
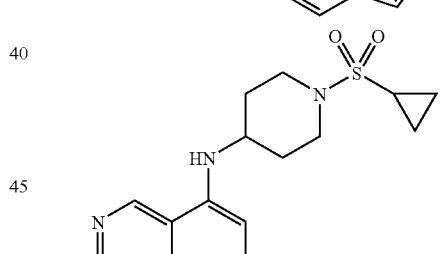
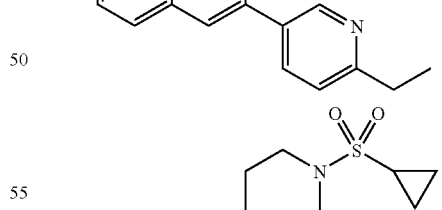
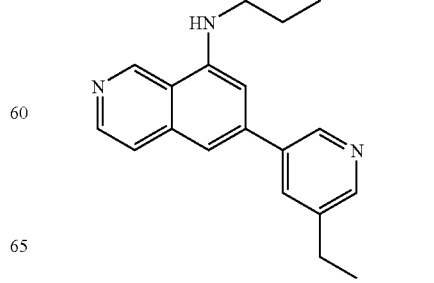

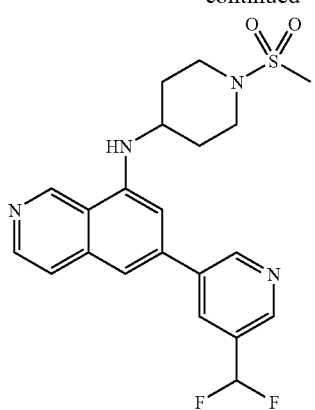
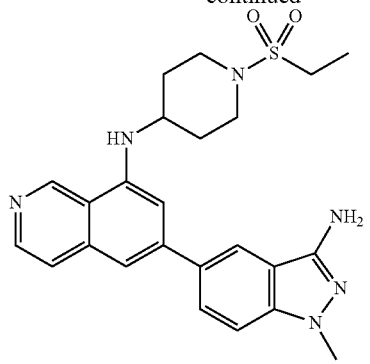
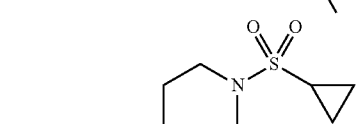
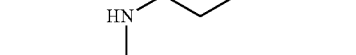
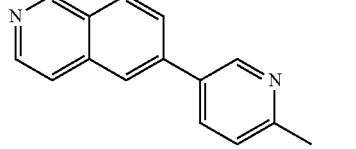

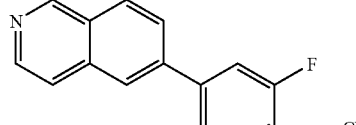
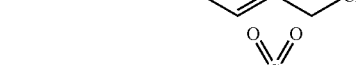
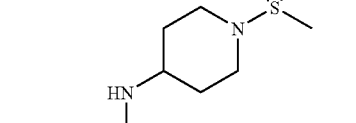

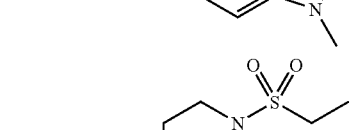

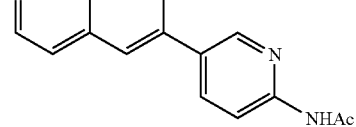

105
-continued
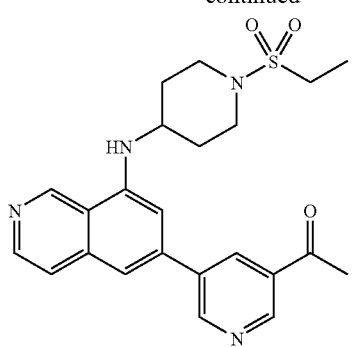
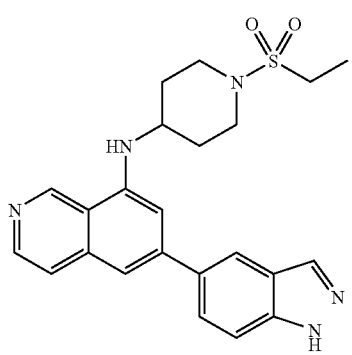
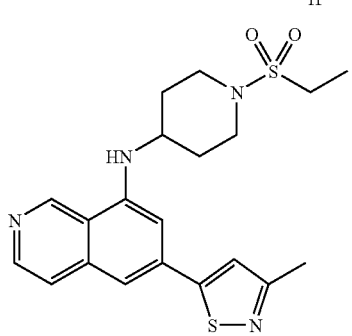
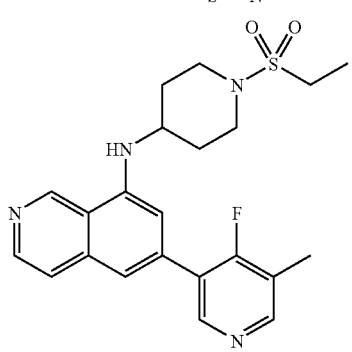
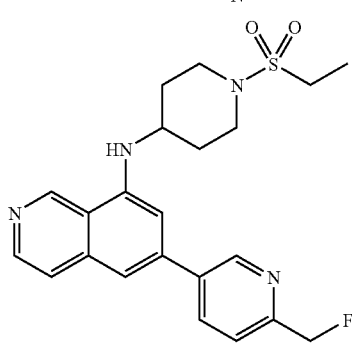
106
-continued
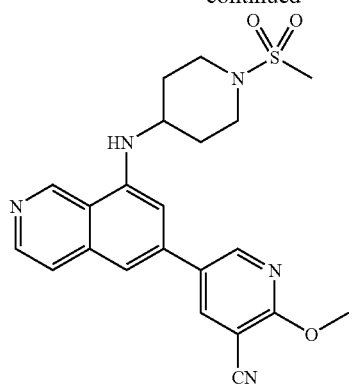
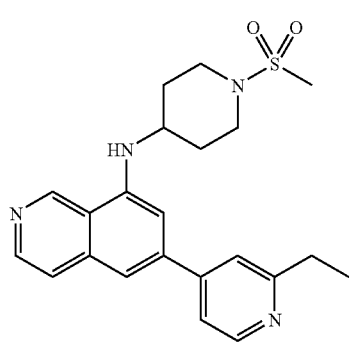
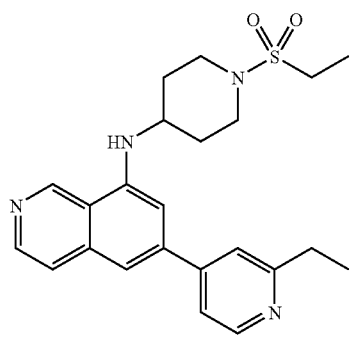
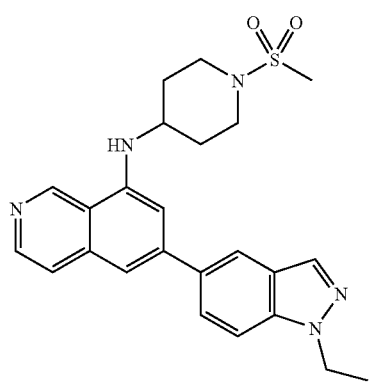

107
-continued
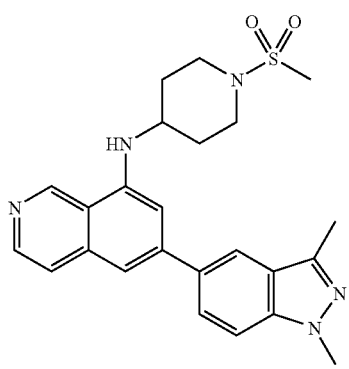
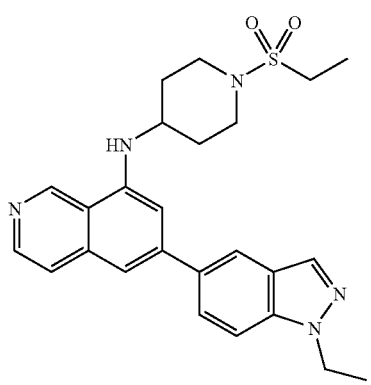
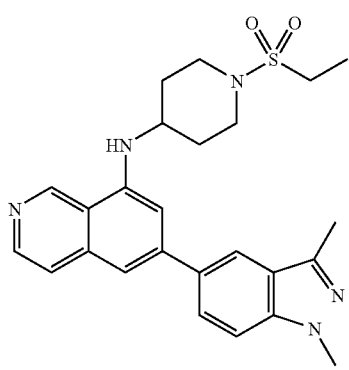
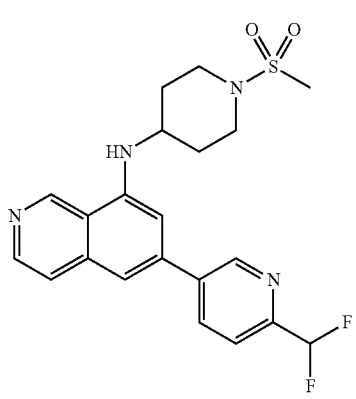
108
-continued
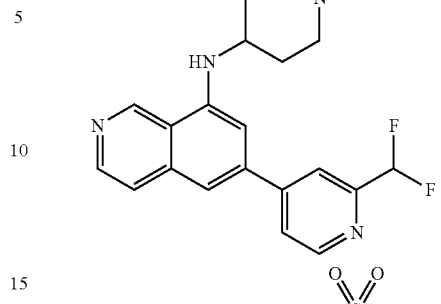
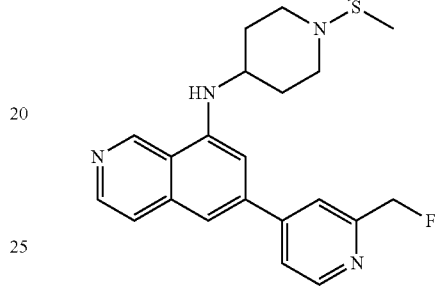
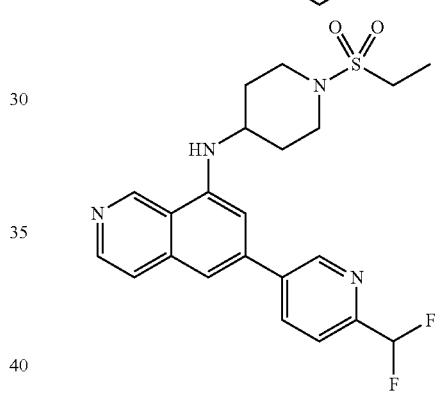
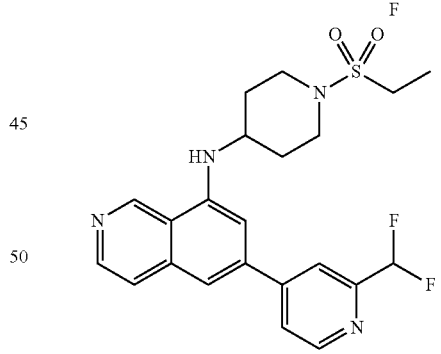
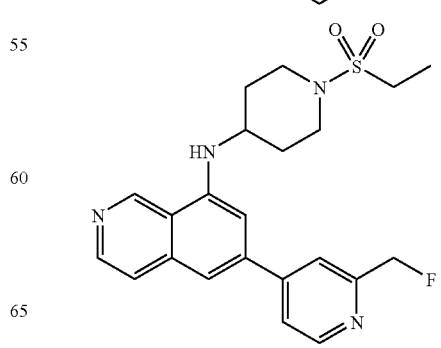

109
-continued
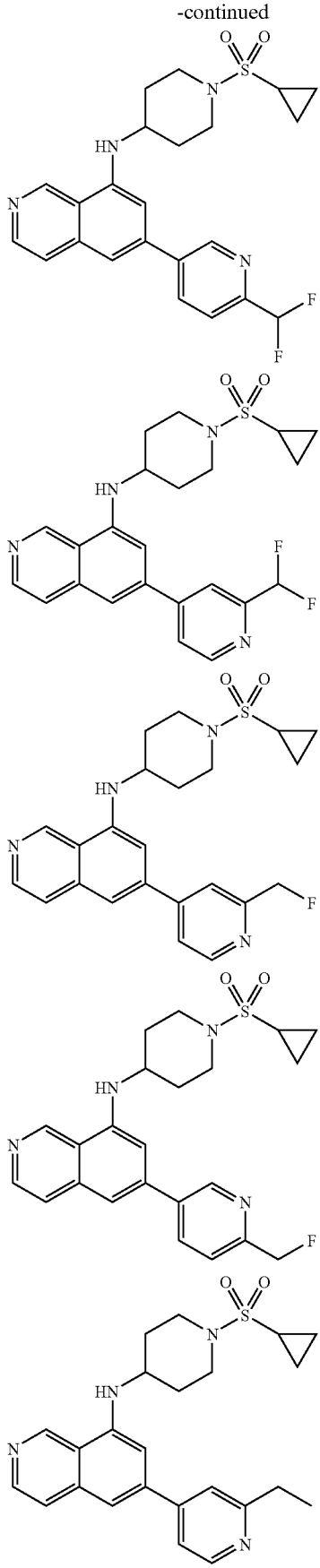
110
-continued
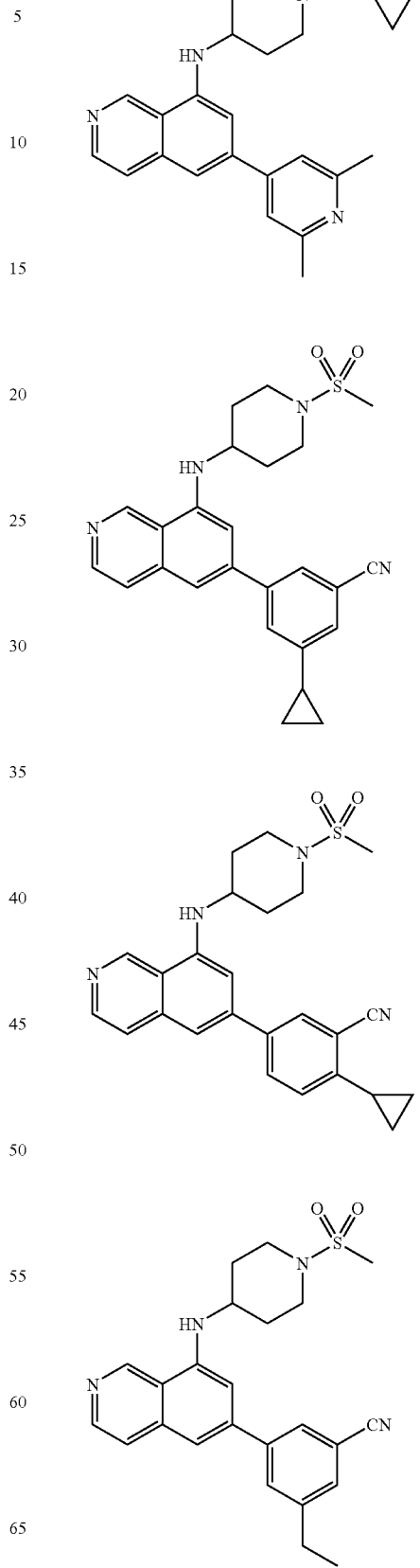

-continued
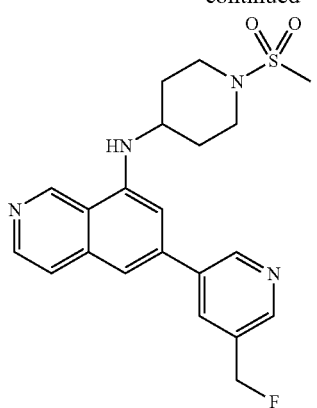
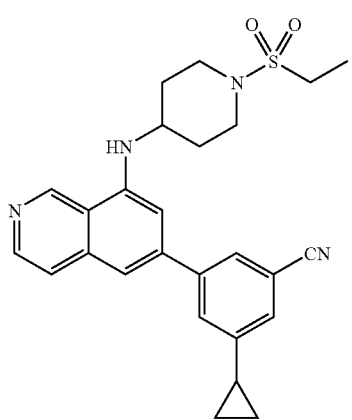
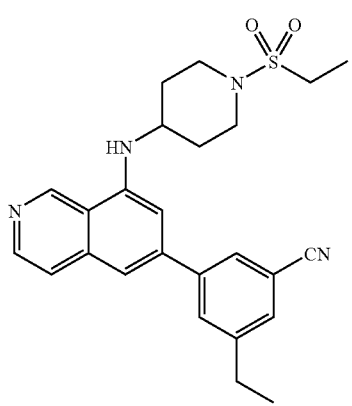
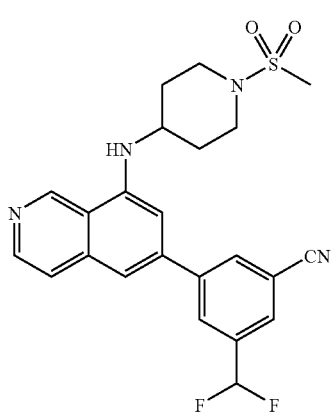
-continued
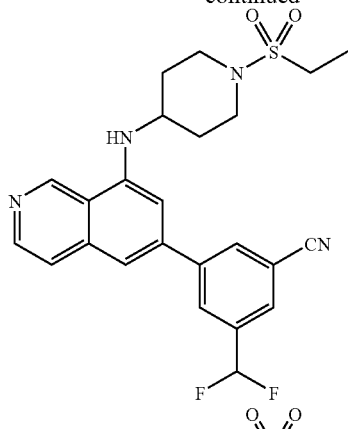
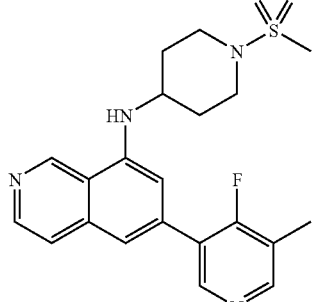
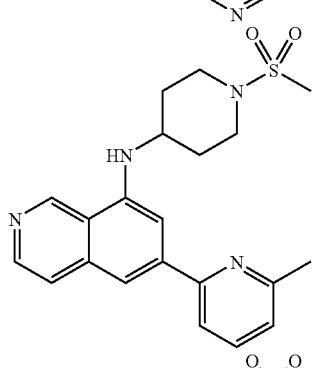
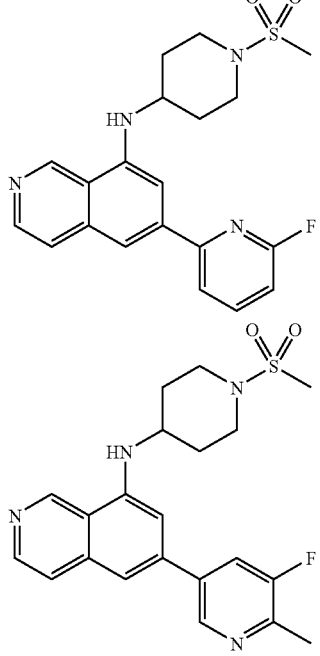

113
-continued
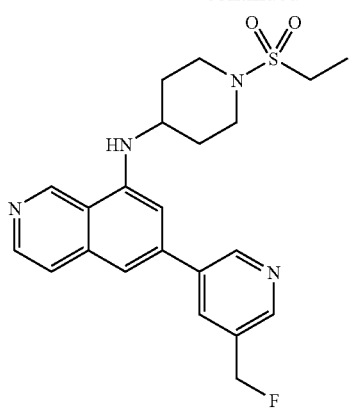
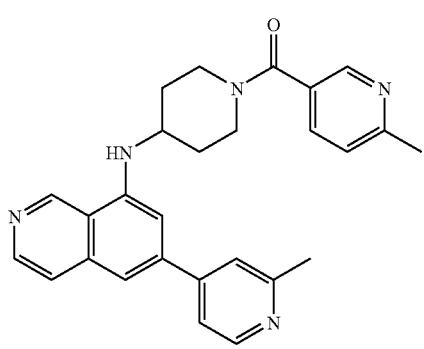
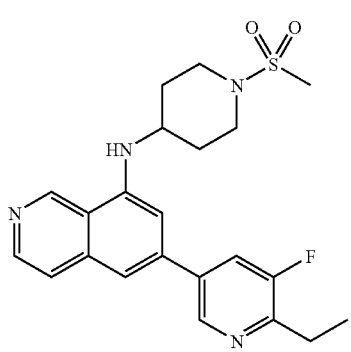
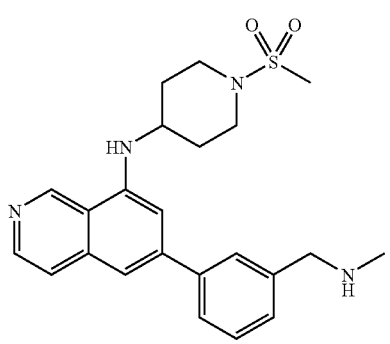
114
-continued
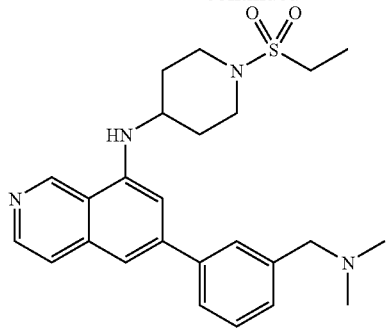
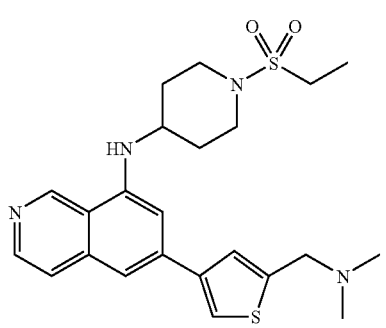
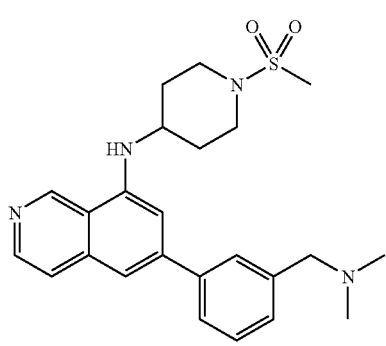
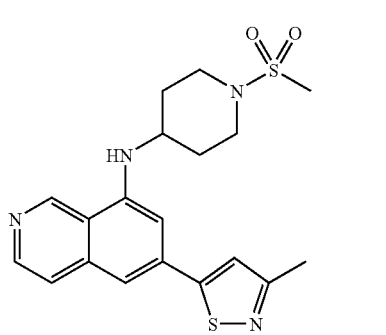
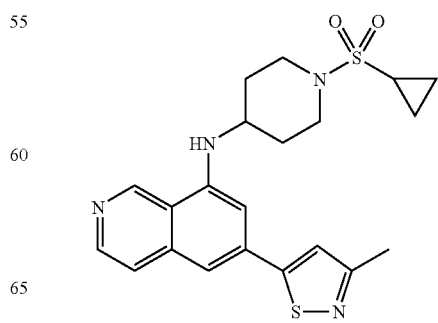

115
-continued
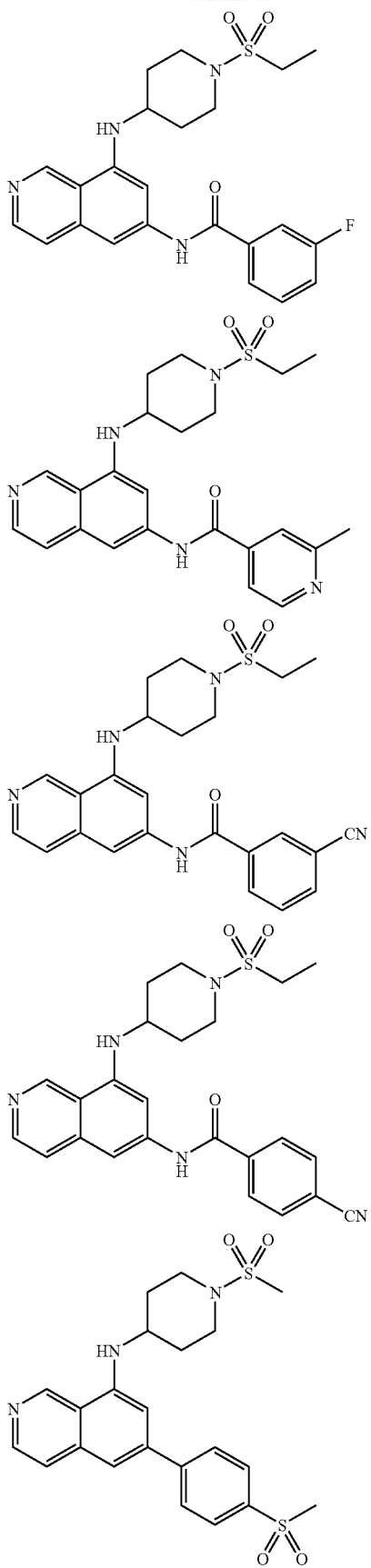
116
-continued
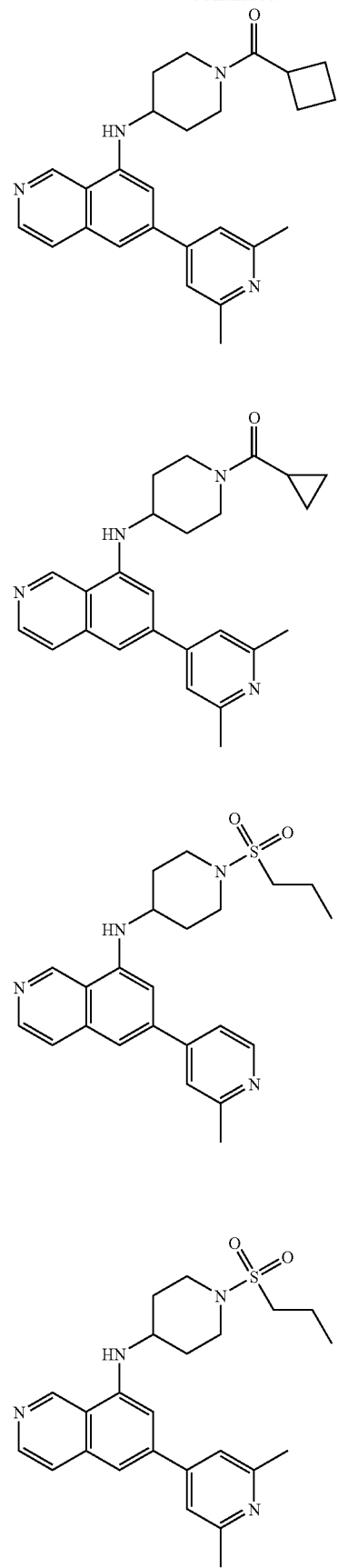

117
-continued
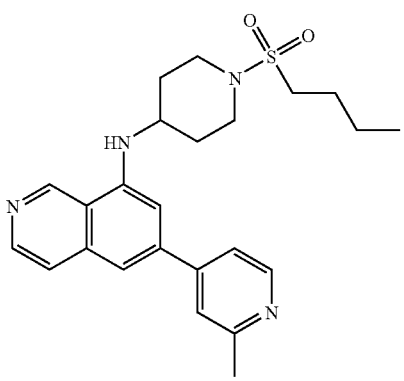
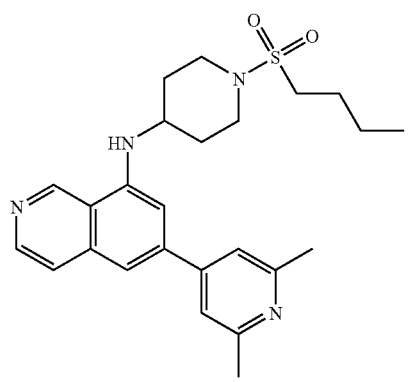
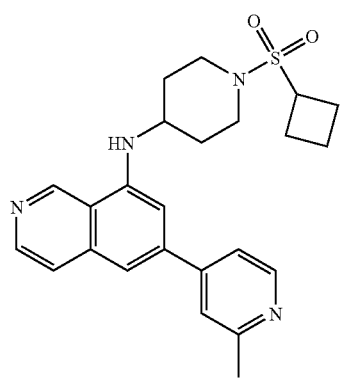
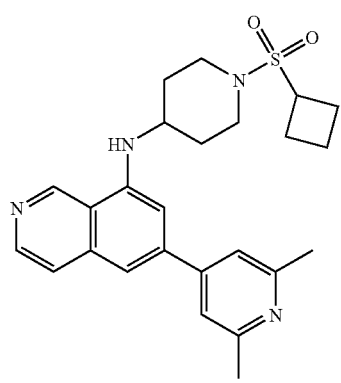
118
-continued
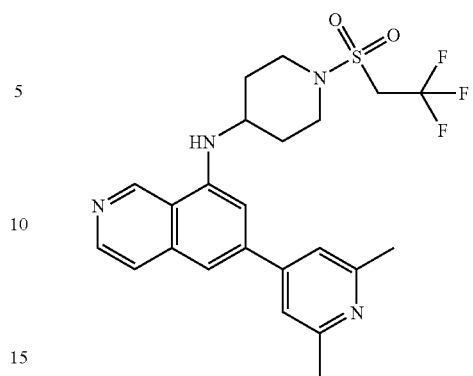
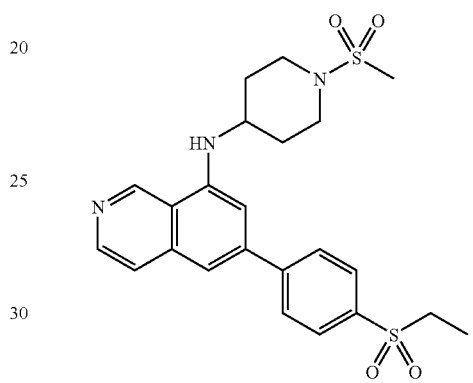
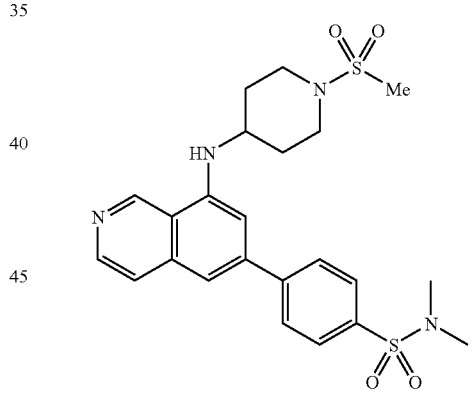
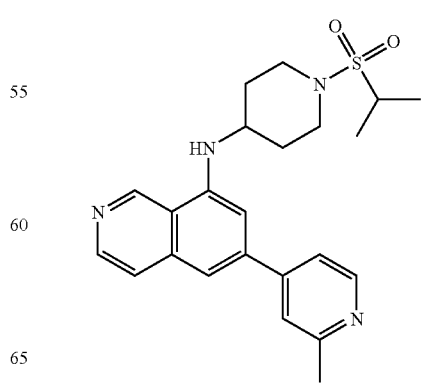

119
-continued
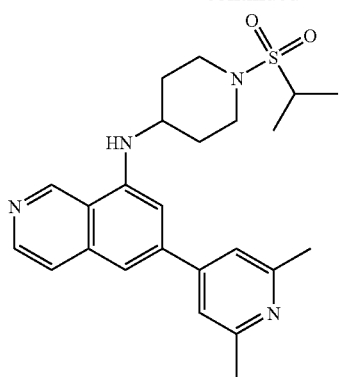
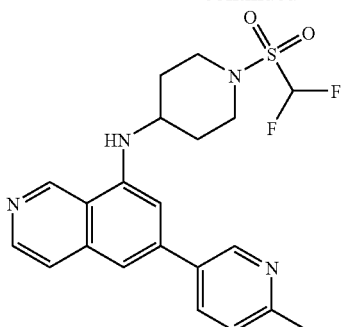
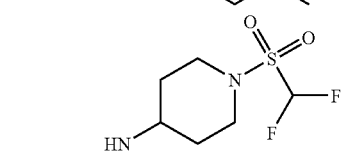
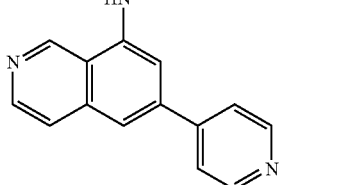
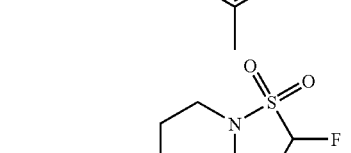
120
-continued
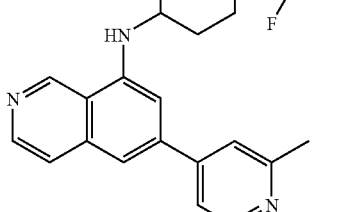
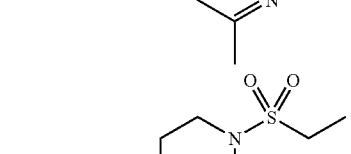
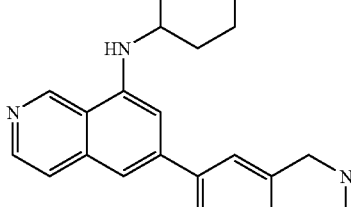
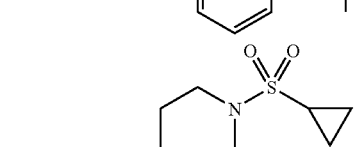
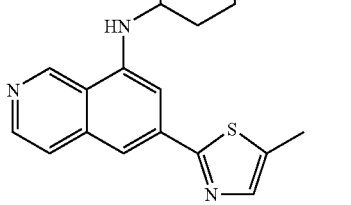

121
-continued
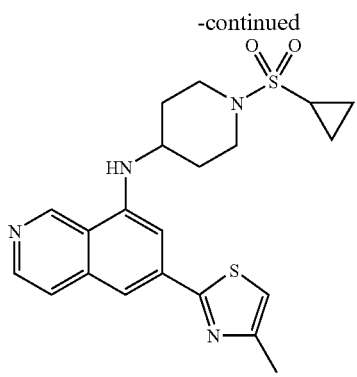
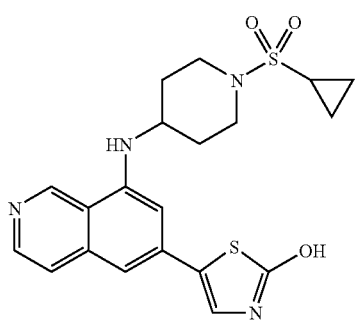
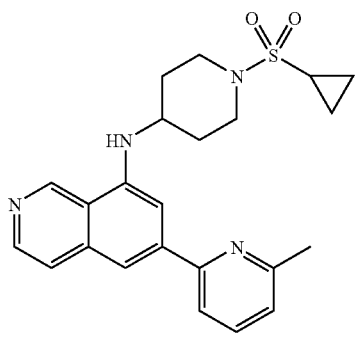
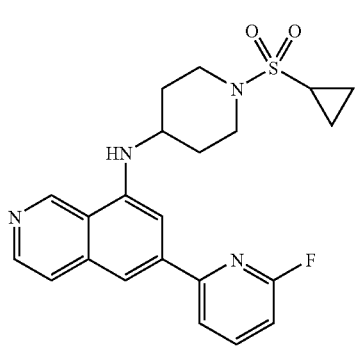
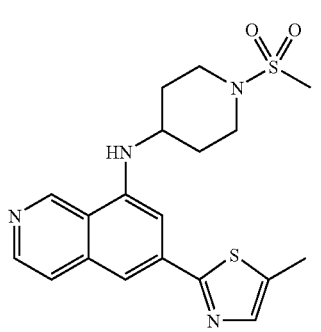
122
-continued
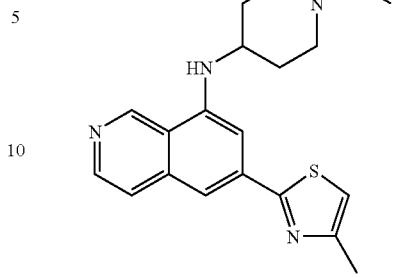
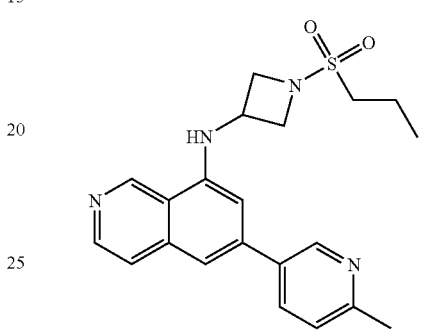
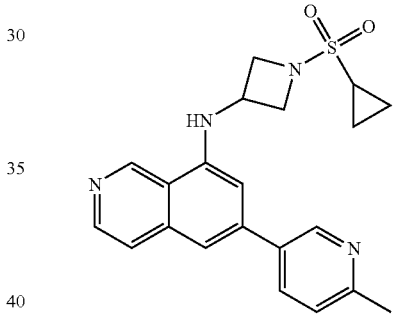
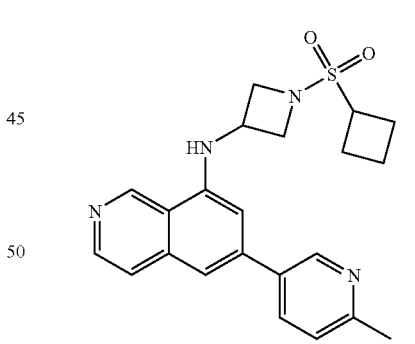
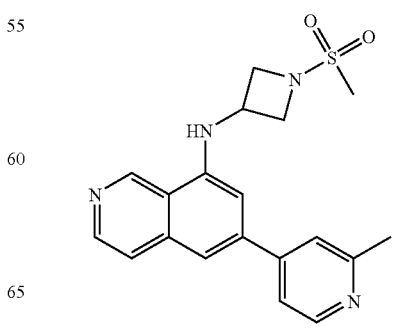

123
-continued
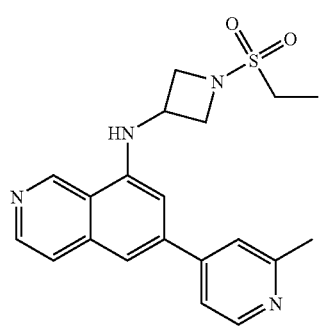
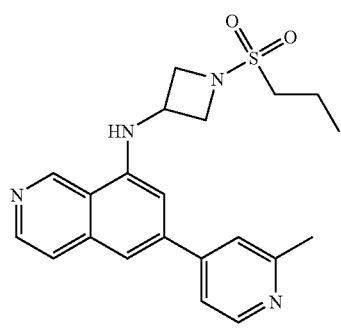
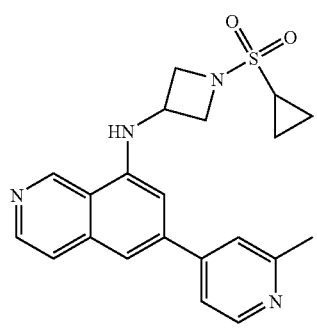
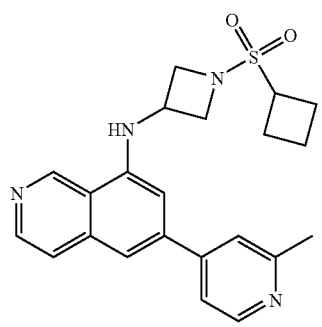
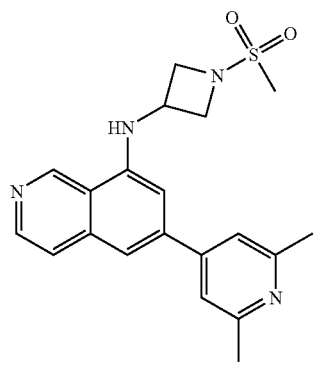
124
-continued
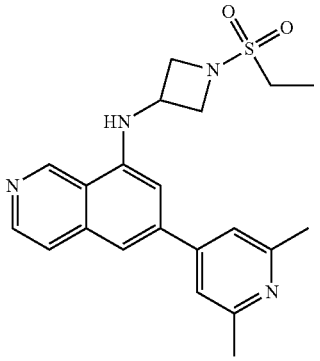
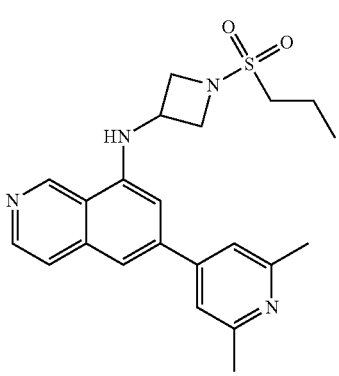
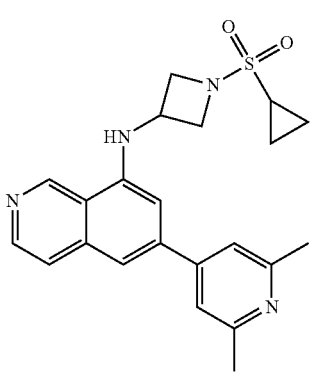
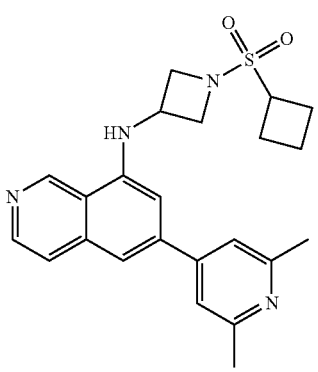

125
-continued
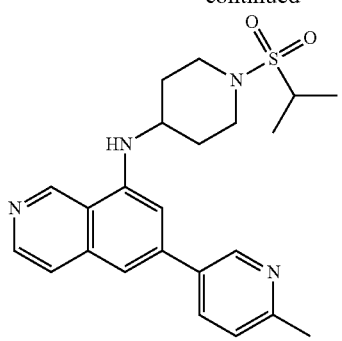
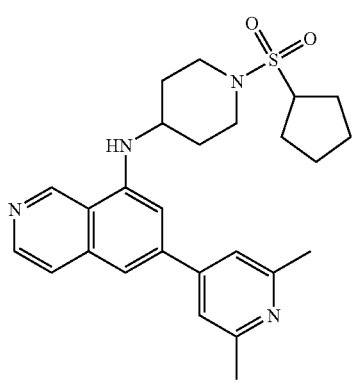
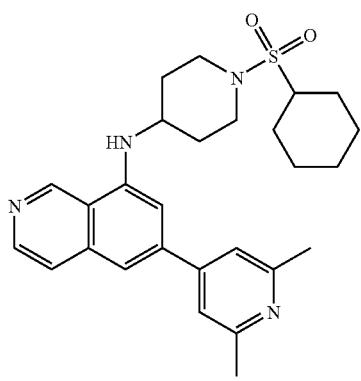
126
-continued
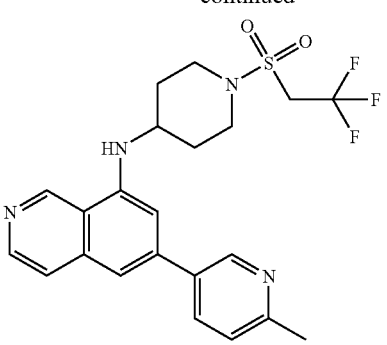
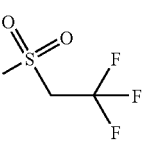
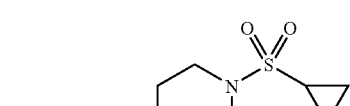
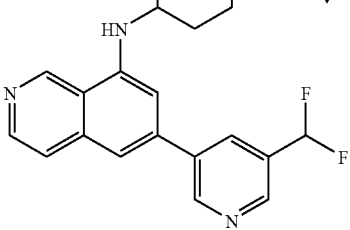

-continued

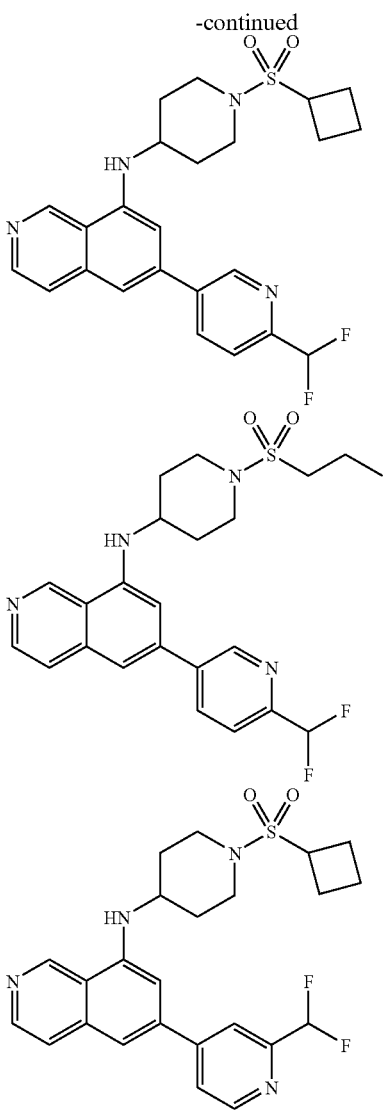

<15> A pharmaceutical composition comprising a compound according to any one of the above <1> to <14> or a pharmaceutically acceptable salt thereof as an active ingredient;

<16> The pharmaceutical composition according to the above <15>, for preventing and/or treatmenting an NF-κB-associated disease or symptom;

<16-2> The pharmaceutical composition according to the above <15>, for preventing and/or treating an NF-κB-associated disease or symptom by inhibiting a NF-κB activation pathway;

<17> The pharmaceutical composition according to the above <15>, for preventing and/or treating an IKKβ-associated disease or symptom;

<17-2> The pharmaceutical composition according to the above <15>, for preventing and/or treating an IKKβ-associated disease or symptom by inhibiting IKKβ;

<17-3> The pharmaceutical composition according to the above <15>, for preventing and/or treating an IKK-associated disease or symptom;

<17-4> The pharmaceutical composition according to the above <15>, for preventing and/or treating an IKK-associated disease or symptom by inhibiting IKK;

<18> The pharmaceutical composition according to the above <15>, for preventing and/or treating a TNF-α-associated disease or symptom;

<18-2> The pharmaceutical composition according to the above <15>, for preventing and/or treating a TNF-α-associated disease or symptom by suppressing TNF-αproduction;

<19> The pharmaceutical composition according to the above <15>, for preventing and/or treating mammal rheumatoid arthritis;

<20> The pharmaceutical composition according to the above <15>, for preventing and/or treating a mammal autoimmune disease;

<21> The pharmaceutical composition according to the above <15>, for preventing and/or treating a mammal inflammatory disease;

<22> The pharmaceutical composition according to the above <15>, used for the prophylactic and/or therapeutic treatment of a mammal cardiovascular disease;

<23> The pharmaceutical composition according to the above <15>, for preventing and/or treating a mammal cancer;

<24> The pharmaceutical composition according to the above <15>, for preventing and/or treating a disease or symptom associated with acute or chronic inflammatory reaction in mammals;

<25> An IKKβ inhibitor, comprising a compound according to any one of the above <1> to <14> or a salt thereof as an active ingredient;

<25-2> An NF-κB activation pathway inhibitor, comprising a compound according to any one of the above <1> to <14> or a salt thereof as an active ingredient;

<25-3> An IKK inhibitor, comprising a compound according to any one of the above <1> to <14> or a salt thereof as an active ingredient;

<25-4> A TNF-αproduction inhibitor, comprising a compound according to any one of the above <1> to <14> or a salt thereof as an active ingredient;

<26> A method for inhibiting IKKβ, comprising administering an effective amount of a compound according to any one of the above <1> to <14> or a pharmaceutically acceptable salt thereof;

<26-2> A method for inhibiting an NF-κB activation pathway, comprising administering an effective amount of a compound according to any one of the above <1> to <14> or a pharmaceutically acceptable salt thereof;

<26-3> A method for inhibiting IKK, comprising administering an effective amount of a compound according to any one of the above <1> to <14> or a pharmaceutically acceptable salt thereof;

<26-4> A method for inhibiting TNF-αproduction, comprising administering an effective amount of a compound according to any one of the above <1> to <14> or a pharmaceutically acceptable salt thereof;

<27> A method for preventing and/or treating an NF-κB-associated disease or symptom comprising administering an effective amount of a compound according to any one of the above <1> to <14> or a pharmaceutically acceptable salt thereof;

<28> A method for preventing and/or treating an IKKβ-associated disease or symptom comprising administering an effective amount of a compound according to any one of the above <1> to <14> or a pharmaceutically acceptable salt thereof;

<28-2> A method for preventing and/or treating an IKK-associated disease or symptom comprising administration of an effective amount of a compound according to any one of the above <1> to <14> or a pharmaceutically acceptable salt thereof;

<28-3> A method for preventing and/or treating an TNF-α-associated disease or symptom comprising administering an effective amount of a compound according to any one of the above <1> to <14> or a pharmaceutically acceptable salt thereof;

<29> A method for preventing and/or treating a disease or symptom associated with acute or chronic inflammatory reaction in mammals comprising administering an effective amount of a compound according to any one of the above <1> to <14> or a pharmaceutically acceptable salt thereof;

<29-2> A method for preventing and/or treating mammal rheumatoid arthritis comprising administering an effective amount of a compound according to any one of the above <1> to <14> or a pharmaceutically acceptable salt thereof;

<29-3> A method for preventing and/or treating a mammal autoimmune disease comprising administering an effective amount of a compound according to any one of the above <1> to <14> or a pharmaceutically acceptable salt thereof;

<29-4> A method for preventing and/or treating a mammal inflammatory disease comprising administering an effective amount of a compound according to any one of the above <1> to <14> or a pharmaceutically acceptable salt thereof;

<29-5> A method for preventing and/or treating a mammal cardiovascular disease comprising administering an effective amount of a compound according to any one of the above <1> to <14> or a pharmaceutically acceptable salt thereof;

<29-6> A method for preventing and/or treating a mammal cancer comprising administering an effective amount of a compound according to any one of the above <1> to <14> or a pharmaceutically acceptable salt thereof;

<30> The compound according to any one of the above <1> to <14> or a pharmaceutically acceptable salt thereof, for preventing and/or treating an NF-κB-associated disease or symptom;

<30-2> The compound according to any one of the above <1> to <14> or a pharmaceutically acceptable salt thereof, for preventing and/or treating an IKKβ-associated disease or symptom;

<30-3> The compound according to any one of the above <1> to <14> or a pharmaceutically acceptable salt thereof, for preventing and/or treating an TNF-α-associated disease or symptom;

<31> A compound represented by the following formula (2a) or a salt thereof:

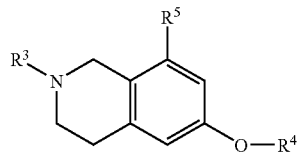

(2a)

wherein
R$^3$ represents a hydrogen atom or an alkyl group that may be substituted;
R$^4$ represents a hydrogen atom, an alkyl group that may be substituted, or an aralkyl group that may be substituted; and
R$^5$ represents a halogen atom;

<31-2> The compound according to the above <31> or a salt thereof, wherein R$^3$ represents a hydrogen atom;

<31-3> The compound according to the above <31> or <31-2> or a salt thereof, wherein R$^4$ represents an alkyl group that may be substituted;

<31-4> The compound according to the above <31> or <31-2> or a salt thereof, wherein R$^4$ represents a methyl group that may be substituted;

<31-5> The compound according to any of the above <31> to <31-4> or a salt thereof, wherein R$^3$ represents a bromine atom;

<32> A compound represented by the following formula (2b) or a salt thereof:

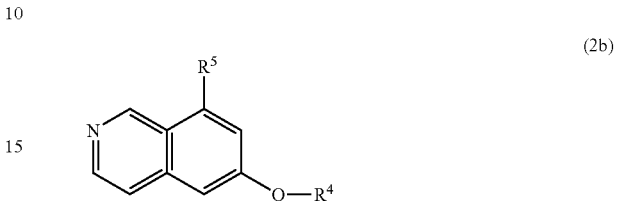

(2b)

wherein
R$^4$ represents a hydrogen atom, an alkyl group that may be substituted, or an aralkyl group that may be substituted; and
R$^5$ represents a halogen atom.

<32-2> The compound according to the above <32> or a salt thereof, wherein R$^4$ represents an alkyl group that may be substituted;

<32-3> The compound according to the above <32> or <32-2> or a salt thereof, wherein R$^4$ represents a methyl group;

<32-4> The compound according to any of the above <32> to <32-3> or a salt thereof, wherein R$^5$ represents a bromine atom;

Advantages of the Invention

The "compound represented by general formula (1) or a salt thereof" (which hereinafter may be simply referred to as "the compound of the present invention") has an excellent IKKβ inhibiting activity. Besides, the compound of the present invention has a TNF-α production suppressing activity. Furthermore, the compound of the present invention has an anti-inflammatory effect. As a result, the compound of the present invention has an NF-κB activation inhibiting effect and characteristics of being useful in the prevention and/or treatment of NF-κB associated diseases and symptoms, for example, autoimmune diseases, inflammatory diseases, cardiovascular diseases, and cancer when administered to humans and animals and very safe.

BRIEF DESCRIPTION OF THE DRAWINGS

FIG. 1 illustrates effects of Example Compound 1-N-6 by Method A on a mouse collagen-induced arthritis model in Test Example 5. In the figure, the horizontal axis represents experiment days and the vertical axis represents clinical scores;

FIG. 2 illustrates effects of Example Compound 2-N-100 by Method B on a mouse collagen-induced arthritis model (only the results at doses of 10 and 30 mg/kg are shown) in Test Example 5. In the figure, the horizontal axis represents experiment days and the vertical axis represents clinical scores; and FIG. 3 illustrates effects of Example Compound 3-NP-24 on a rat Streptococcus cell wall (SCW)-induced arthritis model in Test Example 6. In the figure, the horizontal axis represents experiment days and the vertical axis represents thickness of the ankle joint.

MODE FOR CARRYING OUT THE INVENTION

Hereafter, the present invention will be specifically described.

In the present specification, unless otherwise specified, a "halogen atom" refers to a fluorine atom, a chlorine atom, a bromine atom, or an iodine atom.

Preferred examples of halogen atoms include a chlorine atom, a bromine atom, and an iodine atom. In one embodiment of the present invention, a chlorine atom or a bromine atom is more preferred as a halogen atom and a chlorine atom is particularly preferred. In another embodiment of the present invention, a fluorine atom may be more preferred.

In the present specification, an "alkyl group" refers to a straight, branched, or cyclic saturated hydrocarbon group or a combination thereof. Preferred examples of alkyl groups include lower alkyl groups.

In the present specification, "lower" means that a certain functional group has 1 to 6 carbon atoms. Among lower alkyl groups, alkyl groups having 1 to 3 carbon atoms are particularly preferred. In other substituents having an alkyl moiety (for example, an alkoxy group) a lower alkyl moiety is similarly preferred as the alkyl moiety and an alkyl moiety having 1 to 3 carbon atoms is particularly preferred as a lower alkyl moiety.

Preferred examples of alkyl groups having 1 to 3 carbon atoms include a methyl group, an ethyl group, an n-propyl group, an isopropyl group, and a cyclopropyl group.

Preferred examples of alkyl groups having 4 to 6 carbon atoms include an n-butyl group, an isobutyl group, an s-butyl group, a t-butyl group, a cyclobutyl group, a cyclopropylmethyl group, an n-pentyl group, a cyclopentyl group, a cyclopropylethyl group, a cyclobutylmethyl group, an n-hexyl group, a cyclohexyl group, a cyclopropylpropyl group, a cyclobutylethyl group, and a cyclopentylmethyl group. Particularly preferred examples of such alkyl groups include a methyl group, an ethyl group, an n-propyl group, an isopropyl group, and a cyclopropyl group.

In the present specification, an "alkoxy group" refers to a structure in which the above-mentioned alkyl group binds to an oxygen atom. Examples thereof include straight, branched, or cyclic saturated alkoxy groups and combinations thereof and lower alkoxy groups are preferred. Among the lower alkoxy groups, alkoxy groups having 1 to 4 carbon atoms are particularly preferred.

Preferred examples of alkoxy groups having 1 to 4 carbon atoms include a methoxy group, an ethoxy group, an n-propoxy group, an isopropoxy group, a cyclopropoxy group, an n-butoxy group, an isobutoxy group, an s-butoxy group, a t-butoxy group, a cyclobutoxy group, and a cyclopropylmethoxy group. Preferred examples of alkoxy groups having 5 or 6 carbon atoms include an n-pentyloxy group, a cyclopentyloxy group, a cyclopropylethyloxy group, a cyclobutylmethyloxy group, an n-hexyloxy group, a cyclohexyloxy group, a cyclopropylpropyloxy group, a cyclobutylethyloxy group, and a cyclopentylmethyloxy group.

In the present specification, an "alkylene" refers to a divalent group comprising a straight, branched, or cyclic saturated hydrocarbon or a combination thereof and examples thereof include divalent groups comprising a saturated hydrocarbon having 1 to 6 carbon atoms. In one embodiment, alkylenes having 1 to 3 carbon atoms are preferred. In another embodiment, alkylenes having 4 to 6 carbon atoms may be preferred. Straight or branched alkylenes are preferred, and straight alkylenes are particularly preferred.

Preferred examples of alkylenes include methylene, ethylene, trimethylene, tetramethylene, pentamethylene, and hexamethylene. Particularly preferred examples of alkyl groups include methylene, ethylene, and trimethylene.

In the present specification, an "aryl group" refers to a substituent derived from an aromatic hydrocarbon and examples thereof include monocyclic aromatic groups and fused polycyclic aromatic groups. Examples thereof include monovalent substituents derived from the following aryl rings by removing one arbitrary hydrogen atom.

Examples of aryl rings include monocyclic aromatic rings and fused polycyclic aromatic rings.

In the present specification, partially unsaturated monocyclic or fused-bicyclic carbon rings and heterocyclic rings and the like are also included in monocyclic aromatic rings and fused polycyclic aromatic rings. An aryl ring may be an aromatic hydrocarbon ring and may contain one or more, for example, 1 to 3 hetero atoms of one or more types selected from the group consisting of a nitrogen atom, a sulfur atom, and an oxygen atom as ring-constituting atoms other than carbon atoms.

Examples of the monocyclic aromatic rings include monocyclic aromatic hydrocarbon rings and monocyclic aromatic heterocyclic rings containing one or more hetero atoms and examples thereof include a benzene ring and 5- or 6-membered aromatic heterocyclic rings containing one or more hetero atoms. Specifically, preferred examples of 5- or 6-membered aromatic heterocyclic rings include thiophene, pyridine, furan, thiazole, oxazole, pyrazole, pyrazine, pyrimidine, pyrrole, imidazole, pyridazine, isothiazole, isoxazole, 1,2,4-oxadiazole, 1,3,4-oxadiazole, 1,2,4-thiadiazole, 1,3,4-thiadiazole, and furazan.

Examples of the fused polycyclic aromatic rings include fused polycyclic aromatic hydrocarbon rings and fused polycyclic aromatic heterocyclic rings containing one or more hetero atoms. Examples of fused polycyclic aromatic hydrocarbon rings include bicyclic or tricyclic aromatic hydrocarbon rings having 9 to 14 carbon atoms and specific preferred examples thereof include naphthalene, 1,2,3,4-tetrahydronaphthalene, indene, 2,3-dihydroindene (indane), fluorene, phenanthrene, 9,10-dihydrophenanthrene, and anthracene.

Examples of fused polycyclic aromatic heterocyclic rings include 9- to 14-membered, preferably 9- or 10-membered fused polycyclic aromatic heterocyclic rings containing one or more, for example, 1 to 4 hetero atoms and specific preferred examples thereof include benzofuran, 2,3-dihydrobenzofuran, benzothiophene, 2,3-dihydrobenzothiophene, benzimidazole, benzoxazole, benzisoxazole, benzothiazole, benzisothiazole, naphtho[2,3-b]thiophene, quinoline, isoquinoline, 1,2-dihydroisoquinoline, 3,4-dihydroisoquinoline, 1,2-dihydroquinoline, 3,4-dihydroquinoline, 1,2,3,4-tetrahydroisoquinoline, 1,2,3,4-tetrahydroquinoline, indole, indoline, quinoxaline, phenanthridine, phenothiazine, phenoxazine, phthalazine, naphthyridine, quinazoline, cinnoline, carbazole, β-carboline, acridine, phenazine, phthalimide, and thioxanthene.

In the present specification, examples of monocyclic aromatic groups as aryl groups include monovalent groups derived from the above-mentioned monocyclic aromatic rings by removing one arbitrary hydrogen atom and specific preferred examples thereof include a phenyl group, a thienyl group (2- or 3-thienyl group), a pyridyl group (2-, 3-, or 4-pyridyl group), a furyl group (2- or 3-furyl group), a thiazolyl group (2-, 4-, or 5-thiazolyl group), an oxazolyl group (2-, 4-, or 5-oxazolyl group), a pyrazolyl group (1-, 3-, or 4-pyrazolyl group), a 2-pyrazinyl group, a pyrimidinyl group (2-, 4-, or 5-pyrimidinyl group), a pyrrolyl group (1-, 2-, or 3-pyrrolyl group), an imidazolyl group (1-, 2-, or 4-imidazolyl group), a pyridazinyl group (3- or 4-pyridazinyl group), an 3-isothiazolyl group, an 3-isooxazolyl group, an 1,2,4-oxadiazol-5-yl group, and an 1,2,4-oxadiazol-3-yl group.

In the present specification, examples of fused polycyclic aromatic groups as aryl groups include monovalent groups derived from the above-mentioned fused polycyclic aromatic ring comprising 2 to 4, preferably 2 or 3 rings by removing one arbitrary hydrogen atom and specific preferred examples thereof include a 1-naphthyl group, a 2-naphthyl group, an 1-indenyl group, an 2-indenyl group, a 2,3-dihydroinden-1-yl group, a 2,3-dihydroinden-2-yl group, an 2-anthryl group, an indazolyl group (3-, 4-, 5-, 6-, or 7-indazolyl group), a quinolyl group (2-, 3-, 4-, 5-, 6-, 7-, or 8-quinolyl group), an isoquinolyl group (1-, 3-, 4-, 5-, 6-, 7-, or 8-isoquinolyl group), a 1,2-dihydroisoquinolyl or 1,2,3,4-tetrahydroisoquinolyl group (substituted at the same position as in an isoquinolyl group), an indolyl group (1-, 2-, 3-, 4-, 5-, 6-, or 7-indolyl group), an isoindolyl group (1-, 2-, 4-, or 5-isoindolyl group), a phthalazinyl group (1-, 5-, or 6-phthalazinyl group), a quinoxalinyl group (2-, 3-, or 5-quinoxalinyl group), a benzofuranyl group (2-, 3-, 4-, 5-, or 6-benzofuranyl group), a 2,3-dihydrobenzofuran-1-yl group, a 2,3-dihydrobenzofuran-2-yl group, a 2,3-dihydrobenzothiophen-1-yl group, a 2,3-dihydrobenzothiophen-2-yl group, a benzothiazolyl group (2-, 4-, 5- or 6-benzothiazolyl group), a benzimidazolyl group (1-, 2-, 4-, 5- or 6-benzimidazolyl group), a fluorenyl group (1-, 2-, 3-, or 4-fluorenyl group), and a thioxanthenyl group.

In the present specification, an "aryloxy group" refers to a group to which the above-mentioned aryl group binds via an oxygen atom. The aryl moiety of an aryloxy group is preferably a monocyclic aromatic group and examples of aryloxy groups include a phenoxy group, a 2-thienyloxy group, a 3-thienyloxy group, a 2-pyridyloxy group, a 3-pyridyloxy group, a 4-pyridyloxy group, a 2-furyloxy group, a 3-furyloxy group, a 2-thiazolyloxy group, a 4-thiazolyloxy group, a 5-thiazolyloxy group, an 2-oxazolyloxy group, an 4-oxazolyloxy group, an 5-oxazolyloxy group, a 1-pyrazolyloxy group, a 3-pyrazolyloxy group, a 4-pyrazolyloxy group, a 2-pyrazinyloxy group, a 2-pyrimidinyloxy group, a 4-pyrimidinyloxy group, a 5-pyrimidinyloxy group, a 1-pyrrolyloxy group, a 2-pyrrolyloxy group, a 3-pyrrolyloxy group, an 1-imidazolyloxy group, an 2-imidazolyloxy group, an 4-imidazolyloxy group, a 3-pyridazinyloxy group, a 4-pyridazinyloxy group, an 3-isothiazolyloxy group, an 3-isoxazolyloxy group, an 1,2,4-oxadiazol-5-yloxy group, and an 1,2,4-oxadiazol-3-yloxy group. A phenoxy group, a 2-thienyloxy group, a 3-thienyloxy group, a 2-furyloxy group, a 3-furyloxy group, a 2-pyridyloxy group, a 3-pyridyloxy group, a 4-pyridyloxy group, and the like are particularly preferred.

In the present specification, an "aralkyl group" refers to an alkyl group substituted with an aryl group (arylalkyl group). Here, an alkyl moiety of an aralkyl group is the same as the above-mentioned alkyl group, and an aryl moiety is the same as the above-mentioned aryl group. An aryl moiety of an aralkyl group is preferably a monocyclic aromatic group.

Examples of aralkyl groups include a benzyl group, a 2-thienylmethyl group, a 3-thienylmethyl group, a 2-pyridylmethyl group, a 3-pyridylmethyl group, a 4-pyridylmethyl group, a 2-furylmethyl group, a 3-furylmethyl group, a 2-thiazolylmethyl group, a 4-thiazolylmethyl group, a 5-thiazolylmethyl group, an 2-oxazolylmethyl group, an 4-oxazolylmethyl group, an 5-oxazolylmethyl group, a 1-pyrazolylmethyl group, a 3 pyrazolylmethyl group, a 4-pyrazolylmethyl group, a 2-pyrazinylmethyl group, a 2-pyrimidinylmethyl group, a 4-pyrimidinylmethyl group, a 5-pyrimidinylmethyl group, a 1-pyrrolylmethyl group, a 2-pyrrolylmethyl group, a 3-pyrrolylmethyl group, an 1-imidazolylmethyl group, an 2-imidazolylmethyl group, an 4-imidazolylmethyl group, a 3-pyridazinylmethyl group, a 4-pyridazinylmethyl group, an 3-isothiazolylmethyl group, an 3-isooxazolylmethyl group, an 1,2,4-oxadiazol-5-ylmethyl group, and an 1,2,4-oxadiazol-3-ylmethyl group. In one embodiment, a benzyl group, a 2-thienylmethyl group, a 3-thienylmethyl group, a 2-furylmethyl group, a 3-furylmethyl group, a 2-pyridylmethyl group, a 3-pyridylmethyl group, a 4-pyridylmethyl group, and the like are particularly preferred.

Furthermore, examples of aralkyl groups include a 2-phenylethyl group, a 2-(2-thienyl)ethyl group, a 2-(3-thienyl)ethyl group, a 2-(2-pyridyl)ethyl group, a 2-(3-pyridyl)ethyl group, a 2-(4-pyridyl)ethyl group, a 2-(2-furyl)ethyl group, a 2-(3-furyl)ethyl group, a 2-(2-thiazolyl)ethyl group, a 2-(4-thiazolyl)ethyl group, a 2-(5-thiazolyl)ethyl group, an 2-(2-oxazolyl)ethyl group, an 2-(4-oxazolyl)ethyl group, an 2-(5-oxazolyl)ethyl group, a 2-(1-pyrazolyl)ethyl group, a 2-(3-pyrazolyl)ethyl group, a 2-(4-pyrazolyl)ethyl group, a 2-(2-pyrazinyl)ethyl group, a 2-(2-pyrimidinyl)ethyl group, a 2-(4-pyrimidinyl)ethyl group, a 2-(5-pyrimidinyl)ethyl group, a 2-(1-pyrrolyl)ethyl group, a 2-(2-pyrrolyl)ethyl group, a 2-(3-pyrrolyl)ethyl group, an 2-(1-imidazolyl)ethyl group, an 2-(2-imidazolyl)ethyl group, an 2-(4-imidazolyl)ethyl group, a 2-(3-pyridazinyl)ethyl group, a 2-(4-pyridazinyl)ethyl group, an 2-(3-isothiazolyl)ethyl group, an 2-(3-isooxazolyl)ethyl group, an 2-(1,2,4-oxadiazol-5-yl)ethyl group, and an 2-(1,2,4-oxadiazol-3-yl)ethyl group. In one embodiment, a 2-phenylethyl group, a 2-(2-thienyl)ethyl group, a 2-(3-thienyl)ethyl group, a 2-(2-furyl)ethyl group, a 2-(3-furyl)ethyl group, a 2-(2-pyridyl)ethyl group, a 2-(3-pyridyl)ethyl group, and a 2-(4-pyridyl)ethyl group are particularly preferred.

Furthermore, examples of aralkyl groups also include a 1-phenylethyl group, a 1-(2-thienyl)ethyl group, a 1-(3-thienyl)ethyl group, a 1-(2-pyridyl)ethyl group, a 1-(3-pyridyl)ethyl group, a 1-(4-pyridyl)ethyl group, a 1-(2-furyl)ethyl group, a 1-(3-furyl)ethyl group, a 1-(2-thiazolyl)ethyl group, a 1-(4-thiazolyl)ethyl group, a 1-(5-thiazolyl)ethyl group, an 1-(2-oxazolyl)ethyl group, an 1-(4-oxazolyl)ethyl group, an 1-(5-oxazolyl)ethyl group, a 1-(1-pyrazolyl)ethyl group, a 1-(3-pyrazolyl)ethyl group, a 1-(4-pyrazolyl)ethyl group, a 1-(2-pyrazinyl)ethyl group, a 1-(2-pyrimidinyl)ethyl group, a 1-(4-pyrimidinyl)ethyl group, a 1-(5-pyrimidinyl)ethyl group, a 1-(1-pyrrolyl)ethyl group, a 1-(2-pyrrolyl)ethyl group, a 1-(3-pyrrolyl)ethyl group, a 1-(1-imidazolyl)ethyl group, an 1-(2-imidazolyl)ethyl group, an 1-(4-imidazolyl)ethyl group, a 1-(3-pyridazinyl)ethyl group, a 1-(4-pyridazinyl)ethyl group, an 1-(3-isothiazolyl)ethyl group, an 1-(3-isooxazolyl)ethyl group, an 1-(1,2,4-oxadiazol-5-yl)ethyl group, and an 1-(1,2,4-oxadiazol-3-yl)ethyl group. In one embodiment, a 1-phenylethyl group, a 1-(2-thienyl)ethyl group, a 1-(3-thienyl)ethyl group, a 1-(2-furyl)ethyl group, a 1-(3-furyl)ethyl group, a 1-(2-pyridyl)ethyl group, a 1-(3-pyridyl)ethyl group, and a 1-(4-pyridyl)ethyl group are particularly preferred.

In the present specification, a "saturated heterocyclic group" refers to a saturated ring group containing a hetero atom as a constituent of the ring and examples thereof include monocyclic saturated heterocyclic groups. The ring contains preferably 1 or 2 hetero atoms, more preferably one hetero atom. Furthermore, the monocyclic saturated heterocyclic group is, for example, a 3- to 7-membered ring group, particularly preferably a 5- or 6-membered ring group. Specific preferred examples of saturated heterocyclic groups include a tetrahydropyranyl group (3- or 4-tetrahydropyranyl group), a 3-tetrahydrofuryl group, a piperidyl group (3- or 4-piperidyl group), a 3-pyrrolidyl group, a tetrahydrothiopyranyl group (3- or 4-tetrahydrothiopyranyl group), a 3-tetrahydrothiofuryl group, and a morpholino group (2- or 3-morpholino group). A particularly preferred example is a morpholino group.

In the present specification, an "amino group" refers to a —NH$_2$ group.

In the present specification, examples of a substituent on an alkyl group that may be substituted include a hydroxyl group, a halogen atom, a carboxy group, a cyano group, a saturated heterocyclic group, an alkylsulfonylamino group, and an aminocarbonylamino group. A hydroxyl group and a halogen atom are more preferred.

An alkyl group that may be substituted is preferably one group selected from the group consisting of a trifluoromethyl group, a difluoromethyl group, a hydroxymethyl group, and a 2-hydroxyethyl group in addition to the above-mentioned preferred examples of alkyl groups. A methyl group, an ethyl group, an n-propyl group, an isopropyl group, a cyclopropyl group, a trifluoromethyl group, a difluoromethyl group, a hydroxymethyl group, and a 2-hydroxyethyl group are more preferred, and a methyl group is particularly preferred.

In the present specification, examples of a substituent in an alkoxy group that may be substituted include the same substituents as substituents in the above-mentioned alkyl groups that may be substituted, and one or more halogen atoms are particularly preferred.

A substituted alkoxy groups is preferably, for example, an alkoxy group substituted arbitrarily with one or more halogen atoms, more preferably an alkoxy group having 1 to 4 carbon atoms substituted arbitrarily with one or more halogen atoms. When an alkoxy group is substituted with 2 or more halogen atoms, the halogen atom may be identical to or different from each other. An alkoxy group that may be substituted is preferably one group selected from the group consisting of a monofluoromethoxy group, a difluoromethoxy group, a trifluoromethoxy group, and a 2,2,2-trifluoroethoxy group in addition to the above-mentioned preferred examples of alkoxy groups having 1 to 6 carbon atoms. One group selected from the group consisting of a trifluoromethoxy group and a 2,2,2-trifluoroethoxy group in addition to the above-mentioned preferred examples of alkoxy groups having 1 to 6 carbon atoms is particularly preferred.

In the present specification, a substituent in an alkylene that may be substituted is preferably one group selected from the group consisting of a trifluoromethyl group, a difluoromethyl group, a hydroxymethyl group, and a 2-hydroxyethyl group in addition to the same groups as the above-mentioned substituents in an alkyl group that may be substituted, more preferably a methyl group, an ethyl group, an n-propyl group, an isopropyl group, a cyclopropyl group, a trifluoromethyl group, a difluoromethyl group, a hydroxymethyl group, and a 2-hydroxyethyl group, particularly preferably a methyl group.

In the present specification, substituents in an aryl group that may be substituted and an aryloxy group that may be substituted are the same as the above-mentioned substituents in an alkyl group that may be substituted.

In the present specification, substituents in an aralkyl group that may be substituted are the same as, for example, the above-mentioned substituents in an alkyl group that may be substituted.

In the present specification, preferred examples of aralkyl groups that may be substituted in one embodiment include the above-mentioned preferred examples of aralkyl groups. Furthermore, in another embodiment, an aralkyl group may be preferably substituted with an alkyl group, an alkoxy group, an amino group, a hydroxyl group, a cyano group, or a halogen atom on a carbon atom among constituents forming an aryl ring of the above-mentioned aralkyl group. Specific examples thereof include a 4-methylphenylmethyl group, a 4-methoxyphenylmethyl group, an 4-aminophenylmethyl group, a 4-hydroxyphenylmethyl group, a 4-fluorophenylmethyl group, a 5-methyl-2-furylmethyl group, a 4-methyl-2-furylmethyl group, a 5-methyl-3-furylmethyl group, a 5-methyl-2-pyrrolylmethyl group, a 4-methyl-2-pyrrolylmethyl group, a 5-methyl-3-pyrrolylmethyl group, a 5-methyl-2-thienylmethyl group, a 4-methyl-2-thienylmethyl group, and a 5-methyl-3-thienylmethyl group. Furthermore, in another embodiment, an aralkyl group may be preferably substituted with an alkyl group or an alkoxy group on a nitrogen atom among constituents forming an aryl ring of an aralkyl group. Specific examples thereof include a 1-methyl-2-pyrrolylmethyl group, a 1-ethyl-2-pyrrolylmethyl group, and a 1-methyl-3-pyrrolylmethyl group.

In the present specification, substituents in a saturated heterocyclic group that may be substituted are the same as, for example, the above-mentioned substituents of an alkyl group that may be substituted.

In the present specification, saturated heterocyclic groups that may be substituted are preferably the above-mentioned preferred examples of saturated heterocyclic groups.

In the present specification, examples of amino groups that may be substituted include an —NH$_2$ group, an alkylamino group, a dialkylamino group, an acylamino group, an alkylcarbonylamino group, and an alkylsulfonylamino group. Furthermore, examples of amino groups that may be substituted also include an amino group substituted with 1 or 2 alkyl groups that may be substituted, an amino group substituted with 1 or 2 aryl groups that may be substituted, and an amino group substituted with an aryl group that may be substituted and an alkyl group that may be substituted.

Specific examples of amino groups that may be substituted include a methylamino group, an ethylamino group, an n-propylamino group, an isopropylamino group, a dimethylamino group, an ethyl(methyl)amino group, a diethylamino group, a methyl(n-propyl)amino group, an acetylamino group, a propanoylamino group, a methylsulfonylamino group, an ethylsulfonylamino group, an n-propylsulfonylamino group, an isopropylsulfonylamino group, and a cyclopropylsulfonylamino group.

Hereafter, the structure of the compound represented by the formula (1) (also simply referred to as "the compound of the formula (1)") will be described in detail.

In the compound of the formula (1), $D^1$ represents a single bond, —N($R^{11}$)—, —O—, —S—, —S(O)—, or —S(O)$_2$—, preferably a single bond, —N($R^{11}$)—, —O—, and —S—, more preferably a single bond, —N($R^{11}$)—, and —O—. In one embodiment, —N($R^{11}$)— may be particularly preferred and —O— may be particularly preferred in another embodiment. —S(O)— and —S(O)$_2$— may be preferred in yet another embodiment.

$R^{11}$ represents a hydrogen atom or an alkyl group that may be substituted, and a hydrogen atom is preferred in one embodiment. In another embodiment, a lower alkyl group is preferred, an alkyl group having 1 to 3 carbon atoms is more preferred, a methyl group and an ethyl group are yet more preferred, and a methyl group is particularly preferred.

$A^1$ represents a single bond, an alkylene that may be substituted, or any of divalent groups selected from the following formulas (1a-1) to (1a-6):

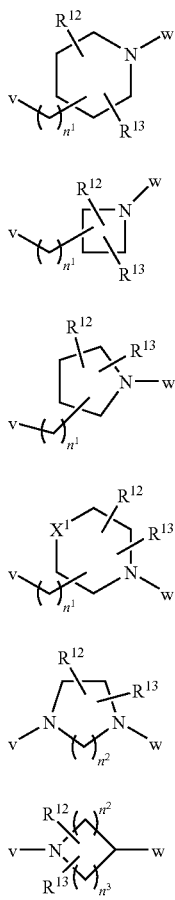

(1a-1)

(1a-2)

(1a-3)

(1a-4)

(1a-5)

(1a-6)

preferably an alkylene that may be substituted or any of divalent groups selected from the formulas (1a-1) to (1a-6). In one embodiment, the formulas (1a-1), (1a-2), and (1a-5) are more preferred, the formulas (1a-1) and (1a-2) are yet more preferred, and the formula (1a-1) is particularly preferred. In another embodiment, the formula (1a-2) may be preferred. In yet another embodiment, the formulas (1a-3), (1a-4), and (1a-6) may be more preferred, the formulas (1a-3) and (1a-4) may be yet more preferred, and the formula (1a-3) may be particularly preferred. In yet another embodiment, the formula (1a-4) may be preferred.

Preferred examples of $A^1$ include the following formulas (1a-1-1), (1a-2-1), and (1a-5-1):

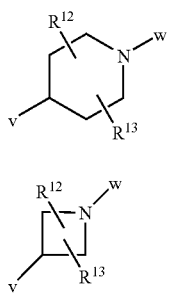

(1a-1-1)

(1a-2-1)

-continued

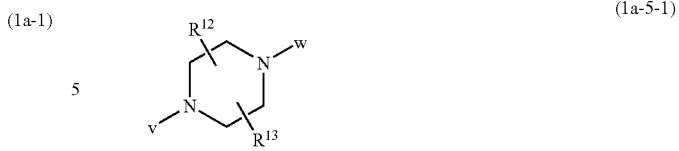

(1a-5-1)

wherein $R^{12}$, $R^{13}$, v, and w have the same meaning as defined above, and the formula (1a-1-1) is more preferred in one embodiment. In another embodiment, the formula (1a-2-1) may be more preferred. In yet another embodiment, the formula (1a-5-1) may be more preferred.

When $D^1$ represents a single bond, $A^1$ represents the formula (1a-5) or (1a-6), preferably the formula (1a-5).

When $D^1$ represents —N($R^{11}$)—, —O—, —S—, —S(O)—, or —S(O)$_2$—, $A^1$ represents a single bond, an alkylene that may be substituted, or any of divalent groups selected from the above-mentioned formulas (1a-1) to (1a-4).

When $A^1$ represents a single bond, $D^2$ represents an alkylene that may be substituted or -E-C(O)—.

When $R^1$ represents an amino group that may be substituted, $D^2$ represents an alkylene that may be substituted or -E-C(O)—.

$n^1$ is an integer of 0, 1, or 2, and 0 or 1 is preferred. In one embodiment, 0 is particularly preferred. In another embodiment, 1 may be preferred.

$n^2$ is an integer of 2 or 3. In one embodiment, 2 is preferred. In another embodiment, 3 may be preferred.

$n^3$ is an integer of 1 or 2. In one embodiment, 1 is preferred. In another embodiment, 2 may be preferred.

$R^{12}$ and $R^{13}$ each independently represent a hydrogen atom, a hydroxyl group, or an alkyl group that may be substituted, preferably a hydrogen atom or an alkyl group that may be substituted. In one embodiment, a hydrogen atom is more preferred. In another embodiment, an alkyl group that may be substituted may be preferred. Preferred examples of alkyl groups that may be substituted include a methyl group, an ethyl group, an n-propyl group, an i-propyl group, and a trifluoromethyl group and a methyl group is more preferred.

$X^1$ represents —N($R^{14}$)—, —O—, or —S—, and —N($R^{14}$)— or —O— is preferred. In one embodiment, —O— or —S— is more preferred, and —O— is particularly preferred. In another embodiment, —N($R^{14}$)— may be preferred.

$R^{14}$ represents a hydrogen atom or an alkyl group that may be substituted, and a hydrogen atom is preferred in one embodiment. In another embodiment, an alkyl group that may be substituted may be preferred. Examples of an alkyl group that may be substituted in $R^{14}$ include alkyl groups having 1 to 3 carbon atoms.

v represents a bond with $D^1$, and w represents a bond with $D^2$.

$D^2$ represents a single bond, an alkylene that may be substituted, —C(O)—, —C(S)—, —S(O)$_2$—, —C(O)—N($R^{15}$)—, —C(S)—N($R^{15}$)—, or -E-C(O)—, preferably a single bond or an alkylene that may be substituted. In one embodiment, an alkylene that may be substituted is more preferred. An alkylene that may be substituted is preferably a straight or branched alkylene having 1 to 3 carbon atoms. Examples thereof include methylene, ethylene, and trimethylene and methylene and ethylene are preferred. In another embodiment, a single bond may be preferred. In yet another embodiment, —C(O)—, —S(O)$_2$—, or -E-C(O)— may be preferred and —C(O)— may be more preferred. In yet another embodiment, —S(O)$_2$— may be preferred.

$R^{15}$ represents a hydrogen atom or an alkyl group, preferably a hydrogen atom.

E represents an alkylene that may be substituted. An alkylene is preferably a straight or branched alkylene having 1 to 4 carbon atoms, more preferably an alkylene having 1 to 3 carbon atoms. Examples of alkylenes include methylene, ethylene, and trimethylene and methylene and ethylene are preferred.

$R^1$ represents a hydrogen atom, an alkyl group that may be substituted, an amino group that may be substituted, a saturated heterocyclic group that may be substituted, an aralkyl group that may be substituted, an aryl group that may be substituted, a carbamimidoyl group, or any of groups selected from the following formulas (1b-1) to (1b-4):

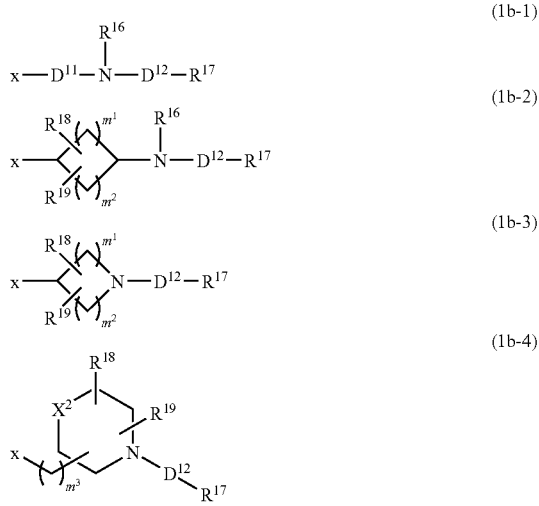

preferably a hydrogen atom, an alkyl group that may be substituted, a saturated heterocyclic group that may be substituted, an aralkyl group that may be substituted, an aryl group that may be substituted, or any of groups selected from the formulas (1b-1) to (1b-4), more preferably an alkyl group that may be substituted, an aralkyl group that may be substituted, an aryl group that may be substituted, or any of groups selected from the formulas (1b-1) to (1b-4). In one embodiment, an alkyl group that may be substituted, an aralkyl group that may be substituted, or an aryl group that may be substituted is more preferred, and an alkyl group that may be substituted is particularly preferred. In another embodiment, an aralkyl group that may be substituted may be preferred. In yet another embodiment, an aryl group that may be substituted may be preferred. Examples of an alkyl group that may be substituted include the above-mentioned preferred examples of an alkyl group that may be substituted. An alkyl group having 1 to 6 carbon atoms is preferred, and an alkyl group having 1 to 4 carbon atoms is more preferred. Examples of an alkyl group include a methyl group, an ethyl group, an n-propyl group, an i-propyl group, a cyclopropyl group, and a trifluoromethyl group. Examples of an aralkyl group that may be substituted include the above-mentioned preferred examples of an aralkyl group that may be substituted, for example, an alkyl group having 1 to 3 carbon atoms that is substituted with an aryl group. Examples of an aralkyl group include a benzyl group, a 2-pyridylmethyl group, a 3-pyridylmethyl group, and a 4-pyridylmethyl group. Examples of an aryl group that may be substituted include the above-mentioned preferred examples of an aryl group that may be substituted, for example, a phenyl group, a thienyl group (2- or 3-thienyl group), a pyridyl group (2-, 3-, or 4-pyridyl group), a furyl group (2- or 3-furyl group), a naphthyl group (1- or 2-naphthyl group), a quinolyl group (2-, 3-, 4-, 5-, 6-, 7-, or 8-quinolyl group), and substitution products thereof, and a phenyl group or a pyridyl group (2-, 3-, or 4-pyridyl group) is preferred. In one embodiment, a phenyl group is particularly preferred. In another embodiment, a pyridyl group may be preferred.

In another embodiment, $R^1$ preferably represents a hydrogen atom, a saturated heterocyclic group that may be substituted, or any of groups selected from the formulas (1b-1) to (1b-4). In one embodiment, a saturated heterocyclic group that may be substituted or the formula (1b-1) or (1b-3) is preferred. In another embodiment, the formula (1b-2) or (1b-4) may be preferred. Examples of a saturated heterocyclic group that may be substituted include a morpholino group (2- or 3-morpholino group), an azetidyl group (2- or 3-azetidyl group), a piperidyl group (2-, 3-, or 4-piperidyl group), and a pyrrolidyl group (2- or 3-pyrrolidyl group). In another embodiment, a hydrogen atom may be preferred.

$m^1$ is an integer of 0, 1, or 2. In one embodiment, 0 or 1 is preferred and 1 is more preferred. In another embodiment, 2 may be preferred.

$m^2$ is an integer of 1 or 2 and 1 is preferred.

$m^3$ is an integer of 0, 1, or 2 and 0 or 1 is preferred.

$X^2$ represents —N($R^{14}$)—, —O—, or —S—. —O— or —S— is preferred, and —O— is particularly preferred.

$D^{11}$ represents an alkylene that may be substituted. An alkylene is preferably a straight or branched alkylene having 1 to 4 carbon atoms, more preferably an alkylene having 1 to 3 carbon atoms. Examples of alkylenes include methylene, ethylene, and trimethylene and methylene or ethylene is preferred.

$D^{12}$ represents a single bond, an alkylene that may be substituted, —C(O)—, —S(O)$_2$—, or —C(O)—N($R^{15}$)—. In one embodiment, a single bond or an alkylene that may be substituted is preferred. In another embodiment, —C(O)— or —S(O)$_2$— is preferred and —C(O)— is particularly preferred. In yet another embodiment, —S(O)$_2$— may be preferred.

$R^{16}$, $R^{18}$, and $R^{19}$ may be identical to or different from one another and each independently represents a hydrogen atom or an alkyl group that may be substituted. In one embodiment, a hydrogen atom is preferred. In another embodiment, an alkyl group that may be substituted may be preferred. Examples of an alkyl group that may be substituted include alkyl groups having 1 to 3 carbon atoms. A methyl group, an ethyl group, or an n-propyl group is preferred, and a methyl group is more preferred.

$R^{17}$ represents a hydrogen atom, an alkyl group that may be substituted, an aralkyl group that may be substituted, or an aryl group that may be substituted. A hydrogen atom, an alkyl group that may be substituted, or an aryl group that may be substituted is preferred, and an alkyl group that may be substituted or an aryl group that may be substituted is more preferred. An alkyl group that may be substituted is preferably an alkyl group having 1 to 6 carbon atoms, more preferably an alkyl group having 1 to 4 carbon atoms. Examples of an alkyl group include a methyl group, an ethyl group, an n-propyl group, an i-propyl group, a cyclopropyl group, and a trifluoromethyl group. Examples of an aryl group that may be substituted include a phenyl group, a thienyl group (2- or 3-thienyl group), a pyridyl group (2-, 3-, or 4-pyridyl group), a furyl group (2- or 3-furyl group), a naphthyl group (a 1- or 2-naphthyl group), and a quinolyl group (2-, 3-, 4-, 5-, 6-, 7-, or 8-quinolyl group) and substitution products thereof. A phenyl group and a pyridyl group (2-, 3-, or 4-pyridyl group) are preferred.

x represents a bond with $D^2$.

When $R^{17}$ represents a hydrogen atom, $D^{12}$ represents a single bond.

$D^3$ represents a single bond, —N($R^{21}$)—, —O—, —N($R^{21}$)—C(O)—, or —S—, preferably a single bond, —O—, or —N($R^{21}$)—C(O)—, more preferably a single bond or —N($R^{21}$)—C(O)—. In one embodiment, a single bond is particularly preferred. In another embodiment, —N($R^{21}$)—C(O)— may be preferred.

$R^{21}$ represents a hydrogen atom or an alkyl group that may be substituted. In one embodiment, a hydrogen atom is preferred. In another embodiment, an alkyl group that may be substituted may be preferred. Examples of an alkyl group that may be substituted include alkyl groups having 1 to 3 carbon atoms. A methyl group, an ethyl group, and an n-propyl group are preferred and a methyl group is more preferred.

$R^2$ represents an alkyl group that may be substituted or a group represented by the following formula (2a-1):

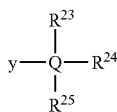

(2a-1)

In one embodiment, a group represented by the formula (2a-1) is preferred. In another embodiment, an alkyl group that may be substituted may be preferred. Examples of an alkyl group that may be substituted include the above-mentioned preferred examples of an alkyl group that may be substituted. An alkyl group having 1 to 6 carbon atoms is preferred and an alkyl group having 1 to 3 carbon atoms is more preferred.

Q represents an aryl group that may be substituted. Examples of an aryl group include the above-mentioned preferred examples of aryl group. In one embodiment, a monocyclic aromatic group is preferred. In another embodiment, a fused polycyclic aromatic group or the like may be preferred. Examples of monocyclic aromatic groups include a phenyl group, a thienyl group (2- or 3-thienyl group), a pyridyl group (2-, 3-, or 4-pyridyl group), and a furyl group (2- or 3-furyl group). In one embodiment, a phenyl group is particularly preferred. In another embodiment, a pyridyl group may be preferred. In yet another embodiment, a thienyl group may be preferred.

Examples of fused polycyclic aromatic groups include a 1-naphthyl group, a 2-naphthyl group, a quinolyl group (2-, 3-, 4-, 5-, 6-, 7-, or 8-quinolyl group), an isoquinolyl group (1-, 3-, 4-, 5-, 6-, 7-, or 8-isoquinolyl group), an indazolyl group (3-, 4-, 5-, 6-, or 7-indazolyl group), and an indolyl group (2-, 3-, 4-, 5-, 6-, or 7-indolyl group). In yet another embodiment, examples include a pyrrolyl group, a pyrimidinyl group, a pyridazinyl group, an imidazolyl group, a quinazolinyl group, and a quinolyl group. In one embodiment, a pyrrolyl group is preferred. In yet another embodiment, a pyrazolyl group may be preferred.

y represents a bond with W.

$R^{23}$, $R^{24}$, and $R^{25}$ may be identical to or different from one another and each independently represents a hydrogen atom, a halogen atom, a cyano group, an alkyl group that may be substituted, an alkoxy group that may be substituted, an amino group that may be substituted, an aryl group that may be substituted, an aryloxy group that may be substituted, an aralkyl group that may be substituted, or a group represented by the following formula (2b-1):

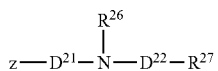

(2b-1)

1 or 2 of $R^{23}$, $R^{24}$, and $R^{25}$ preferably represent a hydrogen atom. In one embodiment, it is particularly preferred that any two of $R^{23}$, $R^{24}$, and $R^{25}$ represent a hydrogen atom. In another embodiment, it may be preferred that any one of $R^{23}$, $R^{24}$, and $R^{25}$ represents a hydrogen atom. In yet another embodiment, it is possible that none of $R^{23}$, $R^{24}$, and $R^{25}$ represent a hydrogen atom. $R^{23}$, $R^{24}$, and $R^{25}$ preferably represent a halogen atom, a cyano group, an alkyl group that may be substituted, an alkoxy group that may be substituted, an amino group that may be substituted, or a group represented by the formula (2b-1). In one embodiment, a halogen atom or a cyano group is particularly preferred. In another embodiment, an alkoxy group that may be substituted or an amino group that may be substituted may be preferred. In yet another embodiment, a group represented by the formula (2b-1) may be preferred.

Examples of Q substituted with $R^{23}$, $R^{24}$, and $R^{25}$ include a phenyl group, a 2-, 3-, or 4-methylphenyl group, a 2-, 3-, or 4-trifluoromethylphenyl group, a 2-, 3-, or 4-methanesulfonylphenyl group, a 2-, 3-, or 4-cyanophenyl group, a 2-, 3-, or 4-fluorophenyl group, a 2-, 3-, or 4-chlorophenyl group, a 2-, 3-, or 4-methoxyphenyl group, an 2-, 3-, or 4-aminophenyl group, a 2-, 3-, or 4-hydroxy phenyl group, a 2-, 3-, or 4-hydroxymethylphenyl group, an 2-, 3-, or 4-aminomethylphenyl group, a 2-, 3-, or 4-cyanomethylphenyl group, a 2-, 3-, or 4-(2-cyanoethyl)phenyl group, an 2-, 3-, or 4-acetylphenyl group, a 2-, 3-, or 4-pyridyl group, a 2- or 3-thienyl group, a 2- or 3-furyl group, a 3,4-difluorophenyl group, a 3-chloro-4-fluorophenyl group, a 4-cyano-3-methylphenyl group, a 3-cyano-4-fluorophenyl group, an 4-amino-3-cyanophenyl group a 3-cyano-5-fluorophenyl group, a 3-fluoro-4-cyanophenyl group, a 5-cyanothiophen-2-yl group, a 4-methylthiophen-3-yl group, a 6-methoxypyridin-3-yl group, and a 6-fluoropyridin-3-yl group. Examples thereof further include a 2-cyanopyridin-3-yl group, a 4-cyanopyridin-3-yl group, a 5-cyanopyridin-3-yl group, a 6-cyanopyridin-3-yl group, a 2-cyanopyridin-4-yl group, a 3-cyanopyridin-4-yl group, a 2-fluoropyridin-3-yl group, a 4-fluoropyridin-3-yl group, a 5-fluoropyridin-3-yl group, a 2-fluoropyridin-4-yl group, a 3-fluoropyridin-4-yl group, a 2-methylpyridin-3-yl group, 4-methylpyridin-3-yl group, a 5-methylpyridin-3-yl group, a 6-methylpyridin-3-yl group, a 2-methylpyridin-4-yl group, a 3-methylpyridin-4-yl group, a 2-difluoromethylpyridin-3-yl group, a 4-difluoromethylpyridin-3-yl group, a 5-difluoromethylpyridin-3-yl group, a 6-difluoromethylpyridin-3-yl group, a 2-difluoromethylpyridin-4-yl group, a 3-difluoromethylpyridin-4-yl group, an 2-ethylpyridin-3-yl group, an 4-ethylpyridin-3-yl group, an 5-ethylpyridin-3-yl group, an 6-ethylpyridin-3-yl group, an 2-ethylpyridin-4-yl group, an 3-ethylpyridin-4-yl group, an 4-, 5-, 6-, or 7-indazolyl group, and a 3-, 4-, or 5-pyrazolyl group.

$D^{21}$ represents a single bond or an alkylene that may be substituted. In one embodiment, a single bond is preferred. In another embodiment, an alkylene that may be substituted may be preferred. Examples of an alkylene that may be substituted include alkylenes having 1 to 3 carbon atoms. Examples of alkylenes include methylene, ethylene, and trimethylene.

$D^{22}$ represents a single bond, an alkylene that may be substituted, —C(O)—, —S(O)$_2$—, or —C(O)—N(R$^{28}$)—, preferably a single bond, an alkylene that may be substituted, —C(O)—, or —S(O)$_2$—. In one embodiment, —C(O)— or —S(O)$_2$— is more preferred. In another embodiment, a single bond may be preferred. $R^{26}$, $R^{27}$, and $R^{28}$ may be identical to or different from one another and each independently represents a hydrogen atom or an alkyl group that may be substituted. In one embodiment, a hydrogen atom is preferred. In another embodiment, an alkyl group that may be substituted may be preferred. An alkyl group that may be substituted is preferably an alkyl group having 1 to 6 carbon atoms, more preferably an alkyl group having 1 to 4 carbon atoms. Examples of alkyl groups include a methyl group, an ethyl group, and a cyclopropyl group.

z represents a bond with Q.

When $D^{22}$ represents a single bond, $R^{27}$ represents a hydrogen atom.

Combinations of substituents in the compound of the present invention are not particularly limited so long as the compound of the present invention has an intended IKKβ inhibiting activity and the preferred examples thereof include compounds having the following combinations of substituents or salts thereof:

[1] the compound of the formula (1), wherein $R^2$ represents a substituted phenyl group or a substituted pyridyl group, or a salt thereof;

[2] the compound of the formula (1), wherein $D^3$ represents a single bond And $R^2$ represents a substituted phenyl group or a substituted pyridyl group, or a salt thereof;

[3] the compound of the formula (1), wherein $D^3$ represents a single bond and $R^2$ represents a substituted phenyl group, or a salt thereof;

[4] the compound of the formula (1), wherein $D^3$ represents a single bond and $R^2$ represents a substituted pyridyl group, or a salt thereof;

[5] the compound of the formula (1), wherein $D^1$ represents —N(R$^{11}$)—, —O—, or —S—, or a salt thereof;

[6] the compound of the formula (1), wherein $D^1$ represents —N(R$^{11}$)—, or a salt thereof;

[7] the compound of the formula (1), wherein $D^1$ represents —O—, or a salt thereof;

[8] the compound of the formula (1), wherein $D^1$ represents —S—, or a salt thereof;

[9] the compound of the formula (1), wherein $A^1$ represents a divalent group represented by the formula (1a-1), (1a-2), or (1a-5), or a salt thereof;

[10] the compound of the formula (1), wherein $A^1$ represents a divalent group represented by the formula (1a-1) or (1a-2), or a salt thereof;

[11] the compound of the formula (1), wherein $D^2$ represents —C(O)—, —S(O)$_2$—, or —C(O)—N(R$^{15}$)—, or a salt thereof;

[12] the compound of the formula (1), wherein $A^1$ represents a divalent group represented by the formula (1a-1), (1a-2), or (1a-5) and $D^2$ represents —C(O)—, —S(O)$^2$—, or —C(O)—N(R$^{15}$)—, or a salt thereof;

[13] the compound of the formula (1), wherein $R^2$ represents a substituted phenyl group or a substituted pyridyl group and $D^1$ represents —N(R$^{11}$)—, —O—, or —S—, or a salt thereof; and

[14] the compound of the formula (1), wherein $R^2$ represents a substituted phenyl group or a substituted pyridyl group, $D^1$ represents —N(R$^{11}$)—, —O—, or —S—, and $A^1$ represents a divalent group represented by the formula (1a-1), (1a-2), or (1a-5), or a salt thereof.

Examples of the compound of the present invention include the following examples, but the compound of the present invention is not limited to these examples.

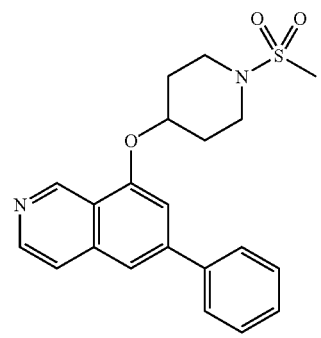

EXA1-1

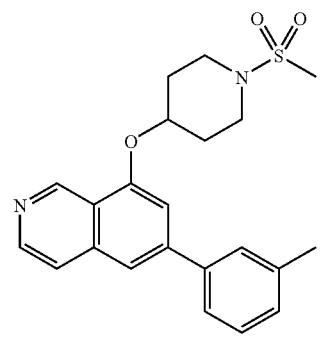

EXA1-2

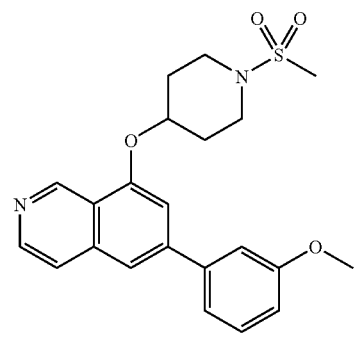

EXA1-3

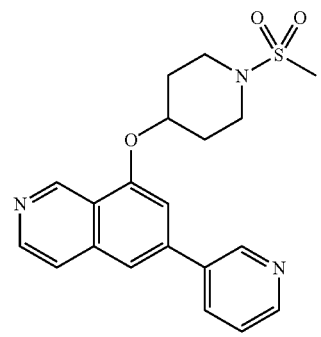

EXA1-4

EXA1-5
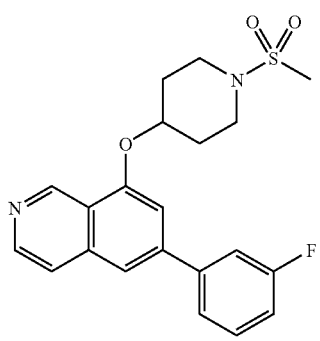
EXA1-9
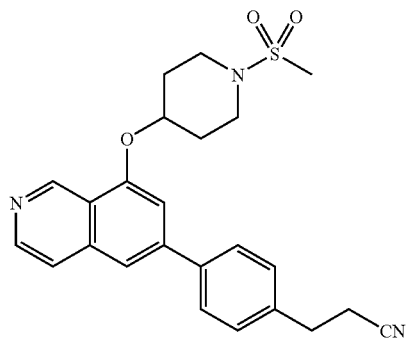
EXA1-6
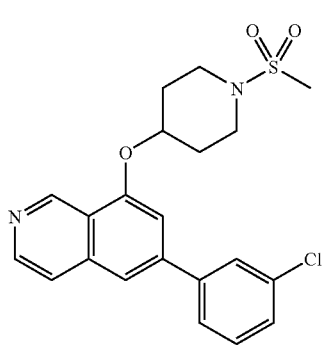
EXA1-10
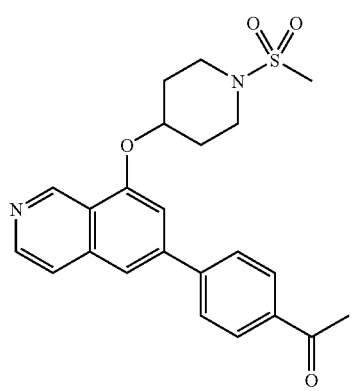
EXA1-7
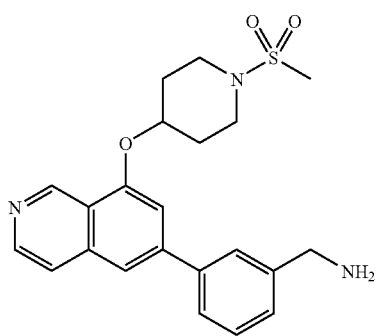
EXA1-11
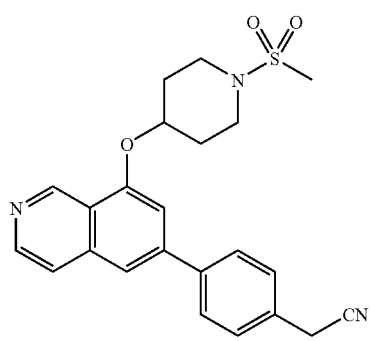
EXA1-8
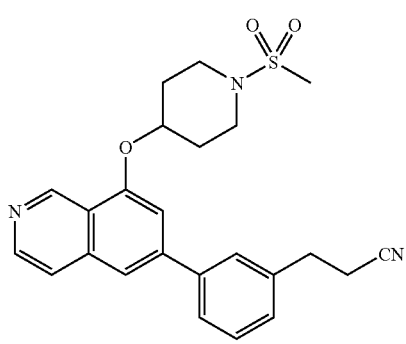
EXA1-12
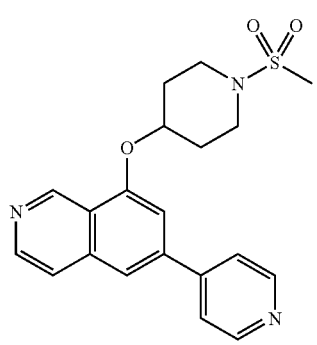

EXA1-13
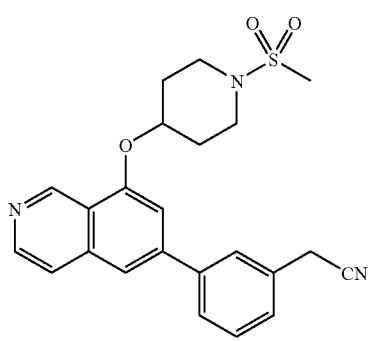
EXA1-17
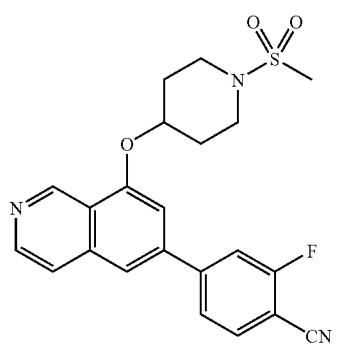
EXA1-14
EXA1-18
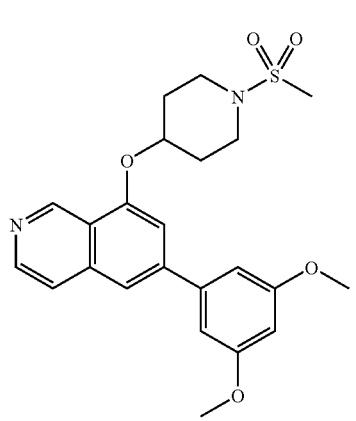
EXA1-15
EXA1-19
EXA1-16
EXA1-20
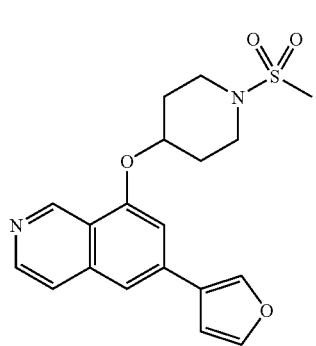
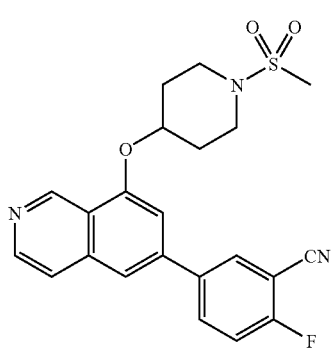

EXA1-21
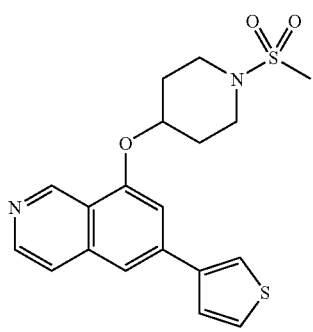
EXA2-4
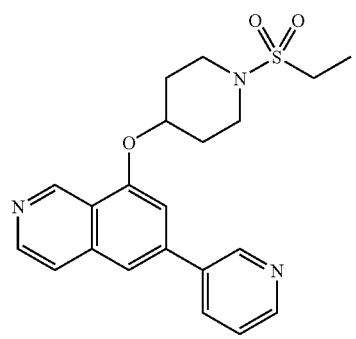
EXA2-1
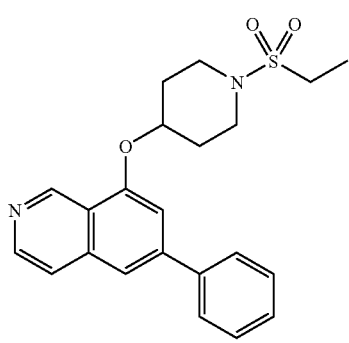
EXA2-5
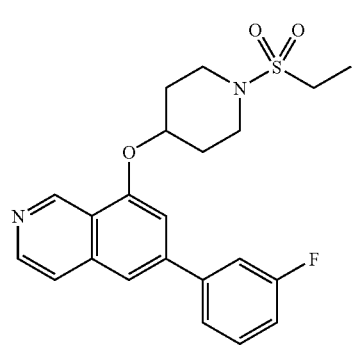
EXA2-2
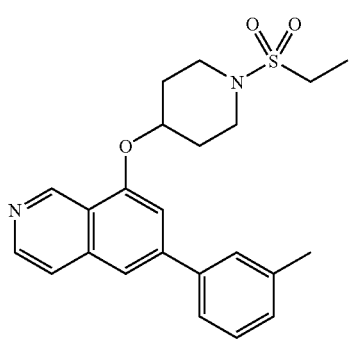
EXA2-6
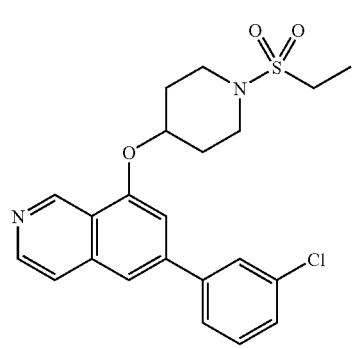
EXA2-3
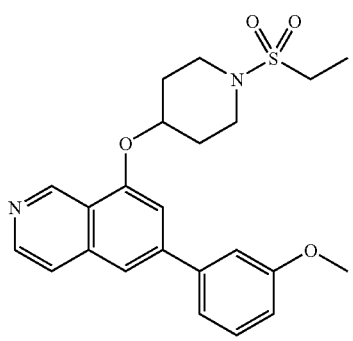
EXA2-7
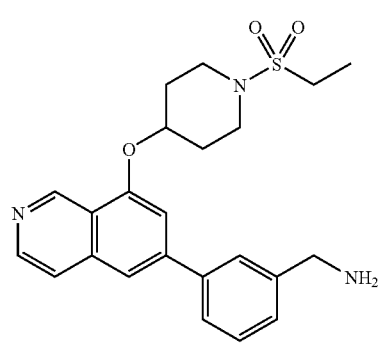

-continued
EXA2-8
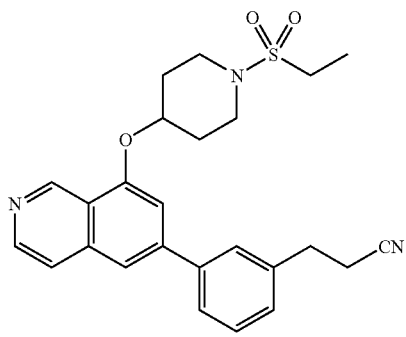
EXA2-9
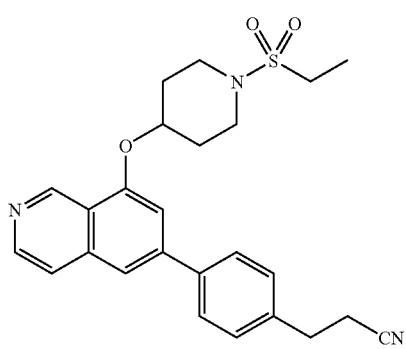
EXA2-10
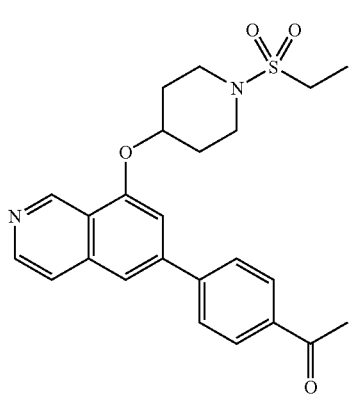
EXA2-11
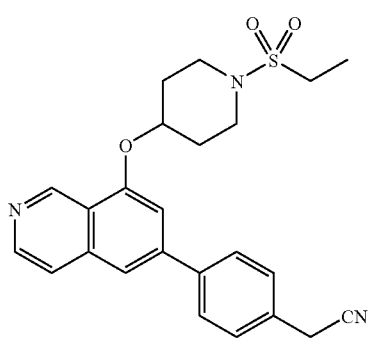
-continued
EXA2-12
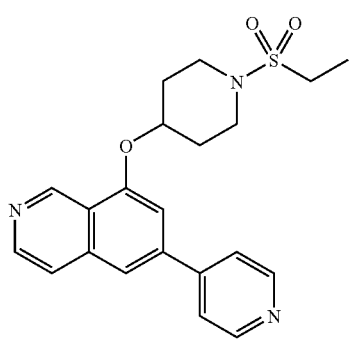
EXA2-13
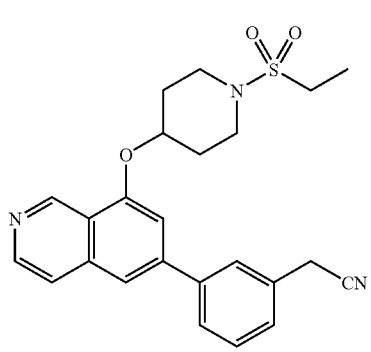
EXA2-14
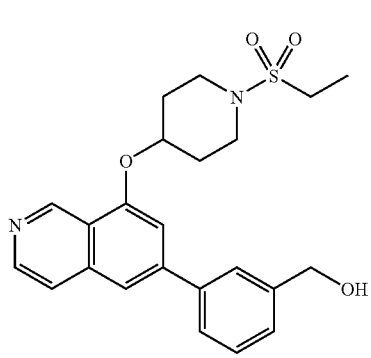
EXA2-15
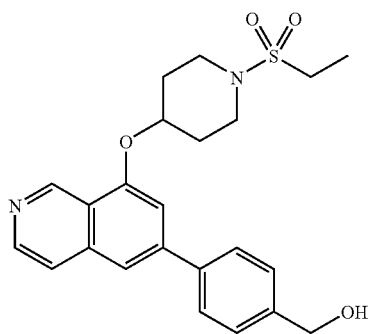

| EXA2-16 | EXA2-20 |
|---|---|
| 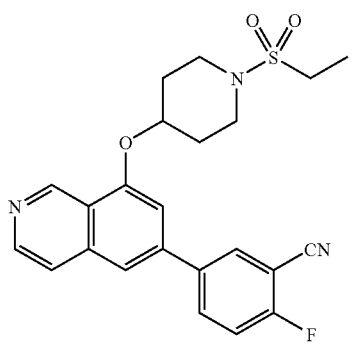 | 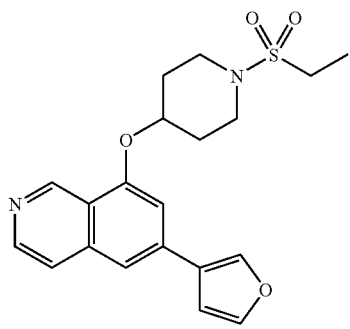 |
| EXA2-17 | EXA2-21 |
| 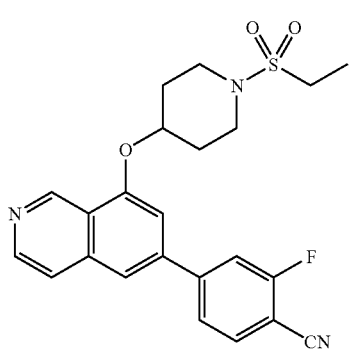 | 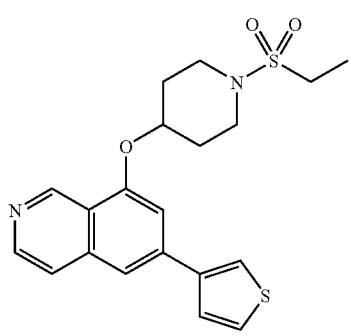 |
| EXA2-18 | EXA3-1 |
| 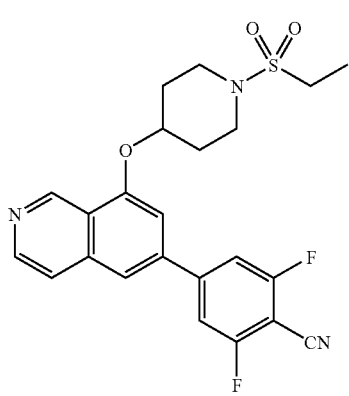 | 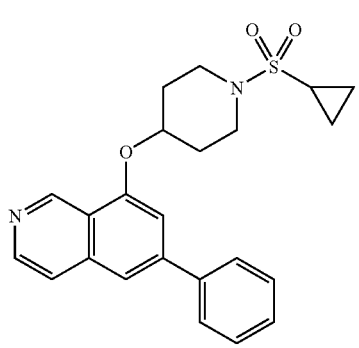 |
| EXA2-19 | EXA3-2 |
| 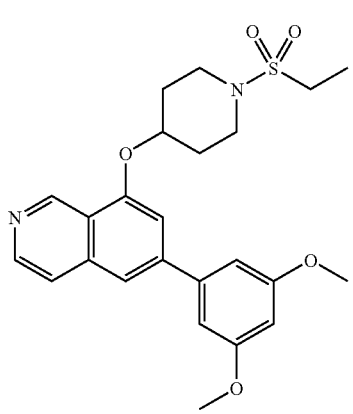 | 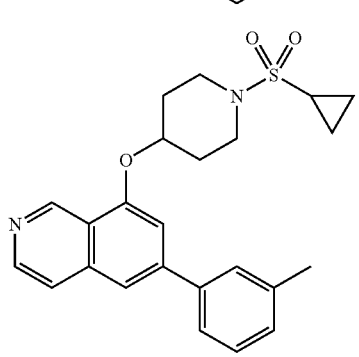 |
| | EXA3-3 |
| | 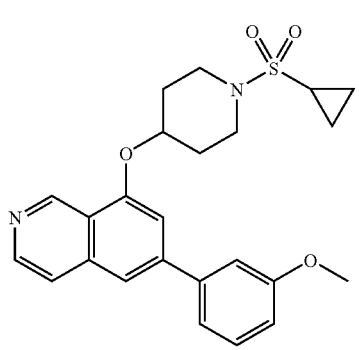 |

-continued
EXA3-4
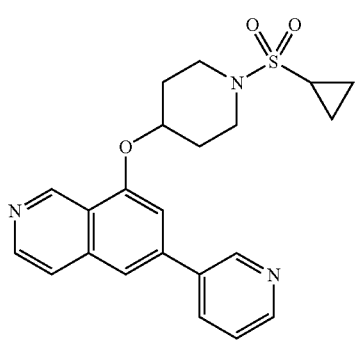
EXA3-5
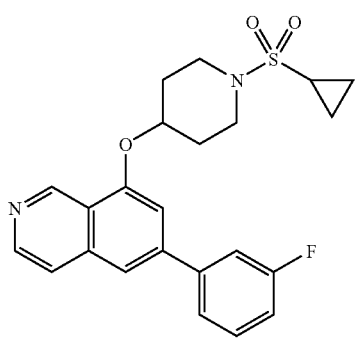
EXA3-6
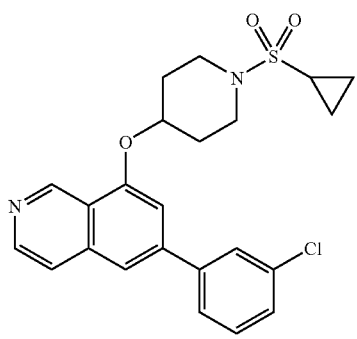
EXA3-7
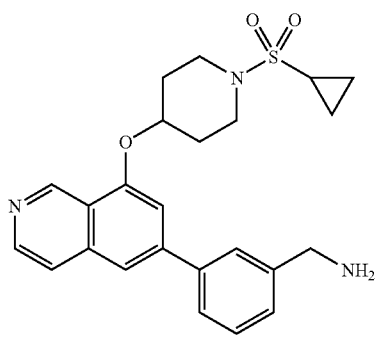
-continued
EXA3-8
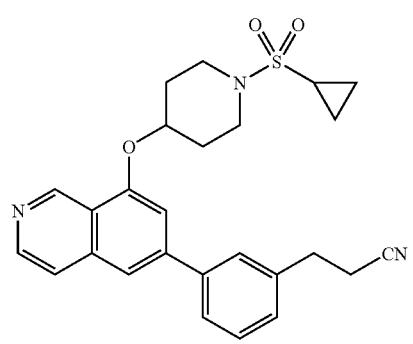
EXA3-9
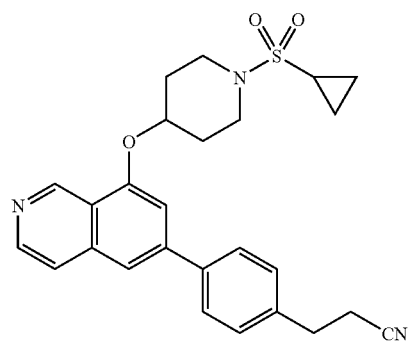
EXA3-10
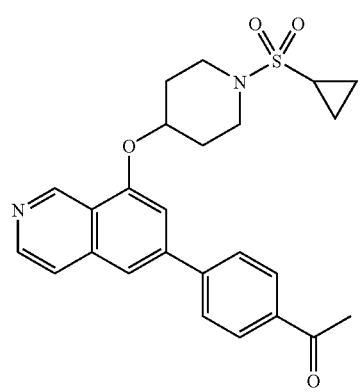
EXA3-11
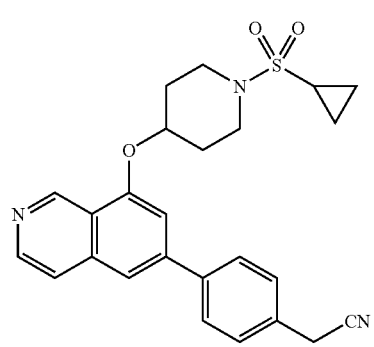

EXA3-12 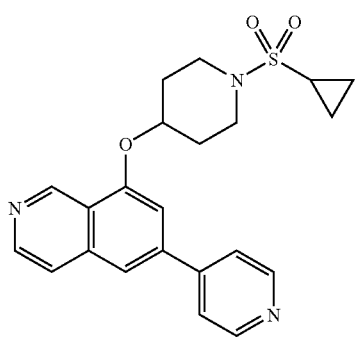
EXA3-16 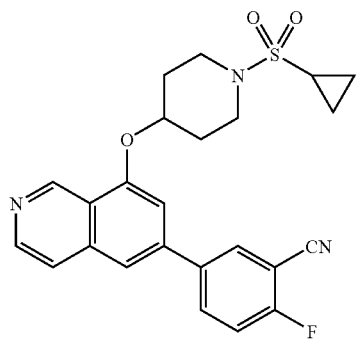
EXA3-13 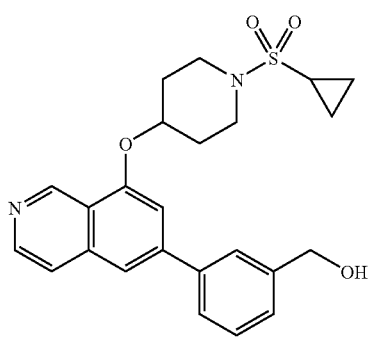
EXA3-17 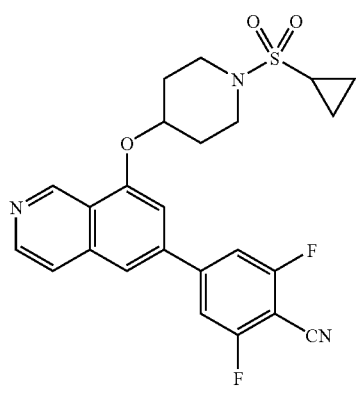
EXA3-14 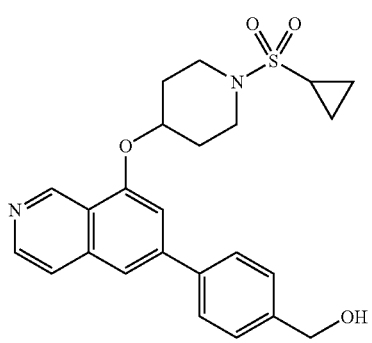
EXA3-18 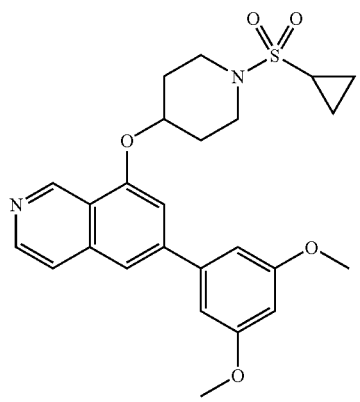
EXA3-15
EXA3-19

-continued

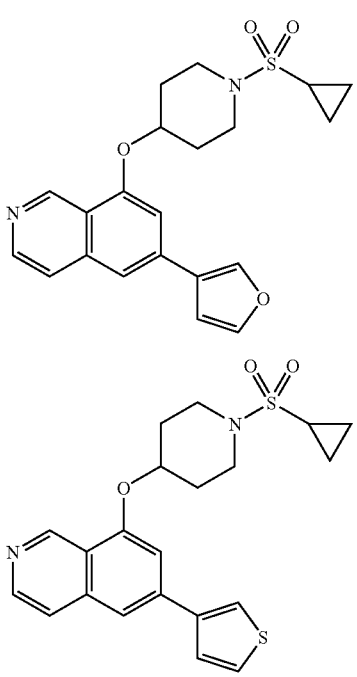

EXA3-20

EXA3-21

The compound of the present invention may have one or more asymmetric center, and a stereoisomer such as an optical enantiomer or a diastereoisomer based on such an asymmetric center may exist. Stereoisomers in a pure form and arbitrary mixtures or racemates of stereoisomers all fall within the scope of the present invention. In one embodiment, mixtures of racemates and the like may be preferred due to easiness of production. Furthermore, when the compound of the present invention has an olefinic double bond or a cyclic structure, two or more stereoisomers may exist, and arbitrary stereoisomers in a pure form or arbitrary mixtures of stereoisomers all fall within the scope of the present invention. Furthermore, the compound of the present invention may exist as a tautomer. Existence of tautomers is apparent for those skilled in the art and all tautomers fall within the scope of the present invention.

In the present specification, "the compound represented by the formula (1)" is generally understood as a compound, in a free form, represented by the formula (1).

The compound represented by the formula (1) may exist as a salt and such a salt also fall within the scope of the present invention. The form of the salt is not particularly limited and an acid addition salt is generally formed. A base addition salt may be formed depending on the type of a substituent.

Salts are preferably pharmaceutically acceptable salts. Acids and bases that form pharmaceutically acceptable salts are known to those skilled in the art and examples thereof include the salts described by Berge et al. in J. Pharm. Sci., 1977, pp. 1-19.

Examples of acid addition salts include mineral acid salts such as hydrochlorides, hydrobromates, hydroiodides, nitrates, sulfates, hydrogen sulfates, phosphates, and hydrogen phosphates and organic acid salts such as acetates, trifluoroacetates, gluconates, lactates, salicylates, citrates, tartarates, ascorbates, succinates, maleates, fumarates, formates, benzoates, methanesulfonates, ethanesulfonates, and p-toluenesulfonates.

For example, when one or more substituents include an acidic moiety, examples of base addition salts include alkali metal salts such as sodium salts and potassium salts, alkaline earth metal salts such as magnesium salts and calcium salts, organic amine salts such as triethylamine salts, pyridine salts, procaine salts, picoline salts, dicyclohexylamine salts, diethanolamine salts, triethanolamine salts, tris(hydroxymethyl) aminomethane salts, and amino acid addition salts such as arginine salts, lysine salts, ornithine salts, serine salts, glycine salts, aspartic acid salts, and glutamic acid salts.

The compound of the present invention may be a nonhydrate. Furthermore, the compound of the present invention is preferably a hydrate in one embodiment.

In one embodiment, the compound of the present invention is preferably a solvate. In another embodiment, a nonsolvate may be preferred.

The compound of the present invention may be crystalline or amorphous. The crystalline compound may be of a single crystal or a mixture of multiple crystalline forms. Alternatively, the compound of the present invention may be of an arbitrary mixture of crystalline and amorphous forms.

In one embodiment, it is preferred that "the compound represented by the formula (1)" is neither a hydrate nor a solvate (this compound may be referred to as a "free compound"). In another embodiment, it may be preferred that "the compound represented by the formula (1)" is either a hydrate or a solvate.

In one embodiment, it is preferred that "a salt of the compound represented by the formula (1)" is neither a hydrate nor a solvate. In another embodiment, it may be preferred that "a salt of the compound represented by the formula (1)" is either a hydrate or a solvate. Furthermore, preferred examples include crystals of these substances.

In one embodiment, the above-mentioned compound of the present invention is preferably crystalline.

A prodrug of the compound of the present invention also falls within the scope of the present invention.

A prodrug can be produced from the compound of the present invention by, for example, suitably introducing a group constituting a prodrug into one or more arbitrary groups selected from hydroxyl groups and amino groups in the compound of the present invention according to a usual method using a prodrug forming reagent such as a corresponding halogenated compound and then suitably isolating and purifying according to a usual method as intended. Furthermore, a prodrug of the compound of the present invention can also be produced by suitably introducing a group constituting a prodrug into a carboxyl group in the compound of the present invention according to a usual method using a prodrug forming reagent such as a corresponding alcohol or amine. When the prodrug of the present invention is produced, a protective group existing in a compound represented by the formula (2) described later may be utilized.

The prodrug of the compound of the present invention is not particularly limited so long as a metabolite thereof exhibits an intended pharmacological effect and examples thereof include compounds in which a group constituting a prodrug is introduced into one or more arbitrary groups selected from hydroxyl groups, amino groups, and carboxyl groups in the compound of the present invention. Examples of the group that can constitute a prodrug when introduced into a hydroxyl group or an amino group include an acyl group and an alkoxycarbonyl group and preferred examples include an acetyl group, a propionyl group, a methoxycarbonyl group, and an ethoxycarbonyl group. In one embodiment, an ethoxycarbonyl group is particularly preferred. In another embodiment, an acetyl group, a propionyl group, or a methoxycarbonyl group may be preferred. Examples of the group that can constitute a prodrug when introduced into a carboxyl group include a methyl group, an ethyl group, an n-propyl group, an isopropyl group, an n-butyl group, an isobutyl group, an s-butyl group, a t-butyl group, an amino group, a methylamino group, an ethylamino group, a dimethylamino group, and a diethylamino group and preferred examples include an ethyl group, an n-propyl group, and an isopropyl group. In one embodiment, an ethyl group is particularly preferred. In another embodiment, an n-propyl group or an isopropyl group may be preferred.

Hereafter, the structure of the compound represented by the formula (2a) (which may also be simply referred to as "the compound of the formula (2a)") will be described in detail.

In the compound of the formula (2a), $R^3$ represents a hydrogen atom or an alkyl group that may be substituted, preferably a hydrogen atom. In another embodiment, a lower alkyl group is preferred, an alkyl group having 1 to 3 carbon atoms is more preferred, a methyl group or an ethyl group is even more preferred, and a methyl group is particularly preferred.

$R^4$ represents a hydrogen atom, an alkyl group that may be substituted, or an aralkyl group that may be substituted. An alkyl group that may be substituted or an aralkyl group that may be substituted are preferred and an alkyl group that may be substituted is more preferred. In another embodiment, an aralkyl group that may be substituted may be preferred. In yet another embodiment, a hydrogen atom may be preferred.

$R^5$ represents a halogen atom, preferably a bromine atom, a chlorine atom, or a fluorine atom, more preferably a bromine atom or a chlorine atom, yet more preferably a bromine atom. In another embodiment, a chlorine atom may be preferred.

Hereafter, the structure of the compound represented by the formula (2b) (which may also be simply referred to as "the compound of the formula (2b)" will be described in detail.

In the compound of the formula (2b), $R^4$ represents a hydrogen atom, an alkyl group that may be substituted, or an aralkyl group that may be substituted, preferably an alkyl group that may be substituted or an aralkyl group that may be substituted, more preferably an alkyl group that may be substituted. In another embodiment, an aralkyl group that may be substituted may be preferred. In yet another embodiment, a hydrogen atom may be preferred.

$R^5$ represents a halogen atom, preferably a bromine atom, a chlorine atom, or a fluorine atom, more preferably a bromine atom or a chlorine atom, yet more preferably a bromine atom. In another embodiment, a chlorine atom may be preferred.

The compound represented by the formula (2a) or (2b) is generally a free compound represented by the formula (2a) or (2b), respectively. Furthermore, the compound represented by the formula (2a) or (2b) may exist as a salt thereof, and such a salt thereof also falls within the scope of the present invention. The form of the salt can be the same as those of the compound represented by the formula (1).

The compound represented by the formula (2a) or (2b) or a salt thereof may be a nonhydrate. Furthermore, in one embodiment, the compound represented by the formula (2a) or (2b) or a salt thereof is preferably a hydrate.

In one embodiment, the compound represented by the formula (2a) or (2b) or a salt thereof is preferably a solvate. In another embodiment, it may be preferred that the compound represented by the formula (2a) or (2b) is a nonsolvate.

The compound represented by the formula (2a) or (2b) may be crystalline or amorphous. The crystalline compound may be of a single crystal or a mixture of multiple crystalline forms. Alternatively, the compound represented by the formula (2a) or (2b) may be of an arbitrary mixture of crystalline and amorphous forms.

In one embodiment, it is preferred that "the compound represented by the formula (2a) or (2b)" is neither a hydrate nor a solvate (this compound may be referred to as a "free compound"). In another embodiment, it may be preferred that "the compound represented by the formula (2a) or (2b)" is either a hydrate or a solvate.

In one embodiment, it is preferred that a "salt of the compound represented by the formula (2a) or (2b)" is neither a hydrate nor a solvate. In another embodiment, it may be preferred that a "salt of the compound represented by the formula (2a) or (2b)" is either a hydrate or a solvate. Furthermore, preferred examples include crystals of those substances.

In one embodiment, the above-mentioned compound represented by the formula (2a) or (2b) or a salt thereof is preferably crystalline.

A prodrug of the compound represented by the formula (2a) or (2b) or a salt thereof also falls within the scope of the present invention. The form and the production method of the prodrug of the compound represented by the formula (2a) or (2b) or a salt thereof can be the same as those of the compound represented by the formula (1) or a salt thereof.

Production Methods

The compound of the present invention can be produced by, for example, the following methods, but the production methods thereof are not limited to the following Production Methods.

In the following Production Methods, the reaction time of each reaction is not particularly limited and it is sufficient to terminate the reaction in each reaction when an intended yield is obtained. The progression of the reaction can be readily followed by the analytical measure described later.

Each reaction in the following Production Methods can be carried out in an inert gas atmosphere, such as, for example, a nitrogen or argon flow, if necessary.

Furthermore, protection by a protective group and subsequent deprotection in each reaction in the following Production Methods can be performed suitably with reference to the methods described later if necessary.

Examples of the protective group used in the following Production Methods include a protective group for a carboxyl group (—COOH), a protective group for a hydroxyl group (—OH), a protective group for a formyl group (—CHO), and a protective group for an amino group (—NH$_2$).

Examples of the protective group for a carboxyl group include an alkyl group having 1 to 4 carbon atoms, an alkenyl group having 2 to 4 carbon atoms, an alkyl group having 1 to 4 carbon atoms that is substituted with an alkoxy group having 1 to 4 carbon atoms, an alkyl group having 1 to 4 carbon atoms that is substituted with 1 to 3 halogen atoms and specific examples include a methyl group, an ethyl group, a t-butyl group, an allyl group, a methoxyethyl group, and a trichloroethyl group.

Examples of the protective group for a hydroxyl group include an alkyl group having 1 to 4 carbon atoms, an alkenyl group having 2 to 4 carbon atoms, an alkyl group having 1 to 4 carbon atoms that is substituted with an alkoxy group having 1 to 4 carbon atoms, an alkyl group having 1 to 4 carbon atoms that is substituted with 1 to 3 halogen atoms, a silyl group substituted with 3 identical or different alkyl groups having 1 to 4 carbon atoms or phenyl groups, a tetrahydropyranyl group, a tetrahydrofuryl group, a propargyl group, and a trimethylsilylethyl group and specific examples include a methyl group, an ethyl group, a t-butyl group, an allyl group, a methoxymethyl (MOM) group, a methoxyethyl (MEM) group, a trichloroethyl group, a phenyl group, a methylphenyl group, a chlorophenyl group, a benzyl group, a methyl benzyl group, a chlorobenzyl group, a dichlorobenzyl group, a fluorobenzyl group, a trifluoromethylbenzyl group, a nitrobenzyl group, a methoxybenzyl group, an N-methylaminobenzyl group, an N,N-dimethylaminobenzyl group, a phenacyl group, a trityl group, an 1-ethoxyethyl (EE) group, a tetrahydropyranyl (THP) group, a tetrahydrofuryl group, a propargyl group, a trimethylsilyl (TMS) group, a triethylsilyl (TES) group, a t-butyldimethylsilyl (TBDMS) group, a t-butyldiphenylsilyl (TBDPS) group, an acetyl (Ac) group, a pivaloyl group, a benzoyl group, an allyloxycarbonyl (Alloc) group, and a 2,2,2-trichloroethoxycarbonyl (Troc) group.

Examples of the protective group for a formyl group include an acetal group and specific examples include dimethyl acetal.

Examples of the protective group for an amino group include a benzyl group, a, methylbenzyl group, a chlorobenzyl group, a dichlorobenzyl group, a fluorobenzyl group, a trifluoromethylbenzyl group, a nitrobenzyl group, a methoxyphenyl group, an N-methylaminobenzyl group, an N,N-dimethylaminobenzyl group, a phenacyl group, an acetyl group, a trifluoroacetyl group, a pivaloyl group, a benzoyl group, an allyloxycarbonyl group, a 2,2,2-trichloroethoxycarbonyl group, a benzyloxycarbonyl (Cbz) group, a t-butoxycarbonyl (Boc) group, a 1-methyl-1-(4-biphenyl)ethoxycarbonyl (Bpoc) group, a 9-fluorenylmethoxycarbonyl group, a benzyloxy methyl (BOM) group, and a 2-(trimethylsilyl)ethoxymethyl (SEM) group.

During the production step or at the final stage in the following Production Methods, the compound can be converted to a target compound by deprotecting an introduced protective group at the same time as or successively after the production step. The protection and deprotection reactions can be performed by a known method, for example, the method described in Protective Groups in Organic Synthesis, John Wiley and Sons (2007), and deprotection can be performed by, for example, the following methods (1) to (6) and the like.

(1) Deprotection reaction under an acidic condition. This reaction is performed, for example, in an organic solvent (dichloromethane, chloroform, dioxane, ethyl acetate, methanol, anisole, etc.) in the presence of an acid such as an organic acid (acetic acid, trifluoroacetic acid, methanesulfonic acid, p-toluenesulfonic acid, etc.), a Lewis acid (boron tribromide, boron trifluoride, bromide aluminium, aluminium chloride, etc.) or an inorganic acid (hydrochloric acid, hydrobromic acid, sulfuric acid, etc.) or a mixture thereof (hydrobromic acid/acetic acid, etc.) at −10 to 100° C. In some methods, ethanethiol, 1,2-ethanedithiol, or the like may be added as an additive. The amount of an acid used is preferably 1 to 100 molar equivalents based on the starting compound. The reaction time is usually 0.1 hours or longer, preferably, for example, 0.5 to 48 hours. Since the reaction progression can be followed by thin layer chromatography (TLC), high performance liquid chromatography (HPLC), or the like, the reaction can be suitably terminated when an intended yield of a target compound is obtained.

(2) Deprotection reaction by alkali hydrolysis. This reaction is performed by, for example, reacting the compound with a base in a reaction solvent such as a polar solvent. Examples of the base include alkali metal bases such as sodium hydroxide, potassium hydroxide, lithium hydroxide, barium hydroxide, calcium hydroxide, sodium carbonate, potassium carbonate, sodium methoxide, and potassium t-butoxide and organic bases such as triethylamine. The amount of a alkali metal base used is usually 1 to 20 molar equivalents per mole of a reactant, preferably, for example, 1 to 10 molar equivalents and that of an organic base is, for example, 1 molar equivalent to a large excess. The reaction solvent is usually an inactive medium that does not interfere with an reaction, preferably a polar solvent. Examples of the polar solvent include water, methanol, ethanol, tetrahydrofuran, and dioxane. If necessary, these solvents can be mixed. As the reaction temperature, for example, a suitable temperature from −10° C. to reflux temperature of a solvent is selected. The reaction time, is usually 0.5 to 72 hours or longer, preferably, for example, 1 to 48 hours. When an organic base is used, the reaction time is, for example, 5 hours to 14 days.

(3) Deprotection reaction by hydrogenolysis. This reaction is performed, for example, in a solvent [an ether solvent (tetrahydrofuran, dioxane, dimethoxyethane, diethyl ether, etc.), an alcohol solvent (methanol, ethanol, etc.), a benzene solvent (benzene, toluene, etc.), a ketone solvent (acetone, methyl ethyl ketone, etc.), a nitrile solvent (acetonitrile, etc.), an amide solvent (dimethylformamide, etc.), an ester solvent (ethyl acetate, etc.), water, acetic acid, a mixed solvent of two or more of these solvents, etc.] in the presence of a catalyst (a palladium carbon powder, platinum oxide ($PtO_2$), activated nickel, etc.) and a hydrogen source such as a hydrogen gas, ammonium formate, or hydrazine hydrate under normal pressure or increased pressure at −10 to 100° C.

(4) Deprotection reaction of a silyl group. This reaction is performed by, for example, using tetra-n-butylammonium fluoride or the like in an organic solvent that can be mixed with water (tetrahydrofuran, acetonitrile, etc.) at −10 to 60° C.

(5) Deprotection reaction using a metal. This reaction is performed, for example, in an acidic solvent (acetic acid, a buffer of pH 4.2 to 7.2, or a mixture of these solutions and an organic solvent such as tetrahydrofuran) in the presence of a zinc powder at −10 to 60° C. with or without applying ultrasound waves.

(6) Deprotection reaction using a metal complex. This reaction is performed by, for example, using a metal complex [tetrakis triphenylphosphine palladium(0), bis(triphenylphosphine)palladium(II) dichloride, palladium(II) acetate, tris(triphenylphosphine)rhodium(I) chloride, etc.] in an organic solvent (dichloromethane, dimethylformamide, tetrahydrofuran, ethyl acetate, acetonitrile, dioxane, ethanol, etc.), water, or a mixed solvent thereof in the presence of a trap reagent (tributyltin hydride, triethyl silane, dimedon, morpholine, diethylamine, pyrrolidine, etc.), an organic acid (acetic acid, formic acid, 2-ethylhexanoic acid, etc.) and/or an organic acid salt (sodium 2-ethylhexanoate, potassium 2-ethylhexanoate, etc.) and in the presence or absence of a phosphine reagent (triphenylphosphine, etc.) at −10 to 60° C.

Production Methods 1 and 2 will be described as examples of production methods of the compound of the present invention.

(Production Method 1)

The compound of the formula (1) can be produced along the reaction pathway shown in Scheme 1. In the following scheme, "Step" means a step. For example, "Step 1-1" is step 1-1.

Scheme 1
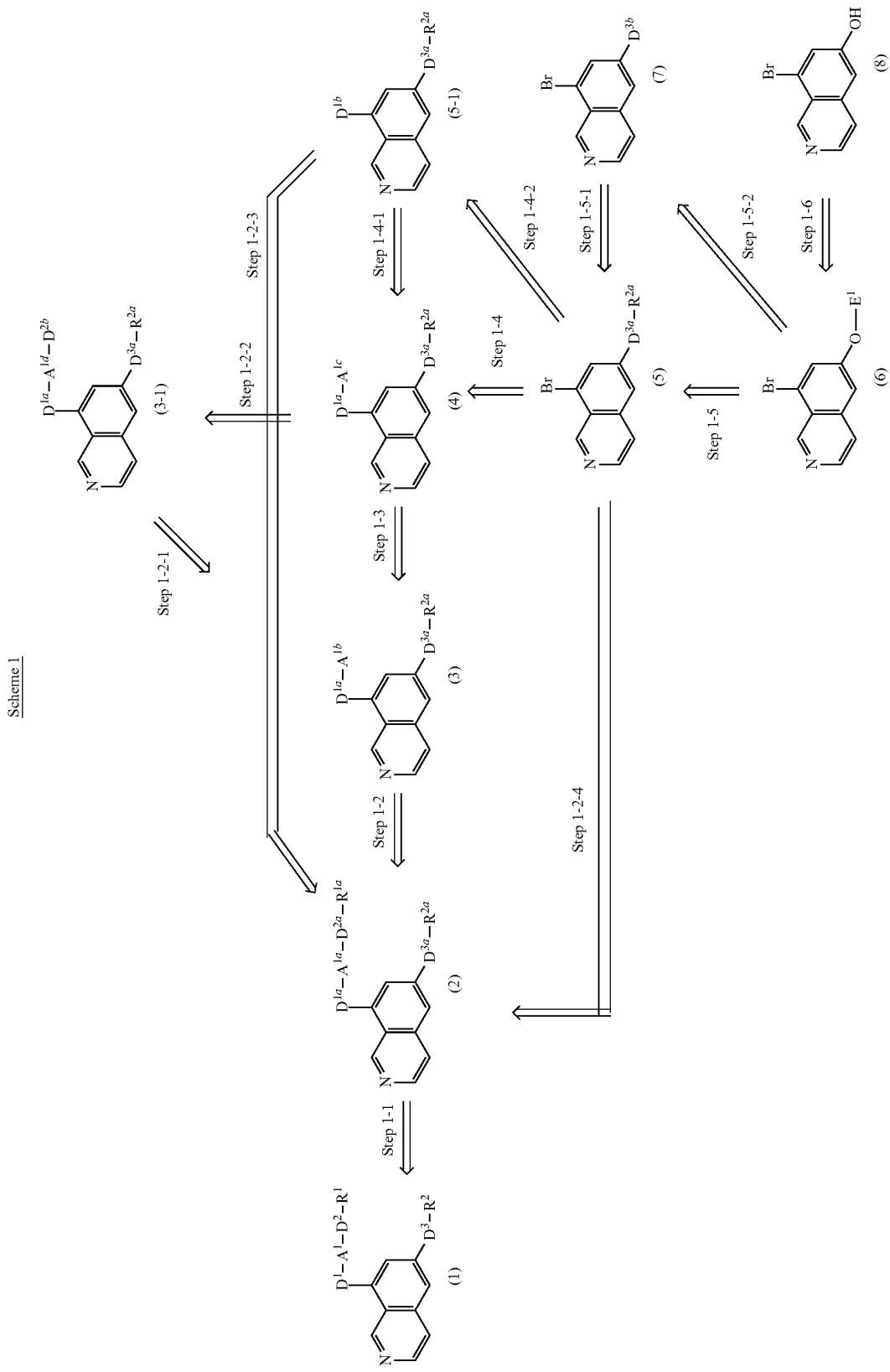

Step 1-1

The compound of the present invention can be produced by performing a deprotection reaction in the compound of the formula (2), wherein $D^{1a}$, $A^{1a}$, $D^{2a}$, $R^{1a}$, $D^{3a}$, and $R^{2a}$ each have the same meaning as $D^1$, $A^1$, $D^2$, $R^1$, $D^3$, and $R^2$, respectively, in Scheme 1 (Step 1-1).

When $D^{1a}$, $A^{1a}$, $D^{2a}$, $R^{1a}$, $D^{3a}$ and $R^{2a}$ in the compound of the formula (2) are the same groups as $D^1$, $A^1$, $D^2$, $R^1$, $D^3$, and $R^2$, respectively, in the compound of the formula (1), Step 1-1 is unnecessary.

As described above, this deprotection reaction can be performed according to a known method, for example, the method described in Protective Groups in Organic Synthesis, John Wiley and Sons (2007) or the like.

A deprotection reaction using an acid can be performed with reference to the conditions in the above-mentioned "Deprotection reaction under an acidic condition." For example, when the compound of the formula (2) having a Boc group is deprotected to produce the compound of the formula (1), examples of a solvent used for a reaction include nonsolvents, water, alcohol, acetonitrile, and ether solvents such as 1,4-dioxane and a mixed solvent thereof. Furthermore, examples of the acid include mineral acids and organic acids and specific examples include hydrochloric acid, sulfuric acid, nitric acid, acetic acid, methanesulfonic acid, and phosphoric acid. Hydrochloric acid is preferred. The amount of an acid used is preferably 1 to 100 molar equivalents per mole of the compound of the formula (2). A reaction is preferably performed in the range of room temperature to reflux temperature of a solvent, more preferably from room temperature to 80° C. The compound of the formula (1) can also be produced by deprotecting the compound of the formula (2) having a Boc group using trifluoroacetic acid. In this case, trifluoroacetic acid can be used solely or as a mixed solvent with water or dichloromethane. The reaction can be performed in the temperature range of 0 to 100° C., preferably in the range of room temperature to 50° C. It is preferred to use 1 to 100 molar equivalents of trifluoroacetic acid per mole of the compound of the formula (2).

When a salt is formed with the acid used by the compound of the formula (1) as a solid after the reaction, a salt of the compound of the formula (1) can be obtained by isolating and purifying this solid by a usual method. Furthermore, when the compound of the formula (1) forms an acid adduct after the reaction, a free base (free compound) can be obtained by neutralizing this acid adduct by a usual method, and then an intended acid adduct can also be obtained.

A compound of the formula (2) wherein $D^{1a}$ represents —S(O)— or —S(O)$_2$— can be produced by oxidizing a compound of the formula (2) wherein $D^{1a}$ represents —S— (Compound 1-1U) according to, for example, the following method (1-1-i) or (1-1-ii).

(1-1-i) A compound of the formula (2) wherein $D^{1a}$ represents —S(O)— can be obtained by oxidizing Compound 1-1U using an oxidizing agent in an inert solvent. Examples of the inert solvent include dichloromethane, chloroform, tetrahydrofuran, 1,4-dioxane, acetonitrile, tert-butanol, acetic acid, trifluoroacetic acid, and water and a mixed solvent thereof. Examples of the oxidizing agent include sodium metaperiodate, 3-chloroperbenzoic acid, and hydrogen peroxide. It is preferred to use 0.3 to 2 molar equivalents of the oxidizing, agent per mole of the starting compound. The reaction time is preferably 0.1 to 48 hours.

(1-1-ii) A compound of the formula (2) wherein $D^{1a}$ represents —S(O)$_2$— can be obtained by oxidizing Compound 1-1U using an oxidizing agent in an inert solvent. The same inert solvents and oxidizing agents as in the above-mentioned (1-1-i) can be used. However, it is preferred to use 2 or more molar equivalents of the oxidizing agent per mole of the starting compound.

A compound of the formula (2) wherein $R^{1a}$ represents any of groups of the formulas (1b-1) to (1b-4) can be produced from a compound of the formula (2) wherein $R^{1a}$ represents any of groups of the following formulas (1b-5) to (1b-8), respectively:

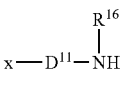
(1b-5)

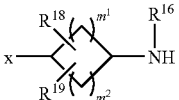
(1b-6)

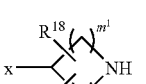
(1b-7)

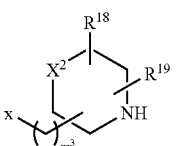
(1b-8)

wherein $D^{11}$, $R^{16}$, $R^{18}$, $R^{19}$, $X^2$, $m^1$, $m^2$, and $m^3$ have the same meaning as defined above and x represents a bond with $D^{2a}$ (Compound 1-2U) by any of the following methods (1-2-i) to (1-2-iv).

Here, a compound of the formula (2) wherein $R^{1a}$ represents a group of formula (1b-1), (1b-2), (1b-3), or (1b-4) can be produced from a compound of the formula (2) wherein $R^{1a}$ represents a group of formula (1b-5), (1b-6), (1b-7), or (1b-8), respectively.

(1-2-i) A compound of the formula (2) wherein $D^{12}$ in groups of the formulas (1b-1) to (1b-4) represents an alkylene that may be substituted can be obtained by, for example, using an alkyl halide (a chloride, a bromide, an iodide, etc.). A reaction can be usually performed in the presence of a base. Preferred examples of the base include inorganic bases such as potassium carbonate, sodium carbonate, cesium carbonate, sodium hydrogencarbonate, potassium hydroxide, and sodium hydroxide and potassium carbonate is particularly preferred. One or more molar equivalents of a halide per mole of Compound 1-2U are preferably used and it is more preferred to use 2 to 10 molar equivalents or more. Examples of a reaction solvent used include water, alcohol solvents such as methanol and ethanol, inert solvents such as N,N-dimethylformamide, tetrahydrofuran, 1,4-dioxane, acetone, 2-butanone, dimethyl sulfoxide, and acetonitrile and a mixed solvent thereof. Water, N,N-dimethylformamide, and acetone are preferred. The reaction temperature is, for example, —10° C. or higher, preferably from 0 to 200° C. The reaction time is usually 0.5 hours or longer, preferably 2 to 36 hours.

A compound of the formula (2) wherein $R^{1a}$ represents any of groups of the formulas (1b-1) to (1b-4) can also be produced by coupling an aldehyde or a ketone corresponding to a substituent to be introduced and Compound 1-2U by a reductive amination reaction. Examples of the method of reductive amination include the method described in The Fourth Series of Experimental Chemistry, The Chemical Society of Japan ed., Maruzen Co., Ltd., vol. 20, pp. 300-302, "Reductive Amination Reaction" or the methods according to the references included in this publication. Preferably, coupling is carried out by allowing a reducing agent to act on the starting compound in a solvent. Examples of the reducing agent include metal hydride reducing agents such as sodium borohydride, zinc borohydride, sodium borohydride triacetate, a borane-dimethyl sulfide complex, a borane-pyridine complex, a borane-triethylamine complex, a borane-tetrahydrofuran complex, and lithium triethylboron and sodium borohydride and sodium borohydride triacetate are preferred. For example, 0.1 or more molar equivalents of a reducing agent per mole of Compound 1-2U are usually used and it is preferred to use 1 to 20 molar equivalents. 1 or more molar equivalents of the corresponding aldehyde or ketone are used and it is preferred to use 2 to 10 molar equivalents. Examples of the solvent include alcohols such as methanol, ethanol, and isopropanol, ethers such as tetrahydrofuran, 1,2-dimethoxyethane, and 1,4-dioxane, halogenated hydrocarbons such as dichloromethane, chloroform, and 1,2-dichloroethane, and N,N-dimethylformamide and methanol, tetrahydrofuran, and 1,2-dichloroethane are preferred. The reaction temperature is 0° C. or higher, preferably from 10° C. to reflux temperature of a solvent. The reaction time is 0.1 hours or longer, preferably 0.5 to 30 hours.

(1-2-ii) A compound of the formula (2) wherein $D^{12}$ in groups of the formulas (1b-1) to (1b-4) represents —C(O)— can be produced by amidating a compound having a carboxyl group (—COOH) and Compound 1-2U by the methods described in The Fourth Series of Experimental Chemistry. The Chemical Society of Japan ed., Maruzen Co., Ltd., vol. 22, pp. 137-151, "Acid Amides and Acid Imides" or according to the references included in this publication. Specifically, a carboxylic acid corresponding to $R^{17}$ in the formulas (1b-1) to (1b-4), that is, a commercially available or preferable $R^{17}$—COOH can be reacted with Compound 1-2U in an inert solvent in the presence of a suitable condensing agent widely used to form a bond with carboxylic acid by a known method. Examples of the condensing agent include dicyclohexylcarbodiimide, diisopropyl carbodiamide, and 1-ethyl-3-(3-dimethylaminopropyl)carbodiimide. 1-Hydroxybenzotriazole, 1-hydroxy-7-azobenzotriazole, and the like may be used as additives in some cases. Examples of the inert solvent include halogen hydrocarbons such as dichloromethane, chloroform, and 1,2-dichloroethane and N,N-dimethylformamide. Two or more types of organic solvents may be mixed. One or more molar equivalents of the carboxylic acid and the condensing agent per mole of Compound 1-2U can usually be used and it is preferred to use 1 to 10 molar equivalents. The reaction temperature is 0° C. or higher, preferably, for example, 0 to 100° C. The reaction time is 0.1 hours or longer, preferably, for example, 0.1 to 48 hours.

Alternatively, the compound of the formula (2) wherein $R^{1a}$ represents any of groups of the formulas (1b-1) to (1b-4) can also be produced by coupling a carboxylic acid chloride or a mixed acid anhydride corresponding to $R^{17}$ in the formulas (1b-1) to (1b-4) and Compound 1-2U in an inert solvent in the presence of a base. Examples of the inert solvent include halogen hydrocarbons such as dichloromethane, chloroform, and 1,2-dichloroethane and acetonitrile. Examples of the base include organic bases such as triethylamine, N,N-diisopropylethylamine, and pyridine and inorganic bases such as potassium carbonate and sodium hydrogencarbonate. 1 to 6 molar equivalents of a base, a carboxylic acid chloride, or a mixed acid anhydride per mole of Compound 1-2U can usually be used, and it is preferred to use 1.1 to 3.3 molar equivalents. The reaction temperature is from −10 to 100° C., preferably approx. 0 to 50° C. The reaction time is preferably 0.1 to 48 hours.

(1-2-iii)

When $D^{12}$ in the formulas (1b-1) to (1b-4) represents —S(O)$_2$— in the compound of the formula (2), the compound of the formula (2) wherein $R^{1a}$ represents any of groups of the formulas (1b-1) to (1b-4) can be produced by coupling Compound 1-2U and a sulfonic acid chloride or a sulfonic acid anhydride corresponding to $R^{17}$ in the formulas (1b-1) to (1b-4) in an inert solvent in the presence of a base by the methods described in The Fourth Series of Experimental Chemistry, The Chemical Society of Japan ed., Maruzen Co., Ltd., vol. 22, pp. 137-151, "Acid Amides and Acid Imides" or the methods according to the references included in this publication. Examples of the inert solvent include halogen hydrocarbons such as dichloromethane, chloroform, and 1,2-dichloroethane and acetonitrile. Dichloromethane is particularly preferred. Examples of the base include organic bases such as triethylamine, N,N-diisopropylethylamine, and pyridine and inorganic bases such as potassium carbonate and sodium hydrogencarbonate. Triethylamine, N,N-diisopropylethylamine, and pyridine are preferred. 1 to 10 molar equivalents of a base and a sulfonic acid chloride per mole of Compound 1-2U can be usually used and it is preferred to use 1.1 to 5 molar equivalents. The reaction temperature is from −10 to 40° C., preferably approx. 0 to 30° C. The reaction time is preferably 0.1 to 48 hours.

(1-2-iv) When $D^{12}$ in the formulas (1b-1) to (1b-4) represents —C(O)—N(R$^{15}$)— in the compound of the formula (2), the compound of the formula (2) wherein $R^{1a}$ represents any of groups of the formulas (1b-1) to (1b-4) can be produced by coupling compound 1-2U and an isocyanate corresponding to $R^{17}$ in the formulas (1b-1) to (1b-4) in an inert solvent in the presence or absence of a base by the method described in The First Series of Experimental Chemistry, The Chemical Society of Japan ed., Maruzen Co., Ltd., vol. 14, pp. 1628-1644, "Ureas" or The Fourth Series of Experimental Chemistry, The Chemical Society of Japan ed., Maruzen Co., Ltd., vol. 20, pp. 360-361, "Ureas" or the methods according to the references included in these publications. Examples of the inert solvent include halogen hydrocarbons such as dichloromethane and chloroform and acetonitrile. Examples of the base include organic bases such as triethylamine, N,N-diisopropylethylamine, pyridine and inorganic bases such as potassium carbonate and sodium hydrogencarbonate. 1 to 10 molar equivalents of a base and an isocyanate per mole of compound 1-2U can usually be used, and it is preferred to use 1.1 to 3.3 molar equivalents. The reaction temperature is from −10 to 40° C., preferably approx. 0 to 30° C. The reaction time is preferably 0.1 to 48 hours.

A compound of the formula (2) wherein $R^{2a}$ represents the above-mentioned formula (2a-1) and one or more of R$^{23}$, R$^{24}$, and R$^{25}$ represents the above-mentioned formula (2b-1) (Compound 1-3T) can be produced from a compound of the formula (2) wherein $R^{2a}$ represents the formula (2a-1) and one or more of R$^{23}$, R$^{24}$, and R$^{25}$ represents the following formula (2b-2):

wherein $D^{21}$, $R^{26}$, and z have the same meaning as defined above (Compound 1-3U) by the following methods (1-3-i) to (1-3-iv).

(1-3-i) Compound 1-3T wherein $D^{22}$ represents an alkylene that may be substituted can be produced from Compound 1-3U according to the same method as in the above-mentioned (1-2-i).

(1-3-ii) Compound 1-3T wherein $D^{22}$ represents —C(O)— can be produced from Compound 1-3U according to the same method as in the above (1-2-ii).

(1-3-iii) Compound 1-3T wherein $D^{22}$ represents —S(O)$_2$— can be produced from Compound 1-3U according to the same method as in the above (1-2-iii).

(1-3-iv) Compound 1-3T wherein $D^{22}$ represents —C(O)—N($R^{28}$)— can be produced from Compound 1-3U according to the same method as in the above (1-2-iv).

Step 1-2

When, in the compound of the formula (2), $D^{1a}$ represents a single bond, —N($R^{11}$)—, —O—, —S—, —S(O)—, or —S(O)$_2$—, $A^{1a}$ represents any of divalent groups of the above-mentioned formulas (1a-1) to (1a-5), and $D^{2a}$ represents a single bond, —S(O)$_2$—, —C(O)—N($R^{15}$)—, or -E-C(O)—, (provided that, when $D^{1a}$ represents a single bond, $A^{1a}$ represents a divalent group of the formula (1a-5), and, when $D^{1a}$ represents —N($R^{11}$)—, —O—, —S—, —S(O)—, or —S(O)$_2$—, $A^{1a}$ represents any of divalent groups of the formulas (1a-1) to (1a-4)), the compound of the formula (2) can be produced from a compound of the formula (3) wherein $A^{1b}$ represents any of groups of the following formulas (1a-7) to (1a-11):

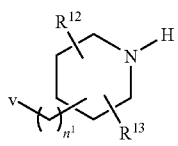
(1a-7)

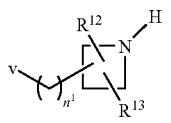
(1a-8)

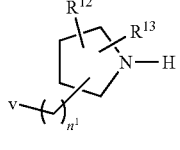
(1a-9)

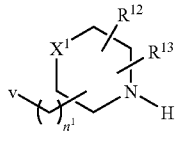
(1a-10)

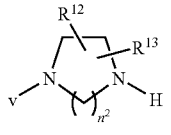
(1a-11)

wherein $D^1a$, $D^{3a}$, $R^{2a}$, $R^{12}$, $R^{13}$, $X^1$, $n^1$, and $n^2$ have the same meaning as defined above, and v represents a bond with $D^{1a}$.

Here, a compound of the formula (2) wherein $A^{1a}$ represents a group of the formula (1a-1), (1a-2), (1a-3), (1a-4), or (1a-5) can be produced from a compound of the formula (3) wherein $A^{1B}$ represents a group of the formula (1a-7), (1a-8), (1a-9), (1a-10), or (1a-11), respectively.

A compound of the formula (2) wherein $D^{2a}$ represents —C(O)—, —S(O)$_2$—, —C(S)—, —C(O)—N($R^{15}$)—, —C(S)—N($R^{15}$)—, or -E-C(O)— can be produced from a compound of formula (3) and commercially available or preparable compound of the following formula (1-2a):

$Y^1$-$D^{2c}$-$R^{1a}$ (1-2a)

wherein $Y^1$ represents a halogen atom or a hydroxyl group, $D^{2c}$ represents —C(O)—, —S(O)$_2$—, —C(S)—, or -E-C(O)—, and $R^{1a}$ has the same meaning as defined above, provided that, when $D^{2c}$ represents alkylene, -E-C(O)—, or —S(O)$_2$—, $Y^1$ represents a halogen atom) according to any of the following methods (1-4-i) to (1-4-v).

(1-4-i) A compound of the formula (2) wherein $D^{2a}$ represents an alkylene or -EC(O)— can be produced from a compound of the formula (3) and a compound of the formula (1-2a) or a commercially available or preparable compound of the following formula (1-2b):

$Y^2$—C(O)-$D^{2b}$-$R^{1a}$ (1-2b)

wherein $Y^2$ represents a hydrogen atom or an alkyl group, $D^{2d}$ is an alkylene or -E-C(O)—, and $R^{1a}$ has the same meaning as defined above, according to the same method as in the above (1-2-i).

(1-4-ii) A compound of the formula (2) wherein $D^{2a}$ represents —C(O)— can be produced from a compound of the formula (3) and a commercially available or preparable compound of the formula (1-2a) according to the same method as in the above (1-2-ii). When $Y^1$ represents a hydroxyl group and $D^{2c}$ represents —C(O)— in a compound of the formula (1-2a), the compound of the formula (1-2a) is carboxylic acid, and this carboxylic acid may be used as it is in a reaction according to the method (1-2-ii) or may be converted to a corresponding anhydride and then used in a reaction according to the method (1-2-ii).

(1-4-iii) A compound of the formula (2) wherein $D^{2a}$ represents —S(O)$_2$— can be produced from a compound of the formula (3) and a commercially available or preparable compound of the formula (1-2a) according to the same method as in the above (1-2-iii).

(1-4-iv) A compound of the formula (2) wherein $D^{2a}$ represents —C(O)—N($R^{15}$)— or —C(S)—N($R^{15}$)— and $R^{15}$ represents a hydrogen atom can be produced from a compound of the formula (3) and a commercially available or preparable compound (for example, preparable according to the methods described in The First Series of Experimental Chemistry, The Chemical Society of Japan ed., Maruzen Co., Ltd., vol. 14, pp. 1490-1508, "Isocyanates" and "Thioisocyanates" or the methods according to the references included in this publication) of the following formula (1-2c) or (1-2d):

O=C—N—($R^{1a}$) (1-2c)

S=C—N—($R^{1a}$) (1-2d)

according to the same method as in the above-mentioned (1-2-iv).

(1-4-v) A compound of the formula (2) wherein $D^{2a}$ represents —C(S)— can be produced from a compound of the formula (3) by, for example, the method described in The First Series of Experimental Chemistry, The Chemical Society of Japan ed., Maruzen Co., Ltd., vol. 14, pp. 1827-1828, "Synthesis of Thiocarboxylic Acid Amide" or the methods described in the references included in this publication. Examples of the method include methods comprising reacting a compound of the formula (3) and a corresponding thiocarboxylic acid ester in a solvent in the presence of a base. Examples also include methods comprising producing from a compound of the formula (2) wherein $D^{2a}$ represents —C(O)— by the method described in The First Series of Experimental Chemistry, The Chemical Society of Japan ed., Maruzen Co., Ltd., vol. 14., pp. 1817-1821, "Thiocarbonyl Compounds" or the methods described in the references included in this publication.

When $D^{2a}$ represents a single bond and $R^{1a}$ represents a hydrogen atom in the compound of the formula (2), Step 1-2 is unnecessary.

Step 1-2-1

A compound of the formula (2) wherein $D^{2a}$ represents -E-C(O)— can be produced from a compound of the formula (3-1) wherein $D^{1a}$ has the same meaning as defined above, $A^{1d}$ represents any of divalent groups of the above-mentioned formulas (1a-1) to (1a-5), provided that, when $D^{1a}$ represents a single bond, $A^{1d}$ represents a divalent group of the formula (1a-5), and, when $D^{1a}$ represents —N($R^{11}$)—, —O—, —S—, —S(O)—, or —S(O)$_2$—, $A^{1d}$ represents any of divalent groups of the formulas (1a-1) to (1a-4), and $D^{2b}$ represents -E-C(O)—OH by an amidation reaction with a commercially available or preparable aminating reagent according to, for example, the method described in The Fourth Series of Experimental Chemistry, The Chemical Society of Japan ed., Maruzen Co., Ltd., vol. 22, pp. 137-151, "Acid Amides and Acid Imides" and the methods according to the references included in this publication. Examples of the aminating reagent include primary amines such as methylamine and secondary amines such as dimethylamine and pyrrolidine.

Step 1-2-2

A compound of the formula (3-1) can be produced by coupling a compound of formula (3) and a commercially available or preparable compound of the following formula (1-2-2a):

(1-2-2a)

wherein $Y^3$ represents a halogen atom and $G^1$ represents a hydrogen atom or a protective group of a carboxyl group) or a commercially available or preparable compound of the following formula (1-2-2b):

(1-2-2b)

wherein $G^1$ has the same meaning as defined above by a method according to the above (1-2-i) and then deprotecting $G^1$. However, when $G^1$ represents hydrogen, deprotection is unnecessary.

Step 1-3

A compound of the formula (3) can be produced by deprotecting the $G^2$ group in a compound of the formula (4) wherein $A^{1c}$ represents any of groups of the following formulas (1a-12) to (1a-16):

(1a-12)

(1a-13)

(1a-14)

(1a-15)

(1a-16)

$D^{1a}$, $D^{3a}$, $R^{2a}$, $R^{12}$, $R^{13}$, $X^1$, $n^1$, $n^2$, and v each have the same meaning as defined above, and $G^2$ represents a protective group of an amino group, provided that, when $D^{1a}$ represents a single bond, $A^{1c}$ represents a divalent group of the formula (1a-16), $D^{1a}$ represents —N($R^{11}$)—, —O—, —S—, —S(O)—, or —S(O)$_2$—, $A^{1c}$ represents any of divalent groups of the formulas (1a-12) to (1a-15).

Here, the compound of the formula (3) wherein $A^{1b}$ represents a group of the formula (1a-7), (1a-8), (1a-9), (1a-10), or (1a-11) can be produced from a compound of the formula (4) wherein $A^{1c}$ represents a group of (1a-12), (1a-13), (1a-14), (1a-15), or (1a-16), respectively.

For example, when $G^2$ represents a Boc group, the above-described "Deprotection reaction under an acidic condition" can be performed as a method for producing a compound of the formula (3) by deprotecting the Boc group in the compound of the formula (4).

Step 1-4

A compound of the formula (4) can be produced by coupling a compound of the formula (5) wherein $D^{1a}$ and $R^{2a}$ each have the same meaning as defined above and any commercially available or preparable compound of the following formulas (1a-17) to (1a-21):

(1a-17)

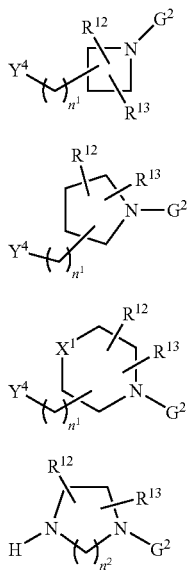

wherein $Y^4$ represents $HN(R^{11})-$, $HO-$, or $HS-$ and $R^{12}$, $R^{13}$, $X^1$, $n^1$, $n^2$, and $G^2$ each have the same meaning as defined above.

Specifically, a compound of the formula (4) wherein $D^{1a}$ represents $-N(R^{11})-$ can be produced by reacting a compound of the formula (5) and any of compounds of the formulas (1a-17) to (1a-20) wherein $Y^4$ represents $HN(R^{11})-$ or a compound of the formula (1a-21) in an inert solvent in the presence of a palladium catalyst, a phosphorus compound, and a base (for example, according to Buchwald, S. L., J. Org. Chem., 2000, pp. 1158 and Buchwald, S. L., Organic Letters, 2000, pp. 1101). Examples of the inert solvent include ether solvents such as tetrahydrofuran, 1,4-dioxane, and 1,2-dimethoxyethane, toluene, and N,N-dimethylformamide. 1,4-Dioxane and toluene are preferred. Examples of the palladium catalyst include commercially available catalysts such as tetrakis(triphenylphosphine)palladium, tetrakis(methyldiphenylphosphine)palladium, dichlorobis(triphenylphosphine)palladium, dichlorobis(tri-o-tolylphosphine) palladium, dichlorobis(tricyclohexylphosphine)palladium, dichlorobis(triethylphosphine)palladium, palladium acetate, palladium chloride, bis(acetonitrile)palladium chloride, bis (dibenzylideneacetone)palladium, tris(dibenzylideneacetone)dipalladium, and bis(diphenylphosphinoferrocene) palladium chloride. These catalysts may be added to a reaction system as they are or catalysts separately prepared and isolated from palladium acetate, tris(dibenzylideneacetone)dipalladium, or the like and an arbitrary ligand may be added. Furthermore, a catalyst that appears to be actually involved in the reaction may be prepared in a reaction system by mixing palladium acetate, tris(dibenzylideneacetone)dipalladium, or the like and an arbitrary ligand. The number of valents in palladium may be 0 or +2. In particular, preferred examples include tris(dibenzylideneacetone)dipalladium(0) and palladium(II) acetate. Examples of the phosphorus compound include phosphine ligands such as trifurylphosphine, tri(o-tolyl)phosphine, tri(cyclohexyl)phosphine, tri(t-butyl) phosphine, dicyclohexylphenylphosphine, 1,1'-bis(di-t-butylphosphino)ferrocene, 2-dicyclohexylphosphino-2'-dimethylamino-1,1'-biphenyl, 2-(di-t-butylphosphino)biphenyl, 2-(dicyclohexylphosphino)biphenyl, 2,2'-bis(diphenylphosphino)-1,1'-binaphthyl, xantphos, and tri(tert-butyl)phosphine. Alternative examples also include 2-dicyclohexylphosphino-2',6'-dimethoxybiphenyl, 2-dicyclohexyl-2',4',6'-triisopropylbiphenyl, and 1,2,3,4,5-pentamethyl-1'-(di-t-butylphosphino)ferrocene). 2-(di-tert-butylphosphino) biphenyl, 2-(dicyclohexylphosphino)biphenyl, 2,2'-bis (diphenylphosphino)-1,1'-binaphthyl, xantphos, tri(tert-butyl)phosphine, and the like are preferred. Preferred examples of a combination of a palladium catalyst and a phosphorus compound include tris(dibenzylideneacetone)dipalladium and 2,2'-bis(diphenylphosphino)-1,1'-binaphthyl. The equivalent amount of a palladium catalyst may be an equal amount or a catalytic amount, but 0.01 mol % or more based on the starting compounds is preferred, and 0.10 to 50.0 mol % is particularly preferred. Examples of the base include sodium tert-butoxide, cesium carbonate, and potassium phosphate. For example, usually, 1 or more molar equivalents of a compound represent by any of the formulas (1a-17) to (1a-21) per mole of a compound of the formula (5) is preferred, and 1 to 5 molar equivalents are more preferred. As the reaction temperature, a suitable temperature from room temperature to reflux temperature of a solvent is selected, and the range of room temperature to 200° C. is preferred. The reaction time is 0.1 hours or longer, preferably 0.1 to 48 hours.

A compound of the formula (4) wherein $D^{1a}$ represents $-O-$ can be produced by reacting a compound of the formula (5) and any of compounds of the formulas (1a-17) to (1a-20) wherein $Y^4$ represents $HO-$ in an inert solvent in the presence of a palladium catalyst, a phosphorus compound, and a base (for example, according to Buchwald, S. L., J. Org. Chem., 2000, pp. 1158 and Buchwald, S. L., Organic Letters, 2000, pp. 1101). Examples of the inert solvent include ether solvents such as tetrahydrofuran, 1,4-dioxane, and 1,2-dimethoxyethane and toluene. Examples of the palladium catalyst include the above-mentioned palladium catalysts, for example, palladium(II) acetate and tris(dibenzylideneacetone)dipalladium(0). Examples of the phosphorus compound include 2-(di-tert-butylphosphino) biphenyl, rac-2-(di-tert-butylphosphino)-1,1'-binaphthyl, and 2-(di-tert-butylphosphino)-2'-dimethylamino-1,1'-binaphthyl. Furthermore, examples of the base include sodium tert-butoxide, potassium tert-butoxide, cesium carbonate, and potassium phosphate. Preferred examples of a combination of a palladium catalyst and a phosphorus compound include palladium acetate and rac-2-(di-tert-butylphosphino)-1,1'-binaphthyl. It is usually preferred to use 1 or more molar equivalents of a compound represented by the formulas (1a-17) to (1a-20) per mole of a compound of the formula (5) and it is more preferred to use 1 to 5 molar equivalents. As the reaction temperature, a suitable temperature from room temperature to reflux temperature of a solvent is selected. The reaction time is preferably 0.1 to 48 hours.

A compound of the formula (4) wherein $D^{1a}$ represents $-S-$ can be produced by reacting a compound of the formula (5) and any of compounds of the formulas (1a-17) to (1a-20) wherein $Y^4$ represents $HS-$ in an inert solvent in the presence of a palladium catalyst, a phosphorus compound, and a base (for example, according to Hartwing et al., J. Am. Chem. Soc., 2000, pp. 2180). Examples of the inert solvent include hydrocarbon solvents such as toluene, xylene, and hexane, halogen hydrocarbon solvents such as dichloromethane, 1,2-dimethoxyethane, and chloroform, and ether solvents such as tetrahydrofuran, dioxane, and diglyme. Examples of the palladium catalyst include the above-mentioned palladium catalysts such as, for example, palladium acetate and bis(dibenzylideneacetone)palladium. Examples of the phosphorus compound include the above-mentioned phosphorus compounds and preferred examples include Josiphos ligands. The amount of a palladium catalyst used may be equal to the starting compound or a catalytic amount, but 0.01 mol % or more based on the starting compound is preferred and 0.10 to 50.0 mol % is particularly preferred. Furthermore, examples of the base include sodium tert-butoxide, potassium tert-butoxide, and cesium carbonate. For example, it is usually preferred to use 1 or more molar equivalents of a compound represented by any of the formulas (1a-17) to (1a-20) per mole of a compound of the formula (5) and it is more preferred to use 1 to 5 molar equivalents. As the reaction temperature, a suitable temperature from room temperature to reflux temperature of a solvent is selected. The reaction time is preferably 0.1 to 48 hours.

A compound of the formula (4) wherein $D^{1a}$ represents —S(O)— or —S(O)$_2$— can be obtained by oxidizing a compound of the formula (4) wherein $D^{1a}$ represents —S—according to the above-mentioned method (1-1-i) or (1-1-ii).

Step 1-4-1

As an alternative method, a compound of formula (4) wherein $D^{1a}$ represents —N(R$^{11}$)— or —O— can be produced by coupling a compound of the formula (5-1) wherein $D^{1b}$ represents —N(R$^{11}$)H or —OH, $D^{1a}$ and $R^{2a}$ have the same meaning as defined above and any of compounds of the following formulas (1a-22) to (1a-25):

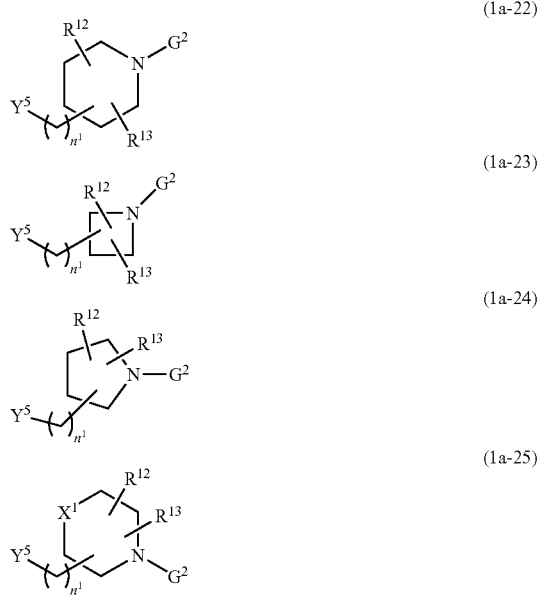

wherein $Y^5$ represents a halogen atom, a hydroxyl group, a methanesulfonyloxy (OMs) group, a p-toluenesulfonyloxy (OTs) group, an alkenyl group, an alkynyl group, or $R^a$—C(O)— wherein $R^a$ represents a hydrogen atom or an alkyl group, and $R^{12}$, $R^{13}$, $X^1$, $G^2$, and $n^1$ have the same meaning as defined above.

Specifically, a compound of formula (4) wherein $D^{1a}$ represents —N(R$^{11}$)— can be produced from a compound of the formula (5-1) wherein $D^{1b}$ represents —N(R$^{11}$)H and any of compounds of the formulas (1a-22) to (1a-25) wherein $Y^5$ represents a halogen atom, an OMs group, an OTs group, or $R^a$—C(O)— according to the same method as in the above (1-2-i). Here, when $Y^5$ represents a halogen atom, OMs, or OTs, $Y^5$ in a detached state binds to $D^{1a}$ in any of compounds of the formulas (1a-22) to (1a-25), and, when $Y^5$ represents $R^a$—C(O)—, a carbonyl moiety in $Y^5$ is converted to methylene and binds to $D^{1a}$ in any of compounds of the formulas (1a-22) to (1a-25).

Furthermore, as an alternative method, a compound of the formula (4) wherein $D^{1a}$ represents —N(R$^{11}$)— can be produced by coupling a compound of the formula (5-1) wherein $D^{1b}$ represents —N(R$^{11}$)H and any of compounds of the formulas (1a-22) to (1a-25) wherein $Y^5$ represents an alkenyl group or an alkynyl group in the presence of a suitable metal catalyst and a ligand (for example, according to Thomas, E. M. & Matthias, B., Chem. Rev., 1998, p. 673). When the compound obtained after this coupling has an unsaturated bond, a usual reduction reaction (for example, according to the methods described in The First Series of Experimental Chemistry, The Chemical Society of Japan ed., Maruzen Co., Ltd., vol. 15-II, pp. 333-448, "Addition of Catalytic hydrogen" or The Fourth Series of Experimental Chemistry, The Chemical Society of Japan ed., Maruzen Co., Ltd., vol. 26, pp. 159-266, "Reduction in General" can be performed.

A compound of formula (4) wherein $D^{1a}$ represents —O— can be produced from a compound of the formula (5-1) wherein $D^{1b}$ represents —OH and any of compounds of the formulas (1a-22) to (1a-25) wherein $Y^5$ represents a hydroxyl group by utilizing a Mitsunobu reaction (for example, according to Mitsunobu, O., SYNTHESIS, 1981, p. 1). Specifically, such a compound can be produced by reacting a compound of the formula (5-1) and any of compounds of the formulas (1a-22) to (1a-25) wherein $Y^5$ represents a hydroxyl group in an organic solvent in the presence of a phosphine such as triphenylphosphine or tributylphosphine and an azo compound such as diethyl azodicarboxylate, diisopropyl azodicarboxylate, N,N,N',N'-tetramethyl azodicarboxamide, 1,1'-(azodicarbonyl)dipiperidine, or N,N,N',N'-tetraisopropyl carboxamide. Examples of the organic solvent include ethers such as diethyl ether, tetrahydrofuran, and dimethoxyethane, halogen solvents such as methylene chloride, and benzenes such as benzene, toluene, and xylene and these solvents can be mixed if necessary. The amount of a phosphine used is usually 1 to 10 molar equivalents per mole of a compound of the formula (5-1), preferably 1.5 to 5 molar equivalents. The amount of an azo compound used is usually 1 to 10 molar equivalents per mole of a compound of the formula (5-1), preferably 1.5 to 5 molar equivalents. For example, the amount of a compound of the formulas (1a-22) to (1a-25) is 1 to 10 times that of a compound of the formula (5-1) in mole, preferably 1.5 to 5 times in mole. The reaction temperature is usually in the range of −20° C. to reflux temperature of a solvent, preferably from 0 to −60° C. The reaction time is generally 1 hour to 3 days, preferably 3 to 24 hours.

As an alternative method, a compound of formula (4) wherein $D^{1a}$ represents —O— can be produced by coupling a compound of the formula (5-1) wherein $D^{1b}$ represents —OH and any of compounds of the formulas (1a-22) to (1a-25) wherein $Y^5$ represents an alkenyl group or an alkynyl group in the presence of a suitable metal catalyst and ligand (for example, according to Francisco, A. et al., Chem. Rev., 2004, p. 3079, or Ian C. S. et al., J. Am. Chem. Soc., 2003, p. 8696). When the compound obtained after this coupling has an unsaturated bond, a usual reduction reaction (for example, according to the methods described in The First Series of Experimental Chemistry, The Chemical Society of Japan ed., Maruzen Co., Ltd., vol. 15-II, pp. 333-448, "Addition of Catalytic Hydrogen" and The Fourth Series of Experimental Chemistry, The Chemical Society of Japan ed., Maruzen Co., Ltd., vol. 26, pp. 159-266, "Reduction in General".

Step 1-2-3

A compound of the formula (2) can also be produced from a compound of the formula (5-1) and a commercially available or separately preparable compound of the following formula (1-2-3a):

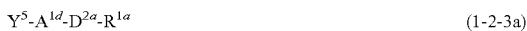   (1-2-3a)

wherein $A^{1d}$ represents an alkylene that may be substituted or any divalent group selected from the following formulas (1a-1a) to (1a-4-a):

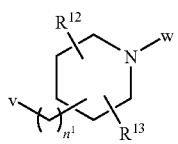   (1a-1a)

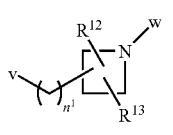   (1a-2a)

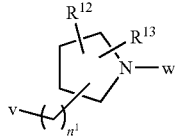   (1a-3a)

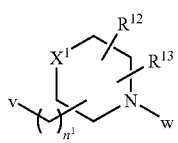   (1a-4a)

wherein $R^{12}$, $R^{13}$, $X^1$, and $n^1$ each have the same meaning as defined above, v represents a bond with $Y^5$, and w represents a bond with $D^{2a}$, and $Y^5$, $D^{2a}$ and $R^{1a}$ have the same meaning as defined above, according to the same method as in Step 1-4-1.

Examples of the method for preparing a compound of the formula (1-2-3a) include a method comprising introducing a moiety corresponding to -$D^{2a}$-$R^{1a}$ by alkylation, amidation, or sulfonamidation of any of compounds of the formulas (1a-22) to (1a-25) or urea formation thereon or the like according to the method of Step 1-2. At this time, a protective group may be introduced and deprotection may be performed if necessary.

Step 1-4-2

A compound of the formula (5-1) can be produced by coupling a compound of the formula (5) and a commercially available or preparable compound of the following formula (1-4-2a) or (1-4-2b):

   (1-4-2a)

wherein $R^{11}$ has the same meaning as defined above and $G^{3a}$ represents a hydrogen atom or a protective group of an amino group;

   (1-4-2b)

wherein $G^{3b}$ represents a hydrogen atom or a protective group of an oxygen atom, according to the method of Step 1-4 and then deprotecting $G^{3a}$ or $G^{3b}$. However, when $G^{3a}$ or $G^{3b}$ represents a hydrogen atom, the deprotection step is unnecessary.

Step 1-2-4

A compound of the formula (2) can also be produced by reacting a compound of the formula (5) and a commercially available or separately preparable compound of the following formula (1-2-4-a):

   (1-2-4-a)

wherein $Y^6$ represents a hydrogen atom, $HN(R^{11})$—, HO—, or HS—, $A^{1e}$ represents an alkylene that may be substituted or any divalent group selected from the formulas (1a-1b) to (1a-6b);

   (1a-1b)

   (1a-2b)

   (1a-3b)

   (1a-4b)

   (1a-5b)

   (1a-6b)

wherein v represents a bond with $Y^6$, w represents a bond with $D^{2a}$, and $R^{12}$, $R^{13}$, $X^1$, $n^1$, and $n^2$ have the same meaning as defined above), $D^{2a}$ and $R^{1a}$ have the same meaning as defined above, provided that, when $Y^6$ represents a hydrogen atom, $A^{1e}$ represents a divalent group of the formula (1a-5b) or (1a-6b), and, when $Y^6$ represents $HN(R^{11})$—, HO—, or HS—, $A^{1e}$ represents any divalent group selected from the formulas (1a-1b) to (1a-4-b), according to method of Step 1-4.

For example, a compound of the formula (1-2-4-a) can be prepared by introducing a moiety corresponding to -$D^{2a}$-$R^{1a}$ by alkylation, amidation, sulfonamidation, conversion to urea, or the like of any of compounds of the following formulas (1a-26) to (1a-30):

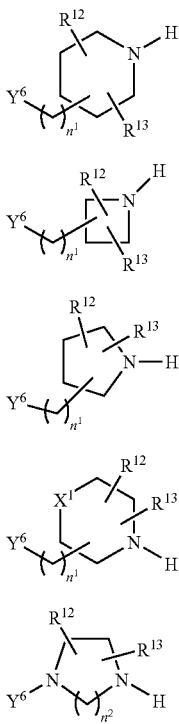

(1a-26)
(1a-27)
(1a-28)
(1a-29)
(1a-30)

wherein $Y^6$, $R^{12}$, $R^{13}$, $X^1$, $n^1$, and $n^2$ each have the same meaning as defined above, according to the method of Step 1-2. At this time, a protective group may be introduced and deprotection may be performed, if necessary.

Step 1-5

A compound of the formula (5) can be produced from a compound of the formula (6) wherein $E^1$ represents a hydrogen atom, a p-toluenesulfonyl (Ts) group, a methanesulfonyl (Ms) group, or a trifluoromethanesulfonyl (Tf) group.

A compound of the formula (5) wherein $D^{3a}$ represents a single bond can be produced by performing a Suzuki reaction of a compound of the formula (6) and a commercially available or preparable organic boronic acid compound or organic boronic acid ester (for example, according to Miyaura et al., Journal Of Organometallic Chemistry, 2000, 611, p. 392). Examples of the palladium catalyst used in the Suzuki reaction include tetrakis(triphenylphosphine)palladium, tetrakis(methyldiphenylphosphine)palladium, dichlorobis(triphenylphosphine)palladium, dichlorobis(tri-o-tolylphosphine)palladium, dichlorobis(tricyclohexylphosphine)palladium, dichlorobis(triethylphosphine)palladium, palladium acetate, palladium chloride, bis(acetonitrile)palladium chloride, tris(dibenzylideneacetone)dipalladium, and bis(diphenylphosphinoferrocene)palladium chloride. Furthermore, a catalyst prepared from palladium acetate, tris(dibenzylideneacetone)dipalladium, or the like and an arbitrary ligand may be used. The number of valents in palladium is, for example, 0 or +2. Examples of a ligand in palladium include phosphine ligands such as trifurylphosphine, trio-tolyl)phosphine, tri(cyclohexyl)phosphine, tri(t-butyl)phosphine, dicyclohexylphenylphosphine, 1,1'-bis(di-t-butylphosphino)ferrocene, 2-dicyclohexylphosphino-2'-dimethylamino-1,1'-biphenyl, 2-dicyclohexylphosphino-2',4',7'-triisopropylbiphenyl, and 2-(di-t-butylphosphino)biphenyl and nonphosphine ligands such as imidazol-2-ylidene carbenes.

The amount of a palladium catalyst used in the Suzuki reaction is preferably 0.01 mol % or more based on the starting compound (a compound of the formula [6]), more preferably 0.1 to 50 mol %. Examples of a base used in the Suzuki reaction include sodium carbonate, potassium carbonate, cesium carbonate, cesium fluoride, potassium fluoride, potassium phosphate, potassium acetate, triethylamine, potassium hydroxide, sodium hydroxide, sodium methoxide, and lithium methoxide.

Examples of an inert solvent used in the Suzuki reaction include hydrocarbon solvents such as toluene, xylene, and hexane, halogen hydrocarbon solvents such as dichloromethane and chloroform, sulfoxide solvents such as dimethyl sulfoxide, amide solvents such as dimethylformamide, ether solvents such as tetrahydrofuran, dioxane, and diglyme, alcohol solvents such as methanol, ethanol, and tert-butanol, nitrile solvents such as acetonitrile, ketone solvents such as acetone and cyclohexanone, ester solvents such as ethyl acetate, and heterocyclic ring solvents such as pyridine. Furthermore, 2 or more organic solvents may be mixed. Furthermore, the solvent system may be a biphasic system of water and an organic solvent or a homogeneous system of hydrous organic solvents or organic solvents.

The reaction temperature varies depending on the starting compound, the catalyst, the base, the type of the solvent, and the like and is, for example, 0 to 150° C., preferably from room temperature to 120° C.

Furthermore, as an alternative method, a compound of the formula (5) wherein $D^{3a}$ represents a single bond can be produced by a Stille reaction of a compound of the formula (6) and a commercially available or preparable organic tin compound (for example, according to Angew. Chem. Int. Ed. Engl., 1986, p. 508).

A compound of the formula (5) wherein $D^{3a}$ represents —N($R^{21}$)— can be produced by coupling a compound of the formula (6) and a commercially available or preparable aminating reagent according to the method of Step 1-4. Examples of the aminating reagent include primary or secondary alkylamines and arylamines.

A compound of the formula (5) wherein $D^{3a}$ represents —O— can be produced by reacting a compound of the formula (6) wherein $E^1$ represents a hydrogen atom and a commercially available or preparable aryl halide or aryl triflate or a compound of the formula (6) wherein $E^1$ represents Ts, Ms, or Tf and an etherifying agent having a hydroxyl group in an inert solvent in the presence of a palladium catalyst, a phosphorus compound, and a base (for example, according to Buchwald, S. L., J. Org. Chem., 2000, p. 1158 and Buchwald, S. L., Organic Letters, 2000, p. 1101). Examples of the inert solvent include ether solvents such as tetrahydrofuran, 1,4-dioxane, and 1,2-dimethoxyethane and toluene. Examples of the palladium catalyst include palladium acetate and tris(dibenzylideneacetone)dipalladium. Examples of the phosphorus compound include 2-(di-tert-butylphosphino)biphenyl, 2-(di-tert-butylphosphino)-1,1'-binaphthyl, and 2-(di-tert-butylphosphino)-2'-dimethylamino-1,1'-binaphthyl. Furthermore, examples of the base include sodium tert-butoxide, potassium tert-butoxide, cesium carbonate, and potassium phosphate. Examples of the etherifying agent include alcohols such as methanol and ethanol and phenols.

A compound of the formula (5) wherein $D^{1a}$ represents —S— can be produced from a compound of the formula (6) wherein $E^1$ represents Ts, Ms, or Tf and an intended compound having a thiol group according to the same method as in Step 1-4. Examples of the compound having a thiol group include alkylthiols such as ethanethiol and thiophenols.

Step 1-5-1

A compound of the formula (5) wherein $D^{3a}$ represents —N($R^{21}$)—C(O)— can be produced from a compound of the formula (7) wherein $D^{3b}$ represents —N($R^{21}$)—H, wherein $R^{21}$ has the same meaning as defined above. Specifically, a compound of the formula (7) and a commercially available or preparable intended compound having a carboxyl group (—COOH), carboxylic acid chloride, or mixed acid anhydride according to the same method as in the above (1-2-ii).

As an alternative method, a compound of the formula (5) wherein $D^{1a}$ represents —N($R^{21}$)— can be produced by coupling a compound of the formula (7) and a commercially available or preparable intended aryl halide or aryl triflate according to the method of above Step 1-4.

Step 1-5-2

A compound of the formula (7) can be produced from a compound of the formula (6). Specifically, by coupling a compound of the formula (6) and a commercially available or preparable compound of the following formula (1-5-2a):

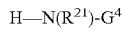   (1-5-2a)

wherein $R^{21}$ has the same meaning as defined above and $G^4$ represents a hydrogen atom or a protective group of an amino group according to the method of Step 1-4 and then deprotecting $G^4$.

Step 1-6

A compound of the formula (6) can be produced from a compound of the formula (8). Specifically, preferred examples include known methods comprising reacting p-toluenesulfonyl chloride, methanesulfonyl chloride, trifluoromethanesulfonyl chloride, methanesulfonic acid anhydride, trifluoromethanesulfonic acid anhydride, or N-phenyl-bis(trifluoromethanesulfonimide) in the presence of a suitable base such as triethylamine, N,N-diisopropylethylamine, pyridine, sodium carbonate, potassium carbonate, or sodium hydrogencarbonate. Examples of the reaction solvent include various organic solvents and chloroform, dichloromethane, and the like are preferred. As the reaction temperature, a suitable temperature is usually selected from −20 to −100° C., preferably −10 to 80° C. The reaction time is generally 1 hour to 3 days, preferably 3 to 24 hours.

A compound of the formula (8) can be produced according to, for example, Reference Examples 1-1 to 1-5 described later.

(Production Method 2)

A compound of the above-mentioned formula (2) wherein $D^{1a}$, $A^{1a}$, $D^{2a}$, $R^{1a}$, $D^{1a}$, and $R^{2a}$ has the same meaning as defined above can be produced along a reaction pathway shown in Scheme 2.

Scheme 2
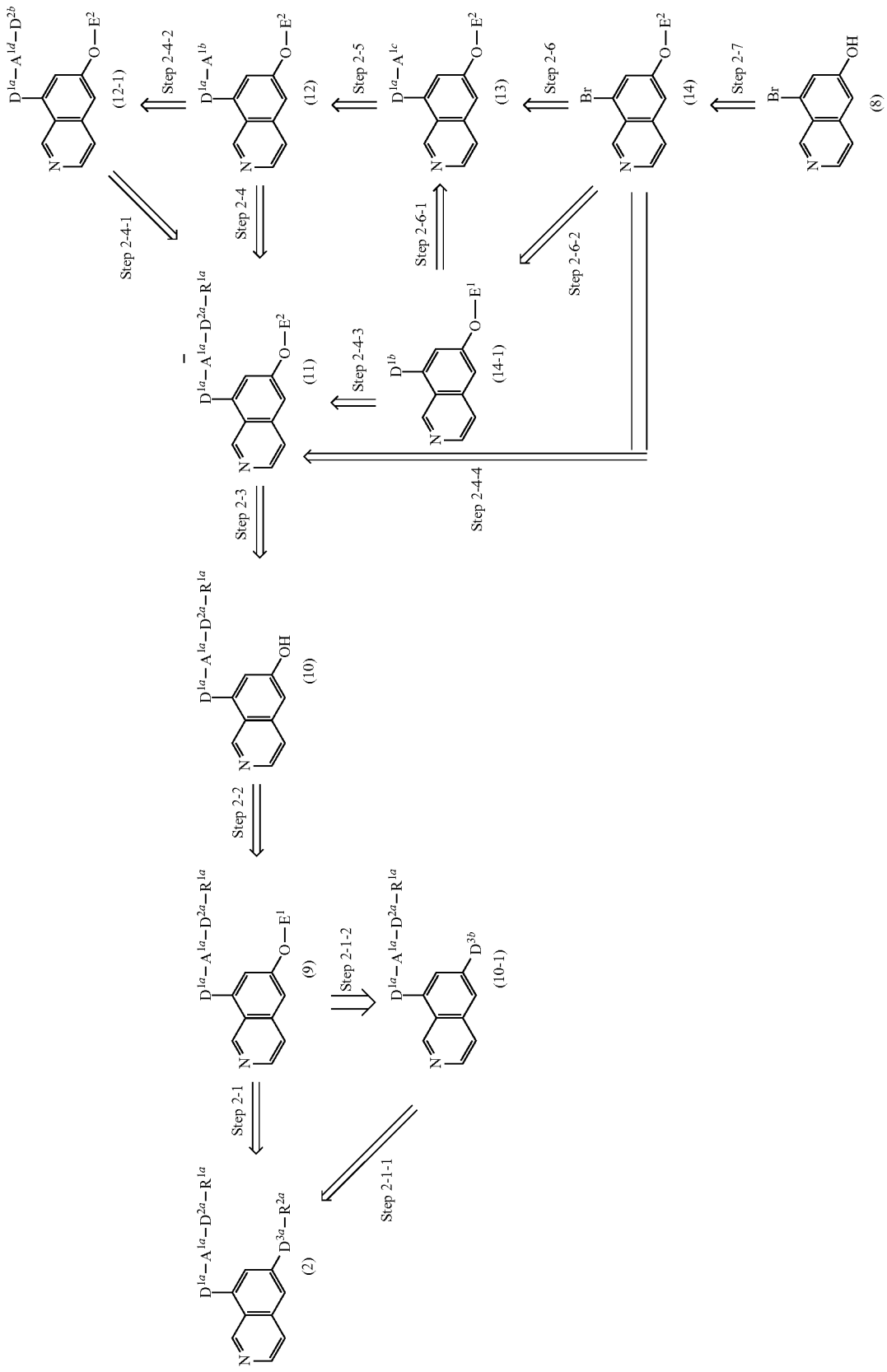

A compound of the formula (2) may be produced suitably by employing the same method as in (1-1-i) to (1-1-ii), (1-2-i) to (1-2-iv), (1-3-i) to (1-3-iv), and (1-4-i) to (1-4-v) in Production Method 1.

Furthermore, a compound of the formula (1) can be produced from a compound of the formula (2) according to the method of Step 1-1 in Production Method 1.

Step 2-1

A compound of the formula (2) can be produced from a compound of the formula (9) wherein $D^{1a}$, $A^{1a}$, $D^{2a}$, $R^{1a}$ and $E^1$ have the same meaning as defined above according to the same method as in Step 1-5 in Production Method 1.

Step 2-1-1

A compound of the formula (2) wherein $D^{3a}$ represents —N($R^{21}$)—C(O)— can be produced from a compound of the formula (10-1) wherein $D^{3b}$ represents —N($R^{21}$)—H and $D^{1a}$, $A^{1a}$, $D^{2a}$, $R^{1a}$, and $R^{21}$ have the same meaning as defined above according to the same method as in Step 1-5-1 in Production Method 1.

As an alternative method, a compound of the formula (2) wherein $D^{3a}$ represents —N($R^{21}$)— can be produced from a compound of the formula (10-1) according to the same method as in Step 1-5-1 in Production Method 1.

Step 2-1-2

A compound of the formula (10-1) can be produced from a compound of the formula (9) according to the same method as in Step 1-5-2 in Production Method 1.

Step 2-2

A compound of the formula (9) can be produced from a compound of the formula (10) wherein $D^{1a}$, $A^{1a}$, $D^{2a}$, and $R^{1a}$ have the same meaning as defined above according to the same method as in Step 1-6 in Production Method 1.

Step 2-3

A compound of the formula (10) can be produced by deprotecting a compound of the formula (11) wherein $D^{1a}$, $A^{1a}$, $D^{2a}$, and $R^{1a}$ have the same meaning as defined above and $E^2$ represents a hydrogen atom or a protective group of a hydroxyl group.

For example, when $E^2$ represents a benzyl group and a compound of the formula (10) is produced by debenzylation, the above-described "Deprotection reaction by hydrogenolysis" can be performed. Examples include methods comprising performing a reaction in an alcohol, an ether solvent such as ethyl acetate, or 1,4-dioxane or a mixed solvent thereof. Examples of a catalyst include a palladium carbon powder. The reaction is performed, for example, at 0 to 100° C., preferably 10 to 80° C. However, when $E^2$ represents a hydrogen atom, Step 2-3 is unnecessary.

Step 2-4

A compound of the formula (11) can be produced from a compound of the formula (12) wherein $D^{1a}$, $A^{1b}$, and $E^2$ have the same meaning as defined above according to the same method as in Step 1-2 in Production Method 1.

Step 2-4-1

A compound of the formula (11) wherein $D^{2a}$ represents -E-C(O)— can be produced from a compound of the formula (12-1) wherein $D^{1a}$, $A^{1b}$, $D^{2b}$, and $E^2$ have the same meaning as defined above according to the method of Step 1-2-1 in Production Method 1.

Step 2-4-2

A compound of the formula (12-1) can be produced from a compound of the formula (12) according to the same method as in Step 1-2-2 in Production Method 1.

Step 2-5

A compound of the formula (12) can be produced from a compound of the formula (13) wherein $D^{1a}$, and $E^2$ have the same meaning as defined above according to the same method as in Step 1-3 in Production Method 1.

Step 2-6

A compound of the formula (13) can be produced from a compound of the formula (14) wherein $E^2$ has the same meaning as defined above according to the method of Step 1-4 in Production Method 1.

Step 2-6-1

As an alternative method, a compound of the formula (13) wherein $D^{1a}$ represents —N($R^{11}$)— or O— can be produced from a compound of the formula (14-1) wherein $D^{1b}$ represents —N($R^{11}$)H or —OH and $E^2$ has the same meaning as defined above according to the same method as in Step 1-4-1 in Production Method 1.

Step 2-4-3

Furthermore, as an alternative method, a compound of the formula (11) can also be produced by using a compound of the formula (14-1) in the method of Step 1-2-3 in Production Method 1.

Step 2-6-2

A compound of the formula (14-1) can be produced from a compound of the formula (14) wherein $E^2$ has the same meaning as defined above according to the same method as in Step 1-4-2 in Production Method 1.

Step 2-4-4

Furthermore, as an alternative method, a compound of the formula (11) can also be produced by using a compound of the formula (14) according to the method of Step 1-2-4 in Production Method 1.

Step 2-7

A compound of the formula (14) can be produced by protecting a hydroxyl group in a compound of the formula (8). The protection reaction of a hydroxyl group can be performed according to a known method, for example, the method described in Protective Groups in Organic Synthesis, John Wiley and Sons (2007). Examples of the protective group of a hydroxyl group include the above-mentioned protective groups of a hydroxyl group, for example, a methyl group, a tert-butyl group, a MOM group, a MEM group, a THP group, a benzyl group, and a TBDMS group. In particular, a compound of the formula (14) wherein $E^2$ represents a methyl group can be produced by the method described in Reference Examples 1-1 to 1-4.

(Production Method 3)

Compounds represented by the formulas (2a) and (2b) can be produced along the reaction pathway shown in Scheme 3. In the following scheme, "Step" means a step, for example, "Step 3-1-1" is Step 3-1-1.

Production Methods shown in the following Scheme 3 are particularly preferred production methods when $R^5$ represents a bromine atom or a chlorine atom in the formulas (2a) and (2b).

and $R^5$ have the same meaning as defined above according to, for example, the method described in The Fifth Series of Experimental Chemistry, The Chemical Society of Japan ed., Maruzen Co., Ltd., vol. 17, pp. 425-427, "Catalytic Dehydrogenation Reaction" and the methods described in the references of this publication.

Step 3-2

In Scheme 3, a compound of the formula (IM2) can be produced by heating a compound of the formula (IM3) wherein $R^4$ and $R^5$ have the same meaning as defined above

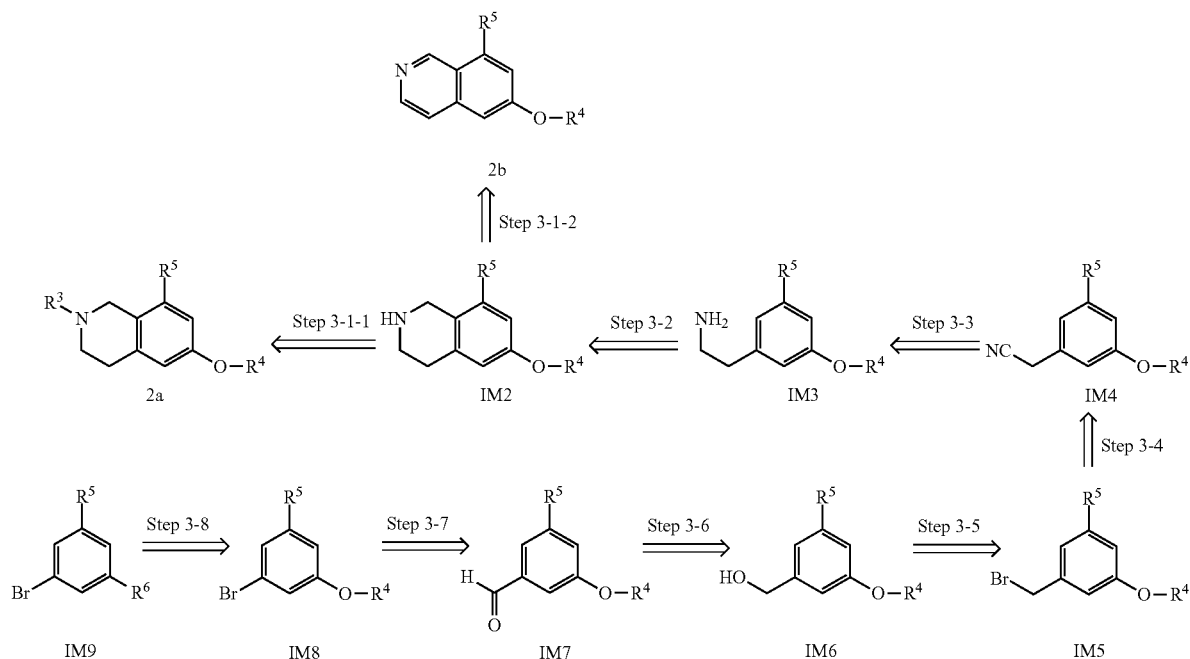

Step 3-1-1

In Scheme 3, a compound of the formula (2a) can be produced from a compound of the formula (IM2) wherein $R^4$, and $R^5$ have the same meaning as defined above and a commercially available or preparable compound of the following formula (3-1a) or (3-1b):

$$Y^7—R^3 \qquad (3\text{-}1a)$$

wherein $Y^7$ represents a halogen atom, and $R^3$ has the same meaning as defined above $$H—C(O)—R^3 \qquad (3\text{-}1b)$$

wherein $R^3$ has the same meaning as defined above according to the same method as in (1-2-i) in Production Method 1. When $R^3$ in the compound of the formula (2a) represents a hydrogen atom, Step 3-1-1 is unnecessary.

For example, a commercially available iodine methane (TCI) can be used as a compound of the formula (3-1a). Furthermore, a commercially available acetaldehyde (TCI) can be used as a compound formula (3-1b).

Step 3-1-2

In Scheme 3, a compound of the formula (2b) can be produced from a compound of the formula (IM2) wherein $R^4$ and formamide in a suitable acid solvent (for example, according to Whaley, W. M. & Govindachari, T. R., Org. React., 1951, 6, p. 74). Examples of the acid solvent include hydrochloric acid, trifluoroacetic acid, and formic acid.

Step 3-3

In Scheme 3, a compound of the formula (IM3) can be produced from a compound of the formula (IM4) wherein $R^4$ and $R^5$ have the same meaning as defined above according to the methods described in, for example, The Fifth Series of Experimental Chemistry, The Chemical Society of Japan ed., Maruzen Co., Ltd., vol. 14, pp. 352-357, "Reduction Reaction of Nitriles" and the methods described in the references of this publication.

Step 3-4

In Scheme 3, a compound of the formula (IM4) can be produced from a compound of the formula (IM5) wherein $R^4$ and $R^5$ have the same meaning as defined above by performing a substitution reaction with a suitable cyaniding agent according to the methods described in, for example, The First Series of Experimental Chemistry, The Chemical Society of Japan ed., Maruzen Co., Ltd., vol. 14, pp. 1433-1439, "Substitution with Metal Cyanides or Hydrogen Cyanides" or the methods described in The Fifth Series of Experimental Chemistry, The Chemical Society of Japan ed., Maruzen Co., Ltd., vol. 14, pp. 517-519, "Synthesis of Nitriles" and the method described in the references of these publications. Examples of the cyanidating agent include sodium cyanide and potassium cyanide.

Step 3-5

In Scheme 3, a compound of the formula (IM5) can be produced from a compound of the formula (IM6) wherein $R^4$ and $R^5$ have the same meaning as defined above according to the methods described in, for example, The Fifth Series of Experimental Chemistry, The Chemical Society of Japan ed., Maruzen Co., Ltd., vol. 13, pp. 393-406, "Generation of C—Cl and C—Br Bonds from C—O Bond and the methods described in the references of this publication.

Step 3-6

In Scheme 3, a compound of the formula (IM6) can be produced from a compound of the formula (IM7) wherein $R^4$ and $R^5$ have the same meaning as defined above according to the methods described in, for example, The Fifth Series of Experimental Chemistry, The Chemical Society of Japan ed., Maruzen Co., Ltd., vol. 14, pp. 1-18, "Synthesis by Reduction Reaction" and the methods described in the references of this publication.

Step 3-7

In Scheme 3, a compound of the formula (IM7) can be produced from a compound of the formula (IM8) wherein $R^4$ and $R^5$ have the same meaning as defined above according to the methods described in, for example, The Fifth Series of Experimental Chemistry, The Chemical Society of Japan ed., Maruzen Co., Ltd., vol. 15, pp. 78-87, "Synthesis by Formylation and Carbonylation" and the methods described in the references of this publication.

Step 3-8

In Scheme 3, a compound of the formula (IM8) can be produced from a compound of the formula (IM9) wherein $R^6$ represents a halogen atom and $R^4$ and $R^5$ have the same meaning as defined above and a commercially available or preparable compound of the following formula (3-8a):

$$R^4\text{—O—}M^4 \qquad (3\text{-}8a)$$

wherein $M^4$ represents an organic metal atom and $R^4$ has the same meaning as defined above according to the methods described in, for example, The Fifth Series of Experimental Chemistry, The Chemical Society of Japan ed., Maruzen Co., Ltd., vol. 14, pp. 241-249, "Synthesis from Aryl Halides" and the methods described in the references of this publication.

For example, as a compound of the formula (3-8a), a commercially available sodium methoxide (WAKO) can be used.

A commercially available compound of the formula (IM9) can also be used. For example, 1,3,5-tribromobenzene (TCI), 1,3-dibromo-5-fluorobenzene (TCI), 1,3-dibromo-5-chlorobenzene (TCI), and 1-bromo-3-chloro-5-fluorobenzene (TCI) can be used.

The compound of the present invention has a IKKβ inhibiting activity.

The compound of the present invention can inhibit the expression of a gene whose expression is regulated by NF-κB by suppressing the activation of NF-κB via inhibition of the IKK activity. Therefore, for example, the compound of the present invention can inhibit the production of inflammatory cytokines (TNF-α, IL-1, etc.), resulting in suppression of inflammatory reactions of these cytokines against various cells. Therefore, the compound of the present invention has an IKKβ inhibiting activity, an IKK inhibiting activity, an NF-κB activation pathway inhibiting activity, a TNF-αproduction suppressing activity, and the like and is useful for the prevention or treatment of diseases or symptoms associated with IKKβ, IKK, NF-κB, TNF-α, and the like. Furthermore, the compound of the present invention is also useful as an IKKβ inhibitor, an IKK inhibitor, an NF-κB activation pathway inhibitor, a TNF-αproduction suppressing agent, and the like.

These and other pharmacological activities of the compound of the present invention can be measured by standard test methods, for example, the methods described below.

Examples of IKK that can be used for the measurement of an IKKβ activity include a known human IKKβ (Accession No. NP_001547) and IKKβ mutants that have a sequence of the amino acid sequence of the human IKKβ in which one or more amino acids are substituted, deleted, or added and have an IKKβ activity. In one embodiment, the human IKKβ(Accession No. NP_001547) is more preferred. In another embodiment, IKKβ mutants that have a sequence of the amino acid sequence of the human IKKβ in which one or more amino acids are substituted, deleted, or added and have an IKKβ activity may be preferred. Furthermore, the IKKβ activity can also be measured according to a method already disclosed by Kishore et al. (J. B. C., 2003, 278, pp. 32861-32871) using a commercially available IKKβ (for example, Carna Biosciences, Japan). A preferred example of IKK used in the measurement of the IKKβ activity inhibiting ability described in Test Example 1 described later is a fusion protein labeled with a histidine tag at the N terminus of the amino acid residue of human IKK obtained in an expression system using baculovirus.

The IKKβ activity inhibiting ability (IKKβ inhibiting activity) and the IKK activity inhibiting ability (IKK inhibiting activity) of the compound of the present invention can be determined by adding a test compound before initiating the enzymatic reaction as in the method described in Test Example 1 described later and measuring the amount of a phosphorylated substrate.

When IKK is activated, IκB is phosphorylated, and the phosphorylated IκB is ubiquitinated and then degraded in the proteasome. The stimulus-dependent degradation of IκB can be measured by the method disclosed in, for example, WO 2004/089913. The IκBα degradation suppressing activity of the compound of the present invention can be determined by adding a test compound before applying a stimulus to cells and measuring degraded IκBα.

When a cell receives an inflammatory stimulus such as bacterial lipopolysaccharide (LPS), an endotoxin, the cell produces inflammatory cytokines such as TNF-α, and IKK is known to be involved therein. Production of an inflammatory cytokine can be measured by the methods already disclosed in WO 2004/089913. The cells to be used may be primary cultured human or animal cells or cultured cell strains such as THP-1 cells as in the method described in Test Example 2 of the present specification. Furthermore, blood can also be used for the measurement as in the method described in Test Example 3 in the present specification. The inflammatory cytokine production inhibiting ability of the compound of the present invention can be determined by adding a test compound before applying an inflammatory stimulus to cells or blood and measuring the amount of inflammatory cytokines produced.

Administration of LPS to animals induces rapid production of TNF-α. This model is used for in-vivo evaluation of a drug that is expected to have a TNF-α production suppressing ability. Specifically, the TNF-α production suppressing ability can be evaluated according to, for example, the method described in Test Example 4 in the present specification and the method already disclosed by Kishore et al. (J. B. C., 2003, 278, pp. 32861-32871). The animals used are not limited to mice and rats. The in-vivo TNF-α production inhibiting ability of the compound of the present invention can be determined by administering a test compound to animals before administering LPS and measuring the amount of inflammatory cytokines produced.

Examples of TNF-α-associated diseases include rheumatoid arthritis, ankylosing spondylarthritis, Crohn's disease, giant cell arteritis, polymyalgia rheumatica, pigmented purpuric lichenoid dermatitis, sarcoidosis, Wegener's granuloma, pyoderma, Behcet's syndrome, TNF-receptor-associated periodic syndrome, SAPHO syndrome, Takayasu's disease, myositis, Still's disease, periarteritis nodosa, relapsing polychondritis, and scleroderma (C. Lacoin et al., European League Against Rheumatism (EULAR) 2008, THU0470.

The compound of the present invention has an IKKβ activity inhibiting ability and is useful for the prevention and treatment of diseases and symptoms associated with IKKβ or NF-κB. Examples of such diseases and symptoms include rheumatoid arthritis, osteoarthritis, inflammatory colitis, asthma, chronic obstructive pulmonary disease, transplant rejection (prevention), cancer, ischemia-reperfusion injury, diabetes, virus infections, and heart diseases descried by Burke et al. (Curr. Opin. Drug Discov. Devel., 2003, 6, pp. 720-728) but are not limited to these examples.

Examples of such diseases and symptoms include autoimmune diseases, inflammatory diseases, cardiovascular diseases, cancer, and diseases associated with acute or chronic inflammatory reactions and more specific examples include systemic anaphylaxis, hypersensitivity reaction, drug allergy, allergy to insect stings, food allergy, Crohn's disease, ulcerative colitis, ileitis, enteritis, vaginitis, psoriasis, dermatitis, eczema, atopic dermatitis, allergic contact dermatitis, pigmented purpuric lichenoid dermatitis, urticarial eruption, vasculitis, spondylarthrosis (including ankylosing spondylarthritis), scleroderma, pyoderma, SAPHO syndrome, allergic asthma, allergic rhinitis, allergic conjunctivitis, hypersensitivity lung disease, rheumatoid arthritis, Still's disease, giant cell arteritis, polymyalgia rheumatica, psoriasis arthritis, systemic lupus erythematosus, type I diabetes, glomerulonephritis, transplantation rejection (including allograft rejection and graft versus host disease), atherosclerosis, myositis, ischemia-reperfusion injury, traumatic brain damage, cerebral circulatory disturbance, closed head trauma, Parkinson's disease, multiple secrosis, Alzheimer's disease, encephalitis, meningitis, osteoporosis, gout, hepatitis, nephritis, gallbladder disease, sepsis, sarcoidosis, conjunctivitis, otitis, chronic obstructive pulmonary disease, sinusitis, Behcet's syndrome, cancer in the breast, the skin, the prostate, the neck, the uterus, the ovaries, the testicles, the bladder, the lungs, the liver, the larynx, the mouth cavity, the colon, the gastrointestinal tracts (for example, the esophagus, the stomach, and the pancreas), the brain, the thyroid gland, blood, and the lymphatic system, Wegener's granuloma, diseases in which vasculogenesis or neovascularization plays a role, obesity, type II diabetes, X syndrome, insulin resistance, hyperglycemia, hyperuricemia, hyperinsulinism, cachexia, hypercholesterolemia, hyperlipidemia, dyslipidemia, mixed dyslipidemia, hypertriglyceridemia, anorexia nervosa, bulimia, bacteremia, septic shock acute heart failure, hypotension, hypertension, angina pectoris, myocardial infarction, cardiomyopathy, congestive heart failure, atherosclerosis, coronary arteries disease, restenosis and angiostenosis, periarteritis nodosa, Takayasu's disease, TNF-receptor-associated periodic syndrome, relapsing polychondritis, immunological diseases, and symptoms associated with these diseases.

Usefulness of the compound of the present invention for the prevention and/or treatment of rheumatoid arthritis can be confirmed by, for example, administering a test compound to a mouse collagen-induced arthritis model (see Test Example 5). The mouse collagen-induced arthritis model shows the same biochemical and pathological features as human chronic rheumatoid arthritis and is widely used to study the disease mechanism and potential therapies of human chronic rheumatoid arthritis (Staines et al., Br. J. Rheumatol., 1994, 33, pp. 798-807 and Feldmann et al., Annu. Rev. Immunol., 1996, 14, pp. 397-440). Usefulness can be confirmed by orally, intravenously, or intraperitoneally administering a test compound at doses of 0.01 to 1000 mg/kg, preferably 0.1 to 100 mg/kg to the mouse collagen-induced arthritis model and evaluating swelling and histology of the four limbs.

Usefulness of the compound of the present invention for the prevention and/or treatment of osteoporosis in patients (including prevention and treatment of bone defect and bone regeneration) can be confirmed by, for example, administering a test compound to an osteoporosis model. Osteoporosis is a term that is widely used for many diseases and symptoms associated with decreased bone mass and includes primary osteoporosis (for example, postmenopausal osteoporosis, senile osteoporosis, and juvenile osteoporosis) and secondary osteoporosis. Examples of secondary osteoporosis include chronic diseases (for example, chronic kidney disease, liver failure, gastrointestinal malabsorption, chronic lack of exercise, and chronic inflammatory diseases including chronic rheumatoid arthritis, osteoarthritis, periodontal disease, and abacterial joint relaxation), diseases associated with endocrine dysfunction (for example, diabetes, hyperthyroidism, hyperparathyroidism, sex dysfunction, and pituitary dysfunction), symptoms associated with drugs and substances (for example, corticosteroids, heparins, anti-convulsants, alcohols, and immunosuppressive agents), and hematological disturbance (for example, metastatic diseases, myeloma, leukemia, Gaucher's disease, and anemia). It has been reported that at least either direct inhibition of IκB or indirect inhibition of the NF-κB pathway is useful for the treatment of osteoporosis and osteoarthritis (WO 2003/104219, WO 2003/103658, WO 2003/029242, WO 2003/065972, and WO 99/65495). Furthermore, it has been reported that destruction of cartilages and bones is observed in the above-mentioned mouse collagen-induced arthritis model, and the IKK inhibiting factor inhibits defects of cartilages and bones in this model (McIntyre et al., Arthritis & Rheumatism, 2003, 48(9), pp. 2652-2659). Usefulness can be confirmed by orally, intravenously, or intraperitoneally administering a test compound to the model animal at doses of 0.01 to 1000 mg/kg, preferably 0.1 to 100 mg/kg and measuring bone density, bone strength, bone metabolism marker, and the like.

Usefulness of the compound of the present invention for the prevention and/or treatment of cerebral circulatory disturbance can be confirmed by, for example, administering a test compound to a mouse cerebral ischemia model (Herrmann et al., Nature Medicine, 2005, 11, pp. 1322-1329). Usefulness can be confirmed by orally, intravenously, or intraperitoneally administering a test compound to the model animal at doses of 0.01 to 1000 mg/kg, preferably 0.1 to 100 mg/kg and measuring the infarct volume and the like.

Usefulness of the compound of the present invention for the prevention and/or treatment of type II diabetes can be confirmed by, for example, administering a test compound to a mouse insulin resistant diabetes model (Arkan et al., Nature Medicine, 2005, 11, pp. 191-198). Usefulness can be confirmed by orally, intravenously, or intraperitoneally administering a test compound to the model animal at doses of 0.01 to 1000 mg/kg, preferably 0.1 to 100 mg/kg and measuring blood glucose concentrations and plasma insulin concentrations.

Usefulness of the compound of the present invention for the prevention and/or treatment of cancer can be confirmed by, for example, administering a test compound to an ultraviolet ray irradiation induced skin cancer mouse model, a cancer cell transplanted immunodeficiency mouse model (Orengo, I. F. et al.; Arch. Dermatol., 2002, 138(6), pp. 823-824, and Clin. Cancer Res., 2006 (12), pp. 5887-5894), or the like. Efficacy can be confirmed by orally, intravenously, or intraperitoneally administering a test compound to the model animal at doses of 0.01 to 1000 mg/kg, preferably 0.1 to 100 mg/kg and observing the growth and disappearance of cancer tissues.

Usefulness of the compound of the present invention as an active ingredient of a pharmaceutical can be confirmed by, for example, performing a metabolism test. Examples of the metabolism test include blood stability test (a method of predicting the in-vivo metabolic clearance from the metabolic rate of a compound in hepatic microsome or the S9 fraction of human or other animal species [refer to Shou, W. Z. et al., J. Mass Spectrom., 40(10), pp. 1347-1356, 2005, Li, C. et al., Drug Metab. Dispos., 34(6), 901-905, 2006, or the like]), metabolite molecular species test, and reactive metabolite test. Usefulness as an active ingredient of a pharmaceutical can be confirmed by clarifying metabolic profiles of the compound using one or more of these methods.

The enzyme inhibition selectivity of the compound of the present invention can be evaluated by measuring the inhibitory effect of the compound using various commercially available kinases under reaction conditions suitable for each enzyme. For example, the inhibitory effect of the compound on ROCK I can be evaluated by measuring enzyme activity using commercially available ROCK I (Carna Biosciences, Japan) and HTRF® KinEASE™-STK S2 Kit (Cisbio Bioassays U.S.) in the presence of the compound according to the methods in the instructions attached to the products. Similarly, the inhibitory effect on JAK2 and PKCθ can also be evaluated by the same method as for ROCK I using a combination of commercially available JAK2 (Carna Biosciences, Japan) and HTRF® KinEASE™-TK Kit (Cisbio Bioassays U.S.) and a combination of PKCθ (Carna Biosciences, Japan) and HTRF® KinEASE™-STK S1 Kit (Cisbio Bioassays U.S.). The enzyme inhibition selectivity of the compound can be evaluated by comparing the inhibitory effect on various kinases measured in this manner and the inhibitory effect on IKKβ.

The present invention also provides methods of prevention and/or treatment for the above-mentioned diseases and symptoms, and the methods include administration of a safe and effective amount of the compound represented by the above-mentioned formula (1) or a pharmaceutically acceptable salt thereof to a mammal requiring the prevention and/or treatment. Furthermore, pharmaceutical compositions or compounds effective in the prevention and/or treatment of the above-mentioned diseases and symptoms can be used in combination. Furthermore, preferred examples of target mammals of the above-mentioned preventing and/or treating methods include humans, pets or companion animals such as dogs and cats, and farm animals.

In the present specification, to "treat" a disease or a symptom includes to prevent the aggravation of, delay the progression of, improve, cure, resolve, or relieve one or more biological signs of the disease or the symptom and prevent one or more biological cascades that can cause the disease or the symptom. Furthermore, in the present specification, to "prevent" a disease or a symptom is to substantially decrease the possibility and/or severity of one or more biological signs of the disease or the symptom and delay the onset thereof.

The present invention also provides a pharmaceutical composition comprising the compound of the present invention as an active ingredient. This pharmaceutical composition can be used against the above-mentioned disease or symptom in mammals, preferably humans, pets or companion animals such as dogs and cats, and farm animals solely or in combination with one or more other preventing or treating agents.

Examples of pharmaceuticals that can be used in combination with the pharmaceutical composition of the present invention include immunosuppressants such as, specifically, tacrolimus, cyclosporin, rapamycin, and mycophenolate mofetil and formulations comprising these drugs; disease modifying antirheumatic drugs and antimetabolites used as a treating agent for chronic rheumatoid arthritis such as, specifically, gold formulations, bucillamine, lobenzarit, hydroxychloroquine, D-penicillamine, salazosulfa pyridine, methotrexate, azathiopurine, mizoribine, and leflunomide and formulations comprising these drugs; receptor antagonists against cytokines such as interleukin (IL)-1, IL-6, and tumor necrosis factor (TNF)-α, anti-cytokine antibody formulations, anti-cytokine receptor antibody formulations, and soluble receptor formulations against these cytokines, which antagonists or formulations are biologics, such as, specifically, anakinra, infliximab, tocilizumab, and etanercept and formulations comprising these drugs; steroid formulations such as, specifically, dexamethasone, betamethasone, prednisolone, fluticasone, and beclomethasone and formulations comprising these drugs, bronchodilators used as a treating agent for chronic bronchial asthma such as, specifically, salmeterol and salbutamol, β2 adrenergic stimulants, and ipratropium, an anticholinergic drug and formulations comprising these drugs; treating agents for allergic diseases such as, for example, theophylline, a xanthine-related drug, and formulations comprising these drugs, anti-allergic drugs such as fexofenadine, epinastatin, cetirizine, ketotifen, disodium cromoglycate, and pemirolast and formulations comprising these drugs, leukotriene antagonists such as zafirlukast, montelukast, pranlukast, iralukast, and pobilukast and formulations comprising these drugs, leukotriene biosynthesis inhibitors such as zileuton and formulations comprising these drugs; nonsteroidal anti-inflammatory drugs (NSAIDs) such as, specifically, propionic acid derivatives (for example, alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen) and formulations comprising these drugs, acetic acid derivatives (for example, indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac) and formulations comprising these drugs, fenamate derivatives (for example, flufenamate, meclofenamic acid, mefenamic acid, niflumic acid, and tolfenamic acid) and formulations comprising these drugs, biphenyl carboxylic acid derivatives (for example, diflunisal and flufenisal) and formulations comprising these drugs, oxicams (for example, isoxicam, piroxicam, sudoxicam, and tenoxicam) and formulations comprising these drugs, salicylates (for example, acetylsalicyl acid and sulfaslazine) and formulations comprising these drugs, pyrazolones (for example, apazone, bezpiperylon, feprazone, mofebutazone, oxyphenbutazone, and phenylbutazone) and formulations comprising these drugs, cyclooxygenase-2 inhibitors (for example, celecoxib and rofecoxib) and formulations comprising these drugs; cytoplasmic phospholipase A2α (cPLA2α) inhibitors and formulations comprising these drugs; other IKK inhibitors and formulations comprising these drugs; antitumor drugs such as, specifically, bortezomib, capecitabine, gemcitabine, irinotecan, fludarabine, 5-fluorouracil or 5-fluorouracil/leucovorin, taxanes (for example, paclitaxel and docetaxel), platinum formulations (for example, cisplatin, carboplatin, and oxaliplatin), anthracyclines (for example, doxorubicin and idarubicin), mitoxantrone, dexamethasone, vincristine, etoposide, prednisone, thalidomide, trastuzumab, temozolomide, alkylating agents such as melphalan, chlorambucil, and cyclophosphamide, and formulations comprising these drugs; anti-diabetic drugs such as, specifically, insulin or pseudo insulin, sulfonylureas (for example, glyburide, meglinatide, tolbutamide, and glipizide) and formulations comprising these drugs, biguanides (for example, metformin) and formulations comprising these drugs, α-glucosidase inhibitors (for example, acarbose) and formulations comprising these drugs, thiazolidinone compounds (for example, rosiglitazone, troglitazone, ciglitazone, pioglitazone, and englitazone) and formulations comprising these drugs. Furthermore, a pharmaceutical composition comprising the compound of the present invention as an active ingredient can also be used in combination with radiation therapy.

An effective amount of the compound of the present invention or a pharmaceutically acceptable salt thereof can be used as it is or mixed with a pharmaceutically acceptable carrier to produce a pharmaceutical composition using a technique known to those skilled in the art. Such a carrier may be, for example, a suspending agent such as carboxymethylcellulose, purified water, physiological saline, or the like in some cases, and other known carriers can also be used. As one example, the compound of the present invention or a pharmaceutically acceptable salt thereof can be suspended or dissolved in purified water containing 0.5% carboxymethylcellulose and used as a pharmaceutical composition.

Examples of the dosage form of the pharmaceutical composition of the present invention include tablet, powder, granule, syrup, suspension, capsule, and injection and these formulations can be produced using various carriers depending on the dosage form by techniques known to those skilled in the art. For example, examples of a carrier for an oral agent include excipient, binder, lubricant, fluidity promoter, and coloring material.

When the pharmaceutical composition of the present invention is a parenteral agent such as an injection, distilled water for injection, physiological saline, aqueous glucose solution, vegetable oil for injection, propylene glycol, polyethylene glycol, or the like can be generally used as a diluent. Furthermore, if necessary, a disinfectant, a preservative, a stabilizer, an isotonizing agent, a soothing agent, or the like may also be added.

When the pharmaceutical composition of the present invention is administered to a mammal, for example, a human, it can be orally administered in the form of tablet, powder, granule, suspension, or capsule or parenterally administered in the form of injection including a drip infusion, suppository, gel, lotion, ointment, cream, or spray. The dose varies depending on the indication, dosage form, patient's age, body weight, severity of the symptom, or the like and the general adult daily dosage is, for example, 0.001 to 2000 mg, which is divided into 1 to 5 times. The pharmaceutical composition of the present invention is generally administered everyday for several days to 2 months, and both the daily dose and the treatment period can be adjusted depending on the patient's symptom.

EXAMPLES

Hereafter, the present invention will be specifically described with reference to Examples and Test Examples (hereinafter referred to as "Examples, etc."). However, the scope of the present invention is not limited to the following Examples, etc.

In the Examples, etc., Precoatedsilica Gel 60 F254 (Merck, Product No. 5715-1M) was used for thin layer chromatography (TLC). After developing with chloroform:methanol (1:0 to 1:1), acetonitrile:acetic acid:water (200:1:1 to 100:4:4), or ethyl acetate:hexane (1:0 to 0:1), the product was confirmed by UV (254 or 365 nm) irradiation, colors produced by iodine solution, aqueous permanganate potassium solution, phosphomolybdic acid (ethanol solution), ninhydrin, dinitrophenylhydrazine hydrochloride solution, or the like.

Anhydrous magnesium sulfate or anhydrous sodium sulfate was used to dry an organic solvent.

Among column chromatography procedures, Quad 1 purification system (Biotage) was used for those indicated with "Quad" and one or several of any cartridge column among KP-Sil-12M, -40S, or -40M manufactured by the corporation were used depending on the amount of a sample. Furthermore, Multi Prep YFLC (Yamazen Corporation) was used for steps indicated with "Yamazen" and any of Ultra Pack Si-40A, 40B, or 40D manufactured by the corporation was used as a column. Furthermore, MORITEX 2-ch Parallel Purification Apparatus "Purif-α2 (50F)" was used for steps indicated with "MORITEX" and PurifPack-Si series manufactured by the corporation was used as a column.

Silica Gel 60N (spherical, neutral, 40 to 100 μm, Kanto Chemical Co., Inc.) was used for flash column chromatography.

One or several of PLC Plate Silica Gel 60 F254, 20×20 cm, layer thickness, 2 mm, with concentration zone (4 cm) (Merck, Product No. 13793-1M) were used for preparative thin layer chromatography (hereinafter referred to as "PTLC") depending on the amount of a sample.

For purification by HPLC, the preparative purification system of Japan Waters was used Develosil C-30-UG-5 (Nomura Chemical Co., Ltd.) or the like was used as a column. A water-acetonitrile solvent containing 0.1% acetic acid was used as an eluate.

Shimadzu LC6A System (Shimadzu Corporation) was used as an HPLC apparatus in "separation of chiral compounds." Chiralcel OJ-RH (20 mm i.d.×250 mm) (Daicel CHEMICAL INDUSTRIES, LTD.) was used as a column for separation. Elution was performed at a flow rate of 10 mL/min using water as Solution A and acetonitrile as Solution B as solvents, with a ratio of 70% Solution B. In purification by HPLC, the solvent was removed by lyophilization to give a target compound, unless otherwise specified. To measure nuclear magnetic resonance spectrum (NMR), Gemini-300 (FT-NMR, Varian, Inc.), or AL-300 (FT-NMR, JEOL Ltd.) was used. Unless otherwise specified, deuterated chloroform was used as the solvent, a chemical shift was measured using tetramethyl silane (TMS) as an internal standard and expressed with δ (ppm), and the binding constant was expressed with J (Hz).

For "LCMS," mass spectrum was measured by liquid chromatography mass spectrometry (LCMS). The following apparatuses (A), (B), and (C) were used depending on the purpose for analyses.

(A) A single quadrupole mass spectrometer, HPLC/SQD System (Waters), was used as a mass spectrometer and measurement was performed by the electrospray (ESI) method. Acquity Ultra Performance LC System was used as the liquid chromatography apparatus. ACQUITY HPLC BEH C18 2.1× 50 mm 1.7 μm (Waters) was used as the separation column. Generally, elution was performed at a flow rate of 0.6 mL/min, using water (containing 0.10 [v/v] acetic acid) as Solution A and acetonitrile (containing 0.1% [v/v] acetic acid) as Solution B, under conditions of a linear gradient of 5 to 90% (v/v) Solution B from 0 minutes to 2.0 minutes and a linear gradient of 90 to 98% (v/v) Solution B from 2.0 minutes to 2.5 minutes.

(B) Platform-LC Mass Spectrometer (Micromass) was used as a mass spectrometer for the measurement by the electrospray (ESI) method. An apparatus of GILSON was used as a liquid chromatography apparatus. Develosil C30-UG-5 (50×4.6 mm) (Nomura Chemical Co., Ltd.) was used as the separation column. Generally, elution was performed at a flow rate of 2 mL/min, using water (containing 0.1% [v/v] acetic acid) as Solution A and acetonitrile (containing 0.1% [v/v] acetic acid) as Solution B, under conditions of a linear gradient of 5 to 98% (v/v) Solution B from 0 minutes to 4 minutes and 980 (v/v) Solution B to 6 minutes.

(C) Micromass ZMD Mass Spectrometer (Waters) was used as the mass spectrometer for the measurement by the electrospray (ESI) method. An apparatus of Waters was used as a liquid chromatography apparatus. Develosil C30-UG-5 (50×4.6 mm) (Nomura Chemical Co., Ltd.) was used as the separation column. Generally, elution was performed at a flow rate 2 mL/min, using water (containing 0.1% [v/v] acetic acid) as Solution A and acetonitrile (containing 0.1% [v/v] acetic acid) as Solution B, under conditions of a linear gradient of 5 to 98% (v/v) Solution B from 0 minutes to 4 minutes, followed by 98% Solution B maintained to 5 minutes, a linear gradient of 98 to 5% (v/v) Solution B from 5 minutes to 5.01 minutes, and 5% Solution B maintained to 7.3 minutes.

In the following Examples, for example, "Example compound 1-N-1" indicates the final product in "Example 1-N-1," 3-(8-(piperidin-4-ylamino)isoquinolin-6-yl)benzonitrile.

Symbols in the tables are defined as follows.

"EXP.": Example number

"exp.": Reference Example number

"SM1" and "SM2": Starting material. "EXP. Example number" is used for a starting material that is an Example compound and "IM. Intermediate number" is used for a starting material that is an intermediate compound (for example, "IM. Br-1" indicates Intermediate Br-1). Abbreviations used in "SM2" refer to compounds corresponding to abbreviations represented in the tables provided later. For example, starting materials shown in "SM1" and "SM2" in EXP1-N-3 of "Table 1-N" correspond to "Intermediate Br-1" and "sa3," respectively. When there is one starting material, only the relevant starting material is shown.

"ST": Structure represented by any of general formulas Qn1 to Qn26, Qn1-1, Qn1-2, Qn8-1, Qn1P to Qn10P, Qo1 to Qo14, Qo1-1 to Qo1-10, Qo2-1 to Qo2-6, Qo9-1, and Qs1 to Qs2. In each of the following general formulas, J represents a structure corresponding to an abbreviation such as "col" in "Table co" and Ar represents a structure corresponding to an abbreviation such as "Ar1" in "Table Ar."

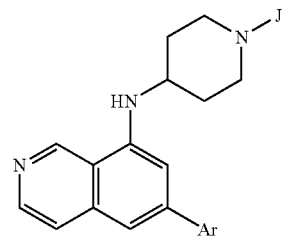

Qn1

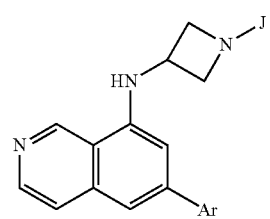

Qn2

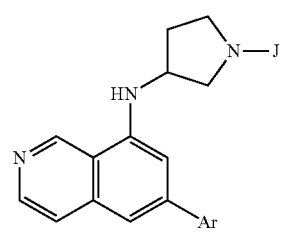

Qn3

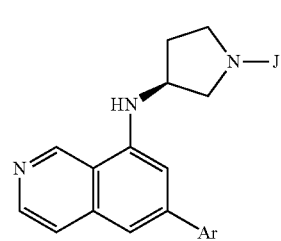

Qn4

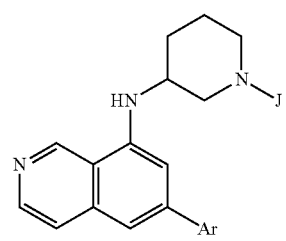

Qn5

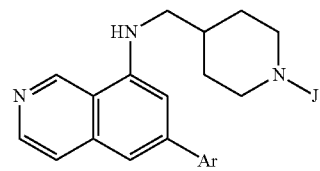

Qn6

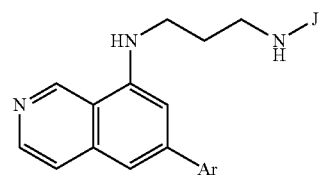

Qn7

Qn8
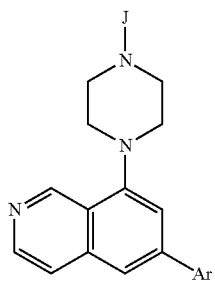
Qn9
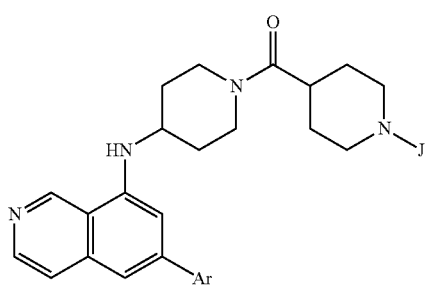
Qn10
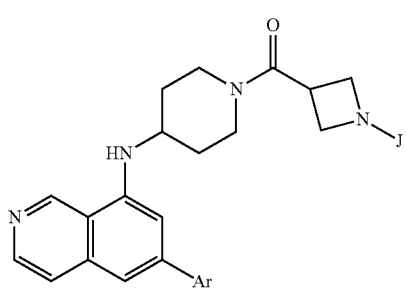
Qn11
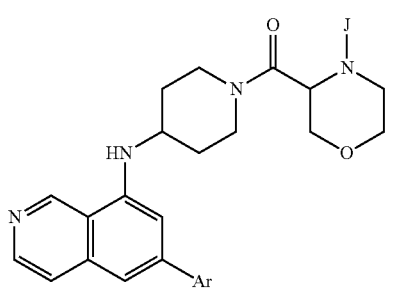
Qn12
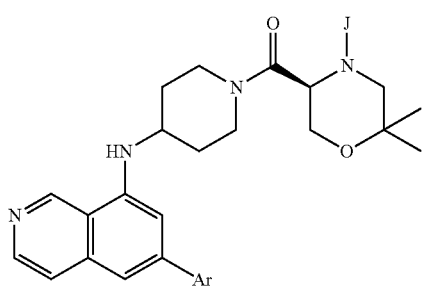
Qn13
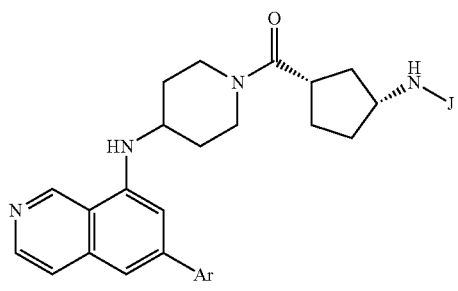
Qn14
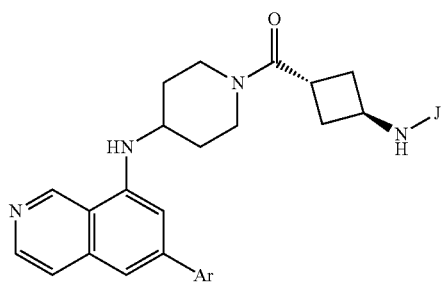
Qn15
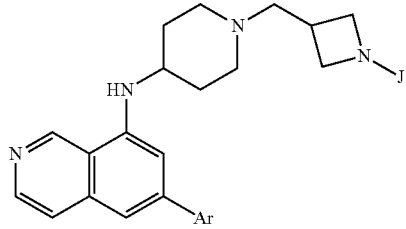
Qn16
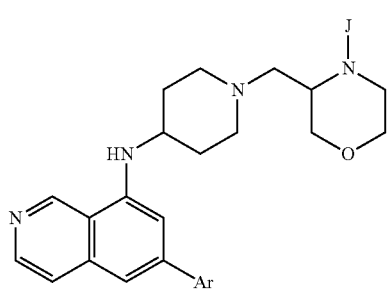
Qn17
Qn18
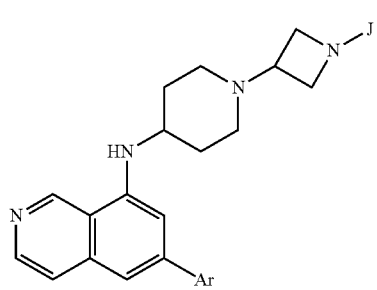

| 205 -continued | | 206 -continued | |
|---|---|---|---|
| 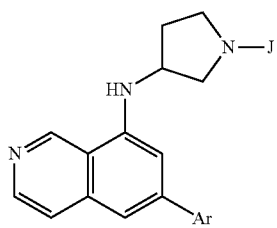 | Qn19 | 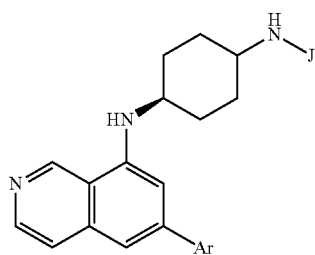 | Qn26 |
| 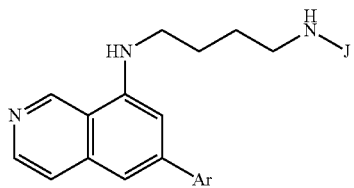 | Qn20 | 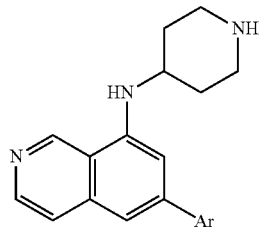 | Qn1-1 |
| 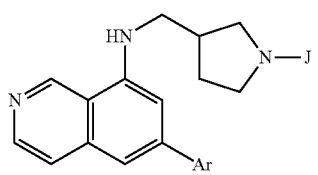 | Qn21 | 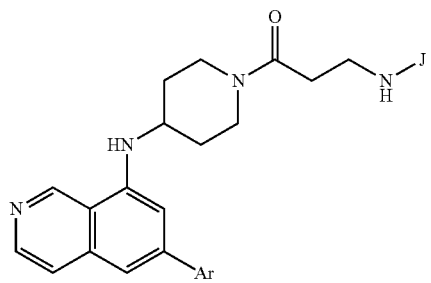 | Qn1-2 |
| 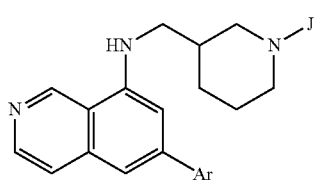 | Qn22 | 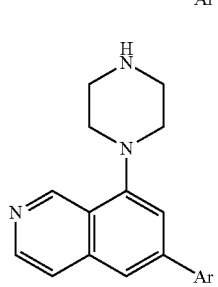 | Qn8-1 |
| 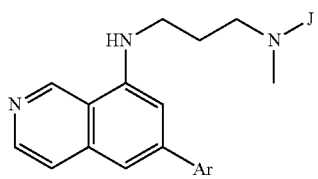 | Qn23 | 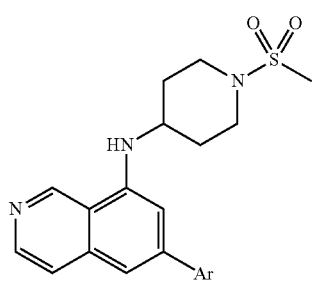 | Qn1P |
| 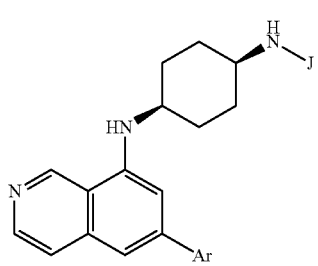 | Qn24 | 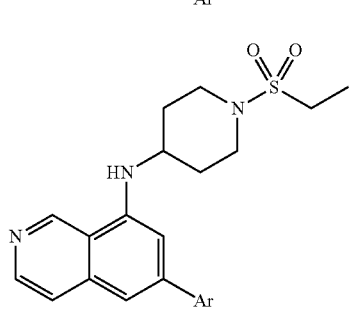 | Qn2P |
| 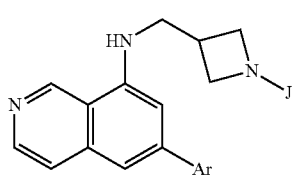 | Qn25 | | |

| | |
|---|---|
| Qn3P 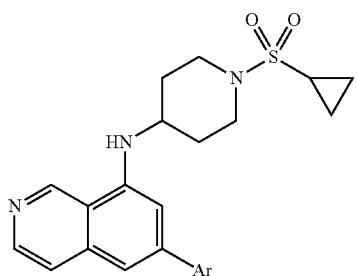 | Qn8P 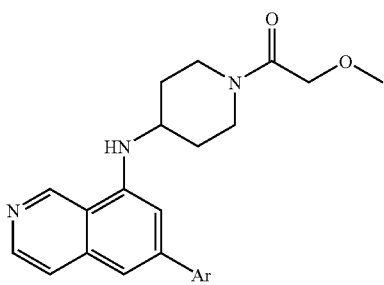 |
| Qn4P 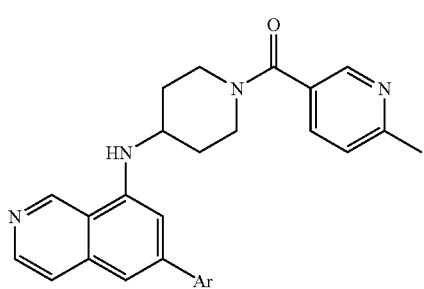 | Qn9P 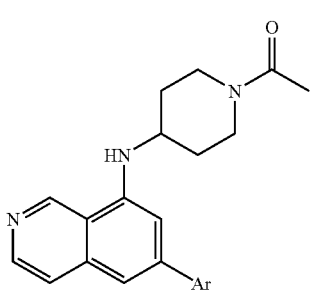 |
| Qn5P 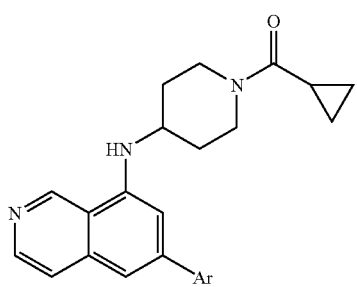 | Qn10P 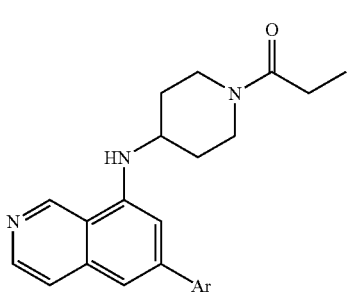 |
| Qn6P 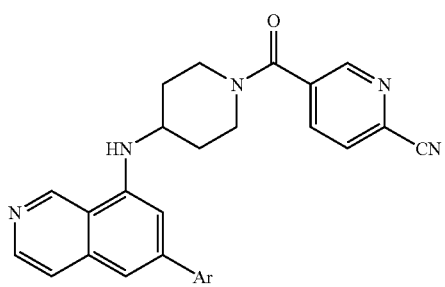 | Qn11P 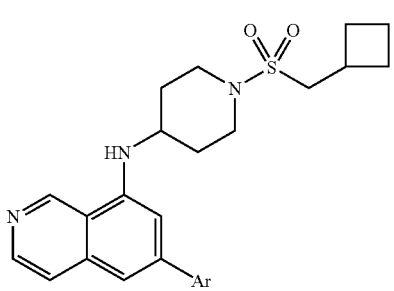 |
| Qn7P 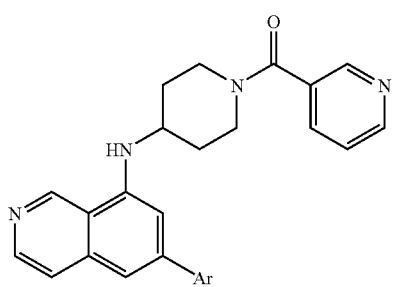 | Qn12P 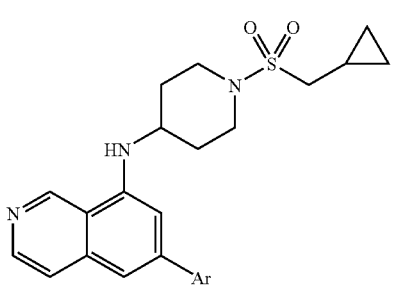 |

Qn13P
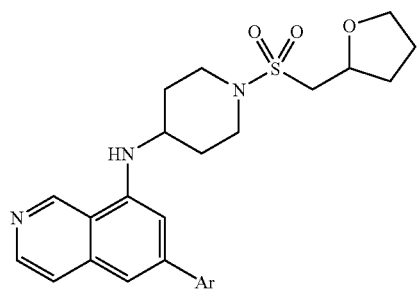
Qn14P
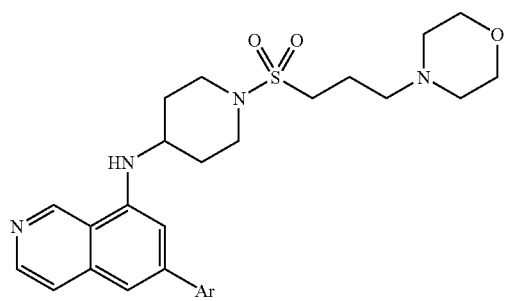
Qn15P
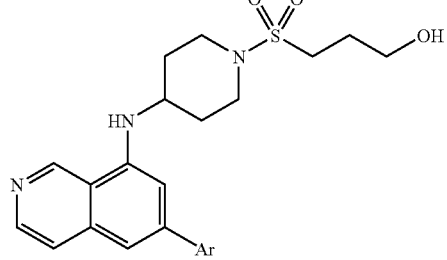
Qn16P
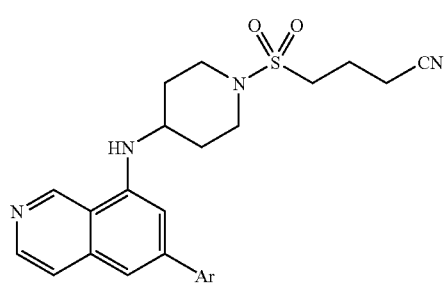
Qn17P
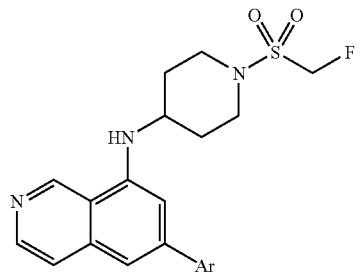
Qn18P
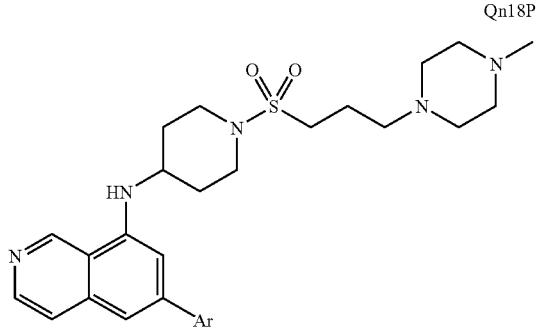
Qn19P
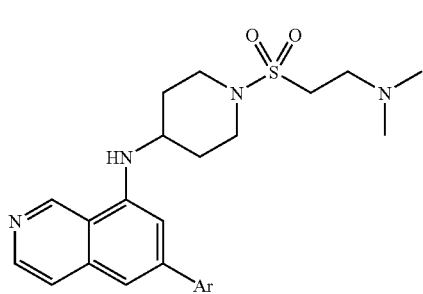
Qn20P
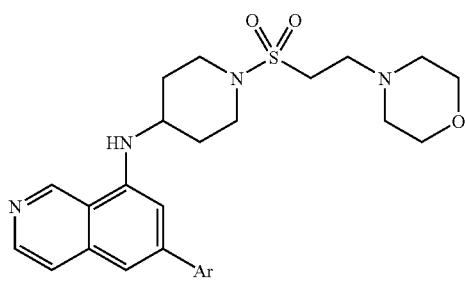
Qn21P
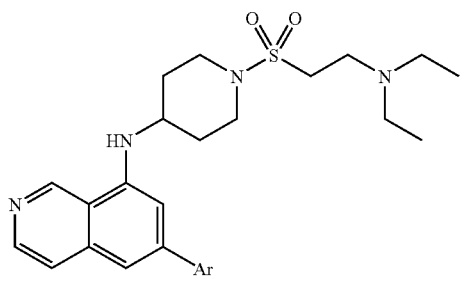
Qn22P
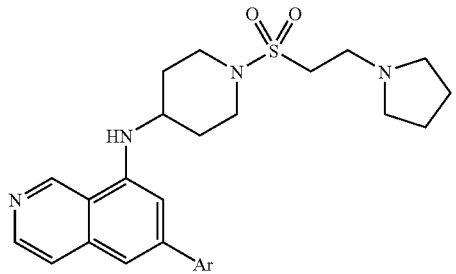

Qn23P
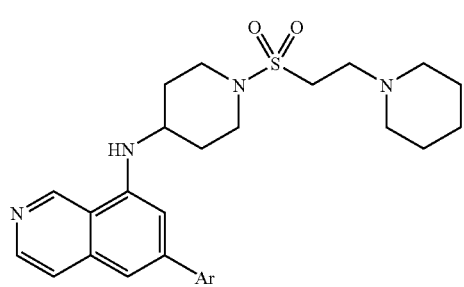
Qn24P
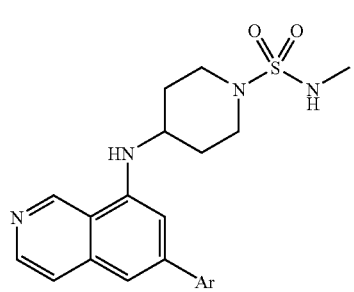
Qn25P
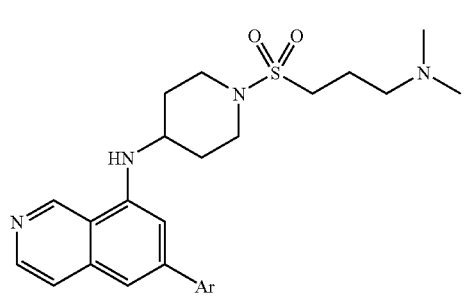
Qn26P
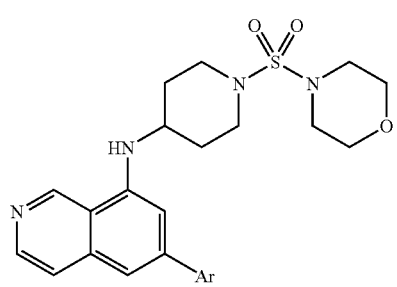
Qn27P
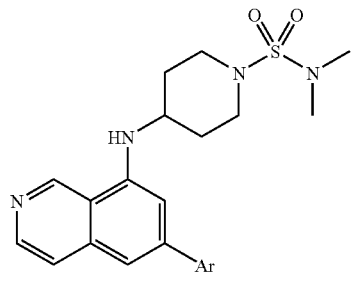
Qn28P
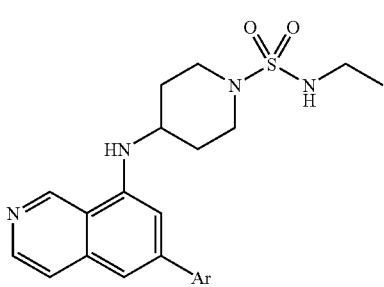
Qn29P
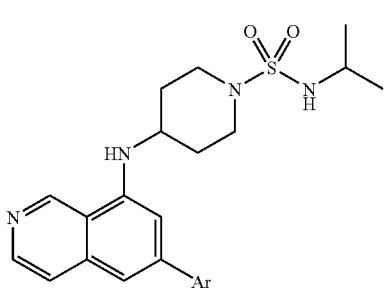
Qn30P
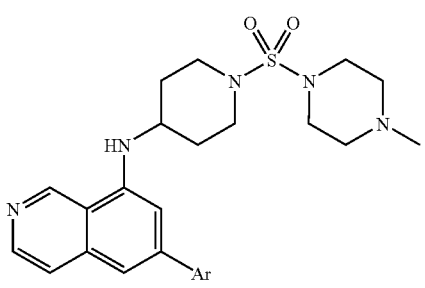
Qn31P
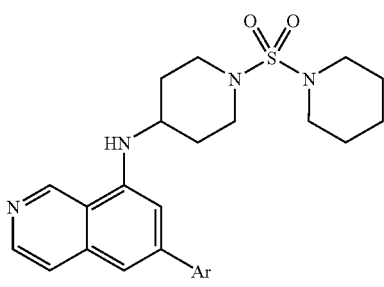
Qn32P
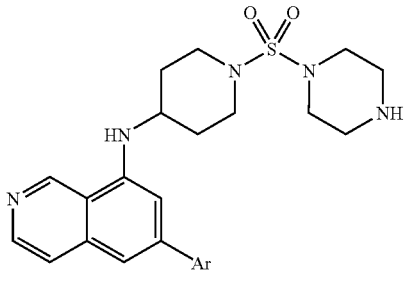
Qo1
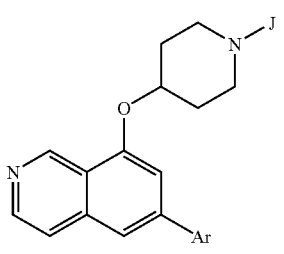

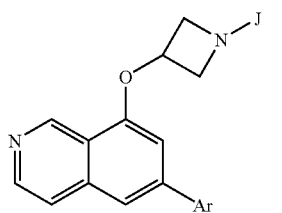
Qo2
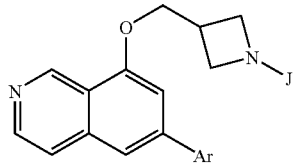
Qo9
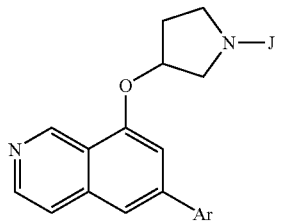
Qo3
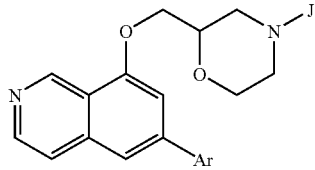
Qo10
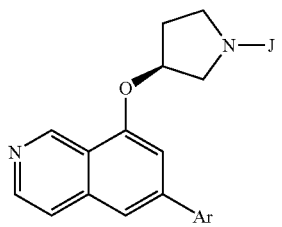
Qo4
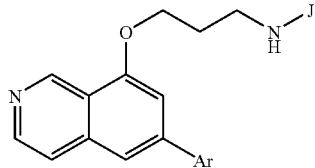
Qo11
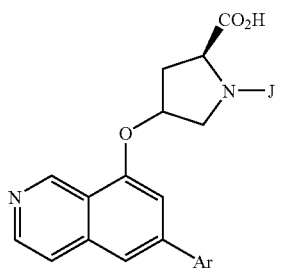
Qo5
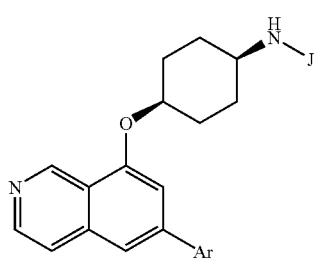
Qo12
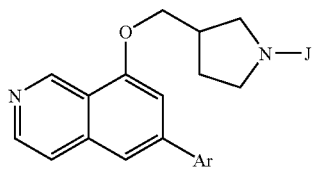
Qo6
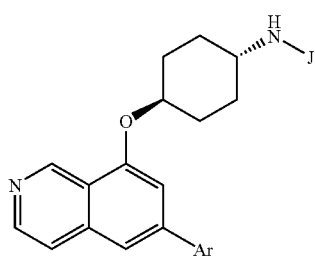
Qo13
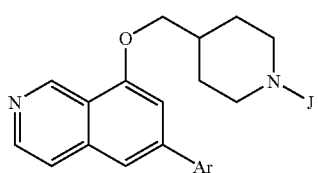
Qo7
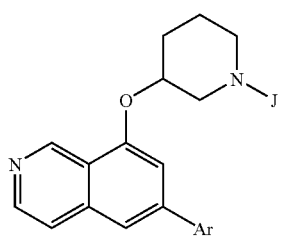
Qo14
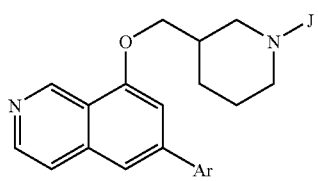
Qo8
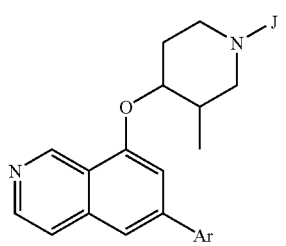
Qo15

Qo1-1
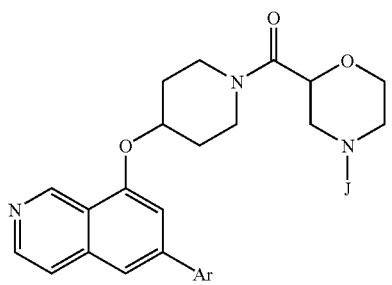
Qo1-2
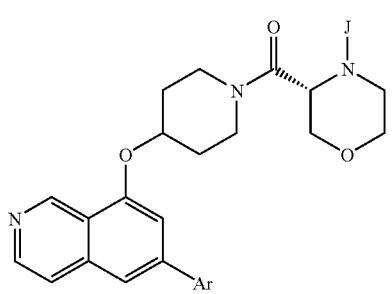
Qo1-3
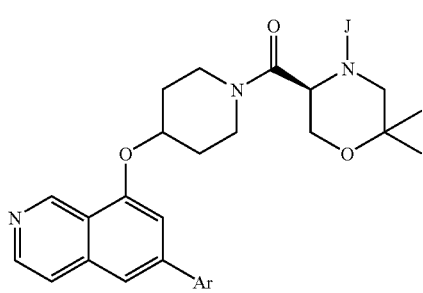
Qo1-4
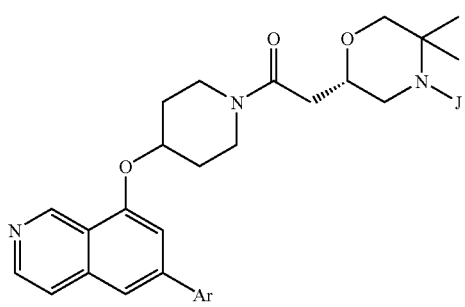
Qo1-5
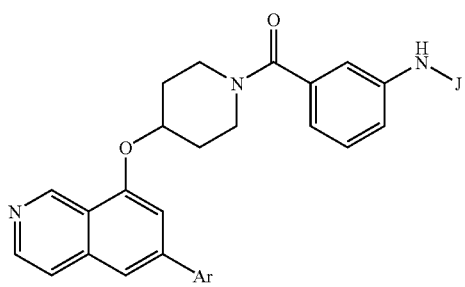
Qo1-6
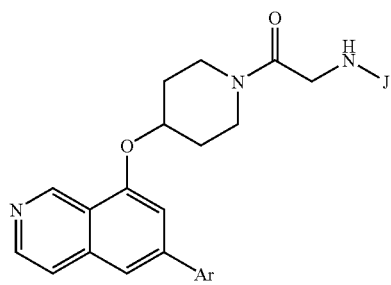
Qo1-7
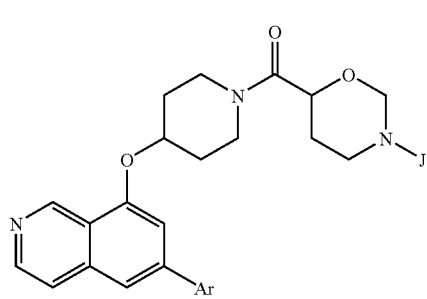
Qo1-8
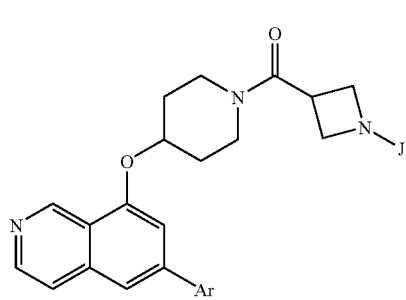
Qo1-9
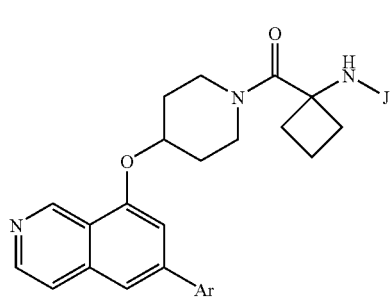
Qo1-10
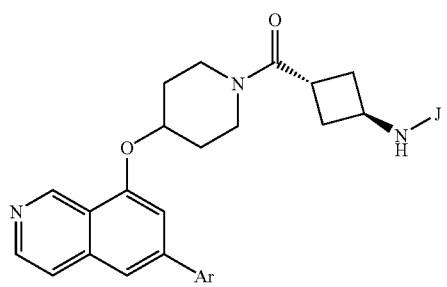

Qo1-11 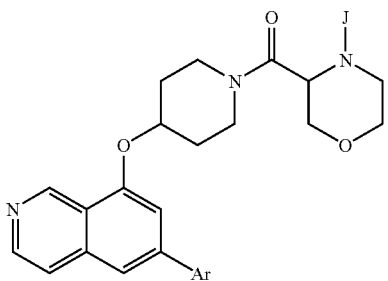

Qo2-1 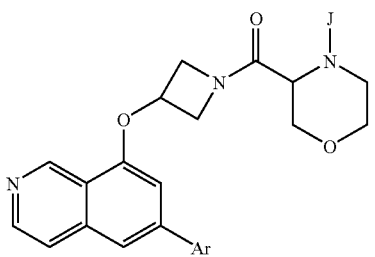

Qo2-2 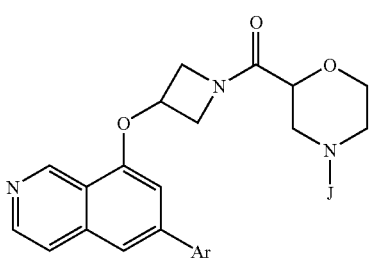

Qo2-3 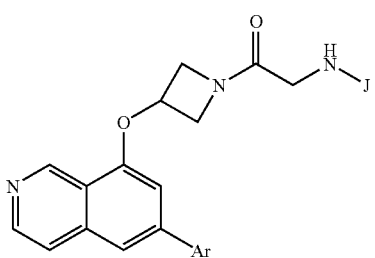

Qo2-3 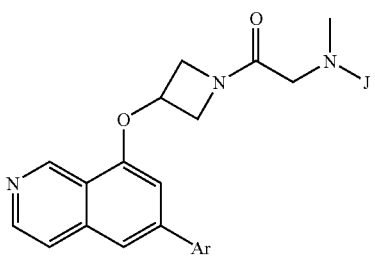

Qo2-5 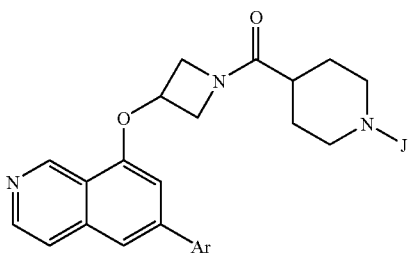

Qo2-6 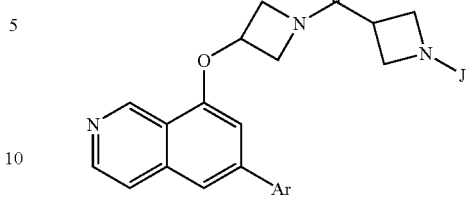

Qo9-1 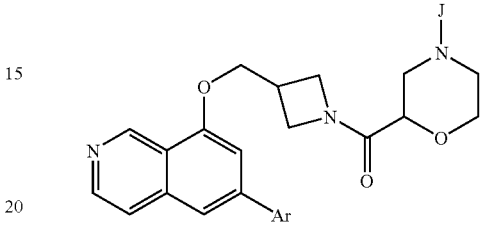

Qs1 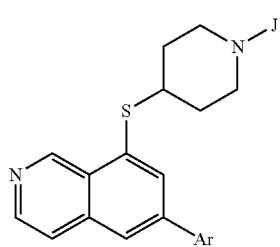

Qs2 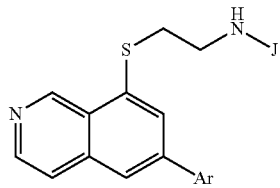

"LCMS": Liquid chromatography mass spectrometry spectrum data (m/z). Specifically, the following "method", "RTime", and "mass" are included.

"method": LCMS conditions. "A" indicates a condition that the above-mentioned "LCMS" apparatus (A) was used. "B" indicates a condition that the above-mentioned "LCMS" apparatus (B) was used. "C" indicates a condition that the above-mentioned "LCMS" apparatus (C) was used. Furthermore, "D" shown in the condition column indicates mass spectrum data measured by fast atom bombardment mass spectrometry (FAB-MS) using JEOL-JMS-SX102 (JEOL Ltd.).

"RTime": Retention time (min) in LCMS.

"mass": Mass spectrum data (MH+ or MH−) (however, "N.D." indicates that the molecular ion peak could not be detected). The m/z value in "mass" items indicates the value of a proton-added molecular ion (MH+) unless otherwise specified.

"Ref.": Example to be referred to for a production method. For example, "EXP. 1-N-2" in the Ref. column indicates that a compound can be synthesized according to the production method described in Example 1-N-2. Furthermore, "EXP. 1-N-1(a)" indicates that a compound can be synthesized according to the production method described in Step a of Example 1-N-1. If a slash appears in the Ref. column, the corresponding Example is described in the main text.

"Spl.": Manufacturer of a reagent used. May be referred to using the following abbreviations:

Tokyo Chemical Industry, TCI; Aldrich, Ald; Sigma-Aldrich, sAld; Kanto Chemical, KANTO; Wako Pure Chemical Industries, WAKO; Lancaster, LANC; Maybridge, MAYB; Acros, Acros; Nacalai Tesque, nakalai; Alfa Aesar, AAesar; Avocado, Avocado; Fluoro Chem, Fchem; Argonaut, Argonaut; ABCR, ABCR; Matrix, Matrix; Array BioPharma, Array; Oakwood, Oak; AstaTech, Ast; Enamin, Ena; Apollo, Apollo; CNH Technologies, CNH; AMRI, AMRI; Tyger, Tyger; Watanabe, Wata; Fluka, Fluka; NEOSYSTEM, NEO; Novabiochem, Nova; BACHEM, BACHEM; FRONTIER, FRON; Combi-Blocks, Combi; Strem, Strem; Life Chemicals, Life; J&W Pharmalab, J&W; Princeton Bio, Princeton; Bionet, Bionet; Otava, Otava; Synchem, Synchem; Asymchem, Asym; Varian, Varian; NeoMPS, NeoMPS; Tront, Tront; ChemBridge, Chemb; Synthonix, Syn; ACB Blocks, ACBB; Labotest, Labo; Focus, Focus; Hande Sciences, Hande; ASDI, ASDI; Bolon Molecular, Boron.

Furthermore, abbreviations in the main text and the tables are defined as follows:

n, normal; i, iso; s, secondary; t, tertiary; c, cyclo; Me, methyl; Et, ethyl; Pr, propyl; Bu, butyl; Pen, pentyl; Hex, hexyl; Hep, heptyl; Ph, phenyl; Bn, benzyl; Py, pyridyl; Indan, indanyl; Ac, acetyl; CHO, formyl; COOH, carboxyl; $NO_2$, nitro; DMA, dimethylamino; $NH_2$, amino; $CF_3$, trifluoromethyl; F, fluoro; Cl, Chloro; Br, bromo; $CF_3$, trifluoromethyl; OMe, methoxy; OH, hydroxy; TFA, trifluoroacetyl; $SO_2$, sulfonyl; CO, carbonyl; THF, tetrahydrofuran; DMF, N,N-dimethylformamide; DMSO, dimethyl sulfoxide; TsOH, p-toluenesulfonic acid; $Tf_2O$, anhydrous trifluoromethanesulfonic acid.

The number given before a substituent indicates the position of substitution. The hyphenated number before an abbreviation of an aromatic ring indicates the position of substitution of the aromatic ring. (S) included in a compound name or a formula indicates that an asymmetric carbon is in the S configuration, and (R) indicates the R configuration. Furthermore, a compound having asymmetric carbon atoms that does not include (R) or (S) indicates a mixture comprising (R) compounds and (S) compounds in an arbitrary ratio. Such a compound may be a racemic mixture of (R) compound and (S) compound.

In the present specification, unless otherwise specified, as apparent for those skilled in the art, A symbol

⋰ represents bonding towards the far side of the page (that is, α-orientation), a symbol

⌁ represents bonding towards the near side of the page (that is, β-orientation), a symbol

∿ represents either α-orientation or β-orientation, or a mixture of both, and a symbol

∕ represents a mixture of α-orientation and β-orientation.

When deprotection was required in a synthesis step of an Example compound in the Table, deprotection was performed by a known method, such as, for example, the methods described in Protective Groups in Organic Synthesis, John Wiley and Sons (2007).

Reference Example 1-1

(3-bromo-5-methoxyphenyl)methanol (Intermediate 1)

$NaBH_4$ (3.85 g; WAKO) was added to an ethanol (80 mL) and THF (20 mL) mixture solution of 3-bromo-5-methoxybenzaldehyde (22 g) with ice cooling and the resulting mixture was stirred at room temperature for 3 hours. The resulting mixture was poured into ice water (300 mL) and ethyl acetate (300 mL) was added thereto to extract the mixture with and the organic layer was washed with saturated aqueous sodium bicarbonate solution (300 mL) and then dried. The solvent was evaporated under reduced pressure to give the title compound (22.05 g).

(Intermediate 1 Rf (TLC)=0.6 (Hex:EtOAc=1:1))

3-Bromo-5-methoxybenzaldehyde can be produced from 1,3,5-tribromobenzene according to the methods described in J. Org. Chem., 2004, 69, p. 8982 and U.S. Patent No. 2004/198736.

Reference Example 1-2

1-bromo-3-(bromomethyl)-5-methoxybenzene (Intermediate 2)

Triphenylphosphine (28 g; KANTO) was added to a dichloromethane (150 mL) solution of Intermediate 1 (22.05 g) with ice cooling, the resulting mixture was stirred for approx. 10 minutes followed by the addition of N-bromosuccinimide (20 g; TCI), and the resulting mixture was stirred at room temperature for 13 hours and 30 minutes. The solvent was evaporated under reduced pressure and the residue was purified by column chromatography (n-hexane/ethyl acetate) to give the title compound (23.94 g).

(Intermediate 2 Rf (TLC)=0.8 (Hex:EtOAc=3:1))

Reference Example 1-3

2-(3-bromo-5-methoxyphenyl)acetonitrile (Intermediate 3)

Sodium cyanide (3.4 g; WAKO) was added to a DMSO (100 mL) solution of Intermediate 2 (16.3 g) at room temperature and the resulting mixture was stirred at 40° C. for 1 hour and 40 minutes. Ethyl acetate (300 mL) and saturated aqueous sodium bicarbonate solution (150 mL), and water (150 mL) were added to extract the reaction mixture, the reaction mixture was washed with saturated brine (300 mL), the organic layer was dried, and the solvent was evaporated under reduced pressure. The residue was purified by column chromatography (Yamazen; n-hexane/ethyl acetate) to give the title compound (11.37 g).

(Intermediate 3 Rf (TLC)=0.4 (Hex:EtOAc=3:1))

Reference Example 1-4

8-bromo-6-methoxyisoquinoline (Intermediate 6)

[Step a] 2-(3-bromo-5-methoxyphenyl)ethanamine (Intermediate 4)

A borane-tetrahydrofuran complex (1 M, 73.6 mL) was added to a THF (36.8 mL) solution of Intermediate 3 at room temperature and the resulting mixture was stirred to reflux at 80° C. for 2 hours. Methanol (26 mL) and 1 N hydrochloric acid (26 mL) were added to the reaction mixture solution and the resulting mixture was stirred at room temperature for 1 hour. The resulting mixture was neutralized with 1 N aqueous sodium hydroxide solution followed by the addition of ethyl acetate (100 mL) to extract the reaction mixture, the organic layer was dried, and then the solvent was evaporated under reduced pressure to give the title compound (8.76 g).

(Intermediate 4 Rf (TLC)=0.1 ($CH_3Cl$:MeOH=10:1))

[Step b]
8-bromo-6-methoxy-1,2,3,4-tetrahydroisoquinoline (Intermediate 5)

Paraformaldehyde (660 mg; WAKO) was added to a formic acid (50 mL) solution of Intermediate 4 (4.33 g) at 50° C. and the resulting mixture was stirred as it was for 13 hours and 30 minutes. The solvent was evaporated under reduced pressure followed by the addition of dichloromethane (100 mL) and 1 N aqueous sodium hydroxide solution (100 mL) to extract the reaction mixture, and the aqueous layer was further extracted with dichloromethane. The organic layer was combined and dried and then the solvent was evaporated under reduced pressure to give the title compound (4.49 g).

(Intermediate 5 LCMS: 242.1 (MH$^+$); retention time: 0.66 min; LCMS; condition A)

[Step c] 8-Bromo-6-methoxy-isoquinoline (Intermediate 6)

Sodium sulfate (2.8 g) and manganese dioxide (7.1 g; Ald) were added to a toluene (60 mL) solution of Intermediate 5 (1.99 g) and the resulting mixture was stirred at 140° C. for 24 hours. The reaction mixture was filtrated through celite followed by the addition of 2 N hydrochloric acid and the resulting mixture was washed with ether. The resulting mixture was neutralized with 5 N aqueous sodium hydroxide solution and then extracted with dichloromethane to give the title compound (698 mg).

(Intermediate 6 LCMS: 238.0 (MH$^+$); retention time: 3.64 min; LCMS; condition A)

$^1$H-NMR (DMSO); δ (ppm) 3.94 (3H, s), 7.44 (1H, d, J=2.2 Hz), 7.66 (1H, d, J=2.2 Hz), 7.76 (1H, d, 5.9 Hz), 8.53 (1H, d, 5.9 Hz), 9.29 (1H, s)

Reference Example 1-5

8-Bromoisoquinolin-6-ol (Intermediate 7)

An aqueous hydrobromic acid (180 mL) solution of Intermediate 6 (30 g) was stirred at 130° C. for 38 hours. The resulting mixture was stirred at room temperature for approx. 10 minutes followed by the addition of water (300 mL) and the precipitate was collected by filtration and dried to give the title compound (21 g).

(Intermediate 7 LCMS: 224.0 (MH$^+$); retention time: 0.63 min; LCMS; condition A)

Reference Example 1-6-1

8-bromoisoquinolin-6-yl trifluoromethanesulfonate (Intermediate 8)

Triethylamine (18 mL; WAKO) and N-phenylbis(trifluoromethanesulfonimide) (14 g; TCI) were added to a chloroform (130 mL) solution of Intermediate 7 (10 g) at room temperature and the resulting mixture was stirred at 40° C. for 12 hours and 30 minutes. The resulting mixture was stirred at room temperature for approx. 10 minutes and washed with saturated brine, the organic layer was dried, the solvent was evaporated under reduced pressure, and the residue was purified by column chromatography (Yamazen; n-hexane/ethyl acetate) to give the title compound (10.2 g).

(Intermediate 8 LCMS: 356.0 (MH$^+$); retention time: 4.62 min; LCMS; condition B)

Reference Example 1-6-2

6-(benzyloxy)-8-bromoisoquinoline (Intermediate 9)

Benzyl alcohol (0.25 mL; Ald), triphenylphosphine (1.29 g), and TMAD (850 mg; Ald) were added to a toluene (30 mL) solution of Intermediate 7 (500 mg) and the resulting mixture was stirred at room temperature for 13 hours. The reaction mixture solution was filtrated, the solvent was evaporated under reduced pressure, and the residue was purified by column chromatography (Yamazen; n-hexane/ethyl acetate) to give the title compound (186 mg).

(Intermediate 9 LCMS: 314.1 (MH$^+$); retention time: 1.71 min; LCMS; condition A)

Reference Example 1-6-3

8-bromoisoquinolin-6-yl 4-methylbenzenesulfonate (Intermediate 10)

Triethylamine (0.137 mL) was added to a dichloromethane (5 mL) solution of Intermediate 7 (100 mg) and p-toluenesulfonic acid chloride (66 mg; WAKO) at room temperature and the resulting mixture was stirred as it was for 15 hours. The resulting mixture was diluted with dichloromethane and washed with water, the organic layer was dried, then the solvent was evaporated under reduced pressure, and the residue was purified by column chromatography (Yamazen; n-hexane/ethyl acetate) to give the title compound (92.9 mg).

(Intermediate 10 LCMS: 377.8 (MH$^+$); retention time: 1.81 min; LCMS; condition A)

Reference Example Br-1

3-(8-bromoisoquinolin-6-yl)benzonitrile (Intermediate Br-1)

An aqueous solution (50 mL) of sodium carbonate (3.5 g) was added to a THF (200 mL) solution of Intermediate 8 (3.9 g), 3-cyanophenylboronic acid (which may be referred to as sbo1; 1.6 g; WAKO), PdCl$_2$dppf.CH$_2$Cl$_2$ (1.78 g; TCI) at room temperature and the resulting mixture was stirred as it was for 6 and half hours. Ethyl acetate (300 mL), saturated brine, and water were added to extract the reaction mixture, then the organic layer was dried, the solvent was evaporated under reduced pressure, and the residue was purified by column chromatography (Yamazen; chloroform/methanol) to give the title compound (2.1 g).

(Intermediate Br-1 LCMS: 309.0 (MH$^+$); retention time: 1.71 min; LCMS; condition A)

Reference Examples Br-2 to Br-7

According to the method of Reference Example Br-1, syntheses in Reference Examples Br-2 to Br-7 were performed using Intermediate 8 as a raw material to synthesize Intermediates Br-2 to Br-7 (Table Br). In Table Br, the Ar column represents "Ar" in the general formula QBr shown below and the structures corresponding to each abbreviation are shown in Table Ar provided later. Further, in Table Br, the SM1 column represents compounds used in each Reference Example corresponding to 3-cyanophenylboronic acid (which may be referred to as sbo1) used in Reference Example Br-1. Further, the Reference Example number of a compound produced in each Reference Example is used as an intermediate number thereof. For example, the compound obtained in Reference Example Br-2 is Intermediate Br-2. In Table Br, "exp." and "LCMS" are defined as described above, and abbreviations such as "sbo1" and "Ar1" represent compounds or groups corresponding to abbreviations in Tables sbo and Ar.

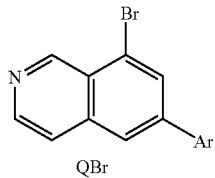

QBr

TABLE BR

| EXP. | SM1 | Ar | method | LCMS RTime | MH+ |
|---|---|---|---|---|---|
| Br-1 | sbo1 | Ar1 | A | 1.17 | 309.0 |
| Br-2 | sbo2 | Ar2 | A | 2.10 | 318.2 |
| Br-3 | sbo3 | Ar3 | A | 1.16 | 285.1 |
| Br-4 | sbo4 | Ar4 | A | 1.73 | 326.9 |
| Br-5 | sbo5 | Ar7 | A | 2.21 | 370.0 |
| Br-6 | sbo6 | Ar8 | A | 1.81 | 413.2 |
| Br-7 | sbo41 | Ar41 | A | 1.79 | 327.2 |
| Br-8 | sbo192 | Ar192 | A | 1.18 | 299.1 |
| Br-9 | sbo186 | Ar186 | A | 1.02 | 299.1 |
| Br-10 | sbo161 | Ar161 | A | 0.94 | 313.3 |

Reference Example N-2

1-(ethylsulfonyl)piperidin-4-amine (Intermediate N-2)

Triethylamine (10 mL) was added to a dichloromethane (90 mL) solution of Benzyl piperidin-4-ylcarbamate (5.09 g) at 0° C. followed by the dropwise addition of ethane sulfonylchloride (which may be referred to as sso10; 3.2 mL; TCI) and the resulting mixture was stirred overnight slowly raising to room temperature. 1 N Hydrochloric acid (90 mL; WAKO) was added to the reaction mixture solution, the resulting mixture was stirred for approx. 10 minutes, then the reaction mixture was extracted with chloroform, the organic layer was dried, the solvent was evaporated under reduced pressure, and the residue was purified by silica gel column chromatography (Yamazen; chloroform/methanol). Palladium hydroxide (20% by weight, Wet-type, 5 g; NECHEM) was added to a methanol (90 mL) solution of this product under a nitrogen atmosphere. The atmosphere in a reaction vessel was replaced with hydrogen at room temperature, the resulting mixture was stirred overnight, the atmosphere in the reaction vessel was returned to a nitrogen atmosphere, the residue was removed by filtration, the solvent was evaporated under reduced pressure, and the residue was dried to give the title compound (3.32 g).

(Intermediate N-2 LCMS: 193.1 (MH$^+$); retention time: 0.28 min; LCMS; condition A)

Reference Example N-1

1-(methylsulfonyl)piperidin-4-amine (Intermediate N-1)

Reference Example N-3

1-(cyclopropylsulfonyl)piperidin-4-amine (Intermediate N-3)

Intermediates N-1 and N-3 were synthesized using mesyl chloride (which may be referred to as sso1) and cyclopropylsulfonyl chloride (which may be referred to as sso4), respectively, instead of ethanesulfonyl chloride described in the step of Reference Example N-2.

Reference Example N-4

(4-aminopiperidin-1-yl)(6-methylpyridin-3-yl) methanone (Intermediate N-4)

Triethylamine (14 mL; WAKO) was added to a dichloromethane (98 mL) solution of Benzyl piperidin-4-ylcarbamate (5.33 g), 6-methylnicotinic acid (which may be referred to as sco100; 4.0 g; Ald), HOAt (4.0 g; Wata) and WSC.HCl (5.7 g; Wata) and the resulting mixture was stirred overnight at room temperature. Saturated sodium hydrogencarbonate solution (50 mL) was added to the reaction mixture solution, the resulting mixture was extracted, the organic layer was dried, the solvent was evaporated under reduced pressure, and the residue was purified by silica gel column chromatography (Yamazen; chloroform/methanol). Palladium carbon (10% by weight, Pe-type, 3.45 g; NECHEM) was added to a methanol (90 mL) solution of this product under a nitrogen atmosphere. The atmosphere in a reaction vessel was replaced with hydrogen at room temperature, the resulting mixture was stirred overnight, the atmosphere in the reaction vessel was returned to a nitrogen atmosphere, the residue was removed by filtration, the solvent was evaporated under reduced pressure, and the residue was dried to give the title compound (4.05 g).

(Intermediate N-4 LCMS: 220.5 (MH$^+$); retention time: 0.28 min; LCMS; condition A)

Reference Example N-5

(4-aminopiperidin-1-yl)(cyclopropyl)methanone (Intermediate N-5)

Reference Example N-6

5-(4-aminopiperidine-1-carbonyl)picolinonitrile (Intermediate N-6)

Reference Example N-7

(4-aminopiperidin-1-yl)(pyridin-3-yl)methanone (Intermediate N-7)

Reference Example N-8

1-(4-aminopiperidin-1-yl)-2-methoxyethanone (Intermediate N-8)

Intermediates N-5, N-6, N-7 and N-8 were synthesized using cyclopropanecarboxylic acid (which may be referred to as sco2), 6-cyanonicotinic acid (which may be referred to as sco6), nicotinic acid (which may be referred to as sco28) and methoxyacetic acid (which may be referred to as sco96), respectively, instead of 6-methylnicotinic acid described in the step of Reference Example N-4.

Reference Example N-9

1-(4-aminopiperidin-1-yl)ethanone (Intermediate N-9)

Reference Example N-10

1-(4-aminopiperidin-1-yl)propan-1-one (Intermediate N-10)

Intermediates N-9 and N-10 were synthesized using acetic anhydride (which may be referred to as sco1) and propionyl chloride (TCI), respectively, instead of ethanesulfonyl chloride described in the step of Reference Example N-2.

Reference Example N-11

1-(cyclobutylmethylsulfonyl)piperidin-4-amine (Intermediate N-11)

Sodium sulfite (1.3 g; WAKO), ethanol (3.9 mL), and water (5.8 mL) were added to (bromomethyl)cyclobutane (0.8 mL; Ald), the resulting mixture was stirred at 100° C. for 2 hours, and the solvent was evaporated under reduced pressure. Toluene (10 mL), DMF (20 µL), and thionyl chloride (1.9 mL; TCI) were successively added to the residue, the resulting mixture was stirred at 110° C. for 5 hours, and the solvent was evaporated under reduced pressure. This residue was used instead of ethanesulfonyl chloride described in the step of Reference Example N-2 to give the title compound.

Reference Example N-12

1-(cyclopropylmethylsulfonyl)piperidin-4-amine (Intermediate N-12)

Reference Example N-13

1-(((tetrahydrofuran-2-yl)methylsulfonyl)piperidin-4-amine (Intermediate N-12)

Intermediates N-12 and N-13 were synthesized using (bromomethyl)cyclopropane and tetrahydrofurfuryl bromide, respectively, instead of (bromomethyl)cyclobutane described in the step of Reference Example N-11.

Reference Example N-14

3-(4-aminopiperidin-1-ylsulfonyl)propyl acetate (Intermediate N-14)

[Step a] benzyl 1-(3-iodopropylsulfonyl)piperidin-4-ylcarbamate (Intermediate N-14-1)

Triethylamine (3 mL) was added to a dichloromethane (200 mL) solution of Benzyl piperidin-4-ylcarbamate (1.2 g) at 0° C. followed by the dropwise addition of 3-chloropropane sulfonylchloride (4.3 mL; TCI) and the resulting mixture was slowly stirred overnight with raising to room temperature. 1 N Hydrochloric acid (90 mL; WAKO) was added to the reaction mixture solution, the resulting mixture was stirred for approx. 10 minutes, then the reaction mixture was extracted with chloroform, the organic layer was dried, the solvent was evaporated under reduced pressure, and the residue was purified by silica gel column chromatography (Yamazen; chloroform/methanol). 100 mg of this purified compound was dissolved in acetone (10 mL) followed by the addition of sodium iodide (KANTO; 44 mg) and the resulting mixture was stirred at room temperature for 12 hours. Sodium iodide (KANTO; 44 mg) was further added, the resulting mixture was stirred at 40° C. for 24 hours followed by the addition of sodium iodide (KANTO; 132 mg), and the resulting mixture was stirred at 60° C. for 24 hours. The reaction mixture solution was cooled to room temperature, the residue was collected by filtration using a Kiriyama funnel to give the title compound (64 mg).

(LCMS: 467.2 (MH$^+$); retention time: 1.68 min; LCMS; condition A)

[Step b] benzyl 1-(3-morpholinopropylsulfonyl)piperidin-4-ylcarbamate (Intermediate N-14-2)

Morpholine (22 µL) and sodium carbonate (27 mg) were added to an acetonitrile (0.5 mL) solution of Intermediate N-14-1 (15 mg) and the resulting mixture was stirred at 80° C. for 12 hours. Water was added to the reaction mixture solution and the resulting mixture was extracted with ethyl acetate. The organic layer was dried and the solvent was evaporated under reduced pressure to give the title compound (13 mg).

(LCMS: 426.3 (MH$^+$); retention time: 1.03 min; LCMS; condition A)

[Step c] 3-(4-aminopiperidin-1-ylsulfonyl)propyl acetate

Palladium/carbon (10% by weight, Wet-type, 6 mg; NECHEM) was added to a methanol (150 µL) solution of Intermediate N-14-2 (13 mg) under a nitrogen atmosphere. The atmosphere in a reaction vessel was replaced with hydrogen at room temperature, the resulting mixture was stirred overnight, the atmosphere in the reaction vessel was returned to a nitrogen atmosphere, the residue was removed by filtration, the solvent was evaporated under reduced pressure, and the residue was dried to give the title compound (8.1 mg).

(LCMS: 292.3 (MH$^+$); retention time: 0.25 min; LCMS; condition A)

Reference Example N-18

1-(3-(4-methylpiperazin-1-yl)propylsulfonyl)piperidin-4-amine (Intermediate N-18)

Reference Example N-25

1-(3-(dimethylamino)propylsulfonyl)piperidin-4-amine (Intermediate N-25)

Intermediates N-18 and N-25 were synthesized using 1-methylpiperazine and dimethylamine, respectively, instead of morpholine described in the step of Reference Example N-14.

Reference Example N-15

3-(4-aminopiperidin-1-ylsulfonyl)propyl acetate (Intermediate N-15)

Potassium acetate (12 mg) was added to a DMF (1 mL) solution of Intermediate N-14-1 (15 mg) and the resulting mixture was stirred at 80° C. for 15 hours. Saturated aqueous sodium bicarbonate solution was added to the reaction mixture solution and the resulting mixture was extracted with ethyl acetate. The organic layer was dried and the solvent was evaporated under reduced pressure. The title compound was obtained from this product according to the method described in Step c of Reference Example N-14.

(LCMS: 265.2 (MH$^+$); retention time: 0.27 min; LCMS; condition A)

Reference Example N-16

4-(4-aminopiperidin-1-ylsulfonyl)butanenitrile (Intermediate N-16)

Sodium cyanide (6 mg) was added to a DMSO (1 mL) solution of Intermediate N-14-1 (15 mg) and the resulting mixture was stirred at 80° C. for 1 hour. Saturated aqueous sodium bicarbonate solution was added to the reaction mixture solution and the resulting mixture was extracted with ethyl acetate. The organic layer was dried and the solvent was evaporated under reduced pressure. The title compound (2.3 mg) was obtained from this product according to the method described in Step c of Reference Example N-14.

(LCMS: 232.2 (MH$^+$); retention time: 0.27 min; LCMS; condition A)

Reference Example N-17

1-(fluoromethylsulfonyl)piperidin-4-amine (Intermediate N-17)

Triethylamine (10 mL) was added to a dichloromethane (90 mL) solution of Benzyl piperidin-4-ylcarbamate (5.09 g) at 0° C. followed by the dropwise addition of methanesulfonyl chloride (which may be referred to as sbo1; 3 mL; TCI) and the resulting mixture was slowly stirred overnight with raising to room temperature. 1 N Hydrochloric acid (90 mL; WAKO) was added to the reaction mixture solution, the resulting mixture was stirred for approx. 10 minute, the resulting mixture was extracted with chloroform, the organic layer was dried, then the solvent was evaporated under reduced pressure, and the residue was purified by silica gel column chromatography (Yamazen; chloroform/methanol). 200 mg of this purified compound was dissolved in THF (4 mL) and the resulting mixture was added dropwise to a THF (5 mL) solution of LDA prepared from diisopropylamine (0.2 mL; WAKO) and normal butyllithium (1.6 M, 1 mL; KANTO) at −78° C. The resulting mixture was stirred for 30 minutes followed by the dropwise addition of THF (3 mL) solution of N-fluorobenzenesulfonimide (320 mg) and the resulting mixture was slowly stirred overnight with raising to room temperature. Saturated aqueous ammonium chloride solution was added to the reaction mixture solution and the resulting mixture was extracted with ethyl acetate. The organic layer was dried, the solvent was evaporated under reduced pressure, and the residue was purified by silica gel column chromatography (Yamazen; chloroform/methanol). The title compound (10 mg) was obtained from this purified product according to the method described in Step c of Reference Example N-14.

(LCMS: 197.2 (MH$^+$); retention time: 0.27 min; LCMS; condition A)

Reference Example N-19

1-(2-(dimethylamino)ethylsulfonyl)piperidin-4-amine (Intermediate N-19)

Triethylamine (3.4 mL) was added to a dichloromethane (300 mL) solution of Benzyl piperidin-4-ylcarbamate (2.2 g) at 0° C. followed by the dropwise addition of 2-chloroethanesulfonyl chloride (2.6 mL; TCI) and the resulting mixture was slowly stirred overnight with raising to room temperature. 1 N Hydrochloric acid (90 mL; WAKO) was added to the reaction mixture solution, the resulting mixture was stirred for approx. 10 minutes, then the reaction mixture was extracted with chloroform, the organic layer was dried, the solvent was evaporated under reduced pressure, and the residue was purified by silica gel column chromatography (Yamazen; chloroform/methanol). 30 mg of this purified compound was dissolved in methanol (1 mL) followed by the addition of dimethylamine (2 M, 0.2 mL; Ald), the resulting mixture was stirred at 100° C. for 2 hours with microwave irradiation, and then the solvent was evaporated under reduced pressure. The title compound was obtained from this residue according to the method described in Step c of Reference Example N-14.

(LCMS: 236.2 (MH$^+$); retention time: 0.27 min; LCMS; condition A)

Reference Example N-20

1-(2-morpholinoethylsulfonyl)piperidin-4-amine (Intermediate N-20)

Reference Example N-21

1-(2-(diethylamino)ethylsulfonyl)piperidin-4-amine (Intermediate N-21)

Reference Example N-22

1-(2-(pyrrolidin-1-yl)ethylsulfonyl)piperidin-4-amine (Intermediate N-22)

Reference Example N-23

1-(2-(piperidin-1-yl)ethylsulfonyl)piperidin-4-amine (Intermediate N-23)

Intermediates N-20, N-21, N-22 and N-23 were synthesized using morpholine, diethylamine, pyrrolidine and piperidine, respectively, instead of dimethylamine described in the step of Reference Example N-19.

Reference Example N-24

4-amino-N-methylpiperidine-1-sulfonamide (Intermediate N-24)

Triethylamine (1.5 mL) was added to a dichloromethane (30 mL) solution of Benzyl piperidin-4-ylcarbamate (580 mg) at 0° C. followed by the dropwise addition of chlorosulfonic acid (290 µL; TCI), the resulting mixture was stirred at room temperature for 4 hours, and the solvent was evaporated under reduced pressure. Benzene (32 mL) and phosphorus pentachloride (0.7 g; WAKO) were added to this residue and the resulting mixture was stirred at 80° C. for 1.5 hours. The reaction mixture solution was cooled to room temperature followed by the addition of 1 N aqueous sodium hydroxide solution (10 mL), the resulting mixture was extracted with dichloromethane, the organic layer was dried, then the solvent was evaporated under reduced pressure, and the residue was purified by silica gel column chromatography (Yamazen; hexane/ethyl acetate). 30 mg of this purified compound was dissolved in dichloromethane (0.4 mL) followed by the addition of 3,5-lutidine (0.4 mL; WAKO) and methylamine (2 M, 70 μL; Ald) and the resulting mixture was stirred at room temperature for 24 hours. 1 N hydrochloric acid (2 mL; WAKO) was added to the reaction mixture solution, the resulting mixture was stirred for approx. 10 minutes, then the reaction mixture was extracted with dichloromethane, the organic layer was dried, and then the solvent was evaporated under reduced pressure. The title compound was obtained from this residue according to the method described in Step c of Reference Example N-14.

(LCMS: 194.1 (MH$^+$); retention time: 0.27 min; LCMS; condition A)

Reference Example N-26

1-(morpholinosulfonyl)piperidin-4-amine (Intermediate N-26)

Reference Example N-27

4-amino-N,N-dimethylpiperidine-1-sulfonamide (Intermediate N-27)

Reference Example N-28

4-amino-N-ethylpiperidine-1-sulfonamide (Intermediate N-28)

Reference Example N-29

4-amino-N-isopropylpiperidine-1-sulfonamide (Intermediate N-29)

Reference Example N-30

1-(4-methylpiperazin-1-ylsulfonyl)piperidin-4-amine (Intermediate N-30)

Reference Example N-31

1-(piperidin-1-ylsulfonyl)piperidin-4-amine (Intermediate N-31)

Reference Example N-32 tert-butyl 4-(4-aminopiperidin-1-ylsulfonyl)piperazine-1-carboxylate (Intermediate N-32)

Intermediates N-26, N-27, N-28, N-29, N-30, N-31 and N-32 were synthesized using morpholine, dimethylamine, ethylamine, isopropylamine, 1-methyl piperazine, piperidine and 1-(tert-butoxycarbonyl)piperazine, respectively, instead of methylamine described in the step of Reference Example N-24.

Reference Example Tf-1

8-(1-(methylsulfonyl)piperidin-4-ylamino)isoquinolin-6-yl trifluoromethanesulfonate (Intermediate Tf-1)

[Step a] 6-methoxy-N-(1-(methylsulfonyl)piperidin-4-yl)isoquinolin-8-amine (Intermediate Tf-1-1)

The title compound (1.09 g) was obtained from Intermediate 6 (2 g) and Intermediate N-1 by the similar method as Step a of Example 1-N-1.

(Intermediate Tf-1-1 LCMS: 336.4 (MH$^+$); retention time: 0.84 min; LCMS; condition A)

[Step b] 8-(1-(methylsulfonyl)piperidin-4-ylamino)isoquinolin-6-ol (Intermediate Tf-1-2)

A dichloromethane solution of boron tribromide (1 M, 44.7 mL; TCI) was added to a dichloromethane solution of Intermediate Tf-1-1 (1.0 g) at 0° C. under a nitrogen atmosphere and the resulting mixture was returned to room temperature and then stirred overnight at 50° C. Methanol was added and then the solvent was evaporated under reduced pressure to give the title compound (1.8 g).

(Intermediate Tf-1-2 LCMS: 322.2 (MH$^+$); retention time: 0.79 min; LCMS; condition A)

[Step c] 8 (1-(methylsulfonyl)piperidin-4-ylamino)isoquinolin-6-yltrifluoromethanesulfonate The title compound (0.62 g) was obtained from Intermediate Tf-1-2 (1.8 g) by the similar method as Reference Example 1-6-1.

(Intermediate Tf-1 LCMS: 454.3 (MH$^+$); retention time: 1.50 min; LCMS; condition A)

Reference Example Tf-2

8-(1-(ethylsulfonyl)piperidin-4-ylamino)isoquinolin-6-yl trifluoromethanesulfonate (Intermediate Tf-2)

Reference Example Tf-3

8 amine 8 (1-(cyclopropylsulfonyl)piperidin-4-ylamino)isoquinolin-6-yl trifluoromethanesulfonate (Intermediate Tf-3)

Intermediates Tf-2 and Tf-3 were synthesized using Intermediates N-2 and N-3, respectively, instead of Intermediate N-1 described in the step of Reference Example Tf-1.

Example 1-N-1

3-(8-(piperidin-4-ylamino)isoquinolin-6-yl)benzonitrile

[Step a] tert-butyl 4-(6-(3-cyanophenyl)isoquinoline-8-ylamino)piperidine-1-carboxylate (Intermediate 1-N-1)

Sodium t-butoxide (1.58 g; TCI) was added to a toluene solution of Intermediate Br-1 (1.7 g), 4-amino-1-N-Boc-piperidine (which may be referred to as sa; 2.2 g; WAKO), Pd$_2$(dba)$_3$ (1.0 g; Ald), and BINAP (1.36 g; Ald) under a nitrogen atmosphere and the resulting mixture was stirred at 80° C. for 8 hours. The resulting mixture was stirred at room temperature for approx. 10 minutes, then the reaction mixture solution was filtrated, and the filtrate was concentrated under reduced pressure. The residue was purified by column chromatography (Yamazen; hexane/ethyl acetate) to give the title compound (1.2 g).

(Intermediate 1-N-1 LCMS: 429.4 (MH$^+$); retention time: 1.48 min; LCMS; condition A)

[Step b] 3-(8-(piperidin-4-ylamino)isoquinolin-6-yl) benzonitrile

A methanol hydrochloride solution (10%, 20 mL; TCI) of Intermediate 1-N-1 (1.2 g) was stirred at 50° C. for 2 and half hours. The resulting mixture was stirred at room temperature for approx. 10 minutes followed by the addition of ether and the precipitate was collected by filtration and dried to give the title compound (997 mg).

(LCMS: 329.3 (MH$^+$); retention time: 0.77 min; LCMS; condition A)

Example 1-N-22

3-(8-(3-(1H-imidazol-1-yl)propylamino)isoquinolin-6-yl)benzonitrile

Sodium t-butoxide (23.1 mg) was added to a toluene solution of Intermediate Br-1 (24.7 mg), N-(3-aminopropyl)imidazole (which may be referred to as sa22; 40.1 mg; TCI), Pd$_2$(dba)$_3$ (14.7 mg), and BINAP (19.9 mg) under a nitrogen atmosphere and the resulting mixture was stirred at 80° C. for 8 hours. The resulting mixture was stirred at room temperature for approx. 10 minutes, then the reaction mixture solution was filtrated, and the solvent was evaporated. The residue was purified by preparative HPLC to give the title compound (6.0 mg).

(LCMS: 354.2 (MH$^+$); retention time: 2.29 min; LCMS; condition B)

Example 1-o-1

3-(8-(piperidin-4-yloxy)isoquinolin-6-yl)benzonitrile

[Step a] tert-butyl 4-(6-(3-cyanophenyl)isoquinoline-8-yloxy)piperidine-1-carboxylate (Intermediate 1-o-1)

Cesium carbonate (958 mg; Ald) was added to a toluene solution of Intermediate Br-1 (300 mg), 4-hydroxy-1-N-Boc-piperidine (which may be referred to as soh1; 604 mg; Ald), Pd(OAc)$_2$ (44.9 mg; WAKO), and 1,1'-binaphthyl-2-yldi-tert-butylphosphine (94.6 mg; Strem) under a nitrogen atmosphere and the resulting mixture was stirred overnight at 70° C. The resulting mixture was stirred at room temperature for approx. 10 minutes, then the reaction mixture solution was filtrated, and the filtrate was concentrated under reduced pressure. The residue was purified by column chromatography (Yamazen; chloroform/methanol) to give the title compound (256 mg).

(Intermediate 1-o-1 LCMS: 430.5 (MH$^+$); retention time: 1.70 min; LCMS; condition A)

[Step b] 3-(8-(piperidin-4-yloxy)isoquinolin-6-yl) benzonitrile

The title compound (186 mg) was obtained from Intermediate 1-o-1 (256 mg) according to the method described in Step b of Example 1-N-1.

(LCMS: 330.0 (MH$^+$); retention time: 0.85 min; LCMS; condition A)

Example 1-o-39

3-(8-(cyclopropylmethoxy)isoquinolin-6-yl)benzonitrile

Cesium carbonate (52.7 mg) was added to a 1,4-dioxane solution of Intermediate Br-1 (24.7 mg), cyclopropylmethanol (which may be referred to as soh39; 29.4 mg; Ald), Pd(OAc)$_2$ (11.1 mg), 1,1'-binaphthyl-2-yldi-tert-butylphosphine (26.0 mg) and the resulting mixture was stirred at 80° C. for 21 hours. The reaction mixture solution was filtrated through celite and then the filtrate was concentrated. The residue was dissolved in dichloromethane (250 µL), the resulting mixture was added to SCX resin (300 mg; Varian) and agitated by shaking for 3 hours. The reaction mixture was filtrated, then the SCX resin was washed with dichloromethane and methanol followed by the addition of 2 M ammonia methanol solution to elute, and the solvent was evaporated to give the title compound (11.0 mg).

(LCMS: 301.3 (MH$^+$); retention time: 1.50 min; LCMS; condition A)

Example 1-s-1

3-(8-(piperidin-4-ylthio)isoquinolin-6-yl)benzonitrile

[Step a] tert-butyl 4-(6-(3-cyanophenyl)isoquinoline-8-ylthio)piperidine-1-calboxylate (Intermediate 1-s-1)

Diisopropylethylamine (211 µL; TCI) was added to 1,4-dioxane solution of Intermediate Br-1 (187 mg), 4-mercapto-1-N-Boc-piperidine (which may be referred to as ssh1; 132 mg; Intermediate 1-s-1), Pd$_2$(dba)$_3$ (55.5 mg), and Xanthphos (70.1 mg; Ald) under a nitrogen atmosphere and the resulting mixture was stirred overnight at 80° C. The resulting mixture was stirred at room temperature for approx. 10 minutes, then the reaction mixture solution was filtrated, and the filtrate was concentrated under reduced pressure. The residue was purified by column chromatography (Yamazen; chloroform/methanol) to give the title compound (1.36 mg).

(Intermediate 1-s-1 LCMS: 446.4 (MH$^+$); retention time: 5.28 min; LCMS; condition B)

[Step b] 3-(8-(piperidin-4-ylthio)isoquinolin-6-yl) benzonitrile

The title compound (90.5 mg) was obtained from Intermediate 1-s-1 (136 mg) according to the method described in Step b of Example 1-N-1.

(LCMS: 346.2 (MH$^+$); retention time: 1.01 min; LCMS; condition A)

Example 1-N-3 to 1-N-62, 1-o-2 to 1-o-56, 1-s-2

Compounds of Examples 1-N-3 to 1-N-62, 1-o-2 to 1-o-56, and 1-s-2 were synthesized according to the method in Example 1-N-1, 1-N-22, 1-o-1, 1-o-39, or 1-s-1 (Tables 1-N, 1-o, and 1-s). At this time, for example, the method described in Step b of Example 1-N-1 was used if deprotection was required. The X and Ar columns in Tables 1-N, 1-o, and 1-s represent "X" and "Ar," respectively, in the following general formula "Q1. "SM1," "SM2," "LCMS," and "Ref" are defined as described above. Abbreviations such as "a1," "Ar1," "sa1," "oh1," "soh1," "sh1," and "ssh1" represent compounds or groups corresponding to abbreviations in Tables a, Ar, sa, oh, soh, sh, and ssh, respectively.

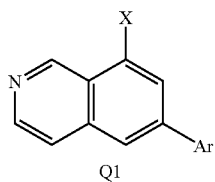

Example compounds 1-o-24, -31, -41 to -44, and -49 to -51 in Table 1-o were finally purified by preparative HPLC.

TABLE 1-N

| EXP. | SM1 | SM2 | K | Ar | LCMS method | RTime | MH+ | Ref. |
|---|---|---|---|---|---|---|---|---|
| 1-N-1 | IM. Br-1 | sa1 | a1 | Ar1 | A | 0.77 | 329.3 | |
| 1-N-2 | IM. Br-1 | sa2 | a2 | Ar1 | C | 2.98 | 329.3 | EXP. 1-N-1(a) |
| 1-N-3 | IM. Br-1 | sa3 | a3 | Ar1 | C | 2.96 | 314.9 | EXP. 1-N-1(a) |
| 1-N-4 | IM. Br-1 | sa4 | a4 | Ar1 | A | 0.74 | 301.3 | EXP. 1-N-22 |
| 1-N-5 | IM. Br-1 | sa5 | a5 | Ar1 | B | 2.01 | 303.2 | EXP. 1-N-1(a) |
| 1-N-6 | IM. Br-1 | sa6 | a6 | Ar1 | C | 3.03 | 315.0 | EXP. 1-N-1(a) |
| 1-N-7 | IM. Br-1 | sa7 | a7 | Ar1 | B | 2.27 | 329.3 | EXP. 1-N-1(a) |
| 1-N-8 | IM. Br-1 | sa8 | a8 | Ar1 | A | 0.84 | 329.3 | EXP. 1-N-1(a) |
| 1-N-9 | IM. Br-1 | sa9 | a9 | Ar1 | A | 0.84 | 329.3 | EXP. 1-N-22 |
| 1-N-10 | IM. Br-1 | sa10 | a10 | Ar1 | A | 0.76 | 315.3 | EXP. 1-N-22 |
| 1-N-11 | IM. Br-1 | sa11 | a11 | Ar1 | A | 0.84 | 343.3 | EXP. 1-N-22 |
| 1-N-12 | IM. Br-1 | sa12 | a12 | Ar1 | A | 0.80 | 343.3 | EXP. 1-N-22 |
| 1-N-13 | IM. Br-1 | sa13 | a13 | Ar1 | A | 0.84 | 343.3 | EXP. 1-N-22 |
| 1-N-14 | IM. Br-1 | sa14 | a14 | Ar1 | A | 0.82 | 343.3 | EXP. 1-N-22 |
| 1-N-15 | IM. Br-1 | sa15 | a15 | Ar1 | A | 0.78 | 329.2 | EXP. 1-N-22 |
| 1-N-16 | IM. Br-1 | sa16 | a16 | Ar1 | A | 0.79 | 329.2 | EXP. 1-N-22 |
| 1-N-17 | IM. Br-1 | sa17 | a17 | Ar1 | A | 0.76 | 315.3 | EXP. 1-N-22 |
| 1-N-18 | IM. Br-1 | sa18 | a18 | Ar1 | B | 3.72 | 328.2 | EXP. 1-N-22 |
| 1-N-19 | IM. Br-1 | sa19 | a19 | Ar1 | B | 2.74 | 337.2 | EXP. 1-N-22 |
| 1-N-20 | IM. Br-1 | sa20 | a20 | Ar1 | B | 2.42 | 343.2 | EXP. 1-N-22 |
| 1-N-21 | IM. Br-1 | sa21 | a21 | Ar1 | B | 2.34 | 359.2 | EXP. 1-N-1(a) |
| 1-N-22 | IM. Br-1 | sa22 | a22 | Ar1 | B | 2.29 | 354.2 | |
| 1-N-23 | IM. Br-1 | sa23 | a23 | Ar1 | A | 0.91 | 290.3 | EXP. 1-N-22 |
| 1-N-24 | IM. Br-1 | sa24 | a24 | Ar1 | A | 0.95 | 304.3 | EXP. 1-N-22 |
| 1-N-25 | IM. Br-1 | sa25 | a25 | Ar1 | A | 0.81 | 320.2 | EXP. 1-N-22 |
| 1-N-26 | IM. Br-1 | sa26 | a26 | Ar1 | B | 2.34 | 343.2 | EXP. 1-N-22 |
| 1-N-27 | IM. Br-1 | sa27 | a27 | Ar1 | A | 0.76 | 315.4 | EXP. 1-N-1(a) |
| 1-N-28 | IM. Br-1 | sa28 | a28 | Ar1 | A | 0.76 | 315.4 | EXP. 1-N-1(a) |
| 1-N-29 | IM. Br-1 | sa29 | a29 | Ar1 | A | 0.81 | 329.3 | EXP. 1-N-1(a) |
| 1-N-30 | IM. Br-1 | sa30 | a30 | Ar1 | A | 0.90 | 343.4 | EXP. 1-N-1(a) |
| 1-N-31 | IM. Br-1 | sa31 | a31 | Ar1 | A | 1.14 | 493.4 | EXP. 1-N-1(a) |
| 1-N-32 | IM. Br-1 | sa32 | a32 | Ar1 | A | 1.06 | 419.5 | EXP. 1-N-1(a) |
| 1-N-34 | IM. Br-3 | sa1 | a1 | Ar3 | B | 2.71 | 305.1 | EXP. 1-N-1(a) |
| 1-N-36 | IM. Br-5 | sa1 | a1 | Ar7 | B | 1.80 | 334.2 | EXP. 1-N-1(a) |
| 1-N-37 | IM. Br-6 | sa1 | a1 | Ar8 | B | 0.42 | 333.3 | EXP. 1-N-1(a) |
| 1-N-38 | IM. Br-3 | sa5 | a5 | Ar3 | A | 0.28 | 279.0 | EXP. 1-N-1(a) |
| 1-N-39 | IM. Br-3 | sa4 | a4 | Ar3 | A | 0.55 | 277.0 | EXP. 1-N-1(a) |
| 1-N-40 | IM. Br-3 | sa12 | a12 | Ar3 | A | 0.60 | 319.1 | EXP. 1-N-1(a) |
| 1-N-41 | IM. Br-3 | sa27 | a27 | Ar3 | A | 0.56 | 291.0 | EXP. 1-N-1(a) |
| 1-N-42 | IM. Br-3 | sa28 | a28 | Ar3 | A | 0.56 | 291.0 | EXP. 1-N-1(a) |
| 1-N-43 | IM. Br-3 | sa2 | a2 | Ar3 | A | 0.57 | 305.0 | EXP. 1-N-1(a) |
| 1-N-44 | IM. Br-4 | sa4 | a4 | Ar4 | A | 0.84 | 319.0 | EXP. 1-N-1(a) |
| 1-N-45 | IM. Br-5 | sa3 | a3 | Ar7 | B | 2.52 | 320.2 | EXP. 1-N-1(a) |
| 1-N-46 | IM. Br-5 | sa5 | a5 | Ar7 | B | 2.06 | 308.3 | EXP. 1-N-1(a) |
| 1-N-47 | IM. Br-3 | sa6 | a6 | Ar3 | C | 2.64 | 291.0 | EXP. 1-N-1(a) |
| 1-N-48 | IM. Br-6 | sa6 | a6 | Ar8 | B | 0.43 | 319.3 | EXP. 1-N-1(a) |
| 1-N-49 | IM. Br-2 | sa1 | a1 | Ar2 | A | 0.91 | 338.0 | EXP. 1-N-1(a) |
| 1-N-50 | IM. Br-2 | sa4 | a4 | Ar2 | A | 0.89 | 310.0 | EXP. 1-N-1(a) |
| 1-N-51 | IM. Br-4 | sa1 | a1 | Ar4 | A | 0.83 | 347.4 | EXP. 1-N-1(a) |
| 1-N-52 | IM. Br-4 | sa3 | a3 | Ar4 | A | 0.81 | 333.4 | EXP. 1-N-1(a) |
| 1-N-53 | IM. Br-4 | sa15 | a15 | Ar4 | A | 0.83 | 347.4 | EXP. 1-N-1(a) |
| 1-N-54 | IM. Br-4 | sa17 | a17 | Ar4 | A | 0.79 | 333.4 | EXP. 1-N-1(a) |
| 1-N-55 | IM. Br-4 | sa13 | a13 | Ar4 | A | 0.89 | 361.4 | EXP. 1-N-1(a) |
| 1-N-56 | IM. Br-4 | sa33 | a33 | Ar4 | A | 0.87 | 361.4 | EXP. 1-N-1(a) |
| 1-N-57 | IM. Br-4 | sa34 | a34 | Ar4 | A | 0.94 | 361.4 | EXP. 1-N-1(a) |
| 1-N-58 | IM. Br-4 | sa5 | a5 | Ar4 | A | 0.83 | 321.4 | EXP. 1-N-1(a) |
| 1-N-59 | IM. Br-4 | sa35 | a35 | Ar4 | A | 0.89 | 335.4 | EXP. 1-N-1(a) |
| 1-N-60 | IM. Br-4 | sa36 | a36 | Ar4 | A | 0.90 | 335.4 | EXP. 1-N-1(a) |
| 1-N-61 | IM. Br-7 | sa1 | a1 | Ar41 | A | 0.87 | 347.4 | EXP. 1-N-1(a) |
| 1-N-62 | IM. Br-7 | sa4 | a4 | Ar41 | A | 0.87 | 319.4 | EXP. 1-N-1(a) |

TABLE 1-N-continued

| EXP. | SM1 | SM2 | K | Ar | LCMS method | RTime | MH+ | Ref. |
|---|---|---|---|---|---|---|---|---|
| 1-N-63 | IM. Br-8 | sa1 | a1 | Ar192 | A | 0.25 | 319.3 | EXP. 1-N-1(a) |
| 1-N-64 | IM. Br-9 | sa1 | a1 | Ar186 | A | 0.25 | 319.3 | EXP. 1-N-1(a) |
| 1-N-65 | IM. Br-10 | sa1 | a1 | Ar161 | A | 0.24 | 333.2 | EXP. 1-N-1(a) |
| 1-N-66 | IM. Br-8 | sa4 | a4 | Ar192 | A | 0.50 | 291.2 | EXP. 1-N-1(a) |
| 1-N-67 | IM. Br-9 | sa4 | a4 | Ar186 | A | 0.50 | 291.2 | EXP. 1-N-1(a) |
| 1-N-68 | IM. Br-10 | sa4 | a4 | Ar161 | A | 0.49 | 305.2 | EXP. 1-N-1(a) |

TABLE 1-O

| EXP. | SM1 | SM2 | K | Ar | LCMS method | RTime | MH+ | Ref. |
|---|---|---|---|---|---|---|---|---|
| 1-o-1 | IM. Br-1 | soh1 | oh1 | Ar1 | A | 0.85 | 330.0 | |
| 1-o-2 | IM. Br-1 | soh2 | oh2 | Ar1 | A | 0.87 | 330.3 | EXP. 1-o-1(a) |
| 1-o-3 | IM. Br-1 | soh3 | oh3 | Ar1 | A | 0.81 | 316.1 | EXP. 1-o-1(a) |
| 1-o-4 | IM. Br-1 | soh4 | oh4 | Ar1 | B | 2.14 | 316.2 | EXP. 1-o-1(a) |
| 1-o-5 | IM. Br-1 | soh5 | oh5 | Ar1 | B | 2.10 | 316.2 | EXP. 1-o-1(a) |
| 1-o-6 | IM. Br-1 | soh6 | oh6 | Ar1 | A | 0.82 | 302.1 | EXP. 1-o-1(a) |
| 1-o-7 | IM. Br-1 | soh7 | oh7 | Ar1 | A | 0.89 | 344.1 | EXP. 1-o-1(a) |
| 1-o-8 | IM. Br-1 | soh8 | oh8 | Ar1 | A | 0.88 | 344.1 | EXP. 1-o-1(a) |
| 1-o-10 | IM. Br-1 | soh10 | oh10 | Ar1 | A | 0.79 | 304.3 | EXP. 1-o-1(a) |
| 1-o-11 | IM. Br-1 | soh11 | oh11 | Ar1 | A | 0.87 | 344.2 | EXP. 1-o-1(a) |
| 1-o-12 | IM. Br-1 | soh12 | oh12 | Ar1 | A | 0.82 | 344.4 | EXP. 1-o-1(a) |
| 1-o-13 | IM. Br-1 | soh13 | oh13 | Ar1 | A | 0.82 | 330.2 | EXP. 1-o-39 |
| 1-o-16 | IM. Br-1 | soh16 | oh16 | Ar1 | A | 0.87 | 316.0 | EXP. 1-o-1(a) |
| 1-o-16 | IM. Br-1 | soh16 | oh16 | Ar1 | A | 0.81 | 316.2 | EXP. 1-o-39 |
| 1-o-18 | IM. Br-1 | sch18 | ch18 | Ar1 | A | 0.86 | 346.0 | EXP. 1-o-1(a) |
| 1-o-19 | IM. Br-1 | sch19 | ch19 | Ar1 | A | 0.81 | 332.3 | EXP. 1-o-39 |
| 1-o-20 | IM. Br-1 | sch20 | ch20 | Ar1 | A | 0.95 | 372.6 | EXP. 1-o-39 |
| 1-o-21 | IM. Br-1 | sch21 | ch21 | Ar1 | A | 0.89 | 358.6 | EXP. 1-o-39 |
| 1-o-23 | IM. Br-1 | sch23 | ch23 | Ar1 | A | 1.51 | 354.4 | EXP. 1-o-39 |
| 1-o-24 | IM. Br-1 | sch24 | ch24 | Ar1 | A | 0.97 | 343.3 | EXP. 1-o-39 |
| 1-o-25 | IM. Br-1 | sch25 | ch25 | Ar1 | A | 0.91 | 332.3 | EXP. 1-o-39 |
| 1-o-26 | IM. Br-1 | sch26 | ch26 | Ar1 | A | 0.81 | 330.3 | EXP. 1-o-39 |
| 1-o-27 | IM. Br-1 | sch27 | ch27 | Ar1 | A | 0.83 | 344.4 | EXP. 1-o-39 |
| 1-o-28 | IM. Br-1 | sch28 | ch28 | Ar1 | A | 0.83 | 382.4 | EXP. 1-o-39 |
| 1-o-33 | IM. Br-1 | sch33 | ch33 | Ar1 | A | 0.98 | 291.3 | EXP. 1-o-1(a) |
| 1-o-34 | IM. Br-1 | sch34 | ch34 | Ar1 | A | 1.04 | 305.3 | EXP. 1-o-39 |
| 1-o-35 | IM. Br-1 | sch35 | ch35 | Ar1 | A | 1.21 | 261.3 | EXP. 1-o-39 |
| 1-o-36 | IM. Br-1 | sch36 | ch36 | Ar1 | A | 1.46 | 289.5 | EXP. 1-o-39 |
| 1-o-37 | IM. Br-1 | sch37 | ch37 | Ar1 | A | 1.64 | 303.3 | EXP. 1-o-39 |
| 1-o-38 | IM. Br-1 | sch38 | ch38 | Ar1 | A | 1.33 | 285.3 | EXP. 1-o-39 |
| 1-o-39 | IM. Br-1 | sch39 | ch39 | Ar1 | A | 1.50 | 301.3 | |
| 1-o-40 | IM. Br-1 | sch40 | ch40 | Ar1 | A | 1.64 | 315.3 | EXP. 1-o-39 |
| 1-o-41 | IM. Br-1 | sch41 | ch41 | Ar1 | A | 0.97 | 343.3 | EXP. 1-o-39 |
| 1-o-42 | IM. Br-1 | sch42 | ch42 | Ar1 | A | 1.59 | 343.3 | EXP. 1-o-39 |
| 1-o-43 | IM. Br-1 | sch43 | ch43 | Ar1 | A | 1.17 | 317.3 | EXP. 1-o-39 |
| 1-o-44 | IM. Br-1 | sch44 | ch44 | Ar1 | A | 1.29 | 381.8 | EXP. 1-o-39 |
| 1-o-45 | IM. Br-1 | sch45 | ch45 | Ar1 | A | 1.48 | 327.3 | EXP. 1-o-1(a) |
| 1-o-47 | IM. Br-1 | sch47 | ch47 | Ar1 | A | 1.18 | 305.3 | EXP. 1-o-1(a) |
| 1-o-49 | IM. Br-1 | sch49 | ch49 | Ar1 | A | 1.54 | 362.4 | EXP. 1-o-39 |
| 1-o-50 | IM. Br-1 | sch50 | ch50 | Ar1 | A | 1.56 | 362.4 | EXP. 1-o-39 |
| 1-o-51 | IM. Br-1 | sch51 | ch51 | Ar1 | A | 0.82 | 360.0 | EXP. 1-o-1(a) |
| 1-o-52 | IM. Br-1 | sch52 | ch52 | Ar1 | A | 1.25 | 373.2 | EXP. 1-o-1(a) |
| 1-o-54 | IM. Br-1 | sch54 | ch54 | Ar1 | A | 1.21 | 338.3 | EXP. 1-o-39 |
| 1-o-55 | IM. Br-3 | sch1 | ch1 | Ar3 | A | 0.62 | 306.1 | EXP. 1-o-1(a) |
| 1-o-56 | IM. Br-4 | sch6 | ch6 | Ar4 | A | 0.90 | 320.3 | EXP. 1-o-1(a) |
| 1-o-57 | IM. Br-4 | sch1 | ch1 | Ar4 | A | 0.95 | 348.4 | EXP. 1-o-1(a) |
| 1-o-58 | IM. Br-41 | sch1 | ch1 | Ar41 | A | 0.98 | 348.4 | EXP. 1-o-1(a) |
| 1-o-69 | IM. Br-4 | sch55 | ch55 | Ar4 | A | 1.01 | 362.4 | EXP. 1-o-1(a) |

TABLE 1-S

| | | | | | LCMS | | |
|---|---|---|---|---|---|---|---|
| EXP. | SM1 | SM2 | x | Ar | method | RTime | MH+ Ref. |
| 1-s-1 | IM.Br-1 | ssh1 | sh1 | Ar1 | A | 1.01 | 346.2 |
| 1-s-2 | IM.Br-1 | ssh2 | sh2 | Ar1 | A | 0.89 | 306.0 EXP. 1-s-1 |

Example 2-N-1

3-(8-(1-acetylpiperidin-4-ylamino)isoquinolin-6-yl)benzonitrile

Triethylamine (103 μL) and acetic anhydride (which may be referred to as sco1; 28 μL; WAKO) were added to a dichloromethane (6 mL) solution of Example compound 1-N-1 (60 mg) at room temperature and the resulting mixture was stirred for 11 hours. Methanol was added to the reaction mixture solution and the resulting mixture was concentrated under reduced pressure and purified by silica gel column chromatography (Yamazen; chloroform/methanol) to give the title compound (69.1 mg).

(LCMS: 371.4 (MH$^+$); retention time: 1.09 min; LCMS; condition A)

Example 2-N-2

3-(8-(1-(cyclopropanecarbonyl)piperidin-4-ylamino)isoquinolin-6-yl)benzonitrile

Triethylamine (35 μL) and cyclopropanecarboxylic acid (which may be referred to as sco2; 12.8 mg; TCI) were added to a DMF (2 mL) solution of Example compound 1-N-1 (20 mg), HOAt (14 mg; TCI), WSC (29 mg; TCI) at room temperature and the resulting mixture was stirred for 12 and half hours at room temperature. Ethyl acetate, saturated brine, and water were added to extract the reaction mixture, then the organic layer was dried, the solvent was evaporated under reduced pressure, and the residue was purified by column chromatography (Yamazen; chloroform/methanol) to give the title compound (17.5 mg).

(LCMS: 397.4 (MH$^+$); retention time: 1.15 min; LCMS; condition A)

Example 2-N-3

3-(8-(1-(2-methylbenzoyl)piperidin-4-ylamino)isoquinolin-6-yl)benzonitrile

PS-DCC resin (N-Cyclohexylcarbodiimide-N'-propyloxymethyl polystyrene; 35.0 mg; Nova), HOAt (6.2 mg), triethylamine (15.4 μL), and 2-methylbenzoic acid (which may be referred to as sco3; 4.6 mg; TCI) were added to a DMF (0.6 mL) solution of Example compound 1-N-1 (10.0 mg) and the resulting mixture was shaken at room temperature for 14 hours under a nitrogen atmosphere. The reaction mixture was filtrated and the residue was washed with DMF (0.25 mL×2). The filtrate and the wash were mixed followed by the addition of MP-Carbonate resin (Macroporous triethylammonium methylpolystyrene carbonate; 50 mg; Argonaut), the resulting mixture was shaken for 1 hour followed by the addition of MP-Carbonate resin (50 mg), the resulting mixture was shaken for 1 hour, MP-Carbonate resin (50 mg) was further added, and the resulting mixture was shaken for 14 hours. The resulting mixture was filtrated followed by the addition of SCX (300 mg) and the resulting mixture was shaken for 2 hours. The reaction mixture was filtrated and the residue was washed with dichloromethane (3 mL) and methanol (4 mL). Then, the mixture was washed with 4 N ammonia methanol solution (4 mL; Ald) and this resulting wash was concentrated. The resulting mixture was dried using a vacuum pump to give the title compound (9.5 mg).

(LCMS: 447.1 (MH$^+$); retention time: 1.30 min; LCMS; condition A)

Example 2-N-4

N-(2-(4-(6-(3-cyanophenyl)isoquinolin-8-ylamino)piperidine-1-carbonyl)phenyl)methanesulfonamide PS-DCC resin (N-Cyclohexylcarbodiimide-N'-propyloxymethylpolystyrene; 35.0 mg; Nova), HOAt (6.2 mg), triethylamine (15.4 μL), and 2-(methylsulfonamide)benzoic acid (which may be referred to as sco4; 9.0 mg; Matrix) were added to a DMF (0.6 mL) solution of Example compound 1-N-1 (10.0 mg) and the resulting mixture was shaken at room temperature for 14 hours under a nitrogen atmosphere. The resulting mixture was filtrated followed by the addition of SCX (300 mg) and the resulting mixture was shaken for 2 hours. The reaction mixture was filtrated and the residue was washed with dichloromethane (3 mL) and methanol (4 mL). Then, the mixture was washed with 4 N ammonia methanol solution (4 mL; Ald) and this resulting wash was concentrated. The resulting mixture was dried using a vacuum pump to give the title compound (3.5 mg).

(LCMS: 526.2 (MH$^+$); retention time: 1.24 min; LCMS; condition A)

Example 2-N-5

3-(8-(1-(3-hydroxypropanoyl)piperidin-4-ylamino)isoquinolin-6-yl)benzonitrile

PS-DCC resin (35.0 mg), HOAt (6.2 mg), triethylamine (15.4 μL), and 3-hydroxypropionic acid (which may be referred to as sco5; 4.0 mg; TCI) were added to a DMF (0.6 mL) solution of Example compound 1-N-1 (10.0 mg) and the resulting mixture was shaken at room temperature for hours under a nitrogen atmosphere. The reaction mixture was filtrated and the residue was washed with DMF (0.25 mL×2). The filtrate and the wash were mixed followed by the addition of MP-Carbonate resin (50 mg), the resulting mixture was shaken for 1 hour followed by the addition of MP-Carbonate resin (50 mg), and the resulting mixture was shaken for 1 hour. MP-Carbonate resin (50 mg) and PS-Isocyanate resin (Polystyrene methylisocyanate; 50 mg; Aid) were further added, and the resulting mixture was shaken for 14 hours. The resulting mixture was filtrated followed by the addition of SCX (300 mg) and the resulting mixture was shaken for 2 hours. The reaction mixture was filtrated and the residue was washed with dichloromethane (3 mL) and methanol (4 mL). Then, the mixture was washed with 4 N ammonia methanol solution (4 mL) and this resulting wash was concentrated. The resulting mixture was dried using a vacuum pump to give the title compound (5.3 mg).

(LCMS: 401.2 (MH$^+$); retention time: 1.02 min; LCMS; condition A)

Example 2-N-6 to 2-N-113, 2-N-201 to 2-N-293, 2-N-301 to 2-N-320, 2-N-401 to 2-N-402, 2-N-501 to 2-N-511, 2-N-601 to 2-N-620, 2-N-701 to 2-N-713, 2-N-801 to 2-N-804 and 2-N-901 to 2-N-990, 2-o-1 to 2-o-257, 2-s-1 to 2-s-6

Compounds of Examples 2-N-6 to 2-N-113, 2-N-201 to 2-N-293, 2-N-301 to 2-N-320, 2-N-401 to 2-N-402, 2-N-501 to 2-N-511, 2-N-601 to 2-N-620, 2-N-701 to 2-N-713, 2-N-801 to 2-N-804 and 2-N-901 to 2-N-990, 2-o-1 to 2-o-257 and 2-s-1 to 2-s-6 were synthesized according to the methods in Example 2-N-1 to 2-N-5 (Tables 2-N, 2-o, and 2-s).

In Tables 2-N, 2-o, and 2-s, the ST column represent the structures represented by the above general formulas, the J and Ar columns represent "J" and "Ar," respectively, in the general formulas shown in the ST column, "ST," "SM1," "SM2," "LCMS," and "Ref" are defined as described above, and abbreviations such as "co1," "Ar1," and "sco1" represent compounds or groups corresponding to the abbreviations in Tables co, Ar, and sco, respectively, provided later. Abbreviations in the tables represent compounds or groups shown in the figures shown earlier or later.

Tables 2-N, 2-o, and 2-s also include compounds finally purified by preparative HPLC, such as those of Examples 2-o-33, 2-o-34, 2-o-52, 2-o-76, 2-o-88, 2-o-89, 2-o-99, 2-o-100, 2-o-120, 2-o-128 to 2-o-132, 2-o-158, 2-o-160, 2-o-170 to 2-o-172, 2-o-181, 2-o-189, 2-o-191 to 2-o-193, 2-o-210, 2-o-211, 2-o-221, 2-o-222, for example.

EXP. 4-N-3, 4-N-4, 4-N-5, and 4-N-7 represent Example compounds 4-N-3, 4-N-4, 4-N-5, and 4-N-7, respectively, described later.

Example 4-NP-419, 4-NP-420, 4-NP-435 to 4-NP-458, 4-NP-469 to 4-NP-471, 4-NP-497 to 4-NP-507, 4-NP-511, 4-NP-517

Compounds of Example 4-NP-419, 4-NP-420, 4-NP-435 to 4-NP-458, 4-NP-469 to 4-NP-471, 4-NP-497 to 4-NP-507, 4-NP-511 and 4-NP-517 were synthesized according to the methods in Examples 2-N-1 to 2-N-5 (Table 2-N2). In Table 2-N2, the ST column represents the structures represented by the above general formulas, the J and Ar columns represent "J" and "Ar" in the general formula represented in the ST column, "ST," "SM1," "SM2," "LCMS," and "Ref" are defined as described above, abbreviations such as "co1," "Ar1," and "sco1" represent compounds or groups corresponding to the abbreviations in Tables co, Ar, and sco, respectively, provided later. Abbreviations in the tables represent compounds or groups shown in the figures shown earlier or later. The compounds in the tables also include compounds finally purified by preparative HPLC.

TABLE 2-N

| EXP. | SM1 | SM2 | ST | J | Ar | LCMS method | RTime | MH+ | Ref. |
|---|---|---|---|---|---|---|---|---|---|
| 2-N-1 | EXP. 1-N-1 | sco1 | Qn1 | co1 | Ar1 | A | 1.09 | 371.4 | |
| 2-N-2 | EXP. 1-N-1 | sco2 | Qn1 | co2 | Ar1 | A | 1.15 | 397.4 | |
| 2-N-3 | EXP. 1-N-1 | sco3 | Qn1 | co3 | Ar1 | A | 1.30 | 447.1 | |
| 2-N-4 | EXP. 1-N-1 | sco4 | Qn1 | co4 | Ar1 | A | 1.24 | 526.2 | |
| 2-N-5 | EXP. 1-N-1 | sco5 | Qn1 | co5 | Ar1 | A | 1.02 | 401.2 | |
| 2-N-6 | EXP. 1-N-1 | sco6 | Qn1 | co6 | Ar1 | A | 1.17 | 459.1 | EXP. 2-N-2 |
| 2-N-7 | EXP. 1-N-1 | sco7 | Qn1 | co7 | Ar1 | A | 1.11 | 366.4 | EXP. 2-N-2 |
| 2-N-8 | EXP. 1-N-1 | sco8 | Qn1 | co8 | Ar1 | A | 1.33 | 447.1 | EXP. 2-N-3 |
| 2-N-9 | EXP. 1-N-1 | sco9 | Qn1 | co9 | Ar1 | A | 1.33 | 447.1 | EXP. 2-N-3 |
| 2-N-10 | EXP. 1-N-1 | sco10 | Qn1 | co10 | Ar1 | A | 1.27 | 451.1 | EXP. 2-N-3 |
| 2-N-11 | EXP. 1-N-1 | sco11 | Qn1 | co11 | Ar1 | A | 1.29 | 451.1 | EXP. 2-N-3 |
| 2-N-12 | EXP. 1-N-1 | sco12 | Qn1 | co12 | Ar1 | A | 1.28 | 451.1 | EXP. 2-N-3 |
| 2-N-13 | EXP. 1-N-1 | sco13 | Qn1 | co13 | Ar1 | A | 1.31 | 467.1 | EXP. 2-N-3 |
| 2-N-14 | EXP. 1-N-1 | sco14 | Qn1 | co14 | Ar1 | A | 1.36 | 457.1 | EXP. 2-N-3 |
| 2-N-15 | EXP. 1-N-1 | sco15 | Qn1 | co15 | Ar1 | A | 1.35 | 467.1 | EXP. 2-N-3 |
| 2-N-16 | EXP. 1-N-1 | sco16 | Qn1 | co16 | Ar1 | A | 1.23 | 458.1 | EXP. 2-N-3 |
| 2-N-17 | EXP. 1-N-1 | sco17 | Qn1 | co17 | Ar1 | A | 1.23 | 458.1 | EXP. 2-N-3 |
| 2-N-18 | EXP. 1-N-1 | sco18 | Qn1 | co18 | Ar1 | A | 1.23 | 458.1 | EXP. 2-N-3 |
| 2-N-19 | EXP. 1-N-1 | sco19 | Qn1 | co19 | Ar1 | A | 1.24 | 491.1 | EXP. 2-N-3 |
| 2-N-20 | EXP. 1-N-1 | sco20 | Qn1 | co20 | Ar1 | A | 1.28 | 491.1 | EXP. 2-N-3 |
| 2-N-21 | EXP. 1-N-1 | sco21 | Qn1 | co21 | Ar1 | A | 1.28 | 491.1 | EXP. 2-N-3 |
| 2-N-22 | EXP. 1-N-1 | sco22 | Qn1 | co22 | Ar1 | A | 1.25 | 463.1 | EXP. 2-N-3 |
| 2-N-23 | EXP. 1-N-1 | sco23 | Qn1 | co23 | Ar1 | A | 1.28 | 463.1 | EXP. 2-N-3 |
| 2-N-24 | EXP. 1-N-1 | sco24 | Qn1 | co24 | Ar1 | A | 1.26 | 463.1 | EXP. 2-N-3 |
| 2-N-25 | EXP. 1-N-1 | sco25 | Qn1 | co25 | Ar1 | A | 1.33 | 476.1 | EXP. 2-N-3 |
| 2-N-26 | EXP. 1-N-1 | sco26 | Qn1 | co26 | Ar1 | A | 1.32 | 476.1 | EXP. 2-N-3 |
| 2-N-27 | EXP. 1-N-1 | sco27 | Qn1 | co27 | Ar1 | A | 1.32 | 478.1 | EXP. 2-N-3 |
| 2-N-28 | EXP. 1-N-1 | sco28 | Qn1 | co28 | Ar1 | A | 1.06 | 434.4 | EXP. 2-N-2 |
| 2-N-29 | EXP. 1-N-1 | sco29 | Qn1 | co29 | Ar1 | A | 1.19 | 526.2 | EXP. 2-N-4 |
| 2-N-30 | EXP. 1-N-1 | sco30 | Qn1 | co30 | Ar1 | A | 1.17 | 526.2 | EXP. 2-N-4 |
| 2-N-31 | EXP. 1-N-1 | sco31 | Qn1 | co31 | Ar1 | A | 1.27 | 433.5 | EXP. 2-N-2 |
| 2-N-32 | EXP. 1-N-1 | sco32 | Qn1 | co32 | Ar1 | A | 1.12 | 463.2 | EXP. 2-N-3 |
| 2-N-33 | EXP. 1-N-1 | sco33 | Qn1 | co33 | Ar1 | A | 1.31 | 476.1 | EXP. 2-N-2 |
| 2-N-34 | EXP. 1-N-1 | sco34 | Qn1 | co34 | Ar1 | A | 1.32 | 463.4 | EXP. 2-N-2 |
| 2-N-35 | EXP. 1-N-1 | sco35 | Qn1 | co35 | Ar1 | A | 1.40 | 479.2 | EXP. 2-N-2 |
| 2-N-36 | EXP. 1-N-1 | sco36 | Qn1 | co36 | Ar1 | A | 1.43 | 477.3 | EXP. 2-N-2 |
| 2-N-37 | EXP. 1-N-1 | sco37 | Qn1 | co37 | Ar1 | A | 1.09 | 434.2 | EXP. 2-N-2 |
| 2-N-38 | EXP. 1-N-1 | sco38 | Qn1 | co38 | Ar1 | A | 1.05 | 434.2 | EXP. 2-N-2 |
| 2-N-39 | EXP. 1-N-1 | sco39 | Qn1 | co39 | Ar1 | A | 1.04 | 435.2 | EXP. 2-N-2 |
| 2-N-40 | EXP. 1-N-1 | sco40 | Qn1 | co40 | Ar1 | A | 1.05 | 435.2 | EXP. 2-N-2 |
| 2-N-41 | EXP. 1-N-1 | sco41 | Qn1 | co41 | Ar1 | A | 1.08 | 435.2 | EXP. 2-N-2 |

TABLE 2-N-continued

| EXP. | SM1 | SM2 | ST | J | Ar | LCMS method | RTime | MH+ | Ref. |
|---|---|---|---|---|---|---|---|---|---|
| 2-N-42 | EXP. 1-N-1 | sco42 | Qn1 | co42 | Ar1 | A | 2.29 | 473.3 | EXP. 2-N-2 |
| 2-N-43 | EXP. 1-N-1 | sco43 | Qn1 | co43 | Ar1 | A | 0.98 | 437.1 | EXP. 2-N-2 |
| 2-N-44 | EXP. 1-N-1 | sco44 | Qn1 | co44 | Ar1 | A | 0.93 | 437.1 | EXP. 2-N-2 |
| 2-N-45 | EXP. 1-N-1 | sco45 | Qn1 | co45 | Ar1 | A | 1.12 | 440.2 | EXP. 2-N-3 |
| 2-N-46 | EXP. 1-N-1 | sco46 | Qn1 | co46 | Ar1 | A | 1.25 | 439.2 | EXP. 2-N-3 |
| 2-N-47 | EXP. 1-N-1 | sco47 | Qn1 | co47 | Ar1 | A | 1.28 | 439.2 | EXP. 2-N-3 |
| 2-N-48 | EXP. 1-N-1 | sco48 | Qn1 | co48 | Ar1 | A | 1.19 | 423.2 | EXP. 2-N-3 |
| 2-N-49 | EXP. 1-N-1 | sco49 | Qn1 | co49 | Ar1 | A | 1.21 | 423.2 | EXP. 2-N-3 |
| 2-N-50 | EXP. 1-N-1 | sco50 | Qn1 | co50 | Ar1 | A | 1.13 | 459.1 | EXP. 2-N-2 |
| 2-N-51 | EXP. 1-N-1 | sco51 | Qn1 | co51 | Ar1 | A | 1.19 | 468.2 | EXP. 2-N-2 |
| 2-N-52 | EXP. 1-N-1 | sco52 | Qn1 | co52 | Ar1 | A | 1.05 | 448.2 | EXP. 2-N-2 |
| 2-N-53 | EXP. 1-N-1 | sco53 | Qn1 | co53 | Ar1 | A | 1.17 | 452.2 | EXP. 2-N-2 |
| 2-N-54 | EXP. 1-N-1 | sco54 | Qn1 | co54 | Ar1 | A | 0.95 | 449.1 | EXP. 2-N-2 |
| 2-N-55 | EXP. 1-N-1 | sco55 | Qn1 | co55 | Ar1 | A | 1.15 | 468.1 | EXP. 2-N-2 |
| 2-N-56 | EXP. 1-N-1 | sco56 | Qn1 | co56 | Ar1 | A | 1.17 | 464.1 | EXP. 2-N-2 |
| 2-N-57 | EXP. 1-N-1 | sco57 | Qn1 | co57 | Ar1 | A | 1.07 | 448.1 | EXP. 2-N-2 |
| 2-N-58 | EXP. 1-N-1 | sco58 | Qn1 | co58 | Ar1 | A | 0.92 | 449.1 | EXP. 2-N-2 |
| 2-N-59 | EXP. 1-N-1 | sco59 | Qn1 | co59 | Ar1 | A | 1.09 | 452.1 | EXP. 2-N-2 |
| 2-N-60 | EXP. 1-N-1 | sco60 | Qn1 | co60 | Ar1 | A | 1.15 | 468.1 | EXP. 2-N-2 |
| 2-N-61 | EXP. 1-N-1 | sco61 | Qn1 | co61 | Ar1 | A | 1.24 | 502.1 | EXP. 2-N-2 |
| 2-N-62 | EXP. 1-N-1 | sco62 | Qn1 | co62 | Ar1 | A | 1.21 | 501.9 | EXP. 2-N-2 |
| 2-N-63 | EXP. 1-N-1 | sco63 | Qn1 | co63 | Ar1 | B | 2.24 | 449.3 | EXP. 2-N-2 |
| 2-N-64 | EXP. 1-N-1 | sco64 | Qn1 | co64 | Ar1 | A | 0.10 | 450.1 | EXP. 2-N-2 |
| 2-N-65 | EXP. 1-N-1 | sco65 | Qn1 | co65 | Ar1 | A | 1.13 | 448.1 | EXP. 2-N-2 |
| 2-N-66 | EXP. 1-N-1 | sco66 | Qn1 | co66 | Ar1 | A | 1.20 | 452.1 | EXP. 2-N-2 |
| 2-N-67 | EXP. 1-N-1 | sco67 | Qn1 | co67 | Ar1 | A | 1.10 | 448.1 | EXP. 2-N-2 |
| 2-N-68 | EXP. 1-N-1 | sco68 | Qn1 | co68 | Ar1 | A | 1.15 | 452.1 | EXP. 2-N-2 |
| 2-N-69 | EXP. 1-N-1 | sco69 | Qn1 | co69 | Ar1 | A | 1.18 | 468.1 | EXP. 2-N-2 |
| 2-N-70 | EXP. 1-N-1 | sco70 | Qn1 | co70 | Ar1 | A | 0.98 | 450.1 | EXP. 2-N-2 |
| 2-N-71 | EXP. 1-N-1 | sco71 | Qn1 | co71 | Ar1 | A | 0.92 | 449.1 | EXP. 2-N-2 |
| 2-N-72 | EXP. 1-N-1 | sco72 | Qn1 | co72 | Ar1 | A | 1.16 | 448.2 | EXP. 2-N-2 |
| 2-N-73 | EXP. 1-N-1 | sco73 | Qn1 | co73 | Ar1 | A | 1.00 | 462.2 | EXP. 2-N-3 |
| 2-N-74 | EXP. 1-N-1 | sco74 | Qn1 | co74 | Ar1 | A | 1.19 | 468.1 | EXP. 2-N-2 |
| 2-N-75 | EXP. 1-N-1 | sco75 | Qn1 | co75 | Ar1 | A | 0.90 | 449.1 | EXP. 2-N-2 |
| 2-N-76 | EXP. 1-N-1 | sco76 | Qn1 | co76 | Ar1 | A | 1.31 | 502.1 | EXP. 2-N-2 |
| 2-N-77 | EXP. 1-N-1 | sco77 | Qn1 | co77 | Ar1 | A | 1.18 | 464.1 | EXP. 2-N-2 |
| 2-N-78 | EXP. 1-N-1 | sco78 | Qn1 | co78 | Ar1 | A | 0.99 | 450.1 | EXP. 2-N-2 |
| 2-N-79 | EXP. 1-N-1 | sco79 | Qn1 | co79 | Ar1 | A | 1.16 | 492.1 | EXP. 2-N-2 |
| 2-N-80 | EXP. 1-N-1 | sco80 | Qn1 | co80 | Ar1 | A | 1.34 | 502.1 | EXP. 2-N-3 |
| 2-N-81 | EXP. 1-N-1 | sco81 | Qn1 | co81 | Ar1 | A | 1.39 | 502.1 | EXP. 2-N-3 |
| 2-N-82 | EXP. 1-N-1 | sco82 | Qn1 | co82 | Ar1 | A | 1.34 | 502.1 | EXP. 2-N-3 |
| 2-N-83 | EXP. 1-N-1 | sco83 | Qn1 | co83 | Ar1 | A | 1.27 | 502.0 | EXP. 2-N-2 |
| 2-N-84 | EXP. 1-N-1 | sco84 | Qn1 | co84 | Ar1 | A | 1.38 | 502.0 | EXP. 2-N-2 |
| 2-N-85 | EXP. 1-N-1 | sco85 | Qn1 | co85 | Ar1 | A | 1.32 | 502.1 | EXP. 2-N-3 |
| 2-N-86 | EXP. 1-N-1 | sco86 | Qn1 | co86 | Ar1 | A | 1.34 | 502.1 | EXP. 2-N-2 |
| 2-N-87 | EXP. 1-N-1 | sco87 | Qn1 | co87 | Ar1 | A | 1.39 | 510.2 | EXP. 2-N-2 |
| 2-N-88 | EXP. 1-N-1 | sco88 | Qn1 | co88 | Ar1 | A | 1.05 | 462.2 | EXP. 2-N-3 |
| 2-N-89 | EXP. 1-N-1 | sco89 | Qn1 | co89 | Ar1 | A | 1.09 | 462.2 | EXP. 2-N-3 |
| 2-N-90 | EXP. 1-N-1 | sco90 | Qn1 | co90 | Ar1 | A | 1.24 | 462.2 | EXP. 2-N-3 |
| 2-N-91 | EXP. 1-N-1 | sco91 | Qn1 | co91 | Ar1 | A | 1.19 | 411.3 | EXP. 2-N-2 |
| 2-N-92 | EXP. 1-N-1 | sco92 | Qn1 | co92 | Ar1 | A | 0.96 | 448.3 | EXP. 2-N-2 |
| 2-N-93 | EXP. 1-N-1 | sco93 | Qn1 | co93 | Ar1 | A | 1.25 | 263.8 | EXP. 2-N-2 |
| 2-N-94 | EXP. 1-N-1 | sco94 | Qn1 | co94 | Ar1 | A | 1.20 | 466.2 | EXP. 2-N-2 |
| 2-N-95 | EXP. 1-N-1 | sco95 | Qn1 | co95 | Ar1 | A | 1.16 | 466.2 | EXP. 2-N-2 |
| 2-N-96 | EXP. 1-N-1 | sco96 | Qn1 | co96 | Ar1 | A | 1.07 | 401.2 | EXP. 2-N-3 |
| 2-N-97 | EXP. 1-N-1 | sco97 | Qn1 | co97 | Ar1 | A | 0.98 | 387.0 | EXP. 2-N-2 |
| 2-N-98 | EXP. 1-N-1 | sco98 | Qn1 | co98 | Ar1 | A | 1.14 | 429.2 | EXP. 2-N-3 |
| 2-N-99 | EXP. 1-N-1 | sco99 | Qn1 | co99 | Ar1 | A | 1.12 | 429.2 | EXP. 2-N-3 |
| 2-N-100 | EXP. 1-N-1 | sco100 | Qn1 | co100 | Ar1 | A | 1.09 | 448.2 | EXP. 2-N-2 |
| 2-N-101 | EXP. 1-N-1 | sco170 | Qn1 | co170 | Ar1 | A | 1.29 | 470.2 | EXP. 2-N-3 |
| 2-N-102 | EXP. 1-N-1 | sco229 | Qn1 | co229 | Ar1 | A | 0.88 | 440.5 | EXP. 2-N-2 |
| 2-N-103 | EXP. 1-N-1 | sco231 | Qn1 | co231 | Ar1 | A | 0.87 | 412.2 | EXP. 2-N-2 |
| 2-N-104 | EXP. 1-N-1 | sco235 | Qn1 | co235 | Ar1 | A | 0.82 | 442.5 | EXP. 2-N-2 |
| 2-N-105 | EXP. 1-N-1 | sco210 | Qn1 | co210 | Ar1 | A | 0.87 | 442.3 | EXP. 2-N-2 |
| 2-N-106 | EXP. 1-N-1 | sco218 | Qn1 | co218 | Ar1 | A | 0.82 | 386.4 | EXP. 2-N-2 |
| 2-N-107 | EXP. 1-N-1 | sco177 | Qn1 | co177 | Ar1 | A | 0.90 | 400.1 | EXP. 2-N-2 |
| 2-N-108 | EXP. 2-N-107 | sco1 | Qn1-2 | co1 | Ar1 | A | 1.02 | 442.1 | EXP. 2-N-1 |
| 2-N-109 | EXP. 1-N-1 | sco211 | Qn1 | co211 | Ar1 | A | 0.83 | 442.1 | EXP. 2-N-2 |
| 2-N-110 | EXP. 1-N-1 | sco178 | Qn1 | co177 | Ar1 | A | 0.85 | 442.1 | EXP. 2-N-2 |
| 2-N-111 | EXP. 1-N-1 | sco212 | Qn1 | co212 | Ar1 | A | 0.99 | 470.1 | EXP. 2-N-2 |
| 2-N-112 | EXP. 1-N-1 | sco179 | Qn1 | co178 | Ar1 | A | 0.93 | 440.1 | EXP. 2-N-2 |
| 2-N-113 | EXP. 1-N-1 | sco262 | Qn1 | co262 | Ar1 | A | 0.91 | 426.1 | EXP. 2-N-2 |
| 2-N-201 | EXP. 1-N-51 | sco1 | Qn1 | co1 | Ar1 | A | 1.12 | 389.1 | EXP. 2-N-1 |
| 2-N-204 | EXP. 1-N-51 | sco100 | Qn1 | co100 | Ar4 | A | 1.17 | 466.1 | EXP. 2-N-2 |
| 2-N-205 | EXP. 1-N-51 | sco6 | Qn1 | co6 | Ar4 | A | 1.30 | 477.1 | EXP. 2-N-2 |
| 2-N-206 | EXP. 1-N-51 | sco44 | Qn1 | co44 | Ar4 | A | 1.06 | 455.1 | EXP. 2-N-2 |

TABLE 2-N-continued

| EXP. | SM1 | SM2 | ST | J | Ar | LCMS method | RTime | MH+ | Ref. |
|---|---|---|---|---|---|---|---|---|---|
| 2-N-207 | EXP. 1-N-51 | sco101 | Qn1 | co101 | Ar4 | A | 1.63 | 527.2 | EXP. 2-N-3 |
| 2-N-208 | EXP. 1-N-51 | sco102 | Qn1 | co102 | Ar4 | A | 1.62 | 527.2 | EXP. 2-N-3 |
| 2-N-209 | EXP. 1-N-51 | sco103 | Qn1 | co103 | Ar4 | A | 1.54 | 527.2 | EXP. 2-N-3 |
| 2-N-210 | EXP. 1-N-51 | sco104 | Qn1 | co104 | Ar4 | A | 1.49 | 479.2 | EXP. 2-N-3 |
| 2-N-211 | EXP. 1-N-51 | sco105 | Qn1 | co105 | Ar4 | A | 1.47 | 479.3 | EXP. 2-N-3 |
| 2-N-212 | EXP. 1-N-51 | sco106 | Qn1 | co106 | Ar4 | A | 1.43 | 479.4 | EXP. 2-N-3 |
| 2-N-213 | EXP. 1-N-51 | sco107 | Qn1 | co107 | Ar4 | A | 1.62 | 493.2 | EXP. 2-N-3 |
| 2-N-214 | EXP. 1-N-51 | sco108 | Qn1 | co108 | Ar4 | A | 1.94 | 563.3 | EXP. 2-N-3 |
| 2-N-215 | EXP. 1-N-51 | sco109 | Qn1 | co109 | Ar4 | A | 1.48 | 547.1 | EXP. 2-N-3 |
| 2-N-216 | EXP. 1-N-51 | sco110 | Qn1 | co110 | Ar4 | A | 1.51 | 499.2 | EXP. 2-N-3 |
| 2-N-217 | EXP. 1-N-51 | sco111 | Qn1 | co111 | Ar4 | A | 1.42 | 499.2 | EXP. 2-N-3 |
| 2-N-218 | EXP. 1-N-51 | sco112 | Qn1 | co112 | Ar4 | A | 1.46 | 501.2 | EXP. 2-N-3 |
| 2-N-219 | EXP. 1-N-51 | sco113 | Qn1 | co113 | Ar4 | A | 1.43 | 483.2 | EXP. 2-N-3 |
| 2-N-220 | EXP. 1-N-51 | sco114 | Qn1 | co114 | Ar4 | A | 1.57 | 533.2 | EXP. 2-N-3 |
| 2-N-221 | EXP. 1-N-51 | sco115 | Qn1 | co115 | Ar4 | A | 1.51 | 533.2 | EXP. 2-N-3 |
| 2-N-222 | EXP. 1-N-51 | sco116 | Qn1 | co116 | Ar4 | A | 1.53 | 533.3 | EXP. 2-N-3 |
| 2-N-223 | EXP. 1-N-51 | sco117 | Qn1 | co117 | Ar4 | A | 1.56 | 587.2 | EXP. 2-N-3 |
| 2-N-224 | EXP. 1-N-51 | sco118 | Qn1 | co118 | Ar4 | A | 1.39 | 487.2 | EXP. 2-N-3 |
| 2-N-225 | EXP. 1-N-51 | sco119 | Qn1 | co119 | Ar4 | A | 1.41 | 505.2 | EXP. 2-N-5 |
| 2-N-226 | EXP. 1-N-51 | sco120 | Qn1 | co120 | Ar4 | A | 1.39 | 487.2 | EXP. 2-N-5 |
| 2-N-227 | EXP. 1-N-51 | sco121 | Qn1 | co121 | Ar4 | A | 1.51 | 537.2 | EXP. 2-N-3 |
| 2-N-228 | EXP. 1-N-51 | sco122 | Qn1 | co122 | Ar4 | A | 1.46 | 503.1 | EXP. 2-N-3 |
| 2-N-229 | EXP. 1-N-51 | sco123 | Qn1 | co123 | Ar4 | A | 1.48 | 547.1 | EXP. 2-N-3 |
| 2-N-230 | EXP. 1-N-51 | sco124 | Qn1 | co124 | Ar4 | A | 1.53 | 537.2 | EXP. 2-N-5 |
| 2-N-231 | EXP. 1-N-51 | sco125 | Qn1 | co125 | Ar4 | A | 1.45 | 505.2 | EXP. 2-N-5 |
| 2-N-232 | EXP. 1-N-51 | sco126 | Qn1 | co126 | Ar4 | A | 1.59 | 553.2 | EXP. 2-N-5 |
| 2-N-233 | EXP. 1-N-51 | sco127 | Qn1 | co127 | Ar4 | A | 1.49 | 547.1 | EXP. 2-N-5 |
| 2-N-234 | EXP. 1-N-51 | sco128 | Qn1 | co128 | Ar4 | A | 1.46 | 501.2 | EXP. 2-N-3 |
| 2-N-235 | EXP. 1-N-51 | sco129 | Qn1 | co129 | Ar4 | A | 1.49 | 501.2 | EXP. 2-N-3 |
| 2-N-236 | EXP. 1-N-51 | sco130 | Qn1 | co130 | Ar4 | A | 1.42 | 527.2 | EXP. 2-N-3 |
| 2-N-237 | EXP. 1-N-51 | sco131 | Qn1 | co131 | Ar4 | A | 1.27 | 541.2 | EXP. 2-N-3 |
| 2-N-238 | EXP. 1-N-51 | sco132 | Qn1 | co132 | Ar4 | A | 1.34 | 511.2 | EXP. 2-N-3 |
| 2-N-239 | EXP. 1-N-51 | sco133 | Qn1 | co133 | Ar4 | A | 1.33 | 511.2 | EXP. 2-N-3 |
| 2-N-240 | EXP. 1-N-51 | sco134 | Qn1 | co134 | Ar4 | A | 1.38 | 511.2 | EXP. 2-N-3 |
| 2-N-241 | EXP. 1-N-51 | sco135 | Qn1 | co135 | Ar4 | A | 1.27 | 511.2 | EXP. 2-N-3 |
| 2-N-242 | EXP. 1-N-51 | sco136 | Qn1 | co136 | Ar4 | A | 1.32 | 541.2 | EXP. 2-N-3 |
| 2-N-243 | EXP. 1-N-51 | sco137 | Qn1 | co137 | Ar4 | A | 1.30 | 541.2 | EXP. 2-N-3 |
| 2-N-244 | EXP. 1-N-51 | sco138 | Qn1 | co138 | Ar4 | A | 1.61 | 525.2 | EXP. 2-N-3 |
| 2-N-245 | EXP. 1-N-51 | sco139 | Qn1 | co139 | Ar4 | A | 1.36 | 499.2 | EXP. 2-N-5 |
| 2-N-246 | EXP. 1-N-51 | sco140 | Qn1 | co140 | Ar4 | A | 1.46 | 509.2 | EXP. 2-N-3 |
| 2-N-247 | EXP. 1-N-51 | sco141 | Qn1 | co141 | Ar4 | A | 1.47 | 495.2 | EXP. 2-N-3 |
| 2-N-248 | EXP. 1-N-51 | sco142 | Qn1 | co142 | Ar4 | A | 1.38 | 495.2 | EXP. 2-N-3 |
| 2-N-249 | EXP. 1-N-51 | sco143 | Qn1 | co143 | Ar4 | A | 1.37 | 495.2 | EXP. 2-N-3 |
| 2-N-250 | EXP. 1-N-51 | sco144 | Qn1 | co144 | Ar4 | A | 1.35 | 545.2 | EXP. 2-N-5 |
| 2-N-251 | EXP. 1-N-51 | sco145 | Qn1 | co145 | Ar4 | A | 1.40 | 517.2 | EXP. 2-N-5 |
| 2-N-252 | EXP. 1-N-51 | sco146 | Qn1 | co146 | Ar4 | A | 1.34 | 526.2 | EXP. 2-N-3 |
| 2-N-253 | EXP. 1-N-51 | sco147 | Qn1 | co147 | Ar4 | A | 1.39 | 526.2 | EXP. 2-N-3 |
| 2-N-254 | EXP. 1-N-51 | sco148 | Qn1 | co148 | Ar4 | A | 1.64 | 552.2 | EXP. 2-N-3 |
| 2-N-255 | EXP. 1-N-51 | sco149 | Qn1 | co149 | Ar4 | A | 1.35 | 526.2 | EXP. 2-N-3 |
| 2-N-256 | EXP. 1-N-51 | sco150 | Qn1 | co150 | Ar4 | A | 1.33 | 539.2 | EXP. 2-N-3 |
| 2-N-257 | EXP. 1-N-51 | sco151 | Qn1 | co151 | Ar4 | A | 1.76 | 579.3 | EXP. 2-N-3 |
| 2-N-258 | EXP. 1-N-51 | sco152 | Qn1 | co152 | Ar4 | A | 1.32 | 501.2 | EXP. 2-N-3 |
| 2-N-259 | EXP. 1-N-51 | sco153 | Qn1 | co153 | Ar4 | A | 1.27 | 603.2 | EXP. 2-N-3 |
| 2-N-260 | EXP. 1-N-51 | sco154 | Qn1 | co154 | Ar4 | A | 1.26 | 485.2 | EXP. 2-N-3 |
| 2-N-261 | EXP. 1-N-51 | sco155 | Qn1 | co155 | Ar4 | A | 1.24 | 485.2 | EXP. 2-N-5 |
| 2-N-262 | EXP. 1-N-51 | sco156 | Qn1 | co156 | Ar4 | A | 1.49 | 617.2 | EXP. 2-N-3 |
| 2-N-263 | EXP. 1-N-51 | sco157 | Qn1 | co157 | Ar4 | A | 1.19 | 522.2 | EXP. 2-N-3 |
| 2-N-264 | EXP. 1-N-51 | sco158 | Qn1 | co158 | Ar4 | A | 1.19 | 527.2 | EXP. 2-N-3 |
| 2-N-265 | EXP. 1-N-51 | sco159 | Qn1 | co159 | Ar4 | A | 1.14 | 512.2 | EXP. 2-N-5 |
| 2-N-266 | EXP. 1-N-51 | sco160 | Qn1 | co160 | Ar4 | A | 1.19 | 522.2 | EXP. 2-N-3 |
| 2-N-267 | EXP. 1-N-51 | sco161 | Qn1 | co161 | Ar4 | A | 1.33 | 528.2 | EXP. 2-N-3 |
| 2-N-268 | EXP. 1-N-51 | sco162 | Qn1 | co162 | Ar4 | A | 1.51 | 534.3 | EXP. 2-N-3 |
| 2-N-269 | EXP. 1-N-51 | sco163 | Qn1 | co163 | Ar4 | A | 1.47 | 516.2 | EXP. 2-N-3 |
| 2-N-270 | EXP. 1-N-51 | sco164 | Qn1 | co164 | Ar4 | A | 1.4 | 539.2 | EXP. 2-N-3 |
| 2-N-271 | EXP. 1-N-51 | sco165 | Qn1 | co165 | Ar4 | A | 1.48 | 531.2 | EXP. 2-N-3 |
| 2-N-272 | EXP. 1-N-51 | sco166 | Qn1 | co166 | Ar4 | A | 1.64 | 579.1 | EXP. 2-N-3 |
| 2-N-273 | EXP. 1-N-51 | sco167 | Qn1 | co167 | Ar4 | A | 1.54 | 549.1 | EXP. 2-N-3 |
| 2-N-274 | EXP. 1-N-51 | sco168 | Qn1 | co168 | Ar4 | A | 1.58 | 541.2 | EXP. 2-N-5 |
| 2-N-275 | EXP. 1-N-51 | sco169 | Qn1 | co169 | Ar4 | A | 1.21 | 503.2 | EXP. 2-N-3 |
| 2-N-276 | EXP. 1-N-51 | sco171 | Qn1 | co171 | Ar4 | A | 1.64 | 527.4 | EXP. 2-N-2 |
| 2-N-277 | EXP. 1-N-51 | sco172 | Qn1 | co172 | Ar4 | A | 1.31 | 500.3 | EXP. 2-N-2 |
| 2-N-278 | EXP. 1-N-51 | sco173 | Qn1 | co173 | Ar4 | A | 1.27 | 477.4 | EXP. 2-N-2 |
| 2-N-279 | EXP. 1-N-51 | sco174 | Qn1 | co174 | Ar4 | A | 1.43 | 475.4 | EXP. 2-N-2 |
| 2-N-280 | EXP. 1-N-51 | sco175 | Qn1 | co175 | Ar4 | A | 1.40 | 633.4 | EXP. 2-N-2 |
| 2-N-281 | EXP. 1-N-49 | sco1 | Qn1 | co1 | Ar2 | A | 1.24 | 380.0 | EXP. 2-N-1 |
| 2-N-282 | EXP. 1-N-49 | sco2 | Qn1 | co2 | Ar2 | A | 1.35 | 405.8 | EXP. 2-N-2 |

TABLE 2-N-continued

| EXP. | SM1 | SM2 | ST | J | Ar | LCMS method | RTime | MH+ | Ref. |
|---|---|---|---|---|---|---|---|---|---|
| 2-N-283 | EXP. 1-N-49 | sco100 | Qn1 | co100 | Ar2 | A | 1.26 | 457.0 | EXP. 2-N-2 |
| 2-N-284 | EXP. 1-N-34 | sco1 | Qn1 | co1 | Ar3 | A | 0.74 | 347.1 | EXP. 2-N-1 |
| 2-N-285 | EXP. 1-N-34 | sco38 | Qn1 | co38 | Ar3 | A | 0.85 | 410.2 | EXP. 2-N-2 |
| 2-N-286 | EXP. 1-N-34 | sco53 | Qn1 | co53 | Ar3 | A | 0.96 | 428.1 | EXP. 2-N-2 |
| 2-N-287 | EXP. 1-N-34 | sco43 | Qn1 | co43 | Ar3 | A | 0.82 | 413.1 | EXP. 2-N-2 |
| 2-N-288 | EXP. 1-N-34 | sco92 | Qn1 | co92 | Ar3 | A | 0.74 | 424.2 | EXP. 2-N-2 |
| 2-N-289 | EXP. 1-N-34 | sco235 | Qn1 | co235 | Ar3 | A | 0.68 | 418.2 | EXP. 2-N-2 |
| 2-N-290 | EXP. 1-N-34 | sco28 | Qn1 | co28 | Ar3 | A | 0.80 | 410.1 | EXP. 2-N-2 |
| 2-N-291 | EXP. 1-N-34 | sco2 | Qn1 | co2 | Ar3 | A | 0.93 | 373.0 | EXP. 2-N-2 |
| 2-N-292 | EXP. 1-N-51 | sco231 | Qn1 | co231 | Ar4 | A | 0.90 | 373.0 | EXP. 2-N-2 |
| 2-N-293 | EXP. 1-N-51 | sco100 | Qn1 | co100 | Ar4 | A | 1.30 | 477.1 | EXP. 2-N-2 |
| 2-N-301 | EXP. 1-N-4 | sco1 | Qn2 | co1 | Ar1 | A | 0.98 | 343.4 | EXP. 2-N-1 |
| 2-N-302 | EXP. 1-N-4 | sco2 | Qn2 | co2 | Ar1 | A | 1.11 | 369.2 | EXP. 2-N-2 |
| 2-N-303 | EXP. 1-N-4 | sco28 | Qn2 | co28 | Ar1 | A | 1.04 | 406.2 | EXP. 2-N-2 |
| 2-N-304 | EXP. 1-N-4 | sco100 | Qn2 | co100 | Ar1 | A | 1.10 | 420.2 | EXP. 2-N-3 |
| 2-N-305 | EXP. 1-N-4 | sco74 | Qn2 | co74 | Ar1 | A | 1.24 | 440.1 | EXP. 2-N-3 |
| 2-N-306 | EXP. 1-N-4 | sco76 | Qn2 | co76 | Ar1 | A | 1.35 | 474.1 | EXP. 2-N-3 |
| 2-N-307 | EXP. 1-N-4 | sco52 | Qn2 | co52 | Ar1 | A | 1.04 | 420.2 | EXP. 2-N-3 |
| 2-N-308 | EXP. 1-N-4 | sco53 | Qn2 | co53 | Ar1 | A | 1.14 | 424.2 | EXP. 2-N-3 |
| 2-N-309 | EXP. 1-N-4 | sco69 | Qn2 | co69 | Ar1 | A | 1.22 | 440.1 | EXP. 2-N-3 |
| 2-N-310 | EXP. 1-N-4 | sco68 | Qn2 | co68 | Ar1 | A | 1.17 | 424.2 | EXP. 2-N-3 |
| 2-N-311 | EXP. 1-N-4 | sco72 | Qn2 | co72 | Ar1 | A | 1.24 | 420.2 | EXP. 2-N-3 |
| 2-N-312 | EXP. 1-N-4 | sco66 | Qn2 | co66 | Ar1 | A | 1.25 | 424.2 | EXP. 2-N-3 |
| 2-N-313 | EXP. 1-N-4 | sco17 | Qn2 | co17 | Ar1 | A | 1.24 | 430.2 | EXP. 2-N-3 |
| 2-N-314 | EXP. 1-N-4 | sco18 | Qn2 | co18 | Ar1 | A | 1.25 | 430.2 | EXP. 2-N-3 |
| 2-N-315 | EXP. 1-N-4 | sco97 | Qn2 | co97 | Ar1 | A | 0.94 | 359.1 | EXP. 2-N-3 |
| 2-N-316 | EXP. 1-N-4 | sco6 | Qn2 | co6 | Ar1 | A | 1.19 | 431.2 | EXP. 2-N-3 |
| 2-N-317 | EXP. 1-N-4 | sco16 | Qn2 | co16 | Ar1 | A | 1.22 | 430.2 | EXP. 2-N-3 |
| 2-N-318 | EXP. 1-N-50 | sco2 | Qn2 | co2 | Ar2 | A | 1.00 | 378.2 | EXP. 2-N-2 |
| 2-N-319 | EXP. 1-N-50 | sco1 | Qn2 | co1 | Ar2 | A | 1.16 | 352.0 | EXP. 2-N-1 |
| 2-N-320 | EXP. 1-N-39 | sco1 | Qn2 | co1 | Ar3 | A | 0.71 | 319.0 | EXP. 2-N-1 |
| 2-N-401 | EXP. 1-N-44 | sco100 | Qn2 | co100 | Ar4 | A | 1.14 | 439.1 | EXP. 2-N-2 |
| 2-N-402 | EXP. 1-N-44 | sco6 | Qn2 | co6 | Ar4 | A | 1.24 | 449.1 | EXP. 2-N-2 |
| 2-N-501 | EXP. 1-N-27 | sco1 | Qn3 | co1 | Ar1 | A | 1.01 | 357.4 | EXP. 2-N-1 |
| 2-N-502 | EXP. 1-N-28 | sco1 | Qn4 | co1 | Ar1 | A | 1.00 | 357.4 | EXP. 2-N-1 |
| 2-N-503 | EXP. 1-N-2 | sco1 | Qn5 | co1 | Ar1 | A | 1.04 | 371.4 | EXP. 2-N-1 |
| 2-N-504 | EXP. 1-N-12 | sco1 | Qn6 | co1 | Ar1 | A | 1.07 | 386.4 | EXP. 2-N-1 |
| 2-N-505 | EXP. 1-N-12 | sco2 | Qn5 | co2 | Ar1 | A | 1.20 | 411.3 | EXP. 2-N-2 |
| 2-N-506 | EXP. 1-N-12 | sco28 | Qn6 | co28 | Ar1 | A | 1.10 | 448.3 | EXP. 2-N-2 |
| 2-N-507 | EXP. 1-N-12 | sco229 | Qn6 | co229 | Ar1 | A | 1.42 | 554.4 | EXP. 2-N-2 |
| 2-N-508 | EXP. 1-N-5 | sco1 | Qn7 | co1 | Ar1 | A | 0.99 | 346.4 | EXP. 2-N-1 |
| 2-N-509 | EXP. 1-N-6 | sco1 | Qn8 | co1 | Ar1 | A | 1.07 | 357.1 | EXP. 2-N-1 |
| 2-N-510 | EXP. 1-N-6 | sco218 | Qn8 | co218 | Ar1 | A | 0.83 | 372.3 | EXP. 2-N-2 |
| 2-N-511 | EXP. 1-N-40 | sco1 | Qn6 | co1 | Ar3 | A | 0.82 | 361.1 | EXP. 2-N-1 |
| 2-N-601 | EXP. 2-N-102 | sco1 | Qn9 | co1 | Ar1 | A | 1.06 | 482.3 | EXP. 2-N-1 |
| 2-N-602 | EXP. 2-N-102 | sco28 | Qn9 | co28 | Ar1 | A | 1.13 | 545.3 | EXP. 2-N-2 |
| 2-N-603 | EXP. 2-N-102 | sco2 | Qn9 | co2 | Ar1 | A | 1.16 | 508.2 | EXP. 2-N-2 |
| 2-N-604 | EXP. 2-N-102 | sco38 | Qn9 | co38 | Ar1 | A | 1.09 | 545.2 | EXP. 2-N-2 |
| 2-N-605 | EXP. 2-N-102 | sco52 | Qn9 | co52 | Ar1 | A | 1.08 | 559.2 | EXP. 2-N-2 |
| 2-N-606 | EXP. 2-N-102 | sco40 | Qn9 | co40 | Ar1 | A | 1.08 | 546.2 | EXP. 2-N-2 |
| 2-N-607 | EXP. 2-N-102 | sco43 | Qn9 | co43 | Ar1 | A | 1.04 | 548.2 | EXP. 2-N-2 |
| 2-N-608 | EXP. 2-N-102 | sco92 | Qn9 | co92 | Ar1 | A | 0.99 | 559.3 | EXP. 2-N-2 |
| 2-N-609 | EXP. 2-N-102 | sco235 | Qn9 | co235 | Ar1 | A | 0.93 | 553.3 | EXP. 2-N-2 |
| 2-N-610 | EXP. 2-N-103 | sco1 | Qn10 | co1 | Ar1 | A | 1.03 | 454.2 | EXP. 2-N-1 |
| 2-N-611 | EXP. 2-N-103 | sco28 | Qn10 | co28 | Ar1 | A | 1.08 | 517.2 | EXP. 2-N-2 |
| 2-N-612 | EXP. 2-N-103 | sco2 | Qn10 | co2 | Ar1 | A | 1.19 | 480.2 | EXP. 2-N-2 |
| 2-N-613 | EXP. 2-N-103 | sco38 | Qn10 | co38 | Ar1 | A | 1.07 | 517.2 | EXP. 2-N-2 |
| 2-N-614 | EXP. 2-N-109 | sco62 | Qn10 | co62 | Ar1 | A | 1.04 | 531.2 | EXP. 2-N-2 |
| 2-N-615 | EXP. 2-N-103 | sco40 | Qn10 | co40 | Ar1 | A | 1.09 | 518.2 | EXP. 2-N-2 |
| 2-N-616 | EXP. 2-N-103 | sco43 | Qn10 | co43 | Ar1 | A | 1.02 | 520.2 | EXP. 2-N-2 |
| 2-N-617 | EXP. 2-N-103 | sco92 | Qn10 | co92 | Ar1 | A | 0.98 | 531.2 | EXP. 2-N-2 |
| 2-N-618 | EXP. 2-N-103 | sco235 | Qn10 | co235 | Ar1 | A | 0.91 | 525.2 | EXP. 2-N-2 |
| 2-N-619 | EXP. 1-N-49 | sco231 | Qn1 | co231 | Ar2 | A | 0.97 | 421.1 | EXP. 2-N-2 |
| 2-N-620 | EXP. 2-N-519 | sco2 | Qn10 | co2 | Ar2 | A | 1.26 | 489.0 | EXP. 2-N-2 |
| 2-N-701 | EXP. 2-N-104 | sco1 | Qn11 | co1 | Ar1 | A | 1.07 | 484.2 | EXP. 2-N-1 |
| 2-N-702 | EXP. 2-N-104 | sco28 | Qn11 | co28 | Ar1 | A | 1.09 | 547.2 | EXP. 2-N-2 |
| 2-N-703 | EXP. 2-N-104 | sco40 | Qn11 | co40 | Ar1 | A | 1.07 | 548.2 | EXP. 2-N-2 |
| 2-N-704 | EXP. 2-N-104 | sco92 | Qn11 | co92 | Ar1 | A | 0.99 | 551.2 | EXP. 2-N-2 |
| 2-N-705 | EXP. 2-N-111 | sco1 | Qn12 | co1 | Ar1 | A | 1.15 | 512.1 | EXP. 2-N-1 |
| 2-N-706 | EXP. 2-N-111 | sco100 | Qn12 | co100 | Ar1 | A | 2.94 | 589.3 | EXP. 2-N-2 |
| 2-N-707 | EXP. 2-N-111 | sco2 | Qn12 | co2 | Ar1 | A | 1.23 | 538.3 | EXP. 2-N-2 |
| 2-N-708 | EXP. 2-N-111 | sco44 | Qn12 | co44 | Ar1 | A | 1.09 | 578.1 | EXP. 2-N-2 |
| 2-N-709 | EXP. 2-N-111 | sco216 | Qn12 | co216 | Ar1 | A | 0.06 | 578.1 | EXP. 2-N-2 |
| 2-N-710 | EXP. 2-N-111 | sco92 | Qn12 | co92 | Ar1 | A | 1.10 | 589.1 | EXP. 2-N-2 |
| 2-N-711 | EXP. 2-N-111 | sco172 | Qn12 | co172 | Ar1 | A | 1.31 | 623.1 | EXP. 2-N-2 |
| 2-N-712 | EXP. 2-N-111 | sco97 | Qn12 | co97 | Ar1 | A | 1.08 | 528.3 | EXP. 2-N-2 |

TABLE 2-N-continued

| EXP. | SM1 | SM2 | ST | J | Ar | LCMS method | RTime | MH+ | Ref. |
|---|---|---|---|---|---|---|---|---|---|
| 2-N-713 | EXP. 2-N-111 | sco176 | Qn12 | co176 | Ar1 | A | 0.95 | 610.2 | EXP. 2-N-2 |
| 2-N-801 | EXP. 4-N-4 | sco1 | Qn15 | co1 | Ar1 | A | 0.85 | 440.1 | EXP. 2-N-1 |
| 2-N-802 | EXP. 4-N-3 | sco1 | Qn16 | co1 | Ar1 | A | 0.84 | 470.1 | EXP. 2-N-1 |
| 2-N-803 | EXP. 4-N-5 | sco1 | Qn17 | co1 | Ar1 | A | 0.83 | 470.1 | EXP. 2-N-1 |
| 2-N-804 | EXP. 4-N-7 | sco1 | Qn18 | co1 | Ar1 | A | 0.88 | 426.1 | EXP. 2-N-1 |
| 2-N-901 | EXP. 1-N-51 | sco94 | Qn1 | co94 | Ar4 | A | 1.33 | 484.4 | EXP. 2-N-2 |
| 2-N-902 | EXP. 1-N-51 | sco95 | Qn1 | co95 | Ar4 | A | 1.30 | 484.4 | EXP. 2-N-2 |
| 2-N-903 | EXP. 1-N-51 | sco181 | Qn1 | co181 | Ar4 | A | 1.42 | 494.4 | EXP. 2-N-2 |
| 2-N-904 | EXP. 1-N-51 | sco182 | Qn1 | co182 | Ar4 | A | 1.42 | 494.4 | EXP. 2-N-2 |
| 2-N-905 | EXP. 1-N-51 | sco183 | Qn1 | co183 | Ar4 | A | 1.96 | 577.3 | EXP. 2-N-3 |
| 2-N-906 | EXP. 1-N-51 | sco184 | Qn1 | co184 | Ar4 | A | 1.47 | 564.1 | EXP. 2-N-3 |
| 2-N-907 | EXP. 1-N-51 | sco185 | Qn1 | co185 | Ar4 | A | 1.35 | 501.1 | EXP. 2-N-3 |
| 2-N-908 | EXP. 1-N-51 | sco186 | Qn1 | co186 | Ar4 | A | 1.50 | 523.2 | EXP. 2-N-3 |
| 2-N-909 | EXP. 1-N-51 | sco187 | Qn1 | co187 | Ar4 | A | 1.27 | 503.2 | EXP. 2-N-3 |
| 2-N-910 | EXP. 1-N-51 | sco188 | Qn1 | co188 | Ar4 | A | 1.22 | 497.2 | EXP. 2-N-3 |
| 2-N-911 | EXP. 1-N-51 | sco189 | Qn1 | co189 | Ar4 | A | 1.20 | 511.2 | EXP. 2-N-3 |
| 2-N-912 | EXP. 1-N-51 | sco190 | Qn1 | co190 | Ar4 | A | 1.29 | 497.2 | EXP. 2-N-3 |
| 2-N-913 | EXP. 1-N-51 | sco191 | Qn1 | co191 | Ar4 | A | 1.25 | 485.2 | EXP. 2-N-3 |
| 2-N-914 | EXP. 1-N-51 | sco192 | Qn1 | co192 | Ar4 | A | 1.22 | 485.2 | EXP. 2-N-3 |
| 2-N-915 | EXP. 1-N-51 | sco193 | Qn1 | co193 | Ar4 | A | 1.29 | 536.2 | EXP. 2-N-3 |
| 2-N-916 | EXP. 1-N-51 | sco194 | Qn1 | co194 | Ar4 | A | 1.48 | 555.2 | EXP. 2-N-3 |
| 2-N-917 | EXP. 1-N-44 | sco53 | Qn2 | co53 | Ar4 | A | 1.25 | 442.3 | EXP. 2-N-3 |
| 2-N-918 | EXP. 1-N-44 | sco52 | Qn2 | co52 | Ar4 | A | 1.14 | 438.4 | EXP. 2-N-3 |
| 2-N-919 | EXP. 1-N-44 | sco50 | Qn2 | co50 | Ar4 | A | 1.23 | 449.3 | EXP. 2-N-3 |
| 2-N-920 | EXP. 1-N-44 | sco68 | Qn2 | co68 | Ar4 | A | 1.29 | 442.3 | EXP. 2-N-3 |
| 2-N-921 | EXP. 1-N-44 | sco66 | Qn2 | co66 | Ar4 | A | 1.36 | 442.3 | EXP. 2-N-3 |
| 2-N-922 | EXP. 1-N-44 | sco6 | Qn2 | co6 | Ar4 | A | 1.34 | 458.3 | EXP. 2-N-3 |
| 2-N-923 | EXP. 1-N-44 | sco76 | Qn2 | co76 | Ar4 | A | 1.45 | 492.1 | EXP. 2-N-3 |
| 2-N-924 | EXP. 1-N-44 | sco89 | Qn2 | co89 | Ar4 | A | 1.16 | 452.4 | EXP. 2-N-3 |
| 2-N-925 | EXP. 1-N-44 | sco94 | Qn2 | co94 | Ar4 | A | 1.28 | 456.3 | EXP. 2-N-3 |
| 2-N-926 | EXP. 1-N-44 | sco95 | Qn2 | co95 | Ar4 | A | 1.26 | 458.3 | EXP. 2-N-3 |
| 2-N-927 | EXP. 1-N-44 | sco93 | Qn2 | co93 | Ar4 | A | 1.33 | 516.3 | EXP. 2-N-3 |
| 2-N-928 | EXP. 1-N-44 | sco17 | Qn2 | co17 | Ar4 | A | 1.35 | 448.3 | EXP. 2-N-3 |
| 2-N-929 | EXP. 1-N-44 | sco18 | Qn2 | co18 | Ar4 | A | 1.35 | 448.3 | EXP. 2-N-3 |
| 2-N-930 | EXP. 1-N-51 | sco97 | Qn1 | co97 | Ar4 | A | 1.12 | 405.4 | EXP. 2-N-2 |
| 2-N-931 | EXP. 1-N-51 | sco5 | Qn1 | co5 | Ar4 | A | 1.10 | 419.4 | EXP. 2-N-2 |
| 2-N-932 | EXP. 1-N-44 | sco195 | Qn2 | co195 | Ar4 | A | 1.41 | 466.3 | EXP. 2-N-3 |
| 2-N-933 | EXP. 1-N-44 | sco1 | Qn2 | co1 | Ar4 | A | 1.10 | 316.3 | EXP. 2-N-1 |
| 2-N-934 | EXP. 1-N-44 | sco96 | Qn2 | co96 | Ar4 | A | 1.13 | 391.4 | EXP. 2-N-3 |
| 2-N-935 | EXP. 1-N-44 | sco196 | Qn2 | co196 | Ar4 | A | 1.15 | 405.4 | EXP. 2-N-3 |
| 2-N-936 | EXP. 1-N-44 | sco197 | Qn2 | co197 | Ar4 | A | 1.20 | 405.4 | EXP. 2-N-3 |
| 2-N-937 | EXP. 1-N-44 | sco198 | Qn2 | co198 | Ar4 | A | 1.11 | 403.3 | EXP. 2-N-3 |
| 2-N-938 | EXP. 1-N-44 | sco98 | Qn2 | co98 | Ar4 | A | 1.17 | 419.4 | EXP. 2-N-3 |
| 2-N-939 | EXP. 1-N-44 | sco99 | Qn2 | co99 | Ar4 | A | 1.15 | 419.4 | EXP. 2-N-3 |
| 2-N-940 | EXP. 1-N-44 | sco199 | Qn2 | co199 | Ar4 | A | 1.11 | 405.4 | EXP. 2-N-3 |
| 2-N-941 | EXP. 1-N-51 | sco96 | Qn1 | co96 | Ar4 | A | 1.18 | 419.4 | EXP. 2-N-3 |
| 2-N-942 | EXP. 1-N-51 | sco98 | Qn1 | co98 | Ar4 | A | 1.26 | 447.4 | EXP. 2-N-3 |
| 2-N-943 | EXP. 1-N-51 | sco99 | Qn1 | co99 | Ar4 | A | 1.22 | 447.4 | EXP. 2-N-3 |
| 2-N-944 | EXP. 1-N-44 | sco97 | Qn2 | co97 | Ar4 | A | 1.04 | 377.3 | EXP. 2-N-2 |
| 2-N-945 | EXP. 1-N-62 | sco1 | Qn2 | co1 | Ar41 | A | 1.08 | 361.4 | EXP. 2-N-1 |
| 2-N-946 | EXP. 1-N-62 | sco68 | Qn2 | co68 | Ar41 | A | 1.28 | 442.4 | EXP. 2-N-3 |
| 2-N-947 | EXP. 1-N-62 | sco53 | Qn2 | co53 | Ar41 | A | 1.23 | 442.4 | EXP. 2-N-3 |
| 2-N-948 | EXP. 1-N-62 | sco68 | Qn2 | co68 | Ar41 | A | 1.35 | 442.4 | EXP. 2-N-3 |
| 2-N-949 | EXP. 1-N-62 | sco58 | Qn2 | co58 | Ar41 | A | 1.25 | 454.4 | EXP. 2-N-3 |
| 2-N-950 | EXP. 1-N-62 | sco93 | Qn2 | co93 | Ar41 | A | 1.31 | 518.3 | EXP. 2-N-3 |
| 2-N-951 | EXP. 1-N-62 | sco94 | Qn2 | co94 | Ar41 | A | 1.28 | 456.4 | EXP. 2-N-3 |
| 2-N-952 | EXP. 1-N-62 | sco95 | Qn2 | co95 | Ar41 | A | 1.24 | 456.4 | EXP. 2-N-3 |
| 2-N-953 | EXP. 1-N-62 | sco89 | Qn2 | co89 | Ar41 | A | 1.15 | 452.4 | EXP. 2-N-3 |
| 2-N-954 | EXP. 1-N-62 | sco2 | Qn2 | co2 | Ar41 | A | 1.17 | 375.4 | EXP. 2-N-3 |
| 2-N-955 | EXP. 1-N-61 | sco253 | Qn1 | co253 | Ar41 | A | 1.17 | 449.4 | EXP. 2-N-2 |
| 2-N-956 | EXP. 1-N-61 | sco254 | Qn1 | co254 | Ar41 | A | 1.42 | 498.4 | EXP. 2-N-2 |
| 2-N-957 | EXP. 1-N-62 | sco96 | Qn2 | co96 | Ar41 | A | 1.15 | 391.4 | EXP. 2-N-3 |
| 2-N-958 | EXP. 1-N-62 | sco98 | Qn2 | co98 | Ar41 | A | 1.18 | 419.4 | EXP. 2-N-3 |
| 2-N-959 | EXP. 1-N-62 | sco99 | Qn2 | co99 | Ar41 | A | 1.17 | 419.4 | EXP. 2-N-3 |
| 2-N-960 | EXP. 1-N-62 | sco201 | Qn2 | co201 | Ar41 | A | 1.31 | 369.5 | EXP. 2-N-3 |
| 2-N-961 | EXP. 1-N-62 | sco97 | Qn2 | co97 | Ar41 | A | 1.05 | 377.4 | EXP. 2-N-3 |
| 2-N-962 | EXP. 1-N-61 | sco53 | Qn1 | co53 | Ar41 | A | 1.33 | 470.4 | EXP. 2-N-3 |
| 2-N-963 | EXP. 1-N-61 | sco55 | Qn1 | co55 | Ar41 | A | 1.37 | 470.4 | EXP. 2-N-3 |
| 2-N-964 | EXP. 1-N-61 | sco56 | Qn1 | co56 | Ar41 | A | 1.36 | 482.5 | EXP. 2-N-3 |
| 2-N-965 | EXP. 1-N-61 | sco94 | Qn1 | co94 | Ar41 | A | 1.37 | 484.5 | EXP. 2-N-3 |
| 2-N-966 | EXP. 1-N-61 | sco201 | Qn1 | co201 | Ar41 | A | 1.37 | 417.5 | EXP. 2-N-3 |
| 2-N-967 | EXP. 1-N-61 | sco97 | Qn1 | co97 | Ar41 | A | 1.18 | 405.5 | EXP. 2-N-3 |
| 2-N-968 | EXP. 1-N-61 | sco98 | Qn1 | co98 | Ar41 | A | 1.29 | 447.5 | EXP. 2-N-3 |
| 2-N-969 | EXP. 1-N-61 | sco99 | Qn1 | co99 | Ar41 | A | 1.26 | 447.5 | EXP. 2-N-3 |
| 2-N-970 | EXP. 1-N-61 | sco96 | Qn1 | co96 | Ar41 | A | 1.21 | 419.5 | EXP. 2-N-3 |
| 2-N-971 | EXP. 1-N-61 | sco255 | Qn1 | co255 | Ar41 | A | 1.26 | 433.5 | EXP. 2-N-3 |

TABLE 2-N-continued

| EXP. | SM1 | SM2 | ST | J | Ar | LCMS method | RTime | MH+ | Ref. |
|---|---|---|---|---|---|---|---|---|---|
| 2-N-972 | EXP. 1-N-61 | sco256 | Qn1 | co256 | Ar41 | A | 1.26 | 433.5 | EXP. 2-N-3 |
| 2-N-973 | EXP. 1-N-61 | sco257 | Qn1 | co257 | Ar41 | A | 1.43 | 429.5 | EXP. 2-N-3 |
| 2-N-974 | EXP. 1-N-61 | sco258 | Qn1 | co258 | Ar41 | A | 1.24 | 461.5 | EXP. 2-N-3 |
| 2-N-975 | EXP. 1-N-61 | sco259 | Qn1 | co259 | Ar41 | A | 1.26 | 445.5 | EXP. 2-N-3 |
| 2-N-976 | EXP. 1-N-61 | sco53 | Qn1 | co53 | Ar18 | A | 1.25 | 452.4 | EXP. 2-N-3 |
| 2-N-977 | EXP. 1-N-61 | sco68 | Qn1 | co68 | Ar18 | A | 1.30 | 452.4 | EXP. 2-N-3 |
| 2-N-978 | EXP. 1-N-61 | sco58 | Qn1 | co58 | Ar18 | A | 1.29 | 464.5 | EXP. 2-N-3 |
| 2-N-979 | EXP. 1-N-61 | sco94 | Qn1 | co94 | Ar18 | A | 1.30 | 466.5 | EXP. 2-N-3 |
| 2-N-980 | EXP. 1-N-61 | sco201 | Qn1 | co201 | Ar18 | A | 1.29 | 399.5 | EXP. 2-N-3 |
| 2-N-981 | EXP. 1-N-61 | sco97 | Qn1 | co97 | Ar18 | A | 1.08 | 387.5 | EXP. 2-N-3 |
| 2-N-982 | EXP. 1-N-61 | sco98 | Qn1 | co98 | Ar18 | A | 1.21 | 429.5 | EXP. 2-N-3 |
| 2-N-983 | EXP. 1-N-61 | sco99 | Qn1 | co99 | Ar18 | A | 1.19 | 429.5 | EXP. 2-N-3 |
| 2-N-984 | EXP. 1-N-61 | sco96 | Qn1 | co96 | Ar18 | A | 1.14 | 401.5 | EXP. 2-N-3 |
| 2-N-985 | EXP. 1-N-61 | sco255 | Qn1 | co255 | Ar18 | A | 1.18 | 415.5 | EXP. 2-N-3 |
| 2-N-986 | EXP. 1-N-61 | sco256 | Qn1 | co256 | Ar18 | A | 1.18 | 415.5 | EXP. 2-N-3 |
| 2-N-987 | EXP. 1-N-61 | sco257 | Qn1 | co257 | Ar18 | A | 1.35 | 411.5 | EXP. 2-N-3 |
| 2-N-988 | EXP. 1-N-61 | sco258 | Qn1 | co258 | Ar18 | A | 1.17 | 443.5 | EXP. 2-N-3 |
| 2-N-989 | EXP. 1-N-61 | sco259 | Qn1 | co259 | Ar18 | A | 1.19 | 427.5 | EXP. 2-N-3 |
| 2-N-990 | EXP. 1-N-62 | sco60 | Qn2 | co60 | Ar41 | A | 1.26 | 449.4 | EXP. 2-N-3 |

TABLE 2-O

| EXP. | SM1 | SM2 | ST | J | Ar | LCMS method | RTime | MH+ | Ref. |
|---|---|---|---|---|---|---|---|---|---|
| 2-o-1 | EXP. 1-o-1 | sco1 | Qo1 | co1 | Ar1 | A | 1.14 | 372.4 | EXP. 2-N-1 |
| 2-o-2 | EXP. 1-o-1 | sco201 | Qo1 | co201 | Ar1 | A | 1.33 | 400.3 | EXP. 2-N-2 |
| 2-o-3 | EXP. 1-o-1 | sco2 | Qo1 | co2 | Ar1 | A | 1.29 | 398.3 | EXP. 2-N-2 |
| 2-o-4 | EXP. 1-o-1 | sco202 | Qo1 | co202 | Ar1 | A | 1.06 | 441.3 | EXP. 2-N-2 |
| 2-o-5 | EXP. 1-o-1 | sco203 | Qo1 | co203 | Ar1 | A | 1.18 | 442.3 | EXP. 2-N-2 |
| 2-o-6 | EXP. 1-o-1 | sco204 | Qo1 | co204 | Ar1 | A | 1.2 | 428.1 | EXP. 2-N-2 |
| 2-o-7 | EXP. 1-o-1 | sco49 | Qo1 | co49 | Ar1 | A | 1.36 | 424.3 | EXP. 2-N-2 |
| 2-o-8 | EXP. 1-o-1 | sco205 | Qo1 | co205 | Ar1 | A | 0.96 | 441.1 | EXP. 2-N-2 |
| 2-o-9 | EXP. 1-o-1 | sco206 | Qo1 | co206 | Ar1 | A | 1.44 | 437.3 | EXP. 2-N-2 |
| 2-o-10 | EXP. 1-o-1 | sco47 | Qo1 | co47 | Ar1 | A | 1.43 | 440.2 | EXP. 2-N-2 |
| 2-o-11 | EXP. 1-o-1 | sco39 | Qo1 | co39 | Ar1 | A | 1.11 | 436.2 | EXP. 2-N-2 |
| 2-o-12 | EXP. 1-o-1 | sco41 | Qo1 | co41 | Ar1 | A | 1.18 | 436.2 | EXP. 2-N-2 |
| 2-o-13 | EXP. 1-o-1 | sco37 | Qo1 | co37 | Ar1 | A | 1.24 | 436.3 | EXP. 2-N-2 |
| 2-o-14 | EXP. 1-o-1 | sco44 | Qo1 | co44 | Ar1 | A | 1.02 | 438.2 | EXP. 2-N-2 |
| 2-o-15 | EXP. 1-o-1 | sco207 | Qo1 | co207 | Ar1 | A | 1.37 | 438.3 | EXP. 2-N-2 |
| 2-o-16 | EXP. 1-o-1 | sco208 | Qo1 | co208 | Ar1 | A | 1.21 | 438.3 | EXP. 2-N-2 |
| 2-o-17 | EXP. 1-o-1 | sco45 | Qo1 | co45 | Ar1 | A | 1.23 | 441.2 | EXP. 2-N-2 |
| 2-o-18 | EXP. 1-o-1 | sco209 | Qo1 | co209 | Ar1 | A | 1.03 | 453.0 | EXP. 2-N-2 |
| 2-o-19 | EXP. 1-o-1 | sco210 | Qo1 | co210 | Ar1 | A | 1.00 | 443.1 | EXP. 2-N-2 |
| 2-o-20 | EXP. 1-o-1 | sco211 | Qo1 | co211 | Ar1 | A | 0.92 | 443.1 | EXP. 2-N-2 |
| 2-o-21 | EXP. 1-o-1 | sco212 | Qo1 | co212 | Ar1 | A | 0.99 | 471.1 | EXP. 2-N-2 |
| 2-o-22 | EXP. 1-o-1 | sco213 | Qo1 | co213 | Ar1 | A | 0.96 | 485.1 | EXP. 2-N-2 |
| 2-o-23 | EXP. 1-o-1 | sco28 | Qo1 | co28 | Ar1 | A | 1.17 | 435.2 | EXP. 2-N-2 |
| 2-o-24 | EXP. 1-o-1 | sco37 | Qo1 | co37 | Ar1 | A | 1.24 | 435.3 | EXP. 2-N-2 |
| 2-o-25 | EXP. 1-o-1 | sco76 | Qo1 | co76 | Ar1 | A | 1.63 | 503.3 | EXP. 2-N-2 |
| 2-o-26 | EXP. 1-o-1 | sco100 | Qo1 | co100 | Ar1 | A | 1.17 | 449.1 | EXP. 2-N-3 |
| 2-o-27 | EXP. 1-o-1 | sco74 | Qo1 | co74 | Ar1 | A | 1.35 | 469.0 | EXP. 2-N-3 |
| 2-o-28 | EXP. 1-o-1 | sco75 | Qo1 | co75 | Ar1 | A | 0.99 | 450.1 | EXP. 2-N-3 |
| 2-o-29 | EXP. 1-o-1 | sco6 | Qo1 | co6 | Ar1 | A | 1.29 | 450.2 | EXP. 2-N-3 |
| 2-o-30 | EXP. 1-o-1 | sco53 | Qo1 | co53 | Ar1 | A | 1.25 | 453.2 | EXP. 2-N-3 |
| 2-o-31 | EXP. 1-o-1 | sco38 | Qo1 | co38 | Ar1 | A | 1.12 | 435.0 | EXP. 2-N-3 |
| 2-o-32 | EXP. 1-o-1 | sco68 | Qo1 | co88 | Ar1 | A | 1.29 | 453.2 | EXP. 2-N-3 |
| 2-o-33 | EXP. 1-o-1 | sco214 | Qo1 | co214 | Ar1 | A | 1.31 | 453.3 | EXP. 2-N-3 |
| 2-o-34 | EXP. 1-o-1 | sco77 | Qo1 | co77 | Ar1 | A | 1.35 | 465.1 | EXP. 2-N-3 |
| 2-o-35 | EXP. 1-o-1 | sco215 | Qo1 | co215 | Ar1 | A | 1.38 | 483.0 | EXP. 2-N-3 |
| 2-o-36 | EXP. 1-o-1 | sco249 | Qo1 | co249 | Ar1 | A | 1.26 | 449.1 | EXP. 2-N-2 |
| 2-o-37 | EXP. 1-o-1 | sco31 | Qo1 | co31 | Ar1 | A | 1.40 | 434.3 | EXP. 2-N-3 |
| 2-o-38 | EXP. 1-o-1 | sco8 | Qo1 | co8 | Ar1 | A | 1.51 | 448.3 | EXP. 2-N-3 |
| 2-o-39 | EXP. 1-o-1 | sco11 | Qo1 | co11 | Ar1 | A | 1.40 | 452.3 | EXP. 2-N-3 |
| 2-o-40 | EXP. 1-o-1 | sco23 | Qo1 | co23 | Ar1 | A | 1.46 | 464.3 | EXP. 2-N-3 |
| 2-o-41 | EXP. 1-o-1 | sco17 | Qo1 | co17 | Ar1 | A | 1.39 | 459.3 | EXP. 2-N-3 |
| 2-o-42 | EXP. 1-o-1 | sco25 | Qo1 | co25 | Ar1 | A | 1.53 | 477.1 | EXP. 2-N-3 |
| 2-o-43 | EXP. 1-o-1 | sco92 | Qo1 | co92 | Ar1 | A | 1.09 | 449.2 | EXP. 2-N-3 |
| 2-o-44 | EXP. 1-o-1 | sco216 | Qo1 | co216 | Ar1 | A | 1.04 | 438.1 | EXP. 2-N-3 |
| 2-o-45 | EXP. 1-o-1 | sco97 | Qo1 | co97 | Ar1 | A | 1.19 | 388.3 | EXP. 2-N-2 |
| 2-o-46 | EXP. 1-o-1 | sco96 | Qo1 | co96 | Ar1 | A | 1.15 | 402.3 | EXP. 2-N-3 |
| 2-o-47 | EXP. 1-o-1 | sco217 | Qo1 | co217 | Ar1 | A | 1.05 | 430.1 | EXP. 2-N-2 |

TABLE 2-O-continued

| EXP. | SM1 | SM2 | ST | J | Ar | LCMS method | RTime | MH+ | Ref. |
|---|---|---|---|---|---|---|---|---|---|
| 2-o-48 | EXP. 1-o-1 | sco218 | Qo1 | co218 | Ar1 | A | 0.87 | 387.0 | EXP. 2-N-2 |
| 2-o-49 | EXP. 1-o-1 | sco219 | Qo1 | co219 | Ar1 | A | 0.93 | 415.1 | EXP. 2-N-2 |
| 2-o-50 | EXP. 1-o-1 | sco220 | Qo1 | co220 | Ar1 | A | 0.93 | 457.1 | EXP. 2-N-2 |
| 2-o-51 | EXP. 1-o-1 | sco221 | Qo1 | co221 | Ar1 | A | 0.90 | 441.1 | EXP. 2-N-2 |
| 2-o-52 | EXP. 1-o-1 | sco222 | Qo1 | co222 | Ar1 | A | 2.37 | 457.2 | EXP. 2-N-2 |
| 2-o-53 | EXP. 1-o-1 | sco223 | Qo1 | co223 | Ar1 | A | 1.13 | 416.1 | EXP. 2-N-3 |
| 2-o-54 | EXP. 1-o-1 | sco224 | Qo1 | co224 | Ar1 | A | 1.29 | 458.1 | EXP. 2-N-3 |
| 2-o-55 | EXP. 1-o-1 | sco225 | Qo1 | co225 | Ar1 | A | 1.32 | 470.3 | EXP. 2-N-3 |
| 2-o-56 | EXP. 1-o-1 | sco98 | Qo1 | co98 | Ar1 | A | 1.16 | 430.1 | EXP. 2-N-3 |
| 2-o-57 | EXP. 1-o-1 | sco99 | Qo1 | co99 | Ar1 | A | 1.15 | 430.1 | EXP. 2-N-3 |
| 2-o-58 | EXP. 1-o-1 | sco226 | Qo1 | co226 | Ar1 | A | 1.70 | 538.1 | EXP. 2-N-3 |
| 2-o-59 | EXP. 1-o-1 | sco227 | Qo1 | co227 | Ar1 | A | 1.39 | 484.3 | EXP. 2-N-3 |
| 2-o-60 | EXP. 1-o-1 | sco228 | Qo1 | co228 | Ar1 | A | 1.06 | 415.1 | EXP. 2-N-3 |
| 2-o-61 | EXP. 1-o-1 | sco229 | Qo1 | co229 | Ar1 | A | 0.96 | 441.2 | EXP. 2-N-2 |
| 2-o-62 | EXP. 1-o-1 | sco230 | Qo1 | co230 | Ar1 | A | 0.91 | 455.1 | EXP. 2-N-2 |
| 2-o-63 | EXP. 1-o-1 | sco231 | Qo1 | co231 | Ar1 | A | 0.93 | 413.2 | EXP. 2-N-2 |
| 2-o-64 | EXP. 1-o-1 | sco232 | Qo1 | co232 | Ar1 | A | 0.94 | 427.2 | EXP. 2-N-2 |
| 2-o-65 | EXP. 1-o-1 | sco252 | Qo1 | co252 | Ar1 | A | 0.93 | 427.1 | EXP. 2-N-2 |
| 2-o-66 | EXP. 1-o-6 | sco1 | Qo2 | co1 | Ar1 | A | 1.07 | 344.1 | EXP. 2-N-1 |
| 2-o-67 | EXP. 1-o-6 | sco39 | Qo2 | co39 | Ar1 | A | 1.01 | 408.2 | EXP. 2-N-4 |
| 2-o-68 | EXP. 1-o-6 | sco41 | Qo2 | co41 | Ar1 | A | 1.20 | 408.1 | EXP. 2-N-2 |
| 2-o-69 | EXP. 1-o-6 | sco40 | Qo2 | co40 | Ar1 | A | 1.10 | 408.0 | EXP. 2-N-2 |
| 2-o-70 | EXP. 1-o-6 | sco44 | Qo2 | co44 | Ar1 | A | 0.97 | 410.2 | EXP. 2-N-4 |
| 2-o-71 | EXP. 1-o-6 | sco43 | Qo2 | co43 | Ar1 | A | 1.04 | 410.1 | EXP. 2-N-2 |
| 2-o-72 | EXP. 1-o-6 | sco233 | Qo2 | co233 | Ar1 | A | 1.22 | 395.2 | EXP. 2-N-4 |
| 2-o-73 | EXP. 1-o-6 | sco207 | Qo2 | co207 | Ar1 | A | 1.23 | 410.1 | EXP. 2-N-2 |
| 2-o-74 | EXP. 1-o-6 | sco234 | Qo2 | co234 | Ar1 | A | 1.20 | 410.1 | EXP. 2-N-2 |
| 2-o-75 | EXP. 1-o-6 | sco235 | Qo2 | co235 | Ar1 | A | 0.89 | 415.1 | EXP. 2-N-2 |
| 2-o-76 | EXP. 1-o-6 | sco210 | Qo2 | co210 | Ar1 | A | 0.95 | 415.2 | EXP. 2-N-2 |
| 2-o-77 | EXP. 1-o-6 | sco28 | Qo2 | co28 | Ar1 | A | 1.08 | 407.2 | EXP. 2-N-4 |
| 2-o-78 | EXP. 1-o-6 | sco76 | Qo2 | co76 | Ar1 | A | 1.49 | 475.1 | EXP. 2-N-2 |
| 2-o-79 | EXP. 1-o-6 | sco53 | Qo2 | co53 | Ar1 | A | 1.24 | 425.1 | EXP. 2-N-2 |
| 2-o-80 | EXP. 1-o-6 | sco100 | Qo2 | co100 | Ar1 | A | 1.13 | 421.1 | EXP. 2-N-3 |
| 2-o-81 | EXP. 1-o-6 | sco74 | Qo2 | co74 | Ar1 | A | 1.33 | 441.0 | EXP. 2-N-3 |
| 2-o-82 | EXP. 1-o-6 | sco75 | Qo2 | co75 | Ar1 | A | 0.94 | 422.0 | EXP. 2-N-3 |
| 2-o-83 | EXP. 1-o-6 | sco6 | Qo2 | co6 | Ar1 | A | 1.26 | 432.0 | EXP. 2-N-3 |
| 2-o-84 | EXP. 1-o-6 | sco38 | Qo2 | co38 | Ar1 | A | 1.09 | 407.0 | EXP. 2-N-3 |
| 2-o-85 | EXP. 1-o-6 | sco58 | Qo2 | co58 | Ar1 | A | 1.25 | 425.0 | EXP. 2-N-3 |
| 2-o-86 | EXP. 1-o-6 | sco236 | Qo2 | co236 | Ar1 | A | 1.28 | 455.2 | EXP. 2-N-3 |
| 2-o-87 | EXP. 1-o-6 | sco215 | Qo2 | co215 | Ar1 | A | 1.34 | 455.0 | EXP. 2-N-3 |
| 2-o-88 | EXP. 1-o-6 | sco214 | Qo2 | co214 | Ar1 | A | 1.27 | 425.1 | EXP. 2-N-3 |
| 2-o-89 | EXP. 1-o-6 | sco77 | Qo2 | co77 | Ar1 | A | 1.32 | 437.1 | EXP. 2-N-3 |
| 2-o-90 | EXP. 1-o-6 | sco31 | Qo2 | co31 | Ar1 | A | 1.36 | 406.3 | EXP. 2-N-3 |
| 2-o-91 | EXP. 1-o-6 | sco8 | Qo2 | co8 | Ar1 | A | 1.45 | 420.3 | EXP. 2-N-3 |
| 2-o-92 | EXP. 1-o-6 | sco11 | Qo2 | co11 | Ar1 | A | 1.40 | 424.3 | EXP. 2-N-3 |
| 2-o-93 | EXP. 1-o-6 | sco23 | Qo2 | co23 | Ar1 | A | 1.39 | 436.3 | EXP. 2-N-3 |
| 2-o-94 | EXP. 1-o-6 | sco17 | Qo2 | co17 | Ar1 | A | 1.33 | 431.2 | EXP. 2-N-3 |
| 2-o-95 | EXP. 1-o-6 | sco25 | Qo2 | co25 | Ar1 | A | 1.46 | 449.1 | EXP. 2-N-3 |
| 2-o-96 | EXP. 1-o-6 | sco237 | Qo2 | co237 | Ar1 | A | 1.26 | 457.1 | EXP. 2-N-2 |
| 2-o-97 | EXP. 1-o-6 | sco92 | Qo2 | co92 | Ar1 | A | 0.97 | 421.2 | EXP. 2-N-2 |
| 2-o-98 | EXP. 1-o-6 | sco238 | Qo2 | co238 | Ar1 | A | 0.97 | 421.1 | EXP. 2-N-2 |
| 2-o-99 | EXP. 1-o-6 | sco239 | Qo2 | co239 | Ar1 | A | 0.99 | 435.1 | EXP. 2-N-2 |
| 2-o-100 | EXP. 1-o-6 | sco216 | Qo2 | co216 | Ar1 | A | 0.91 | 410.0 | EXP. 2-N-2 |
| 2-o-101 | EXP. 1-o-6 | sco240 | Qo2 | co240 | Ar1 | A | 0.97 | 411.2 | EXP. 2-N-4 |
| 2-o-102 | EXP. 1-o-6 | sco241 | Qo2 | co241 | Ar1 | A | 0.95 | 412.2 | EXP. 2-N-4 |
| 2-o-103 | EXP. 1-o-6 | sco242 | Qo2 | co242 | Ar1 | A | 0.88 | 424.2 | EXP. 2-N-2 |
| 2-o-104 | EXP. 1-o-6 | sco243 | Qo2 | co243 | Ar1 | A | 0.89 | 427.2 | EXP. 2-N-2 |
| 2-o-105 | EXP. 1-o-6 | sco97 | Qo2 | co97 | Ar1 | A | 1.10 | 359.8 | EXP. 2-N-2 |
| 2-o-106 | EXP. 1-o-6 | sco244 | Qo2 | co244 | Ar1 | A | 1.00 | 374.1 | EXP. 2-N-2 |
| 2-o-107 | EXP. 1-o-6 | sco245 | Qo2 | co245 | Ar1 | A | 1.48 | 495.3 | EXP. 2-N-2 |
| 2-o-108 | EXP. 1-o-6 | sco223 | Qo2 | co223 | Ar1 | A | 1.01 | 388.1 | EXP. 2-N-3 |
| 2-o-109 | EXP. 1-o-6 | sco224 | Qo2 | co224 | Ar1 | A | 1.20 | 428.1 | EXP. 2-N-3 |
| 2-o-110 | EXP. 1-o-6 | sco227 | Qo2 | co227 | Ar1 | A | 1.22 | 442.1 | EXP. 2-N-3 |
| 2-o-111 | EXP. 1-o-6 | sco98 | Qo2 | co98 | Ar1 | A | 1.05 | 402.1 | EXP. 2-N-3 |
| 2-o-112 | EXP. 1-o-6 | sco99 | Qo2 | co99 | Ar1 | A | 1.04 | 402.1 | EXP. 2-N-3 |
| 2-o-113 | EXP. 1-o-6 | sco226 | Qo2 | co226 | Ar1 | A | 1.61 | 510.2 | EXP. 2-N-3 |
| 2-o-114 | EXP. 1-o-6 | sco227 | Qo2 | co227 | Ar1 | A | 1.28 | 456.3 | EXP. 2-N-3 |
| 2-o-115 | EXP. 1-o-6 | sco226 | Qo2 | co228 | Ar1 | A | 0.97 | 388.1 | EXP. 2-N-3 |
| 2-o-116 | EXP. 1-o-6 | sco218 | Qo2 | co218 | Ar1 | A | 0.82 | 359.0 | EXP. 2-N-2 |
| 2-o-117 | EXP. 1-o-5 | sco245 | Qo2 | co246 | Ar1 | A | 0.82 | 373.0 | EXP. 2-N-2 |
| 2-o-118 | EXP. 1-o-5 | sco219 | Qo2 | co219 | Ar1 | A | 0.94 | 387.1 | EXP. 2-N-2 |
| 2-o-119 | EXP. 1-o-6 | sco229 | Qo2 | co229 | Ar1 | A | 1.46 | 413.2 | EXP. 2-N-2 |
| 2-o-120 | EXP. 1-o-6 | sco230 | Qo2 | co230 | Ar1 | A | 0.87 | 427.2 | EXP. 2-N-2 |
| 2-o-121 | EXP. 1-o-6 | sco230 | Qo2 | co230 | Ar1 | A | 0.81 | 385.2 | EXP. 2-N-2 |
| 2-o-122 | EXP. 1-o-3 | sco1 | Qo3 | co1 | Ar1 | A | 1.08 | 358.4 | EXP. 2-N-2 |
| 2-o-123 | EXP. 1-o-3 | sco215 | Qo3 | co215 | Ar1 | A | 1.29 | 469.0 | EXP. 2-N-3 |

TABLE 2-O-continued

| EXP. | SM1 | SM2 | ST | J | Ar | LCMS method | RTime | MH+ | Ref. |
|---|---|---|---|---|---|---|---|---|---|
| 2-o-124 | EXP. 1-o-3 | sco44 | Qo3 | co44 | Ar1 | A | 0.91 | 424.1 | EXP. 2-N-3 |
| 2-o-125 | EXP. 1-o-3 | sco39 | Qo3 | co39 | Ar1 | A | 0.99 | 422.1 | EXP. 2-N-3 |
| 2-o-126 | EXP. 1-o-3 | sco97 | Qo3 | co97 | Ar1 | A | 0.94 | 374.1 | EXP. 2-N-3 |
| 2-o-128 | EXP. 1-o-76 | sco1 | Qo5 | co1 | Ar1 | A | 0.98 | 402.0 | EXP. 2-N-2 |
| 2-o-129 | EXP. 1-o-76 | sco28 | Qo5 | co28 | Ar1 | A | 0.99 | 465.0 | EXP. 2-N-2 |
| 2-o-130 | EXP. 1-o-76 | sco44 | Qo5 | co44 | Ar1 | A | 0.89 | 468.0 | EXP. 2-N-2 |
| 2-o-131 | EXP. 1-o-76 | sco219 | Qo5 | co219 | Ar1 | A | 0.8 | 445.1 | EXP. 2-N-2 |
| 2-o-132 | EXP. 1-o-76 | sco97 | Qo5 | co97 | Ar1 | A | 0.92 | 418.0 | EXP. 2-N-2 |
| 2-o-133 | EXP. 1-o-13 | sco1 | Qo6 | co1 | Ar1 | A | 1.08 | 372.2 | EXP. 2-N-1 |
| 2-o-134 | EXP. 1-o-13 | sco247 | Qo6 | co247 | Ar1 | A | 1.28 | 453.2 | EXP. 2-N-2 |
| 2-o-135 | EXP. 1-o-13 | sco249 | Qo6 | co249 | Ar1 | A | 1.35 | 423.2 | EXP. 2-N-2 |
| 2-o-136 | EXP. 1-o-13 | sco250 | Qo6 | co250 | Ar1 | A | 1.02 | 424.2 | EXP. 2-N-2 |
| 2-o-137 | EXP. 1-o-13 | sco240 | Qo6 | co240 | Ar1 | A | 1.08 | 439.2 | EXP. 2-N-2 |
| 2-o-138 | EXP. 1-o-11 | sco1 | Qo7 | co1 | Ar1 | A | 1.16 | 386.2 | EXP. 2-N-1 |
| 2-o-139 | EXP. 1-o-12 | sco1 | Qo8 | co1 | Ar1 | A | 1.32 | 386.4 | EXP. 2-N-1 |
| 2-o-140 | EXP. 1-o-15 | sco1 | Qo9 | co1 | Ar1 | A | 1.08 | 358.0 | EXP. 2-N-1 |
| 2-o-141 | EXP. 1-o-15 | sco44 | Qo9 | co44 | Ar1 | A | 1.09 | 424.1 | EXP. 2-N-2 |
| 2-o-142 | EXP. 1-o-15 | sco210 | Qo9 | co210 | Ar1 | B | 2.32 | 429.3 | EXP. 2-N-2 |
| 2-o-143 | EXP. 1-o-15 | sco216 | Qo9 | co216 | Ar1 | B | 2.28 | 424.2 | EXP. 2-N-2 |
| 2-o-144 | EXP. 1-o-15 | sco219 | Qo9 | co219 | Ar1 | A | 0.91 | 401.0 | EXP. 2-N-2 |
| 2-o-145 | EXP. 1-o-18 | sco1 | Qo10 | co1 | Ar1 | B | 2.91 | 388.3 | EXP. 2-N-1 |
| 2-o-146 | EXP. 1-o-18 | sco44 | Qo10 | co44 | Ar1 | B | 2.55 | 454.2 | EXP. 2-N-2 |
| 2-o-147 | EXP. 1-o-10 | sco1 | Qo11 | co1 | Ar1 | A | 0.98 | 346.1 | EXP. 2-N-1 |
| 2-o-148 | EXP. 1-o-7 | sco44 | Qo12 | co44 | Ar1 | A | 1.07 | 452.1 | EXP. 2-N-3 |
| 2-o-149 | EXP. 1-o-7 | sco97 | Qo12 | co97 | Ar1 | A | 1.05 | 402.1 | EXP. 2-N-3 |
| 2-o-150 | EXP. 1-o-8 | sco1 | Qo13 | co1 | Ar1 | A | 1.13 | 386.2 | EXP. 2-N-1 |
| 2-o-151 | EXP. 1-o-8 | sco44 | Qo13 | co44 | Ar1 | A | 1.03 | 452.1 | EXP. 2-N-2 |
| 2-o-152 | EXP. 2-o-19 | sco1 | Qo1-1 | co1 | Ar1 | A | 1.23 | 485.3 | EXP. 2-N-1 |
| 2-o-153 | EXP. 2-o-19 | sco44 | Qo1-1 | co44 | Ar1 | A | 1.13 | 551.1 | EXP. 2-N-2 |
| 2-o-154 | EXP. 2-o-20 | sco1 | Qo1-2 | co1 | Ar1 | A | 1.12 | 485.2 | EXP. 2-N-1 |
| 2-o-155 | EXP. 2-o-20 | sco44 | Qo1-2 | co44 | Ar1 | A | 1.05 | 551.1 | EXP. 2-N-2 |
| 2-o-156 | EXP. 2-o-21 | sco1 | Qo1-3 | co1 | Ar1 | B | 3.16 | 513.3 | EXP. 2-N-1 |
| 2-o-157 | EXP. 2-o-21 | sco44 | Qo1-3 | co44 | Ar1 | B | 2.84 | 578.2 | EXP. 2-N-2 |
| 2-o-158 | EXP. 2-o-22 | sco219 | Qo1-4 | co219 | Ar1 | A | 1.15 | 570.0 | EXP. 2-N-5 |
| 2-o-159 | EXP. 2-o-22 | sco44 | Qo1-4 | co44 | Ar1 | A | 1.13 | 593.1 | EXP. 2-N-5 |
| 2-o-160 | EXP. 2-o-22 | sco97 | Qo1-4 | co97 | Ar1 | A | 1.25 | 543.2 | EXP. 2-N-5 |
| 2-o-161 | EXP. 2-o-22 | sco2 | Qo1-4 | co2 | Ar1 | A | 1.34 | 553.1 | EXP. 2-N-5 |
| 2-o-162 | EXP. 2-o-36 | sco1 | Qo1-5 | co1 | Ar1 | A | 1.25 | 491.2 | EXP. 2-N-1 |
| 2-o-163 | EXP. 2-o-36 | sco44 | Qo1-5 | co44 | Ar1 | A | 1.26 | 557.7 | EXP. 2-N-2 |
| 2-o-164 | EXP. 2-o-48 | sco44 | Qo1-5 | co44 | Ar1 | A | 1.03 | 495.1 | EXP. 2-N-3 |
| 2-o-165 | EXP. 2-o-48 | sco219 | Qo1-6 | co219 | Ar1 | A | 0.96 | 472.1 | EXP. 2-N-3 |
| 2-o-166 | EXP. 2-o-48 | sco39 | Qo1-6 | co39 | Ar1 | A | 1.09 | 493.1 | EXP. 2-N-3 |
| 2-o-167 | EXP. 2-o-48 | sco207 | Qo1-6 | co207 | Ar1 | A | 1.17 | 495.1 | EXP. 2-N-3 |
| 2-o-168 | EXP. 2-o-48 | sco216 | Qo1-6 | co216 | Ar1 | A | 0.98 | 495.1 | EXP. 2-N-3 |
| 2-o-169 | EXP. 2-o-48 | sco217 | Qo1-6 | co217 | Ar1 | A | 1.02 | 486.1 | EXP. 2-N-3 |
| 2-o-170 | EXP. 2-o-48 | sco97 | Qo1-6 | co97 | Ar1 | A | 1.04 | 445.1 | EXP. 2-N-3 |
| 2-o-171 | EXP. 2-o-48 | sco2 | Qo1-6 | co2 | Ar1 | A | 1.17 | 455.1 | EXP. 2-N-3 |
| 2-o-172 | EXP. 2-o-48 | sco49 | Qo1-6 | co49 | Ar1 | A | 1.23 | 481.1 | EXP. 2-N-3 |
| 2-o-173 | EXP. 2-o-61 | sco1 | Qo1-7 | co1 | Ar1 | A | 1.14 | 482.3 | EXP. 2-N-1 |
| 2-o-174 | EXP. 2-o-61 | sco28 | Qo1-7 | co28 | Ar1 | A | 1.17 | 546.0 | EXP. 2-N-2 |
| 2-o-175 | EXP. 2-o-61 | sco39 | Qo1-7 | co39 | Ar1 | A | 1.07 | 547.1 | EXP. 2-N-5 |
| 2-o-176 | EXP. 2-o-61 | sco44 | Qo1-7 | co44 | Ar1 | A | 1.01 | 549.1 | EXP. 2-N-5 |
| 2-o-177 | EXP. 2-o-61 | sco2 | Qo1-7 | co2 | Ar1 | A | 1.2 | 509.1 | EXP. 2-N-5 |
| 2-o-178 | EXP. 2-o-61 | sco219 | Qo1-7 | co219 | Ar1 | A | 0.96 | 526.1 | EXP. 2-N-5 |
| 2-o-179 | EXP. 2-o-61 | sco97 | Qo1-7 | co97 | Ar1 | A | 1.06 | 499.0 | EXP. 2-N-5 |
| 2-o-180 | EXP. 2-o-63 | sco44 | Qo1-8 | co44 | Ar1 | A | 1.02 | 521.1 | EXP. 2-N-2 |
| 2-o-181 | EXP. 2-o-63 | sco28 | Qo1-8 | co28 | Ar1 | A | 1.25 | 518.0 | EXP. 2-N-2 |
| 2-o-182 | EXP. 2-o-63 | sco1 | Qo1-8 | co1 | Ar1 | B | 2.79 | 455.2 | EXP. 2-N-1 |
| 2-o-183 | EXP. 2-o-64 | sco44 | Qo1-9 | co44 | Ar1 | A | 1.03 | 535.1 | EXP. 2-N-2 |
| 2-o-184 | EXP. 2-o-65 | sco44 | Qo1-10 | co44 | Ar1 | A | 0.97 | 535.1 | EXP. 2-N-3 |
| 2-o-185 | EXP. 2-o-65 | sco39 | Qo1-10 | co39 | Ar1 | A | 1.05 | 533.1 | EXP. 2-N-3 |
| 2-o-186 | EXP. 2-o-65 | sco97 | Qo1-10 | co97 | Ar1 | A | 1.00 | 485.1 | EXP. 2-N-3 |
| 2-o-187 | EXP. 2-o-65 | sco4 | Qo1-10 | co4 | Ar1 | A | 1.09 | 532.1 | EXP. 2-N-3 |
| 2-o-188 | EXP. 2-o-75 | sco1 | Qo2-1 | co1 | Ar1 | A | 1.06 | 457.1 | EXP. 2-N-1 |
| 2-o-189 | EXP. 2-o-75 | sco44 | Qo2-1 | co44 | Ar1 | A | 1.01 | 523.1 | EXP. 2-N-2 |
| 2-o-190 | EXP. 2-o-75 | sco1 | Qo2-2 | co1 | Ar1 | A | 1.07 | 457.1 | EXP. 2-N-1 |
| 2-o-191 | EXP. 2-o-76 | sco44 | Qo2-2 | co44 | Ar1 | A | 1.03 | 523.1 | EXP. 2-N-2 |
| 2-o-192 | EXP. 2-o-76 | sco219 | Qo2-2 | co219 | Ar1 | A | 0.98 | 500.1 | EXP. 2-N-3 |
| 2-o-193 | EXP. 2-o-76 | sco97 | Qo2-2 | co97 | Ar1 | A | 1.05 | 473.1 | EXP. 2-N-3 |
| 2-o-194 | EXP. 2-o-116 | sco44 | Qo2-3 | co44 | Ar1 | A | 0.91 | 467.1 | EXP. 2-N-6 |
| 2-o-195 | EXP. 2-o-116 | sco219 | Qo2-3 | co219 | Ar1 | A | 0.83 | 444.1 | EXP. 2-N-6 |
| 2-o-196 | EXP. 2-o-116 | sco97 | Qo2-3 | co97 | Ar1 | A | 0.9 | 417.1 | EXP. 2-N-5 |
| 2-o-197 | EXP. 2-o-116 | sco2 | Qo2-3 | co2 | Ar1 | A | 1.02 | 427.1 | EXP. 2-N-5 |
| 2-o-198 | EXP. 2-o-116 | sco39 | Qo2-3 | co39 | Ar1 | A | 0.95 | 465.0 | EXP. 2-N-5 |
| 2-o-199 | EXP. 2-o-116 | sco28 | Qo2-3 | co28 | Ar1 | A | 0.96 | 464.0 | EXP. 2-N-5 |
| 2-o-200 | EXP. 2-o-116 | sco207 | Qo2-3 | co207 | Ar1 | A | 1.04 | 467.1 | EXP. 2-N-5 |

TABLE 2-O-continued

| EXP. | SM1 | SM2 | ST | J | Ar | LCMS method | RTime | MH+ | Ref. |
|---|---|---|---|---|---|---|---|---|---|
| 2-o-201 | EXP. 2-o-116 | sco216 | Qo2-3 | co216 | Ar1 | A | 0.85 | 467.1 | EXP. 2-N-5 |
| 2-o-202 | EXP. 2-o-116 | sco49 | Qo2-3 | co49 | Ar1 | A | 1.07 | 453.0 | EXP. 2-N-5 |
| 2-o-203 | EXP. 2-o-116 | sco217 | Qo2-3 | co217 | Ar1 | A | 0.69 | 458.1 | EXP. 2-N-5 |
| 2-o-204 | EXP. 2-o-117 | sco44 | Qo2-4 | co44 | Ar1 | A | 0.92 | 481.1 | EXP. 2-N-5 |
| 2-o-205 | EXP. 2-o-117 | sco219 | Qo2-4 | co219 | Ar1 | A | 0.86 | 458.1 | EXP. 2-N-5 |
| 2-o-206 | EXP. 2-o-117 | sco2 | Qo2-4 | co2 | Ar1 | A | 1.09 | 441.1 | EXP. 2-N-5 |
| 2-o-207 | EXP. 2-o-117 | sco39 | Qo2-4 | co39 | Ar1 | A | 0.95 | 479.0 | EXP. 2-N-5 |
| 2-o-208 | EXP. 2-o-117 | sco28 | Qo2-4 | co28 | Ar1 | A | 1.02 | 478.0 | EXP. 2-N-5 |
| 2-o-209 | EXP. 2-o-117 | sco49 | Qo2-4 | co49 | Ar1 | A | 1.12 | 467.0 | EXP. 2-N-5 |
| 2-o-210 | EXP. 2-o-117 | sco97 | Qo2-4 | co97 | Ar1 | A | 1.00 | 431.1 | EXP. 2-N-5 |
| 2-o-211 | EXP. 2-o-117 | sco216 | Qo2-4 | co216 | Ar1 | A | 0.95 | 481.1 | EXP. 2-N-5 |
| 2-o-212 | EXP. 2-o-119 | sco1 | Qo2-5 | co1 | Ar1 | A | 1.05 | 455.2 | EXP. 2-N-1 |
| 2-o-213 | EXP. 2-o-121 | sco1 | Qo2-6 | co1 | Ar1 | A | 0.97 | 427.2 | EXP. 2-N-1 |
| 2-o-214 | EXP. 2-o-121 | sco28 | Qo2-6 | co28 | Ar1 | A | 1.02 | 490.2 | EXP. 2-N-4 |
| 2-o-215 | EXP. 2-o-121 | sco44 | Qo2-6 | co44 | Ar1 | A | 0.93 | 493.2 | EXP. 2-N-4 |
| 2-o-216 | EXP. 2-o-121 | sco92 | Qo2-6 | co92 | Ar1 | A | 0.94 | 504.2 | EXP. 2-N-4 |
| 2-o-217 | EXP. 2-o-121 | sco240 | Qo2-6 | co240 | Ar1 | A | 0.95 | 494.2 | EXP. 2-N-4 |
| 2-o-218 | EXP. 2-o-142 | sco1 | Qo9-1 | co1 | Ar1 | A | 1.14 | 471.1 | EXP. 2-N-1 |
| 2-o-219 | EXP. 2-o-142 | sco44 | Qo9-1 | co44 | Ar1 | A | 1.00 | 537.0 | EXP. 2-N-2 |
| 2-o-220 | EXP. 2-o-142 | sco219 | Qo9-1 | co219 | Ar1 | A | 0.69 | 514.0 | EXP. 2-N-2 |
| 2-o-221 | EXP. 1-o-55 | sco1 | Qo1 | co1 | Ar3 | A | 0.86 | 348.0 | EXP. 2-N-1 |
| 2-o-222 | EXP. 1-o-56 | sco44 | Qo1 | co44 | Ar3 | A | 0.81 | 414.0 | EXP. 2-N-2 |
| 2-o-223 | EXP. 1-o-55 | sco37 | Qo1 | co37 | Ar3 | A | 0.90 | 411.0 | EXP. 2-N-4 |
| 2-o-224 | EXP. 1-o-55 | sco5 | Qo1 | co5 | Ar3 | A | 0.90 | 425.1 | EXP. 2-N-4 |
| 2-o-225 | EXP. 1-o-55 | sco76 | Qo1 | co76 | Ar3 | A | 1.17 | 479.0 | EXP. 2-N-4 |
| 2-o-226 | EXP. 1-o-55 | sco74 | Qo1 | co74 | Ar3 | A | 1.06 | 445.0 | EXP. 2-N-4 |
| 2-o-227 | EXP. 1-o-55 | sco40 | Qo1 | co40 | Ar3 | A | 0.84 | 412.1 | EXP. 2-N-4 |
| 2-o-228 | EXP. 1-o-55 | sco41 | Qo1 | co41 | Ar3 | A | 0.87 | 412.0 | EXP. 2-N-4 |
| 2-o-229 | EXP. 1-o-55 | sco207 | Qo1 | co207 | Ar3 | A | 0.93 | 414.1 | EXP. 2-N-4 |
| 2-o-230 | EXP. 1-o-55 | sco3 | Qo1 | co3 | Ar3 | A | 0.96 | 374.0 | EXP. 2-N-4 |
| 2-o-231 | EXP. 1-o-55 | sco4 | Qo1 | co4 | Ar3 | A | 0.87 | 411.0 | EXP. 2-N-4 |
| 2-o-232 | EXP. 1-o-55 | sco39 | Qo1 | co39 | Ar3 | A | 0.82 | 412.0 | EXP. 2-N-4 |
| 2-o-233 | EXP. 1-o-55 | sco43 | Qo1 | co43 | Ar3 | A | 0.81 | 414.1 | EXP. 2-N-4 |
| 2-o-234 | EXP. 1-o-55 | sco216 | Qo1 | co216 | Ar3 | A | 0.72 | 414.1 | EXP. 2-N-4 |
| 2-o-235 | EXP. 1-o-55 | sco92 | Qo1 | co92 | Ar3 | A | 0.82 | 425.1 | EXP. 2-N-4 |
| 2-o-236 | EXP. 1-o-55 | sco219 | Qo1 | co219 | Ar3 | A | 0.70 | 391.1 | EXP. 2-N-4 |
| 2-o-237 | EXP. 1-o-55 | sco97 | Qo1 | co97 | Ar3 | A | 0.78 | 364.0 | EXP. 2-N-4 |
| 2-o-238 | EXP. 1-o-55 | sco210 | Qo1 | co210 | Ar3 | A | 0.69 | 419.1 | EXP. 2-N-4 |
| 2-o-239 | EXP. 1-o-65 | sco235 | Qo1 | co235 | Ar3 | A | 0.68 | 419.1 | EXP. 2-N-4 |
| 2-o-240 | EXP. 1-o-55 | sco235 | Qo1 | co235 | Ar3 | A | 0.68 | 389.1 | EXP. 2-N-2 |
| 2-o-241 | EXP. 2-o-239 | sco44 | Qo1-11 | co44 | Ar3 | A | 0.74 | 527.1 | EXP. 2-N-5 |
| 2-o-242 | EXP. 2-o-239 | sco219 | Qo1-11 | co219 | Ar3 | A | 0.66 | 504.0 | EXP. 2-N-5 |
| 2-o-243 | EXP. 2-o-238 | sco44 | Qo1-1 | co44 | Ar3 | A | 0.75 | 527.1 | EXP. 2-N-5 |
| 2-o-244 | EXP. 2-o-238 | sco219 | Qo1-1 | co219 | Ar3 | A | 0.69 | 504.1 | EXP. 2-N-5 |
| 2-o-245 | EXP. 2-o-238 | sco97 | Qo1-1 | co97 | Ar3 | A | 0.72 | 477.1 | EXP. 2-N-5 |
| 2-o-246 | EXP. 2-o-238 | sco2 | Qo1-1 | co2 | Ar3 | A | 0.88 | 487.1 | EXP. 2-N-5 |
| 2-o-247 | EXP. 2-o-240 | sco44 | Qo1-8 | co44 | Ar3 | A | 0.87 | 497.0 | EXP. 2-N-5 |
| 2-o-248 | EXP. 2-o-240 | sco219 | Qo1-8 | co219 | Ar3 | A | 0.66 | 474.1 | EXP. 2-N-5 |
| 2-o-249 | EXP. 2-o-240 | sco97 | Qo1-8 | co97 | Ar3 | A | 0.71 | 447.1 | EXP. 2-N-5 |
| 2-o-250 | EXP. 2-o-240 | sco2 | Qo1-8 | co2 | Ar3 | A | 0.85 | 457.1 | EXP. 2-N-5 |
| 2-o-251 | EXP. 2-o-240 | sco39 | Qo1-8 | co39 | Ar3 | A | 0.76 | 495.1 | EXP. 2-N-5 |
| 2-o-252 | EXP. 1-o-56 | sco3 | Qo2 | co3 | Ar4 | A | 1.30 | 388.3 | EXP. 2-N-2 |
| 2-o-253 | EXP. 1-o-56 | sco39 | Qo2 | co39 | Ar4 | A | 1.14 | 426.2 | EXP. 2-N-2 |
| 2-o-254 | EXP. 1-o-56 | sco214 | Qo2 | co214 | Ar4 | A | 1.37 | 443.2 | EXP. 2-N-2 |
| 2-o-255 | EXP. 1-o-56 | sco5 | Qo2 | co5 | Ar4 | A | 1.26 | 439.0 | EXP. 2-N-2 |
| 2-o-256 | EXP. 1-o-56 | sco76 | Qo2 | co76 | Ar4 | A | 1.66 | 493.2 | EXP. 2-N-2 |
| 2-o-257 | EXP. 1-o-2 | sco1 | Qo14 | co1 | Ar1 | A | 1.16 | 372.4 | EXP. 2-N-1 |

TABLE 2-S

| EXP. | SM1 | SM2 | ST | J | Ar | LCMS method | RTime | MH+ | Ref. |
|---|---|---|---|---|---|---|---|---|---|
| 2-s-1 | EXP. 1-s-1 | sco100 | Qs1 | co100 | Ar1 | A | 1.46 | 465.3 | EXP. 2-N-2 |
| 2-s-2 | EXP. 1-s-1 | sco6 | Qs1 | co6 | Ar1 | A | 4.60 | 476.3 | EXP. 2-N-2 |
| 2-s-3 | EXP. 1-s-1 | sco84 | Qs1 | co94 | Ar1 | A | 1.60 | 483.4 | EXP. 2-N-2 |
| 2-s-4 | EXP. 1-s-2 | sco1 | Qs2 | co1 | Ar1 | A | 1.15 | 347.9 | EXP. 2-N-1 |
| 2-s-5 | EXP. 1-s-2 | sco44 | Qs2 | co44 | Ar1 | A | 1.08 | 414.1 | EXP. 2-N-2 |
| 2-s-6 | EXP. 1-s-2 | sco97 | Qs2 | co97 | Ar1 | A | 1.09 | 364.0 | EXP. 2-N-2 |

TABLE 2-N2

| Exp. | SM1 | SM2 | ST | J | Ar | LCMS method | RTime | MH+ | Ref. |
|---|---|---|---|---|---|---|---|---|---|
| 4-NP-419 | EXP. 1-N-66 | sco1 | Qn2 | co1 | Ar192 | A | 0.65 | 333.3 | EXP. 2-N-1 |
| 4-NP-420 | EXP. 1-N-66 | sco2 | Qn2 | co2 | Ar192 | A | 0.73 | 347.3 | EXP. 2-N-3 |
| 4-NP-435 | EXP. 1-N-63 | sco260 | Qn1 | co260 | Ar192 | A | 0.87 | 389.4 | EXP. 2-N-3 |
| 4-NP-436 | EXP. 1-N-64 | sco260 | Qn1 | co260 | Ar186 | A | 0.77 | 389.4 | EXP. 2-N-3 |
| 4-NP-437 | EXP. 1-N-65 | sco260 | Qn1 | co260 | Ar161 | A | 0.73 | 403.4 | EXP. 2-N-3 |
| 4-NP-438 | EXP. 1-N-63 | sco261 | Qn1 | co261 | Ar192 | A | 0.96 | 403.4 | EXP. 2-N-3 |
| 4-NP-439 | EXP. 1-N-64 | sco261 | Qn1 | co261 | Ar186 | A | 0.87 | 403.4 | EXP. 2-N-3 |
| 4-NP-440 | EXP. 1-N-65 | sco261 | Qn1 | co261 | Ar161 | A | 0.82 | 417.4 | EXP. 2-N-3 |
| 4-NP-441 | EXP. 1-N-63 | sco201 | Qn1 | co201 | Ar192 | A | 0.86 | 389.4 | EXP. 2-N-3 |
| 4-NP-442 | EXP. 1-N-64 | sco201 | Qn1 | co201 | Ar186 | A | 0.77 | 389.4 | EXP. 2-N-3 |
| 4-NP-443 | EXP. 1-N-65 | sco201 | Qn1 | co201 | Ar161 | A | 0.73 | 403.4 | EXP. 2-N-3 |
| 4-NP-444 | EXP. 1-N-63 | sco257 | Qn1 | co257 | Ar192 | A | 0.92 | 401.4 | EXP. 2-N-3 |
| 4-NP-445 | EXP. 1-N-64 | sco257 | Qn1 | co257 | Ar186 | A | 0.82 | 401.4 | EXP. 2-N-3 |
| 4-NP-446 | EXP. 1-N-65 | sco257 | Qn1 | co257 | Ar161 | A | 0.78 | 415.4 | EXP. 2-N-3 |
| 4-NP-447 | EXP. 1-N-63 | sco262 | Qn1 | co262 | Ar192 | A | 0.99 | 415.4 | EXP. 2-N-3 |
| 4-NP-448 | EXP. 1-N-64 | sco262 | Qn1 | co262 | Ar186 | A | 0.9 | 415.4 | EXP. 2-N-3 |
| 4-NP-449 | EXP. 1-N-65 | sco262 | Qn1 | co262 | Ar161 | A | 0.85 | 429.4 | EXP. 2-N-3 |
| 4-NP-450 | EXP. 1-N-63 | sco263 | Qn1 | co263 | Ar192 | A | 1.05 | 429.4 | EXP. 2-N-3 |
| 4-NP-451 | EXP. 1-N-64 | sco263 | Qn1 | co263 | Ar186 | A | 0.97 | 429.4 | EXP. 2-N-3 |
| 4-NP-452 | EXP. 1-N-65 | sco263 | Qn1 | co263 | Ar161 | A | 0.91 | 443.5 | EXP. 2-N-3 |
| 4-NP-453 | EXP. 1-N-63 | sco2 | Qn1 | co2 | Ar192 | A | 0.83 | 387.4 | EXP. 2-N-3 |
| 4-NP-454 | EXP. 1-N-64 | sco2 | Qn1 | co2 | Ar186 | A | 0.73 | 387.4 | EXP. 2-N-3 |
| 4-NP-455 | EXP. 1-N-65 | sco2 | Qn1 | co2 | Ar161 | A | 0.69 | 401.4 | EXP. 2-N-3 |
| 4-NP-456 | EXP. 1-N-63 | sco7 | Qn1 | co7 | Ar192 | A | 0.79 | 375.4 | EXP. 2-N-3 |
| 4-NP-457 | EXP. 1-N-64 | sco7 | Qn1 | co7 | Ar186 | A | 0.69 | 375.4 | EXP. 2-N-3 |
| 4-NP-458 | EXP. 1-N-65 | sco7 | Qn1 | co7 | Ar161 | A | 0.65 | 389.4 | EXP. 2-N-3 |
| 4-NP-469 | EXP. 1-N-63 | sco1 | Qn1 | co1 | Ar192 | A | 0.71 | 361.4 | EXP. 2-N-1 |
| 4-NP-470 | EXP. 1-N-64 | sco1 | Qn1 | co1 | Ar186 | A | 0.61 | 361.4 | EXP. 2-N-1 |
| 4-NP-471 | EXP. 1-N-65 | sco1 | Qn1 | co1 | Ar161 | A | 0.58 | 375.4 | EXP. 2-N-1 |
| 4-NP-497 | EXP. 1-N-66 | sco260 | Qn2 | co260 | Ar192 | A | 0.84 | 361.3 | EXP. 2-N-3 |
| 4-NP-498 | EXP. 1-N-66 | sco2 | Qn2 | co2 | Ar192 | A | 0.78 | 359.3 | EXP. 2-N-3 |
| 4-NP-499 | EXP. 1-N-66 | sco257 | Qn2 | co257 | Ar192 | A | 0.87 | 373.3 | EXP. 2-N-3 |
| 4-NP-500 | EXP. 1-N-67 | sco7 | Qn2 | co7 | Ar186 | A | 0.66 | 347.3 | EXP. 2-N-3 |
| 4-NP-501 | EXP. 1-N-67 | sco260 | Qn2 | co260 | Ar186 | A | 0.74 | 361.3 | EXP. 2-N-3 |
| 4-NP-502 | EXP. 1-N-67 | sco2 | Qn2 | co2 | Ar186 | A | 0.69 | 359.3 | EXP. 2-N-3 |
| 4-NP-503 | EXP. 1-N-67 | sco257 | Qn2 | co257 | Ar186 | A | 0.78 | 373.3 | EXP. 2-N-3 |
| 4-NP-504 | EXP. 1-N-68 | sco7 | Qn2 | co7 | Ar161 | A | 0.65 | 361.3 | EXP. 2-N-3 |
| 4-NP-505 | EXP. 1-N-68 | sco260 | Qn2 | co260 | Ar161 | A | 0.72 | 375.4 | EXP. 2-N-3 |
| 4-NP-506 | EXP. 1-N-68 | sco2 | Qn2 | co2 | Ar161 | A | 0.68 | 373.3 | EXP. 2-N-3 |
| 4-NP-507 | EXP. 1-N-68 | sco257 | Qn2 | co257 | Ar161 | A | 0.76 | 387.4 | EXP. 2-N-3 |
| 4-NP-511 | EXP. 1-N-67 | sco1 | Qn2 | co1 | Ar186 | A | 0.57 | 333.3 | EXP. 2-N-1 |
| 4-NP-517 | EXP. 1-N-68 | sco1 | Qn2 | co1 | Ar161 | A | 0.56 | 347.3 | EXP. 2-N-1 |

Example 3-N-1

3-(8-(1-(methylsulfonyl)piperidin-4-ylamino)isoquinolin-6-yl)benzonitrile

Triethylamine (52 µL) and methanesulfonyl chloride (which may be referred to as sso1; 12 µL; TCI) were added to a dichloromethane (3 mL) solution of Example compound 1-N-1 (30 mg) at room temperature and the resulting mixture was stirred for 23 and half hours at room temperature. Further, triethylamine (52 µL) and methanesulfonyl chloride (24 µL) were added to a resulting solution at room temperature and the resulting mixture was stirred for 13 and half hours. Chloroform and water were added to extract the reaction mixture, then the organic layer was dried, the solvent was evaporated under reduced pressure, and the residue was purified by column chromatography (Yamazen; chloroform/methanol) to give the title compound (8.3 mg).

(LCMS: 329.3 (MH$^+$); retention time: 0.77 min; LCMS; condition A)

Example 3-N-2

3-(8-(1-(2,6-dichloropyridin-3-ylsulfonyl)piperidin-4-ylamino)isoquinolin-6-yl)benzonitrile Triethylamine (15.4 µL) and 2,6-dichloropyridine-3-sulfonyl chloride (which may be referred to as sso2; 7.0; J&W) were added to a DCM (1.8 mL) solution of Example compound 1-N-1 (10.0 mg) and the resulting mixture was shaken at room temperature for 14 hours under a nitrogen atmosphere. The resulting mixture was filtrated followed by the addition of SCX (300 mg) and the resulting mixture was shaken for 2 hours. The reaction mixture was filtrated and the residue was washed with dichloromethane (3 mL) and methanol (4 mL). Then, the mixture was washed with 4 N ammonia methanol solution (4 mL) and this resulting wash was concentrated. The resulting mixture was dried using a vacuum pump to give the title compound (6.9 mg).

(LCMS: 538.1 (MH$^+$); retention Time: 1.54 min; LCMS; condition A)

Example 3-N-3 to 3-N-24, 3-N-103 to 3-N-114, 3-N-201 to 3-N-209, 3-N-301 to 3-N-302, 3-N-401 to 3-N-411, 3-N-501 to 3-N-520 and 3-N-601 to 3-N-674, 3-o-1 to 3-o-42, 3-s-1 to 3-s-3

Compounds of Examples 3-N-3 to 3-N-24, 3-N-103 to 3-N-114, 3-N-201 to 3-N-209, 3-N-301 to 3-N-302, 3-N-401 to 3-N-411, 3-N-501 to 3-N-520 and 3-N-601 to 3-N-674, 3-o-1 to 3-o-42 and 3-s-1 to 3-s-3 were synthesized according to the method in Example 3-N-1 or 3-N-2 (Tables 3-N, 3-o, and 3-s). In Tables 3-N, 3-o, and 3-s, the ST column represent the structures represented by the above general formulas, the J and Ar columns represent "J" and "Ar," respectively, in the general formulas shown in the ST column, "ST," "SM1," "SM2," "LCMS," and "Ref" are defined as described above, and abbreviations such as "sol," "Ar1," and "sso1" represent compounds or groups corresponding to the abbreviations in Tables so, Ar, and sso, respectively, provided later. Abbreviations in the tables represent compounds or groups shown in the figures shown earlier or later.

Tables 3-N, 3-o, and 3-s also include compounds finally purified by preparative HPLC, such as those of Example compounds 3-o-11, 3-o-13, 3-o-19, 3-o-22, 3-o-28, 3-o-37 and 3-o-39, for example.

EXP. 4-N-4, 4-N-5, and 4-N-7 represent Example compounds 4-N-4, 4-N-5, and 4-N-7, respectively, described later.

Examples 4-NP-1 to 4-NP-24, 4-NP-27 to 4-NP-30, 4-NP-33 to 4-NP-35, 4-NP-37 to 4-NP-50, 4-NP-73, 4-NP-421 to 4-NP-422, 4-NP-459 to 4-NP-468, 4-NP-474 to 4-NP-484, 4-NP-508 to 4-NP-510, 4-NP-512 to 4-NP-516, 4-NP-518 to 4-NP-522 and 4-NP-526 to 4-NP-531

Compounds of Examples 4-NP-1 to 4-NP-24, 4-NP-27 to 4-NP-30, 4-NP-33 to 4-NP-35, 4-NP-37 to 4-NP-50, 4-NP-73, 4-NP-421 to 4-NP-422, 4-NP-459 to 4-NP-468, 4-NP-474 to 4-NP-484, 4-NP-508 to 4-NP-510, 4-NP-512 to 4-NP-516, 4-NP-518 to 4-NP-522 and 4-NP-526 to 4-NP-531 were synthesized according to the method in Example 3-N-1 or 3-N-2 (Table 3-N2). In Table 3-N2, the ST column represents the structures represented by the above general formulas, the J and Ar columns represent "J" and "Ar" in the general formula represented in the ST column, "ST," "SM1," "SM2," "LCMS," and "Ref" are defined as described above, abbreviations such as "sol," "Ar1," and "sso1" represent compounds or groups corresponding to the abbreviations in Tables so, Ar, and sso, respectively, provided later. Abbreviations in the tables represent compounds or groups shown in the figures shown earlier or later. The compounds in the tables also include compounds finally purified by preparative HPLC.

TABLE 3-N

| Exp. | SM1 | SM2 | ST | J | Ar | LCMS method | RTime | MH+ | Ref. |
|---|---|---|---|---|---|---|---|---|---|
| 3-N-1 | EXP. 1-N-1 | sso1 | Qn1 | so1 | Ar1 | A | 1.12 | 407.4 | |
| 3-N-2 | EXP. 1-N-1 | sso10 | Qn1 | so10 | Ar1 | A | 1.54 | 538.1 | |
| 3-N-3 | EXP. 1-N-1 | sso3 | Qn1 | so3 | Ar1 | A | 1.34 | 435.1 | EXP. 3-N-1 |
| 3-N-4 | EXP. 1-N-1 | sso4 | Qn1 | so4 | Ar1 | A | 1.25 | 433.1 | EXP. 3-N-1 |
| 3-N-5 | EXP. 1-N-1 | sso5 | Qn1 | so5 | Ar1 | A | 1.43 | 469.4 | EXP. 3-N-1 |
| 3-N-6 | EXP. 1-N-1 | sso6 | Qn1 | so6 | Ar1 | A | 1.24 | 470.5 | EXP. 3-N-1 |
| 3-N-7 | EXP. 1-N-1 | sso7 | Qn1 | so7 | Ar1 | A | 1.23 | 470.2 | EXP. 3-N-1 |
| 3-N-8 | EXP. 1-N-1 | sso8 | Qn1 | so8 | Ar1 | A | 1.41 | 483.5 | EXP. 3-N-1 |
| 3-N-9 | EXP. 1-N-1 | sso9 | Qn1 | so9 | Ar1 | A | 1.12 | 473.2 | EXP. 3-N-1 |
| 3-N-10 | EXP. 1-N-1 | sso2 | Qn1 | so2 | Ar1 | A | 1.20 | 421.5 | EXP. 3-N-1 |
| 3-N-11 | EXP. 1-N-1 | sso11 | Qn1 | so11 | Ar1 | A | 1.34 | 562.2 | EXP. 3-N-1 |
| 3-N-12 | EXP. 1-N-1 | sso12 | Qn1 | so12 | Ar1 | A | 1.44 | 512.1 | EXP. 3-N-1 |
| 3-N-13 | EXP. 1-N-1 | sso13 | Qn1 | so13 | Ar1 | A | 1.38 | 494.2 | EXP. 3-N-2 |
| 3-N-14 | EXP. 1-N-1 | sso14 | Qn1 | so14 | Ar1 | A | 1.40 | 494.1 | EXP. 3-N-2 |
| 3-N-15 | EXP. 1-N-1 | sso15 | Qn1 | so15 | Ar1 | A | 1.41 | 494.2 | EXP. 3-N-2 |
| 3-N-16 | EXP. 1-N-1 | sso16 | Qn1 | so16 | Ar1 | A | 1.50 | 483.2 | EXP. 3-N-2 |
| 3-N-17 | EXP. 1-N-1 | sso17 | Qn1 | so17 | Ar1 | A | 1.47 | 487.1 | EXP. 3-N-2 |
| 3-N-18 | EXP. 1-N-1 | sso18 | Qn1 | so18 | Ar1 | A | 1.46 | 499.2 | EXP. 3-N-2 |
| 3-N-19 | EXP. 1-N-1 | sso19 | Qn1 | so19 | Ar1 | A | 1.59 | 537.2 | EXP. 3-N-2 |
| 3-N-20 | EXP. 1-N-1 | sso20 | Qn1 | so20 | Ar1 | A | 1.51 | 535.2 | EXP. 3-N-2 |
| 3-N-21 | EXP. 1-N-1 | sso21 | Qn1 | so21 | Ar1 | A | 1.62 | 553.2 | EXP. 3-N-2 |
| 3-N-22 | EXP. 1-N-1 | sso22 | Qn1 | so22 | Ar1 | A | 1.42 | 500.2 | EXP. 3-N-2 |
| 3-N-23 | EXP. 2-N-75 | sso1 | Qn1 | so30 | Ar1 | A | 1.22 | 605.1 | EXP. 3-N-1 |
| 3-N-24 | EXP. 2-N-107 | sso1 | Qn1-2 | so1 | Ar1 | A | 1.10 | 478.1 | EXP. 3-N-1 |
| 3-N-103 | EXP. 1-N-3 | sso1 | Qn1 | so1 | Ar4 | A | 1.24 | 425.1 | EXP. 3-N-1 |
| 3-N-104 | EXP. 1-N-3 | sso23 | Qn1 | so23 | Ar4 | A | 1.39 | 567.2 | EXP. 3-N-2 |
| 3-N-105 | EXP. 1-N-3 | sso24 | Qn1 | so24 | Ar4 | A | 1.68 | 595.1 | EXP. 3-N-2 |
| 3-N-106 | EXP. 1-N-3 | sso25 | Qn1 | so25 | Ar4 | A | 1.78 | 623.1 | EXP. 3-N-2 |
| 3-N-107 | EXP. 1-N-3 | sso26 | Qn1 | so26 | Ar4 | A | 1.62 | 539.1 | EXP. 3-N-2 |
| 3-N-108 | EXP. 1-N-3 | sso27 | Qn1 | so27 | Ar4 | A | 1.45 | 547.2 | EXP. 3-N-2 |
| 3-N-109 | EXP. 1-N-3 | sso28 | Qn1 | so28 | Ar4 | A | 1.43 | 547.2 | EXP. 3-N-2 |
| 3-N-110 | EXP. 1-N-3 | sso29 | Qn1 | so29 | Ar4 | A | 1.72 | 589.1 | EXP. 3-N-2 |
| 3-N-111 | EXP. 2-N-610 | sso1 | Qn10 | so1 | Ar2 | A | 1.28 | 499.2 | EXP. 3-N-1 |
| 3-N-112 | EXP. 1-N-34 | sso7 | Qn1 | so7 | Ar3 | A | 1.02 | 446.0 | EXP. 3-N-1 |
| 3-N-113 | EXP. 1-N-34 | sso1 | Qn1 | so1 | Ar3 | A | 0.83 | 383.0 | EXP. 3-N-1 |
| 3-N-114 | EXP. 1-N-51 | sso1 | Qn1 | so1 | Ar4 | A | 1.24 | 428.1 | EXP. 3-N-1 |
| 3-N-201 | EXP. 1-N-4 | sso1 | Qn2 | so1 | Ar1 | A | 1.10 | 379.4 | EXP. 3-N-1 |
| 3-N-202 | EXP. 1-N-4 | sso2 | Qn2 | so2 | Ar1 | A | 1.19 | 393.2 | EXP. 3-N-1 |
| 3-N-203 | EXP. 1-N-4 | sso3 | Qn2 | so3 | Ar1 | A | 1.26 | 407.3 | EXP. 3-N-1 |
| 3-N-204 | EXP. 1-N-4 | sso8 | Qn2 | so8 | Ar1 | A | 1.42 | 466.2 | EXP. 3-N-1 |
| 3-N-205 | EXP. 1-N-4 | sso6 | Qn2 | so6 | Ar1 | A | 1.23 | 442.2 | EXP. 3-N-1 |

TABLE 3-N-continued

| Exp. | SM1 | SM2 | ST | J | Ar | LCMS method | RTime | MH+ | Ref. |
|---|---|---|---|---|---|---|---|---|---|
| 3-N-206 | EXP. 1-N-4 | sso4 | Qn2 | so4 | Ar1 | A | 1.21 | 405.1 | EXP. 3-N-1 |
| 3-N-207 | EXP. 1-N-4 | sso5 | Qn2 | so5 | Ar1 | A | 1.36 | 441.1 | EXP. 3-N-1 |
| 3-N-208 | EXP. 1-N-50 | sso1 | Qn2 | so1 | Ar2 | B | 3.23 | 388.1 | EXP. 3-N-1 |
| 3-N-209 | EXP. 1-N-39 | sso1 | Qn2 | so1 | Ar3 | B | 2.10 | 368.2 | EXP. 3-N-1 |
| 3-N-301 | EXP. 1-N-44 | sso1 | Qn2 | so1 | Ar4 | A | 1.18 | 397.0 | EXP. 3-N-1 |
| 3-N-302 | EXP. 1-N-44 | sso4 | Qn2 | so4 | Ar4 | A | 1.28 | 423.1 | EXP. 3-N-1 |
| 3-N-401 | EXP. 1-N-27 | sso1 | Qn3 | so1 | Ar1 | A | 1.01 | 393.4 | EXP. 3-N-1 |
| 3-N-402 | EXP. 1-N-28 | sso1 | Qn4 | so1 | Ar1 | A | 1.08 | 393.4 | EXP. 3-N-1 |
| 3-N-403 | EXP. 1-N-2 | sso1 | Qn5 | so1 | Ar1 | A | 1.16 | 407.4 | EXP. 3-N-1 |
| 3-N-404 | EXP. 1-N-12 | sso1 | Qn6 | so1 | Ar1 | A | 1.18 | 421.5 | EXP. 3-N-1 |
| 3-N-405 | EXP. 1-N-12 | sso2 | Qn6 | so2 | Ar1 | A | 1.22 | 435.2 | EXP. 3-N-1 |
| 3-N-406 | EXP. 1-N-12 | sso3 | Qn6 | so3 | Ar1 | A | 1.31 | 449.2 | EXP. 3-N-1 |
| 3-N-407 | EXP. 1-N-12 | sso8 | Qn6 | so8 | Ar1 | A | 1.42 | 497.2 | EXP. 3-N-1 |
| 3-N-408 | EXP. 1-N-12 | sso6 | Qn6 | so6 | Ar1 | A | 1.29 | 484.2 | EXP. 3-N-1 |
| 3-N-409 | EXP. 1-N-40 | sso1 | Qn6 | so1 | Ar3 | A | 0.90 | 397.1 | EXP. 3-N-1 |
| 3-N-410 | EXP. 1-N-5 | sso1 | Qn7 | so1 | Ar1 | A | 1.04 | 381.2 | EXP. 3-N-1 |
| 3-N-411 | EXP. 1-N-6 | sso1 | Qn8 | so1 | Ar1 | A | 1.22 | 393.3 | EXP. 3-N-1 |
| 3-N-501 | EXP. 2-N-102 | sso1 | Qn9 | so1 | Ar1 | A | 1.14 | 518.3 | EXP. 3-N-1 |
| 3-N-502 | EXP. 2-N-102 | sso3 | Qn9 | so3 | Ar1 | A | 1.26 | 546.2 | EXP. 3-N-2 |
| 3-N-503 | EXP. 2-N-102 | sso6 | Qn9 | so6 | Ar1 | A | 1.26 | 581.2 | EXP. 3-N-2 |
| 3-N-504 | EXP. 2-N-102 | sso9 | Qn9 | so9 | Ar1 | A | 1.17 | 684.2 | EXP. 3-N-2 |
| 3-N-505 | EXP. 2-N-103 | sso1 | Qn10 | so1 | Ar1 | A | 1.09 | 490.1 | EXP. 3-N-1 |
| 3-N-506 | EXP. 2-N-103 | sso3 | Qn10 | so3 | Ar1 | A | 1.24 | 518.2 | EXP. 3-N-2 |
| 3-N-507 | EXP. 2-N-103 | sso6 | Qn10 | so6 | Ar1 | A | 1.23 | 553.1 | EXP. 3-N-2 |
| 3-N-508 | EXP. 2-N-103 | sso9 | Qn10 | so9 | Ar1 | A | 1.13 | 556.2 | EXP. 3-N-2 |
| 3-N-509 | EXP. 2-N-292 | sso1 | Qn10 | so1 | Ar4 | B | 2.94 | 508.2 | EXP. 3-N-1 |
| 3-N-510 | EXP. 2-N-104 | sso1 | Qn11 | so1 | Ar1 | A | 1.13 | 520.2 | EXP. 3-N-1 |
| 3-N-511 | EXP. 2-N-104 | sso6 | Qn11 | so6 | Ar1 | A | 1.15 | 583.2 | EXP. 3-N-1 |
| 3-N-512 | EXP. 2-N-104 | sso9 | Qn11 | so9 | Ar1 | A | 1.16 | 586.3 | EXP. 3-N-1 |
| 3-N-513 | EXP. 2-N-111 | sso1 | Qn12 | so1 | Ar1 | A | 1.33 | 548.1 | EXP. 3-N-1 |
| 3-N-514 | EXP. 2-N-111 | sso6 | Qn12 | so6 | Ar1 | A | 1.35 | 611.1 | EXP. 3-N-2 |
| 3-N-515 | EXP. 2-N-111 | sso9 | Qn12 | so9 | Ar1 | A | 1.20 | 614.1 | EXP. 3-N-2 |
| 3-N-516 | EXP. 2-N-112 | sso1 | Qn13 | so1 | Ar1 | B | 2.91 | 618.3 | EXP. 3-N-1 |
| 3-N-517 | EXP. 2-N-113 | sso1 | Qn14 | so1 | Ar1 | B | 2.77 | 504.3 | EXP. 3-N-1 |
| 3-N-518 | EXP. 4-N-4 | sso1 | Qn15 | so1 | Ar1 | A | 0.89 | 476.1 | EXP. 3-N-1 |
| 3-N-519 | EXP. 4-N-5 | sso1 | Qn17 | so1 | Ar1 | A | 0.92 | 506.0 | EXP. 3-N-1 |
| 3-N-520 | EXP. 4-N-7 | sso1 | Qn18 | so1 | Ar1 | A | 0.97 | 462.0 | EXP. 3-N-1 |
| 3-N-601 | EXP. 1-N-3 | sso37 | Qn1 | so37 | Ar4 | A | 2.11 | 613.3 | EXP. 3-N-2 |
| 3-N-602 | EXP. 1-N-44 | sso38 | Qn2 | so38 | Ar4 | A | 1.55 | 502.3 | EXP. 3-N-2 |
| 3-N-603 | EXP. 1-N-44 | sso13 | Qn2 | so13 | Ar4 | A | 1.48 | 484.3 | EXP. 3-N-2 |
| 3-N-604 | EXP. 1-N-44 | sso14 | Qn2 | so14 | Ar4 | A | 1.50 | 484.3 | EXP. 3-N-2 |
| 3-N-605 | EXP. 1-N-44 | sso15 | Qn2 | so15 | Ar4 | A | 1.51 | 484.3 | EXP. 3-N-2 |
| 3-N-606 | EXP. 1-N-44 | sso16 | Qn2 | so16 | Ar4 | A | 1.57 | 473.3 | EXP. 3-N-2 |
| 3-N-607 | EXP. 1-N-44 | sso17 | Qn2 | so17 | Ar4 | A | 1.55 | 477.3 | EXP. 3-N-2 |
| 3-N-608 | EXP. 1-N-44 | sso18 | Qn2 | so18 | Ar4 | A | 1.53 | 489.3 | EXP. 3-N-2 |
| 3-N-609 | EXP. 1-N-44 | sso20 | Qn2 | so20 | Ar4 | A | 1.59 | 525.3 | EXP. 3-N-2 |
| 3-N-610 | EXP. 1-N-44 | sso39 | Qn2 | so39 | Ar4 | A | 1.67 | 528.2 | EXP. 3-N-2 |
| 3-N-611 | EXP. 1-N-44 | sso40 | Qn2 | so40 | Ar4 | A | 1.65 | 498.3 | EXP. 3-N-2 |
| 3-N-612 | EXP. 1-N-44 | sso41 | Qn2 | so41 | Ar4 | A | 1.60 | 518.3 | EXP. 3-N-2 |
| 3-N-613 | EXP. 1-N-44 | sso2 | Qn2 | so2 | Ar4 | A | 1.30 | 411.3 | EXP. 3-N-2 |
| 3-N-614 | EXP. 1-N-3 | sso38 | Qn1 | so38 | Ar4 | A | 1.55 | 530.3 | EXP. 3-N-2 |
| 3-N-615 | EXP. 1-N-3 | sso13 | Qn1 | so13 | Ar4 | A | 1.48 | 512.3 | EXP. 3-N-2 |
| 3-N-616 | EXP. 1-N-3 | sso14 | Qn1 | so14 | Ar4 | A | 1.50 | 512.3 | EXP. 3-N-2 |
| 3-N-617 | EXP. 1-N-3 | sso15 | Qn1 | so15 | Ar4 | A | 1.50 | 512.3 | EXP. 3-N-2 |
| 3-N-618 | EXP. 1-N-3 | sso16 | Qn1 | so16 | Ar4 | A | 1.61 | 501.3 | EXP. 3-N-2 |
| 3-N-619 | EXP. 1-N-3 | sso17 | Qn1 | so17 | Ar4 | A | 1.57 | 505.3 | EXP. 3-N-2 |
| 3-N-620 | EXP. 1-N-3 | sso18 | Qn1 | so18 | Ar4 | A | 1.58 | 517.3 | EXP. 3-N-2 |
| 3-N-621 | EXP. 1-N-3 | sso20 | Qn1 | so20 | Ar4 | A | 1.60 | 553.3 | EXP. 3-N-2 |
| 3-N-622 | EXP. 1-N-62 | sso46 | Qn1 | so46 | Ar41 | A | 1.67 | 531.4 | EXP. 3-N-2 |
| 3-N-623 | EXP. 1-N-52 | sso1 | Qn19 | so1 | Ar4 | A | 1.20 | 411.4 | EXP. 3-N-2 |
| 3-N-624 | EXP. 1-N-52 | sso4 | Qn19 | so2 | Ar4 | A | 1.25 | 425.5 | EXP. 3-N-2 |
| 3-N-625 | EXP. 1-N-52 | sso4 | Qn19 | so42 | Ar4 | A | 1.35 | 439.4 | EXP. 3-N-2 |
| 3-N-626 | EXP. 1-N-52 | sso4 | Qn19 | so4 | Ar4 | A | 1.29 | 437.4 | EXP. 3-N-2 |
| 3-N-627 | EXP. 1-N-52 | sso3 | Qn19 | so3 | Ar4 | A | 1.33 | 439.4 | EXP. 3-N-2 |
| 3-N-628 | EXP. 1-N-60 | sso1 | Qn20 | so1 | Ar4 | A | 1.17 | 413.4 | EXP. 3-N-2 |
| 3-N-629 | EXP. 1-N-60 | sso2 | Qn20 | so2 | Ar4 | A | 1.23 | 427.4 | EXP. 3-N-2 |
| 3-N-630 | EXP. 1-N-50 | sso4 | Qn20 | so4 | Ar4 | A | 1.29 | 439.4 | EXP. 3-N-2 |
| 3-N-631 | EXP. 1-N-53 | sso1 | Qn21 | so1 | Ar4 | A | 1.22 | 425.4 | EXP. 3-N-2 |
| 3-N-632 | EXP. 1-N-53 | sso2 | Qn21 | so2 | Ar4 | A | 1.27 | 439.4 | EXP. 3-N-2 |
| 3-N-633 | EXP. 1-N-53 | sso42 | Qn21 | so42 | Ar4 | A | 1.37 | 463.4 | EXP. 3-N-2 |
| 3-N-634 | EXP. 1-N-53 | sso4 | Qn21 | so4 | Ar4 | A | 1.31 | 451.4 | EXP. 3-N-2 |
| 3-N-635 | EXP. 1-N-55 | sso1 | Qn22 | so1 | Ar4 | A | 1.29 | 439.4 | EXP. 3-N-2 |
| 3-N-636 | EXP. 1-N-55 | sso2 | Qn22 | so2 | Ar4 | A | 1.34 | 453.4 | EXP. 3-N-2 |
| 3-N-637 | EXP. 1-N-55 | sso42 | Qn22 | so42 | Ar4 | A | 1.44 | 467.4 | EXP. 3-N-2 |
| 3-N-638 | EXP. 1-N-59 | sso2 | Qn23 | so2 | Ar4 | A | 1.28 | 427.4 | EXP. 3-N-2 |
| 3-N-639 | EXP. 1-N-58 | sso1 | Qn7 | so1 | Ar4 | A | 1.12 | 399.4 | EXP. 3-N-2 |

TABLE 3-N-continued

| Exp. | SM1 | SM2 | ST | J | Ar | LCMS method | RTime | MH+ | Ref. |
|---|---|---|---|---|---|---|---|---|---|
| 3-N-640 | EXP. 1-N-58 | sso4 | Qn7 | so4 | Ar4 | A | 1.23 | 425.4 | EXP. 3-N-2 |
| 3-N-641 | EXP. 1-N-57 | sso1 | Qn24 | so1 | Ar4 | A | 1.25 | 439.4 | EXP. 3-N-2 |
| 3-N-642 | EXP. 1-N-54 | sso4 | Qn25 | so4 | Ar4 | A | 1.31 | 437.4 | EXP. 3-N-2 |
| 3-N-643 | EXP. 1-N-54 | sso3 | Qn25 | so3 | Ar4 | A | 1.36 | 439.4 | EXP. 3-N-2 |
| 3-N-644 | EXP. 1-N-59 | sso1 | Qn23 | so1 | Ar4 | A | 1.22 | 413.4 | EXP. 3-N-2 |
| 3-N-645 | EXP. 1-N-59 | sso4 | Qn22 | so4 | Ar4 | A | 1.38 | 465.4 | EXP. 3-N-2 |
| 3-N-646 | EXP. 1-N-59 | sso4 | Qn23 | so4 | Ar4 | A | 1.33 | 439.4 | EXP. 3-N-2 |
| 3-N-647 | EXP. 1-N-56 | sso1 | Qn26 | so1 | Ar4 | A | 1.20 | 439.4 | EXP. 3-N-2 |
| 3-N-648 | EXP. 1-N-56 | sso4 | Qn26 | so4 | Ar4 | A | 1.31 | 465.4 | EXP. 3-N-2 |
| 3-N-649 | EXP. 1-N-51 | sso42 | Qn1 | so42 | Ar4 | A | 1.40 | 456.4 | EXP. 3-N-2 |
| 3-N-650 | EXP. 1-N-51 | sso43 | Qn1 | so43 | Ar4 | A | 1.60 | 479.4 | EXP. 3-N-1 |
| 3-N-651 | EXP. 1-N-51 | sso44 | Qn1 | so44 | Ar4 | A | 1.47 | 493.4 | EXP. 3-N-1 |
| 3-N-652 | EXP. 1-N-51 | sso45 | Qn1 | so45 | Ar4 | A | 1.45 | 487.4 | EXP. 3-N-1 |
| 3-N-653 | EXP. 1-N-60 | sso42 | Qn20 | so42 | Ar4 | A | 1.28 | 441.4 | EXP. 3-N-2 |
| 3-N-654 | EXP. 1-N-60 | sso3 | Qn20 | so3 | Ar4 | A | 1.26 | 441.4 | EXP. 3-N-2 |
| 3-N-655 | EXP. 1-N-53 | sso3 | Qn21 | so3 | Ar4 | A | 1.34 | 453.4 | EXP. 3-N-2 |
| 3-N-656 | EXP. 1-N-53 | sso3 | Qn22 | so3 | Ar4 | A | 1.40 | 467.4 | EXP. 3-N-2 |
| 3-N-657 | EXP. 1-N-58 | sso10 | Qn7 | so10 | Ar4 | A | 1.18 | 413.4 | EXP. 3-N-2 |
| 3-N-658 | EXP. 1-N-58 | sso42 | Qn7 | so42 | Ar4 | A | 1.23 | 427.4 | EXP. 3-N-2 |
| 3-N-659 | EXP. 1-N-57 | sso10 | Qn24 | so10 | Ar4 | A | 1.28 | 453.4 | EXP. 3-N-2 |
| 3-N-660 | EXP. 1-N-57 | sso42 | Qn24 | so42 | Ar4 | A | 1.37 | 467.4 | EXP. 3-N-2 |
| 3-N-661 | EXP. 1-N-57 | sso4 | Qn24 | so4 | Ar4 | A | 1.32 | 466.4 | EXP. 3-N-2 |
| 3-N-662 | EXP. 1-N-54 | sso47 | Qn25 | so47 | Ar4 | A | 1.43 | 453.4 | EXP. 3-N-2 |
| 3-N-663 | EXP. 1-N-59 | sso42 | Qn23 | so42 | Ar4 | A | 1.34 | 441.4 | EXP. 3-N-2 |
| 3-N-664 | EXP. 1-N-59 | sso47 | Qn23 | so47 | Ar4 | A | 1.42 | 455.4 | EXP. 3-N-2 |
| 3-N-665 | EXP. 1-N-56 | sso10 | Qn26 | so10 | Ar4 | A | 1.21 | 453.4 | EXP. 3-N-2 |
| 3-N-666 | EXP. 1-N-51 | sso3 | Qn1 | so3 | Ar4 | A | 1.35 | 453.4 | EXP. 3-N-2 |
| 3-N-667 | EXP. 1-N-62 | sso2 | Qn2 | so2 | Ar41 | A | 1.29 | 411.4 | EXP. 3-N-2 |
| 3-N-668 | EXP. 1-N-62 | sso4 | Qn2 | so4 | Ar41 | A | 1.31 | 423.4 | EXP. 3-N-2 |
| 3-N-669 | EXP. 1-N-61 | sso3 | Qn1 | so3 | Ar41 | A | 1.40 | 453.4 | EXP. 3-N-2 |
| 3-N-670 | EXP. 1-N-61 | sso47 | Qn1 | so47 | Ar41 | A | 1.51 | 467.4 | EXP. 3-N-2 |
| 3-N-671 | EXP. 1-N-61 | sso42 | Qn1 | so42 | Ar41 | A | 1.42 | 453.4 | EXP. 3-N-2 |
| 3-N-672 | EXP. 1-N-61 | sso48 | Qn1 | so48 | Ar41 | A | 1.51 | 467.4 | EXP. 3-N-2 |
| 3-N-673 | EXP. 1-N-61 | sso49 | Qn1 | so49 | Ar41 | A | 1.49 | 502.4 | EXP. 3-N-2 |

TABLE 3-o

| EXP. | SM1 | SM2 | ST | J | Ar | LCMS method | RTime | MH+ | Ref. |
|---|---|---|---|---|---|---|---|---|---|
| 3-o-1 | EXP. 1-o-1 | sso1 | Qo1 | so1 | Ar1 | A | 1.29 | 408.4 | EXP. 3-N-1 |
| 3-o-2 | EXP. 1-o-1 | sso3 | Qo1 | so3 | Ar1 | A | 1.44 | 436.3 | EXP. 3-N-1 |
| 3-o-3 | EXP. 1-o-1 | sso6 | Qo1 | so6 | Ar1 | A | 1.34 | 471.2 | EXP. 3-N-2 |
| 3-o-4 | EXP. 1-o-1 | sso32 | Qo1 | so32 | Ar1 | A | 1.35 | 527.2 | EXP. 3-N-2 |
| 3-o-5 | EXP. 1-o-1 | sso36 | Qo1 | so36 | Ar1 | A | 1.42 | 437.2 | EXP. 3-N-1 |
| 3-o-6 | EXP. 1-o-1 | sso9 | Qo1 | so9 | Ar1 | A | 1.27 | 474.2 | EXP. 3-N-1 |
| 3-o-7 | EXP. 1-o-1 | sso33 | Qo1 | so33 | Ar1 | A | 1.62 | 476.1 | EXP. 3-N-1 |
| 3-o-8 | EXP. 1-o-6 | sso1 | Qo2 | so1 | Ar1 | A | 1.22 | 380.1 | EXP. 3-N-1 |
| 3-o-9 | EXP. 1-o-6 | sso6 | Qo2 | so6 | Ar1 | A | 1.29 | 443.1 | EXP. 3-N-2 |
| 3-o-10 | EXP. 1-o-6 | sso9 | Qo2 | so9 | Ar1 | A | 1.15 | 446.1 | EXP. 3-N-2 |
| 3-o-11 | EXP. 1-o-6 | sso34 | Qo2 | so34 | Ar1 | A | 1.26 | 457.0 | EXP. 3-N-1 |
| 3-o-12 | EXP. 1-o-5 | sso1 | Qo4 | so1 | Ar1 | A | 1.21 | 394.3 | EXP. 3-N-1 |
| 3-o-13 | EXP. 1-o-76 | sso1 | Qo5 | so1 | Ar1 | A | 1.04 | 438.0 | EXP. 3-N-1 |
| 3-o-14 | EXP. 1-o-13 | sso1 | Qo5 | so1 | Ar1 | A | 1.21 | 408.2 | EXP. 3-N-2 |
| 3-o-15 | EXP. 1-o-13 | sso9 | Qo6 | so9 | Ar1 | A | 1.24 | 474.2 | EXP. 3-N-1 |
| 3-o-16 | EXP. 1-o-13 | sso35 | Qo6 | so35 | Ar1 | A | 1.09 | 475.2 | EXP. 3-N-1 |
| 3-o-17 | EXP. 1-o-11 | sso1 | Qo7 | so1 | Ar1 | A | 1.35 | 422.2 | EXP. 3-N-1 |
| 3-o-18 | EXP. 1-o-12 | sso1 | Qo8 | so1 | Ar1 | A | 1.37 | 422.4 | EXP. 3-N-1 |
| 3-o-19 | EXP. 1-o-15 | sso1 | Qo9 | so1 | Ar1 | A | 1.30 | 394.0 | EXP. 3-N-1 |
| 3-o-20 | EXP. 1-o-15 | sso4 | Qo9 | so4 | Ar1 | A | 1.33 | 420.2 | EXP. 3-N-1 |
| 3-o-21 | EXP. 1-o-18 | sso1 | Qo10 | so1 | Ar1 | B | 3.33 | 424.2 | EXP. 3-N-1 |
| 3-o-22 | EXP. 1-o-10 | sso1 | Qo11 | so1 | Ar1 | A | 1.13 | 382.2 | EXP. 3-N-1 |
| 3-o-23 | EXP. 1-o-2 | sso1 | Qo14 | so1 | Ar1 | A | 1.25 | 408.4 | EXP. 3-N-1 |
| 3-o-24 | EXP. 1-o-7 | sso1 | Qo12 | so1 | Ar1 | A | 1.19 | 422.1 | EXP. 3-N-2 |
| 3-o-25 | EXP. 1-o-8 | sso1 | Qo13 | so1 | Ar1 | A | 1.23 | 422.1 | EXP. 3-N-1 |
| 3-o-26 | EXP. 2-o-19 | sso1 | Qo1-1 | so1 | Ar1 | A | 1.35 | 521.3 | EXP. 3-N-1 |
| 3-o-27 | EXP. 2-o-20 | sso1 | Qo1-2 | so1 | Ar1 | A | 1.26 | 521.0 | EXP. 3-N-1 |
| 3-o-28 | EXP. 2-o-22 | sso1 | Qo1-4 | so1 | Ar1 | A | 1.37 | 563.1 | EXP. 3-N-2 |
| 3-o-29 | EXP. 2-o-36 | sso1 | Qo1-5 | so1 | Ar1 | A | 1.30 | 527.2 | EXP. 3-N-1 |
| 3-o-30 | EXP. 2-o-61 | sso1 | Qo1-7 | so1 | Ar1 | A | 1.23 | 519.3 | EXP. 3-N-1 |
| 3-o-31 | EXP. 2-o-63 | sso9 | Qo1-8 | so9 | Ar1 | A | 1.16 | 557.1 | EXP. 3-N-1 |
| 3-o-32 | EXP. 2-o-75 | sso1 | Qo2-1 | so1 | Ar1 | A | 1.18 | 493.0 | EXP. 3-N-1 |

TABLE 3-o-continued

| EXP. | SM1 | SM2 | ST | J | Ar | LCMS method | RTime | MH+ | Ref. |
|---|---|---|---|---|---|---|---|---|---|
| 3-o-33 | EXP. 2-o-76 | sso1 | Qo2-2 | so1 | Ar1 | A | 1.29 | 493.0 | EXP. 3-N-1 |
| 3-o-34 | EXP. 2-o-117 | sso1 | Qo2-4 | so1 | Ar1 | A | 1.09 | 451.0 | EXP. 3-N-2 |
| 3-o-35 | EXP. 2-o-119 | sso1 | Qo2-5 | so1 | Ar1 | A | 1.13 | 491.2 | EXP. 3-N-2 |
| 3-o-36 | EXP. 2-o-121 | sso34 | Qo2-6 | so34 | Ar1 | A | 1.18 | 526.1 | EXP. 3-N-2 |
| 3-o-37 | EXP. 2-o-121 | sso9 | Qo2-6 | so9 | Ar1 | A | 1.11 | 529.2 | EXP. 3-N-2 |
| 3-o-38 | EXP. 2-o-142 | sso1 | Qo9-1 | so1 | Ar1 | A | 1.24 | 507.2 | EXP. 3-N-1 |
| 3-o-39 | EXP. 1-o-55 | sso1 | Qo1 | so1 | Ar3 | A | 0.97 | 384.0 | EXP. 3-N-1 |
| 3-o-40 | EXP. 2-o-239 | sso1 | Qo1-11 | so1 | Ar3 | A | 0.86 | 497.0 | EXP. 3-N-2 |
| 3-o-41 | EXP. 2-o-238 | sso1 | Qo1-1 | so1 | Ar3 | A | 0.87 | 497.0 | EXP. 3-N-2 |
| 3-o-42 | EXP. 1-o-66 | sso4 | Qo2 | so4 | Ar4 | A | 1.43 | 424.2 | EXP. 3-N-1 |

TABLE 3-s

| EXP. | SM1 | SM2 | ST | J | Ar | LCMS method | RTime | MH+ | Ref. |
|---|---|---|---|---|---|---|---|---|---|
| 3-s-1 | EXP. 1-s-1 | sso1 | Qs1 | so1 | Ar1 | A | 1.59 | 424.3 | EXP. 3-N-1 |
| 3-s-2 | EXP. 1-s-1 | sso3 | Qs1 | so3 | Ar1 | A | 1.68 | 460.3 | EXP. 3-N-1 |
| 3-s-3 | EXP. 1-s-2 | sso1 | Qs2 | so1 | Ar1 | A | 1.16 | 347.9 | EXP. 3-N-1 |

TABLE 3-N2

| Exp. | SM1 | SM2 | ST | J | Ar | LCMS method | RTime | MH+ | Ref. |
|---|---|---|---|---|---|---|---|---|---|
| 4-NP-1 | EXP. 1-N-61 | sso50 | Qn1 | so50 | Ar41 | A | 1.29 | 469.4 | EXP. 3-N-1 |
| 4-NP-2 | EXP. 1-N-4 | sso51 | Qn2 | so51 | Ar1 | A | 1.20 | 421.4 | EXP. 3-N-1 |
| 4-NP-3 | EXP. 1-N-61 | sso52 | Qn1 | so52 | Ar41 | A | 1.41 | 522.4 | EXP. 3-N-2 |
| 4-NP-4 | EXP. 1-N-61 | sso9 | Qn1 | so9 | Ar41 | A | 1.16 | 491.4 | EXP. 3-N-2 |
| 4-NP-5 | EXP. 1-N-61 | sso53 | Qn1 | so53 | Ar41 | A | 1.26 | 491.4 | EXP. 3-N-2 |
| 4-NP-6 | EXP. 1-N-61 | sso35 | Qn1 | so35 | Ar41 | A | 1.13 | 492.4 | EXP. 3-N-2 |
| 4-NP-7 | EXP. 1-N-61 | sso54 | Qn1 | so54 | Ar41 | A | 1.36 | 491.4 | EXP. 3-N-2 |
| 4-NP-8 | EXP. 1-N-62 | sso55 | Qn2 | so55 | Ar41 | A | 1.57 | 465.4 | EXP. 3-N-2 |
| 4-NP-9 | EXP. 1-N-62 | sso56 | Qn2 | so56 | Ar41 | A | 1.48 | 540.3 | EXP. 3-N-2 |
| 4-NP-10 | EXP. 1-N-62 | sso57 | Qn2 | so57 | Ar41 | A | 1.49 | 494.3 | EXP. 3-N-2 |
| 4-NP-11 | EXP. 1-N-62 | sso52 | Qn2 | so52 | Ar41 | A | 1.42 | 494.3 | EXP. 3-N-2 |
| 4-NP-12 | EXP. 1-N-62 | sso58 | Qn2 | so58 | Ar41 | A | 1.40 | 531.4 | EXP. 3-N-2 |
| 4-NP-13 | EXP. 1-N-62 | sso9 | Qn2 | so9 | Ar41 | A | 1.16 | 463.4 | EXP. 3-N-2 |
| 4-NP-14 | EXP. 1-N-62 | sso53 | Qn2 | so53 | Ar41 | A | 1.24 | 463.4 | EXP. 3-N-2 |
| 4-NP-15 | EXP. 1-N-62 | sso59 | Qn2 | so59 | Ar41 | A | 1.44 | 494.3 | EXP. 3-N-2 |
| 4-NP-16 | EXP. 1-N-62 | sso35 | Qn2 | so35 | Ar41 | A | 1.10 | 464.4 | EXP. 3-N-2 |
| 4-NP-17 | EXP. 1-N-62 | sso50 | Qn2 | so60 | Ar41 | A | 1.11 | 463.4 | EXP. 3-N-2 |
| 4-NP-18 | EXP. 1-N-51 | sso56 | Qn1 | so56 | Ar4 | A | 1.48 | 558.3 | EXP. 3-N-2 |
| 4-NP-19 | EXP. 1-N-51 | sso57 | Qn1 | so57 | Ar4 | A | 1.47 | 522.4 | EXP. 3-N-2 |
| 4-NP-20 | EXP. 1-N-51 | sso58 | Qn1 | so58 | Ar4 | A | 1.38 | 559.4 | EXP. 3-N-2 |
| 4-NP-21 | EXP. 1-N-51 | sso9 | Qn1 | so9 | Ar4 | A | 1.13 | 491.4 | EXP. 3-N-2 |
| 4-NP-22 | EXP. 1-N-51 | sso53 | Qn1 | so53 | Ar4 | A | 1.22 | 491.4 | EXP. 3-N-2 |
| 4-NP-23 | EXP. 1-N-51 | sso35 | Qn1 | so35 | Ar4 | A | 1.15 | 492.4 | EXP. 3-N-2 |
| 4-NP-24 | EXP. 1-N-51 | sso64 | Qn1 | so54 | Ar4 | A | 1.34 | 491.4 | EXP. 3-N-2 |
| 4-NP-27 | EXP. 1-o-57 | sso2 | Qo1 | so2 | Ar4 | A | 1.48 | 440.4 | EXP. 3-N-1 |
| 4-NP-28 | EXP. 1-o-57 | sso3 | Qo1 | so3 | Ar4 | A | 1.55 | 452.4 | EXP. 3-N-1 |
| 4-NP-29 | EXP. 1-o-58 | sso2 | Qo1 | so2 | Ar41 | A | 1.54 | 440.4 | EXP. 3-N-1 |
| 4-NP-30 | EXP. 1-o-58 | sso3 | Qo1 | so3 | Ar41 | A | 1.58 | 452.4 | EXP. 3-N-1 |
| 4-NP-33 | EXP. 1-o-69 | sso1 | Qo15 | so1 | Ar4 | A | 1.49 | 440.4 | EXP. 3-N-1 |
| 4-NP-34 | EXP. 1-o-69 | sso2 | Qo15 | so2 | Ar4 | A | 1.58 | 454.4 | EXP. 3-N-1 |
| 4-NP-35 | EXP. 1-o-69 | sso3 | Qo15 | so3 | Ar4 | A | 1.62 | 466.4 | EXP. 3-N-1 |
| 4-NP-37 | EXP. 1-N-61 | sso55 | Qn1 | so55 | Ar41 | A | 1.56 | 493.4 | EXP. 3-N-2 |
| 4-NP-38 | EXP. 1-N-61 | sso56 | Qn1 | so56 | Ar41 | A | 1.51 | 558.3 | EXP. 3-N-2 |
| 4-NP-39 | EXP. 1-N-61 | sso57 | Qn1 | so57 | Ar41 | A | 1.51 | 522.3 | EXP. 3-N-2 |
| 4-NP-40 | EXP. 1-N-61 | sso61 | Qn1 | so61 | Ar41 | A | 1.34 | 451.4 | EXP. 3-N-2 |
| 4-NP-41 | EXP. 1-N-61 | sso58 | Qn1 | so58 | Ar41 | A | 1.43 | 559.4 | EXP. 3-N-2 |
| 4-NP-42 | EXP. 1-N-61 | sso59 | Qn1 | so59 | Ar41 | A | 1.43 | 522.4 | EXP. 3-N-2 |
| 4-NP-43 | EXP. 1-N-61 | sso60 | Qn1 | so60 | Ar41 | A | 1.10 | 491.4 | EXP. 3-N-2 |
| 4-NP-44 | EXP. 1-N-62 | sso62 | Qn2 | so62 | Ar41 | A | 1.45 | 451.4 | EXP. 3-N-2 |
| 4-NP-45 | EXP. 1-N-62 | sso61 | Qn2 | so61 | Ar41 | A | 1.33 | 423.4 | EXP. 3-N-2 |
| 4-NP-46 | EXP. 1-N-62 | sso54 | Qn2 | so54 | Ar41 | A | 1.38 | 463.4 | EXP. 3-N-2 |
| 4-NP-47 | EXP. 1-N-51 | sso55 | Qn1 | so55 | Ar4 | A | 1.54 | 493.4 | EXP. 3-N-2 |
| 4-NP-48 | EXP. 1-N-51 | sso41 | Qn1 | so41 | Ar4 | A | 1.34 | 451.4 | EXP. 3-N-2 |
| 4-NP-49 | EXP. 1-N-51 | sso52 | Qn1 | so52 | Ar4 | A | 1.39 | 522.4 | EXP. 3-N-2 |

TABLE 3-N2-continued

| Exp. | SM1 | SM2 | ST | J | Ar | LCMS method | RTime | MH+ | Ref. |
|---|---|---|---|---|---|---|---|---|---|
| 4-NP-50  | EXP. 1-N-51 | sso59 | Qn1 | so59 | Ar4   | A | 1.41 | 522.4 | EXP. 3-N-2 |
| 4-NP-73  | EXP. 1-N-51 | sso63 | Qn1 | so63 | Ar4   | A | 1.55 | 467.4 | EXP. 3-N-1 |
| 4-NP-421 | EXP. 1-N-66 | sso1  | Qn2 | so1  | Ar192 | A | 0.73 | 369.2 | EXP. 3-N-2 |
| 4-NP-422 | EXP. 1-N-66 | sso2  | Qn2 | so2  | Ar192 | A | 0.83 | 383.3 | EXP. 3-N-2 |
| 4-NP-459 | EXP. 1-N-63 | sso42 | Qn1 | so42 | Ar192 | A | 0.86 | 425.4 | EXP. 3-N-2 |
| 4-NP-460 | EXP. 1-N-64 | sso42 | Qn1 | so42 | Ar186 | A | 0.86 | 425.4 | EXP. 3-N-2 |
| 4-NP-461 | EXP. 1-N-65 | sso42 | Qn1 | so42 | Ar161 | A | 0.81 | 439.4 | EXP. 3-N-2 |
| 4-NP-462 | EXP. 1-N-63 | sso63 | Qn1 | so63 | Ar192 | A | 1.07 | 439.4 | EXP. 3-N-2 |
| 4-NP-463 | EXP. 1-N-64 | sso63 | Qn1 | so63 | Ar186 | A | 0.97 | 439.4 | EXP. 3-N-2 |
| 4-NP-464 | EXP. 1-N-65 | sso63 | Qn1 | so63 | Ar161 | A | 0.9  | 453.4 | EXP. 3-N-2 |
| 4-NP-465 | EXP. 1-N-63 | sso64 | Qn1 | so64 | Ar192 | A | 0.98 | 437.4 | EXP. 3-N-2 |
| 4-NP-466 | EXP. 1-N-64 | sso64 | Qn1 | so64 | Ar186 | A | 0.87 | 437.4 | EXP. 3-N-2 |
| 4-NP-467 | EXP. 1-N-65 | sso64 | Qn1 | so64 | Ar161 | A | 0.82 | 451.4 | EXP. 3-N-2 |
| 4-NP-468 | EXP. 1-N-65 | sso44 | Qn1 | so44 | Ar161 | A | 0.87 | 479.4 | EXP. 3-N-2 |
| 4-NP-474 | EXP. 1-N-63 | sso64 | Qn1 | so65 | Ar192 | A | 1.06 | 533.4 | EXP. 3-N-2 |
| 4-NP-475 | EXP. 1-N-64 | sso64 | Qn1 | so55 | Ar186 | A | 0.98 | 533.4 | EXP. 3-N-2 |
| 4-NP-476 | EXP. 1-N-65 | sso64 | Qn1 | so65 | Ar151 | A | 0.92 | 547.5 | EXP. 3-N-2 |
| 4-NP-477 | EXP. 1-N-64 | sso3  | Qn1 | so3  | Ar186 | A | 0.84 | 425.4 | EXP. 3-N-2 |
| 4-NP-478 | EXP. 1-N-65 | sso3  | Qn1 | so3  | Ar181 | A | 0.8  | 439.4 | EXP. 3-N-2 |
| 4-NP-479 | EXP. 1-N-63 | sso62 | Qn1 | so62 | Ar192 | A | 1.08 | 451.4 | EXP. 3-N-2 |
| 4-NP-480 | EXP. 1-N-64 | sso62 | Qn1 | so62 | Ar185 | A | 0.97 | 451.4 | EXP. 3-N-2 |
| 4-NP-481 | EXP. 1-N-64 | sso55 | Qn1 | so55 | Ar186 | A | 1.08 | 465.4 | EXP. 3-N-2 |
| 4-NP-482 | EXP. 1-N-63 | sso66 | Qn1 | so66 | Ar192 | A | 1.02 | 433.3 | EXP. 3-N-2 |
| 4-NP-483 | EXP. 1-N-64 | sso66 | Qn1 | so66 | Ar186 | A | 0.91 | 433.3 | EXP. 3-N-2 |
| 4-NP-484 | EXP. 1-N-65 | sso66 | Qn1 | so66 | Ar161 | A | 0.85 | 447.3 | EXP. 3-N-2 |
| 4-NP-508 | EXP. 1-N-66 | sso7  | Qn2 | so7  | Ar192 | A | 0.93 | 397.3 | EXP. 3-N-2 |
| 4-NP-509 | EXP. 1-N-66 | sso4  | Qn2 | so4  | Ar192 | A | 0.85 | 395.3 | EXP. 3-N-2 |
| 4-NP-510 | EXP. 1-N-66 | sso64 | Qn2 | so54 | Ar186 | A | 0.95 | 409.3 | EXP. 3-N-2 |
| 4-NP-512 | EXP. 1-N-67 | sso1  | Qn2 | so1  | Ar186 | A | 0.64 | 369.3 | EXP. 3-N-2 |
| 4-NP-513 | EXP. 1-N-67 | sso2  | Qn2 | so2  | Ar186 | A | 0.72 | 383.3 | EXP. 3-N-2 |
| 4-NP-514 | EXP. 1-N-67 | sso42 | Qn2 | so42 | Ar186 | A | 0.82 | 397.3 | EXP. 3-N-2 |
| 4-NP-515 | EXP. 1-N-67 | sso4  | Qn2 | so4  | Ar186 | A | 0.76 | 395.3 | EXP. 3-N-2 |
| 4-NP-516 | EXP. 1-N-67 | sso64 | Qn2 | so64 | Ar186 | A | 0.84 | 409.3 | EXP. 3-N-2 |
| 4-NP-518 | EXP. 1-N-68 | sso1  | Qn2 | so1  | Ar161 | A | 0.56 | 383.2 | EXP. 3-N-2 |
| 4-NP-519 | EXP. 1-N-68 | sso2  | Qn2 | so2  | Ar161 | A | 0.7  | 397.3 | EXP. 3-N-2 |
| 4-NP-520 | EXP. 1-N-68 | sso42 | Qn2 | so42 | Ar161 | A | 0.83 | 411.3 | EXP. 3-N-2 |
| 4-NP-521 | EXP. 1-N-68 | sso4  | Qn2 | so4  | Ar161 | A | 0.73 | 409.3 | EXP. 3-N-2 |
| 4-NP-522 | EXP. 1-N-68 | sso64 | Qn2 | so64 | Ar161 | A | 0.82 | 423.3 | EXP. 3-N-2 |
| 4-NP-526 | EXP. 1-N-63 | sso3  | Qn1 | so3  | Ar192 | A | 0.95 | 426.4 | EXP. 3-N-2 |
| 4-NP-527 | EXP. 1-N-65 | sso62 | Qn1 | so62 | Ar161 | A | 0.9  | 465.4 | EXP. 3-N-2 |
| 4-NP-528 | EXP. 1-N-63 | sso62 | Qn1 | so62 | Ar192 | A | 1.17 | 465.4 | EXP. 3-N-2 |
| 4-NP-529 | EXP. 1-N-65 | sso55 | Qn1 | so55 | Ar161 | A | 0.99 | 479.4 | EXP. 3-N-2 |
| 4-NP-530 | EXP. 1-N-63 | sso44 | Qn1 | so44 | Ar192 | A | 1.04 | 465.3 | EXP. 3-N-2 |
| 4-NP-531 | EXP. 1-N-64 | sso44 | Qn1 | so44 | Ar186 | A | 0.93 | 465.3 | EXP. 3-N-2 |

Example 4-N-1

3-(8-(1-(2-aminoethyl)piperidin-4-ylamino)isoquinolin-6-yl)benzonitrile

[Step a] tert-butyl 2-(4-(6-(3-cyanophenyl)isoquinolin-8-ylamino)piperidin-1-yl)ethylcarbamate (Intermediate 4-N-1)

Triethylamine (52 μL) and sodium triacetoxyhydroborate (32 mg; Ald) were added to a 1,2-dichloroethane (3 mL) solution of Example compound 1-N-1 (30 mg) and t-butyl n-(2-oxoethyl)carbamate (24 mg; Ald) at room temperature and the resulting mixture was stirred for 16 hours at room temperature. Chloroform and saturated aqueous sodium bicarbonate solution were added to extract the reaction mixture, then the organic layer was dried, the solvent was evaporated under reduced pressure, and the residue was purified by column chromatography (Yamazen; chloroform/methanol) to give the title compound (40.3 mg).

[Step b] 3-(8-(1-(2-aminoethyl)piperidin-4-ylamino)isoquinolin-6-yl)benzonitrile The title compound (28.5 mg) was obtained from Intermediate 4-N-1 (40.3 mg) according to the method described in Step b of Example 1-N-1.

(LCMS: 372.4 (MH$^+$); retention time: 0.70 min; LCMS; condition A)

Example 4-N-2

3-(8-(1-(pyridin-3-ylmethyl)piperidin-4-ylamino)isoquinolin-6-yl)benzonitrile

The title compound (8.8 mg) was obtained from Example compound 1-N-1 (20 mg) and 3-pyridine carbaldehyde (10 μL; WAKO) according to the method described in Step a of Example 4-N-1.

(LCMS: 420.5 (MH$^+$); retention time: 0.87 min; LCMS; condition A)

Example 4-N-3

3-(8-(1-(morpholin-3-ylmethyl)piperidin-4-ylamino) isoquinolin-6-yl)benzonitrile

[Step a] tert-butyl 3-(hydroxymethyl)morpholine-4-carboxylate (Intermediate 4-N-3-1)

Ethyl chlorocarbonate (149 µL; TCI) was added to a THF (8 mL) solution of morpholine-3, 4-dicarboxylic acid 4-tert-butyl ester (300 mg; Ast) and diisopropylethylamine (560 µL; WAKO) with ice cooling and the resulting mixture was stirred at room temperature for 1 and half hours. Sodium tetrahydroborate (197 mg; WAKO) was added at room temperature, the resulting mixture was stirred for 15 minutes followed by the addition of methanol (1.2 mL) with ice cooling, and the resulting mixture was stirred at room temperature for 2 hours. The reaction mixture solution was concentrated under reduced pressure, ethyl acetate and saturated aqueous sodium bicarbonate solution were added to extract the reaction mixture, then the organic layer was dried, and the solvent was evaporated under reduced pressure to give the title compound (209 mg).

(Intermediate 4-N-3-1 Rf (TLC)=0.4 (CH$_3$Cl:MeOH=10: 1))

[Step b] tert-butyl 3-formylmorpholine-4-carboxylate (Intermediate 4-N-3-2)

Oxalyl dichloride (60 µL; WAKO) was added to DMSO (82 µL) and dichloromethane (5 mL) at −78° C., the resulting mixture was stirred as it was for 15 minutes followed by the addition of a dichloromethane (2 mL) solution of Intermediate 4-N-3-1 (100 mg), and the resulting mixture was stirred at −78° C. for 1 hour. Diisopropylethylamine (320 µL) was added, the resulting mixture was gradually returned to room temperature and stirred for 2 and half hours. The reaction mixture solution was concentrated under reduced pressure followed by the addition of ethyl acetate, the resulting mixture was washed successively with saturated aqueous sodium bicarbonate solution and water, then the organic layer was dried, and the solvent was evaporated under reduced pressure to give the title compound (101 mg).

(Intermediate 4-N-3-2 Rf (TLC)=0.5 (CH$_3$Cl:MeOH=10: 1))

[Step c] tert-butyl 3-((4-(6-(3-cyanophenyl)isoquinolin-8-ylamino)piperidin-1-yl)methyl)morpholine-4-carboxylate (Intermediate 4-N-3-3)

The title compound (31 mg) was obtained from Example compound 1-N-1 (30 mg) and Intermediate 4-N-3-2 (40 mg) according to the method described in Step a of Example 4-N-1.

(Intermediate 4-N-3-3 LCMS: 528.1 (MH$^+$); retention time: 1.06 min; LCMS; condition A)

[Step d] 3-(8-(1-(morpholin-3-ylmethyl)piperidin-4-ylamino)isoquinolin-6-yl)benzonitrile The title compound (22 mg) was obtained from Intermediate 4-N-3-3 (31 mg) according to the method described in Step b of Example 1-N-1.

(LCMS: 428.1 (MH$^+$); retention time: 0.83 min; LCMS; condition A)

Example 4-N-4

3-(8-(1-(azetidin-3-ylmethyl)piperidin-4-ylamino) isoquinolin-6-yl)benzonitrile

[Step a] tert-butyl 3-(hydroxymethyl)azetidine-1-carboxylate (Intermediate 4-N-4-1)

A methanol hydrochloride solution (10%, 0.5 mL) was added to a methanol (7 mL) solution of 1-(diphenylmethyl)-3-(hydroxymethyl)azetidine (500 mg; Oak) followed by the addition of 20% palladium hydroxide-active carbon (15 mg; WAKO) under a nitrogen atmosphere and the resulting mixture was stirred at room temperature for 17 and half hours under a hydrogen atmosphere. The insoluble matter was filtrated and the solvent was evaporated under reduced pressure. The residue was dissolved in a mixed solvent of chloroform and methanol, the resulting mixture passed through a sodium bicarbonate column, and the solvent was evaporated under reduced pressure. The residue was dissolved in acetonitrile (5 mL) followed by the addition of an acetonitrile (3 mL) solution of dicarbonate di-t-butyl (520 mg; WAKO) at room temperature and the resulting mixture was stirred at room temperature for 14 hours. Di-t-butyl dicarbonate (100 mg) was further added, the resulting mixture was stirred for 2 hours, then chloroform (20 mL×3) and saturated aqueous sodium bicarbonate solution (20 mL) were added to the reaction mixture solution to extract the reaction mixture, then the organic layer was dried, and the solvent was evaporated under reduced pressure. The residue was purified by column chromatography (Yamazen; chloroform/methanol) to give the title compound (237 mg).

(Intermediate 4-N-4-1 Rf (TLC)=0.4 (CH$_3$Cl:MeOH=10: 1))

[Step b] tert-butyl 3-formylazetidine-1-carboxylate (Intermediate 4-N-4-2)

The title compound (118 mg) was obtained from Intermediate 4-N-4-1 (118 mg) according to the method described in Step b of Example 4-N-3.

(Intermediate 4-N-4-2 Rf (TLC)=0.5 (CH$_3$Cl:MeOH=10: 1))

[Step c] tert-butyl 3-((4-(6-(3-cyanophenyl)isoquinolin-8-ylamino)piperidin-1-yl)methyl)azetidine-1-carboxylate (Intermediate 4-N-4-3)

The title compound (45 mg) was obtained from Example compound 1-N-1 (50 mg) and Intermediate 4-N-4-2 (50 mg) according to the method described in Step a of Example 4-N-1.

(Intermediate 4-N-4-3 LCMS: 498.1 (MH$^+$); retention time: 1.04 min; LCMS; condition A)

[Step d] 3-(8-(1-(azetidin-3-ylmethyl)piperidin-4-ylamino)isoquinolin-6-yl)benzonitrile The title compound (34 mg) was obtained from Intermediate 4-N-4-3 (45 mg) according to the method described in Step b of Example 1-N-1.

(LCMS: 398.1 (MH$^+$); retention time: 0.68 min; LCMS; condition A)

Example 4-N-5

3-(8-(1-(morpholin-2-ylmethyl)piperidin-4-ylamino) isoquinolin-6-yl)benzonitrile

[Step a] tert-butyl 2-(hydroxymethyl)morpholine-4-carboxylate (Intermediate 4-N-5-1)

The title compound (199.6 mg) was obtained from 4-(tert-butoxycarbonyl)morpholine-2-carboxylic acid (300 mg; NeoMPS) according to the method described in Step a of Example 4-N-3.

(Intermediate 4-N-5-1 Rf (TLC)=0.4 (CH$_3$Cl:MeOH=10:1))

[Step b] tert-butyl 2-formylmorpholine-4-carboxylate (Intermediate 4-N-5-2)

The title compound (229 mg) was obtained from Intermediate 4-N-5-1 (199 mg) according to the method described in Step b of Example 4-N-3.

(Intermediate 4-N-5-2 Rf (TLC)=0.5 (CH$_3$Cl:MeOH=10:1))

[Step c] tert-butyl 2-((4-(6-(3-cyanophenyl)isoquinolin-8-ylamino)piperidin-1-yl)methyl)morpholine-4-carboxylate (Intermediate 4-N-5-3)

The title compound (68 mg) was obtained from Example compound 1-N-1 (50 mg) and Intermediate 4-N-5-2 (89 mg) according to the method described in Step a of Example 4-N-1.

(Intermediate 4-N-5-3 LCMS: 528.1 (MH$^+$); retention time: 1.06 min; LCMS; condition A)

[Step d] 3-(8-(1-(morpholin-2-ylmethyl)piperidin-4-ylamino)isoquinolin-6-yl)benzonitrile The title compound (54 mg) was obtained from Intermediate 4-N-5-3 (68 mg) according to the method described in Step b of Example 1-N-1.

(LCMS: 428.1 (MH$^+$); retention time: 0.71 min; LCMS; condition A)

Example 4-N-6

3-(8-(1-(2-hydroxyethyl)piperidin-4-ylamino)isoquinolin-6-yl)benzonitrile

Potassium carbonate (52 mg; WAKO) was added to a DMF (2 mL) solution of Example compound 1-N-1 (30 mg) and (2-bromoethoxy)-tert-butyldimethylsilane (64 μL; Ald) at room temperature and the resulting mixture was stirred at 50° C. for 12 and half hours. The resulting mixture was stirred at room temperature for approx. 10 minutes, then diluted with ethyl acetate (6 mL), and washed successively with water and saturated brine, then the organic layer was dried, and the solvent was evaporated under reduced pressure. Chloroform was added to the residue and the insoluble matter was filtrated to give the title compound (18.6 mg).

(LCMS: 373.4 (MH$^+$); retention time: 0.79 min; LCMS; condition A)

Example 4-N-7

3-(8-(1-(azetidin-3-yl)piperidin-4-ylamino)isoquinolin-6-yl)benzonitrile

[Step a] tert-butyl 3-oxoazetidine-1-carboxylate (Intermediate 4-N-7-1)

A DMSO (10 mL) solution of a sulfur trioxide-pyridine complex (2.2 g; Ald) was added to a triethylamine (4 mL) solution of 1-Boc-3-(hydroxy)azetidine (500 mg; CNH) at room temperature and the resulting mixture was stirred 50° C. for 2 and half hours. The resulting mixture was stirred for approx. 10 minutes at room temperature, then the reaction mixture was poured into ice water (40 mL) and extracted with ethyl acetate (40 mL), the organic layer was dried, and the solvent was evaporated under reduced pressure to give the title compound (305 mg).

[Step b] tert-butyl 3-(4-(6-(3-cyanophenyl)isoquinolin-8-ylamino)piperidin-1-yl)azetidine-1-carboxylate (Intermediate 4-N-7-2)

Chloroform and saturated aqueous sodium bicarbonate solution were added to Example compound 1-N-1 to extract the compound, then the organic layer was dried, the solvent was evaporated under reduced pressure to give resulting residue (17 mg). Sodium triacetoxyhydroborate (33 mg) was added to a dichloromethane (5 mL) solution of the resulting residue, Intermediate 4-N-7-1 (25 mg), and acetic acid (30 μL) at room temperature, and the resulting mixture was stirred at room temperature for 13 hours. Chloroform and saturated aqueous sodium bicarbonate solution were added to the reaction mixture solution to extract the reaction mixture, then the organic layer was dried, the solvent was evaporated under reduced pressure, and the residue was purified by column chromatography (Yamazen; chloroform/methanol) to give the title compound (12.9 mg).

(Intermediate 4-N-7-2 LCMS: 484.1 (MH$^+$); retention time: 1.06 min; LCMS; condition A)

[Step c] 3-(8-(1-(azetidin-3-yl)piperidin-4-ylamino) isoquinolin-6-yl)benzonitrile The title compound (8.9 mg) was obtained from Intermediate 4-N-7-2 (12.9 mg) according to the method described in Step b of Example 1-N-1.

(LCMS: 384.1 (MH$^+$); retention time: 0.81 min; LCMS; condition A)

Example 4-N-8

3-(8-(1,4'-bipiperidin-4-ylamino)isoquinolin-6-yl) benzonitrile

[Step a] tert-butyl 4-(6-(3-cyanophenyl)isoquinolin-8-ylamino)-1,4'-bipiperidine-1'-carboxylate (Intermediate 4-N-8-1)

The title compound (3.8 mg) was obtained from Example compound 1-N-1 (15 mg) and 1-BOC-4-piperidone (18 mg; WAKO) according to the method described in Step b of Example 4-N-7.

(Intermediate 4-N-7-2 LCMS: 512.1 (MH$^+$); retention time: 1.34 min; LCMS; condition A)

[Step b] 3-(8-(1,4'-bipiperidin-4-ylamino)isoquinolin-6-yl)benzoNitrile

Intermediate 4-N-8-1 (3.8 mg) was dissolved in 95% aqueous TFA solution and the resulting mixture was allowed to stand at room temperature for 2 hours. The solvent was evaporated to give the title compound (5.2 mg).
(LCMS: 412.1 (MH$^+$); retention time: 0.65 min; LCMS; condition A)

Example 4-N-9

3-(8-(1-(1-methylazetidin-3-yl)piperidin-4-ylamino)isoquinolin-6-yl)benzonitrile An aqueous formaldehyde solution (37% by weight; 45 µL; Ald) and triethylamine (8 µL) were added to an acetonitrile (2 mL) solution of Example compound 4-N-7 (10 mg) and triacetoxy sodium hydroborate (13 mg) at room temperature and the resulting mixture was stirred at room temperature for 15 hours. Chloroform and saturated aqueous sodium bicarbonate solution were added to extract the reaction mixture, then the organic layer was dried, the solvent was evaporated under reduced pressure, and the residue was purified by column chromatography (Yamazen; chloroform/methanol) to give the title compound (3.3 mg).
(LCMS: 398.1 (MH$^+$); retention time: 0.88 min; LCMS; condition A)

Example 4-N-10

3-(8-(1-((4-methylmorpholin-2-yl)methyl)piperidin-4-ylamino)isoquinolin-6-yl)benzonitrile The title compound (6.3 mg) was obtained from Example compound 4-N-5 (10 mg) according to the method described in Example 4-N-9.
(LCMS: 442.2 (MH$^+$); retention time: 0.79 min; LCMS; condition A)

Example 4-N-11

3-(8-(1-(2-oxo-2-(pyrrolidin-1-yl)ethyl)piperidin-4-ylamino)isoquinolin-6-yl)benzonitrile

[Step a] 2-(4-(6-(3-cyanophenyl)isoquinolin-8-ylamino)piperidin-yl)acetic acid (Intermediate 4-N-11-1)

Sodium cyanotrihydroborate (15 mg; TCI) was added to a methanol (3 mL) solution of Example compound 1-N-1 (30 mg), glyoxylic acid (6.9 M in water; 21 µL; TCI), and triethylamine (52 µL) at room temperature and the resulting mixture was stirred at room temperature for 15 hours. Water (0.2 mL) was added to the reaction mixture solution and the solvent was evaporated under reduced pressure. Methanol and diethyl ether were added to the residue and the precipitate was filtrated and dried to give the title compound (43 mg).
(Intermediate 4-N-11-1 LCMS: 387.1 (MH$^+$); retention time: 0.83 min; LCMS; condition A)

[Step b] 3-(8-(1-(2-oxo-2-(pyrrolidin-1-yl)ethyl)piperidin-4-ylamino)isoquinolin-6-yl)benzonitrile The title compound (4.7 mg) was obtained from Intermediate 4-N-11-1 (20 mg) and pyrrolidine (7.3 mg; TCI) according to the method described in Example 2-N-2.
(LCMS: 440.1 (MH$^+$); retention time: 0.89 min; LCMS; condition A)

Example 4-N-12

3-(8-(1-(2-morpholino-2-oxoethyl)piperidin-4-ylamino)Isoquinolin-6-yl)benzonitrile The title compound (8.4 mg) was obtained from Intermediate 4-N-11-1 (20 mg) and morpholine (9.0 mg; Ald) according to the method described in Example 2-N-2.
(LCMS: 456.1 (MH$^4$); retention time: 0.87 min; LCMS; condition A)

Examples 4-o-1 to 4-o-13

Compounds of Examples 4-o-1 to 4-o-13 were synthesized according to the method in Step a of Example 4-N-1 (Table 4-o). In Table 4-o, the ST column represents the structures represented by the above general formulas, the J and Ar columns represent "J" and "Ar," respectively, in the general formulas shown in the ST column, "ST," "SM1," "SM2," "LCMS," and "Ref" are defined as described above, and abbreviations such as "ch202," "Ar1," and "sch202" represent compounds or groups corresponding to the abbreviations in Tables ch, Ar, and sch, respectively, provided later. Abbreviations in the tables represent compounds or groups shown in the figures shown earlier or later.

Table 4-o also includes compounds finally purified by preparative HPLC, such as those of Examples 4-o-1, 4-o-3, 4-o-8 and 4-o-13 for example.

TABLE 4-o

| EXP. | SM1 | SM2 | ST | J | Ar | LCMS method | RTime | MH+ | Ref. |
|---|---|---|---|---|---|---|---|---|---|
| 4-o-1 | EXP. 1-o-1 | sch202 | QO1 | ch202 | Ar1 | B | 2.34 | 421.2 | EXP. 4-N-1(a) |
| 4-o-2 | EXP. 1-o-1 | sch203 | QO1 | ch203 | Ar1 | A | 0.84 | 424.1 | EXP. 4-N-1(a) |
| 4-o-3 | EXP. 1-o-1 | sch204 | QO1 | ch204 | Ar1 | B | 2.41 | 388.2 | EXP. 4-N-1(a) |
| 4-o-4 | EXP. 1-o-6 | sch201 | QO2 | ch201 | Ar1 | A | 0.81 | 316.1 | EXP. 4-N-1(a) |
| 4-o-5 | EXP. 1-o-6 | sch202 | QO2 | ch202 | Ar1 | A | 0.89 | 393.2 | EXP. 4-N-1(a) |
| 4-o-6 | EXP. 1-o-6 | sch205 | QO2 | ch205 | Ar1 | A | 1.06 | 392.1 | EXP. 4-N-1(a) |
| 4-o-7 | EXP. 1-o-6 | sch206 | QO2 | ch206 | Ar1 | A | 0.88 | 386.0 | EXP. 4-N-1(a) |
| 4-o-8 | EXP. 1-o-76 | sch201 | QO5 | ch201 | Ar1 | A | 0.84 | 374.0 | EXP. 4-N-1(a) |
| 4-o-9 | EXP. 1-o-15 | sch201 | QO9 | ch201 | Ar1 | A | 0.88 | 330.0 | EXP. 4-N-1(a) |
| 4-o-10 | EXP. 1-o-18 | sch201 | QO10 | ch201 | Ar1 | B | 2.26 | 360.2 | EXP. 4-N-1(a) |
| 4-o-11 | EXP. 2-o-19 | sch201 | QO1-1 | ch201 | Ar1 | A | 0.96 | 457.0 | EXP. 4-N-1(a) |
| 4-o-12 | EXP. 2-o-63 | sch201 | QO1-8 | ch201 | Ar1 | B | 2.35 | 427.2 | EXP. 4-N-1(a) |
| 4-o-13 | EXP. 2-o-76 | sch201 | QO2-2 | ch201 | Ar1 | A | 0.95 | 429.1 | EXP. 4-N-1(a) |

Example 5-N-1

4-(6-(3-cyanophenyl)isoquinolin-8-ylamino)piperidine-1-carboxamide

Triethylamine (52 μL), 4-Dimethylaminopyridine (1 mg), and trimethylsilyl isocyanate (which may be referred to as son1; 99 μL; TCI) were added to a dichloromethane solution of Example compound 1-N-1 (30 mg) and the resulting mixture was stirred at room temperature for 16 and half hours. Diethyl ether was added to the reaction mixture solution, the insoluble matter was filtrated, and the filtrate was concentrated under reduced pressure. The residue was purified by preparative HPLC to give the title compound (2.2 mg).

(LCMS: 372.4 (MH$^+$); retention time: 0.98 min; LCMS; condition A)

Example 5-N-2

4-(6-(3-cyanophenyl)isoquinolin-8-ylamino)-N-ethylpiperidine-1-carboxamide

Triethylamine (35 μL) and ethyl isocyanate (which may be referred to as son2; 10 mg; TCI) were added to a dichloromethane solution of Example compound 1-N-1 (20 mg) and the resulting mixture was stirred at room temperature for 13 and half hours. Dichloromethane and water were added to extract the reaction mixture, then the organic layer was dried, the solvent was evaporated under reduced pressure, and the residue was purified by column chromatography (Yamazen; chloroform/methanol) to give the title compound (15.9 mg).

(LCMS: 400.5 (MH$^+$); retention time: 1.07 min; LCMS; condition A)

Example 5-N-15

4-(6-(6-methylpyridin-3-yl)isoquinolin-8-ylamino)-N-propylpiperidine-1-carboxamide Triethylamine (48 μL) and propyl isocyanate (which may be referred to as son7; 8.9 mg; TCI) were added to a DMF solution of Example compound 1-N-63 (15 mg) and the resulting mixture was stirred at room temperature for 12 and half hours. The solvent of the reaction mixture solution was evaporated, the residue was dissolved in chloroform (0.7 ml) and methanol (0.3 ml), and SCX (500 mg) was added and shaken for 1 hour. The reaction mixture was filtrated and the residue was washed with chloroform (3.5 mL) and methanol (4 mL). Then, the mixture was washed with 2 N ammonia methanol solution (4 mL) and this resulting wash was concentrated. The resulting mixture was dried using a vacuum pump to give the title compound (12.8 mg).

(LCMS: 404.3 (MH$^+$); retention time: 0.86 min; LCMS; condition A)

Example 5-N-3 to 5-N-32 and 5-o-1 to 5-o-10

Compounds of Examples 5-N-3 to 5-N-32 and 5-o-1 to 5-o-10 were synthesized according to the methods in Examples 5-N-1, 5-N-2 and 5-N-15 (Tables 5-N and 5-o). In Tables 5-N and 5-o, the ST column represents the structures represented by the above general formulas, the J and Ar columns represent "J" and "Ar," respectively, in the general formulas shown in the ST column, "ST," "SM1," "SM2," "LCMS," and "Ref" are defined as described above, and abbreviations such as "on1," "Ar1," and "son1" represent compounds or groups corresponding to the abbreviations in Tables on, Ar, and son, respectively, provided later. Abbreviations in the tables represent compounds or groups shown in the figures shown earlier or later.

TABLE 5-N

| Exp. | SM1 | SM2 | ST | J | Ar | LCMS method | Rtime | MH$^+$ | Ref. |
|---|---|---|---|---|---|---|---|---|---|
| 5-N-1 | EXP. 1-N-1 | son1 | Qn1 | on1 | Ar1 | A | 0.99 | 372.4 | |
| 5-N-2 | EXP. 1-N-1 | son2 | Qn1 | on2 | Ar1 | A | 1.07 | 400.5 | |
| 5-N-3 | EXP. 1-N-1 | son3 | Qn1 | on3 | Ar1 | A | 1.32 | 454.5 | EXP. 5-N-2 |
| 5-N-4 | EXP. 1-N-1 | son4 | Qn1 | on4 | Ar1 | A | 1.26 | 448.5 | EXP. 5-N-2 |
| 5-N-5 | EXP. 1-N-1 | son5 | Qn1 | on5 | Ar1 | A | 1.29 | 476.6 | EXP. 5-N-2 |
| 5-N-6 | EXP. 1-N-1 | son6 | Qn1 | on6 | Ar1 | A | 0.98 | 449.5 | EXP. 5-N-2 |
| 5-N-7 | EXP. 1-N-27 | son1 | Qn3 | on1 | Ar1 | A | 0.94 | 358.4 | EXP. 5-N-2 |
| 5-N-8 | EXP. 1-N-5 | son1 | Qn7 | on1 | Ar1 | A | 0.98 | 345.4 | EXP. 5-N-2 |
| 5-N-9 | EXP. 1-N-2 | son1 | Qn5 | on1 | Ar1 | A | 0.99 | 372.3 | EXP. 5-N-2 |
| 5-N-10 | EXP. 1-N-12 | son1 | Qn6 | on1 | Ar1 | A | 1.01 | 386.4 | EXP. 5-N-2 |
| 5-N-11 | EXP. 1-N-28 | son1 | Qn4 | on1 | Ar1 | A | 0.94 | 358.4 | EXP. 5-N-2 |
| S-N-12 | EXP. 1-N-4 | son1 | Qn2 | on1 | Ar1 | A | 0.94 | 344.4 | EXP. 5-N-2 |
| 5-N-13 | EXP. 1-N-12 | son2 | Qn6 | on2 | Ar1 | A | 1.12 | 414.3 | EXP. 5-N-2 |
| 5-N-14 | EXP. 1-N-4 | son2 | Qn2 | on2 | Ar1 | A | 1.03 | 372.3 | EXP. 5-N-2 |
| 5-N-16 | EXP. 1-N-64 | son7 | Qn1 | on7 | Ar186 | A | 0.75 | 404.3 | EXP. 5-N-15 |
| 5-N-17 | EXP. 1-N-65 | son7 | Qn1 | on7 | Ar161 | A | 0.72 | 418.3 | EXP. 5-N-15 |
| 5-N-18 | EXP. 1-N-63 | son8 | Qn1 | on8 | Ar192 | A | 0.96 | 418.3 | EXP. 5-N-15 |
| 5-N-19 | EXP. 1-N-64 | son8 | Qn1 | on8 | Ar186 | A | 0.86 | 418.3 | EXP. 5-N-15 |
| 5-N-20 | EXP. 1-N-65 | son8 | Qn1 | on8 | Ac161 | A | 0.82 | 432.3 | EXP. 5-N-15 |
| 5-N-21 | EXP. 1-N-63 | son9 | Qn1 | on9 | Ar192 | A | 0.85 | 404.3 | EXP. 5-N-15 |
| 5-N-22 | EXP. 1-N-64 | son9 | Qn1 | on9 | Ar186 | A | 0.76 | 404.3 | EXP. 5-N-15 |
| 5-N-23 | EXP. 1-N-65 | son9 | Qn1 | on9 | Ar161 | A | 0.72 | 418.3 | EXP. 5-N-15 |
| 5-N-24 | EXP. 1-N-63 | son10 | Qn1 | on10 | Ar192 | A | 0.98 | 430.3 | EXP. 5-N-15 |
| 5-N-25 | EXP. 1-N-64 | son10 | Qn1 | on10 | Ar186 | A | 0.88 | 430.3 | EXP. 5-N-15 |
| 5-N-26 | EXP. 1-N-65 | son10 | Qn1 | on10 | Ar161 | A | 0.83 | 444.3 | EXP. 5-N-15 |
| 5-N-27 | EXP. 1-N-63 | son3 | Qn1 | on3 | Ar192 | A | 1.05 | 444.3 | EXP. 5-N-15 |
| 5-N-28 | EXP. 1-N-64 | son3 | Qn1 | on3 | Ar186 | A | 0.96 | 444.3 | EXP. 5-N-15 |
| 5-N-29 | EXP. 1-N-65 | son3 | Qn1 | on3 | Ar161 | A | 0.91 | 458.4 | EXP. 5-N-15 |
| 5-N-30 | EXP. 1-N-63 | son2 | Qn1 | on2 | Ar192 | A | 0.78 | 390.3 | EXP. 5-N-15 |
| 5-N-31 | EXP. 1-N-64 | son2 | Qn1 | on2 | Ar186 | A | 0.69 | 390.3 | EXP. 5-N-15 |
| 5-N-32 | EXP. 1-N-65 | son2 | Qn1 | on2 | Ar161 | A | 0.66 | 404.3 | EXP. 5-N-15 |

TABLE 5-o

| EXP. | SM1 | SM2 | ST | J | Ar | LCMS method | RTime | MH+ | Ref. |
|---|---|---|---|---|---|---|---|---|---|
| 5-o-1 | EXP. 1-o-1 | son1 | Qo1 | on1 | Ar1 | A | 1.02 | 373.4 | EXP. 5-N-2 |
| 5-o-2 | EXP. 1-o-1 | son2 | Qo1 | on2 | Ar1 | A | 1.18 | 401.3 | EXP. 5-N-2 |
| 5-o-3 | EXP. 1-o-1 | son3 | Qo1 | on3 | Ar1 | A | 1.42 | 455.3 | EXP. 5-N-2 |
| 5-o-4 | EXP. 1-o-1 | son4 | Qo1 | on4 | Ar1 | A | 1.42 | 449.3 | EXP. 5-N-2 |
| 5-o-5 | EXP. 1-o-2 | son1 | QO14 | on1 | Ar1 | A | 1.03 | 373.4 | EXP. 5-N-2 |
| 5-o-6 | EXP. 1-o-6 | son1 | QO2 | on1 | Ar1 | A | 0.98 | 345.1 | EXP. 5-N-2 |
| 5-o-7 | EXP. 1-o-13 | son1 | QO6 | on1 | Ar1 | A | 1.05 | 373.2 | EXP. 5-N-2 |
| 5-o-8 | EXP. 1-o-10 | son1 | QO11 | on1 | Ar1 | A | 0.96 | 347.1 | EXP. 5-N-2 |
| 5-o-9 | EXP. 1-o-12 | son1 | Qo8 | on1 | Ar1 | A | 1.13 | 387.4 | EXP. 5-N-2 |
| 5-o-10 | EXP. 1-o-11 | son1 | Qo7 | on1 | Ar1 | A | 1.11 | 387.2 | EXP. 5-N-2 |

Example 6-o-1

3-(8-(1-(pyridin-3-yl)piperidin-4-yloxy)isoquinolin-6-yl)benzonitrile

Sodium t-butoxide (10.7 mg) was added to a toluene solution of Example compound 1-o-1 (15 mg), 3-iodinepyridine (22.8 mg; TCI), Pd$_2$(dba)$_3$ (55.5 mg), and BINAP (9.2 mg) under a nitrogen atmosphere and the resulting mixture was stirred overnight at 70° C. The resulting mixture was stirred at room temperature for approx. 10 minutes, then the reaction mixture solution was filtrated, and the filtrate was concentrated under reduced pressure. The residue was purified by preparative HPLC to give the title compound (0.8 mg).

(LCMS: 407.0 (MH$^+$); retention time: 1.12 min; LCMS; condition A)

Example 6-o-2

3-(8-(1-(pyrimidin-5-yl)piperidin-4-yloxy)isoquinolin-6-yl)benzonitrile

Sodium t-butoxide (10.7 mg) was added to a toluene solution of Example compound 1-o-1 (15 mg), 5-bromopyrimidine (17.6 mg; Ald), Pd$_2$(dba)$_3$ (55.5 mg), and BINAP (9.2 mg) under a nitrogen atmosphere and the resulting mixture was stirred overnight at 70° C. The resulting mixture was stirred at room temperature for approx. 10 minutes, then the reaction mixture solution was filtrated, and the filtrate was concentrated under reduced pressure. The residue was purified by column chromatography (Yamazen; chloroform/methanol) followed by the addition of a suitable amount of a methanol hydrochloride solution (100; TCI), the resulting mixture was stirred at room temperature for approx. 10 minutes followed by the addition of ether, and the precipitate was collected by filtration and dried to give the title compound (7.0 mg).

(LCMS: 408.3 (MH$^+$); retention time: 1.23 min; LCMS; condition A)

Example 6-o-3

3-(8-(1-(pyridin-3-yl)azetidin-3-yloxy)isoquinolin-6-yl)benzonitrile

The title compound (3.6 mg) was obtained from Example compound 1-o-6 (15 mg) and 3-iodopyridine (24.6 mg; TCI) according to the method described in Example 6-o-1.

(LCMS: 379.0 (MH$^+$); retention time: 1.09 min; LCMS; condition A)

Example 7-o-1

3-(6-(3-cyanophenyl)isoquinolin-8-yloxy)azetidine-1-carboximidamide

Example compound 1-o-6 (15 mg), 5-tert-butyl (1H-pyrazol-1-yl)methanediylidene dicarbamate (14.9 mg; ADVANCE CHEMTECH), and triethylamine (11.2 µL; WAKO) were added to an acetonitrile solution and the resulting mixture was stirred at room temperature for 3 days. Chloroform and water were added to the reaction mixture solution to extract the reaction mixture, the organic layer was dried, and the solvent was evaporated under reduced pressure. The residue was purified by column chromatography (Yamazen; chloroform/methanol) followed by the addition of a suitable amount of a methanol hydrochloride solution (10%; TCI) and the resulting mixture was stirred at 50° C. for 2 hours. The resulting mixture was stirred at room temperature for approx. 10 minutes followed by the addition of ether and the precipitate was collected by filtration and dried to give the title compound (14.3 mg).

(LCMS: 344.1 (MH$^+$); retention time: 0.85 min; LCMS; condition A)

Example 1-NP-1

N-(1-(ethylsulfonyl)piperidin-4-yl)-6-(3-isopropylphenyl)isoquinolin-8-amine

[Step a] 6-(benzyloxy)-N-(1-(ethylsulfonyl)piperidin-4-yl)isoquinolin-8-amine (Intermediate 1-NP-1-1)

The title compound (759 mg) was obtained from Intermediate 9 (700 mg) and Intermediate N-2 (846 mg) according to the method described in Step a of Example 1-N-1.

(Intermediate 1-NP-1-1 LCMS: 426.3 (MH$^+$); retention time: 1.11 min; LCMS; condition A)

[Step b] 8-(1-(ethylsulfonyl)piperidin-4-ylamino)isoquinolin-6-yltrifluoromethanesulfonate (Intermediate 1-NP-1-2)

Palladium carbon (10% by weight, PE-type, 230 mg; NECHEM) was added to a methanol (10 mL) and THF (5 mL) solution of Intermediate 1-NP-1-1 (750 mg) under a nitrogen atmosphere and the resulting mixture was stirred at room temperature for 15 and half hours under a hydrogen gas atmosphere. The atmosphere was replaced with a nitrogen gas, then the insoluble matter was removed by filtration through celite, and the solvent was evaporated under reduced pressure. Dichloromethane (30 mL), N-phenylbis(trifluoromethanesulfonimide) (691 mg), and triethylamine (2.2 mL) were added to the residue and the resulting mixture was stirred at 50° C. for 13 hours. The resulting mixture was stirred at room temperature for approx. 10 minutes, then the solvent was evaporated under reduced pressure, and the residue was purified by column chromatography (Yamazen; chloroform/methanol) to give the title compound (260 mg).

(Intermediate 1-NP-1-2 LCMS: 468.2 (MH$^+$); retention time: 1.51 min; LCMS; condition A)

[Step c] N-(1-(ethylsulfonyl)piperidin-4-yl)-6-(3-isopropylphenyl)isoquinolin-8-amine Aqueous sodium carbonate solution (0.6 M, 0.18 mL) was added to a THF (0.72 mL) solution of Intermediate 1-NP-1-2 (16.4 mg), 3-isopropylphenylboronic acid (which may be referred to as sbo9; 23 mg), and PdCl$_2$dppf.CH$_2$Cl$_2$ (94.3 mg) at room temperature and the resulting mixture was stirred at 60° C. for 17 hours. The reaction mixture solution was filtrated through celite and then the solvent was evaporated under reduced pressure. The residue was dissolved in dichloromethane (1 mL) and methanol (1 mL) followed by the addition of SCX resin (150 mg) and the resulting mixture was agitated by shaking for 5 hours. The reaction mixture was filtrated, then SCX resin was washed with dichloromethane (1 mL×4) and methanol (1 mL×4) followed by the addition of 2 M ammonia methanol solution (0.5 mL×3) to elute, and the solvent was evaporated to give the title compound (10.2 mg).

(LCMS: 438.2 (MH$^+$); retention time: 1.59 min; LCMS; condition A)

Examples 1-NP-2 to 1-NP-43

Compounds of Examples 1-NP-2 to 1-NP-43 were synthesized according to the method in Example 1-NP-1 (Table 1-NP). At this time, for example, the method described in Step b of Example 1-N-1 was used if deprotection is required. In Table 1-NP, the ST column represents the structures represented by the above general formulas and the Ar column represents "Ar" in the general formulas shown in the ST column. In Table 1-NP, the SM1 column represents compounds used in respective Examples corresponding to Intermediate N-2 used in Step a of Example 1-NP-1 and the SM2 column represents compounds used in respective Examples corresponding to 3-isopropylphenyl boronic acid (which may be referred to as sbo9) used in Step c of Example 1-NP-1. For example, in Example 1-NP-15, Intermediate N-7 was used as "SM1" toward Intermediate 9 to perform Step a of Example 1-NP-1 and 3-methylboronic acid (which may be referred to as sbo19) was used as "SM2" to perform Step c of Example 1-NP-1. In Table 1-NP, "LCMS" was defined as described above, abbreviations such as "Ar9" and "sbo9" represent compounds or groups corresponding to abbreviations in Tables Ar and sbo, respectively, provided later.

Example compounds in Table 1-NP also include compounds purified by column chromatography.

TABLE 1-NP

| EXP. | SM1 | SM2 | ST | Ar | method | Rtime | MH$^+$ |
|---|---|---|---|---|---|---|---|
| 1-NP-1 | IM. N-2 | sbo9 | Qn2P | Ar9 | A | 1.59 | 438.2 |
| 1-NP-2 | IM. N-2 | sbo10 | Qn2P | Ar10 | A | 1.47 | 464.1 |
| 1-NP-3 | IM. N-2 | sbo11 | Qn2P | Ar11 | A | 1.19 | 438.2 |
| 1-NP-4 | IM. N-2 | sbo12 | Qn2P | Ar12 | A | 1.05 | 411.2 |

TABLE 1-NP-continued

| EXP. | SM1 | SM2 | ST | Ar | method | Rtime | MH$^+$ |
|---|---|---|---|---|---|---|---|
| 1-NP-5 | IM. N-2 | sbo13 | Qn2P | Ar13 | A | 1.34 | 414.2 |
| 1-NP-6 | IM. N-2 | sbo2 | Qn2P | Ar2 | A | 1.43 | 430.1 |
| 1-NP-7 | IM. N-2 | sbo14 | Qn2P | Ar14 | A | 0.79 | 425.2 |
| 1-NP-8 | IM. N-2 | sbo15 | Qn2P | Ar15 | A | 1.32 | 414.2 |
| 1-NP-9 | IM. N-2 | sbo16 | Qn2P | Ar16 | A | 1.25 | 402.1 |
| 1-NP-10 | IM. N-2 | sbo4 | Qn2P | Ar4 | A | 1.29 | 439.1 |
| 1-NP-11 | IM. N-2 | sbo25 | Qn2P | Ar25 | A | 1.29 | 396.2 |
| 1-NP-12 | IM. N-2 | sbo17 | Qn2P | Ar17 | A | 1.29 | 426.1 |
| 1-NP-13 | IM. N-2 | sbo18 | Qn2P | Ar18 | A | 1.21 | 421.2 |
| 1-NP-14 | IM. N-2 | sbo3 | Qn2P | Ar3 | A | 0.94 | 397.2 |
| 1-NP-15 | IM. N-7 | sbo19 | Qn7P | Ar19 | A | 1.24 | 423.1 |
| 1-NP-16 | IM. N-7 | sbo13 | Qn7P | Ar13 | A | 1.18 | 427.1 |
| 1-NP-17 | IM. N-7 | sbo11 | Qn7P | Ar11 | A | 1.04 | 451.1 |
| 1-NP-18 | IM. N-7 | sbo4 | Qn7P | Ar4 | A | 1.14 | 452.1 |
| 1-NP-19 | IM. N-7 | sbo20 | Qn7P | Ar20 | A | 1.10 | 452.1 |
| 1-NP-20 | IM. N-7 | sbo21 | Qn7P | Ar21 | A | 1.04 | 451.1 |
| 1-NP-21 | IM. N-7 | sbo16 | Qn7P | Ar16 | A | 1.08 | 415.1 |
| 1-NP-22 | IM. N-7 | sbo22 | Qn7P | Ar22 | A | 0.82 | 413.1 |
| 1-NP-23 | IM. N-7 | sbo23 | Qn7P | Ar23 | A | 0.93 | 439.1 |
| 1-NP-24 | IM. N-7 | sbo14 | Qn7P | Ar14 | A | 0.69 | 438.1 |
| 1-NP-25 | IM. N-7 | sbo5 | Qn7P | Ar7 | A | 0.88 | 439.1 |
| 1-NP-26 | IM. N-7 | sbo25 | Qn7P | Ar25 | A | 1.13 | 409.1 |
| 1-NP-27 | IM. N-7 | sbo18 | Qn7P | Ar18 | A | 1.09 | 434.1 |
| 1-NP-28 | IM. N-7 | sbo2 | Qn7P | Ar2 | A | 1.26 | 443.1 |
| 1-NP-29 | sa1 | sbo25 | Qn1-1 | Ar25 | A | 0.81 | 304.3 |
| 1-NP-30 | sa1 | sbo19 | Qn1-1 | Ar19 | A | 0.90 | 318.3 |
| 1-NP-31 | sa1 | sbo17 | Qn1-1 | Ar17 | A | 0.84 | 334.3 |
| 1-NP-32 | sa1 | sbo11 | Qn1-1 | Ar11 | A | 0.77 | 346.4 |
| 1-NP-33 | sa1 | sbo2 | Qn1-1 | Ar2 | A | 0.93 | 338.3 |
| 1-NP-34 | sa1 | sbo74 | Qn1-1 | Ar74 | A | 0.93 | 338.3 |
| 1-NP-36 | sa6 | sbo18 | Qn1-1 | Ar18 | A | 0.77 | 329.3 |
| 1-NP-37 | sa6 | sbo16 | Qn1-1 | Ar16 | A | 0.74 | 310.2 |
| 1-NP-38 | sa6 | sbo26 | Qn8-1 | Ar25 | A | 0.79 | 290.3 |
| 1-NP-39 | sa6 | sbo18 | Qn8-1 | Ar18 | A | 0.79 | 315.3 |
| 1-NP-40 | sa6 | sbo16 | Qn8-1 | Ar16 | A | 0.71 | 296.2 |
| 1-NP-41 | sa6 | sbo19 | Qn8-1 | Ar19 | A | 0.89 | 304.3 |
| 1-NP-42 | sa6 | sbo17 | Qn8-1 | Ar17 | A | 0.83 | 320.3 |
| 1-NP-43 | sa6 | sbo2 | Qn8-1 | Ar2 | A | 0.94 | 324.3 |

Example 1-oP-2 (1-methyl-1H-imidazol-5-yl)(4-(6-phenylisoquinolin-8-yloxy)piperidin-1-yl)methanone

[Step a] 6-(benzyloxy)-8-(piperidin-4-yloxy) isoquinoline (Intermediate 1-oP-2-1)

The title compound (443 mg) was obtained from Intermediate 9 (700 mg) and 1-BOC-4-hydroxypiperidine (soh1; 1.35 g; Ald) according to the method described in Steps a and b of Example 1-o-1.

(Intermediate 1-oP-2-1 LCMS: 335.0 (MH$^+$); retention time: 0.86 min; LCMS; condition A)

[Step b] (4-(6-(benzyloxy)isoquinolin-8-yloxy)piperidin-1-yl)(1-methyl-1H-imidazol-5-yl)methanone (Intermediate 1-oP-2-2)

The title compound (400 mg) was obtained from Intermediate 1-oP-1-1 (443 mg) and 1-methyl-1H-imidazole-5-carboxylic acid (which may be referred to as sco44; 275 mg; MAYB) according to the method described in Example 2-N-2.

(Intermediate 1-oP-2-2 LCMS: 443.1 (MH$^+$); retention time: 1.00 min; LCMS; condition A)

[Step c] 8-(1-(1-methyl-1H-imidazole-5-carbonyl)piperidin-4-yloxy)isoquinolin-6-Y$^1$ trifluoromethanesulfonate (Intermediate 1-oP-2-3)

The title compound (150 mg) was obtained from Intermediate 1-oP-2-2 (400 mg) according to the method described in Step b of Example 1-NP-1.

(Intermediate 1-oP-2-3 LCMS: 485.0 (MH$^+$); retention time: 1.31 min; LCMS; condition A)

[Step d] (1-methyl-1H-imidazol-5-yl)(4-(6-phenyl-isoquinolin-8-yloxy)piperidin-1-yl)methanone The title compound (5.7 mg) was obtained from Intermediate 1-oP-2-3 (10 mg) and phenylboronic acid (which may be referred to as sbo25; TCI) according to the method described in Step c of Example 1-NP-1.

(LCMS: 413.1 (MH$^+$); retention time: 1.02 min; LCMS; condition A)

Examples 1-oP-1 to 1-oP-43

Compounds of Examples 1-oP-1 to 1-oP-43 were synthesized according to the method in Example 1-oP-2 (Table 1-oP). At this time, for example, the method described in Step b of Example 1-N-1 was used if deprotection is required. In Table 1-oP, the ST column represents the structures represented by the above general formulas and the Ar column represents "Ar" in the general formulas shown in the ST column. The SM1 column represents compounds used in respective Examples corresponding to 1-BOC-4-hydroxypiperidine (which may be referred to as soh1) used in Step a of Example 1-oP-2 and the SM2 column represents compounds used in respective Examples corresponding to phenylboronic acid (which may be referred to as sbo25) used in Step d of Example 1-oP-2. For example, in Example 1-oP-17, 1-BOC-3hydroxy azetidine (which may be referred to as soh6) was used as "SM1" toward Intermediate 9 to perform Step a of Example 1-oP-2. Subsequently, after Steps b and c of Example 1-oP-2 were performed, 3-methylboronic acid (which may be referred to as sbo19) was then used as "SM2" to perform Step d of Example 1-oP-2. In Table 1-oP, "LCMS" was defined as described above. Abbreviations in the tables represent compounds or groups of abbreviations in figures provided later.

In Table 1-oP, the compound of Example 1-oP-14 was purified by column chromatography and the compounds of Example 1-oP-12, 1-oP-13, 1-oP-35 to 1-oP-37, and 1-oP-41 were finally purified by preparative HPLC.

TABLE 1-oP

| EXP. | SM1 | SM2 | ST | Ar | LCMS method | RTime | MH+ |
|---|---|---|---|---|---|---|---|
| 1-oP-1 | soh1 | sbo18 | QoP1 | Ar18 | A | 1.02 | 438.2 |
| 1-oP-2 | soh1 | sbo25 | QoP1 | Ar25 | A | 0.98 | 413.1 |
| 1-oP-3 | soh1 | sbo19 | QoP1 | Ar19 | A | 1.09 | 427.1 |
| 1-oP-4 | soh1 | sbo13 | QoP1 | Ar13 | A | 1.05 | 431.0 |
| 1-oP-5 | soh1 | sbo2 | QoP1 | Ar2 | A | 1.16 | 447.0 |
| 1-oP-6 | soh1 | sbo16 | QoP1 | Ar16 | A | 0.91 | 419.0 |
| 1-oP-7 | soh1 | sbo4 | QoP1 | Ar4 | A | 1.03 | 456.0 |
| 1-oP-8 | soh1 | sbo20 | QoP1 | Ar20 | A | 1.01 | 456.0 |
| 1-oP-9 | soh1 | sbo14 | QoP1 | Ar14 | A | 0.57 | 442.1 |
| 1-oP-10 | soh1 | sbo26 | QoP1 | Ar26 | A | 1.15 | 402.1 |
| 1-oP-11 | soh1 | sbo23 | QoP1 | Ar23 | A | 1.25 | 443.1 |
| 1-oP-12 | soh1 | sbo12 | QoP1 | Ar12 | A | 0.80 | 428.1 |
| 1-oP-13 | soh1 | sbo24 | QoP1 | Ar24 | A | 0.87 | 432.0 |
| 1-oP-14 | soh6 | sbo12 | QoP2 | Ar12 | A | 0.87 | 400.1 |
| 1-oP-15 | soh6 | sbo35 | QoP2 | Ar35 | A | 1.43 | 491.1 |
| 1-oP-16 | soh6 | sbo17 | QoP2 | Ar17 | A | 1.08 | 415.1 |
| 1-oP-17 | soh6 | sbo19 | QoP2 | Ar19 | A | 1.16 | 399.1 |
| 1-oP-18 | soh6 | sbo27 | QoP2 | Ar27 | A | 1.42 | 461.1 |
| 1-oP-19 | soh6 | sbo25 | QoP2 | Ar25 | A | 1.05 | 385.0 |
| 1-oP-20 | soh6 | sbo28 | QoP2 | Ar28 | A | 0.87 | 375.0 |
| 1-oP-21 | soh6 | sbo13 | QoP2 | Ar13 | A | 1.12 | 403.0 |
| 1-oP-22 | soh6 | sbo2 | QoP2 | Ar2 | A | 1.23 | 419.0 |
| 1-oP-23 | soh6 | sbo10 | QoP2 | Ar10 | A | 1.31 | 453.0 |
| 1-oP-24 | soh6 | sbo29 | QoP2 | Ar29 | A | 0.88 | 463.0 |
| 1-oP-25 | soh6 | sbo11 | QoP2 | Ar11 | A | 0.99 | 427.1 |
| 1-oP-26 | soh6 | sbo30 | QoP2 | Ar30 | A | 0.76 | 428.1 |
| 1-oP-27 | soh6 | sbo31 | QoP2 | Ar31 | A | 0.84 | 442.0 |
| 1-oP-28 | soh6 | sbo18 | QoP2 | Ar18 | A | 1.04 | 410.0 |
| 1-oP-31 | soh6 | sbo22 | QoP2 | Ar22 | A | 0.69 | 389.0 |
| 1-oP-32 | soh6 | sbo16 | QoP2 | Ar16 | A | 0.96 | 391.0 |
| 1-oP-33 | soh6 | sbo4 | QoP2 | Ar4 | A | 1.11 | 428.0 |
| 1-oP-34 | soh6 | sbo32 | QoP2 | Ar32 | A | 0.70 | 387.0 |
| 1-oP-35 | soh6 | sbo33 | QoP2 | Ar33 | A | 1.24 | 464.9 |
| 1-oP-36 | soh6 | sbo34 | QoP2 | Ar34 | A | 0.99 | 410.0 |
| 1-oP-37 | soh6 | sbo35 | QoP2 | Ar35 | A | 0.85 | 401.0 |
| 1-oP-38 | soh6 | sbo36 | QoP2 | Ar36 | A | 0.94 | 391.0 |
| 1-oP-39 | soh6 | sbo37 | QoP2 | Ar37 | A | 0.99 | 416.0 |
| 1-oP-40 | soh6 | sbo38 | QoP2 | Ar38 | A | 1.14 | 424.9 |
| 1-oP-41 | soh6 | sbo39 | QoP2 | Ar39 | A | 2.52 | 428.1 |
| 1-oP-42 | soh6 | sbo23 | QoP2 | Ar23 | A | 2.12 | 415.2 |
| 1-oP-43 | soh6 | sbo40 | QoP2 | Ar40 | A | 0.84 | 429.0 |

Example 2-NP-1

4-(8-(1-(cyclopropanecarbonyl)piperidin-4-ylamino)isoquinolin-6-yl)benzonitrile

[Step a] 8-(1-(cyclopropanecarbonyl)piperidin-4-ylamino)isoquinolin-6-yl 4-methylbenzenesulfonate (Intermediate 2-NP-1-1)

Cesium carbonate (1.5 g) was added to a dioxane solution of Intermediate 10 (576 mg), Intermediate N-5 (308 mg), Pd$_2$(dba)$_3$ (280 mg), and Xanthphos (354 mg) at room temperature under a nitrogen atmosphere and the resulting mixture was stirred at 80° C. for 15 hours. The resulting mixture was stirred at room temperature for approx. 10 minutes and then filtrated and the solvent was evaporated under reduced pressure. The residue was purified by column chromatography (chloroform/methanol) to give the title compound (785 mg).

(Intermediate 2-NP-1-1 LCMS: 466.2 (MH$^+$); retention time: 3.22 min; LCMS; condition B)

[Step b] 4-(8-(1-(cyclopropanecarbonyl)piperidin-4-ylamino)isoquinolin-6-yl)benzonitrile 2-Dicyclohexylphosphino-2',4',6'-triisopropylbiphenyl (20 mg), potassium phosphate (34 mg), and 4-cyanophenylboronic acid (which may be referred to as sbo18; 25 mg; WAKO) were added to a t-butanol (3 mL) solution of Intermediate 2-NP-1-1 (20 mg) and palladium acetate (10 mg; Aid) and t-butanol (3 mL) was further added. The resulting mixture was stirred to reflux under a nitrogen atmosphere at 110° C. for 20 hours. The resulting mixture was stirred at room temperature for approx. 10 minutes, then the solvent was evaporated, the resulting residue was dissolved in ethyl acetate (5.4 mL) and methanol (0.6 mL), the resulting mixture was filtrated, and the solvent was evaporated under reduced pressure. The residue was dissolved in dichloromethane (2 mL) and methanol (2 mL) followed by the addition of SCX resin (150 mg) and the resulting mixture was stirred by shaking for 3 hours. The reaction mixture was filtrated, SCX resin was washed with dichloromethane (3 mL×2) and methanol (3 mL×2) followed by the addition of 2 M ammonia methanol solution (0.5 mL×3) to elute, and the solvent was evaporated. The residue was purified by preparative HPLC to give the title compound (1.3 mg).

(LCMS: 397.2 (MH$^{4+}$); retention time: 1.18 min; LCMS; condition A)

Examples 2-NP-2 to 2-NP-58

Compounds of Examples 2-NP-2 to 2-NP-58 were synthesized according to the method in Example 2-NP-1 (Table 2-NP). At this time, for example, the method described in Step b of Example 1-N-1 was used if deprotection is required. In Table 2-NP, the ST column represents the structures represented by the above general formulas and the Ar column represents "Ar" in the general formulas shown in the ST column. The SM1 column represents compounds used in respective Examples corresponding to Intermediate N-5 used in Step a of Example 2-NP-1 and the SM2 column represents compounds used in respective Examples corresponding to 4-cyanophenylboronic acid (which may be referred to as sbo18) used in Step b of Example 2-NP-1. For example, in Example 2-NP-24, Intermediate N-4 was used as "SM1" toward Intermediate 10 to perform Step a of Example 2-NP-1 and then phenylboronic acid (which may be referred to as sbo25) was used as "SM2" to perform Step b of Example 2-NP-1. In Table 2-NP, "LCMS" was defined as described above, abbreviations such as "Ar16" and "sbo16" represent compounds or groups corresponding to abbreviations in Tables Ar and sbo, respectively, provided later.

Example compounds in Table 2-NP include compounds purified by column chromatography and those finally purified by preparative HPLC.

TABLE 2-NP

| EXP. | SM1 | SM2 | ST | Ar | LCMS method | Rtime | MH+ |
|---|---|---|---|---|---|---|---|
| 2-NP-1 | IM. N-5 | sbo16 | Qn5P | Ar16 | A | 1.12 | 378.3 |
| 2-NP-2 | IM. N-5 | sbo64 | Qn5P | Ar64 | A | 1.20 | 392.3 |
| 2-NP-3 | IM. N-5 | sbo28 | Qn5P | Ar28 | A | 1.09 | 362.0 |
| 2-NP-4 | IM. N-5 | sbo24 | Qn5P | Ar24 | A | 1.01 | 391.0 |
| 2-NP-5 | IM. N-5 | sbo65 | Qn5P | Ar65 | A | 1.06 | 403.3 |
| 2-NP-6 | IM. N-5 | sbo66 | Qn5P | Ar66 | A | 1.07 | 403.3 |
| 2-NP-7 | IM. N-5 | sbo67 | Qn5P | Ar67 | A | 0.92 | 409.1 |
| 2-NP-8 | IM. N-5 | sbo14 | Qn5P | Ar14 | A | 0.76 | 401.0 |
| 2-NP-9 | IM. N-5 | sbo25 | Qn5P | Ar25 | A | 1.19 | 372.3 |
| 2-NP-10 | IM. N-5 | sbo19 | Qn5P | Ar19 | A | 1.29 | 386.1 |
| 2-NP-11 | IM. N-5 | sbo9 | Qn5P | Ar9 | A | 1.45 | 414.3 |
| 2-NP-12 | IM. N-5 | sbo68 | Qn5P | Ar68 | A | 1.10 | 411.3 |
| 2-NP-13 | IM. N-5 | sbo12 | Qn5P | Ar12 | A | 0.98 | 387.1 |
| 2-NP-14 | IM. N-5 | sbo21 | Qn5P | Ar21 | A | 1.10 | 414.3 |
| 2-NP-15 | IM. N-5 | sbo69 | Qn5P | Ar69 | A | 1.06 | 411.3 |
| 2-NP-16 | IM. N-5 | sbo70 | Qn5P | Ar70 | A | 1.28 | 408.3 |
| 2-NP-17 | IM. N-5 | sbo71 | Qn5P | Ar71 | A | 1.38 | 424.0 |
| 2-NP-18 | IM. N-5 | sbo20 | Qn5P | Ar20 | A | 1.16 | 415.1 |
| 2-NP-19 | IM. N-5 | sbo17 | Qn5P | Ar17 | B | 2.90 | 466.2 |
| 2-NP-20 | IM. N-5 | sbo18 | Qn5P | Ar18 | A | 1.19 | 397.2 |
| 2-NP-21 | IM. N-5 | sbo13 | Qn5P | Ar13 | A | 1.28 | 390.1 |
| 2-NP-22 | IM. N-5 | sbo5 | Qn5P | Ar5 | A | 1.50 | 458.1 |
| 2-NP-23 | IM. N-5 | sbo4 | Qn5P | Ar4 | B | 2.99 | 415.2 |
| 2-NP-24 | IM. N-4 | sbo25 | Qn4P | Ar25 | A | 1.14 | 423.1 |
| 2-NP-25 | IM. N-4 | sbo19 | Qn4P | Ar19 | A | 1.23 | 437.1 |
| 2-NP-26 | IM. N-4 | sbo9 | Qn4P | Ar9 | A | 1.39 | 465.1 |
| 2-NP-27 | IM. N-4 | sbo68 | Qn4P | Ar68 | A | 1.06 | 462.0 |
| 2-NP-28 | IM. N-4 | sbo12 | Qn4P | Ar12 | A | 0.93 | 438.1 |
| 2-NP-29 | IM. N-4 | sbo21 | Qn4P | Ar21 | A | 1.04 | 465.1 |
| 2-NP-30 | IM. N-4 | sbo69 | Qn4P | Ar69 | A | 1.02 | 462.1 |
| 2-NP-31 | IM. N-4 | sbo70 | Qn4P | Ar70 | A | 1.21 | 459.0 |
| 2-NP-32 | IM. N-4 | sbo71 | Qn4P | Ar71 | A | 1.31 | 475.0 |
| 2-NP-33 | IM. N-4 | sbo20 | Qn4P | Ar20 | A | 1.10 | 466.0 |
| 2-NP-34 | IM. N-4 | sbo24 | Qn4P | Ar24 | A | 0.99 | 442.0 |
| 2-NP-35 | IM. N-4 | sbo65 | Qn4P | Ar65 | A | 1.07 | 464.1 |
| 2-NP-36 | IM. N-4 | sbo23 | Qn4P | Ar23 | B | 2.54 | 453.3 |
| 2-NP-37 | IM. N-4 | sbo14 | Qn4P | Ar14 | A | 0.74 | 462.1 |
| 2-NP-38 | IM. N-4 | sbo5 | Qn4P | Ar7 | B | 2.34 | 453.3 |
| 2-NP-42 | IM. N-1 | sbo19 | Qn1P | Ar19 | A | 1.31 | 396.0 |
| 2-NP-43 | IM. N-1 | sbo68 | Qn1P | Ar68 | A | 1.12 | 421.0 |
| 2-NP-44 | IM. N-1 | sbo12 | Qn1P | Ar12 | A | 0.96 | 397.0 |
| 2-NP-45 | IM. N-1 | sbo21 | Qn1P | Ar21 | A | 1.10 | 424.0 |
| 2-NP-46 | IM. N-1 | sbo69 | Qn1P | Ar69 | A | 1.09 | 421.0 |
| 2-NP-47 | IM. N-1 | sbo70 | Qn1P | Ar70 | A | 1.29 | 418.0 |
| 2-NP-48 | IM. N-1 | sbo71 | Qn1P | Ar71 | A | 1.37 | 433.9 |
| 2-NP-49 | IM. N-1 | sbo16 | Qn1P | Ar16 | A | 1.14 | 388.0 |
| 2-NP-50 | IM. N-1 | sbo64 | Qn1P | Ar64 | A | 1.23 | 401.9 |
| 2-NP-51 | IM. N-1 | sbo24 | Qn1P | Ar24 | A | 0.99 | 401.0 |
| 2-NP-52 | IM. N-1 | sbo65 | Qn1P | Ar65 | A | 1.07 | 413.0 |
| 2-NP-53 | IM. N-1 | sbo66 | Qn1P | Ar66 | A | 1.10 | 413.0 |
| 2-NP-54 | IM. N-1 | sbo67 | Qn1P | Ar67 | A | 0.78 | 383.0 |
| 2-NP-55 | IM. N-1 | sbo23 | Qn1P | Ar23 | B | 2.43 | 412.2 |
| 2-NP-56 | IM. N-1 | sbo14 | Qn1P | Ar14 | A | 0.82 | 411.2 |
| 2-NP-57 | IM. N-1 | sbo5 | Qn1P | Ar7 | B | 2.42 | 412.2 |
| 2-NP-58 | IM. N-1 | sbo25 | Qn1P | Ar25 | A | 1.19 | 382.0 |

Example 3-NP-1

N-(1-(cyclopropylsulfonyl)piperidin-4-yl)-6-m-tolyl-isoquinolin-8-amine

Aqueous sodium carbonate solution (0.6 M, 0.7 mL) was added to a THF (2.8 mL) solution of Intermediate 8 (50 mg), 3-methylphenylboronic acid (which may be referred to as sbo19; 20.9 mg; Ald), and $PdCl_2dppf.CH_2Cl_2$ (22.9 mg) at room temperature and the resulting mixture was stirred as it was for 6 and half hours. The reaction mixture solution was filtrated through celite and then the solvent was evaporated under reduced pressure. The residue was dissolved in dichloromethane (1 mL) and methanol (1 mL) followed by the addition of SCX resin (700 mg) and the resulting mixture was agitated by shaking for 3 hours. The reaction mixture was filtrated, then SCX resin was washed with dichloromethane and methanol followed by the addition of 2 M ammonia methanol solution to elute, and the solvent was evaporated. Sodium t-butoxide (28.8 mg) was added to a dioxane solution of the residue, Intermediate N-3 (40.9 mg), $Pd_2(dba)_3$ (18.3 mg), and BINAP (24.9 mg) at room temperature and the resulting mixture was stirred at 80° C. for 8 hours. The resulting mixture was stirred at room temperature for approx. 10 minutes, then the reaction mixture solution was filtrated, the solvent was evaporated under reduced pressure, and the residue was purified by Quad. The residue was dissolved in dichloromethane (1 mL) and methanol (1 mL) followed by the addition of SCX resin (300 mg) and the resulting mixture was agitated by shaking for 3 hours. The reaction mixture was filtrated, the SCX resin was washed with dichloromethane and methanol followed by the addition of 2 M ammonia methanol solution to elute, the solvent was evaporated to give the title compound (28.4 mg).

Examples 3-NP-2 to 3-NP-149

Compounds of Examples 3-NP-2 to 3-NP-149 were synthesized according to the method in Example 3-NP-1 (Table 3-NP). At this time, for example, the method described in Step b of Example 1-N-1 was used if deprotection is required. In Table 3-NP, the SM1 column represents compounds used in respective Examples corresponding to Intermediate N-3 used in Example 3-NP-1 and the SM2 column represents compounds used in respective Examples corresponding to 3-methylphenylboronic acid (which may be referred to as sbo19) used in Example 3-NP-1. For example, in Example 3-NP-24, toward Intermediate 9, Intermediate N-2 was used as "SM1" and 4-cyano-3-fluoroboronic acid (which may be referred to as sbo41) was used as "SM2" to perform the step of Example 3-NP-1. In Table 3-NP, "LCMS" was defined as described above, abbreviations such as "Ar19" and "sbo19" represent compounds or groups corresponding to abbreviations in Tables Ar and sbo, respectively, provided later.

Example compounds in Table 3-NP include compounds purified by column chromatography and/or compounds finally purified by preparative HPLC.

Example 4-NP-25, 4-NP-26, 4-NP-31, 4-NP-32, 4-NP-36, 4-NP-51 to 4-NP-72, 4-NP-74 to 4-NP-82, 4-NP-86, 4-NP-87, 4-NP-95 to 4-NP-97, 4-NP-99, 4-NP-100, 4-NP-109, 4-NP-128, 4-NP-130 to 4-NP-134, 4-NP-145, 4-NP-162 to 4-NP-167, 4-NP-186, 4-NP-187, 4-NP-216, 4-NP-408 and 4-NP-409

Compounds of Examples 4-NP-25, 4-NP-26, 4-NP-31, 4-NP-32, 4-NP-36, 4-NP-51 to 4-NP-72, 4-NP-74 to 4-NP-82, 4-NP-86, 4-NP-87, 4-NP-95 to 4-NP-97, 4-NP-99, 4-NP-100, 4-NP-109, 4-NP-128, 4-NP-130 to 4-NP-134, 4-NP-145, 4-NP-162 to 4-NP-167, 4-NP-186, 4-NP-187, 4-NP-216, 4-NP-408 and 4-NP-409 were synthesized according to the method in Example 3-NP-1 (Table 3-NP2). At this time, for example, the method described in Step b of Example 1-N-1 was used if deprotection is required. In Table 3-NP2, the SM1, SM2, ST, Ar and LCMS columns are similar as in Table 3-NP, respectively. Example compounds in Table 3-NP2 include compounds purified by column chromatography and/or compounds finally purified by preparative HPLC.

TABLE 3-NP

| EXP. | SM1 | SM2 | ST | Ar | LCMS method | Rtime | MH+ |
|---|---|---|---|---|---|---|---|
| 3-NP-1 | IM. N-3 | sbo19 | Qn3P | Ar19 | A | 1.40 | 422.1 |
| 3-NP-2 | IM. N-3 | sbo13 | Qn3P | Ar13 | A | 1.42 | 426.1 |
| 3-NP-3 | IM. N-3 | sbo12 | Qn3P | Ar12 | A | 1.15 | 423.1 |
| 3-NP-4 | IM. N-3 | sbo21 | Qn3P | Ar21 | A | 1.23 | 450.1 |
| 3-NP-5 | IM. N-3 | sbo69 | Qn3P | Ar69 | A | 1.27 | 447.1 |
| 3-NP-6 | IM. N-3 | sbo70 | Qn3P | Ar70 | A | 1.43 | 444.1 |
| 3-NP-7 | IM. N-3 | sbo71 | Qn3P | Ar71 | A | 1.56 | 460.1 |
| 3-NP-8 | IM. N-3 | sbo20 | Qn3P | Ar20 | A | 1.32 | 451.1 |
| 3-NP-9 | IM. N-3 | sbo16 | Qn3P | Ar16 | A | 1.31 | 414.1 |
| 3-NP-10 | IM. N-3 | sbo64 | Qn3P | Ar64 | A | 1.37 | 428.1 |
| 3-NP-11 | IM. N-3 | sbo28 | Qn3P | Ar28 | A | 1.24 | 398.1 |
| 3-NP-12 | IM. N-3 | sbo72 | Qn3P | Ar72 | A | 1.19 | 427.1 |
| 3-NP-13 | IM. N-3 | sbo65 | Qn3P | Ar65 | A | 1.20 | 439.1 |
| 3-NP-14 | IM. N-3 | sbo66 | Qn3P | Ar66 | A | 1.24 | 439.1 |
| 3-NP-15 | IM. N-3 | sbo67 | Qn3P | Ar67 | A | 0.91 | 409.1 |
| 3-NP-16 | IM. N-3 | sbo73 | Qn3P | Ar73 | A | 1.23 | 427.1 |
| 3-NP-17 | IM. N-3 | sbo23 | Qn3P | Ar23 | A | 1.10 | 438.1 |
| 3-NP-18 | IM. N-3 | sbo14 | Qn3P | Ar14 | A | 0.80 | 437.1 |
| 3-NP-19 | IM. N-3 | sbo37 | Qn3P | Ar37 | A | 1.30 | 439.0 |
| 3-NP-20 | IM. N-3 | sbo18 | Qn3P | Ar18 | A | 1.24 | 433.1 |
| 3-NP-21 | IM. N-3 | sbo2 | Qn3P | Ar2 | A | 1.45 | 442.0 |
| 3-NP-22 | IM. N-3 | sbo25 | Qn3P | Ar25 | A | 1.26 | 408.3 |
| 3-NP-23 | IM. N-3 | sbo4 | Qn3P | Ar4 | A | 1.34 | 461.2 |
| 3-NP-24 | IM. N-2 | sbo41 | Qn2P | Ar41 | A | 1.28 | 439.1 |
| 3-NP-25 | IM. N-4 | sbo41 | Qn4P | Ar41 | A | 1.16 | 466.2 |
| 3-NP-26 | IM. N-3 | sbo41 | Qn3P | Ar41 | A | 1.31 | 451.3 |
| 3-NP-27 | IM. N-5 | sbo41 | Qn5P | Ar41 | A | 1.24 | 415.2 |
| 3-NP-28 | IM. N-4 | sbo42 | Qn4P | Ar42 | A | 1.10 | 475.2 |
| 3-NP-29 | IM. N-2 | sbo42 | Qn2P | Ar42 | A | 1.20 | 449.2 |
| 3-NP-30 | IM. N-3 | sbo42 | Qn3P | Ar42 | A | 1.22 | 461.2 |
| 3-NP-31 | IM. N-5 | sbo42 | Qn5P | Ar42 | A | 1.16 | 425.2 |
| 3-NP-32 | IM. N-4 | sbo43 | Qn4P | Ar43 | A | 1.17 | 462.2 |
| 3-NP-33 | IM. N-2 | sbo43 | Qn2P | Ar43 | A | 1.27 | 435.2 |
| 3-NP-34 | IM. N-3 | sbo43 | Qn3P | Ar43 | A | 1.31 | 447.2 |
| 3-NP-35 | IM. N-5 | sbo43 | Qn5P | Ar43 | A | 1.24 | 411.2 |
| 3-NP-36 | IM. N-4 | sbo44 | Qn4P | Ar44 | A | 1.18 | 466.2 |
| 3-NP-37 | IM. N-2 | sbo44 | Qn2P | Ar44 | A | 1.30 | 439.1 |

TABLE 3-NP-continued

| EXP. | SM1 | SM2 | ST | Ar | LCMS method | Rtime | MH+ |
|---|---|---|---|---|---|---|---|
| 3-NP-38 | IM. N-3 | sbo44 | Qn3P | Ar44 | A | 1.34 | 451.1 |
| 3-NP-39 | IM. N-5 | sbo44 | Qn5P | Ar44 | A | 1.25 | 415.2 |
| 3-NP-40 | IM. N-6 | sbo44 | Qn6P | Ar44 | A | 1.28 | 477.1 |
| 3-NP-41 | IM. N-4 | sbo45 | Qn4P | Ar45 | A | 0.95 | 463.2 |
| 3-NP-42 | IM. N-2 | sbo45 | Qn2P | Ar45 | A | 1.07 | 436.1 |
| 3-NP-43 | IM. N-3 | sbo45 | Qn3P | Ar45 | A | 1.09 | 448.1 |
| 3-NP-44 | IM. N-3 | sbo46 | Qn3P | Ar46 | A | 1.47 | 469.3 |
| 3-NP-45 | IM. N-2 | sbo46 | Qn2P | Ar46 | A | 1.42 | 457.3 |
| 3-NP-46 | IM. N-4 | sbo47 | Qn4P | Ar47 | A | 1.22 | 493.4 |
| 3-NP-47 | IM. N-3 | sbo47 | Qn3P | Ar47 | A | 1.39 | 478.3 |
| 3-NP-48 | IM. N-4 | sbo48 | Qn4P | Ar48 | A | 1.39 | 508.4 |
| 3-NP-49 | IM. N-3 | sbo48 | Qn3P | Ar48 | A | 1.54 | 493.3 |
| 3-NP-50 | IM. N-2 | sbo48 | Qn2P | Ar48 | A | 1.50 | 481.3 |
| 3-NP-51 | IM. N-4 | sbo49 | Qn4P | Ar49 | A | 1.30 | 456.4 |
| 3-NP-52 | IM. N-3 | sbo49 | Qn3P | Ar49 | A | 1.44 | 441.4 |
| 3-NP-53 | IM. N-2 | sbo49 | Qn2P | Ar49 | A | 1.41 | 429.4 |
| 3-NP-54 | IM. N-5 | sbo49 | Qn5P | Ar49 | A | 1.37 | 404.4 |
| 3-NP-55 | IM. N-4 | sbo50 | Qn4P | Ar50 | A | 1.18 | 472.4 |
| 3-NP-56 | IM. N-3 | sbo50 | Qn3P | Ar50 | A | 1.31 | 457.3 |
| 3-NP-57 | IM. N-2 | sbo50 | Qn2P | Ar50 | A | 1.28 | 445.4 |
| 3-NP-58 | IM. N-5 | sbo50 | Qn5P | Ar50 | A | 1.24 | 420.4 |
| 3-NP-59 | IM. N-2 | sbo63 | Qn2P | Ar63 | A | 1.43 | 457.4 |
| 3-NP-60 | IM. N-3 | sbo63 | Qn3P | Ar63 | A | 1.48 | 469.4 |
| 3-NP-61 | IM. N-2 | sbo52 | Qn2P | Ar52 | A | 1.27 | 435.4 |
| 3-NP-62 | IM. N-2 | sbo53 | Qn2P | Ar53 | A | 1.44 | 489.4 |
| 3-NP-63 | IM. N-2 | sbo54 | Qn2P | Ar54 | A | 1.41 | 489.4 |
| 3-NP-64 | IM. N-2 | sbo55 | Qn2P | Ar55 | A | 1.46 | 489.4 |
| 3-NP-65 | IM. N-2 | sbo56 | Qn2P | Ar56 | A | 1.14 | 449.4 |
| 3-NP-66 | IM. N-2 | sbo57 | Qn2P | Ar57 | A | 1.46 | 482.4 |
| 3-NP-67 | IM. N-2 | sbo58 | Qn2P | Ar58 | A | 1.39 | 424.4 |
| 3-NP-68 | IM. N-2 | sbo59 | Qn2P | Ar59 | A | 1.34 | 442.4 |
| 3-NP-69 | IM. N-2 | sbo60 | Qn2P | Ar60 | A | 1.13 | 456.4 |
| 3-NP-70 | IM. N-2 | sbo61 | Qn2P | Ar61 | A | 1.18 | 440.4 |
| 3-NP-71 | IM. N-2 | sbo62 | Qn2P | Ar62 | A | 1.30 | 460.4 |
| 3-NP-72 | IM. N-3 | sbo52 | Qn3P | Ar52 | A | 1.30 | 447.4 |
| 3-NP-73 | IM. N-3 | sbo53 | Qn3P | Ar53 | A | 1.48 | 501.4 |
| 3-NP-74 | IM. N-3 | sbo54 | Qn3P | Ar54 | A | 1.45 | 501.4 |
| 3-NP-75 | IM. N-3 | sbo55 | Qn3P | Ar55 | A | 1.49 | 501.4 |
| 3-NP-76 | IM. N-3 | sbo56 | Qn3P | Ar56 | A | 1.18 | 461.4 |
| 3-NP-77 | IM. N-3 | sbo57 | Qn3P | Ar57 | A | 1.49 | 494.4 |
| 3-NP-78 | IM. N-3 | sbo58 | Qn3P | Ar58 | A | 1.44 | 436.4 |
| 3-NP-79 | IM. N-3 | sbo59 | Qn3P | Ar59 | A | 1.40 | 454.4 |
| 3-NP-80 | IM. N-3 | sbo60 | Qn3P | Ar60 | A | 1.16 | 469.4 |
| 3-NP-81 | IM. N-3 | sbo61 | Qn3P | Ar61 | A | 1.24 | 452.4 |
| 3-NP-82 | IM. N-3 | sbo62 | Qn3P | Ar62 | A | 1.35 | 472.4 |
| 3-NP-83 | IM. N-2 | sbo75 | Qn2P | Ar75 | A | 1.42 | 440.5 |
| 3-NP-84 | IM. N-2 | sbo76 | Qn2P | Ar76 | A | 1.32 | 456.5 |
| 3-NP-85 | IM. N-2 | sbo77 | Qn2P | Ar77 | A | 1.26 | 456.4 |
| 3-NP-86 | IM. N-2 | sbo78 | Qn2P | Ar78 | A | 1.29 | 456.4 |
| 3-NP-87 | IM. N-2 | sbo79 | Qn2P | Ar79 | A | 1.40 | 458.4 |
| 3-NP-88 | IM. N-2 | sbo81 | Qn2P | Ar81 | A | 1.26 | 461.4 |
| 3-NP-89 | IM. N-3 | sbo80 | Qn3P | Ar80 | A | 1.35 | 456.4 |
| 3-NP-90 | IM. N-3 | sbo81 | Qn3P | Ar81 | A | 1.29 | 463.4 |
| 3-NP-91 | IM. N-1 | sbo50 | Qn1P | Ar50 | A | 1.22 | 430.4 |
| 3-NP-92 | IM. N-1 | sbo62 | Qn1P | Ar62 | A | 1.31 | 446.4 |
| 3-NP-93 | IM. N-1 | sbo44 | Qn1P | Ar44 | A | 1.28 | 425.4 |
| 3-NP-94 | IM. N-1 | sbo56 | Qn1P | Ar56 | A | 1.13 | 435.4 |
| 3-NP-95 | IM. N-1 | sbo53 | Qn1P | Ar53 | A | 1.41 | 475.4 |
| 3-NP-96 | IM. N-1 | sbo42 | Qn1P | Ar42 | A | 1.15 | 435.5 |
| 3-NP-97 | IM. N-8 | sbo50 | Qn8P | Ar50 | A | 1.13 | 424.5 |
| 3-NP-98 | IM. N-8 | sbo62 | Qn8P | Ar62 | A | 1.23 | 440.4 |
| 3-NP-99 | IM. N-8 | sbo81 | Qn8P | Ar81 | A | 1.09 | 431.5 |
| 3-NP-100 | IM. N-8 | sbo56 | Qn8P | Ar56 | A | 1.04 | 429.5 |
| 3-NP-101 | IM. N-8 | sbo53 | Qn8P | Ar53 | A | 1.32 | 469.4 |
| 3-NP-102 | IM. N-8 | sbo42 | Qn8P | Ar42 | A | 1.09 | 429.5 |
| 3-NP-103 | IM. N-2 | sbo82 | Qn2P | Ar82 | A | 1.26 | 444.4 |
| 3-NP-104 | IM. N-2 | sbo83 | Qn2P | Ar83 | A | 1.43 | 474.4 |
| 3-NP-105 | IM. N-2 | sbo84 | Qn2P | Ar84 | A | 1.36 | 455.4 |
| 3-NP-106 | IM. N-3 | sbo83 | Qn3P | Ar83 | A | 1.50 | 486.4 |
| 3-NP-107 | IM. N-3 | sbo84 | Qn3P | Ar84 | A | 1.39 | 467.3 |
| 3-NP-108 | IM. N-3 | sbo85 | Qn3P | Ar85 | A | 1.43 | 470.4 |
| 3-NP-109 | IM. N-1 | sbo84 | Qn1P | Ar84 | A | 1.26 | 441.3 |
| 3-NP-110 | IM. N-1 | sbo41 | Qn1P | Ar41 | A | 1.26 | 425.4 |
| 3-NP-111 | IM. N-8 | sbo44 | Qn8P | Ar44 | A | 1.18 | 419.4 |
| 3-NP-112 | IM. N-8 | sbo52 | Qn8P | Ar52 | A | 1.21 | 415.5 |

TABLE 3-NP-continued

| EXP. | SM1 | SM2 | ST | Ar | method | Rtime | MH+ |
|---|---|---|---|---|---|---|---|
| 3-NP-113 | IM. N-8 | sbo41 | Qn8P | Ar41 | A | 1.17 | 419.4 |
| 3-NP-114 | IM. N-1 | sbo18 | Qn1P | Ar18 | A | 1.60 | 479.4 |
| 3-NP-115 | IM. N-2 | sbo86 | Qn2P | Ar86 | A | 1.47 | 493.4 |
| 3-NP-116 | IM. N-1 | sbo87 | Qn1P | Ar87 | A | 1.32 | 441.3 |
| 3-NP-117 | IM. N-2 | sbo87 | Qn2P | Ar87 | A | 1.38 | 455.3 |
| 3-NP-118 | IM. N-3 | sbo87 | Qn3P | Ar87 | A | 1.43 | 467.3 |
| 3-NP-119 | IM. N-1 | sbo20 | Qn1P | Ar20 | A | 1.19 | 425.4 |
| 3-NP-120 | IM. N-2 | sbo20 | Qn2P | Ar20 | A | 1.25 | 439.4 |
| 3-NP-121 | IM. N-1 | sbo60 | Qn1P | Ar60 | A | 1.10 | 442.4 |
| 3-NP-122 | IM. N-2 | sbo88 | Qn2P | Ar88 | A | 1.35 | 455.4 |
| 3-NP-123 | IM. N-2 | sbo89 | Qn2P | Ar89 | A | 1.19 | 454.4 |
| 3-NP-124 | IM. N-2 | sbo47 | Qn2P | Ar47 | A | 1.33 | 465.4 |
| 3-NP-125 | IM. N-1 | sbo81 | Qn1P | Ar81 | A | 1.15 | 437.4 |
| 3-NP-126 | IM. N-9 | sbo41 | Qn9P | Ar41 | A | 1.17 | 389.4 |
| 3-NP-127 | IM. N-9 | sbo18 | Qn9P | Ar18 | A | 1.00 | 371.4 |
| 3-NP-128 | IM. N-9 | sbo42 | Qn9P | Ar42 | A | 0.99 | 399.4 |
| 3-NP-129 | IM. N-9 | sbo56 | Qn9P | Ar56 | A | 0.96 | 399.4 |
| 3-NP-130 | IM. N-9 | sbo20 | Qn9P | Ar20 | A | 1.05 | 389.4 |
| 3-NP-131 | IM. N-9 | sbo81 | Qn9P | Ar81 | A | 1.03 | 401.4 |
| 3-NP-132 | IM. N-9 | sbo50 | Qn9P | Ar50 | A | 1.04 | 394.4 |
| 3-NP-133 | IM. N-9 | sbo60 | Qn9P | Ar60 | A | 0.94 | 406.4 |
| 3-NP-134 | IM. N-9 | sbo43 | Qn9P | Ar43 | A | 1.09 | 385.4 |
| 3-NP-135 | IM. N-9 | sbo63 | Qn9P | Ar63 | A | 1.28 | 439.4 |
| 3-NP-136 | IM. N-9 | sbo44 | Qn9P | Ar44 | A | 1.13 | 389.4 |
| 3-NP-137 | IM. N-9 | sbo46 | Qn9P | Ar46 | A | 1.25 | 405.4 |
| 3-NP-138 | IM. N-10 | sbo41 | Qn10P | Ar41 | A | 1.25 | 403.4 |
| 3-NP-139 | IM. N-10 | sbo18 | Qn10P | Ar18 | A | 1.10 | 385.4 |
| 3-NP-140 | IM. N-10 | sbo42 | Qn10P | Ar42 | A | 1.07 | 413.4 |
| 3-NP-141 | IM. N-10 | sbo56 | Qn10P | Ar56 | A | 1.02 | 413.4 |
| 3-NP-142 | IM. N-10 | sbo20 | Qn10P | Ar20 | A | 1.14 | 403.4 |
| 3-NP-143 | IM. N-10 | sbo81 | Qn10P | Ar81 | A | 1.14 | 415.4 |
| 3-NP-144 | IM. N-10 | sbo60 | Qn10P | Ar60 | A | 1.15 | 408.4 |
| 3-NP-145 | IM. N-10 | sbo60 | Qn10P | Ar60 | A | 1.04 | 420.4 |
| 3-NP-146 | IM. N-10 | sbo43 | Qn10P | Ar43 | A | 1.21 | 399.4 |
| 3-NP-147 | IM. N-10 | sbo90 | Qn10P | Ar90 | A | 1.03 | 386.4 |
| 3-NP-148 | IM. N-10 | sbo53 | Qn10P | Ar53 | A | 1.39 | 453.4 |
| 3-NP-149 | IM. N-10 | sbo44 | Qn10P | Ar44 | A | 1.21 | 403.4 |

TABLE 3-NP2

| Exp. | SM1 | SM2 | ST | Ar | method | R-time | MH+ |
|---|---|---|---|---|---|---|---|
| 4-NP-25 | IM. N-2 | sbo34 | Qn2P | Ar34 | A | 1.20 | 421.4 |
| 4-NP-26 | IM. N-3 | sbo34 | Qn3P | Ar34 | A | 1.24 | 433.4 |
| 4-NP-31 | IM. N-1 | sbo88 | Qn1P | Ar88 | A | 1.29 | 441.4 |
| 4-NP-32 | IM. N-3 | sbo88 | Qn3P | Ar88 | A | 1.42 | 467.3 |
| 4-NP-36 | IM. N-2 | sbo91 | Qn2P | Ar91 | A | 1.24 | 470.4 |
| 4-NP-51 | IM. N-1 | sbo92 | Qn1P | Ar92 | A | 1.21 | 430.4 |
| 4-NP-52 | IM. N-1 | sbo15 | Qn1P | Ar15 | A | 1.2 | 400.4 |
| 4-NP-53 | IM. N-1 | sbo17 | Qn1P | Ar17 | A | 1.19 | 412.4 |
| 4-NP-54 | IM. N-1 | sbo93 | Qn1P | Ar93 | A | 1.13 | 426.4 |
| 4-NP-55 | IM. N-1 | sbo86 | Qn1P | Ar86 | A | 1.25 | 430.4 |
| 4-NP-56 | IM. N-1 | sbo82 | Qn1P | Ar82 | A | 1.16 | 430.4 |
| 4-NP-57 | IM. N-1 | sbo89 | Qn1P | Ar89 | A | 1.11 | 440.4 |
| 4-NP-58 | IM. N-1 | sbo13 | Qn1P | Ar13 | A | 1.19 | 400.4 |
| 4-NP-59 | IM. N-1 | sbo2 | Qn1P | Ar2 | A | 1.31 | 416.4 |
| 4-NP-60 | IM. N-1 | sbo94 | Qn1P | Ar94 | A | 1.18 | 421.4 |
| 4-NP-61 | IM. N-1 | sbo52 | Qn1P | Ar52 | A | 1.22 | 421.4 |
| 4-NP-62 | IM. N-1 | sbo54 | Qn1P | Ar54 | A | 1.35 | 475.4 |
| 4-NP-63 | IM. N-1 | sbo55 | Qn1P | Ar55 | A | 1.37 | 475.3 |
| 4-NP-64 | IM. N-3 | sbo92 | Qn3P | Ar92 | A | 1.32 | 456.4 |
| 4-NP-65 | IM. N-3 | sbo15 | Qn3P | Ar15 | A | 1.3 | 426.4 |
| 4-NP-66 | IM. N-3 | sbo17 | Qn3P | Ar17 | A | 1.27 | 438.4 |
| 4-NP-67 | IM. N-3 | sbo93 | Qn3P | Ar93 | A | 1.24 | 452.5 |
| 4-NP-68 | IM. N-3 | sbo86 | Qn3P | Ar86 | A | 1.36 | 456.4 |
| 4-NP-69 | IM. N-3 | sbo82 | Qn3P | Ar82 | A | 1.28 | 456.4 |
| 4-NP-70 | IM. N-3 | sbo89 | Qn3P | Ar89 | A | 1.23 | 466.4 |
| 4-NP-71 | IM. N-3 | sbo70 | Qn3P | Ar70 | A | 1.36 | 444.4 |
| 4-NP-72 | IM. N-2 | sbo92 | Qn2P | Ar92 | A | 1.26 | 444.4 |

TABLE 3-NP2-continued

| Exp. | SM1 | SM2 | ST | Ar | method | R-time | MH+ |
|---|---|---|---|---|---|---|---|
| 4-NP-74 | IM. N-11 | sbo4 | Qn11P | Ar4 | A | 1.56 | 479.4 |
| 4-NP-75 | IM. N-11 | sbo41 | Qn11P | Ar41 | A | 1.57 | 479.4 |
| 4-NP-76 | IM. N-1 | sbo95 | Qn1P | Ar95 | A | 1.17 | 425.3 |
| 4-NP-77 | IM. N-2 | sbo95 | Qn2P | Ar95 | A | 1.24 | 439.4 |
| 4-NP-78 | IM. N-3 | sbo95 | Qn3P | Ar95 | A | 1.27 | 451.4 |
| 4-NP-79 | IM. N-12 | sbo4 | Qn12P | Ar4 | A | 1.43 | 465.3 |
| 4-NP-80 | IM. N-17 | sbo4 | Qn17P | Ar4 | A | 1.34 | 443.3 |
| 4-NP-81 | IM. N-13 | sbo4 | Qn13P | Ar4 | A | 1.38 | 495.3 |
| 4-NP-82 | IM. N-13 | sbo18 | Qn13P | Ar18 | A | 1.30 | 477.3 |
| 4-NP-86 | IM. N-1 | sbo98 | Qn1P | Ar98 | A | 1.17 | 425.3 |
| 4-NP-87 | IM. N-2 | sbo98 | Qn2P | Ar98 | A | 1.28 | 439.3 |
| 4-NP-95 | IM. N-15 | sbo4 | Qn15P | Ar4 | A | 1.19 | 469.5 |
| 4-NP-96 | IM. N-16 | sbo4 | Qn16P | Ar4 | A | 1.35 | 478.4 |
| 4-NP-97 | IM. N-14 | sbo4 | Qn14P | Ar4 | A | 1.05 | 638.5 |
| 4-NP-99 | IM. N-2 | sbo106 | Qn2P | Ar106 | A | 1.24 | 465.2 |
| 4-NP-109 | IM. N-1 | sbo96 | Qn1P | Ar96 | A | 0.96 | 408.3 |
| 4-NP-100 | IM. N-2 | sbo107 | Qn2P | Ar107 | A | 1.35 | 444.2 |
| 4-NP-128 | IM. N-18 | sbo4 | Qn18P | Ar4 | A | 1.03 | 551.3 |
| 4-NP-130 | IM. N-19 | sbo4 | Qn19P | Ar4 | A | 1.00 | 482.3 |
| 4-NP-131 | IM. N-20 | sbo4 | Qn20P | Ar4 | A | 1.11 | 524.3 |
| 4-NP-132 | IM. N-21 | sbo4 | Qn21P | Ar4 | A | 1.15 | 510.3 |
| 4-NP-133 | IM. N-22 | sbo4 | Qn22P | Ar4 | A | 1.10 | 508.3 |
| 4-NP-134 | IM. N-23 | sbo4 | Qn23P | Ar4 | A | 1.15 | 522.3 |
| 4-NP-145 | IM. N-24 | sbo4 | Qn24P | Ar4 | A | 1.31 | 440.2 |
| 4-NP-162 | IM. N-25 | sbo4 | Qn25P | Ar4 | A | 1.10 | 496.2 |
| 4-NP-163 | IM. N-26 | sbo4 | Qn26P | Ar4 | A | 1.34 | 469.2 |
| 4-NP-164 | IM. N-27 | sbo4 | Qn27P | Ar4 | A | 1.39 | 454.4 |
| 4-NP-165 | IM. N-28 | sbo4 | Qn28P | Ar4 | A | 1.40 | 454.2 |
| 4-NP-166 | IM. N-29 | sbo4 | Qn29P | Ar4 | A | 1.48 | 468.2 |
| 4-NP-167 | IM. N-30 | sbo4 | Qn30P | Ar4 | A | 1.07 | 509.2 |
| 4-NP-186 | IM. N-31 | sbo4 | Qn31P | Ar4 | A | 1.61 | 494.0 |
| 4-NP-187 | IM. N-32 | sbo4 | Qn32P | Ar4 | A | 1.04 | 495.2 |
| 4-NP-216 | IM. N-2 | sbo175 | Qn2P | Ar175 | A | 1.35 | 456.4 |
| 4-NP-408 | IM. N-9 | sbo186 | Qn9P | Ar186 | A | 0.64 | 361.3 |
| 4-NP-409 | IM. N-4 | sbo186 | Qn4P | Ar186 | A | 0.73 | 438.3 |

Example 4-NP-8

5-(8-(1-(ethylsulfonyl)piperidin-4-ylamino)isoquinolin-6-yl)nicotinonitrile

Aqueous sodium carbonate solution (0.1 M, 0.5 mL) was added to a THF (2.0 mL) solution of Intermediate Tf-2 (20 mg), 3-cyanopyridine-5-boronic acid pinacol ester (which may be referred to as sbo96; 29.0 mg; FRON), and PdCl$_2$dppf.CH$_2$Cl$_2$ (4.0 mg) at room temperature and the resulting mixture was stirred at 60° C. for 15 hours. The reaction mixture solution was filtrated through celite and then the solvent was evaporated under reduced pressure. The residue was purified by column chromatography (Yamazen; chloroform/methanol) to give the title compound (18.3 mg).

(LCMS: 422.3 (MH$^+$); retention time: 1.09 min; LCMS; condition A)

Example 4-NP-113

N-(1-(ethylsulfonyl)piperidin-4-yl)-6-(1-methyl-1H-indazol-5-yl)isoquinolin-8-amine Water (0.5 mL) was added to a THF (2.0 mL) solution of Intermediate Tf-2 (20 mg), 1-methyl-1H-indazole-5-boronic acid (which may be referred to as sbo118; 15.1 mg; Syn), PdCl$_2$dppf.CH$_2$Cl$_2$ (7.0 mg), and sodium carbonate (13.6 mg) at room temperature and the resulting mixture was stirred at 80° C. for 17 and half hours. The reaction mixture solution was filtrated through celite and then the solvent was evaporated under reduced pressure. The residue was dissolved in dichloromethane (1 mL) and methanol (1 mL) followed by the addition of SCX resin (200 mg) and the resulting mixture was agitated by shaking for 3 hours. The reaction mixture was filtrated, then SCX resin was washed with dichloromethane and methanol followed by the addition of 2 M ammonia methanol solution to elute, and the solvent was evaporated to give the title compound (19.5 mg).

(LCMS: 450.3 (MH$^+$); retention time: 1.13 min; LCMS; condition A)

Example 4-NP-83 to 4-NP-85, 4-NP-92 to 4-NP-94, 4-NP-101 to 4-NP-127, 4-NP-135, 4-NP-136, 4-NP-138 to 4-NP-144, 4-NP-146, 4-NP-147, 4-NP-149 to 4-NP-156, 4-NP-160, 4-NP-161, 4-NP-169 to 4-NP-180, 4-NP-182, 4-NP-185, 4-NP-188 to 4-NP-202, 4-NP-204 to 4-NP-214, 4-NP-217 to 4-NP-227, 4-NP-231 to 4-NP-244, 4-NP-248 to 4-NP-260, 4-NP-264 to 4-NP-275, 4-NP-278 to 4-NP-297, 4-NP-301 to 4-NP-303, 4-NP-307, 4-NP-309 to 4-NP-311, 4-NP-313 to 4-NP-330, 4-NP-332 to 4-NP-347, 4-NP-349 to 4-NP-357, 4-NP-359, 4-NP-361 to 4-NP-394, 4-NP-404, 4-NP-406, 4-NP-407, 4-NP-410 to 4-NP-418, 4-NP-430 to 4-NP-434, 4-NP-472 and 4-NP-473

Compounds of Examples 4-NP-83 to 4-NP-85, 4-NP-92 to 4-NP-94, 4-NP-101 to 4-NP-127, 4-NP-135, 4-NP-136, 4-NP-138 to 4-NP-144, 4-NP-146, 4-NP-147, 4-NP-149 to 4-NP-156, 4-NP-160, 4-NP-161, 4-NP-169 to 4-NP-180, 4-NP-182, 4-NP-185, 4-NP-188 to 4-NP-202, 4-NP-204 to 4-NP-214, 4-NP-217 to 4-NP-227, 4-NP-231 to 4-NP-244, 4-NP-248 to 4-NP-260, 4-NP-264 to 4-NP-275, 4-NP-278 to 4-NP-297, 4-NP-301 to 4-NP-303, 4-NP-307, 4-NP-309 to 4-NP-311, 4-NP-313 to 4-NP-330, 4-NP-332 to 4-NP-347, 4-NP-349 to 4-NP-357, 4-NP-359, 4-NP-361 to 4-NP-394, 4-NP-404, 4-NP-406, 4-NP-407, 4-NP-410 to 4-NP-418, 4-NP-430 to 4-NP-434, 4-NP-472 and 4-NP-473 were synthesized according to the method in Example 4-NP-113 (Table 4-NP). At this time, for example, the method described in Step b of Example 1-N-1 was used if deprotection is required. In Table 4-NP, the SM1 column represents compounds used in respective Examples corresponding to Intermediate Tf-2 used in Example 4-NP-113 and the SM2 column represents compounds used in respective Examples corresponding to 1-methyl-1H-indazole-5-boronic acid (which may be referred to as sbo118) used in Example 4-NP-113. For example, in Example 4-NP-83, Intermediate Tf-2 was used as "SM1" and 5-(4,4,5,5-tetramethyl-1,3,2-dioxaborolan-2-yl) nicotinonitrile (which may be referred to as sbo96) was used as "SM2" to perform the steps of Example 4-NP-113. In Table 4-NP, "LCMS" was defined as described above, abbreviations such as "Ar19" and "sbo19" represent compounds or groups corresponding to abbreviations in Tables Ar and sbo, respectively, provided later.

Example compounds in Table 4-NP also include compounds purified by column chromatography and/or compounds finally purified by preparative HPLC.

Further, the Example compounds in Table 4-NP also include compounds synthesized by reacting at 80 to 90° C. using 1,4-dioxane instead of THF in the method in Example 4-NP-113, such as the following Example compounds 4-NP-355, 4-NP-356, 4-NP-365, 4-NP-366, 4-NP-367, and 4-NP-368.

TABLE 4-NP

| Exp. | SM1 | SM2 | ST | Ar | LCMS method | Rtime | MH$^+$ |
|---|---|---|---|---|---|---|---|
| 4-NP-83 | Tf-2 | sbo96 | Qn2P | Ar96 | A | 1.09 | 422.3 |
| 4-NP-84 | Tf-2 | sbo90 | Qn2P | Ar90 | A | 1.14 | 422.3 |
| 4-NP-85 | Tf-2 | sbo97 | Qn2P | Ar97 | A | 0.96 | 432.1 |
| 4-NP-92 | Tf-2 | sbo103 | Qn2P | Ar103 | A | 0.94 | 457.3 |
| 4-NP-93 | Tf-2 | sbo104 | Qn2P | Ar104 | A | 1.47 | 436.3 |
| 4-NP-94 | Tf-2 | sbo105 | Qn2P | Ar105 | A | 1.17 | 435.3 |
| 4-NP-101 | Tf-2 | sbo108 | Qn2P | Ar108 | B | 3.15 | 439.0 |
| 4-NP-102 | Tf-2 | sbo109 | Qn2P | Ar109 | B | 3.16 | 449.3 |
| 4-NP-103 | Tf-2 | sbo110 | Qn2P | Ar110 | B | 2.97 | 481.5 |
| 4-NP-104 | Tf-2 | sbo111 | Qn2P | Ar111 | A | 1.36 | 451.3 |
| 4-NP-105 | Tf-2 | sbo112 | Qn2P | Ar112 | A | 1.17 | 444.3 |
| 4-NP-106 | Tf-2 | sbo113 | Qn2P | Ar113 | A | 1.23 | 440.3 |
| 4-NP-107 | Tf-2 | sbo114 | Qn2P | Ar114 | A | 1.26 | 451.3 |
| 4-NP-108 | Tf-2 | sbo115 | Qn2P | Ar115 | A | 1.29 | 446.3 |
| 4-NP-110 | Tf-2 | sbo73 | Qn2P | Ar73 | A | 1.13 | 415.2 |
| 4-NP-111 | Tf-2 | sbo116 | Qn2P | Ar116 | A | 1.29 | 449.2 |
| 4-NP-112 | Tf-2 | sbo117 | Qn2P | Ar117 | A | 1.35 | 433.2 |
| 4-NP-113 | Tf-2 | sbo118 | Qn2P | Ar118 | A | 1.13 | 450.3 |
| 4-NP-114 | Tf-2 | sbo119 | Qn2P | Ar119 | A | 1.19 | 447.3 |
| 4-NP-115 | Tf-2 | sbo120 | Qn2P | Ar120 | A | 0.91 | 439.3 |
| 4-NP-116 | Tf-2 | sbo121 | Qn2P | Ar121 | A | 1.01 | 453.3 |
| 4-NP-117 | Tf-2 | sbo122 | Qn2P | Ar122 | A | 0.86 | 439.3 |
| 4-NP-118 | Tf-2 | sbo123 | Qn2P | Ar123 | A | 0.98 | 453.3 |
| 4-NP-119 | Tf-2 | sbo124 | Qn2P | Ar124 | A | 0.95 | 457.3 |
| 4-NP-120 | Tf-2 | sbo125 | Qn2P | Ar125 | A | 1.09 | 454.3 |
| 4-NP-121 | Tf-2 | sbo126 | Qn2P | Ar126 | A | 0.83 | 386.3 |
| 4-NP-122 | Tf-2 | sbo127 | Qn2P | Ar127 | A | 0.76 | 494.4 |
| 4-NP-123 | Tf-2 | sbo128 | Qn2P | Ar128 | A | 0.91 | 400.3 |
| 4-NP-124 | Tf-2 | sbo129 | Qn2P | Ar129 | A | 1.1 | 437.2 |
| 4-NP-125 | Tf-2 | sbo130 | Qn2P | Ar130 | A | 1.04 | 430.4 |
| 4-NP-126 | Tf-2 | sbo131 | Qn2P | Ar131 | A | 1.29 | 494.4 |
| 4-NP-127 | Tf-2 | sbo132 | Qn2P | Ar132 | A | 1.14 | 466.5 |
| 4-NP-135 | Tf-2 | sbo134 | Qn2P | Ar134 | A | 1.13 | 425.3 |
| 4-NP-136 | Tf-2 | sbo135 | Qn2P | Ar135 | A | 1.12 | 429.3 |
| 4-NP-138 | Tf-2 | sbo136 | Qn2P | Ar136 | A | 0.92 | 451.1 |
| 4-NP-139 | Tf-2 | sbo137 | Qn2P | Ar137 | A | 1.33 | 466.3 |
| 4-NP-140 | Tf-1 | sbo90 | Qn1P | Ar90 | B | 2.78 | 407.8 |
| 4-NP-141 | Tf-1 | sbo123 | Qn1P | Ar123 | B | 2.57 | 439.3 |
| 4-NP-142 | Tf-1 | sbo130 | Qn1P | Ar130 | B | 2.74 | 416.1 |
| 4-NP-143 | Tf-1 | sbo73 | Qn1P | Ar73 | A | 1.10 | 401.2 |
| 4-NP-144 | Tf-1 | sbo118 | Qn1P | Ar118 | A | 1.15 | 436.3 |
| 4-NP-146 | Tf-1 | sbo192 | Qn1P | Ar192 | A | 0.87 | 397.2 |
| 4-NP-147 | Tf-2 | sbo192 | Qn2P | Ar192 | A | 0.94 | 411.2 |
| 4-NP-149 | Tf-1 | sbo22 | Qn1P | Ar22 | A | 0.89 | 386.0 |
| 4-NP-150 | Tf-1 | sbo194 | Qn1P | Ar194 | A | 1.26 | 428.3 |
| 4-NP-151 | Tf-1 | sbo195 | Qn1P | Ar195 | A | 1.30 | 462.2 |
| 4-NP-152 | Tf-1 | sbo186 | Qn1P | Ar186 | A | 0.76 | 397.2 |
| 4-NP-153 | Tf-1 | sbo157 | Qn1P | Ar157 | A | 1.16 | 411.2 |
| 4-NP-154 | Tf-1 | sbo158 | Qn1P | Ar158 | A | 1.14 | 411.2 |
| 4-NP-155 | Tf-1 | sbo147 | Qn1P | Ar147 | A | 1.15 | 417.2 |
| 4-NP-156 | Tf-1 | sbo196 | Qn1P | Ar196 | A | 0.68 | 481.2 |
| 4-NP-160 | Tf-1 | sbo148 | Qn1P | Ar148 | A | 0.69 | 398.2 |
| 4-NP-161 | Tf-1 | sbo300 | Qn1P | Ar300 | A | 0.74 | 399.2 |
| 4-NP-169 | Tf-1 | sbo111 | Qn1P | Ar111 | A | 1.27 | 437.4 |
| 4-NP-170 | Tf-1 | sbo139 | Qn1P | Ar139 | A | 0.94 | 397.2 |
| 4-NP-171 | Tf-1 | sbo140 | Qn1P | Ar140 | A | 1.09 | 409.4 |
| 4-NP-172 | Tf-1 | sbo141 | Qn1P | Ar141 | A | 1.07 | 434.4 |
| 4-NP-173 | Tf-1 | sbo142 | Qn1P | Ar142 | A | 1.13 | 415.5 |
| 4-NP-174 | Tf-1 | sbo143 | Qn1P | Ar143 | A | 1.17 | 434.4 |
| 4-NP-175 | Tf-1 | sbo144 | Qn1P | Ar144 | A | 1.13 | 415.4 |
| 4-NP-176 | Tf-1 | sbo47 | Qn1P | Ar47 | A | 1.28 | 451.4 |
| 4-NP-177 | Tf-1 | sbo145 | Qn1P | Ar145 | A | 1.02 | 413.2 |
| 4-NP-178 | Tf-1 | sbo146 | Qn1P | Ar146 | A | 0.69 | 398.2 |
| 4-NP-179 | Tf-2 | sbo147 | Qn2P | Ar147 | A | 1.22 | 431.0 |
| 4-NP-180 | Tf-2 | sbo148 | Qn2P | Ar148 | A | 0.69 | 412.3 |
| 4-NP-182 | Tf-2 | sbo150 | Qn2P | Ar150 | A | 1.19 | 422.2 |
| 4-NP-185 | Tf-1 | sbo153 | Qn1P | Ar153 | A | 1.10 | 413.2 |
| 4-NP-188 | Tf-2 | sbo153 | Qn2P | Ar153 | A | 1.21 | 427.3 |
| 4-NP-189 | Tf-2 | sbo154 | Qn2P | Ar154 | A | 1.09 | 412.2 |
| 4-NP-190 | Tf-2 | sbo155 | Qn2P | Ar155 | A | 1.15 | 431.2 |
| 4-NP-191 | Tf-2 | sbo139 | Qn2P | Ar139 | A | 1.02 | 411.2 |
| 4-NP-192 | Tf-2 | sbo144 | Qn2P | Ar144 | A | 1.21 | 429.5 |
| 4-NP-193 | Tf-2 | sbo142 | Qn2P | Ar142 | A | 1.28 | 429.4 |
| 4-NP-194 | Tf-2 | sbo156 | Qn2P | Ar156 | A | 1.37 | 445.2 |
| 4-NP-195 | Tf-2 | sbo157 | Qn2P | Ar157 | A | 1.32 | 425.2 |

TABLE 4-NP-continued

| Exp. | SM1 | SM2 | ST | Ar | method | Rtime | MH+ |
|---|---|---|---|---|---|---|---|
| 4-NP-196 | Tf-2 | sbo158 | Qn2P | Ar158 | A | 1.29 | 425.2 |
| 4-NP-197 | Tf-2 | sbo159 | Qn2P | Ar159 | A | 0.93 | 411.2 |
| 4-NP-198 | Tf-1 | sbo160 | Qn1P | Ar160 | A | 1.18 | 439.4 |
| 4-NP-199 | Tf-1 | Ar161 | Qn1P | Ar161 | A | 0.77 | 411.2 |
| 4-NP-200 | Tf-1 | sbo162 | Qn1P | Ar162 | A | 1.35 | 447.2 |
| 4-NP-201 | Tf-1 | sbo163 | Qn1P | Ar163 | A | 0.99 | 422.4 |
| 4-NP-202 | Tf-1 | sbo150 | Qn1P | Ar150 | A | 1.09 | 408.4 |
| 4-NP-204 | Tf-1 | sbo165 | Qn1P | Ar165 | A | 1.01 | 401.5 |
| 4-NP-205 | Tf-1 | sbo166 | Qn1P | Ar166 | A | 1.23 | 431.5 |
| 4-NP-206 | Tf-1 | sbo156 | Qn1P | Ar156 | A | 1.20 | 431.4 |
| 4-NP-207 | Tf-1 | sbo167 | Qn1P | Ar167 | A | 1.06 | 414.5 |
| 4-NP-208 | Tf-1 | sbo168 | Qn1P | Ar168 | A | 0.89 | 439.5 |
| 4-NP-209 | Tf-1 | sbo169 | Qn1P | Ar169 | A | 1.00 | 465.0 |
| 4-NP-210 | Tf-1 | sbo170 | Qn1P | Ar170 | A | 0.95 | 401.5 |
| 4-NP-211 | Tf-1 | sbo171 | Qn1P | Ar171 | A | 1.22 | 431.5 |
| 4-NP-212 | Tf-1 | sbo172 | Qn1P | Ar172 | A | 0.93 | 478.5 |
| 4-NP-213 | Tf-1 | sbo173 | Qn1P | Ar173 | A | 1.25 | 421.5 |
| 4-NP-214 | Tf-1 | sbo174 | Qn1P | Ar174 | A | 1.19 | 439.0 |
| 4-NP-217 | Tf-2 | sbo176 | Qn2P | Ar176 | A | 1.12 | 431.2 |
| 4-NP-218 | Tf-2 | sbo177 | Qn2P | Ar177 | A | 0.93 | 387.2 |
| 4-NP-219 | Tf-2 | sbo178 | Qn2P | Ar178 | A | 0.839 | 411.2 |
| 4-NP-220 | Tf-2 | sbo179 | Qn2P | Ar179 | A | 1.07 | 455.2 |
| 4-NP-221 | Tf-2 | sbo180 | Qn2P | Ar180 | A | 0.88 | 411.2 |
| 4-NP-222 | Tf-2 | sbo181 | Qn2P | Ar181 | A | 1.24 | 445.2 |
| 4-NP-223 | Tf-2 | sbo182 | Qn2P | Ar182 | A | 1.31 | 451.5 |
| 4-NP-224 | Tf-2 | sbo161 | Qn2P | Ar161 | A | 0.81 | 425.2 |
| 4-NP-225 | Tf-2 | sbo163 | Qn2P | Ar163 | A | 1.01 | 436.0 |
| 4-NP-226 | Tf-2 | sbo165 | Qn2P | Ar165 | A | 1.05 | 415.5 |
| 4-NP-227 | Tf-2 | sbo167 | Qn2P | Ar167 | A | 1.15 | 428.1 |
| 4-NP-231 | Tf-1 | sbo186 | Qn1P | Ar186 | A | 0.74 | 397.3 |
| 4-NP-232 | Tf-1 | sbo145 | Qn1P | Ar145 | A | 0.98 | 413.2 |
| 4-NP-233 | Tf-1 | sbo187 | Qn1P | Ar187 | A | 1.30 | 466.5 |
| 4-NP-234 | Tf-1 | sbo188 | Qn1P | Ar188 | A | 0.91 | 386.3 |
| 4-NP-235 | Tf-1 | sbo189 | Qn1P | Ar189 | A | 1.12 | 482.3 |
| 4-NP-236 | Tf-1 | sbo190 | Qn1P | Ar190 | A | 0.95 | 414.3 |
| 4-NP-237 | Tf-1 | sbo191 | Qn1P | Ar191 | A | 1.01 | 454.3 |
| 4-NP-238 | Tf-1 | sbo154 | Qn1P | Ar154 | A | 0.64 | 398.2 |
| 4-NP-239 | Tf-2 | sbo191 | Qn2P | Ar191 | A | 1.09 | 468.3 |
| 4-NP-240 | Tf-3 | sbo192 | Qn3P | Ar192 | A | 1.02 | 423.2 |
| 4-NP-241 | Tf-3 | sbo139 | Qn3P | Ar139 | A | 1.03 | 423.2 |
| 4-NP-242 | Tf-3 | sbo186 | Qn3P | Ar186 | A | 0.88 | 423.2 |
| 4-NP-243 | Tf-2 | sbo170 | Qn2P | Ar170 | A | 1.05 | 416.0 |
| 4-NP-244 | Tf-2 | sbo188 | Qn2P | Ar188 | A | 0.98 | 400.2 |
| 4-NP-248 | Tf-2 | sbo202 | Qn2P | Ar202 | A | 1.37 | 449.1 |
| 4-NP-249 | Tf-2 | sbo203 | Qn2P | Ar203 | A | 0.98 | 454.2 |
| 4-NP-250 | Tf-2 | sbo204 | Qn2P | Ar204 | A | 1.26 | 400.5 |
| 4-NP-251 | Tf-2 | sbo205 | Qn2P | Ar205 | A | 1.34 | 416.4 |
| 4-NP-252 | Tf-2 | sbo206 | Qn2P | Ar206 | A | 1.35 | 416.2 |
| 4-NP-253 | Tf-1 | sbo207 | Qn1P | Ar207 | A | 0.71 | 412.2 |
| 4-NP-254 | Tf-2 | sbo207 | Qn2P | Ar207 | A | 0.76 | 426.2 |
| 4-NP-255 | Tf-1 | sbo208 | Qn1P | Ar208 | A | 0.72 | 412.2 |
| 4-NP-256 | Tf-1 | sbo209 | Qn1P | Ar209 | A | 0.74 | 426.3 |
| 4-NP-257 | Tf-2 | sbo208 | Qn2P | Ar208 | A | 0.72 | 426.3 |
| 4-NP-258 | Tf-2 | sbo209 | Qn2P | Ar209 | A | 0.80 | 440.3 |
| 4-NP-259 | Tf-1 | sbo210 | Qn1P | Ar210 | A | 1.18 | 451.5 |
| 4-NP-260 | Tf-1 | sbo211 | Qn1P | Ar211 | A | 1.06 | 415.0 |
| 4-NP-264 | Tf-1 | sbo215 | Qn1P | Ar215 | A | 1.08 | 417.4 |
| 4-NP-265 | Tf-1 | sbo216 | Qn1P | Ar216 | A | 0.88 | 460.9 |
| 4-NP-266 | Tf-1 | sbo217 | Qn1P | Ar217 | A | 0.62 | 422.2 |
| 4-NP-267 | Tf-1 | sbo218 | Qn1P | Ar218 | A | 0.74 | 436.2 |
| 4-NP-268 | Tf-1 | sbo219 | Qn1P | Ar219 | A | 0.91 | 400.5 |
| 4-NP-269 | Tf-1 | sbo220 | Qn1P | Ar220 | A | 0.82 | 400.0 |
| 4-NP-270 | Tf-1 | sbo221 | Qn1P | Ar221 | A | 1.06 | 385.0 |
| 4-NP-271 | Tf-1 | sbo222 | Qn1P | Ar222 | A | 1.28 | 435.6 |
| 4-NP-272 | Tf-1 | sbo223 | Qn1P | Ar223 | A | 0.94 | 417.4 |
| 4-NP-273 | Tf-1 | sbo224 | Qn1P | Ar224 | A | 1.11 | 448.0 |
| 4-NP-274 | Tf-1 | sbo225 | Qn1P | Ar225 | A | 0.84 | 400.3 |
| 4-NP-275 | Tf-1 | sbo226 | Qn1P | Ar226 | A | 1.03 | 401.4 |
| 4-NP-278 | Tf-1 | sbo229 | Qn1P | Ar229 | A | 0.56 | 412.2 |
| 4-NP-279 | Tf-1 | sbo230 | Qn1P | Ar230 | A | 0.53 | 412.2 |
| 4-NP-280 | Tf-2 | sbo230 | Qn2P | Ar230 | A | 0.58 | 426.3 |
| 4-NP-281 | Tf-1 | sbo231 | Qn1P | Ar231 | A | 0.90 | 464.3 |
| 4-NP-282 | Tf-1 | sbo232 | Qn1P | Ar232 | A | 0.77 | 440.2 |
| 4-NP-283 | Tf-3 | sbo219 | Qn3P | Ar219 | A | 1.01 | 426.5 |
| 4-NP-284 | Tf-3 | sbo167 | Qn3P | Ar167 | A | 1.07 | 440.5 |
| 4-NP-285 | Tf-3 | sbo233 | Qn3P | Ar233 | A | 1.12 | 462.3 |
| 4-NP-286 | Tf-3 | sbo157 | Qn3P | Ar157 | A | 1.20 | 437.3 |
| 4-NP-287 | Tf-3 | sbo148 | Qn3P | Ar148 | A | 0.63 | 424.2 |
| 4-NP-288 | Tf-3 | sbo90 | Qn3P | Ar90 | A | 1.09 | 435.2 |
| 4-NP-289 | Tf-3 | sbo165 | Qn3P | Ar165 | A | 1.04 | 428.2 |
| 4-NP-290 | Tf-3 | sbo171 | Qn3P | Ar171 | A | 1.23 | 458.2 |
| 4-NP-291 | Tf-3 | sbo117 | Qn3P | Ar117 | A | 1.32 | 446.2 |
| 4-NP-292 | Tf-3 | sbo128 | Qn3P | Ar128 | A | 0.89 | 413.2 |
| 4-NP-293 | Tf-3 | sbo161 | Qn3P | Ar161 | A | 0.73 | 437.2 |
| 4-NP-294 | Tf-2 | sbo234 | Qn2P | Ar234 | A | 1.24 | 456.4 |
| 4-NP-295 | Tf-2 | sbo235 | Qn2P | Ar235 | A | 1.16 | 452.5 |
| 4-NP-296 | Tf-2 | sbo210 | Qn2P | Ar210 | A | 1.22 | 465.5 |
| 4-NP-297 | Tf-2 | sbo236 | Qn2P | Ar236 | A | 1.27 | 461.4 |
| 4-NP-301 | Tf-2 | sbo240 | Qn2P | Ar240 | A | 1.07 | 467.1 |
| 4-NP-302 | Tf-2 | sbo241 | Qn2P | Ar241 | A | 1.09 | 481.3 |
| 4-NP-303 | Tf-2 | sbo242 | Qn2P | Ar242 | A | 1.14 | 483.3 |
| 4-NP-307 | Tf-1 | sbo246 | Qn1P | Ar246 | A | 0.97 | 436.5 |
| 4-NP-309 | Tf-2 | sbo248 | Qn2P | Ar248 | A | 0.92 | 475.2 |
| 4-NP-310 | Tf-2 | sbo249 | Qn2P | Ar249 | A | 1.14 | 503.2 |
| 4-NP-311 | Tf-2 | sbo186 | Qn2P | Ar186 | A | 0.74 | 411.2 |
| 4-NP-313 | Tf-3 | sbo96 | Qn3P | Ar96 | A | 1.04 | 435.2 |
| 4-NP-314 | Tf-3 | sbo150 | Qn3P | Ar150 | A | 1.12 | 435.2 |
| 4-NP-315 | Tf-3 | sbo158 | Qn3P | Ar158 | A | 1.14 | 437.3 |
| 4-NP-316 | Tf-3 | sbo156 | Qn3P | Ar156 | A | 1.27 | 457.1 |
| 4-NP-317 | Tf-3 | sbo231 | Qn3P | Ar231 | A | 1.08 | 480.3 |
| 4-NP-318 | Tf-3 | sbo232 | Qn3P | Ar232 | A | 0.95 | 466.3 |
| 4-NP-319 | Tf-3 | sbo232 | Qn3P | Ar232 | A | 0.99 | 448.2 |
| 4-NP-320 | Tf-1 | sbo251 | Qn1P | Ar251 | A | 1.13 | 450.4 |
| 4-NP-321 | Tf-1 | sbo233 | Qn1P | Ar233 | A | 1.11 | 450.4 |
| 4-NP-322 | Tf-1 | sbo252 | Qn1P | Ar252 | A | 1.13 | 450.4 |
| 4-NP-323 | Tf-1 | sbo253 | Qn1P | Ar253 | A | 0.97 | 423.3 |
| 4-NP-324 | Tf-2 | sbo253 | Qn2P | Ar253 | A | 1.04 | 437.4 |
| 4-NP-325 | Tf-1 | sbo254 | Qn1P | Ar254 | A | 0.90 | 411.3 |
| 4-NP-326 | Tf-1 | sbo255 | Qn1P | Ar255 | A | 0.94 | 411.3 |
| 4-NP-327 | Tf-2 | sbo254 | Qn2P | Ar254 | A | 0.97 | 425.4 |
| 4-NP-328 | Tf-2 | sbo255 | Qn2P | Ar255 | A | 1.00 | 425.2 |
| 4-NP-329 | Tf-2 | sbo173 | Qn2P | Ar173 | A | 1.25 | 435.5 |
| 4-NP-330 | Tf-2 | sbo256 | Qn2P | Ar256 | A | 1.19 | 445.3 |
| 4-NP-332 | Tf-2 | sbo258 | Qn2P | Ar258 | A | 1.12 | 431.3 |
| 4-NP-333 | Tf-2 | sbo246 | Qn2P | Ar246 | A | 1.08 | 450.4 |
| 4-NP-334 | Tf-2 | sbo219 | Qn2P | Ar219 | A | 0.97 | 414.3 |
| 4-NP-335 | Tf-2 | sbo259 | Qn2P | Ar259 | A | 0.92 | 465.3 |
| 4-NP-336 | Tf-2 | sbo260 | Qn2P | Ar260 | A | 0.98 | 479.3 |
| 4-NP-337 | Tf-2 | sbo261 | Qn2P | Ar261 | A | 1.06 | 437.2 |
| 4-NP-338 | Tf-2 | sbo266 | Qn2P | Ar266 | A | 1.29 | 449.3 |
| 4-NP-339 | Tf-2 | sbo263 | Qn2P | Ar263 | A | 1.32 | 463.4 |
| 4-NP-340 | Tf-2 | sbo265 | Qn2P | Ar264 | A | 0.81 | 427.3 |
| 4-NP-341 | Tf-2 | sbo265 | Qn2P | Ar265 | A | 1.21 | 441.3 |
| 4-NP-342 | Tf-3 | sbo233 | Qn3P | Ar233 | A | 1.13 | 463.4 |
| 4-NP-343 | Tf-3 | sbo252 | Qn3P | Ar252 | A | 1.19 | 462.3 |
| 4-NP-344 | Tf-2 | sbo233 | Qn2P | Ar233 | A | 1.1 | 450.4 |
| 4-NP-345 | Tf-2 | sbo252 | Qn2P | Ar252 | A | 1.15 | 450.4 |
| 4-NP-346 | Tf-1 | sbo262 | Qn1P | Ar262 | A | 1.01 | 427.3 |
| 4-NP-347 | Tf-2 | sbo262 | Qn2P | Ar262 | A | 1.08 | 441.3 |
| 4-NP-349 | Tf-2 | sbo267 | Qn2P | Ar267 | A | 0.94 | 439.3 |
| 4-NP-350 | Tf-3 | sbo254 | Qn3P | Ar254 | A | 1.02 | 437.1 |
| 4-NP-351 | Tf-3 | sbo255 | Qn3P | Ar255 | A | 1.04 | 437.4 |
| 4-NP-352 | Tf-1 | sbo268 | Qn1P | Ar268 | A | 0.96 | 433.1 |
| 4-NP-353 | Tf-2 | sbo268 | Qn2P | Ar268 | A | 1.03 | 447.1 |
| 4-NP-354 | Tf-1 | sbo269 | Qn1P | Ar269 | A | 0.91 | 415.5 |
| 4-NP-355 | Tf-1 | sbo270 | Qn1P | Ar270 | A | 0.88 | 451.4 |
| 4-NP-356 | Tf-1 | sbo270 | Qn1P | Ar270 | A | 0.93 | 465.4 |
| 4-NP-357 | Tf-2 | sbo274 | Qn2P | Ar274 | A | 0.87 | 454.2 |
| 4-NP-359 | Tf-2 | sbo276 | Qn2P | Ar276 | A | 0.98 | 465.3 |
| 4-NP-361 | Tf-2 | sbo269 | Qn2P | Ar269 | A | 0.96 | 429.0 |
| 4-NP-362 | Tf-1 | sbo236 | Qn1P | Ar236 | A | 1.06 | 438.5 |
| 4-NP-363 | Tf-1 | sbo271 | Qn1P | Ar271 | A | 0.79 | 411.1 |
| 4-NP-364 | Tf-1 | sbo271 | Qn2P | Ar271 | A | 0.85 | 425.3 |
| 4-NP-365 | Tf-1 | sbo272 | Qn1P | Ar272 | A | 1.09 | 450.3 |
| 4-NP-366 | Tf-1 | sbo273 | Qn1P | Ar273 | A | 1.05 | 450.3 |
| 4-NP-367 | Tf-2 | sbo272 | Qn2P | Ar272 | A | 1.15 | 464.5 |
| 4-NP-368 | Tf-2 | sbo273 | Qn2P | Ar273 | A | 1.11 | 464.5 |
| 4-NP-369 | Tf-1 | sbo278 | Qn1P | Ar278 | A | 0.99 | 433.0 |
| 4-NP-370 | Tf-1 | sbo279 | Qn1P | Ar279 | A | 0.98 | 433.0 |
| 4-NP-371 | Tf-1 | sbo280 | Qn1P | Ar280 | A | 0.88 | 415.3 |

TABLE 4-NP-continued

| Exp. | SM1 | SM2 | ST | Ar | LCMS method | Rtime | MH+ |
|---|---|---|---|---|---|---|---|
| 4-NP-372 | Tf-2 | sbo278 | Qn2P | Ar278 | A | 1.06 | 447.0 |
| 4-NP-373 | Tf-2 | sbo279 | Qn2P | Ar279 | A | 1.06 | 447.1 |
| 4-NP-374 | Tf-2 | sbo280 | Qn2P | Ar280 | A | 0.96 | 429.3 |
| 4-NP-375 | Tf-3 | sbo278 | Qn3P | Ar278 | A | 1.13 | 459.3 |
| 4-NP-376 | Tf-3 | sbo279 | Qn3P | Ar279 | A | 1.1 | 459.1 |
| 4-NP-377 | Tf-3 | sbo280 | Qn3P | Ar280 | A | 0.99 | 441.1 |
| 4-NP-378 | Tf-3 | sbo269 | Qn3P | Ar269 | A | 1.01 | 441.1 |
| 4-NP-379 | Tf-3 | sbo271 | Qn3P | Ar271 | A | 0.88 | 437.3 |
| 4-NP-380 | Tf-3 | sbo161 | Qn3P | Ar161 | A | 0.73 | 437.3 |
| 4-NP-381 | Tf-1 | sbo281 | Qn1P | Ar281 | A | 1.27 | 447.1 |
| 4-NP-382 | Tf-1 | sbo282 | Qn1P | Ar282 | A | 1.23 | 447.3 |
| 4-NP-383 | Tf-1 | sbo283 | Qn1P | Ar283 | A | 1.26 | 435.1 |
| 4-NP-384 | Tf-1 | sbo284 | Qn1P | Ar284 | A | 0.84 | 415.5 |
| 4-NP-385 | Tf-2 | sbo281 | Qn2P | Ar281 | A | 1.32 | 461.1 |
| 4-NP-386 | Tf-2 | sbo282 | Qn2P | Ar282 | A | 1.29 | 461.1 |
| 4-NP-387 | Tf-2 | sbo283 | Qn2P | Ar283 | A | 1.31 | 449.6 |
| 4-NP-388 | Tf-2 | sbo284 | Qn2P | Ar284 | A | 0.91 | 429.5 |
| 4-NP-389 | Tf-1 | sbo285 | Qn1P | Ar285 | A | 0.76 | 411.3 |
| 4-NP-390 | Tf-2 | sbo285 | Qn2P | Ar285 | A | 0.83 | 425.3 |
| 4-NP-391 | Tf-3 | sbo285 | Qn3P | Ar285 | A | 0.87 | 437.3 |
| 4-NP-392 | Tf-1 | sbo286 | Qn1P | Ar286 | A | 1.18 | 457.1 |
| 4-NP-393 | Tf-2 | sbo286 | Qn2P | Ar286 | A | 1.24 | 471.1 |
| 4-NP-394 | Tf-3 | sbo286 | Qn3P | Ar286 | A | 1.28 | 483.1 |
| 4-NP-404 | Tf-2 | sbo288 | Qn2P | Ar288 | A | 1.01 | 429.3 |
| 4-NP-406 | Tf-2 | sbo289 | Qn2P | Ar289 | A | 1.06 | 429.5 |
| 4-NP-407 | Tf-1 | sbo289 | Qn1P | Ar289 | A | 1.00 | 415.3 |
| 4-NP-410 | Tf-1 | sbo290 | Qn1P | Ar290 | A | 1.17 | 443.6 |
| 4-NP-411 | Tf-2 | sbo290 | Qn2P | Ar290 | A | 1.11 | 429.5 |
| 4-NP-412 | Tf-1 | sbo291 | Qn1P | Ar291 | A | 1.14 | 440.5 |
| 4-NP-413 | Tf-1 | sbo292 | Qn1P | Ar292 | A | 0.87 | 461.2 |
| 4-NP-414 | Tf-1 | sbo293 | Qn1P | Ar293 | A | 1.12 | 454.3 |
| 4-NP-415 | Tf-1 | sbo294 | Qn1P | Ar294 | A | 1.17 | 468.6 |
| 4-NP-416 | Tf-1 | sbo295 | Qn1P | Ar295 | A | 1.18 | 468.4 |
| 4-NP-417 | Tf-1 | sbo296 | Qn1P | Ar296 | A | 1.45 | 454.5 |
| 4-NP-418 | Tf-1 | sbo297 | Qn1P | Ar297 | A | 1.08 | 455.3 |
| 4-NP-430 | Tf-1 | sbo304 | Qn1P | Ar304 | A | 0.73 | 399.3 |
| 4-NP-431 | Tf-1 | sbo305 | Qn1P | Ar305 | A | 0.94 | 426.1 |
| 4-NP-432 | Tf-1 | sbo306 | Qn1P | Ar306 | A | 0.89 | 441.3 |
| 4-NP-433 | Tf-1 | sbo307 | Qn1P | Ar307 | A | 0.83 | 461.6 |
| 4-NP-434 | Tf-1 | sbo308 | Qn1P | Ar308 | A | 0.91 | 460.6 |
| 4-NP-472 | Tf-1 | sbo309 | Qn1P | Ar309 | A | 1.11 | 489.5 |
| 4-NP-473 | Tf-1 | sbo310 | Qn1P | Ar310 | A | 1.04 | 474.4 |

Example 4-NP-88

N-(4-(8-(1-(ethylsulfonyl)piperidin-4-ylamino)iso-quinolin-6-yl)benzyl)-6-methylnicotinamide

[Step a]

tert-butyl 4-(8-bromoisoquinolin-6-yl)benzylcarbamate (Intermediate 4-NP-88-1)

The title compound was obtained as a crude product (166 mg) by the similar method as the method described in Example 4-NP-8 using Intermediate 6 (120 mg) and 4-((tert-butoxycarbonylamino)methyl)phenylboronic acid (76.1 mg; Combi).

(Intermediate 4-NP-88-1 LCMS: 415.3 (MH+); retention time: 1.89 min; LCMS; condition A)

[Step b]

6-(4-(aminomethyl)phenyl)-N-(1-(ethylsulfonyl)piperidin-4-yl)isoquinolin-8-amine (Intermediate 4-NP-88-2)

The title compound (49.2 mg) was obtained using Intermediate 4-NP-88-1 (166 mg) and Intermediate N-2 (81.6 mg) by the similar method as the method described in Example 1-N-1.

(Intermediate 4-NP-88-2 LCMS: 425.4 (MH+); retention time: 0.69 min; LCMS; condition A)

[Step c]

N-(4-(8-(1-(ethylsulfonyl)piperidin-4-ylamino)iso-quinolin-6-yl)benzyl)-6-methylnicotinamide (Example 4-NP-88)

The title compound (1.3 mg) was obtained using Intermediate 4-NP-88-2 (19.4 mg) and 6-methylnicotinic acid (which may be referred to as sco100; 8.0 mg; Ald) by the similar method as the method described in Example 2-N-2.

(Example 4-NP-88 LCMS: 544.3 (MH+); retention time: 1.02 min; LCMS; condition A)

Example 4-NP-89

N-(4-(8-(1-(ethylsulfonyl)piperidin-4-ylamino)iso-quinolin-6-yl)benzyl)-2-hydroxyacetamide The title compound (6.4 mg) was obtained using Intermediate 4-NP-88-2 (19.4 mg) and 2-hydroxyacetic acid (which may be referred to as sco97; 3.3 mg; WAKO) by the similar method as the method described in Example 2-N-2.

(Example 4-NP-89 LCMS: 483.3 (MH+); retention time: 0.92 min; LCMS; condition A)

Example 4-NP-90

N-(4-(8-(1-(ethylsulfonyl)piperidin-4-ylamino)iso-quinolin-6-yl)phenethyl)-6-methylnicotinamide

[Step a]

tert-butyl 4-(8-bromoisoquinolin-6-yl)phenethylcarbamate (Intermediate 4-NP-90-1)

The title compound was obtained as a crude product (162 mg) using Intermediate 6 (100 mg) and tert-butyl 4-(4,4,5,5-tetramethyl-1,3,2-dioxaborolan-2-yl)phenethylcarbamate (which may be referred to as sbo400; 135 mg) by the similar method as the method described in Example 4-NP-8.

(Intermediate 4-NP-90-1 LCMS: 427.2 (MH+); retention time: 5.36 min; LCMS; condition B)

[Step b]

6-(4-(2-aminoethyl)phenyl)-N-(1-(ethylsulfonyl)piperidin-4-yl)isoquinolin-8-amine (Intermediate 4-NP-90-2)

The title compound (39.6 mg) was obtained using Intermediate 4-NP-90-1 (162 mg) and Intermediate N-2 (58.4 mg) by the similar method as the method described in Example 1-N-1.

(Intermediate 4-NP-90-2 LCMS: 439.4 (MH+); retention time: 0.81 min; LCMS; condition A)

[Step c]

N-(4-(8-(1-(ethylsulfonyl)piperidin-4-ylamino)isoquinolin-6-yl)phenethyl)-6-methylnicotinamide (Example 4-NP-90)

The title compound (8.4 mg) was obtained using Intermediate 4-NP-90-2 (20 mg) and 6-methylnicotinic acid (which may be referred to as sco100; 8.0 mg; Ald) by the similar method as the method described in Example 2-N-2.
(Example 4-NP-90 LCMS: 558.4 (MH$^+$); retention time: 1.09 min; LCMS; condition A)

Example 4-NP-91

N-(4-(8-(1-(ethylsulfonyl)piperidin-4-ylamino)isoquinolin-6-yl)phenethyl)-2-hydroxyacetamide The title compound (0.9 mg) was obtained using Intermediate 4-NP-90-2 (20 mg) and 2-hydroxyacetic acid (which may be referred to as sco97; 3.3 mg; WAKO) by the similar method as the method described in Example 2-N-2.
(Example 4-NP-91 LCMS: 497.4 (MH$^+$); retention time: 0.96 min; LCMS; condition A)

Example 4-NP-98

4-(6-(3-cyano-4-fluorophenyl)isoquinolin-8-ylamino)-N,N-dimethylpiperidine-1-carboxamide The title compound was obtained as a byproduct in the reaction in the step of Example 4-NP-79.
(LCMS: 418.5 (MH$^+$); retention time: 1.19 min; LCMS; condition A)

Example 4-NP-148

2-hydroxy-N-(3-(8-(1-(methylsulfonyl)piperidin-4-ylamino)isoquinolin-6-yl)phenyl)acetamide

[Step a]

6-(3-aminophenyl)-N-(1-(methylsulfonyl)piperidin-4-yl)isoquinolin-8-amine (Intermediate 4-NP-148-1)

The title compound (32.1 mg) was obtained using Intermediate Tf-1 (40 mg) and 3-aminophenylboronic acid (24.1 mg; TCI) by the similar method as the method described in Example 4-NP-8.
(Intermediate 4-NP-148-1 LCMS: 397.2 (MH$^+$); retention time: 0.94 min; LCMS; condition A)

[Step b]

2-hydroxy-N-(3-(8-(1-(methylsulfonyl)piperidin-4-ylamino)isoquinolin-6-yl)phenyl)acetamide (Example 4-NP-148)

The title compound was synthesized according to the following publications using Intermediate 4-NP-148-1 (16 mg) and 2-hydroxyacetic acid (which may be referred to as sco97; 3.7 mg; WAKO) to give the title compound (4.5 mg).
(Document: U.S. Pat. No. 5,366,987)
(Example 4-NP-148 LCMS: 455.2 (MH$^+$); retention time: 0.95 min; LCMS; condition A)

Example 4-NP-157

N-(1-(ethylsulfonyl)piperidin-4-yl)-6-(3-(piperazin-1-ylmethyl)phenyl)isoquinolin-8-amine

[Step a] 3-(8-(1-(ethylsulfonyl)piperidin-4-ylamino)isoquinolin-6-yl)benzaldehyde (Intermediate 4-NP-157-1)

Aqueous sodium carbonate solution (0.1 M, 0.5 mL) was added to a THF (2.0 mL) solution of Intermediate Tf-2 (80 mg), 3-formylphenylboronic acid (51.0 mg; Ald), and PdCl$_2$dppf.CH$_2$Cl$_2$ (14.0 mg) at room temperature and the resulting mixture was stirred at 60° C. for 11 hours. The reaction mixture solution was filtrated through celite and then the solvent was evaporated under reduced pressure. The residue was purified by column chromatography (Yamazen; chloroform/methanol) to give the title compound (81.0 mg).
(LCMS: 424.4 (MH$^+$); retention time: 1.16 min; LCMS; condition A)

[Step b]

tert-butyl-4-(3-(8-(1-(ethylsulfonyl)piperidin-4-ylamino)isoquinolin-6-yl)benzyl)piperazine-1-carboxylate (Intermediate 4-NP-157-2)

Sodium cyanoborohydride (5 mg; WAKO) was added to a methanol solution of Intermediate 4-NP-157-1 (25 mg), 1-BOC-PIPERAZINE (110 mg; Ald), acetic acid (7 ul) at room temperature and the resulting mixture was stirred for 13 hours at room temperature. Chloroform and saturated aqueous sodium bicarbonate solution were added to extract the reaction mixture, then the organic layer was dried, the solvent was evaporated under reduced pressure, and the residue was purified by column chromatography (Yamazen; chloroform/methanol) to give the title compound (19.6 mg).
(LCMS: 594.3 (MH$^+$); retention time: 1.16 min; LCMS; condition A)

[Step c]

N-(1-(ethylsulfonyl)piperidin-4-yl)-6-(3-(piperazin-1-ylmethyl)phenyl)isoquinolin-8-amine A methanol hydrochloride solution (10%, 2 ml) of Intermediate 4-NP-157-2(19.6 mg) was stirred at 50° C. for 2 hours. The reaction solution was evaporated under reduced pressure, ethanol and ether were added to the residue, and the residue was collected by filtration to give the title compound (13.9 mg).
(LCMS: 494.3 (MH$^+$); retention time: 0.82 min; LCMS; condition A)

Example 4-NP-159

N-(1-(ethylsulfonyl)piperidin-4-yl)-6-(3-(morpholinomethyl)phenyl)isoquinolin-8-amine The title compound (2.2 mg) was obtained from Intermediate 4-NP-157-1 (25 mg) and morpholine (10 ul; Ald) by the similar method as Step b of Example 4-NP-157.
(LCMS: 495.2 (MH$^+$); retention time: 0.83 min; LCMS; condition A)

Example 4-NP-184

6-(3-((4-aminopiperidin-1-yl)methyl)phenyl)-N-(1-(ethylsulfonyl)piperidin-4-yl)isoquinolin-8-amine The title compound (9.6 mg) was obtained from Intermediate 4-NP-157-1 (25 mg) and 4-(tert-butoxycarbonylamino)piperidine (118 mg; TCI) using the similar method as Steps b and c of Example 4-NP-157 sequentially.

(LCMS: 508.3 (MH$^+$); retention time: 0.69 min; LCMS; condition A)

Example 4-NP-181

N-(1-(ethylsulfonyl)piperidin-4-yl)-6-(5-(piperazin-1-ylmethyl)pyridin-3-yl)isoquinolin-8-amine

[Step a] 5-(8-(1-(ethylsulfonyl)piperidin-4-ylamino)isoquinolin-6-yl)nicotinaldehyde (Intermediate 4-NP-181-1)

The title compound (34.0 mg) was obtained from Intermediate Tf-2 (60.0 mg) and 5-formyl pyridine-3-boronic acid pinacol ester (55.0 mg) by the similar method as Step a of Example 4-NP-157.

(LCMS: 425.3 (MH$^+$); retention time: 0.99 min; LCMS; condition A)

[Step b]

tert-butyl4-((5-(8-(1-(ethylsulfonyl)piperidin-4-ylamino)isoquinolin-6-yl)pyridin-3-yl)methyl)piperazine-1-carboxylate (Intermediate 4-NP-181-2)

The title compound (54.7 mg) was obtained from Intermediate 4-NP-181-1 (34.0 mg) by the similar method as Step b of Example 4-NP-157.

(LCMS: 595.3 (MH$^+$); retention time: 1.06 min; LCMS; condition A)

[Step c]

N-(1-(ethylsulfonyl)piperidin-4-yl)-6-(5-(piperazin-1-ylmethyl)pyridin-3-yl)isoquinolin-8-amine The title compound (15.8 mg) was obtained from Intermediate 4-NP-181-2 (22.4 mg) by the similar method as Step c of Example 4-NP-157.

(LCMS: 495.3 (MH$^+$); retention time: 0.71 min; LCMS; condition A)

Example 4-NP-183

(5-(8-(1-(ethylsulfonyl)piperidin-4-ylamino)isoquinolin-6-yl)pyridin-3-yl)methanol The title compound (30.6 mg) was obtained as a byproduct in the reaction in the step b of Example 4-NP-181.

(LCMS: 427.2 (MH$^+$); retention time: 0.83 min; LCMS; condition A)

Example 4-NP-228

6-(3-(cyclopropylmethylamino)-4-fluorophenyl)-N-(1-(methylsulfonyl)piperidin-4-yl)isoquinolin-8-amine

[Step a]

6-(3-amino-4-fluorophenyl)-N-(1-(methylsulfonyl)piperidin-4-yl)isoquinolin-8-amine (Intermediate 4-NP-228-1)

The title compound (164 mg) was obtained using Intermediate Tf-1 (200 mg) and 3-amino-4-fluorophenylboronic acid (137 mg; Asymchem) by the similar method as the method described in Example 4-NP-8.

(Intermediate 4-NP-228-1 LCMS: 415.2 (MH$^+$); retention time: 1.11 min; LCMS; condition A)

[Step b]

6-(3-(cyclopropylmethylamino)-4-fluorophenyl)-N-(1-(methylsulfonyl)piperidin-4-yl)isoquinolin-8-amine (Example 4-NP-228)

The title compound was synthesized by the method described in Step a of Example 1-N-1 using Intermediate 4-NP-228-1 (20 mg) and cyclopropanecarbaldehyde (9.6 μL; Ald) and the product was purified by preparative HPLC to give the title compound (4.9 mg).

(Example 4-NP-228 LCMS: 469.3 (MH$^+$); retention time: 1.49 min; LCMS; condition A)

Example 4-NP-229

4-(8-(1-(methylsulfonyl)piperidin-4-ylamino)isoquinolin-6-yl)pyridin-2-ol

2 M Hydrochloric acid-dioxane (2 M; KOKUSAN) was added to the product obtained by the similar method as the method described in Example 4-NP-8 using Intermediate Tf-1 (20 mg) and 2-methoxypyridin-4-ylboronic acid (20.2 mg; Combi) and the product was purified by preparative HPLC to give the title compound (1.3 mg).

(Intermediate 4-NP-229 LCMS: 399.2 (MH$^+$); retention time: 0.72 min; LCMS; condition A)

Example 4-NP-348

N8-(1-(ethylsulfonyl)piperidin-4-yl)-N-6-m-tolylisoquinoline-6,8-diamine

Sodium t-butoxide (1.28 mg; TCI) was added to a 1,4-dioxane solution of Intermediate Tf-2 (20.0 mg), 3-methylaniline (17.9 mg; WAKO), Pd$_2$(dba)$_3$ (3.1 mg; Ald), and BINAP (4.2 mg; Ald) under a nitrogen atmosphere and the resulting mixture was stirred at 80° C. for 4 hours. The resulting mixture was stirred at room temperature for approx. 10 minutes, then the reaction mixture solution was filtrated, and the filtrate was concentrated under reduced pressure. The residue was purified by column chromatography (Yamazen; chloroform/methanol) to give the title compound (2.4 mg).

(LCMS: 425.4 (MH$^+$); retention time: 1.23 min; LCMS; condition A)

Example 4-NP-400

3-(8-(1-(ethylsulfonyl)piperidin-4-ylamino)isoquinolin-6-ylamino)benzonitrile (LCMS: 436.3 (MH$^+$); retention time: 1.07 min; LCMS; condition A)

Example 4-NP-401

N8-(1-(ethylsulfonyl)piperidin-4-yl)-N-6-(3-fluorophenyl)isoquinoline-6,8-diamine (LCMS: 429.3 (MH$^+$); retention time: 1.16 min; LCMS; condition A)

Example 4-NP-402

N8-(1-(ethylsulfonyl)piperidin-4-yl)-N-6-p-tolylisoquinoline-6,8-diamine
(LCMS: 425.3 (MH$^+$); retention time: 1.21 min; LCMS; condition A)

Example 4-NP-403

N8-(1-(ethylsulfonyl)piperidin-4-yl)-N-6-(4-fluorophenyl)isoquinoline-6,8-diamine (LCMS: 429.3 (MH$^+$); retention time: 1.13 min; LCMS; condition A)

Compounds of Examples 4-NP-400, 4-NP-401, 4-NP-402 and 4-NP-403 were synthesized using 3-aminobenzonitrile, 3-fluoroaniline, 4-methylaniline, and 4-fluoroaniline respectively, instead of 3-methylaniline described in the step of Example 4-NP-348.

Example 4-NP-423

6-(3-((methylamino)methyl)phenyl)-N-(1-(methylsulfonyl)piperidin-4-yl)isoquinolin-8-amine

[Step a] 3-(8-(1-(methylsulfonyl)piperidin-4-ylamino) isoquinolin-6-yl)benzaldehyde (Intermediate 4-NP-423-1)

The title compound (21 mg) was obtained from Intermediate Tf-1 (30 mg) and 3-formylphenylboronic acid (which may be referred to as sbo298; 32 mg; Ald) by the similar method as Step a of Example 1-N-1.
(LCMS: 410.5 (MH$^+$); retention time: 0.99 min; LCMS; condition A)

[Step b]

6-(3-((methylamino)methyl)phenyl)-N-(1-(methylsulfonyl)piperidin-4-yl)isoquinolin-8-amine Methylamine (2 M, 110 μL; Ald) and sodium cyanoborohydride (1 M, 77 μL; Ald) were added successively to a methanol (900 μL) solution of Intermediate 4-NP-423-1 (21 mg), the resulting mixture was stirred at room temperature for 12 hours, then the solvent was evaporated under reduced pressure, and the residue was purified by silica gel column chromatography (Yamazen; chloroform/methanol) to give the title compound (3.3 mg).
(LCMS: 425.3 (MH$^+$); retention time: 0.64 min; LCMS; condition A)

Example 4-NP-424

6-(3-((ethylamino)methyl)phenyl)-N-(1-(methylsulfonyl)piperidin-4-yl)isoquinolin-8-amine (LCMS: 439.3 (MH$^+$); retention time: 0.68 min; LCMS; condition A)

Example 4-NP-427

6-(3-((dimethylamino)methyl)phenyl)-N-(1-(methylsulfonyl)piperidin-4-yl)isoquinolin-8-amine (LCMS: 439.4 (MH$^+$); retention time: 0.67 min; LCMS; condition A)

Compounds of Examples 4-NP-424 and 4-NP-427 were synthesized using ethylamine and dimethylamine, respectively, instead of methylamine described in the step b of Example 4-NP-423.

Example 4-NP-245

N-(1-(ethylsulfonyl)piperidin-4-yl)-6-(6-fluoropyridin-2-yl)isoquinolin-8-amine

A DMF solution of Intermediate Tf-1 (10 mg), 2-fluoro-6-(tri-n-butylstannyl)pyridine (19.3 μL), tetrakis(triphenylphosphine)palladium (2.6 mg), and lithium chloride (1.8 mg) was stirred at 100° C. for 12 hours under a nitrogen atmosphere. The solvent of the reaction mixture was evaporated and the residue was purified by column chromatography (Yamazen; chloroform/methanol) to give the title compound (3.6 mg).
(LCMS: 415.2 (MH$^+$); retention time: 1.26 min; LCMS; condition A)

Example 4-NP-425

6-(3-((dimethylamino)methyl)phenyl)-N-(1-(ethylsulfonyl)piperidin-4-yl)isoquinolin-8-amine Methanol (900 μL), dimethylamine (2 M, 110 μL; Ald), and sodium cyanoborohydride (1 M, 77 μL; Ald) were added successively to the residue obtained from Intermediate Tf-2 (30 mg) and 3-formylphenylboronic acid (which may be referred to as sbo298; 32 mg; Ald) by the similar method as Step a of Example 1-N-1, the resulting mixture was stirred at room temperature for 12 hours, then the solvent was evaporated under reduced pressure, and the residue was purified by silica gel column chromatography (Yamazen; chloroform/methanol) to give the title compound (7.6 mg).
(LCMS: 453.4 (MH$^+$); retention time: 0.72 min; LCMS; condition A)

Example 4-NP-485

N-(1-(ethylsulfonyl)piperidin-4-yl)-6-(3-((methylamino)methyl)phenyl)isoquinolin-8-amine (LCMS: 439.3 (MH$^+$); retention time: 0.75 min; LCMS; condition A)

Example 4-NP-486

N-(1-(ethylsulfonyl)piperidin-4-yl)-6-(3-((isopropylamino)methyl)phenyl)isoquinolin-8-amine (LCMS: 467.3 (MH$^+$); retention time: 0.74 min; LCMS; condition A)

Compounds of Examples 4-NP-485 and 4-NP-486 were synthesized using methylamine and isopropylamine, respectively, instead of dimethylamine described in Example 4-NP-425.

Example 4-NP-426

6-(5-((dimethylamino)methyl)thiophen-3-yl)-N-(1-(ethylsulfonyl)piperidin-4-yl)isoquinolin-8-amine The compound was synthesized using 4-formylthiophene-2-ylboronic acid instead of 3-formylphenylboronic acid described in Example 4-NP-425.

(LCMS: 459.3 (MH$^+$); retention time: 0.63 min; LCMS; condition A)

Example 4-NP-487

N-(1-(ethylsulfonyl)piperidin-4-yl)-6-(3-(1-(methylamino)ethyl)phenyl)isoquinolin-8-amine The compound was synthesized using 3-acetylphenylboronic acid and methylamine, respectively, instead of 3-formylphenylboronic acid and dimethylamine described in Example 4-NP-425.

(LCMS: 453.3 (MH$^+$); retention time: 0.75 min; LCMS; condition A)

Example 4-NP-488

N-(1-(ethylsulfonyl)piperidin-4-yl)-6-(3-(1-(methylamino)ethyl)phenyl)isoquinolin-8-amine The compound was synthesized using 3-acetylphenylboronic acid and ethylamine, respectively, instead of 3-formylphenylboronic acid and dimethylamine described in Example 4-NP-425.

(LCMS: 467.4 (MH$^+$); retention time: 0.77 min; LCMS; condition A)

Example 4-NP-496

(5-methyl-2-oxo-1,3-dioxol-4-yl)methyl 3-(8-(1-(ethylsulfonyl)piperidin-4-ylamino)isoquinolin-6-yl)benzyl(methyl)carbamate (5-methyl-2-oxo-1,3-dioxol-4-yl)methyl 4-nitrophenyl carbonate (4.5 mg) and triethylamine (5 µL) were added successively to a DMF (400 µL) solution of Example compound 4-NP-485 (6.2 mg), the resulting mixture was stirred at room temperature for 12 hours, then the solvent was evaporated under reduced pressure, and the residue was purified by silica gel column chromatography (Yamazen; chloroform/methanol) to give the title compound.

(LCMS: 595.4 (MH$^+$); retention time: 1.26 min; LCMS; condition A) (5-methyl-2-oxo-1,3-dioxol-4-yl)methyl 4-nitrophenyl carbonate was prepared by the method described in the Journal of Medicinal Chemistry, 42 (1999), 3994-4000.

Example 4-NP-532

N-(1-(methylsulfonyl)piperidin-4-yl)-6-(phenylthio)isoquinolin-8-amine

Diisopropylethylamine (11.4 mg) was added to a 1,4-dioxane solution of Intermediate Tf-1 (20 mg), thiophenol (8 mg; Ald), Pd2(dba)$_3$ (1.0 mg) and Xantphos (1.28 mg) and the resulting mixture was stirred to reflux for 10 hours. Ethyl acetate and saturated brine were added to extract the reaction mixture, then the organic layer was dried, the solvent was evaporated under reduced pressure, and the residue was purified by column chromatography (Yamazen; chloroform/methanol) to give the title compound (7.8 mg).

(LCMS: 414.2 (MH$^+$); retention time: 1.31 min; LCMS; condition A)

Example 4-NP-543

6-(3-chlorophenylthio)-N-(1-(methylsulfonyl)piperidin-4-yl)isoquinolin-8-amine

The title compound was synthesized using 3-chlorothiophenol instead of thiophenol described in Example 5-NP-532.

(LCMS: 449.2 (MH$^+$); retention time: 1.38 min; LCMS; condition A)

Example 5-NP-1

N-(1-(methylsulfonyl)piperidin-4-yl)-6-(pyridin-2-yl)isoquinolin-8-amine

A DMF solution of Intermediate Tf-1 (20 mg), tri-n-butyl (2-pyridyl)tin (21.1 ul), and tetrakis(triphenylphosphine)palladium(0) (5.1 mg) was stirred at 100° C. for 12 hours under a nitrogen atmosphere. The solvent of the reaction mixture solution was evaporated and the residue was purified by column chromatography (Yamazen; chloroform/methanol) to give the title compound (4.3 mg).

(LCMS: 383.4 (MH$^+$); retention time: 0.96 minute; LCMS condition: A)

Examples 5-NP-2 to 5-NP-18

Compounds of Examples 5-NP-2 to 5-NP-18 were synthesized according to the method in Example 5-NP-1 (Table 5-NP). At this time, for example, the method described in Step b of Example 1-N-1 was used if deprotection is required. In Table 5-NP, SM1 column represents compounds used in respective Examples corresponding to Intermediate Tf-1 used in Example 5-NP-1 and the SM2 column represents compounds used in respective Examples corresponding to tri-n-butyl(2-pyridyl)tin (which may be referred to as sbo138) used in Example 5-NP-1. For example, in Example 5-NP-2, toward Intermediate, Intermediate Tf-1 was used as "SM1" and 6-(tributylstannyl)nicotinonitrile (which may be referred to as sbo164) was used as "SM2" to perform the step of Example 5-NP-1. In 5-NP, "LCMS" was defined as described above, abbreviations such as "Ar19" and "sbo19" represent compounds or groups corresponding to abbreviations in Tables Ar and sbo, respectively, provided later.

Example compounds in Table 5-NP include compounds purified by column chromatography and/or compounds finally purified by preparative HPLC.

TABLE 5-NP

| Exp. | SM1 | SM2 | ST | Ar | LCMS method | Rtime | MH+ |
|---|---|---|---|---|---|---|---|
| 5-NP-2 | Tf-1 | sbo164 | Qn1P | Ar164 | A | 1.11 | 408.2 |
| 5-NP-3 | Tf-1 | sbo185 | Qn1P | Ar185 | A | 0.76 | 384.0 |
| 5-NP-4 | Tf-2 | sbo199 | Qn2P | Ar199 | A | 1.26 | 416.2 |
| 5-NP-5 | Tf-2 | sbo200 | Qn2P | Ar200 | A | 1.36 | 427.2 |
| 5-NP-6 | Tf-2 | sbo201 | Qn2P | Ar201 | A | 1.18 | 411.2 |
| 5-NP-7 | Tf-2 | sbo237 | Qn2P | Ar237 | A | 1.16 | 411.3 |
| 5-NP-8 | Tf-2 | sbo238 | Qn2P | Ar238 | A | 1.16 | 411.3 |
| 5-NP-9 | Tf-2 | sbo239 | Qn2P | Ar239 | A | 1.20 | 417.4 |
| 5-NP-10 | Tf-2 | sbo247 | Qn2P | Ar247 | A | 1.10 | 417.5 |
| 5-NP-11 | Tf-2 | sbo257 | Qn2P | Ar257 | A | 0.94 | 433.3 |
| 5-NP-12 | Tf-2 | sbo275 | Qn2P | Ar275 | A | 1.10 | 417.2 |
| 5-NP-13 | Tf-2 | sbo277 | Qn2P | Ar277 | A | 1.01 | 429.2 |
| 5-NP-14 | Tf-1 | sbo277 | Qn1P | Ar277 | A | 0.93 | 415.3 |
| 5-NP-15 | Tf-1 | sbo287 | Qn1P | Ar287 | A | 1.15 | 435.0 |
| 5-NP-16 | Tf-1 | sbo237 | Qn1P | Ar237 | A | 0.96 | 397.3 |
| 5-NP-17 | Tf-1 | sbo199 | Qn1P | Ar199 | A | 1.00 | 401.5 |
| 5-NP-18 | Tf-2 | sbo287 | Qn2P | Ar287 | A | 1.23 | 449.2 |

Example 6-NP-1

N-(8-(1-(ethylsulfonyl)piperidin-4-ylamino)iso-quinolin-6-yl)-3-fluorobenzamide

[Step a] N8-(1-(ethylsulfonyl)piperidin-4-yl)iso-quinoline-6,8-diamine (Intermediate 6-NP-1-1)

Intermediate Tf-2 (600.0 mg) and benzophenone imine (258 μL; TCI) were added to a toluene (5.1 mL) solution of $Pd_2(dba)_3$ (58.8 mg; Ald), 1,1-bis(diphenylphosphino)ferrocene (106.7 mg; TCI), and sodium t-butoxide (246.7 mg; TCI) under a nitrogen atmosphere and the resulting mixture was stirred at 80° C. for 6 hours. The resulting mixture was stirred at room temperature for approx. 10 minutes, then dichloromethane (2 mL) was added to the reaction mixture solution, the resulting mixture was filtrated through celite, and the filtrate was concentrated under reduced pressure. Methanol (77 mL), hydroxylammonium chloride (178.4 mg; KANTO), and sodium acetate (273.3 mg; WAKO) were added successively to the residue, then the resulting mixture was stirred at room temperature for 1 hour, then the solvent was evaporated under reduced pressure, and the residue was purified by silica gel column chromatography (Yamazen; chloroform/methanol) to give the title compound (391.1 mg).

(LCMS: 335.3 (MH+); retention time: 0.77 min; LCMS; condition A)

[Step b]

N-(8-(1-(ethylsulfonyl)piperidin-4-ylamino)iso-quinolin-6-yl)-3-fluoroBenzamide

3-Fluorobenzoic acid (16.8 mg; TCI), HOAt (16.3 mg; Wata), WSC (34.4 mg; TCI), and triethylamine (42 μL) were added to a DMF (2 mL) solution of Intermediate 6-NP-1-1 (20 mg) and the resulting mixture was stirred at room temperature for 12 and half hours. The solvent was evaporated, then dichloromethane and 1 N aqueous sodium hydroxide solution were added to extract the reaction mixture, the solvent was evaporated under reduced pressure, and the residue was purified by column chromatography (Yamazen; chloroform/methanol) to give the title compound (9.8 mg).

(LCMS: 457.5 (MH+); retention time: 1.11 min; LCMS; condition A)

Example 6-NP-2

N-(8-(1-(ethylsulfonyl)piperidin-4-ylamino)iso-quinolin-6-yl)-4-(1H-imidazol-1-yl)benzamide (LCMS: 505.4 (MH+); retention time: 0.75 min; LCMS; condition A)

Example 6-NP-3

N-(8-(1-(ethylsulfonyl)piperidin-4-ylamino)iso-quinolin-6-yl)-2-methylisonicotinamide (LCMS: 454.3 (MH+); retention time: 0.86 min; LCMS; condition A)

Example 6-NP-4

3-cyano-N-(8-(1-(ethylsulfonyl)piperidin-4-ylamino)isoquinolin-6-yl)benzamide (LCMS: 464.3 (MH+); retention time: 1.05 min; LCMS; condition A)

Example 6-NP-5

4-cyano-N-(8-(1-(ethylsulfonyl)piperidin-4-ylamino)isoquinolin-6-yl)benzamide (LCMS: 464.5 (MH+); retention time: 1.01 min; LCMS; condition A)

Example 6-NP-6

4-cyano-N-(8-(1-(ethylsulfonyl)piperidin-4-ylamino)isoquinolin-6-yl)-3-fluorobenzamide (LCMS: 482.3 (MH+); retention time: 1.12 min; LCMS; condition A)

Example 6-NP-7

N-(8-(1-(ethylsulfonyl)piperidin-4-ylamino)iso-quinolin-6-yl)-6-methylnicotinamide (LCMS: 454.3 (MH+); retention time: 0.89 min; LCMS; condition A)

Example 6-NP-8

N-(8-(1-(ethylsulfonyl)piperidin-4-ylamino)iso-quinolin-6-yl)-2-methylbenzamide (LCMS: 453.5 (MH+); retention time: 1.13 min; LCMS; condition A)

Example 6-NP-9

N-(8-(1-(ethylsulfonyl)piperidin-4-ylamino)iso-quinolin-6-yl)benzamide (LCMS: 439.3 (MH+); retention time: 1.12 min; LCMS; condition A)

Example 6-NP-10

N-(8-(1-(ethylsulfonyl)piperidin-4-ylamino)iso-
quinolin-6-yl)isonicotinamide (LCMS: 440.2 (MH⁺); retention time: 0.85 min; LCMS; condition A)

Example 6-NP-11

N-(8-(1-(ethylsulfonyl)piperidin-4-ylamino)iso-
quinolin-6-yl)nicotinamide (LCMS: 440.3 (MH⁺); retention time: 0.85 min; LCMS; condition A)

Compounds of Examples 6-NP-2, 6-NP-3, 6-NP-4, 6-NP-5, 6-NP-6, 6-NP-7, 6-NP-8, 6-NP-9, 6-NP-10, and 6-NP-11 were synthesized by using 4-(1H-imidazol-1-yl)benzoic acid, 2-methylpyridine-4-carboxylic acid, 3-cyanobenzoic acid, 4-cyanobenzoic acid, 4-cyano-3-fluorobenzoic acid, 6-methylnicotinic acid, 2-toluoylic acid, benzoic acid, isonicotinic acid, nicotinic acid, respectively, instead of 3-fluorobenzoic acid described in Step b of Example 6-NP-1.

Tables Ar, a, oh, sh, co, so, ch, on, sbo, sa, sch, ssh, sco, sso, sch, and son are shown as below.

TABLE Ar

| Ar | Str. |
|---|---|
| Ar1 | 3-cyanophenyl |
| Ar2 | 3-chlorophenyl |
| Ar3 | pyridin-3-yl |
| Ar4 | 3-cyano-4-fluorophenyl |
| Ar5 | 4-(tert-butoxymethyl)phenyl |
| Ar6 | 4-((Boc-amino)methyl)phenyl |
| Ar7 | 4-(hydroxymethyl)phenyl |
| Ar8 | 4-(aminomethyl)phenyl |
| Ar9 | 3-isopropylphenyl |
| Ar10 | 3-(trifluoromethyl)phenyl |
| Ar11 | 3-acetylphenyl |
| Ar12 | 3-aminophenyl |
| Ar13 | 3-fluorophenyl |
| Ar14 | 3-(aminomethyl)phenyl |
| Ar15 | 4-fluorophenyl |
| Ar16 | thiophen-3-yl |
| Ar17 | 3-methoxyphenyl |
| Ar18 | 4-cyanophenyl |
| Ar19 | 3-methylphenyl |
| Ar20 | 3-cyano-4-fluorophenyl |

TABLE Ar-continued

| Ar | Str. |
|---|---|
| Ar21 | 4-acetylphenyl |
| Ar22 | 1-methyl-1H-pyrazol-4-yl |
| Ar23 | 3-(hydroxymethyl)phenyl |
| Ar24 | 2-fluoropyridin-3-yl |
| Ar25 | phenyl |
| Ar26 | 1H-pyrrol-2-yl |
| Ar27 | biphenyl-3-yl |
| Ar28 | furan-3-yl |
| Ar29 | 3-(methylsulfonyl)phenyl |
| Ar30 | 3-carbamoylphenyl |
| Ar31 | 3-acetamidophenyl |
| Ar32 | pyrimidin-5-yl |

TABLE Ar-continued

| Ar | Str. |
|---|---|
| Ar33 | 3-bromophenyl |
| Ar34 | 2-cyanophenyl |
| Ar35 | 3-hydroxyphenyl |
| Ar36 | thiophen-2-yl |
| Ar37 | 5-cyanothiophen-2-yl |
| Ar38 | 5-chlorothiophen-2-yl |
| Ar39 | 3-(dimethylamino)phenyl |
| Ar40 | 3-carboxyphenyl |
| Ar41 | 4-cyano-3-fluorophenyl |
| Ar42 | 3-(2-cyanoethyl)phenyl |
| Ar43 | 4-cyano-3-methylphenyl |
| Ar44 | 3-cyano-5-fluorophenyl |
| Ar45 | 4-amino-3-cyanophenyl |

TABLE Ar-continued
| Ar | Str. |
|---|---|
| Ar46 | 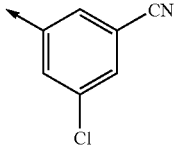 |
| Ar47 | 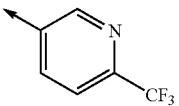 |
| Ar48 | 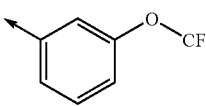 |
| Ar49 | 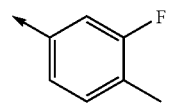 |
| Ar50 | 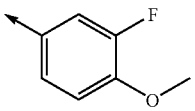 |
| Ar52 | 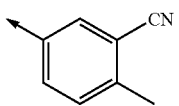 |
| Ar53 | 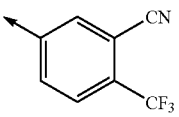 |
| Ar54 | 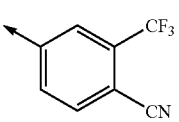 |
| Ar55 | 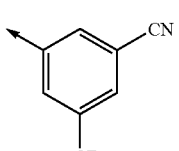 |
| Ar56 | 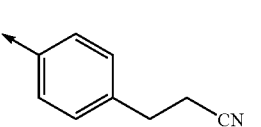 |
| Ar57 | 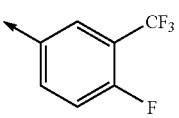 |
| Ar58 | 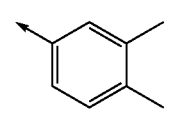 |
TABLE Ar-continued
| Ar | Str. |
|---|---|
| Ar59 | 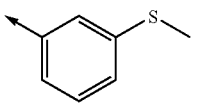 |
| Ar60 | 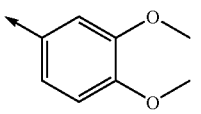 |
| Ar61 | 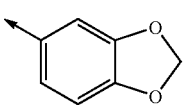 |
| Ar62 | 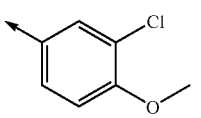 |
| Ar63 | 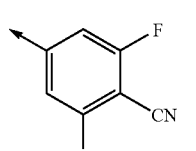 |
| Ar64 | 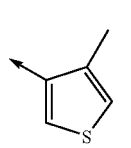 |
| Ar65 | 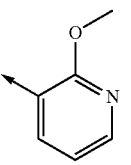 |
| Ar66 | 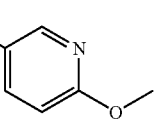 |
| Ar67 | 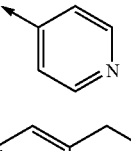 |
| Ar68 | 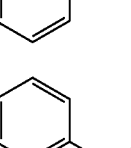 |
| Ar69 | 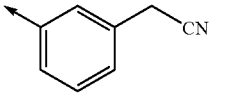 |
| Ar70 | 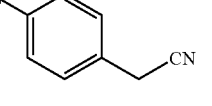 |

TABLE Ar-continued
| Ar | Str. |
|---|---|
| Ar71 | 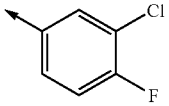 |
| Ar72 | 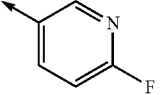 |
| Ar73 | 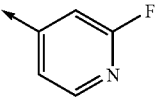 |
| Ar74 | 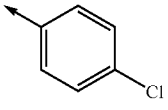 |
| Ar75 | 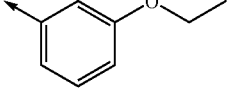 |
| Ar76 | 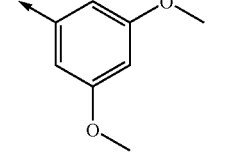 |
| Ar77 | 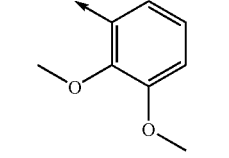 |
| Ar78 | 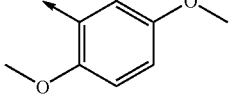 |
| Ar79 | 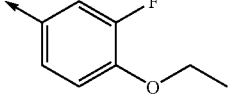 |
| Ar80 | 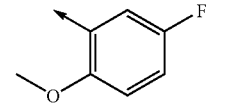 |
| Ar81 | 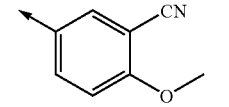 |
| Ar82 | 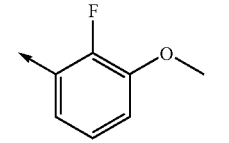 |
TABLE Ar-continued
| Ar | Str. |
|---|---|
| Ar83 | 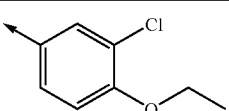 |
| Ar84 | 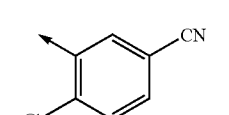 |
| Ar85 | 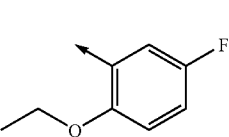 |
| Ar86 | 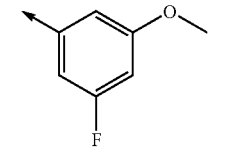 |
| Ar87 | 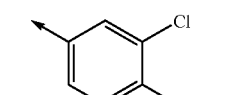 |
| Ar88 | 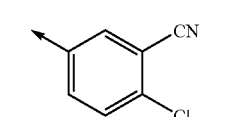 |
| Ar89 | 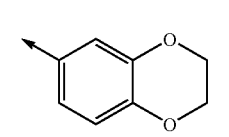 |
| Ar90 | 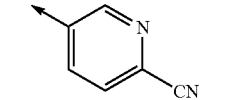 |
| Ar91 | 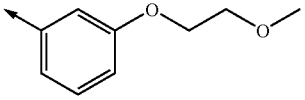 |
| Ar92 | 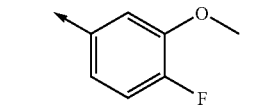 |
| Ar93 | 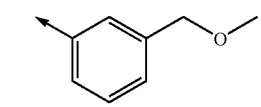 |
| Ar94 | 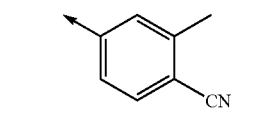 |

TABLE Ar-continued
| Ar | Str. |
|---|---|
| Ar95 | 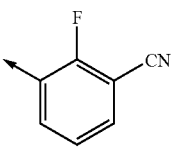 |
| Ar96 | 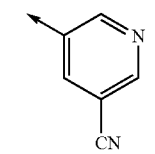 |
| Ar97 | 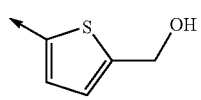 |
| Ar98 | 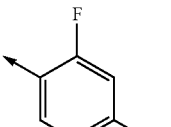 |
| Ar99 | 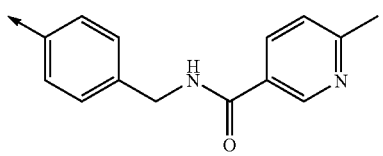 |
| Ar100 | 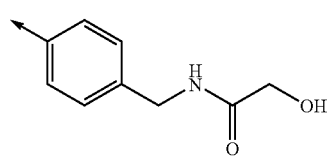 |
| Ar101 | 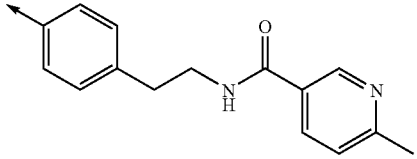 |
| Ar102 | 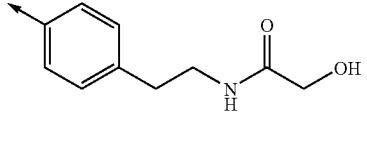 |
| Ar103 | 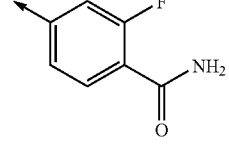 |
| Ar104 | 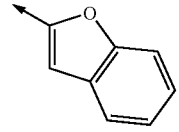 |
TABLE Ar-continued
| Ar | Str. |
|---|---|
| Ar105 | 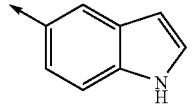 |
| Ar106 | 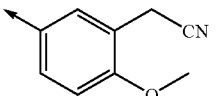 |
| Ar107 | 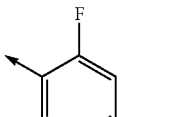 |
| Ar108 | 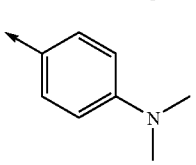 |
| Ar109 | 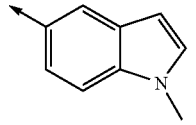 |
| Ar110 | 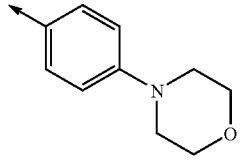 |
| Ar111 | 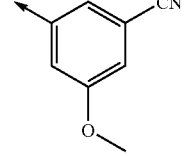 |
| Ar112 | 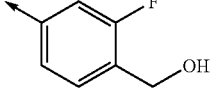 |
| Ar113 | 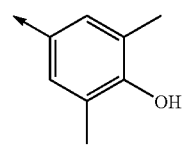 |
| Ar114 | 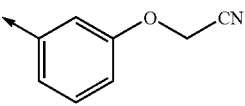 |
| Ar115 | 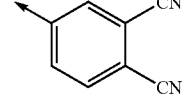 |

TABLE Ar-continued
| Ar | Str. |
|---|---|
| Ar116 | 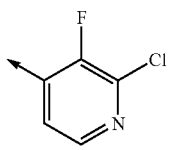 |
| Ar117 | 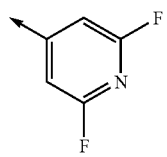 |
| Ar118 | 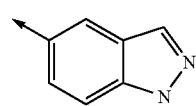 |
| Ar119 | 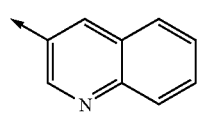 |
| Ar120 | 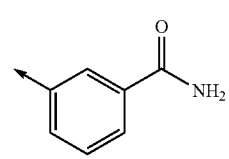 |
| Ar121 | 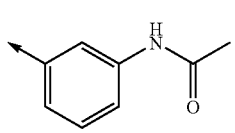 |
| Ar122 | 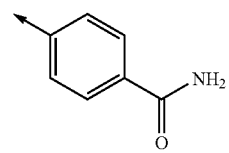 |
| Ar123 | 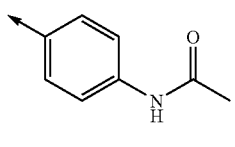 |
| Ar124 | 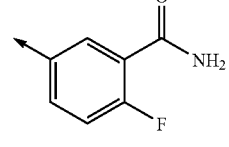 |
| Ar125 | 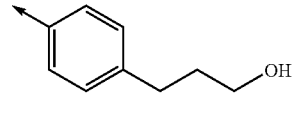 |
| Ar126 | 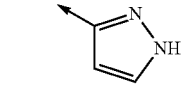 |
TABLE Ar-continued
| Ar | Str. |
|---|---|
| Ar127 | 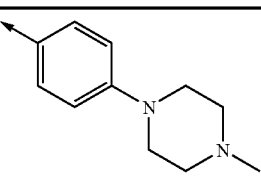 |
| Ar128 | 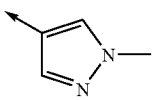 |
| Ar129 | 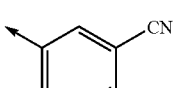 |
| Ar130 | 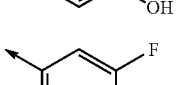 |
| Ar131 | 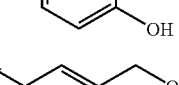 |
| Ar132 | 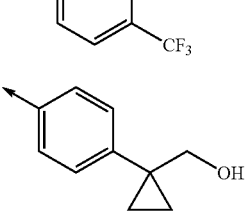 |
| Ar133 | 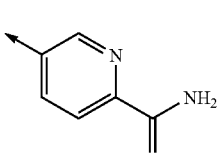 |
| Ar134 | 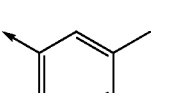 |
| Ar135 | 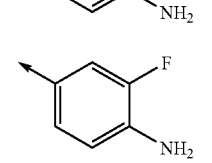 |
| Ar136 |  |
| Ar137 | 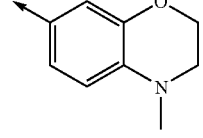 |
| Ar138 | 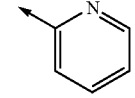 |

TABLE Ar-continued
| Ar | Str. |
|---|---|
| Ar139 | 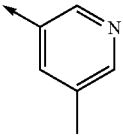 |
| Ar140 | 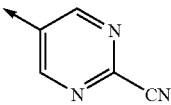 |
| Ar141 | 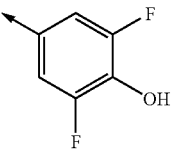 |
| Ar142 | 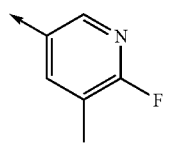 |
| Ar143 | 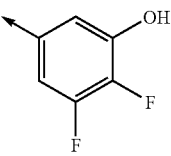 |
| Ar144 | 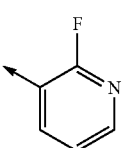 |
| Ar145 | 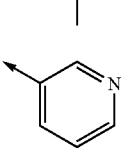 |
| Ar146 | 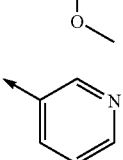 |
| Ar147 | 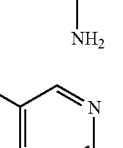 |
| Ar148 | 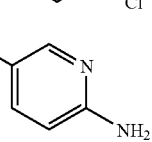 |
TABLE Ar-continued
| Ar | Str. |
|---|---|
| Ar149 | 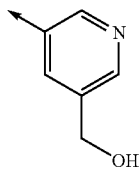 |
| Ar150 | 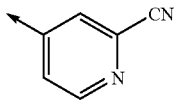 |
| Ar151 | 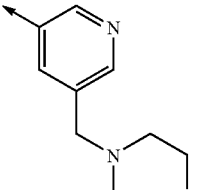 |
| Ar152 | 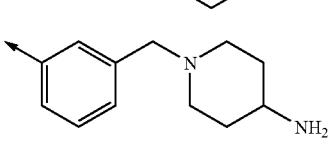 |
| Ar153 | 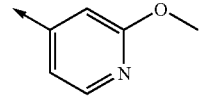 |
| Ar154 | 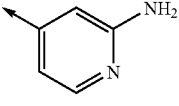 |
| Ar155 | 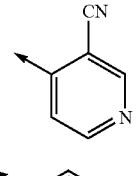 |
| Ar156 | 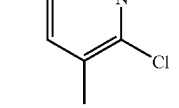 |
| Ar157 | 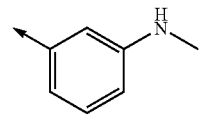 |
| Ar158 | 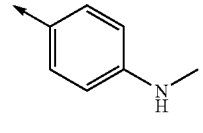 |
| Ar159 | 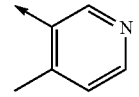 |

TABLE Ar-continued
| Ar | Str. |
|---|---|
| Ar160 | 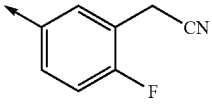 |
| Ar161 | 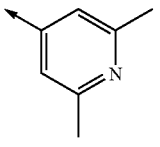 |
| Ar162 | 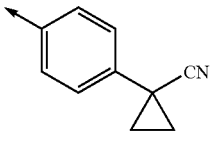 |
| Ar163 | 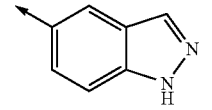 |
| Ar164 | 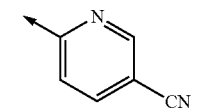 |
| Ar165 | 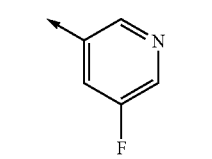 |
| Ar166 | 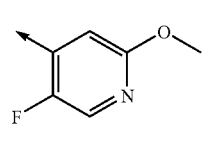 |
| Ar167 | 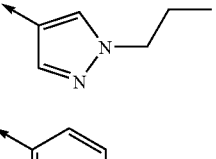 |
| Ar168 | 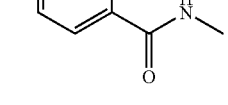 |
| Ar169 | 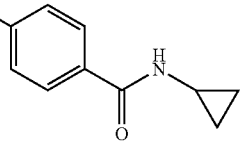 |
| Ar170 | 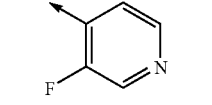 |
| Ar171 |  |
| Ar172 | 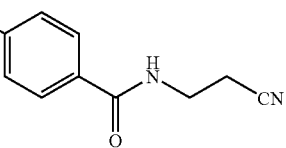 |
| Ar173 | 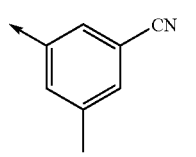 |
| Ar174 | 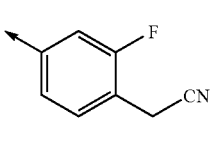 |
| Ar175 | 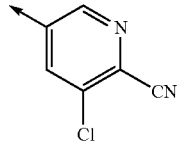 |
| Ar176 | 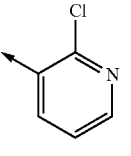 |
| Ar177 | 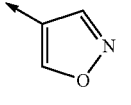 |
| Ar178 | 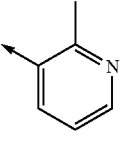 |
| Ar179 | 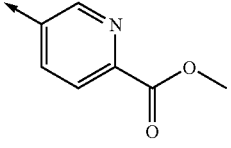 |
| Ar180 | 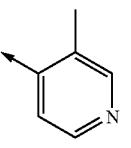 |

US 8,299,055 B2
TABLE Ar-continued
| Ar | Str. |
|---|---|
| Ar181 | 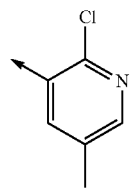 |
| Ar182 | 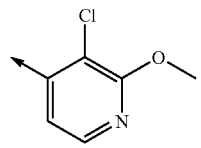 |
| Ar183 | 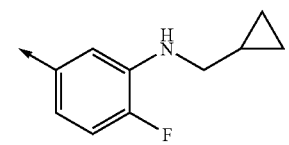 |
| Ar184 | 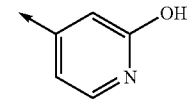 |
| Ar185 | 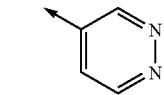 |
| Ar186 | 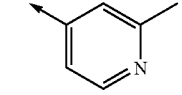 |
| Ar187 | 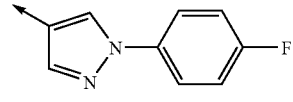 |
| Ar188 | 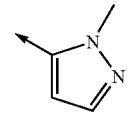 |
| Ar189 | 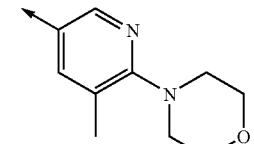 |
| Ar190 | 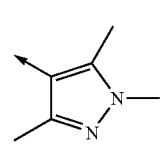 |
| Ar191 | 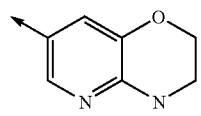 |
TABLE Ar-continued
| Ar | Str. |
|---|---|
| Ar192 | 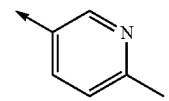 |
| Ar193 | 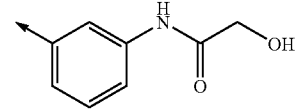 |
| Ar194 | 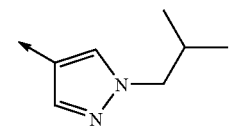 |
| Ar195 | 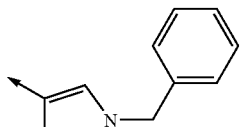 |
| Ar196 | 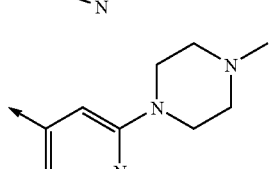 |
| Ar197 | 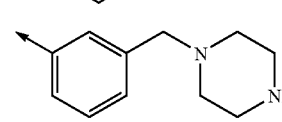 |
| Ar198 | 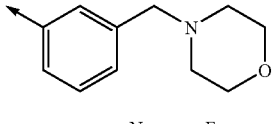 |
| Ar199 | 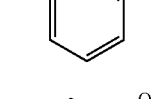 |
| Ar200 | 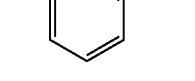 |
| Ar201 | 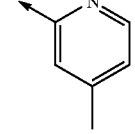 |
| Ar202 | 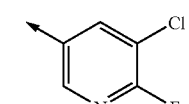 |
| Ar203 | 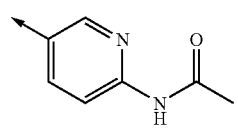 |

TABLE Ar-continued

| Ar | Str. |
|---|---|
| Ar204 | (2,5-dimethylfuran) |
| Ar205 | (2,5-dimethylthiophene) |
| Ar206 | (2,4-dimethylthiophene) |
| Ar207 | (2-amino-3-methylpyridin-5-yl) |
| Ar208 | (2-methylaminopyridin-5-yl) |
| Ar209 | (2-ethylaminopyridin-5-yl) |
| Ar210 | (5-trifluoromethylpyridin-3-yl) |
| Ar211 | (2-fluoro-6-methylpyridin-3-yl) |
| Ar212 | (3-cyclobutylaminophenyl) |
| Ar213 | (3-isobutylamino-4-fluorophenyl) |
| Ar214 | (2-methyl-4-isobutylaminophenyl) |

TABLE Ar-continued

| Ar | Str. |
|---|---|
| Ar215 | (5-chloropyridin-3-yl) |
| Ar216 | (5-methylsulfonylpyridin-3-yl) |
| Ar217 | (imidazo[1,2-a]pyridin-6-yl) |
| Ar218 | (1-methylbenzimidazol-6-yl) |
| Ar219 | (1-ethylpyrazol-4-yl) |
| Ar220 | (1,5-dimethylpyrazol-4-yl) |
| Ar221 | (1-methylpyrrol-2-yl) |
| Ar222 | (1-methylindol-2-yl) |
| Ar223 | (2,4-dimethylthiazol-5-yl) |
| Ar224 | (4-(pyrazol-1-yl)phenyl) |
| Ar225 | (1,3-dimethylpyrazol-4-yl) |

TABLE Ar-continued
| Ar | Str. |
|---|---|
| Ar226 | 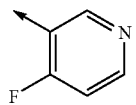 |
| Ar227 | 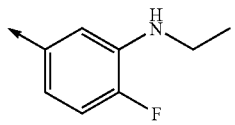 |
| Ar228 | 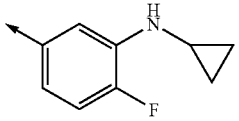 |
| Ar229 | 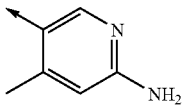 |
| Ar230 | 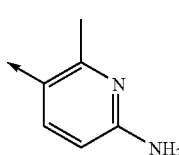 |
| Ar231 | 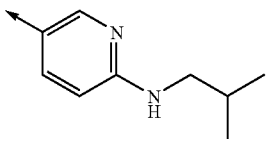 |
| Ar232 | 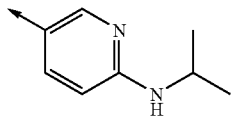 |
| Ar233 | 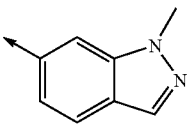 |
| Ar234 | 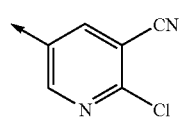 |
| Ar235 | 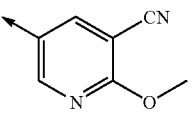 |
| Ar236 | 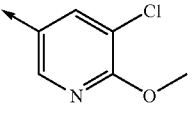 |
| Ar237 | 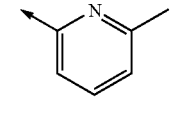 |
TABLE Ar-continued
| Ar | Str. |
|---|---|
| Ar238 | 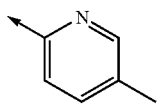 |
| Ar239 | 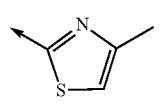 |
| Ar240 | 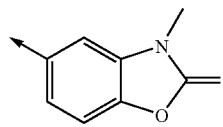 |
| Ar241 | 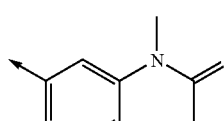 |
| Ar242 | 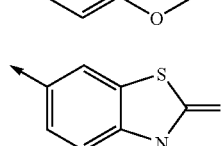 |
| Ar243 | 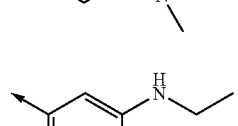 |
| Ar244 | 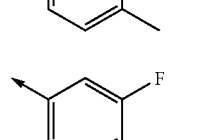 |
| Ar245 | 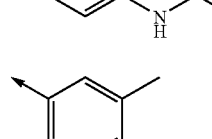 |
| Ar246 | 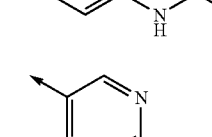 |
| Ar247 | 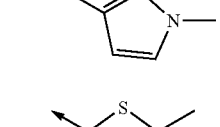 |
| Ar248 | 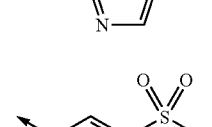 |

TABLE Ar-continued
| Ar | Str. |
|---|---|
| Ar249 | 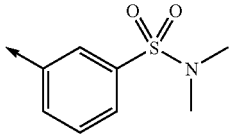 |
| Ar250 | 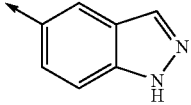 |
| Ar251 | 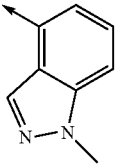 |
| Ar252 | 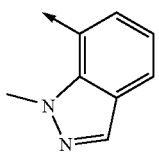 |
| Ar253 | 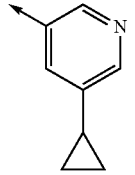 |
| Ar254 | 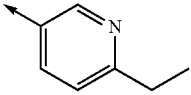 |
| Ar255 | 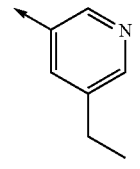 |
| Ar256 | 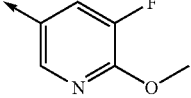 |
| Ar257 | 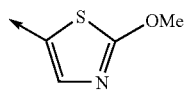 |
| Ar258 | 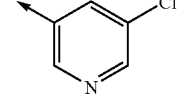 |
| Ar259 | 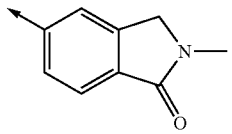 |
TABLE Ar-continued
| Ar | Str. |
|---|---|
| Ar260 | 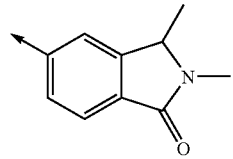 |
| Ar261 | 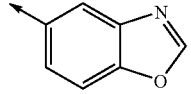 |
| Ar262 | 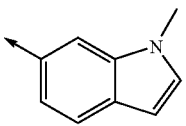 |
| Ar263 | 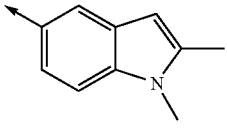 |
| Ar264 | 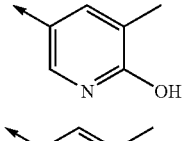 |
| Ar265 | 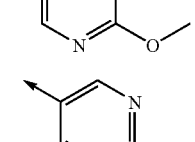 |
| Ar266 | 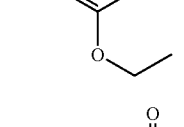 |
| Ar267 | 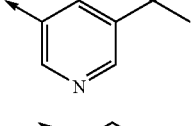 |
| Ar268 | 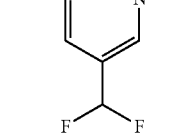 |
| Ar269 | 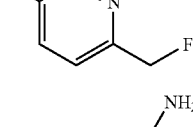 |
| Ar270 | 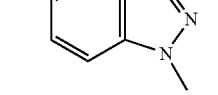 |

TABLE Ar-continued
| Ar | Str. |
|---|---|
| Ar271 | 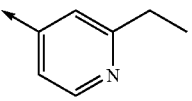 |
| Ar272 | 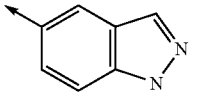 |
| Ar273 | 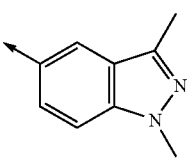 |
| Ar274 | 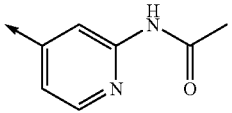 |
| Ar275 | 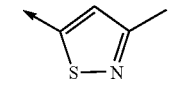 |
| Ar276 | 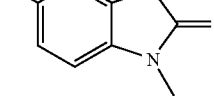 |
| Ar277 | 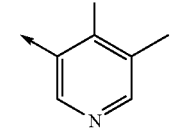 |
| Ar278 | 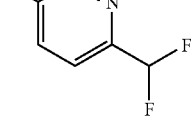 |
| Ar279 | 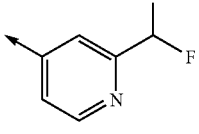 |
| Ar280 | 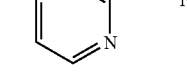 |
| Ar281 | 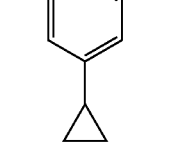 |
TABLE Ar-continued
| Ar | Str. |
|---|---|
| Ar282 | 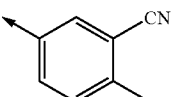 |
| Ar283 | 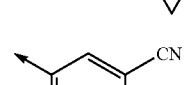 |
| Ar284 | 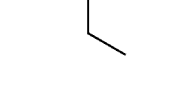 |
| Ar285 | 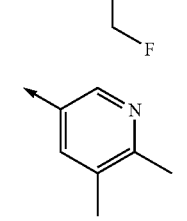 |
| Ar286 | 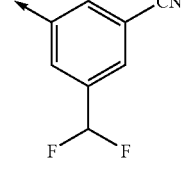 |
| Ar287 | 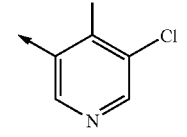 |
| Ar288 | 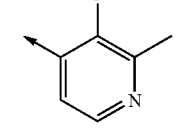 |
| Ar289 | 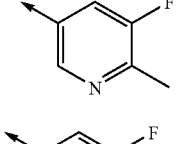 |
| Ar290 | 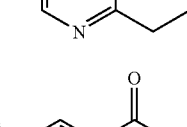 |
| Ar291 | 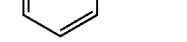 |

TABLE Ar-continued
| Ar | Str. |
|---|---|
| Ar292 | 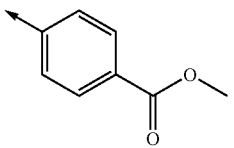 |
| Ar293 | 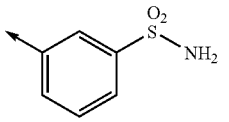 |
| Ar294 | 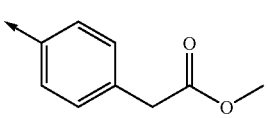 |
| Ar295 | 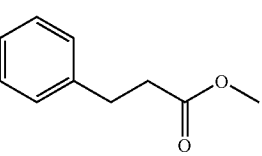 |
| Ar296 | 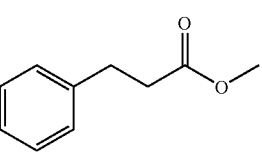 |
| Ar297 | 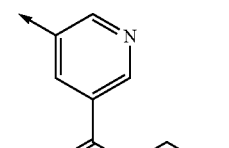 |
| Ar300 | 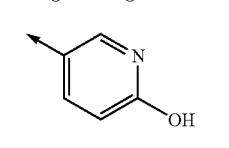 |
| Ar304 | 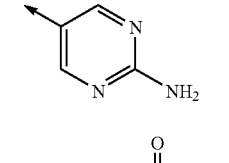 |
| Ar305 | 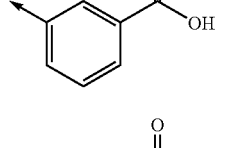 |
| Ar306 | 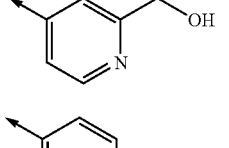 |
| Ar307 | 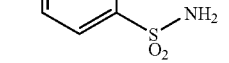 |
TABLE Ar-continued
| Ar | Str. |
|---|---|
| Ar308 | 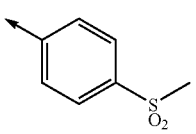 |
| Ar309 | 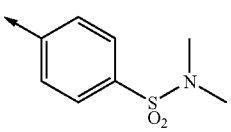 |
| Ar310 | 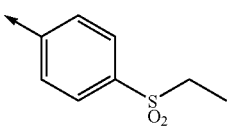 |
| Ar312 | 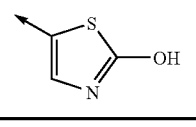 |
TABLE a
| a | Str. |
|---|---|
| a1 | 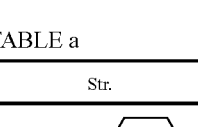 |
| a2 | 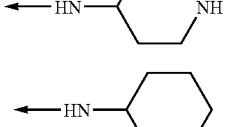 |
| a3 | 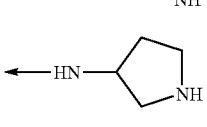 |
| a4 | 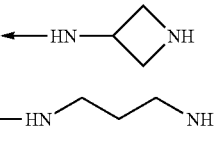 |
| a5 | 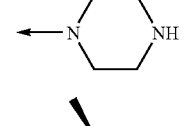 |
| a6 | 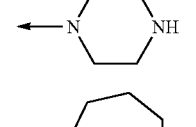 |
| a7 | 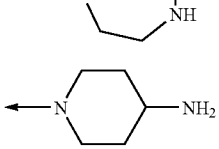 |
| a8 |  |
| a9 |  |

TABLE a-continued

| a | Str. |
|---|---|
| a10 | pyrrolidine with NH2 |
| a11 | cyclohexane-1,4-diamine linker |
| a12 | CH2-piperidine (4-) |
| a13 | CH2-piperidine (3-) |
| a14 | CH2-piperidine (2-) |
| a15 | CH2-pyrrolidine (3-) |
| a16 | CH2-pyrrolidine (2-) |
| a17 | CH2-azetidine |
| a18 | cyclohexyl |
| a19 | CH2-pyridin-3-yl |
| a20 | CH2CH2-pyrrolidine |
| a21 | CH2CH2-morpholine |
| a22 | (CH2)3-imidazol-1-yl |
| a23 | CH2CH2OH |
| a24 | (CH2)3OH |

TABLE a-continued

| a | Str. |
|---|---|
| a25 | CH(CH2OH)2 |
| a26 | 1-methylpiperidin-4-yl |
| a27 | (R)-pyrrolidin-3-yl |
| a28 | (S)-pyrrolidin-3-yl |
| a29 | 4-methylpiperazin-1-yl |
| a30 | N-methyl-piperidin-4-yl |
| a31 | N-methyl-[1-(2,6-dimethoxybenzyl)piperidin-4-yl] |
| a32 | 1-benzylpyrrolidin-3-yl |
| a33 | cis-4-aminocyclohexyl |
| a34 | trans-4-aminocyclohexyl |
| a35 | (CH2)3NHCH3 |
| a36 | (CH2)4NH2 |

TABLE oh

| oh | Str. |
|---|---|
| oh1 | O-piperidin-4-yl |

TABLE oh-continued
| oh | Str. |
|---|---|
| oh2 | 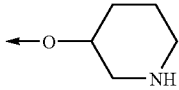 |
| oh3 | 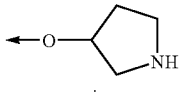 racine |
| oh4 | 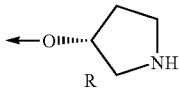 R |
| oh5 | 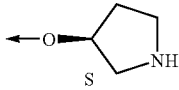 S |
| oh6 | 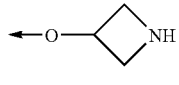 |
| oh7 | 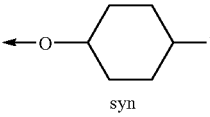 syn |
| oh8 | 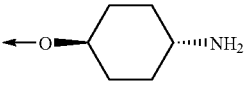 anti |
| oh10 | 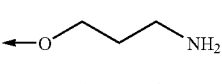 |
| oh11 | 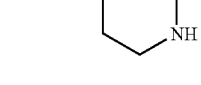 |
| oh12 | 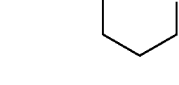 |
| oh13 | 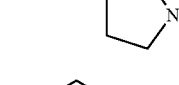 |
| oh15 | 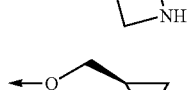 |
| oh16 |  syn |
| oh18 | 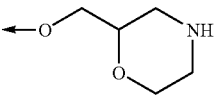 |
TABLE oh-continued
| oh | Str. |
|---|---|
| oh19 | 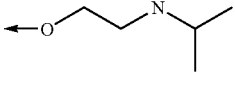 |
| oh20 | 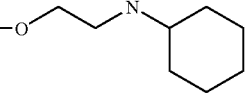 |
| oh21 | 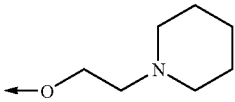 |
| oh23 | 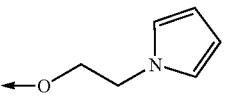 |
| oh24 | 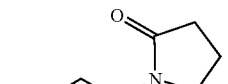 |
| oh25 | 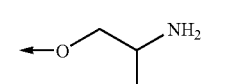 |
| oh26 | 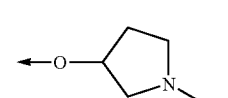 |
| oh27 | 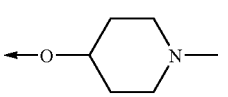 |
| oh28 | 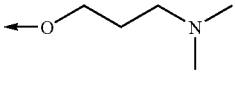 |
| oh33 | 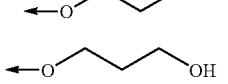 |
| oh34 | 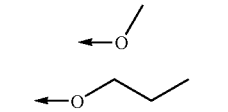 |
| oh35 | 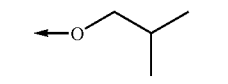 |
| oh36 | 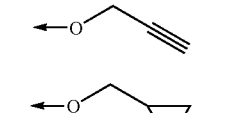 |
| oh37 | 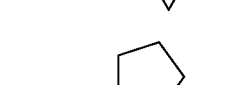 |
| oh38 | 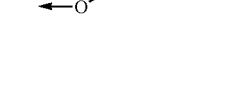 |
| oh39 |  |
| oh40 |  |

TABLE oh-continued

| oh | Str. |
|---|---|
| oh41 | ←O-CH2-(2-thienyl) |
| oh42 | ←O-CH2-(3-thienyl) |
| oh43 | ←O-(tetrahydrofuran-3-yl) |
| oh44 | ←O-CH2-(tetrahydrofuran-2-yl) |
| oh45 | ←O-CH2-(furan-2-yl) |
| oh47 | ←O-CH2CH2-O-CH3 |
| oh49 | ←O-CH2-(3-cyanophenyl) |
| oh50 | ←O-CH2-(4-cyanophenyl) |
| oh51 | (2S,4R)-4-oxy-pyrrolidine-2-carboxylic acid |
| oh52 | 4-oxy-cyclohexane-1-carboxylic acid |
| oh54 | ←O-CH2-(pyridin-2-yl) |
| oh55 | ←O-(3-methylpiperidin-4-yl) |

TABLE sh

| sh | Str. | sh | Str. |
|---|---|---|---|
| sh1 | ←S-(piperidin-4-yl) | sh2 | ←S-CH2CH2-NH2 |

TABLE co

| co | Str. |
|---|---|
| co1 | ←C(=O)CH3 |
| co2 | ←C(=O)-cyclopropyl |
| co3 | ←C(=O)-(2-methylphenyl) |
| co4 | ←C(=O)-(2-(methylsulfonylamino)phenyl) |
| co5 | ←C(=O)CH2CH2OH |
| co6 | ←C(=O)-(6-cyanopyridin-3-yl) |
| co7 | ←C(=O)CH2CH3 |
| co8 | ←C(=O)-(3-methylphenyl) |
| co9 | ←C(=O)-(4-methylphenyl) |

TABLE co-continued

| co | Str. |
|---|---|
| co10 | 2-fluorobenzoyl |
| co11 | 3-fluorobenzoyl |
| co12 | 4-fluorobenzoyl |
| co13 | 2-chlorobenzoyl |
| co14 | 3-chlorobenzoyl |
| co15 | 4-chlorobenzoyl |
| co16 | 2-cyanobenzoyl |
| co17 | 3-cyanobenzoyl |
| co18 | 4-cyanobenzoyl |
| co19 | 2-(COOMe)benzoyl |

TABLE co-continued

| co | Str. |
|---|---|
| co20 | 3-(COOMe)benzoyl |
| co21 | 4-(COOMe)benzoyl |
| co22 | 2-methoxybenzoyl |
| co23 | 3-methoxybenzoyl |
| co24 | 4-methoxybenzoyl |
| co25 | 2-(NMe$_2$)benzoyl |
| co26 | 3-(NMe$_2$)benzoyl |
| co27 | 4-(NMe$_2$)benzoyl |
| co28 | pyridine-3-carbonyl |

TABLE co-continued
| co | Str. |
|---|---|
| co29 | 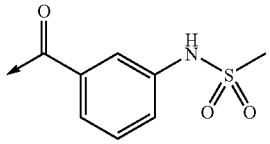 |
| co30 | 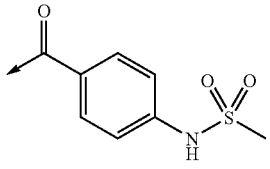 |
| co31 | 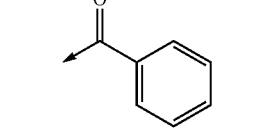 |
| co32 | 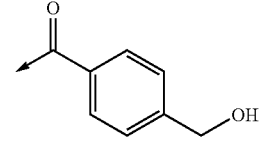 |
| co33 | 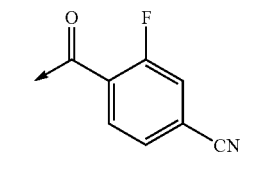 |
| co34 | 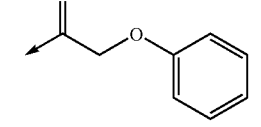 |
| co35 | 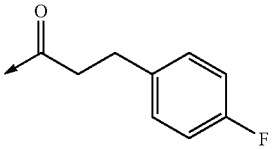 |
| co36 | 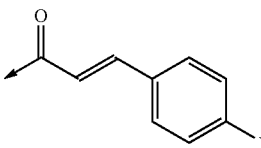 |
| co37 | 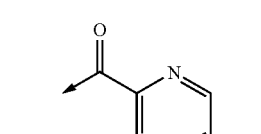 |
TABLE co-continued
| co | Str. |
|---|---|
| co38 | 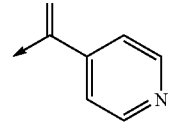 |
| co39 | 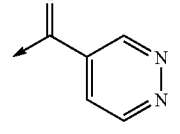 |
| co40 | 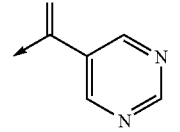 |
| co41 | 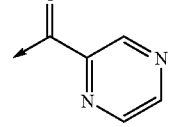 |
| co42 | 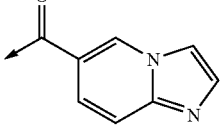 |
| co43 | 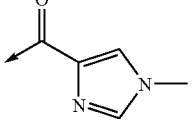 |
| co44 | 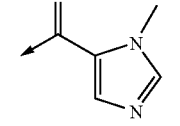 |
| co45 | 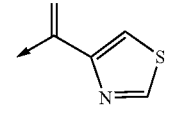 |
| co46 | 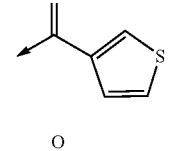 |
| co47 | 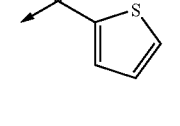 |

| co | Str. |
|---|---|
| co48 | 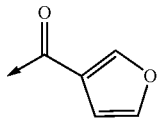 |
| co49 | 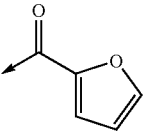 |
| co50 | 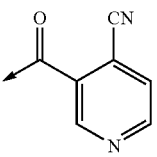 |
| co51 | 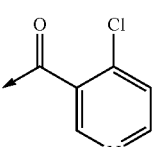 |
| co52 | 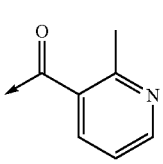 |
| co53 | 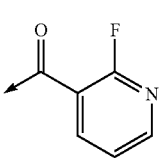 |
| co54 | 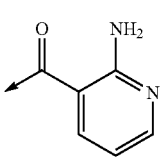 |
| co55 | 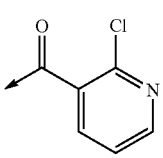 |
| co56 | 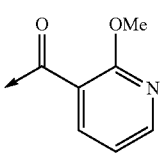 |
| co57 | 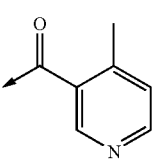 |
| co58 | 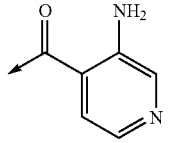 |
| co59 | 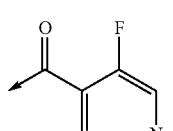 |
| co60 | 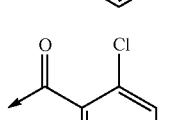 |
| co61 | 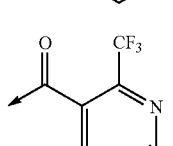 |
| co62 | 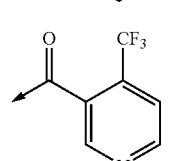 |
| co63 | 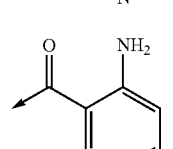 |
| co64 | 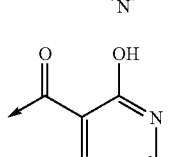 |
| co65 | 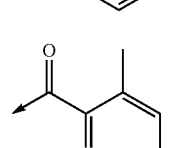 |
| co66 | 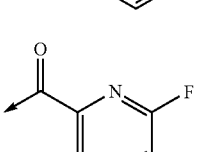 |
| co67 | 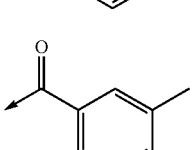 |

TABLE co-continued
| co | Str. |
|---|---|
| co68 | 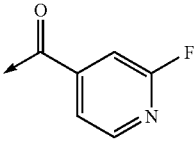 |
| co69 | 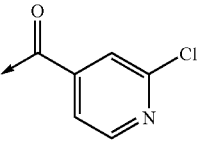 |
| co70 | 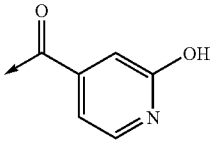 |
| co71 | 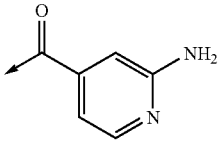 |
| co72 | 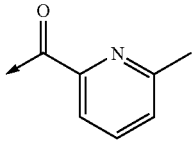 |
| co73 | 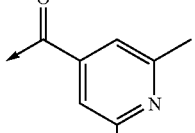 |
| co74 | 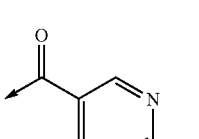 |
| co75 | 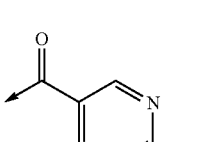 |
| co76 | 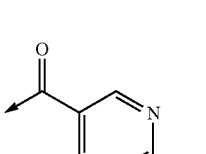 |
TABLE co-continued
| co | Str. |
|---|---|
| co77 | 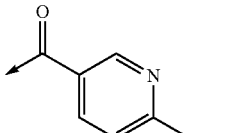 |
| co78 | 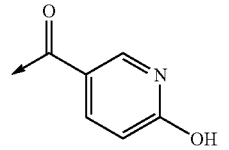 |
| co79 | 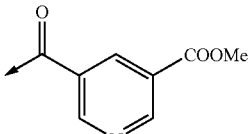 |
| co80 | 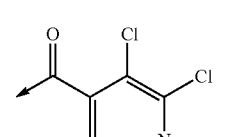 |
| co81 | 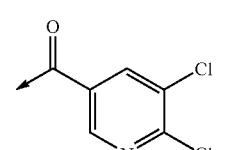 |
| co82 | 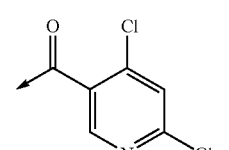 |
| co83 | 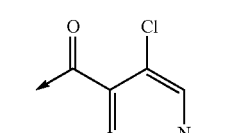 |
| co84 | 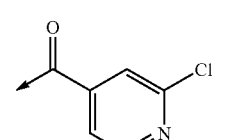 |
| co85 | 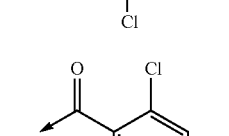 |

TABLE co-continued
| co | Str. |
|---|---|
| co86 | 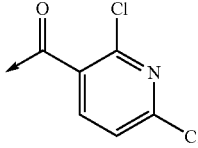 |
| co87 | 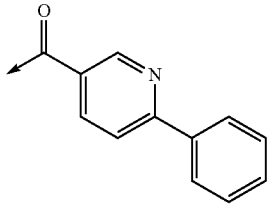 |
| co88 | 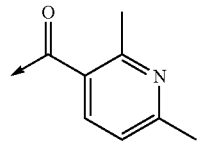 |
| co89 | 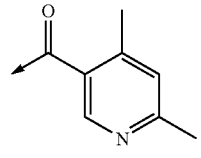 |
| co90 | 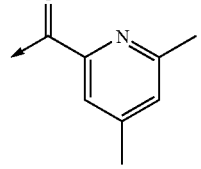 |
| co91 | 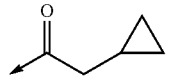 |
| co92 | 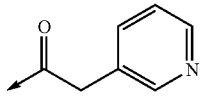 |
| co93 | 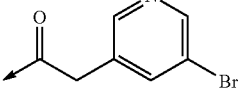 |
| co94 | 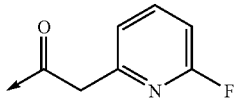 |
| co95 | 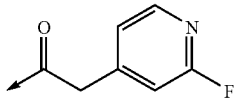 |
| co96 | 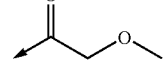 |
TABLE co-continued
| co | Str. |
|---|---|
| co97 | 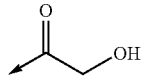 |
| co98 | 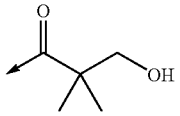 |
| co99 | 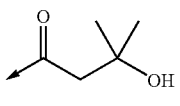 |
| co100 | 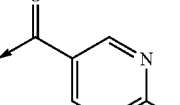 |
| co101 | 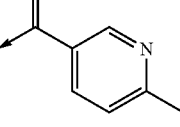 |
| co102 | 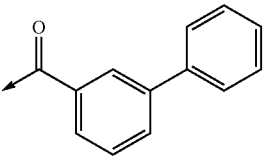 |
| co103 | 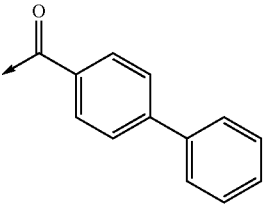 |
| co104 | 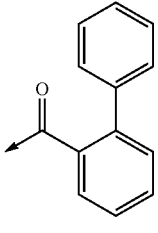 |
| co105 | 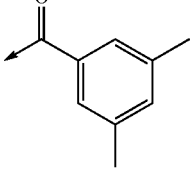 |

TABLE co-continued

| co | Str. |
|---|---|
| co106 | 2,3-dimethylbenzoyl |
| co107 | 2,4,5-trimethylbenzoyl |
| co108 | 3,5-di-tert-butylbenzoyl |
| co109 | 4-bromo-2-fluorobenzoyl |
| co110 | 3-chloro-4-methylbenzoyl |
| co111 | 2-chloro-6-methylbenzoyl |
| co112 | 2,3-difluoro-4-methylbenzoyl |
| co113 | 4-fluoro-3-methylbenzoyl |
| co114 | 4-methyl-3-(trifluoromethyl)benzoyl |

TABLE co-continued

| co | Str. |
|---|---|
| co115 | 4-methyl-2-(trifluoromethyl)benzoyl |
| co116 | 2-methyl-3-(trifluoromethyl)benzoyl |
| co117 | 3,5-bis(trifluoromethyl)benzoyl |
| co118 | 3,4-difluorobenzoyl |
| co119 | 2,4,5-trifluorobenzoyl |
| co120 | 3,5-difluorobenzoyl |
| co121 | 4-fluoro-3-(trifluoromethyl)benzoyl |
| co122 | 3-chloro-4-fluorobenzoyl |
| co123 | 3-bromo-4-fluorobenzoyl |

TABLE co-continued
| co | Str. |
|---|---|
| co124 | 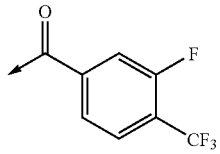 |
| co125 | 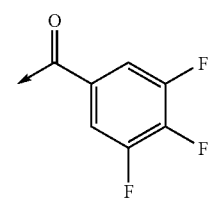 |
| co126 | 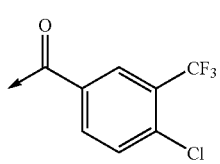 |
| co127 | 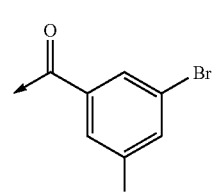 |
| co128 | 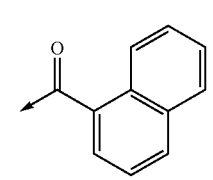 |
| co129 | 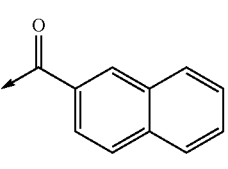 |
| co130 | 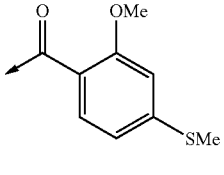 |
| co131 | 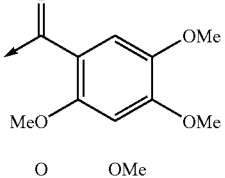 |
| co132 | 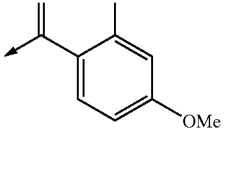 |
TABLE co-continued
| co | Str. |
|---|---|
| co133 | 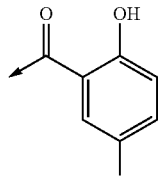 |
| co134 | 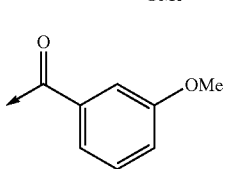 |
| co135 | 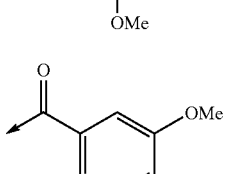 |
| co136 | 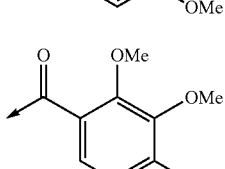 |
| co137 | 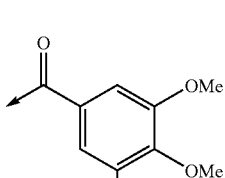 |
| co138 | 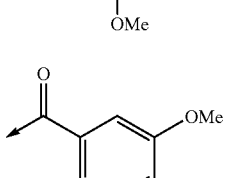 |
| co139 | 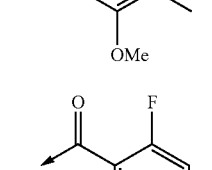 |
| co140 | 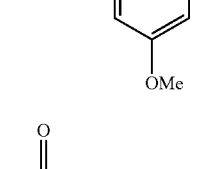 |

TABLE co-continued
| co | Str. |
|---|---|
| co141 | 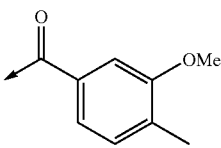 |
| co142 | 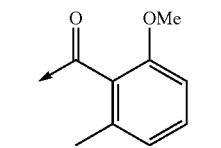 |
| co143 | 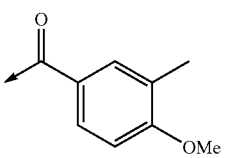 |
| co144 | 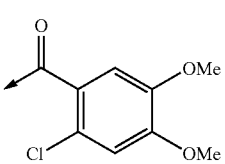 |
| co145 | 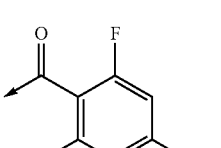 |
| co146 | 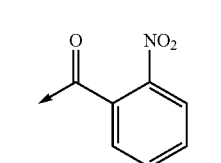 |
| co147 | 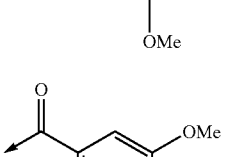 |
| co148 | 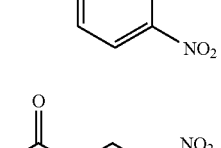 |
| co149 | 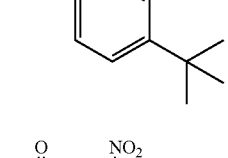 |
TABLE co-continued
| co | Str. |
|---|---|
| co150 | 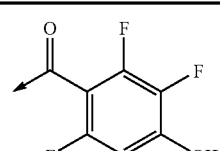 |
| co151 | 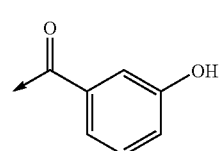 |
| co152 | 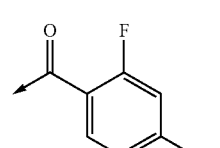 |
| co153 | 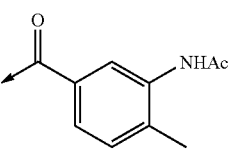 |
| co154 | |
| co155 | |
| co156 | |
| co157 | |

TABLE co-continued
| co | Str. |
|---|---|
| co158 | 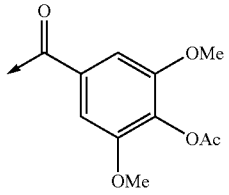 |
| co159 | 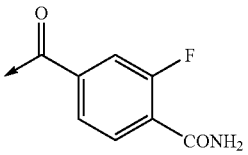 |
| co160 | 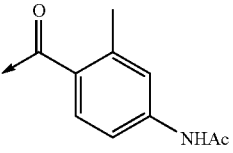 |
| co161 | 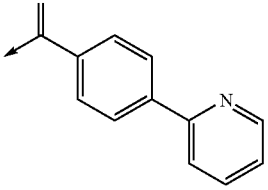 |
| co162 | 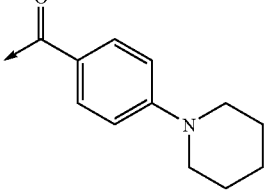 |
| co163 | 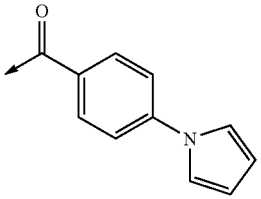 |
| co164 | 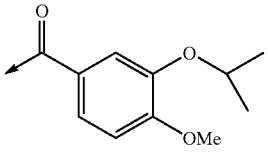 |
| co165 | 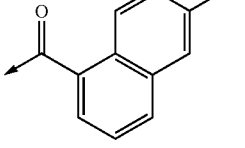 |
TABLE co-continued
| co | Str. |
|---|---|
| co166 | 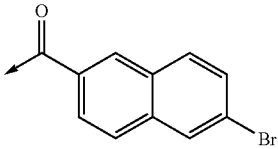 |
| co167 | 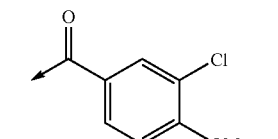 |
| co168 | 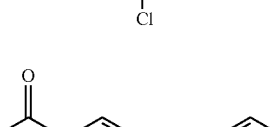 |
| co169 | 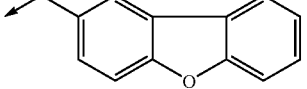 |
| co170 | 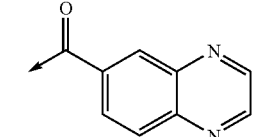 |
| co171 | 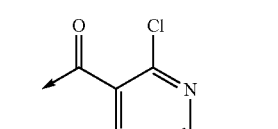 |
| co172 | 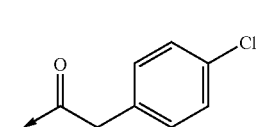 |
| co173 | 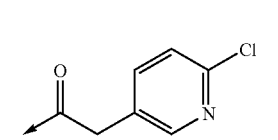 |
| co174 | 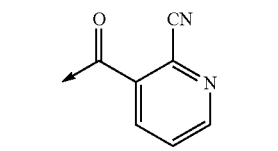 |

TABLE co-continued
| co | Str. |
|---|---|
| co175 | 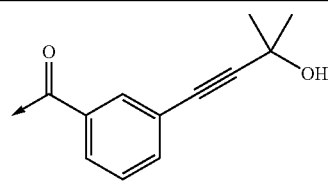 |
| co176 | 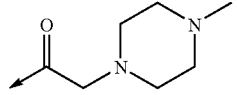 |
| co177 | 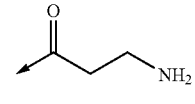 |
| co178 | 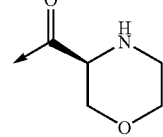 |
| co179 | 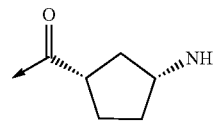 |
| co180 | 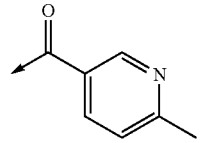 |
| co181 | 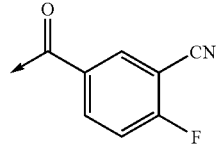 |
| co182 | 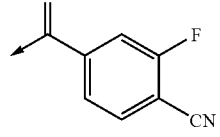 |
| co183 | 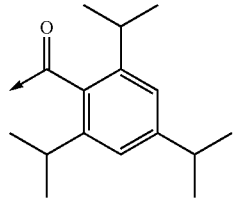 |
| co184 | 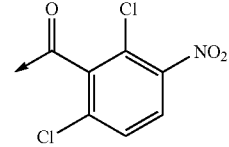 |
TABLE co-continued
| co | Str. |
|---|---|
| co185 | 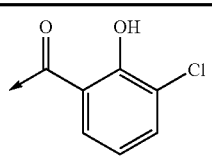 |
| co186 | 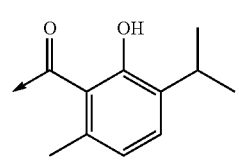 |
| co187 | 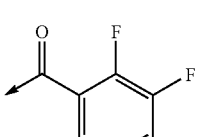 |
| co188 | 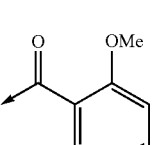 |
| co189 | 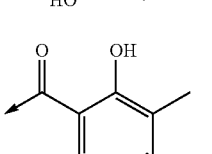 |
| co190 | 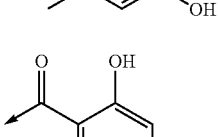 |
| co191 | 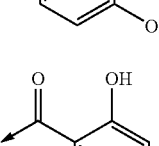 |
| co192 | 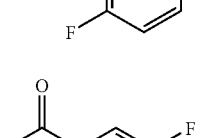 |
| co193 | 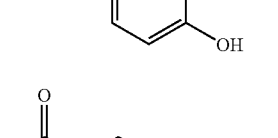 |

| co | Str. |
|---|---|
| co194 | 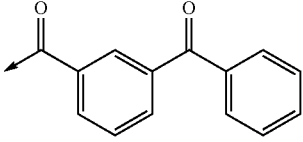 |
| co195 | 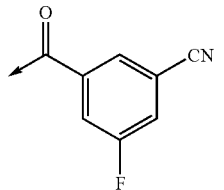 |
| co196 | 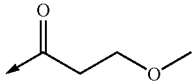 |
| co197 | 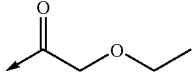 |
| co198 | 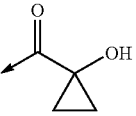 |
| co199 | 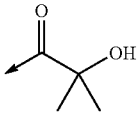 |
| co201 | 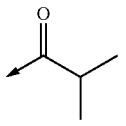 |
| co202 | 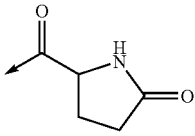 |
| co203 | 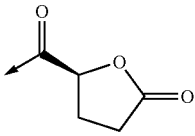 |
| co204 | 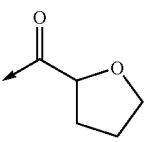 |
| co205 | 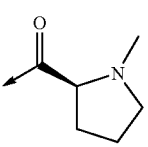 |
| co | Str. |
|---|---|
| co206 | 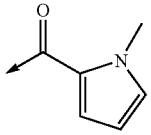 |
| co207 | 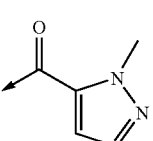 |
| co208 | 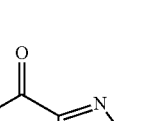 |
| co209 | 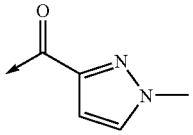 |
| co210 | 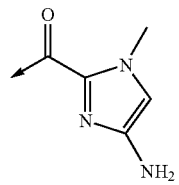 |
| co211 | 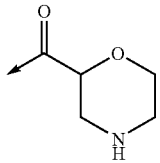 |
| co212 | 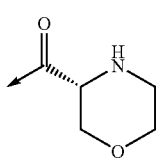 |
| co213 | 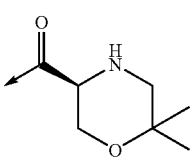 |
| co214 | 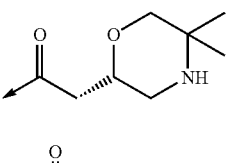 |

TABLE co-continued
| co | Str. |
|---|---|
| co215 | 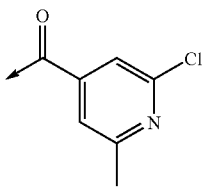 |
| co216 | 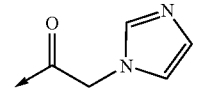 |
| co217 | 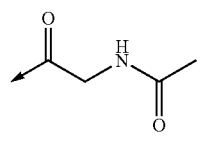 |
| co218 | 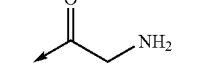 |
| co219 | 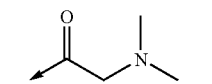 |
| co220 | 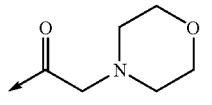 |
| co221 | 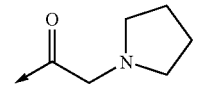 |
| co222 | 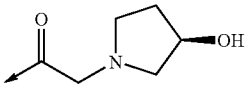 |
| co223 | 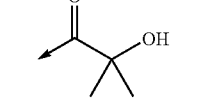 |
| co224 | 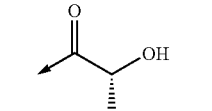 |
| co225 | 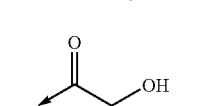 |
| co226 | 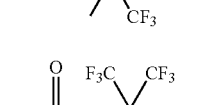 |
| co227 | 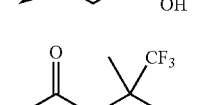 |
TABLE co-continued
| co | Str. |
|---|---|
| co228 | 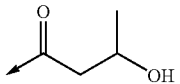 |
| co229 | 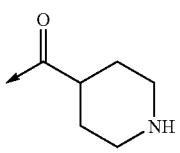 |
| co230 | 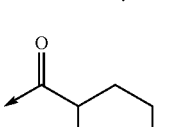 |
| co231 | 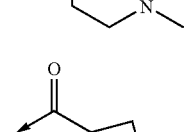 |
| co232 | 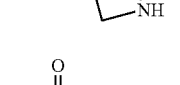 |
| co233 | 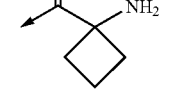 |
| co234 | 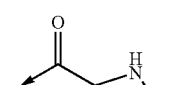 |
| co235 | 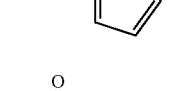 |
| co236 | 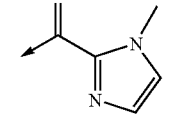 |
| co237 | 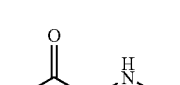 |

TABLE co-continued
| co | Str. |
|---|---|
| co238 | 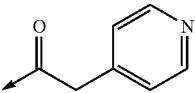 |
| co239 | 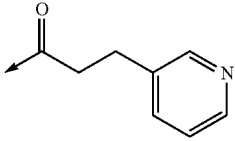 |
| co240 | 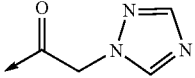 |
| co241 | 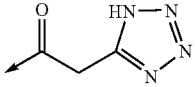 |
| co242 | 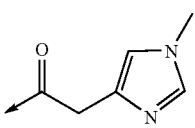 |
| co243 | 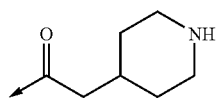 |
| co244 | 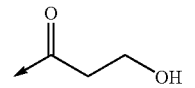 |
| co245 | 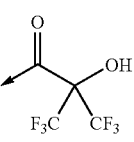 |
| co246 | 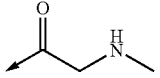 |
| co247 | 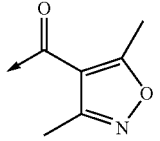 |
| co249 | 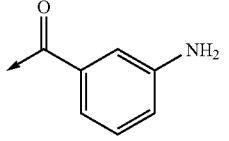 |
| co250 | 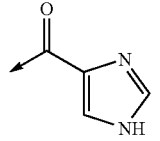 |
TABLE co-continued
| co | Str. |
|---|---|
| co252 |  |
| co253 | 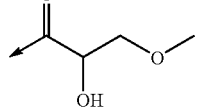 |
| co254 | 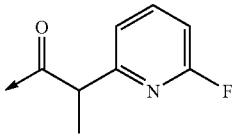 |
| co255 | 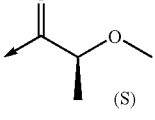 (S) |
| co256 | 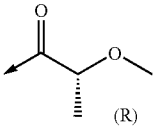 (R) |
| co257 | 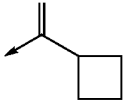 |
| co258 | 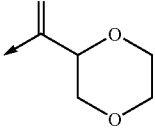 |
| co259 | 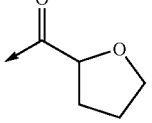 |
| co260 | 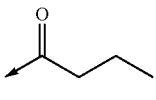 |
| co261 | 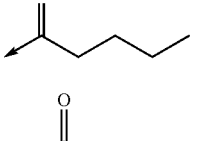 |
| co262 | 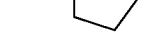 |

TABLE co-continued
| co | Str. |
|---|---|
| co263 | 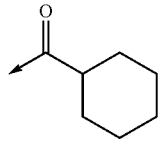 |
| co264 | 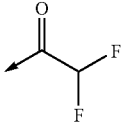 |
TABLE so
| so | Str. |
|---|---|
| so1 |  |
| so2 | 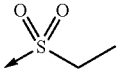 |
| so3 | 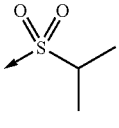 |
| so4 | 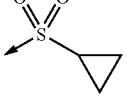 |
| so5 | 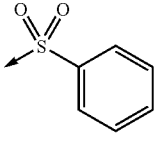 |
| so6 | 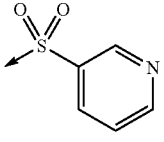 |
| so7 | 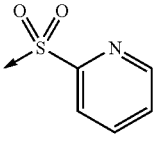 |
| so8 | 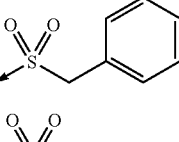 |
| so9 | 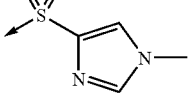 |
TABLE so-continued
| so | Str. |
|---|---|
| so10 |  |
| so11 | 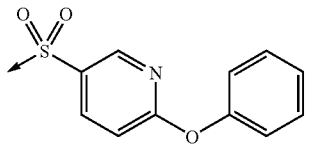 |
| so12 | 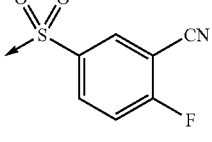 |
| so13 | 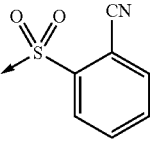 |
| so14 | 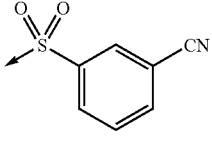 |
| so15 | 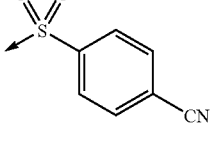 |
| so16 | 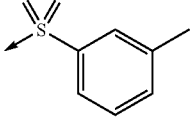 |
| so17 | 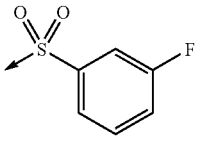 |
| so18 | 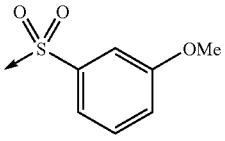 |
| so19 | 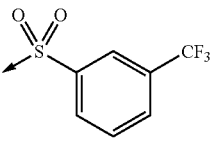 |

TABLE so-continued

| so | Str. |
|---|---|
| so20 | 3-(difluoromethoxy)phenyl methylsulfone |
| so21 | 3-(trifluoromethoxy)phenyl methylsulfone |
| so22 | 6-methoxypyridin-3-yl sulfone |
| so23 | 4-(1-methyl-1H-pyrazol-5-yl)phenyl sulfone |
| so24 | 5-bromo-2-methoxyphenyl sulfone |
| so25 | 3,5-bis(trifluoromethyl)phenyl sulfone |
| so26 | 3-chloro-4-fluorophenyl sulfone |
| so27 | 2,5-dimethoxyphenyl sulfone |
| so28 | 3,4-dimethoxyphenyl sulfone |

TABLE so-continued

| so | Str. |
|---|---|
| so29 | 2-chloro-4-(trifluoromethyl)phenyl sulfone |
| so30 | 6-(methylsulfonamido)pyridin-3-yl sulfone |
| so32 | 4-acetamidophenyl sulfone |
| so33 | thiophen-2-yl sulfone |
| so34 | (pyridin-3-yl)methyl sulfone |
| so35 | 5-methylisoxazol-4-yl sulfone |
| so36 | N,N-dimethylsulfamoyl |
| so37 | 2,4,6-triisopropylphenyl sulfone |
| so38 | 3-cyano-4-fluorophenyl sulfone |
| so39 | 5,6-dichloropyridin-3-yl sulfone |

TABLE so-continued
| so | Str. |
|---|---|
| so40 | 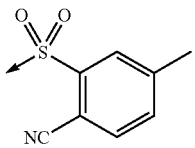 |
| so41 | 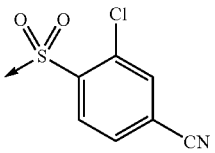 |
| so42 | 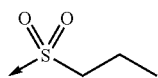 |
| so43 | 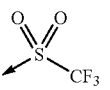 |
| so44 | 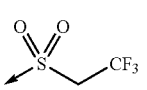 |
| so45 | 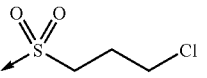 |
| so46 | 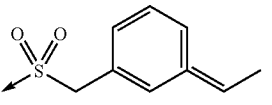 |
| so47 | 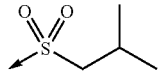 |
| so48 | 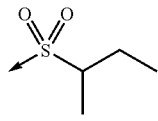 |
| so49 | 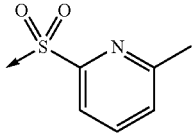 |
| so50 | 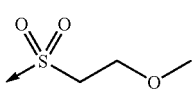 |
| so51 | 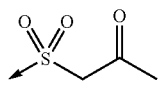 |
| so52 | 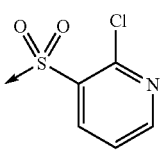 |
TABLE so-continued
| so | Str. |
|---|---|
| so53 | 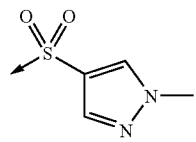 |
| so54 | 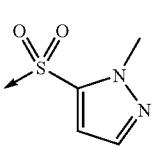 |
| so55 | 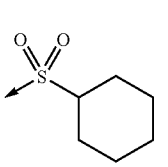 |
| so56 | 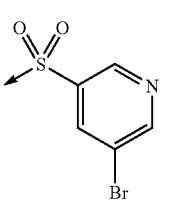 |
| so57 | 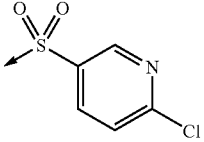 |
| so58 | 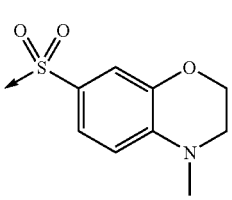 |
| so59 | 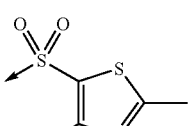 |
| so60 | 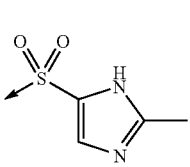 |
| so61 | 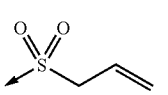 |
| so62 | 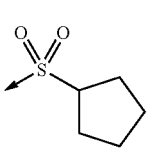 |

TABLE so-continued

| so | Str. |
|---|---|
| so63 | [structure: sulfonyl-butyl] |
| so64 | [structure: sulfonyl-cyclobutyl] |
| so65 | [structure: sulfonyl-pyrazole-tetrahydropyran] |
| so66 | [structure: sulfonyl-CHF2] |

TABLE on

| on | Str. |
|---|---|
| on1 | [structure: C(=O)NH2] |
| on2 | [structure: C(=O)NH-ethyl] |
| on3 | [structure: C(=O)NH-cyclohexyl] |
| on4 | [structure: C(=O)NH-phenyl] |
| on5 | [structure: C(=O)NH-CH2CH2-phenyl] |
| on6 | [structure: C(=O)NH-pyridazine] |
| on7 | [structure: C(=O)NH-propyl] |
| on8 | [structure: C(=O)NH-butyl] |
| on9 | [structure: C(=O)NH-isopropyl] |
| on10 | [structure: C(=O)NH-cyclopentyl] |

TABLE ch

| ch | Str |
|---|---|
| ch201 | —CH₃ |
| ch202 | [structure: CH2-pyridine] |
| ch203 | [structure: CH2-N-methylimidazole] |
| ch204 | [structure: CH2-CO2H] |
| ch205 | [structure: CH2-phenyl] |
| ch206 | [structure: CH2-tetrahydrofuran] |

TABLE sbo

| sbo | Str. | Spl. |
|---|---|---|
| sbo1 | (HO)₂B—[phenyl]—CN | WAKO |
| sbo2 | (HO)₂B—[phenyl]—Cl | Ald |
| sbo3 | (HO)₂B—[pyridine] | WAKO |

TABLE sbo-continued
| sbo | Str. | Spl. |
|---|---|---|
| sbo4 | 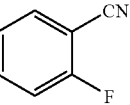 | WAKO |
| sbo5 | 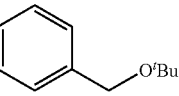 | FRON |
| sbo6 | 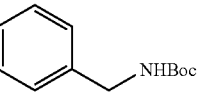 | Combi |
| sbo9 | 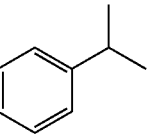 | WAKO |
| sbo10 | 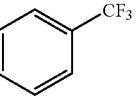 | WAKO |
| sbo11 | 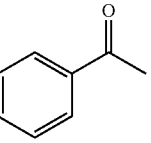 | WAKO |
| sbo12 | 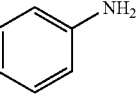 | Acros |
| sbo13 | 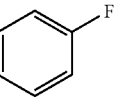 | Ald |
| sbo14 | 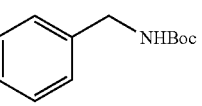 | Combi |
| sbo15 | 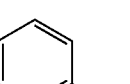 | TCI |
| sbo16 | 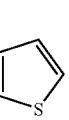 | Ald |
| sbo17 | 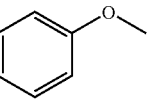 | TCI |
| sbo18 |  | FRON |
| sbo19 |  | Ald |
| sbo20 |  | Combi |
| sbo21 | 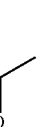 | Ald |
| sbo22 | 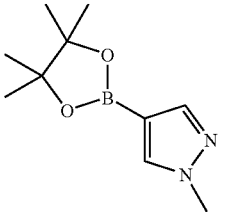 | WAKO |
| sbo23 |  | Matrix |
| sbo24 |  | AAesar |
| sbo25 |  | TCI |
| sbo26 |  | FRON |
| sbo27 |  | Ald |
| sbo28 |  | FRON |

TABLE sbo-continued
| sbo | Str. | Spl. |
|---|---|---|
| sbo29 | 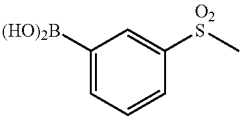 | FRON |
| sbo30 | 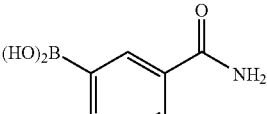 | FRON |
| sbo31 | 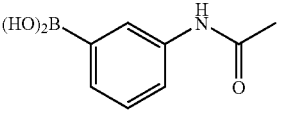 | LANC |
| sbo32 | 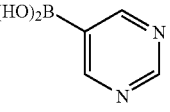 | FRON |
| sbo33 | 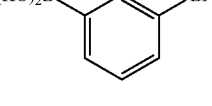 | Ald |
| sbo34 | 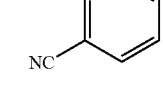 | Ald |
| sbo35 | 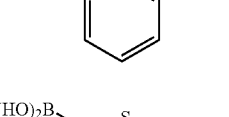 | Ald |
| sbo36 | 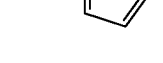 | Ald |
| sbo37 | 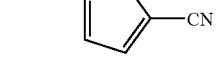 | LANC |
| sbo38 | 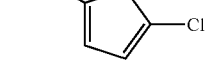 | Ald |
| sbo39 | 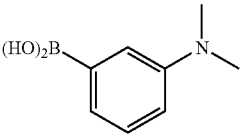 | FRON |
| sbo40 | 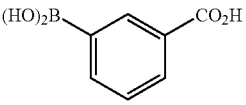 | Ald |
| sbo41 | 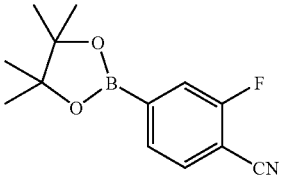 | |
| sbo42 | 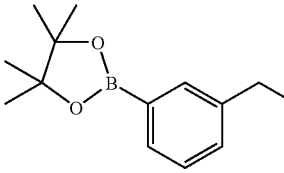 | |
| sbo43 | 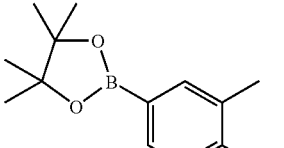 | |
| sbo44 | 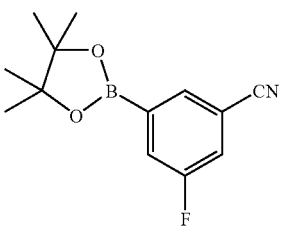 | |
| sbo45 | 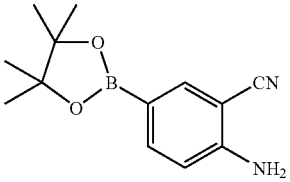 | |
| sbo46 | 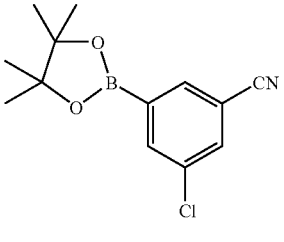 | |
| sbo47 | 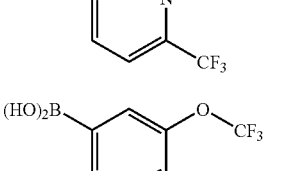 | Apollo |
| sbo48 | 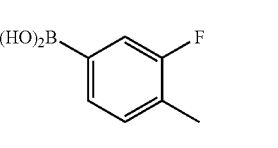 | Ald |
| sbo49 |  | Ald |

TABLE sbo-continued

| sbo | Str. | Spl. |
|---|---|---|
| sbo50 | (HO)₂B-C₆H₃(F)(OMe) | Ald |
| sbo52 | pinacol boronate-C₆H₃(CN)(Me) | |
| sbo53 | pinacol boronate-C₆H₃(CN)(CF₃) | |
| sbo54 | pinacol boronate-C₆H₃(CF₃)(CN) | |
| sbo55 | pinacol boronate-C₆H₃(CN)(CF₃) | |
| sbo56 | pinacol boronate-C₆H₄-CH₂CH₂CN | |
| sbo57 | (HO)₂B-C₆H₃(CF₃)(F) | WAKO |
| sbo58 | (HO)₂B-C₆H₃(Me)(Me) | LANC |
| sbo59 | (HO)₂B-C₆H₄-SMe | Acros |
| sbo60 | (HO)₂B-C₆H₃(OMe)(OMe) | Ald |
| sbo61 | (HO)₂B-benzodioxole | Ald |
| sbo62 | (HO)₂B-C₆H₃(Cl)(OMe) | Ald |
| sbo63 | pinacol boronate-C₆H₂(F)(CN)(F) | |
| sbo64 | (HO)₂B-(4-methylthiophene) | Ald |
| sbo65 | (HO)₂B-(2-methoxypyridin-3-yl) | AAesar |
| sbo66 | (HO)₂B-(6-methoxypyridin-3-yl) | WAKO |
| sbo67 | (HO)₂B-(pyridin-4-yl) | WAKO |
| sbo68 | (HO)₂B-C₆H₄-CH₂CN | Combi |
| sbo69 | (HO)₂B-C₆H₄-CH₂CN | Combi |
| sbo70 | (HO)₂B-C₆H₃(F)(F) | Ald |
| sbo71 | (HO)₂B-C₆H₃(Cl)(F) | Ald |

TABLE sbo-continued

| sbo | Str. | Spl. |
|---|---|---|
| sbo72 | (HO)₂B-pyridine-F (2-fluoro-5-pyridyl) | Ald |
| sbo73 | (HO)₂B-pyridine-F (2-fluoro-4-pyridyl) | FRON |
| sbo74 | (HO)₂B-C₆H₄-Cl (4-chlorophenyl) | Ald |
| sbo75 | (HO)₂B-C₆H₄-OEt (3-ethoxyphenyl) | Kanto |
| sbo76 | (HO)₂B-C₆H₃(OMe)₂ (3,5-dimethoxyphenyl) | Kanto |
| sbo77 | (HO)₂B-C₆H₃(OMe)₂ (2,3-dimethoxyphenyl) | Kanto |
| sbo78 | (HO)₂B-C₆H₃(OMe)₂ (2,5-dimethoxyphenyl) | Acros |
| sbo79 | (HO)₂B-C₆H₃(F)(OEt) (3-fluoro-4-ethoxyphenyl) | Kanto |
| sbo80 | (HO)₂B-C₆H₃(F)(OMe) (5-fluoro-2-methoxyphenyl) | Kanto |
| sbo81 | pinacol boronate-C₆H₃(CN)(OMe) | — |
| sbo82 | (HO)₂B-C₆H₃(F)(OMe) (2-fluoro-3-methoxyphenyl) | Kanto |
| sbo83 | (HO)₂B-C₆H₃(Cl)(OEt) (3-chloro-4-ethoxyphenyl) | Kanto |
| sbo84 | (HO)₂B-C₆H₃(CN)(Cl) | Kanto |
| sbo85 | (HO)₂B-C₆H₃(F)(OEt) | Kanto |
| sbo86 | (HO)₂B-C₆H₃(OMe)(F) (3-methoxy-5-fluorophenyl) | Kanto |
| sbo87 | pinacol boronate-C₆H₃(Cl)(CN) | — |
| sbo88 | (HO)₂B-C₆H₃(CN)(Cl) | Combi |
| sbo89 | (HO)₂B-benzodioxane (2,3-dihydro-1,4-benzodioxin-6-yl) | WAKO |
| sbo90 | pinacol boronate-pyridine-CN (6-cyano-3-pyridyl) | FRON |
| sbo91 | pinacol boronate-C₆H₄-O-CH₂CH₂-OMe | — |
| sbo92 | (HO)₂B-C₆H₃(OMe)(F) (3-methoxy-4-fluorophenyl) | Combi |
| sbo93 | (HO)₂B-C₆H₃(CH₂OMe)(F) | FRON |

TABLE sbo-continued
| sbo | Str. | Spl. |
|---|---|---|
| sbo94 | 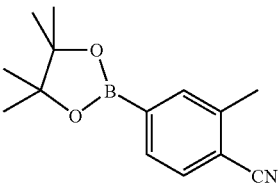 | Combi |
| sbo95 | 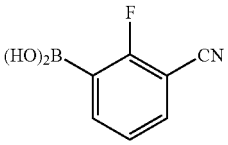 | |
| sbo96 | 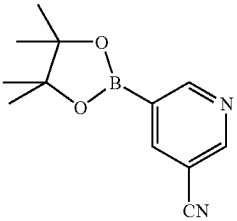 | |
| sbo97 | 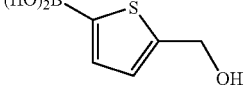 | Asym-chem |
| sbo98 | 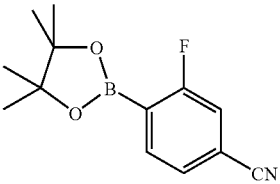 | |
| sbo103 | 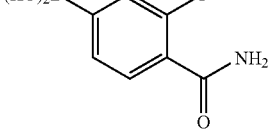 | Combi |
| sbo104 | 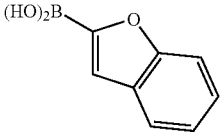 | FRON |
| sbo105 | 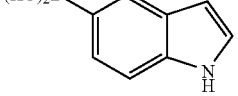 | FRON |
| sbo106 | 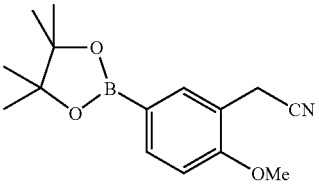 | |
| sbo107 | 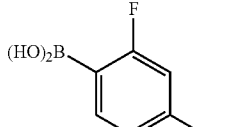 | LANC |
| sbo108 | 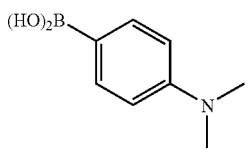 | Ald |
| sbo109 | 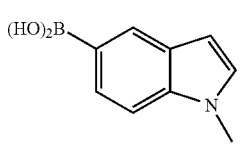 | Ald |
| sbo110 |  | WAKO |
| sbo111 | 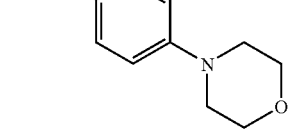 | |
| sbo112 |  | |
| sbo113 | 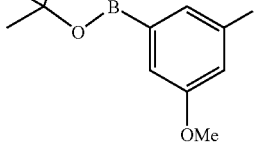 | WAKO |
| sbo114 | 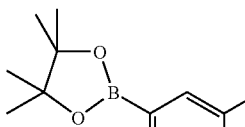 | |

TABLE sbo-continued
| sbo | Str. | Spl. |
|---|---|---|
| sbo115 | 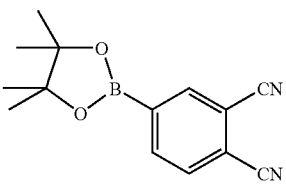 | |
| sbo116 |  | FRON |
| sbo117 | 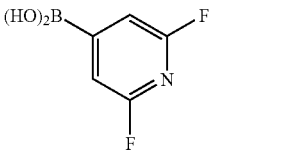 | FRON |
| sbo118 | 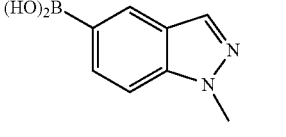 | Syn |
| sbo119 | 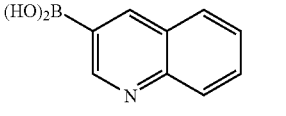 | FRON |
| sbo120 | 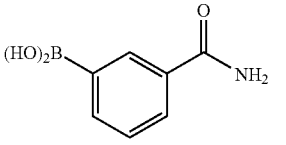 | FRON |
| sbo121 | 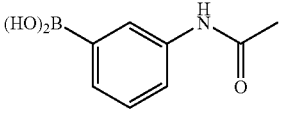 | LANC |
| sbo122 | 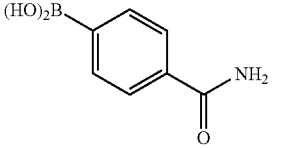 | WAKO |
| sbo123 | 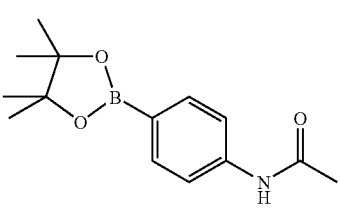 | Ald |
| sbo124 |  | Combi |
| sbo125 | 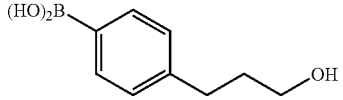 | Combi |
| sbo126 | 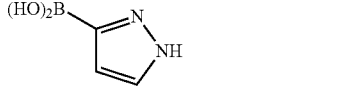 | FRON |
| sbo127 | 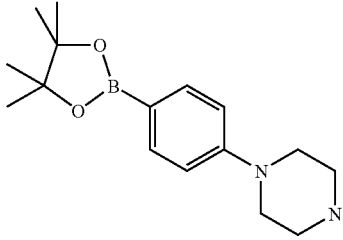 | WAKO |
| sbo128 | 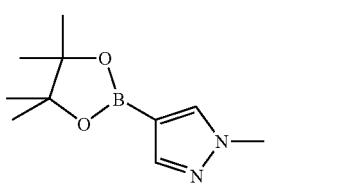 | WAKO |
| sbo129 | 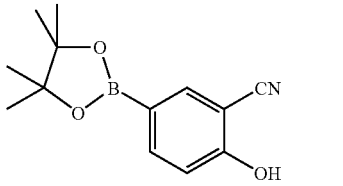 | |
| sbo130 | 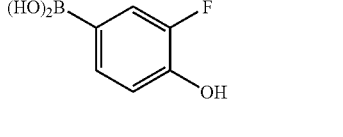 | Combi |
| sbo131 | 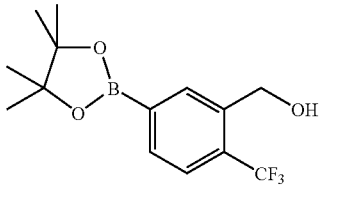 | |
| sbo132 | 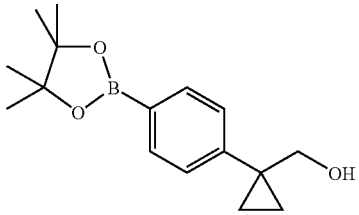 | |

TABLE sbo-continued

| sbo | Str. | Spl. |
|---|---|---|
| sbo134 | 4,4,5,5-tetramethyl-1,3,2-dioxaborolane with 3-methyl-4-aminophenyl | |
| sbo135 | 4,4,5,5-tetramethyl-1,3,2-dioxaborolane with 3-fluoro-4-aminophenyl | |
| sbo136 | 4,4,5,5-tetramethyl-1,3,2-dioxaborolane with 2-oxoindolin-5-yl | |
| sbo137 | 4,4,5,5-tetramethyl-1,3,2-dioxaborolane with 4-methyl-3,4-dihydro-2H-benzo[b][1,4]oxazin-7-yl | May |
| sbo138 | Bu₃Sn-pyridin-2-yl | TCI |
| sbo139 | (HO)₂B-5-methylpyridin-3-yl | Combi |
| sbo140 | 4,4,5,5-tetramethyl-1,3,2-dioxaborolane with 2-cyanopyrimidin-5-yl | FRON |
| sbo141 | 4,4,5,5-tetramethyl-1,3,2-dioxaborolane with 3,5-difluoro-4-hydroxyphenyl | |
| sbo142 | (HO)₂B-6-fluoro-5-methylpyridin-3-yl | FRON |
| sbo143 | 4,4,5,5-tetramethyl-1,3,2-dioxaborolane with 3-hydroxy-4,5-difluorophenyl | |
| sbo144 | 4,4,5,5-tetramethyl-1,3,2-dioxaborolane with 2-fluoro-5-methylpyridin-3-yl | Combi |
| sbo145 | 4,4,5,5-tetramethyl-1,3,2-dioxaborolane with 5-methoxypyridin-3-yl | FRON |
| sbo146 | 4,4,5,5-tetramethyl-1,3,2-dioxaborolane with 5-aminopyridin-3-yl | Apollo |
| sbo147 | 4,4,5,5-tetramethyl-1,3,2-dioxaborolane with 6-chloropyridin-3-yl | Ald |
| sbo148 | 4,4,5,5-tetramethyl-1,3,2-dioxaborolane with 6-aminopyridin-3-yl | WAKO |

TABLE sbo-continued

| sbo | Str. | Spl. |
|---|---|---|
| sbo150 | 4-(4,4,5,5-tetramethyl-1,3,2-dioxaborolan-2-yl)picolinonitrile | |
| sbo153 | (2-methoxypyridin-4-yl)boronic acid | Combi |
| sbo154 | tert-butyl (4-(4,4,5,5-tetramethyl-1,3,2-dioxaborolan-2-yl)pyridin-2-yl)carbamate | |
| sbo155 | (3-chloropyridin-4-yl)boronic acid | FRON |
| sbo156 | (6-chloro-5-methylpyridin-3-yl)boronic acid | Combi |
| sbo157 | N-methyl-3-(4,4,5,5-tetramethyl-1,3,2-dioxaborolan-2-yl)aniline | |
| sbo158 | N-methyl-4-(4,4,5,5-tetramethyl-1,3,2-dioxaborolan-2-yl)aniline | |
| sbo159 | (4-methylpyridin-3-yl)boronic acid | FRON |
| sbo160 | 2-(2-fluoro-5-(4,4,5,5-tetramethyl-1,3,2-dioxaborolan-2-yl)phenyl)acetonitrile | |
| sbo161 | 2,6-dimethyl-4-(4,4,5,5-tetramethyl-1,3,2-dioxaborolan-2-yl)pyridine | |
| sbo162 | 1-(4-(4,4,5,5-tetramethyl-1,3,2-dioxaborolan-2-yl)phenyl)cyclopropanecarbonitrile | |
| sbo163 | tert-butyl 5-(4,4,5,5-tetramethyl-1,3,2-dioxaborolan-2-yl)-1H-indazole-1-carboxylate | MAYB |
| sbo164 | 6-(tributylstannyl)nicotinonitrile | |
| sbo165 | (5-fluoropyridin-3-yl)boronic acid | Combi |
| sbo166 | (5-fluoro-2-methoxypyridin-4-yl)boronic acid | Asym |
| sbo167 | 1-propyl-4-(4,4,5,5-tetramethyl-1,3,2-dioxaborolan-2-yl)-1H-pyrazole | Oak |
| sbo168 | (4-(methylcarbamoyl)phenyl)boronic acid | Apollo |
| sbo169 | (4-(cyclopropylcarbamoyl)phenyl)boronic acid | Combi |

TABLE sbo-continued
| sbo | Str. | Spl. |
|---|---|---|
| sbo170 |  | FRON |
| sbo171 |  | Combi |
| sbo172 | 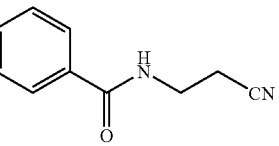 | Combi |
| sbo173 | 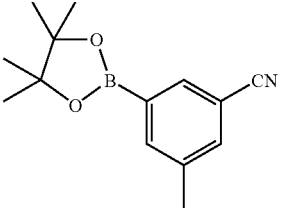 | |
| sbo174 | 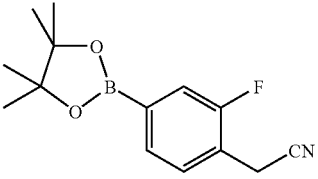 | |
| sbo175 | 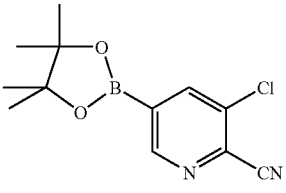 | |
| sbo176 | 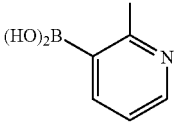 | LANC |
| sbo177 | 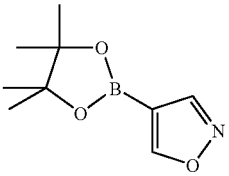 | FRON |
| sbo178 | 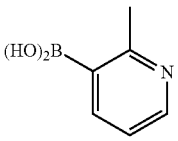 | Combi |
TABLE sbo-continued
| sbo | Str. | Spl. |
|---|---|---|
| sbo179 | 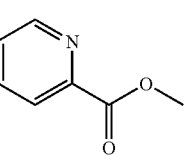 | Combi |
| sbo180 | 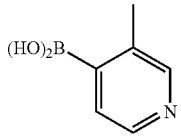 | Combi |
| sbo181 | 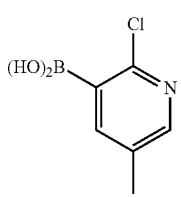 | Combi |
| sbo182 | 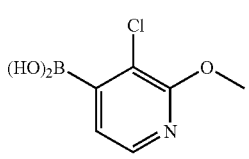 | Combi |
| sbo185 | 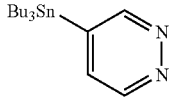 | |
| sbo186 | 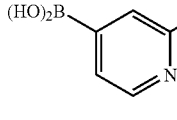 | Syn |
| sbo187 | 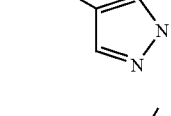 | Combi |
| sbo188 | 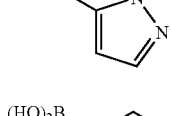 | Combi |
| sbo189 | 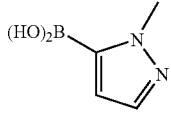 | ASDI |
| sbo190 | 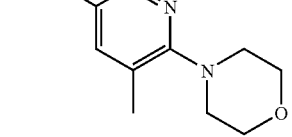 | MAY |

TABLE sbo-continued

| sbo | Str. | Spl. |
|---|---|---|
| sbo191 | | MAY |
| sbo192 | (HO)₂B-pyridine-methyl | FRON |
| sbo194 | | Ald |
| sbo195 | | Boron |
| sbo196 | | WAKO |
| sbo199 | Bu₃Sn-(2-fluoropyridine) | Apollo |
| sbo200 | Bu₃Sn-(2-methoxypyridine) | Apollo |
| sbo201 | Bu₃Sn-(4-methylpyridine) | Apollo |
| sbo202 | | |
| sbo203 | | Ald |
| sbo204 | | Ald |
| sbo205 | | Ald |
| sbo206 | | Ald |
| sbo207 | | |
| sbo208 | | |
| sbo209 | | |
| sbo210 | | Focus |

TABLE sbo-continued
| sbo | Str. | Spl. |
|---|---|---|
| sbo211 | 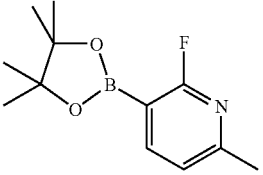 | |
| sbo212 | 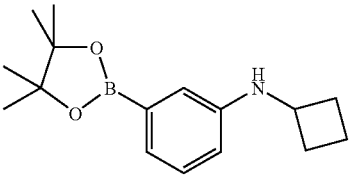 | |
| sbo213 | 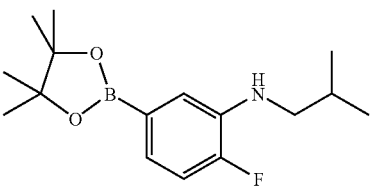 | |
| sbo214 | 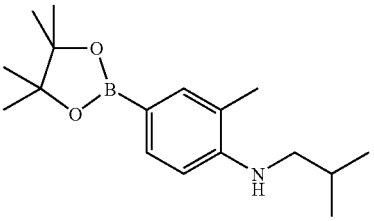 | |
| sbo215 | 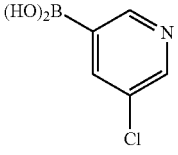 | Apollo |
| sbo216 | 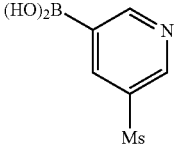 | Combi |
| sbo217 | 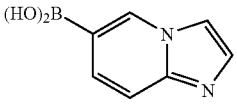 | Combi |
| sbo218 | 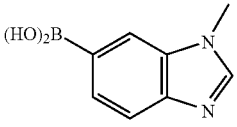 | Combi |
| sbo219 | 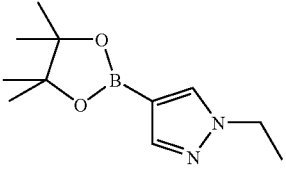 | Oak |
| sbo220 | 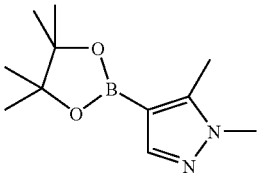 | Combi |
| sbo221 | 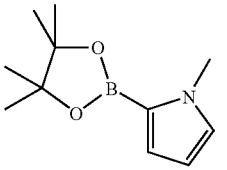 | Combi |
| sbo222 | 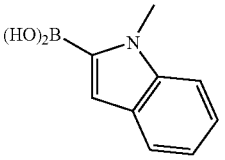 | Combi |
| sbo223 | 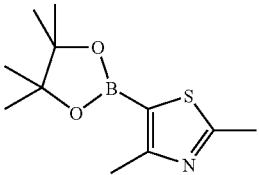 | MAY |
| sbo224 | 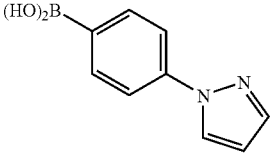 | Combi |
| sbo225 | 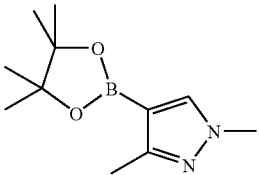 | Combi |
| sbo226 | 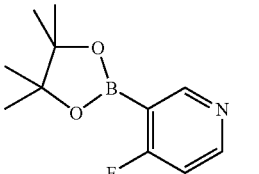 | |
| sbo227 | 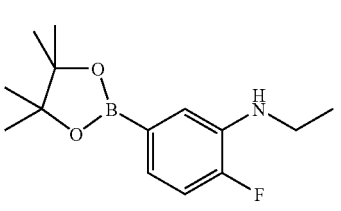 | |

TABLE sbo-continued
| sbo | Str. | Spl. |
|---|---|---|
| sbo228 | 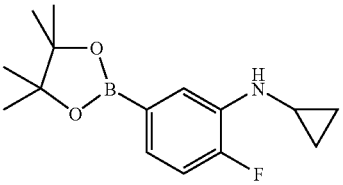 | |
| sbo229 | 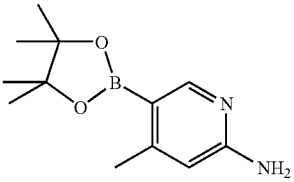 | |
| sbo230 | 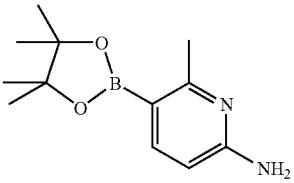 | |
| sbo231 | 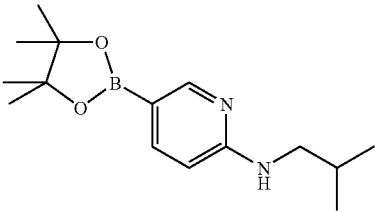 | |
| sbo232 | 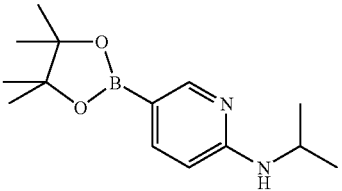 | |
| sbo233 | 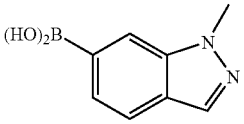 | Syn |
| sbo234 | 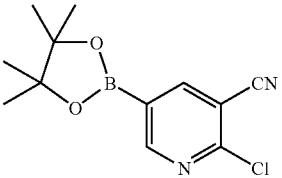 | |
| sbo235 | 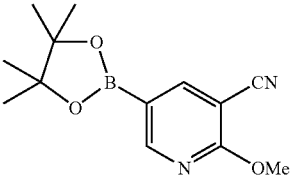 | |
| sbo236 | 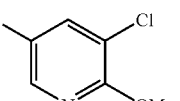 | Combi |
| sbo237 | 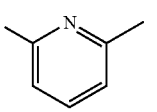 | Syn |
| sbo238 | 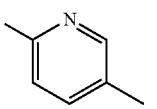 | Apollo |
| sbo239 | 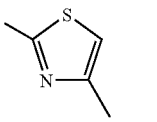 | Apollo |
| sbo240 | 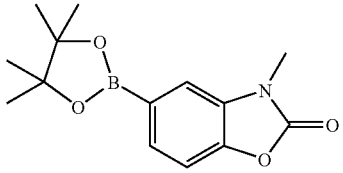 | |
| sbo241 | 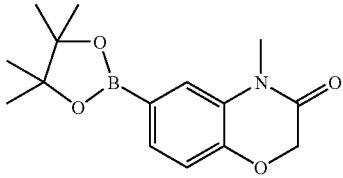 | |
| sbo242 | 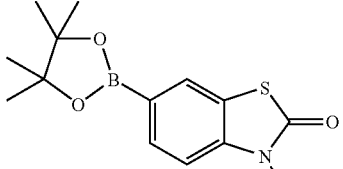 | |
| sbo243 | 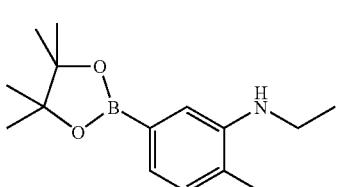 | |
| sbo244 | 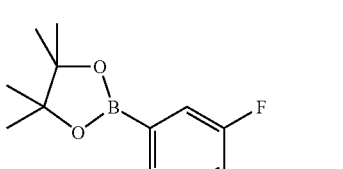 | |

TABLE sbo-continued

| sbo | Str. | Spl. |
|---|---|---|
| sbo245 | 4-(4,4,5,5-tetramethyl-1,3,2-dioxaborolan-2-yl)-2-methyl-N-ethylaniline | |
| sbo246 | 5-(4,4,5,5-tetramethyl-1,3,2-dioxaborolan-2-yl)-1-methyl-1H-pyrrolo[2,3-b]pyridine | |
| sbo247 | Bu₃Sn-(5-methylthiazol-2-yl) | Apollo |
| sbo248 | 3-(4,4,5,5-tetramethyl-1,3,2-dioxaborolan-2-yl)benzenesulfonamide | FRON |
| sbo249 | (HO)₂B-3-(N,N-dimethylsulfamoyl)phenyl | Apollo |
| sbo250 | 5-(4,4,5,5-tetramethyl-1,3,2-dioxaborolan-2-yl)-1-Boc-1H-indazole | MAYB |
| sbo251 | (HO)₂B-1-methyl-1H-indazol-4-yl | Syn |
| sbo252 | (HO)₂B-1-methyl-1H-indazol-7-yl | Syn |
| sbo253 | 3-(4,4,5,5-tetramethyl-1,3,2-dioxaborolan-2-yl)-5-cyclopropylpyridine | |
| sbo254 | 5-(4,4,5,5-tetramethyl-1,3,2-dioxaborolan-2-yl)-2-ethylpyridine | |
| sbo255 | 3-(4,4,5,5-tetramethyl-1,3,2-dioxaborolan-2-yl)-5-ethylpyridine | |
| sbo256 | (HO)₂B-3-fluoro-2-methoxypyridin-5-yl | Combi |
| sbo257 | Bu₃Sn-(2-methoxythiazol-5-yl) | |
| sbo258 | (HO)₂B-5-chloropyridin-3-yl | Apollo |
| sbo259 | 5-(4,4,5,5-tetramethyl-1,3,2-dioxaborolan-2-yl)-2-methylisoindolin-1-one | |
| sbo260 | 5-(4,4,5,5-tetramethyl-1,3,2-dioxaborolan-2-yl)-2,3-dimethylisoindolin-1-one | |

TABLE sbo-continued

| sbo | Str. | Spl. |
|---|---|---| sbo261: 5-(4,4,5,5-tetramethyl-1,3,2-dioxaborolan-2-yl)benzo[d]oxazole sbo262: 3-ethoxy-5-(4,4,5,5-tetramethyl-1,3,2-dioxaborolan-2-yl)pyridine sbo263: 1,2-dimethyl-5-(4,4,5,5-tetramethyl-1,3,2-dioxaborolan-2-yl)-1H-indole sbo265: 3-chloro-2-methoxy-5-(4,4,5,5-tetramethyl-1,3,2-dioxaborolan-2-yl)pyridine sbo266: 1-methyl-6-(4,4,5,5-tetramethyl-1,3,2-dioxaborolan-2-yl)-1H-indole sbo267: 1-(5-(4,4,5,5-tetramethyl-1,3,2-dioxaborolan-2-yl)pyridin-3-yl)ethanone sbo268: 3-(difluoromethyl)-5-(4,4,5,5-tetramethyl-1,3,2-dioxaborolan-2-yl)pyridine TABLE sbo-continued

| sbo | Str. | Spl. |
|---|---|---| sbo269: 2-(fluoromethyl)-5-(4,4,5,5-tetramethyl-1,3,2-dioxaborolan-2-yl)pyridine sbo270: 1-methyl-5-(4,4,5,5-tetramethyl-1,3,2-dioxaborolan-2-yl)-1H-indazol-3-amine sbo271: 2-ethyl-4-(4,4,5,5-tetramethyl-1,3,2-dioxaborolan-2-yl)pyridine sbo274: N-(4-(4,4,5,5-tetramethyl-1,3,2-dioxaborolan-2-yl)pyridin-2-yl)acetamide sbo275: 3-methyl-5-(tributylstannyl)isothiazole sbo276: 1-methyl-5-(4,4,5,5-tetramethyl-1,3,2-dioxaborolan-2-yl)indolin-2-one sbo277: 4-fluoro-5-methyl-3-(tributylstannyl)pyridine sbo278: 2-(difluoromethyl)-5-(4,4,5,5-tetramethyl-1,3,2-dioxaborolan-2-yl)pyridine TABLE sbo-continued

| sbo | Str. | Spl. |
|---|---|---|
| sbo279 | 2-(difluoromethyl)pyridin-4-yl pinacol boronate | |
| sbo280 | 2-(fluoromethyl)pyridin-4-yl pinacol boronate | |
| sbo281 | 3-cyano-5-cyclopropylphenyl pinacol boronate | |
| sbo282 | 3-cyano-4-cyclopropylphenyl pinacol boronate | |
| sbo283 | 3-cyano-5-ethylphenyl pinacol boronate | |
| sbo284 | 5-(fluoromethyl)pyridin-3-yl pinacol boronate | |
| sbo285 | 5,6-dimethylpyridin-3-yl pinacol boronate | |
| sbo286 | 3-cyano-5-(difluoromethyl)phenyl pinacol boronate | |
| sbo287 | 3-chloro-4-fluoro-5-(tributylstannyl)pyridine | |
| sbo288 | 3-fluoro-2-methylpyridin-4-yl pinacol boronate | |
| sbo289 | 3-fluoro-2-methylpyridin-5-yl pinacol boronate | |
| sbo290 | 3-fluoro-2-ethylpyridin-5-yl pinacol boronate | |
| sbo291 | methyl 3-(pinacolboronate)benzoate | WAKO |
| sbo292 | methyl 4-(pinacolboronate)benzoate | Ald |
| sbo293 | 3-(pinacolboronate)benzenesulfonamide | FRON |

TABLE sbo-continued

| sbo | Str. | Spl. |
|---|---|---|
| sbo294 | 4-(HO)$_2$B-C$_6$H$_4$-CH$_2$-C(O)OCH$_3$ | WAKO |
| sbo295 | 4-(HO)$_2$B-C$_6$H$_4$-CH$_2$CH$_2$-C(O)OCH$_3$ | Combi |
| sbo296 | 3-(HO)$_2$B-C$_6$H$_4$-CH$_2$CH$_2$-C(O)OCH$_3$ | Combi |
| sbo297 | 5-(pinacolboronate)-pyridine-3-C(O)OEt | FRON |
| sbo298 | 3-(HO)$_2$B-C$_6$H$_4$-CHO | Ald |
| sbo300 | 5-(pinacolboronate)-pyridin-3-ol | WAKO |
| sbo304 | 5-(pinacolboronate)-2-aminopyrimidine | WAKO |
| sbo305 | 3-(pinacolboronate)-C$_6$H$_4$-C(O)OH | WAKO |
| sbo306 | 4-(pinacolboronate)-pyridine-2-C(O)OCH$_3$ | Combi |
| sbo307 | 4-(pinacolboronate)-C$_6$H$_4$-S(O)$_2$NH$_2$ | FRON |
| sbo308 | 4-(HO)$_2$B-C$_6$H$_4$-S(O)$_2$CH$_3$ | FRON |
| sbo309 | 4-(HO)$_2$B-C$_6$H$_4$-S(O)$_2$N(CH$_3$)$_2$ | Apollo |
| sbo310 | 4-(HO)$_2$B-C$_6$H$_4$-S(O)$_2$CH$_2$CH$_3$ | WAKO |
| sbo312 | 5-Bu$_3$Sn-2-hydroxythiazole | |

In Table sbo, compounds with no entry in the Spl. column were synthesized according to the method described in Tetrahedron, 2001, 57, 9813-9816 using a commercially available aryl halide as a raw material.

Alternatively, compounds were synthesized by the methods described in the following Reference Examples.

Reference Example sbo 91

2-(3-(2-methoxyethoxy)phenyl)-4,4,5,5-tetramethyl-1,3,2-dioxaborolane (sbo 91)

Sodium hydride (462 mg; WAKO) was added to a DMF solution (5 mL) of 3-bromophenol (1 g; TCI) with ice cooling, the resulting mixture was stirred for a certain period followed by the addition of 2-bromomethylethyl ether (1.0 mL; TCI), and the resulting mixture was stirred at room temperature for 12 hours. Water was added to the reaction mixture solution, the reaction mixture was extracted with ethyl acetate, and the organic layer was washed with water and saturated brine. The organic layer was dried and the solvent was evaporated under reduced pressure. The title compound (1.5 g) was synthesized according to the method described in Tetrahedron, 2001, 57, pp. 9813-9816 using the residue.

Reference Example sbo 114

2-(3-(4,4,5,5-tetramethyl-1,3,2-dioxaborolan-2-yl)phenoxy)acetonitrile (sbo 114)

Potassium carbonate (7 g) and bromoacetonitrile (2.3 ml; TCI) were added to an acetone solution (40 mL) of 3-bromophenol (3 g; TCI) at room temperature and the resulting mixture was stirred at 50° C. for 12 hours. The reaction mixture solution was filtrated through celite and the filtrate was evaporated under reduced pressure.

The residue was purified by column chromatography (Yamazen; hexane/ethyl acetate) and then the title compound was synthesized according to the method described in Tetrahedron, 2001, 57, pp. 9813-9816.

Reference Example sbo 164

6-(tributylstannyl)nicotinonitrile (sbo 164)

The title compound was synthesized according to the method described in WO 2006/097691.

Reference Example sbo 208

N-methyl-5-(4,4,5,5-tetramethyl-1,3,2-dioxaborolan-2-yl)pyridin-2-amine (sbo 208)

Methyl iodide (170 µL) was added to a DMF solution of 2-amino-5-bromopyridine (500 mg; TCI) and sodium hydride (123 mg) and the resulting mixture was stirred at room temperature for 13 hours. Ethyl acetate and saturated brine were added to extract the reaction mixture, the organic layer was dried, and the solvent was evaporated under reduced pressure. The residue was purified by column chromatography (Yamazen; hexane/ethyl acetate) and then the title compound was synthesized according to the method described in Tetrahedron, 2001, 57, pp. 9813-9816.

Reference Example sbo 209

N-ethyl-5-(4,4,5,5-tetramethyl-1,3,2-dioxaborolan-2-yl)pyridin-2-amine (sbo 209)

The title compound was synthesized by the similar method as Reference Example sbo208 using ethyl iodide instead of methyl iodide.

Reference Example sbo 262

3-ethoxy-5-(4,4,5,5-tetramethyl-1,3,2-dioxaborolan-2-yl)pyridine (sbo 262)

The title compound was synthesized by the similar method as Reference Example sbo208 using 3-bromo-5-hydroxypyridine (FRON) instead of 2-amino-5-bromo pyridine and ethyl iodide instead of methyl iodide.

Reference Example sbo 212

N-cyclobutyl-3-(4,4,5,5-tetramethyl-1,3,2-dioxaborolan-2-yl)benzenamine (sbo 212)

An amino group was introduced into an aromatic ring according to the method described in WO 2008/156831A2 using 1-bromo-3-chlorobenzene (TCI) and cyclobutanamine (TCI) and the title compound was obtained according to the similar method as the method described in Tetrahedron, 2001, 57, pp. 9813-9816.

Reference Example sbo 213

2-fluoro-N-isobutyl-5-(4,4,5,5-tetramethyl-1,3,2-dioxaborolan-2-yl)aniline (sbo 21)

Reference Example sbo 214

N-isobutyl-2-methyl-4-(4,4,5,5-tetramethyl-1,3,2-dioxaborolan-2-yl)aniline (sbo 214)

Reference Example sbo 227

N-ethyl-2-fluoro-5-(4,4,5,5-tetramethyl-1,3,2-dioxaborolan-2-yl)aniline (sbo 227)

Reference Example sbo 228

N-cyclopropyl-2-fluoro-5-(4,4,5,5-tetramethyl-1,3,2-dioxaborolan-2-yl)aniline (sbo 228)

Reference Example sbo 243

N-ethyl-2-methyl-5-(4,4,5,5-tetramethyl-1,3,2-dioxaborolan-2-yl)aniline (sbo 243)

Reference Example sbo 244

N-ethyl-2-fluoro-4-(4,4,5,5-tetramethyl-1,3,2-dioxaborolan-2-yl)aniline (sbo 244)

Reference Example sbo 245

N-ethyl-2-methyl-4-(4,4,5,5-tetramethyl-1,3,2-dioxaborolan-2-yl)aniline (sbo 245)

Compounds of Reference Examples sbo213, sbo214, sbo227, sbo228, sbo243, sbo244, and sbo245 were synthesized according to the method described in Reference Example sbo212 using commercially available 2-bromo-4-chloro-1-fluorobenzene (Ald), 1-bromo-4-chloro-2-methylbenzene (TCI), 2-bromo-4-chloro-1-fluorobenzene (Ald), 2-bromo-4-chloro-1-fluorobenzene(Ald), 2-bromo-4-chloro-1-methylbenzene (WAKO), 1-bromo-4-chloro-2-fluorobenzene (WAKO), 1-bromo-4-chloro-2-methylbenzene (TCI) and commercially available corresponding amine compounds instead of 1-bromo-3-chlorobenzene (TCI) described in Reference Example sbo212.

Reference Example sbo 231

N-isobutyl-5-(4,4,5,5-tetramethyl-1,3,2-dioxaborolan-2-yl)pyridin-2-amine (sbo 231)

Acetic acid (97 µL) was added to a 1,2-dichloroethane solution of 2-amino-5-bromopyridine (300 mg; TCI), isobutyl aldehyde (232 µL; TCI), and sodium triacetoxyborohydride (504 mg) at room temperature and the resulting mixture was stirred for 14 hours. Water was added to the reaction mixture solution, then the reaction mixture was extracted with chloroform, the organic layer was dried, and the solvent was evaporated under reduced pressure. The residue was purified by column chromatography (Yamazen; hexane/ethyl acetate) and then the title compound was synthesized according to the method described in Tetrahedron, 2001, 57, pp. 9813-9816.

Reference Example sbo 232

N-isopropyl-5-(4,4,5,5-tetramethyl-1,3,2-dioxaborolan-2-yl)pyridin-2-amine

The title compound was synthesized by the similar method as Reference Example sbo231 using acetone instead of isobutyl aldehyde.

Reference Example sbo 240

3-methyl-5-(4,4,5,5-tetramethyl-1,3,2-dioxaborolan-2-yl)benzo[d]oxazol-2(3H)-one (sbo 240)

Sodium hydride (67 mg; WAKO) was added to a THF solution (3 mL) of 5-bromo-2-benzoxazolinone (222 mg; Ald) with ice cooling, the resulting mixture was stirred for a certain period followed by the addition of methyl iodide (83 µL; TCI), and the resulting mixture was stirred at room temperature for 3 hours. Saturated aqueous ammonium chloride was added to the reaction mixture solution, the reaction mixture was extracted with diethyl ether, and the organic layer was washed with saturated brine. The organic layer was dried and the solvent was evaporated under reduced pressure. Using the residue, the title compound was synthesized from the residue according to the method described in the Tetrahedron, 2001, 57, pp. 9813-9816.

Reference Example sbo 241

4-methyl-6-(4,4,5,5-tetramethyl-1,3,2-dioxaborolan-2-yl)-2H-benzo[b][1,4]oxazin-3(4H)-one (sbo 241)

Reference Example sbo 242

3-methyl-6-(4,4,5,5-tetramethyl-1,3,2-dioxaborolan-2-yl)benzo[d]thiazol-2(3H)-one (sbo 243)

Reference Example sbo 246 methyl-5-(4,4,5,5-tetramethyl-1,3,2-dioxaborolan-2-yl)-1H-pyrrolo[2,3-b]pyridine (sbo 246)

Reference Example sbo 263

1,2-dimethyl-5-(4,4,5,5-tetramethyl-1,3,2-dioxaborolan-2-yl)-1H-indole (sbo 263)

Reference Example sbo 266 methyl-6-(4,4,5,5-tetramethyl-1,3,2-dioxaborolan-2-yl)-1H-indole (sbo 266)

Reference Example sbo 276

1-methyl-5-(4,4,5,5-tetramethyl-1,3,2-dioxaborolan-2-yl)indolin-2-one (sbo 276)

Compounds of Reference Example sbo241, sbo242, sbo246, sbo263, sbo266, and sbo276 were synthesized according to the method described in Reference Example 240 using 6-bromo-2H-1,4-benzoxazine-3(4H)-one, 6-bromo-2-benzothiazolinone, 5-bromo-7-azaindole, 5-bromo-2-methylindole, 6-bromoindole, and 5-bromooxyindole, respectively, instead of 5-bromo-2-benzoxazolinone described in the step of Reference Example sbo240.

Reference Example sbo 259

2-methyl-5-(4,4,5,5-tetramethyl-1,3,2-dioxaborolan-2-yl)isoindolin-1-one (sbo 259)

Reference Example sbo 260

2,3-dimethyl-5-(4,4,5,5-tetramethyl-1,3,2-dioxaborolan-2-yl)isoindolin-1-one (sbo 260)

Reference Examples sbo259 and sbo260 were synthesized using 5-bromoisoindolin-1-one instead of 5-bromo-2-benzoxazolinone described in Reference Example sbo240 and separated by silica gel column chromatography (Yamazen; hexane/ethyl acetate).

Reference Example sbo 253

3-cyclopropyl-5-(4,4,5,5-tetramethyl-1,3,2-dioxaborolan-2-yl)pyridine (sbo 253)

3-Bromo-5-cyclopropylpyridine, a known compound, was obtained by the similar method as the method described in WO 2008/091681 using 3,5-dibromopyridine (TCI) and cyclopropylboronic acid (Ald). The title compound was obtained by the similar method as the method described in Tetrahedron, 2001, 57, pp. 9813-9816 using the product thereof.

Reference Example sbo 281

3-cyclopropyl-5-(4,4,5,5-tetramethyl-1,3,2-dioxaborolan-2-yl)benzonitrile (sbo 281)

Reference Example sbo 282

2-cyclopropyl-5-(4,4,5,5-tetramethyl-1,3,2-dioxaborolan-2-yl)benzonitrile (sbo 282)

Reference Examples sbo281 and sbo282 were synthesized according to the method described in Reference Example sbo253 using 3-bromo-5-chlorobenzonitrile (WAKO) and 2-bromo-5-chlorobenzonitrile (Apollo) instead of 3,5-dibromopyridine (TCI) described in Reference Example sbo253 and using potassium cyclopropyltrifluoroborate (Ald) as a substitute of cyclopropylboronic acid (Ald) by the similar method as the method described in Organic Letter, 2004, 6, pp. 357-360.

Reference Example sbo 254

2-ethyl-5-(4,4,5,5-tetramethyl-1,3,2-dioxaborolan-2-yl)pyridine (sbo 254)

An alkyl group was introduced into a pyridine derivative by the similar method as the method described in U.S. Pat. No. 5,436,344A1 using 2-bromo-5-chloropyridine (TCI) and ethylmagnesium bromide (KANTO), a commercially available Grignard reagent, in the presence of a nickel catalyst and the title compound was obtained by the similar method as the method described in Tetrahedron, 2001, 57, pp. 9813-9816 using the product thereof.

Reference Example sbo 255

3-ethyl-5-(4,4,5,5-tetramethyl-1,3,2-dioxaborolan-2-yl)pyridine (sbo 255)

Reference Example sbo 271

2-ethyl-4-(4,4,5,5-tetramethyl-1,3,2-dioxaborolan-2-yl)pyridine (sbo 271)

Reference Examples sbo 255 and sbo 271 were synthesized according to the method described in Reference Example sbo254 using 3,5-dibromopyridine (TCI) and 2-bromo-4-chloropyridine (Oak) instead of 2-bromo-5-chloropyridine (TCI) described in Reference Example sbo254.

Reference Example sbo 285

2,3-dimethyl-5-(4,4,5,5-tetramethyl-1,3,2-dioxaborolan-2-yl)pyridine (sbo 285)

Reference Example sbo285 was synthesized according to the method described in Reference Example sbo254 using 2-bromo-5-chloro-3-methylpyridine (Asym) instead of 2-bromo-5-chloropyridine (TCI) described in Reference Example sbo254 and methylmagnesium bromide (KANTO) instead of ethylmagnesium bromide (KANTO).

Reference Example sbo 257

2-methoxy-5-(tributylstannyl)thiazole (sbo 257)

A diethyl ether (1.8 mL) solution of 5-bromo-2-methoxythiazole (200 mg) was cooled to −78° C. followed by the dropwise addition of normal butyllithium (1.6 M, 0.7 mL; KANTO). The resulting mixture was stirred as it was for 1 hour, followed by the addition of tri-n-butyltin chloride (0.35 mL; TCI), and the resulting mixture was slowly raised to room temperature and then stirred for 2 hours. Saturated aqueous sodium bicarbonate solution was added to the reaction mixture solution, the reaction mixture was extracted with ethyl acetate, and the organic layer was washed with saturated brine. The organic layer was dried and the solvent was evaporated under reduced pressure to give the'title compound.

Reference Example sbo 275

3-methyl-5-(tributylstannyl)isothiazole (sbo 275)

5-Bromo-3-methylisothiazole was synthesized from 5-amino-3-methylisothiazole (Ald) by the method described in US2004/2545. The title compound was obtained by the method described in Reference Example sbo257 using this product.

Reference Example sbo 272

1-ethyl-5-(4,4,5,5-tetramethyl-1,3,2-dioxaborolan-2-yl)-1H-indazole (sbo 272)

Sodium hydride (44 mg) was added to a THF solution of 5-bromoindazole (200 mg; Ast) at 0° C., the resulting mixture was stirred for a certain period followed by the addition of ethyl iodide (156 μL), and the resulting mixture was stirred at room temperature for 11 hours. 1 N hydrochloric acid was added to the reaction mixture, the reaction mixture was extracted with ethyl acetate, the organic layer was dried, and the solvent was evaporated under reduced pressure. The residue was purified by column chromatography (Yamazen; hexane/ethyl acetate) and then the title compound was synthesized according to the method described in Tetrahedron, 2001, 57, pp. 9813-9816.

Reference Example sbo 273

1,3-dimethyl-5-(4,4,5,5-tetramethyl-1,3,2-dioxaborolan-2-yl)-1H-indazole (sbo 273)

The title compound was synthesized by the similar method using 5-bromo-3-methylindazole (J&W) instead of 5-bromoindazole in Reference Example sbo272 and ethyl iodide instead of methyl iodide.

Reference Example sbo 277

4-fluoro-3-methyl-5-(tributylstannyl)pyridine (sbo 277)

A THF (1 mL) solution of diisopropylamine (160 μL; WAKO) was cooled to −78° C. under a nitrogen atmosphere followed by the dropwise addition of normal butyllithium (2.6 M, 430 μL; KANTO). The resulting mixture was stirred as it was for 30 minutes followed by the dropwise addition of a THF (1 mL) solution of 4-fluoro-3-methylpyridine (111 mg) and the resulting mixture was further stirred for 1 hour. Then tri-n-butyltin chloride (330 μL; TCI) was added and the resulting mixture was slowly raised to room temperature and then stirred for 2 hours. Saturated aqueous sodium bicarbonate solution was added to the reaction mixture solution, to the reaction mixture was extracted with ethyl acetate, and the organic layer was washed with saturated brine. The organic layer was dried and the solvent was evaporated under reduced pressure to give the title compound.

Reference Example sbo 287

3-chloro-4-fluoro-5-(tributylstannyl)pyridine (sbo 287)

The title compound was synthesized according to the method described in Reference Example sbo277 using 3-chloro-4-fluoropyridine instead of 4-fluoro-3-methyl pyridine described in the Step of Reference Example sbo277.

Reference Example sbo 278

2-(difluoromethyl)-5-(4,4,5,5-tetramethyl-1,3,2-dioxaborolan-2-yl)pyridine (sbo 278)

5-Bromo-2-(difluoromethyl)pyridine, a known compound, was obtained by the similar method as the method described in WO 2006/109729 using 5-bromopicolinaldehyde (May) and DEOXO-FLUOR (Ald). The title compound was obtained by the similar method as the method described in Tetrahedron, 2001, 57, pp. 9813-9816 using the product.

Reference Example sbo 268

3-(difluoromethyl)-5-(4,4,5,5-tetramethyl-1,3,2-dioxaborolan-2-yl)pyridine (sbo 268)

Reference Example sbo 279

2-(difluoromethyl)-4-(4,4,5,5-tetramethyl-1,3,2-dioxaborolan-2-yl)pyridine (sbo 279)

Compounds of Reference Example sbo268 and 279 were synthesized according to the method described in Reference Example sbo278 using 5-bromonicotinaldehyde (Ald) and 4-chloropicolinaldehyde (Bionet), respectively, instead of 5-bromopicolinaldehyde (May) described in Reference Example sbo278.

Reference Example sbo 286

3-(difluoromethyl)-5-(4,4,5,5-tetramethyl-1,3,2-dioxaborolan-2-yl)benzonitrile (sbo 2286)

A formyl group was introduced into an aromatic ring by the similar method as the method described in WO 2004/20414A1 using 3-bromo-5-chlorobenzonitrile (WAKO) and the title compound was obtained by using the product thereof in the similar manner as Reference Example sbo278.

Reference Example sbo 269

2-(fluoromethyl)-5-(4,4,5,5-tetramethyl-1,3,2-dioxaborolan-2-yl)pyridine (sbo 269)

The title compound was obtained according to the method described in U.S. Patent No. 2007/254892, WO 2005/123703, Reference Example sbo278, or the like using (5-bromopyridin-2-yl)methanol (May) and DEOXO-FLUOR (Ald).

Reference Example sbo 280

2-(fluoromethyl)-4-(4,4,5,5-tetramethyl-1,3,2-dioxaborolan-2-yl)pyridine (sbo 280)

Reference Example sbo 284

3-(fluoromethyl)-5-(4,4,5,5-tetramethyl-1,3,2-dioxaborolan-2-yl)pyridine (sbo 284)

Compounds of Reference Examples sbo 280 and sbo 284 were synthesized according to the method described in Reference Example sbo269 using (4-chloropyridin-2-yl)methanol (Combi) and (5-bromopyridin-3-yl)methanol (Apollo), respectively, instead of (5-bromopyridin-2-yl)methanol (May) described in Reference Example sbo269.

Reference Example sbo 283

3-ethyl-5-(4,4,5,5-tetramethyl-1,3,2-dioxaborolan-2-yl)benzonitrile

A vinylbenzene derivative was obtained by the similar method as the method described in Journal of Organic Chemistry, 2006, 71, pp. 9681-9686 using 3-bromo-5-chlorobenzonitrile (WAKO) and potassium vinyltrifluoroborate (Ald). Further, a vinyl group was reduced by the similar method as the method described in U.S. Pat. No. 5,863,947 and the title compound was obtained by the similar method as the method described in Tetrahedron, 2001, 57, pp. 9813-9816 using the resulting product.

Reference Example sbo 288

3-fluoro-2-methyl-5-(4,4,5,5-tetramethyl-1,3,2-dioxaborolan-2-yl)pyridine (sbo 288)

Tetrakis triphenylphosphine palladium (0.15 g; Ald) was added to a DMF (3.6 mL) solution of 2,5-dichloro-3-fluoropyridine (0.2 g; Combi) and then trimethyl aluminium (2 M, 660 μL; Ald) was slowly added dropwise. Then the resulting mixture was heated to 70° C. and stirred for 3 hours. The reaction mixture solution was cooled to room temperature followed by the addition of water (3 mL), the reaction mixture was extracted with ethyl acetate, the organic layer was dried, the solvent was evaporated under reduced pressure, and the residue was purified by silica gel column chromatography (Yamazen; hexane/ethyl acetate). The title compound was synthesized according to the method described in Tetrahedron, 2001, 57, pp. 9813-9816 using this purified product.

Reference Example sbo 289

2-ethyl-3-fluoro-5-(4,4,5,5-tetramethyl-1,3,2-dioxaborolan-2-yl)pyridine (sbo 289)

Reference Example sbo289 was synthesized according to the method described in Reference Example sbo288 using triethylaluminium instead of trimethylaluminium described in Reference Example sbo288.

Reference Example sbo 400 tert-butyl 4-(4,4,5,5-tetramethyl-1,3,2-dioxaborolan-2-yl)phenethylcarbamate

A Boc protective group was bonded to an amino group of 2-(4-chlorophenyl)ethanamine (Ald) by a usual method and the title compound was synthesized in the similar manner as the method described in Tetrahedron, 2001, 57, pp. 9813-9816.

TABLE sa

| sa | Str. | Spl. |
|---|---|---|
| sa1 | 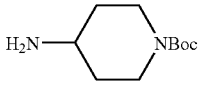 | WAKO |
| sa2 | 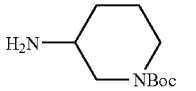 | Ast |
| sa3 | 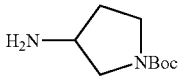 | Ast |
| sa4 | 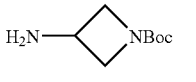 | Ast |
| sa5 | 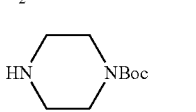 | TCI |
| sa6 |  | TCI |
| sa7 | 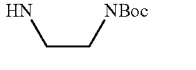 | WAKO |
| sa8 | 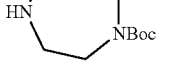 | ALD |

TABLE sa-continued

| sa | Str. | Spl. |
|---|---|---|
| sa9 | (piperidine with NHBoc at 4-position, NH) | TCI |
| sa10 | (pyrrolidine with NHBoc, NH) | TCI |
| sa11 | (cyclohexane-1,4-diamine, one NHBoc, one H₂N) | |
| sa12 | H₂N-CH₂-(piperidine-4-yl), NBoc | Ast |
| sa13 | H₂N-CH₂-(piperidine-3-yl), NBoc | Ast |
| sa14 | H₂N-CH₂-(piperidine-2-yl), NBoc | Ast |
| sa15 | H₂N-CH₂-(pyrrolidine-3-yl), NBoc | Ast |
| sa16 | H₂N-CH₂-(pyrrolidine-2-yl), NBoc | Ast |
| sa17 | H₂N-CH₂-(azetidine-3-yl), NBoc | Ast |
| sa18 | H₂N-cyclohexyl | TCI |
| sa19 | H₂N-CH₂-(pyridin-3-yl) | TCI |
| sa20 | H₂N-CH₂CH₂-(pyrrolidin-1-yl) | AAesar |
| sa21 | H₂N-CH₂CH₂-(morpholin-4-yl) | TCI |
| sa22 | H₂N-CH₂CH₂CH₂-(imidazol-1-yl) | TCI |

TABLE sa-continued

| sa | Str. | Spl. |
|---|---|---|
| sa23 | H₂N-CH₂CH₂-OTBDMS | |
| sa24 | H₂N-CH₂CH₂CH₂-OTBDMS | |
| sa25 | H₂N-CH(CH₂OTBDMS)₂ | |
| sa26 | H₂N-(1-methylpiperidin-4-yl) | TCI |
| sa27 | H₂N-(pyrrolidin-3-yl), NBoc (stereo) | Ald |
| sa28 | H₂N-(pyrrolidin-3-yl), NBoc | Ald |
| sa29 | HN-(4-methylpiperazine) | TCI |
| sa30 | MeHN-(piperidin-4-yl), NBoc | |
| sa31 | MeHN-(piperidin-4-yl)-N-CH₂-(2,6-dimethoxyphenyl) | Matrix |
| sa32 | MeHN-(pyrrolidin-3-yl)-N-benzyl | TCI |
| sa33 | trans-cyclohexane-1,4-diamine, mono-NHBoc | Ast |
| sa34 | cis-cyclohexane-1,4-diamine, mono-NHBoc | AMRI |
| sa35 | H₂N-CH₂CH₂CH₂-N(Me)Boc | Ast |
| sa36 | H₂N-CH₂CH₂CH₂CH₂-NHBoc | TCI |

In Table sa, the compound represented by sa23 to 25 was protected with an alcohol by a usual method using a commercially available aminoalcohol as a raw material. Furthermore, the compound represented by sa11 was prepared as a racemate by mixing the compounds represented by sa33 and sa34, which are chiral compounds, in equal amounts.

Reference Example sa 30 tert-butyl 4-(methylamino)piperidine-1-carboxylate (sa 30)

[Step a] tert-butyl 4-(2,2,2-trifluoroacetamido)piperidine-1-carboxylate (Intermediate sa 30-1)

Anhydrous trifluoroacetic acid (1.4 mL) and triethylamine (1.4 mL) were added to a dichloromethane solution (10 mL) of tert-butyl4-aminopiperidine-1-carboxylate (1 g) and the resulting mixture was stirred at room temperature for 13 and half hours.
Dichloromethane and water were added to the reaction mixture solution to extract the reaction mixture, the organic layer was dried, and the solvent was evaporated under reduced pressure to give the title compound (1.7 g).
(Intermediate sa 30-1 Rf (TLC)=0.4 (Hex:EtOAc=3:1))

[Step b] tert-butyl 4-(2,2,2-trifluoro-N-methylacetamido)piperidine-1-carboxylate (Intermediate sa 30-2)

Methyl iodide (1.25 mL; Ald) and potassium carbonate (3.5 g) were added to a DMF solution (10 mL) of Intermediate sa30-1 (1.5 g) at room temperature and the resulting mixture was stirred for 13 hours. Ethyl acetate and water were added to extract the reaction mixture, the reaction mixture was washed with saturated brine, the organic layer was dried, the solvent was evaporated under reduced pressure, and the residue was purified by column chromatography (Yamazen; hexane/ethyl acetate) to give the title compound (1.14 g).
(Intermediate sa 30-2 Rf (TLC)=0.5 (Hex:EtOAc=3:1))

[Step c] tert-butyl 4-(methylamino)piperidine-1-carboxylate

2 N aqueous sodium hydroxide solution (0.6 mL) was added to a methanol solution (4 mL) of Intermediate sa30-2 (370 mg) at room temperature, the resulting mixture was stirred for 4 hours, then 2 N aqueous sodium hydroxide solution (0.6 mL) was further added, and the resulting mixture was stirred for 1 hour. The reaction mixture solution was concentrated under reduced pressure and chloroform and water were added to the residue to extract the reaction mixture. The organic layer was dried and the solvent was evaporated under reduced pressure to give the title compound (249 mg).
(LCMS: 215.2 (MH$^+$); retention time: 1.37 min; LCMS; condition A)

TABLE soh

| soh | Str. | Spl. |
|---|---|---|
| soh1 | | Ald |
| soh2 | | MAYB |
| soh3 | | |
| soh4 | | WAKO |
| soh5 | | WAKO |
| soh6 | | CNH |
| soh7 | syn | AMRI |
| soh8 | anti | Oak |
| soh10 | | TCI |
| soh11 | | Ald |
| soh12 | | Apollo |
| soh13 | | Matrix |
| soh15 | | |
| soh16 | syn | AMRI |
| soh18 | | Tyger |
| soh19 | | |

TABLE soh-continued

| soh | Str. | Spl. |
|---|---|---|
| soh20 | 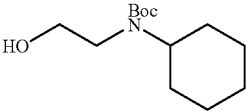 | |
| soh21 | 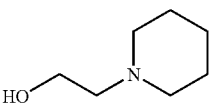 | TCI |
| soh23 | 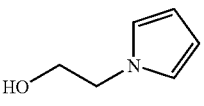 | TCI |
| soh24 | 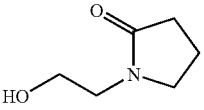 | TCI |
| soh25 | 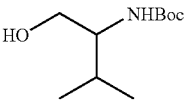 | |
| soh26 | 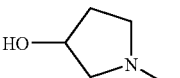 | Ald |
| soh27 | 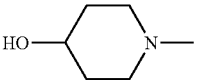 | TCI |
| soh28 | 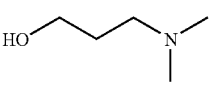 | TCI |
| soh33 | 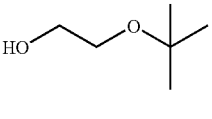 | TCI |
| soh34 | 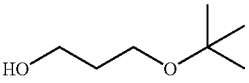 | nacalai |
| soh35 |  | WAKO |
| soh36 | 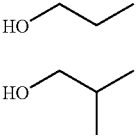 | TCI |
| soh37 |  | TCI |
| soh38 | 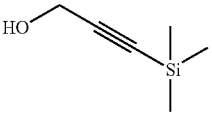 | TCI |
| soh39 | 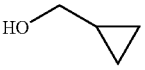 | Ald |
| soh40 | 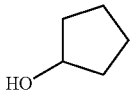 | Ald |
| soh41 | 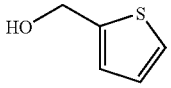 | TCI |
| soh42 | 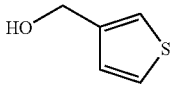 | Ald |
| soh43 | 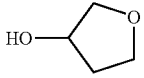 | |
| soh44 | 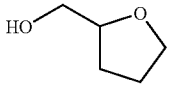 | Ald |
| soh45 | 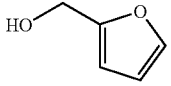 | TCI |
| soh47 | 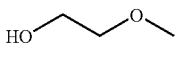 | TCI |
| soh49 | 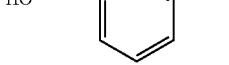 | TCI |
| soh50 | 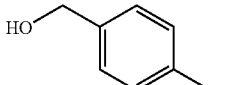 | Fluka |
| soh51 | 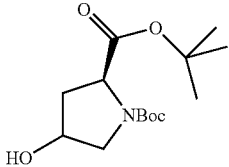 | Wata |
| soh52 | 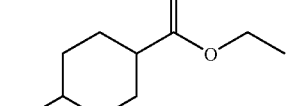 | Ald |
| soh54 | 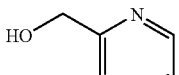 | TCI |
| soh55 | 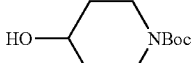 | |

Compounds represented by soh3, 25, and 43 in Table soh were prepared as a racemate by mixing commercially available R-configured and S-configured chiral compounds. Compounds represented by son19 and 20 were protected with amines by a usual method using a commercially available aminoalcohol as a raw material. A compound represented by soh15 was synthesized according to Step a of Example 4-N-4.

TABLE ssh

| ssh | Str. | Spl. |
|---|---|---|
| ssh1 | [structure: 1,4-cyclohexane with HS and NBoc] | |
| ssh2 | [structure: HS-CH2CH2-NHBoc] | Ald |

A compound represented by ssh1 in Table ssh was prepared with reference to Bioorg. Med. Chem. Lett. 2000, 10, pp. 805-809 and U.S. Pat. No. 5,317,025.

TABLE sco

| sco | Str. | Spl. |
|---|---|---|
| sco1 | [acetic anhydride] | WAKO |
| sco2 | HOOC-cyclopropyl | TCI |
| sco3 | HOOC-(2-methylphenyl) | TCI |
| sco4 | HOOC-(2-(methylsulfonylamino)phenyl) | Matrix |
| sco5 | HOOC-CH2CH2-OH | TCI |
| sco6 | HOOC-(pyridine-CN) | Ald |
| sco7 | HOOC-CH2CH3 (propanoic acid) | TCI |
| sco8 | HOOC-(3-methylphenyl) | TCI |
| sco9 | HOOC-(4-methylphenyl) | Ald |
| sco10 | HOOC-(2-fluorophenyl) | TCI |
| sco11 | HOOC-(3-fluorophenyl) | TCI |
| sco12 | HOOC-(4-fluorophenyl) | TCI |
| sco13 | HOOC-(2-chlorophenyl) | TCI |
| sco14 | HOOC-(3-chlorophenyl) | TCI |
| sco15 | HOOC-(4-chlorophenyl) | TCI |
| sco16 | HOOC-(2-cyanophenyl) | Ald |
| sco17 | HOOC-(3-cyanophenyl) | TCI |
| sco18 | HOOC-(4-cyanophenyl) | Ald |
| sco19 | HOOC-(2-COOMe-phenyl) | WAKO |
| sco20 | HOOC-(3-COOMe-phenyl) | WAKO |
| sco21 | HOOC-(4-COOMe-phenyl) | TCI |

TABLE sco-continued

| sco | Str. | Spl. |
|---|---|---|
| sco22 | 2-methoxybenzoic acid (HOOC, OMe at ortho) | TCI |
| sco23 | 3-methoxybenzoic acid (HOOC, OMe at meta) | TCI |
| sco24 | 4-methoxybenzoic acid (HOOC, OMe at para) | WAKO |
| sco25 | 2-(dimethylamino)benzoic acid | AAesar |
| sco26 | 3-(dimethylamino)benzoic acid | TCI |
| sco27 | 4-(dimethylamino)benzoic acid | TCI |
| sco28 | nicotinic acid (pyridine-3-carboxylic acid) | TCI |
| sco29 | 3-(methanesulfonamido)benzoic acid | WAKO |
| sco30 | 4-(methanesulfonamido)benzoic acid | WAKO |
| sco31 | benzoic acid | WAKO |
| sco32 | 4-(hydroxymethyl)benzoic acid | TCI |
| sco33 | 4-cyano-2-fluorobenzoic acid | AAesar |
| sco34 | phenoxyacetic acid (HOOC–CH$_2$–O–Ph) | TCI |
| sco35 | 3-(4-fluorophenyl)propanoic acid | Ald |
| sco36 | (E)-3-(4-fluorophenyl)acrylic acid | TCI |
| sco37 | pyridine-2-carboxylic acid | TCI |
| sco38 | pyridine-4-carboxylic acid (isonicotinic acid) | TCI |
| sco39 | pyridazine-4-carboxylic acid | Ald |
| sco40 | pyrimidine-5-carboxylic acid | MAYB |
| sco41 | pyrazine-2-carboxylic acid | TCI |
| sco42 | imidazo[1,2-a]pyridine-6-carboxylic acid | MAYB |
| sco43 | 1-methyl-1H-imidazole-4-carboxylic acid | MAYB |
| sco44 | 1-methyl-1H-imidazole-5-carboxylic acid | MAYB |
| sco45 | thiazole-4-carboxylic acid | Matrix |
| sco46 | thiophene-3-carboxylic acid | Acros |

TABLE sco-continued
| sco | Str. | Spl. |
|---|---|---|
| sco47 | 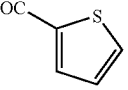 | TCI |
| sco48 | 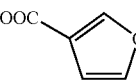 | TCI |
| sco49 | 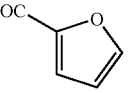 | TCI |
| sco50 | 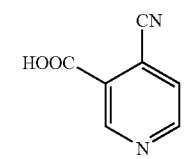 | |
| sco51 | 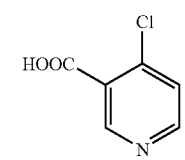 | Ald |
| sco52 | 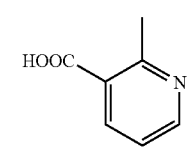 | Ald |
| sco53 | 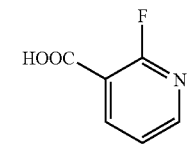 | Ald |
| sco54 | 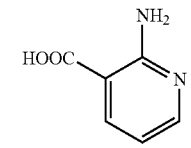 | TCI |
| sco55 | 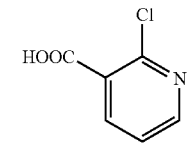 | TCI |
| sco56 | 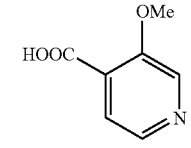 | WAKO |
| sco57 | 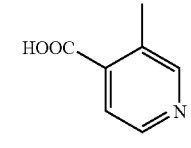 | Ald |
TABLE sco-continued
| sco | Str. | Spl. |
|---|---|---|
| sco58 | 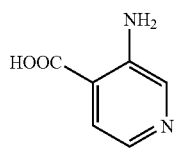 | MAYB |
| sco59 | 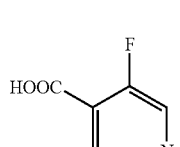 | Matrix |
| sco60 | 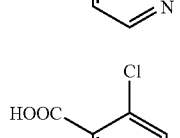 | Ald |
| sco61 | 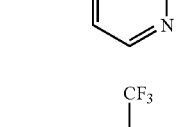 | Ald |
| sco62 | 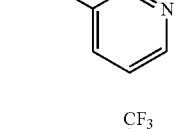 | MAYB |
| sco63 | 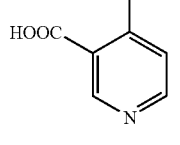 | TCI |
| sco64 | 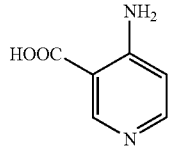 | TCI |
| sco65 | 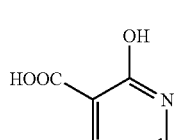 | TCI |
| sco66 | 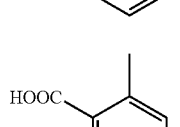 | Ald |
| sco67 | 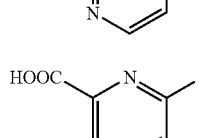 | LANC |

TABLE sco-continued

| sco | Str. | Spl. |
|---|---|---|
| sco68 | HOOC-pyridine-F (4-carboxy, 2-F) | Ald |
| sco69 | HOOC-pyridine-Cl (4-carboxy, 2-Cl) | TCI |
| sco70 | HOOC-pyridine-OH (4-carboxy, 2-OH) | Matrix |
| sco71 | HOOC-pyridine-NH₂ (4-carboxy, 2-NH₂) | LANC |
| sco72 | HOOC-pyridine-Me (2-carboxy, 6-Me) | Ald |
| sco73 | HOOC-pyridine-diMe (4-carboxy, 2,6-diMe) | Life |
| sco74 | HOOC-pyridine-Cl (3-carboxy, 6-Cl) | TCI |
| sco75 | HOOC-pyridine-NH₂ (3-carboxy, 6-NH₂) | TCI |
| sco76 | HOOC-pyridine-CF₃ (3-carboxy, 6-CF₃) | Ald |
| sco77 | HOOC-pyridine-OMe (3-carboxy, 6-OMe) | Matrix |
| sco78 | HOOC-pyridine-OH (3-carboxy, 6-OH) | Ald |
| sco79 | HOOC-pyridine-COOMe (3-carboxy, 5-COOMe) | — |
| sco80 | HOOC-pyridine-diCl (4-carboxy, 2,3-diCl) | Apollo |
| sco81 | HOOC-pyridine-diCl (3-carboxy, 5,6-diCl) | Matrix |
| sco82 | HOOC-pyridine-diCl (3-carboxy, 4,6-diCl) | Bionet |
| sco83 | HOOC-pyridine-diCl (4-carboxy, 3,5-diCl) | TCI |
| sco84 | HOOC-pyridine-diCl (4-carboxy, 2,6-diCl) | TCI |
| sco85 | HOOC-pyridine-diCl (2-carboxy, 3,6-diCl) | Matrix |
| sco86 | HOOC-pyridine-diCl (3-carboxy, 2,6-diCl) | Ald |
| sco87 | HOOC-pyridine-Ph (3-carboxy, 6-Ph) | MAYB |
| sco88 | HOOC-pyridine-diMe (3-carboxy, 2,6-diMe) | J&W |

TABLE sco-continued
| sco | Str. | Spl. |
|---|---|---|
| sco89 | 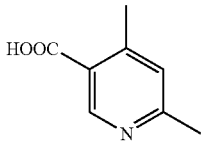 | Princeton |
| sco90 | 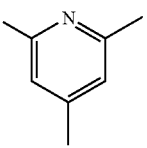 | Otava |
| sco91 |  | WAKO |
| sco92 | 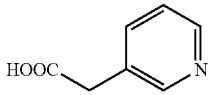 | TCI |
| sco93 | 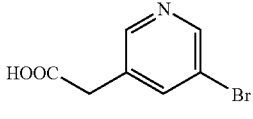 | AAesar |
| sco94 | 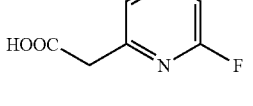 | |
| sco95 | 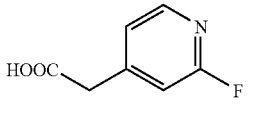 | |
| sco96 | 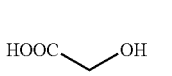 | TCI |
| sco97 |  | WAKO |
| sco98 | 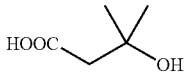 | TCI |
| sco99 | 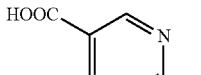 | TCI |
| sco100 |  | Ald |
| sco101 | 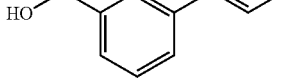 | WAKO |
| sco102 | 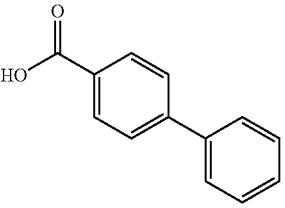 | TCI |
| sco103 | 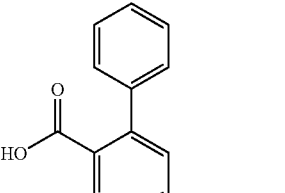 | TCI |
| sco104 | 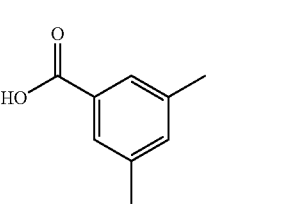 | Ald |
| sco105 | 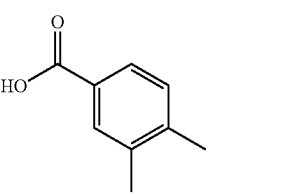 | TCI |
| sco106 | 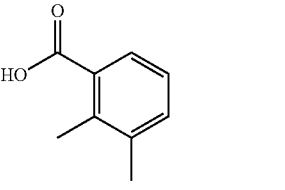 | TCI |
| sco107 | 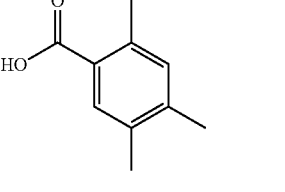 | Ald |
| sco108 | 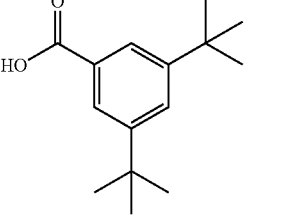 | TCI |

TABLE sco-continued

| sco | Str. | Spl. |
|---|---|---|
| sco109 | 2-fluoro-4-bromobenzoic acid | TCI |
| sco110 | 3-chloro-4-methylbenzoic acid | Matrix |
| sco111 | 2-methyl-6-chlorobenzoic acid | LANC |
| sco112 | 2,3-difluoro-4-methylbenzoic acid | Oak |
| sco113 | 3-methyl-4-fluorobenzoic acid | Ald |
| sco114 | 3-trifluoromethyl-4-methylbenzoic acid | AAesar |
| sco115 | 2-trifluoromethyl-4-methylbenzoic acid | ABCR |
| sco116 | 2-methyl-3-trifluoromethylbenzoic acid | Apollo |
| sco117 | 3,5-bis(trifluoromethyl)benzoic acid | Ald |
| sco118 | 3,4-difluorobenzoic acid | TCI |
| sco119 | 2,4,5-trifluorobenzoic acid | Ald |
| sco120 | 3,5-difluorobenzoic acid | Ald |
| sco121 | 3-trifluoromethyl-4-fluorobenzoic acid | Ald |
| sco122 | 3-chloro-4-fluorobenzoic acid | TCI |
| sco123 | 3-bromo-4-fluorobenzoic acid | LANC |
| sco124 | 3-fluoro-4-trifluoromethylbenzoic acid | Ald |
| sco125 | 3,4,5-trifluorobenzoic acid | TCI |
| sco126 | 3-trifluoromethyl-4-chlorobenzoic acid | Fchem |

TABLE sco-continued

| sco | Str. | Spl. |
|---|---|---|
| sco127 | 3-bromo-5-fluorobenzoic acid | WAKO |
| sco128 | naphthalene-1-carboxylic acid | TCI |
| sco129 | naphthalene-2-carboxylic acid | TCI |
| sco130 | 2-methoxy-4-(methylthio)benzoic acid | Ald |
| sco131 | 2,4,5-trimethoxybenzoic acid | Ald |
| sco132 | 2,4-dimethoxybenzoic acid | TCI |
| sco133 | 2,5-dimethoxybenzoic acid | Acros |
| sco134 | 3,5-dimethoxybenzoic acid | TCI |
| sco135 | 3,4-dimethoxybenzoic acid | TCI |
| sco136 | 2,3,4-trimethoxybenzoic acid | TCI |
| sco137 | 3,4,5-trimethoxybenzoic acid | TCI |
| sco138 | 3,5-dimethoxy-4-methylbenzoic acid | LANC |
| sco139 | 2-fluoro-5-methoxybenzoic acid | Apollo |
| sco140 | 3,5-dimethyl-4-methoxybenzoic acid | Acros |
| sco141 | 3-methoxy-4-methylbenzoic acid | TCI |
| sco142 | 2-methoxy-6-methylbenzoic acid | Ald |
| sco143 | 3-methyl-4-methoxybenzoic acid | Ald |

TABLE sco-continued
| sco | Str. | Spl. |
|---|---|---|
| sco144 | 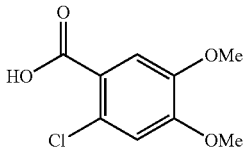 | Matrix |
| sco145 | 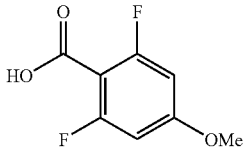 | Matrix |
| sco146 | 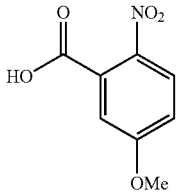 | Ald |
| sco147 | 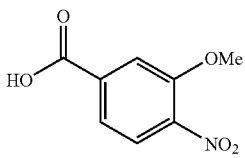 | Ald |
| sco148 | 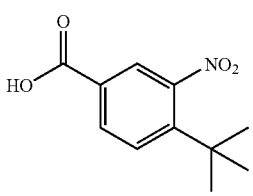 | Ald |
| sco149 | 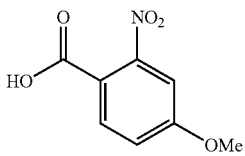 | Ald |
| sco150 | 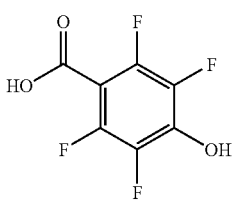 | Ald |
| sco151 | 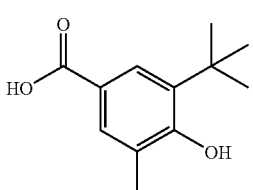 | TCI |
| sco152 | 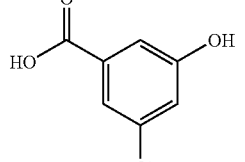 | J&W |
| sco153 |  | Apollo |
| sco154 | 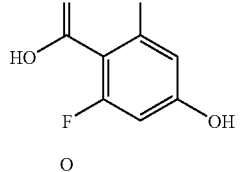 | Matrix |
| sco155 | 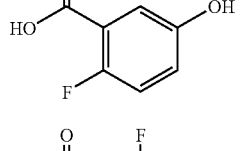 | Matrix |
| sco156 | 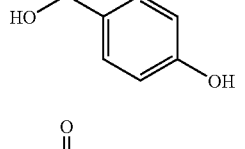 | LANC |
| sco157 | 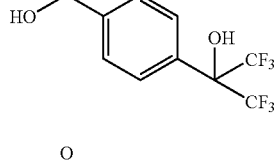 | Ald |
| sco158 | 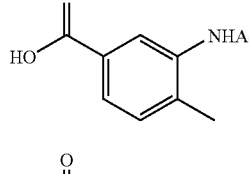 | Ald |
| sco159 | 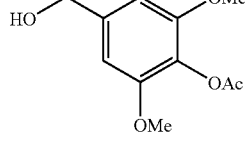 | Matrix |
| sco160 | 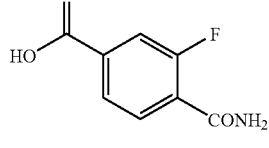 | WAKO |

TABLE sco-continued
| sco | Str. | Spl. |
|---|---|---|
| sco161 | 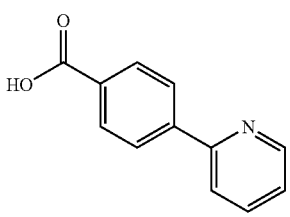 | Synchem |
| sco162 | 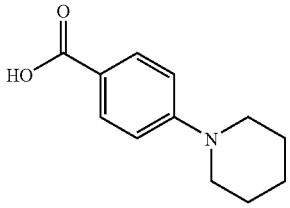 | MAYB |
| sco163 | 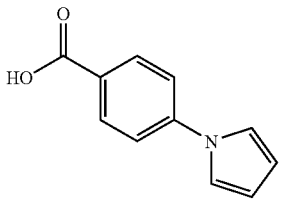 | Ald |
| sco164 | 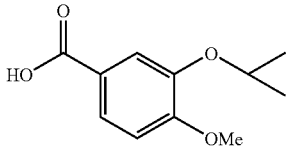 | MAYB |
| sco165 | 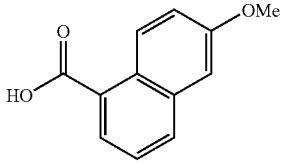 | Ald |
| sco166 | 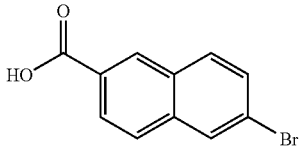 | LANC |
| sco167 | 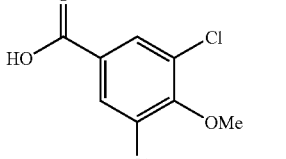 | Apollo |
| sco168 | 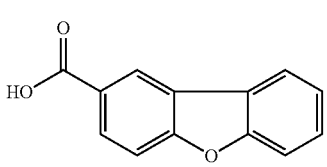 | Ald |
| sco169 | 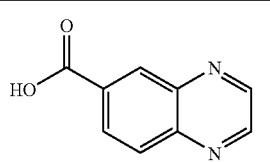 | MAYB |
| sco170 |  | Apollo |
| sco171 | 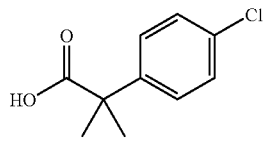 | Acros |
| sco172 | 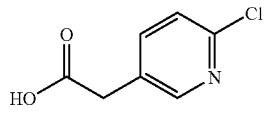 | Asymchem |
| sco173 | 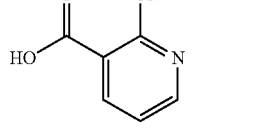 | |
| sco174 | 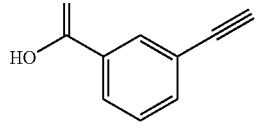 | J&W |
| sco175 | 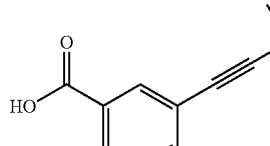 | |
| sco176 | 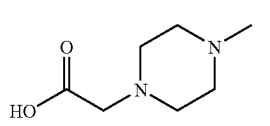 | Matrix |
| sco177 | 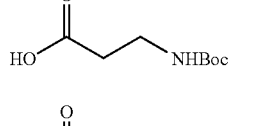 | TCI |
| sco178 | 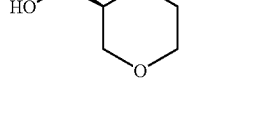 | Ast |

TABLE sco-continued

| sco | Str. | Spl. |
|---|---|---|
| sco179 | (1S,3R)-3-(Boc-amino)cyclopentanecarboxylic acid | Acros |
| sco180 | 6-methylnicotinic acid | WAKO |
| sco181 | 3-cyano-4-fluorobenzoic acid | Apollo |
| sco182 | 4-cyano-3-fluorobenzoic acid | Apollo |
| sco183 | 2,4,6-triisopropylbenzoic acid | WAKO |
| sco184 | 2,6-dichloro-3-nitrobenzoic acid | Ald |
| sco185 | 3-chloro-2-hydroxybenzoic acid | Ald |
| sco186 | 2-hydroxy-3-isopropyl-6-methylbenzoic acid | Ald |
| sco187 | 2,3-difluoro-4-hydroxybenzoic acid | Apollo |
| sco188 | 2-hydroxy-6-methoxybenzoic acid | Ald |
| sco189 | 2,4-dihydroxy-3,6-dimethylbenzoic acid | LANC |
| sco190 | 2-hydroxy-4-methoxybenzoic acid | Ald |
| sco191 | 6-fluoro-2-hydroxybenzoic acid | Ald |
| sco192 | 3-fluoro-4-hydroxybenzoic acid | WAKO |
| sco193 | 4-morpholinobenzoic acid | WAKO |
| sco194 | 3-benzoylbenzoic acid | Ald |
| sco195 | 3-cyano-5-fluorobenzoic acid | Matrix |
| sco196 | 3-methoxypropanoic acid | Ald |
| sco197 | 2-ethoxyacetic acid | TCI |

TABLE sco-continued
| sco | Str. | Spl. |
|---|---|---|
| sco198 | 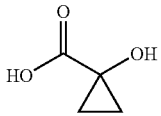 | Ald |
| sco199 | 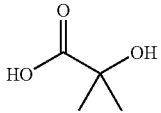 | TCI |
| sco201 | 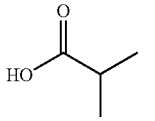 | TCI |
| sco202 | 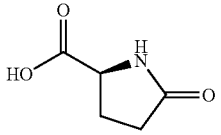 | TCI |
| sco203 | 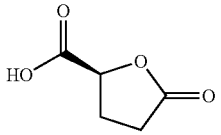 | TCI |
| sco204 | 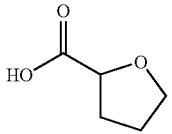 | Ald |
| sco205 | 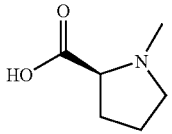 | Wata |
| sco206 | 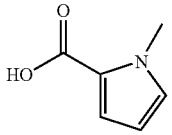 | Ald |
| sco207 | 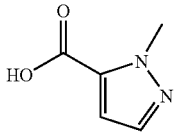 | MAYB |
| sco208 | 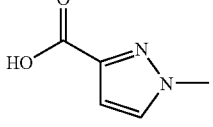 | Fchem |
| sco209 | 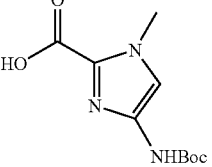 | Oak |
| sco210 | 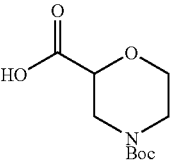 | NEO |
| sco211 | 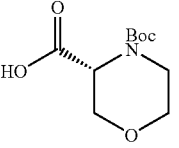 | Ast |
| sco212 | 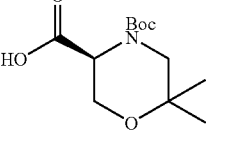 | |
| sco213 | 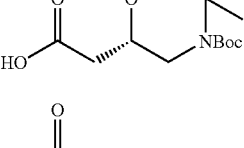 | |
| sco214 | 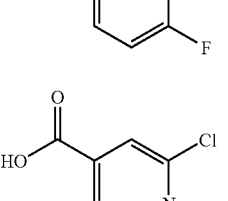 | Ald |
| sco215 | 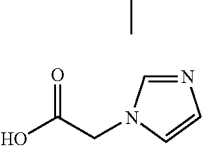 | Ald |
| sco216 | 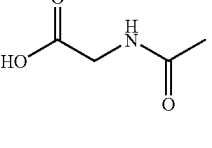 | MAYB |
| sco217 | 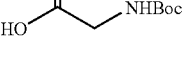 | TCI |
| sco218 | | WAKO |

TABLE sco-continued
| sco | Str. | Spl. |
|---|---|---|
| sco219 | 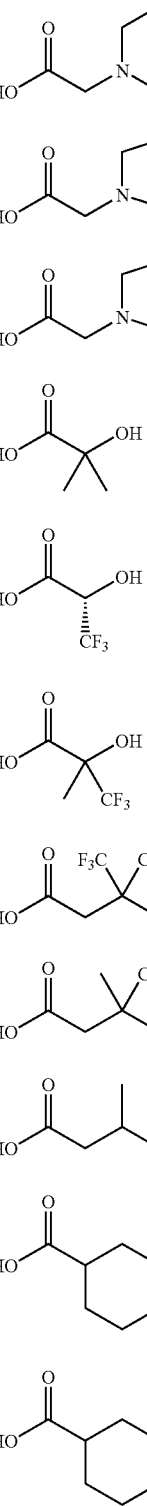 | WAKO |
| sco220 | | Matrix |
| sco221 | | Matrix |
| sco222 | | Tyger |
| sco223 | | TCI |
| sco224 | | Ald |
| sco225 | | Oak |
| sco226 | | WAKO |
| sco227 | | WAKO |
| sco228 | | TCI |
| sco229 | | BACHEM |
| sco230 | | Oak |
| sco231 | 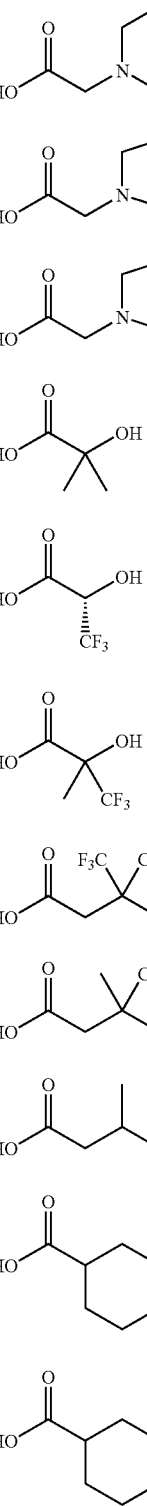 | Wata |
| sco232 | | Ald |
| sco233 | | WAKO |
| sco234 | | Wata |
| sco235 | | Ast |
| sco236 | | TCI |
| sco237 | | MAYB |
| sco238 | | TCI |
| sco239 | | Ald |
| sco240 | | Apollo |
| sco241 | | Ald |

TABLE sco-continued

| sco | Str. | Spl. |
|---|---|---|
| sco242 | 1-methylimidazol-4-yl acetic acid HCl | sAld |
| sco243 | 2-(N-Boc-piperidin-4-yl)acetic acid | Ast |
| sco244 | 3-hydroxypropanoic acid | TCI |
| sco245 | 3,3,3-trifluoro-2-hydroxy-2-(trifluoromethyl)propanoic acid | LANC |
| sco246 | N-Boc-N-methylglycine | WAKO |
| sco247 | 3,5-dimethylisoxazole-4-carboxylic acid | AAesar |
| sco249 | 3-(N-Boc-amino)benzoic acid | Wata |
| sco250 | 1H-imidazole-4-carboxylic acid | Tyger |
| sco252 | trans-3-(N-Boc-amino)cyclobutanecarboxylic acid | AMRI |
| sco253 | 2-hydroxy-3-methoxypropanoic acid | |
| sco254 | 2-(6-fluoropyridin-2-yl)propanoic acid | |
| sco255 | (S)-2-methoxypropanoic acid | Acros |
| sco256 | (R)-2-methoxypropanoic acid | Toront |
| sco257 | cyclobutanecarboxylic acid | TCI |
| sco258 | 1,4-dioxane-2-carboxylic acid | Chemb |
| sco259 | tetrahydrofuran-2-carboxylic acid | Aldrich |
| sco260 | butanoic acid | TCI |
| sco261 | pentanoic acid | TCI |
| sco262 | cyclopentanecarboxylic acid | TCI |
| sco263 | cyclohexanecarboxylic acid | TCI |
| sco264 | 2,2-difluoroacetic acid | Ald |

A compound represented by sco50 in Table sco was prepared by the described method in Tetrahedron Lett., 2005, 46, pp. 135-137. A compound represented by sco79 was prepared from 3,5-pyridinedicarboxylic acid by a usual method. A compound represented by sco94 was prepared by the described method in Synlett, 2000, pp. 1488-1490. A compound represented by sco95 was prepared by the described method in Chem. Pharm. Bull., 1984, pp. 4866-4872. A compound represented by sco173 was prepared by the method described in Tetrahedron Lett., 2005, 46, pp. 135-137. A compound represented by sco176 was prepared from 3-iodobenzoic acid by a usual method. A compound represented by sco212 was prepared by the described method in WO 2004/092167. A compound represented by sco213 was prepared from a commercially available morpholine derivative by a usual method by protecting an amino group. A compound represented by sco253 was prepared by the method described in U.S. Pat. No. 5,348,978. A compound represented by sco254 was prepared from propionitrile and 2,6-difluoropyridine by the method described in Synlett, 2000, pp. 1488-1490.

TABLE sso

| sso | Str. | Spl. |
|---|---|---|
| sso1 | | TCI |
| sso2 | | J&W |
| sso3 | | TCI |
| sso4 | | Ald |
| sso5 | | TCI |
| sso6 | | WAKO |
| sso7 | | |
| sso8 | | Ald |
| sso9 | | WAKO |
| sso10 | | TCI |
| sso11 | | MAYB |
| sso12 | | WAKO |
| sso13 | | TCI |
| sso14 | | TCI |
| sso15 | | TCI |
| sso16 | | Ald |
| sso17 | | Ald |
| sso18 | | AAesar |
| sso19 | | Ald |

US 8,299,055 B2
TABLE sso-continued
| sso | Str. | Spl. |
|---|---|---|
| sso20 | 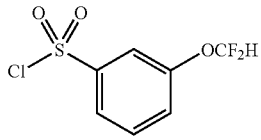 | Ald |
| sso21 | 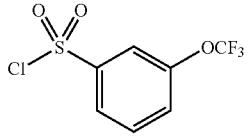 | Ald |
| sso22 | 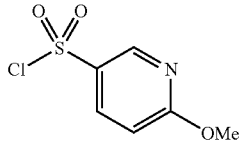 | J&W |
| sso23 | 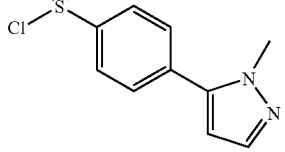 | MAYB |
| sso24 | 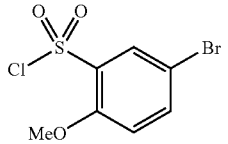 | Avocado |
| sso25 | 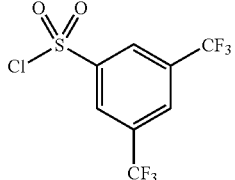 | WAKO |
| sso26 | 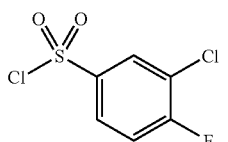 | Avocado |
| sso27 | 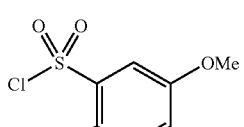 | Ald |
| sso28 | 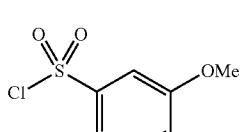 | Ald |
TABLE sso-continued
| sso | Str. | Spl. |
|---|---|---|
| sso29 | 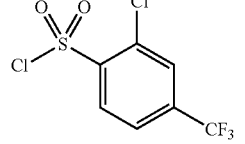 | TCI |
| sso32 | 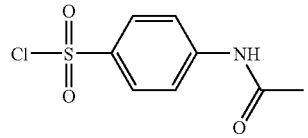 | Ald |
| sso33 | 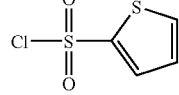 | WAKO |
| sso34 | 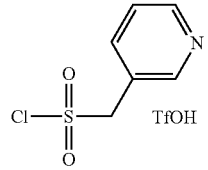 | Array |
| sso35 | 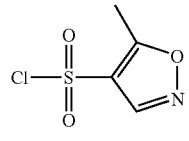 | MAYB |
| sso36 | 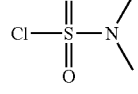 | TCI |
| sso37 | 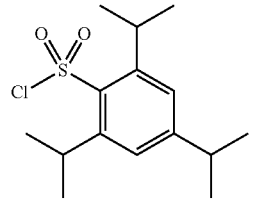 | TCI |
| sso38 | 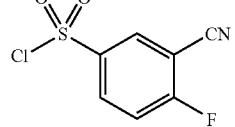 | Ald |
| sso39 | 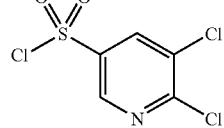 | Apollo |
| sso40 | 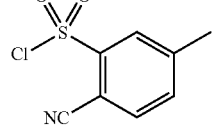 | MAYB |

TABLE sso-continued

| sso | Str. | Spl. |
|---|---|---|
| sso41 | 2-chloro-4-cyanobenzenesulfonyl chloride | Ald |
| sso42 | propane-1-sulfonyl chloride | Ald |
| sso43 | trifluoromethanesulfonyl chloride | TCI |
| sso44 | 2,2,2-trifluoroethanesulfonyl chloride | Acros |
| sso45 | 3-chloropropane-1-sulfonyl chloride | Ald |
| sso46 | (3-methoxyphenyl)methanesulfonyl chloride |  |
| sso47 | 2-methylpropane-1-sulfonyl chloride | Ald |
| sso48 | butane-2-sulfonyl chloride | oak |
| sso49 | 6-methylpyridine-2-sulfonyl chloride |  |
| sso50 | 2-methoxyethanesulfonyl chloride | Otava |
| sso51 | prop-1-yne-1-sulfonyl chloride |  |
| sso52 | 3-chloropyridine-4-sulfonyl chloride | Ena |
| sso53 | 1-methyl-1H-pyrazole-4-sulfonyl chloride | Ena |

TABLE sso-continued

| sso | Str. | Spl. |
|---|---|---|
| sso54 | 1-methyl-1H-pyrazole-5-sulfonyl chloride | MAYB |
| sso55 | cyclohexanesulfonyl chloride | Apollo |
| sso56 | 5-bromopyridine-3-sulfonyl chloride | MAYB |
| sso57 | 6-chloropyridine-3-sulfonyl chloride | Ena |
| sso58 | 4-methyl-3,4-dihydro-2H-pyrido[3,2-b][1,4]oxazine-7-sulfonyl chloride | MAYB |
| sso59 | 2,4-dimethylthiazole-5-sulfonyl chloride | MAYB |
| sso60 | 2-methyl-1H-imidazole-5-sulfonyl chloride | ACBB |
| sso61 | prop-2-ene-1-sulfonyl chloride | Matrix |
| sso62 | cyclopentanesulfonyl chloride | Labo |
| sso63 | butane-1-sulfonyl chloride | TCI |

TABLE sso-continued

| sso | Str. | Spl. |
|---|---|---|
| sso64 | cyclobutanesulfonyl chloride | Hande |
| sso65 | 1-(tetrahydropyran-2-yl)-1H-pyrazole-4-sulfonyl chloride | |
| sso66 | difluoromethanesulfonyl chloride | Ena |

In Table sso, a compound represented by sso46 was prepared from sulfuryl chloride and 3-methoxyphenylmethylmagnesium chloride by the method described in U.S. Patent No. 2007/99825. A compound represented by sso49 was prepared from sulfuryl chloride and 6-methyl-2-pyridylmagnesium bromide (Rieke Metals) by the method described in U.S. Patent No. 2007/99825.

Reference Example sso 51 propyne-1-sulfonyl chloride (sso 51)

A THF solution of 1-propynylmagnesium bromide (0.5 N, 140 μL; Ald) was cooled to −78° C. followed by the addition of sulfuryl chloride (10 L; TCI) and the resulting mixture was stirred for 1 hour. The resulting mixture was stirred at room temperature for 2 hours and the reaction mixture solution was concentrated to give the title compound.

TABLE sch

| sch | Str. | Spl. |
|---|---|---|
| sch201 | HCHO | Ald |
| sch202 | OHC-pyridine | WAKO |
| sch203 | OHC-(N-methylimidazole) | Ald |
| sch204 | OHC-CO₂H | WAKO |
| sch205 | OHC-phenyl | nacalai |

TABLE sch-continued

| sch | Str. | Spl. |
|---|---|---|
| sch206 | OHC-(tetrahydrofuran) | Ald |

TABLE son

| son | Str. | Spl. |
|---|---|---|
| son1 | (CH₃)₃Si-N=C=O | TCI |
| son2 | ethyl isocyanate | TCI |
| son3 | cyclohexyl isocyanate | TCI |
| son4 | phenyl isocyanate | TCI |
| son5 | phenethyl isocyanate | Ald |
| son6 | 3-pyridyl isocyanate | Oak |
| son7 | propyl isocyanate | TCI |
| son8 | butyl isocyanate | TCI |
| son9 | isopropyl isocyanate | TCI |
| son10 | cyclopentyl isocyanate | Ald |

Example IM 1-1

1,3-dibromo-5-methoxybenzene

Sodium methoxide (25 g; WAKO) was added to a DMF (250 mL) solution of 1,3,5-tribromobenzene (75 g; TCI) and the resulting mixture was stirred at 90° C. for 15 minutes. The reaction mixture was concentrated, aqueous ammonium chloride (400 mL) and ethyl acetate (400 mL) were added to extract the reaction mixture, the organic layer was washed with saturated brine (200 mL×2), and the organic layer was dried. The solvent was evaporated under reduced pressure and the residue was purified by column chromatography (n-hexane) to give the title compound (39.2 g).

$^1$H-NMR (CDCl$_3$); δ (ppm) 3.97 (3H, s), 6.98 (2H, m), 7.25 (1H, m)

Example IM 1-2

3-bromo-5-methoxybenzaldehyde

Butylmagnesium chloride (2.0 M, THF; Ald) (31 mL) was cooled to −10° C. followed by the addition of butyllithium (1.6 M, Hex; Ald) (79 mL) and the resulting mixture was stirred for 30 minutes. A toluene solution (220 mL) of Example compound IM1-1 (45 g) was further added and the resulting mixture was further stirred for 30 minutes. A toluene solution (50 mL) of DMF (18 mL; WAKO) was added and the resulting mixture was stirred for 1 hour and then stirred at room temperature for 30 minutes. Aqueous ammonium chloride (300 mL) and ethyl acetate (300 mL) were added to extract the reaction mixture and the organic layer was washed with saturated brine (300 mL) and dried. The solvent was evaporated under reduced pressure and the residue was purified by column chromatography (n-hexane/ethyl acetate) to give the title compound (25.8 g).

$^1$H-NMR (CDCl$_3$); δ (ppm) 3.87 (3H, s), 7.32 (2H, m), 7.58 (1H, t, 1.5 Hz) 9.91 (1H, s)

Example IM 1-3

(3-bromo-5-methoxyphenyl)methanol

NaBH$_4$ (3.85 g; WAKO) was added to an ethanol (80 mL) and THF (20 mL) mixture solution of Example compound IM1-2 (22 g) with ice cooling and the resulting mixture was stirred at room temperature for 3 hours. The resulting mixture was poured into ice water (300 mL), then ethyl acetate (300 mL) was added to extract the reaction mixture, and the organic layer was washed with saturated aqueous sodium bicarbonate solution (300 mL) and then dried. The solvent was evaporated under reduced pressure to give the title compound (22.05 g).

$^1$H-NMR (CDCl$_3$); δ (ppm) 1.86 (1H, s), 3.79 (3H, s), 4.63 (2H, s), 6.84 (1H, m), 6.97 (1H, m), 7.09 (1H, m)

Example IM 1-4

1-bromo-3-(bromomethyl)-5-methoxybenzene

Triphenylphosphine (28 g; KANTO) was added to a dichloromethane (150 mL) solution of Example compound IM1-3 (22.05 g) with ice cooling, the resulting mixture was stirred for approx. 10 minutes followed by the addition of N-bromosuccinimide (20 g; TCI), and the resulting mixture was stirred at room temperature for 13 hours and 30 minutes. The solvent was evaporated under reduced pressure and the residue was purified by column chromatography (n-hexane/ethyl acetate) to give the title compound (23.94 g).

$^1$H-NMR (CDCl3); δ (ppm) 3.80 (3H, s), 4.38 (2H, s), 6.85 (1H, m), 6.98 (1H, m), 7.13 (1H, m)

Example IM 1-5

2-(3-bromo-5-methoxyphenyl)acetonitrile

Sodium cyanide (3.4 g; WAKO) was added to a DMSO (100 mL) solution of Example compound IM1-4 (16.3 g) at room temperature and the resulting mixture was stirred at 40° C. for 1 hour and 40 minutes. Ethyl acetate (300 mL), saturated aqueous sodium bicarbonate solution (150 mL), and water (150 mL) were added to the reaction mixture to extract the reaction mixture, the organic layer was washed with saturated brine (300 mL) and then dried, and then the solvent was evaporated under reduced pressure. The residue was purified by column chromatography (Yamazen; n-hexane/ethyl acetate) to give the title compound (11.37 g).

$^1$H-NMR (CDCl$_3$); δ (ppm) 3.69 (2H, s), 3.81 (3H, s), 6.81 (1H, m), 7.02 (1H, m), 7.06 (1H, m)

Example IM 1-6

8-bromo-6-methoxyisoquinoline

[Step a] 2-(3-bromo-5-methoxyphenyl)ethanamine (Intermediate IM 1-6-1)

A borane-tetrahydrofuran complex (1 M, 73.6 mL) was added to a THF (36.8 mL) solution of Example compound IM1-5 at room temperature and the resulting mixture was stirred to reflux at 80° C. for 2 hours. Methanol (26 mL) and 1 N hydrochloric acid (26 mL) were added to the reaction mixture solution and the resulting mixture was stirred for 1 hour at room temperature. The resulting mixture was neutralized with 1 N aqueous sodium hydroxide solution, then ethyl acetate (100 mL) was added to extract the reaction mixture, the organic layer was dried, and the solvent was evaporated under reduced pressure to give the title compound (8.76 g).

(Intermediate IM 1-6-1 Rf (TLC)=0.1 (CH$_3$Cl:MeOH=10:1))

[Step b] 8-bromo-6-methoxy-1,2,3,4-tetrahydroisoquinoline (Intermediate IM 1-6-2)

Paraformaldehyde (660 mg; WAKO) was added to a formic acid (50 mL) solution of Intermediate IM1-6-1 (4.33 g) obtained by the above-mentioned method at 50° C. and the resulting mixture was stirred for 13 hours and 30 minutes. The solvent was evaporated under reduced pressure, dichloromethane (100 mL) and 1 N aqueous sodium hydroxide solution (100 mL) were added to extract the reaction mixture, and the aqueous layer was further extracted with dichloromethane. The organic layer was combined and dried and the solvent was evaporated under reduced pressure to give the title compound (4.49 g).

(Intermediate IM 1-6-2 LCMS: 242.1 (MH$^+$); retention time: 0.66 min; LCMS; condition A)

$^1$H-NMR (CDCl3); δ (ppm) 1.90 (1H, s), 2.75 (2H, m), 3.06 (2H, m), 3.76 (3H, s), 3.91 (2H, s), 6.61 (1H, d, J=2.6 Hz), 6.96 (1H, d, J=2.6 Hz)

[Step c] 8-Bromo-6-methoxy-isoquinoline

Sodium sulfate (2.8 g) and manganese dioxide (7.1 g; Ald) were added to a toluene (60 mL) solution of Intermediate IM1-6-2 (1.99 g) obtained by the above-mentioned method and the resulting mixture was stirred at 140° C. for 24 hours. The resulting mixture was filtrated through celite followed by the addition of 2 N hydrochloric acid, and the resulting mixture was washed with ether. The resulting mixture was neutralized with 5 N aqueous sodium hydroxide solution and extracted with dichloromethane to give the title compound (698 mg).

(LCMS: 238.0 (MH$^+$); retention time: 3.64 min; LCMS; condition A)

$^1$H-NMR (DMSO); δ (ppm) 3.94 (3H, s), 7.44 (1H, d, J=2.2 Hz), 7.66 (1H, d, J=2.2 Hz), 7.76 (1H, d, J=5.9 Hz), 8.53 (1H, d, 5.9 Hz), 9.29 (1H, s)

Test Example 1

Measurement of IKKβ Activity Inhibiting Ability

The IKKβ activity inhibiting ability of the compound of the present invention was evaluated by time-resolved fluorescence resonance energy transfer (TR-FRET) assay. IKKβ, which was used in the assay, was obtained from Sf9 cells as a host using Bac-to-Bac System of Invitrogen (U.S.) according to the manufacturer's instruction.

Specifically, 6 μL of a mixed solution of an assay buffer (50 mM HEPES pH 7.2, 10 mM MgCl$_2$, 1 mM EGTA, 0.01% Briji, 0.01% BSA) and a biotinylated substrate (GST-IκBα [amino acid residues 1 to 54]-biotin; final concentration 0.25 μM)/ATP (final concentration 25 μM) was added to a well containing 2 μL of a test compound at various concentrations or DMSO (final concentration 0.1%). Then, 2 μL of IKKβ (final concentration 1 nM) diluted with the above-mentioned assay buffer was added to initiate a reaction and incubated at room temperature for 30 minutes, followed by the addition of 2 μL of 500 mM EDTA to terminate the reaction. A detection reagent (3 μL) comprising a buffer (20 mM Tris-HCl pH 7.5, 600 mM KF, 0.1% BSA) containing an avidin reagent (Cisbio, France) labeled with APC and anti-phosphoserine-IκBα monoclonal antibody 9A7K labeled with europium cryptate (Cisbio, France), which recognizes phosphorylated IκBα and does not recognize non-phosphorylated IκBα, was added and the reactant was further incubated at room temperature for 60 minutes. The extent of phosphorylation of the biotinylated substrate peptides was measured as a ratio of the specific energy transfer signal at 665 nm to the reference europium signal at 615 nm using Perkin-Elmer Envision (Perkin Elmer, U.S.). In order to obtain monoclonal antibody 9A7K, a partial IκBα peptide (amino acid residues 28 to 39) phosphorylated the serine residues corresponding to 32nd and 36th amino acid residues in IκBα protein was conjugated to keyhole limpet hemocyanin, mixed with an adjuvant, and used to immunize a C3H/He mouse. Then, 9A7K was obtained from the mouse using a conventional method.

Measurement Results

Among the compounds of the present invention, the test compounds, Example compounds 1-N-1 to 1-N-17, 1-N-19 to 1-N-30, 1-N-32, 1-N-34, 1-N-36 to 1-N-43, 1-N-45 to 1-N-51, 2-N-301, 2-N-2 to 2-N-113, 2-N-201 to 2-N-213, 2-N-215 to 2-N-291, 2-N-1, 2-N-302 to 2-N-320, 2-N-401, 2-N-402, 2-N-501 to 2-N-511, 2-N-601 to 2-N-619, 2-N-701 to 2-N-713, 2-N-801 to 2-N-804, 3-N-1 to 3-N-24, 3-N-101 to 3-N-114, 3-N-201 to 3-N-209, 3-N-301, 3-N-302, 3-N-401 to 3-N-411, 3-N-501 to 3-N-520, 1-o-1 to 1-o-6, 1-o-10 to 1-o-13, 1-o-15, 1-o-16, 1-o-18, 1-o-20, 1-o-21, 1-o-24, 1-o-26 to 1-o-28, 1-o-33 to 1-o-35, 1-o-38, 1-o-43, 1-o-44, 1-o-47, 1-o-51, 1-o-52, 1-s-1, 1-s-2, 2-o-1 to 2-o-21, 2-o-23 to 2-o-35, 2-o-37 to 2-o-50, 2-o-52 to 2-o-57, 2-o-59 to 2-o-64, 2-o-66 to 2-o-120, 2-o-123 to 2-o-134, 2-o-136 to 2-o-138, 2-o-140, 2-o-141, 2-o-143 to 2-o-147, 2-o-149 to 2-o-162, 2-o-164 to 2-o-203, 2-o-205 to 2-o-224, 2-o-226 to 2-o-228, 2-o-232, 2-o-234, 2-o-235, 2-o-237, 2-o-247 to 2-o-256, 2-s-1 to 2-s-6, 3-o-1 to 3-o-11, 3-o-14 to 3-o-22, 3-o-24 to 3-o-39, 3-o-42, 3-s-1 to 3-s-3, 4-o-1, 4-o-3 to 4-o-13, 5-o-1, 5-o-2, 5-o-5 to 5-o-8, 5-o-10, 1-oP-2 to 1-oP-12, 1-oP-14, 1-oP-16, 1-oP-17, 1-oP-19 to 1-oP-22, 1-oP-31 to 1-oP-33, 1-oP-35, 1-oP-37 to 1-oP-39, 1-oP-42, 1-NP-1 to 1-NP-34, 1-NP-36, 1-NP-38 to 1-NP-43, 6-o-1 to 6-o-3, 7-o-1, 3-NP-1 to 3-NP-84, 3-NP-87, 3-NP-88, 3-NP-90 to 3-NP-102, 5-N-1 to 5-N-14, 2-NP-1 to 2-NP-4, 2-NP-6 to 2-NP-10, 2-NP-12 to 2-NP-21, 2-NP-23 to 2-NP-34, 2-NP-36 to 2-NP-38, 2-NP-42 to 2-NP-51, 2-NP-53 to 2-NP-58, exhibited 50% or higher IKKβ activity inhibiting ability at 1 μM or lower.

Furthermore, the test compounds, Example compounds 4-NP-1 to 4-NP-11, 4-NP-13 to 4-NP-36, 4-NP-38 to 4-NP-40, 4-NP-42 to 4-NP-45, 4-NP-47 to 4-NP-157, 4-NP-159 to 4-NP-184, 4-NP-186 to 4-NP-201, 4-NP-203 to 4-NP-229, 4-NP-231 to 4-NP-244, 4-NP-248 to 4-NP-297, 4-NP-301 to 4-NP-320, 4-NP-322 to 4-NP-330, 4-NP-332 to 4-NP-338, 4-NP-340 to 4-NP-342, 4-NP-344, 4-NP-346 to 4-NP-347, 4-NP-349 to 4-NP-357, 4-NP-361 to 4-NP-394, 4-NP-399, 4-NP-404, 4-NP-406 to 4-NP-427, 4-NP-430 to 4-NP-473, 5-NP-2 to 5-NP-20, 6-NP-1 to 6-NP-11, also exhibited 50% or higher IKKβactivity inhibiting ability at 1 μM or lower.

These results confirmed that the compounds of present invention had a potent IKKβ activity inhibiting ability.

Test Example 2

Measurement of TNF-αProduction Suppressing Ability (In Vitro)-1

Effects of the compound of the present invention on TNF-αproduced when human monocyte established cell line THP-1 having properties of a monocyte was stimulated with endotoxin (LPS) were measured as follows.

THP-1 cells which were cultured in RPMI1640 (Invitrogen Corporation, U.S.) supplemented with 10% inactivated fetal bovine serum (FBS) added to a 96-well culture plate at 1×10$^5$ cells/160 μL/well, 20 μL of a test compound having various concentrations or DMSO (final concentration 1%) was further added, and the resulting mixture was preincubated at 37° C. for 1 hour. Then, LPS (Sigma, U.S.) was added to each well at a final concentration of 2 μg/mL. The resulting mixture was incubated at 37° C. for 4 hours and then the culture supernatant was collected. The TNF-αconcentrations in the culture supernatant were measured using TNF-αELISA Kit (R&D Systems, U.S.) or TNF-αHTRF Kit (Cisbio, France). The TNF-αsuppression rate in the test compound at each concentration was obtained assuming the TNF-αconcentration in the culture supernatant to which DMSO was added as 100% production (suppression rate 0%). Furthermore, the cell survival rate was measured using Cell Counting Kit-8 (DOJINDO, Japan).

Measurement Results

Among the compound of the present invention, the representative test compounds, Example compounds 1-N-1 to 1-N-6, 1-N-11 to 1-N-15, 1-N-17, 1-N-20 to 1-N-24, 1-N-26 to 1-N-28, 1-N-34, 1-N-38 to 1-N-43, 1-N-47, 1-N-49, 2-N-301, 2-N-1 to 2-N-34, 2-N-36 to 2-N-63, 2-N-65 to 2-N-70, 2-N-72 to 2-N-77, 2-N-79 to 2-N-113, 2-N-201, 2-N-203 to 2-N-207, 2-N-211, 2-N-215, 2-N-216, 2-N-219, 2-N-224 to 2-N-226, 2-N-228 to 2-N-231, 2-N-233, 2-N-234, 2-N-236 to 2-N-243, 2-N-245, 2-N-247 to 2-N-253, 2-N-255, 2-N-256, 2-N-258 to 2-N-261, 2-N-263, 2-N-264, 2-N-266 to 2-N-271, 2-N-273 to 2-N-275, 2-N-277 to 2-N-280, 2-N-284, 2-N-286 to 2-N-288, 2-N-290, 2-N-291, 2-N-302 to 2-N-319, 2-N-401, 2-N-402, 2-N-501 to 2-N-508, 2-N-601 to 2-N-619, 2-N-701 to 2-N-708, 2-N-710 to 2-N-713, 2-N-801 to 2-N-804, 3-N-1 to 3-N-24, 3-N-101 to 3-N-114, 3-N-201 to 3-N-209, 3-N-301, 3-N-302, 3-N-401, 3-N-402, 3-N-404, 3-N-405, 3-N-410, 3-N-501 to 3-N-518, 3-N-520, 1-o-4, 1-o-5, 1-o-10, 1-o-15, 1-o-16, 1-o-18, 1-o-26, 1-o-33, 1-o-43, 1-s-1, 1-s-2, 2-0-5,2-o-6, 2-o-11 to 2-o-15, 2-o-19, 2-o-20, 2-o-23 to 2-o-26, 2-o-28, 2-o-29, 2-o-31, 2-o-32, 2-o-35, 2-o-43 to 2-o-45, 2-o-53, 2-o-56, 2-o-57, 2-o-63, 2-o-64, 2-o-66 to 2-o-71, 2-o-73 to 2-o-78, 2-o-80 to 2-o-85, 2-o-92, 2-o-93, 2-o-97 to 2-o-101, 2-o-103 to 2-o-106, 2-o-108 to 2-o-112, 2-o-114 to 2-o-118, 2-o-120, 2-o-124, 2-o-125, 2-o-134, 2-o-137, 2-o-138, 2-o-140, 2-o-141, 2-o-144, 2-o-152 to 2-o-154, 2-o-160, 2-o-162, 2-o-164 to 2-o-167, 2-o-172, 2-o-174, 2-o-179 to 2-o-185, 2-o-187 to 2-o-195, 2-o-197, 2-o-199, 2-o-200, 2-o-202, 2-o-205, 2-o-206, 2-o-208, 2-o-209, 2-o-214, 2-o-222, 2-o-253, 2-o-256, 2-s-1 to 2-s-3, 2-s-6, 3-o-1 to 3-o-3, 3-o-6, 3-o-8, 3-o-11, 3-o-15, 3-o-18, 3-o-19, 3-o-25, 3-o-26, 3-o-28 to 3-o-2835, 3-o-42, 3-s-1, 3-s-2, 4-o-4, 4-o-5, 4-o-7, 4-o-9, 4-o-11 to 4-o-14, 1-oP-17, 1-oP-21, 1-oP-22, 1-oP-32, 1-oP-33, 1-oP-35, 1-oP-43, 1-NP-2 to 1-NP-31, 1-NP-33, 1-NP-38, 1-NP-40, 6-o-3, 7-o-1, 3-NP-1 to 3-NP-9, 3-NP-11, 3-NP-12, 3-NP-14 to 3-NP-53, 3-NP-55 to 3-NP-62, 3-NP-64, 3-NP-65, 3-NP-68 to 3-NP-73, 3-NP-75, 3-NP-76, 3-NP-79 to 3-NP-81, 3-NP-83, 3-NP-87, 3-NP-88, 3-NP-90 to 3-NP-96, 3-NP-99, 3-NP-100, 3-NP-102, 5-N-1 to 5-N-4, 5-N-6 to 5-N-14, 2-NP-1 to 2-NP-3, 2-NP-6, 2-NP-8 to 2-NP-10, 2-NP-12, 2-NP-14, 2-NP-15, 2-NP-19 to 2-NP-21, 2-NP-24, 2-NP-25, 2-NP-27 to 2-NP-32, 2-NP-36 to 2-NP-38, 2-NP-42 to 2-NP-47, 2-NP-49, 2-NP-50, 2-NP-53 to 2-NP-58, showed TNF-αproduction suppression rates of 50% or higher at 5 μM or lower.

Furthermore, the test compounds, Example compounds 4-NP-1 to 4-NP-7, 4-NP-10, 4-NP-19 to 4-NP-24, 4-NP-27, 4-NP-31 to 4-NP-32, 4-NP-36, 4-NP-43, 4-NP-47 to 4-NP-89, 4-NP-91 to 4-NP-99, 4-NP-101 to 4-NP-150, 4-NP-152 to 4-NP-157, 4-NP-159 to 4-NP-160, 4-NP-162 to 4-NP-164, 4-NP-167 to 4-NP-170, 4-NP-172 to 4-NP-182, 4-NP-186 to 4-NP-189, 4-NP-191 to 4-NP-196, 4-NP-198 to 4-NP-201, 4-NP-203 to 4-NP-216, 4-NP-224 to 4-NP-228, 4-NP-231 to 4-NP-235, 4-NP-237 to 4-NP-244, 4-NP-248 to 4-NP-261, 4-NP-263 to 4-NP-264, 4-NP-266 to 4-NP-268, 4-NP-270, 4-NP-273 to 4-NP-275, 4-NP-277, 4-NP-281 to 4-NP-296, 4-NP-301 to 4-NP-309, 4-NP-311 to 4-NP-315, 4-NP-318, 4-NP-320, 4-NP-322 to 4-NP-334, 4-NP-341, 4-NP-344, 4-NP-346, 4-NP-349 to 4-NP-356, 4-NP-361 to 4-NP-388, 4-NP-392 to 4-NP-394, 4-NP-399, 4-NP-404, 4-NP-406 to 4-NP-411, 4-NP-414, 4-NP-421, 4-NP-423 to 4-NP-427, 4-NP-430, 4-NP-433 to 4-NP-434, 4-NP-436 to 4-NP-437, 4-NP-439 to 4-NP-448, 4-NP-451, 4-NP-454 to 4-NP-455, 4-NP-457, 4-NP-459 to 4-NP-468, 4-NP-470 to 4-NP-473, 5-NP-2 to 5-NP-10, 5-NP-12 to 5-NP-17, 5-NP-19 to 5-NP-20, 6-NP-1, 6-NP-4, 6-NP-5, 6-NP-9, also showed TNF-αproduction suppression rates of 50% or higher at 5 μM or lower. These results confirmed that the compounds of the present invention potently suppressed the TNF-αproduction by LPS stimulus in THP-1 cells.

Test Example 3-1

Measurement of TNF-α Production Suppressing Ability (In Vitro)-2

Effects of the compound of the present invention on TNF-αproduced when LPS was added to mouse blood were measured as follows.

Blood collected from a BALB/c mouse was added to each well of a 96-well plate at 85 μL/well, 10 μL of a test compound having various concentrations or a DMSO solution (final concentration 0.1%) was further added, and the resulting mixture was preincubated at 37° C. for 30 minutes. Then, LPS (Sigma, U.S.) was added to each well at a final concentration of 5 μg/mL. The resulting mixture was incubated at 37° C. for 4 hours and centrifuged and a plasma fraction was collected. The TNF-α concentrations in the plasma fraction were measured using TNF-α ELISA Kit (R&D Systems, U.S.). The TNF-α suppression rate in the test compound at each concentration was obtained assuming the TNF-α concentration in the plasma fraction to which DMSO was added as 100% production (suppression rate 0%).

Measurement Results

Among the compound of the present invention, the representative test compounds, Example compounds 1-N-1, 1-N-3, 1-N-4, 1-N-6, 1-N-12, 1-N-13, 1-N-15, 1-N-17, 1-N-19, 1-N-20, 1-N-21, 1-N-24, 1-N-26 to 1-N-28, 1-N-36, 2-N-301, 2-N-2, 2-N-5 to 2-N-8, 2-N-11, 2-N-14, 2-N-16 to 2-N-18, 2-N-23, 2-N-26, 2-N-28, 2-N-31, 2-N-32, 2-N-34, 2-N-37, 2-N-38, 2-N-40, 2-N-45, 2-N-47, 2-N-49, 2-N-50, 2-N-60, 2-N-61, 2-N-65, 2-N-68, 2-N-69, 2-N-72, 2-N-74 to 2-N-76, 2-N-84, 2-N-86, 2-N-88, 2-N-89, 2-N-91 to 2-N-100, 2-N-106, 2-N-108, 2-N-203 to 2-N-206, 2-N-241, 2-N-260, 2-N-267, 2-N-277, 2-N-1, 2-N-302 to 2-N-304, 2-N-307, 2-N-310, 2-N-312, 2-N-314, 2-N-315, 2-N-401, 2-N-402, 2-N-501, 2-N-502, 2-N-504, 2-N-508, 2-N-509, 2-N-601, 2-N-612, 2-N-619, 2-N-801, 3-N-1, 3-N-3 to 3-N-6, 3-N-8 to 3-N-10, 3-N-12, 3-N-18, 3-N-23, 3-N-101 to 3-N-103, 3-N-111, 3-N-112, 3-N-201, 3-N-202, 3-N-206, 3-N-301, 3-N-401, 3-N-402, 3-N-404, 3-N-405, 3-N-410, 3-N-509, 3-N-513, 1-o-4 to 1-o-6, 1-o-43, 2-o-1, 2-o-11, 2-o-14, 2-o-15, 2-o-23, 2-o-25, 2-o-44, 2-o-45, 2-o-67, 2-o-70, 2-o-71, 2-o-73, 2-o-78, 2-o-105, 2-o-111, 2-o-117, 2-o-144, 2-o-167, 2-o-174, 2-o-195, 2-o-205, 3-o-1 to 3-o-3, 3-o-14, 3-o-18, 3-o-30, 3-o-34, 3-s-1, 3-s-2, 4-o-4, 4-o-9, 5-o-1, 1-oP-33, 1-oP-43, 1-NP-6, 1-NP-10, 1-NP-11, 1-NP-13, 1-NP-16, 1-NP-18, 1-NP-23, 1-NP-40, 3-NP-1 to 3-NP-3, 3-NP-5 to 3-NP-8, 3-NP-11, 3-NP-1,2,3-NP-15 to 3-NP-26, 3-NP-28 to 3-NP-31, 3-NP-33, 3-NP-34, 3-NP-36 to 3-NP-40, 3-NP-42, 3-NP-43, 3-NP-45, 3-NP-56, 3-NP-57, 3-NP-59, 3-NP-64, 3-NP-65, 3-NP-69 to 3-NP-72, 3-NP-87, 3-NP-88, 3-NP-91 to 3-NP-96, 5-N-1 to 5-N-4, 5-N-6 to 5-N-8, 2-NP-9, 2-NP-12, 2-NP-15, 2-NP-24, 2-NP-25, 2-NP-27 to 2-NP-31, 2-NP-37, 2-NP-42, 2-NP-45 to 2-NP-47, 2-NP-49, 2-NP-54 to 2-NP-56, 2-NP-58, showed TNF-αproduction suppression rates of 50% or higher at 10 μM or lower.

Furthermore, the test compounds, Example compounds 4-NP-1 to 4-NP-2, 4-NP-4 to 4-NP-5, 4-NP-19, 4-NP-21 to 4-NP-22, 4-NP-31 to 4-NP-32, 4-NP-48, 4-NP-51 to 4-NP-63, 4-NP-65, 4-NP-67 to 4-NP-68, 4-NP-71 to 4-NP-74, 4-NP-76 to 4-NP-78, 4-NP-96 to 4-NP-97, 4-NP-104 to 4-NP-112, 4-NP-116 to 4-NP-121, 4-NP-123, 4-NP-128 to 4-NP-136, 4-NP-138, 4-NP-140 to 4-NP-150, 4-NP-152 to 4-NP-155, 4-NP-159 to 4-NP-160, 4-NP-162 to 4-NP-164, 4-NP-167, 4-NP-169 to 4-NP-170, 4-NP-173, 4-NP-175 to 4-NP-180, 4-NP-182, showed TNF-αproduction suppression rates of 50% or higher at 10 μM or lower. These results confirmed that the compound of the present invention potently suppressed the TNF-αproduced when LPS was added to mouse blood.

Test Example 3-2

Measurement of TNF-α Production Suppressing Ability (In Vitro)-3

Effects of the compound of the present invention on TNF-αproduced when LPS was added to rat blood were measured as follows.

Blood collected from a Lewis rat was added to each well of a 96-well plate at 85 μL/well, 10 μL of a test compound having various concentrations or a DMSO solution (final concentration 0.1%) was further added, and the resulting mixture was preincubated at 37° C. for 30 minutes. Then, LPS (Sigma, U.S.) was added to each well at a final concentration of 20 μg/mL. The resulting mixture was incubated at 37° C. for 4 hours and centrifuged and a plasma fraction was collected. The TNF-α concentrations in the plasma fraction were measured using TNF-αELISA Kit (R&D Systems, U.S.). The TNF-α suppression rate in the test compound at each concentration was obtained assuming the TNF-α concentration in the plasma fraction to which DMSO was added as 100% production (suppression rate 0%).

Measurement Results

Among the compound of the present invention, the representative test compounds, Example compounds 4-NP-53, 4-NP-61, 4-NP-144 to 4-NP-147, 4-NP-149 to 4-NP-150, 4-NP-152 to 4-NP-154, 4-NP-163 to 4-NP-164, 4-NP-167, 4-NP-169 to 4-NP-170, 4-NP-173, 4-NP-177, 4-NP-179, 4-NP-181 to 4-NP-182, 4-NP-189, 4-NP-191, 4-NP-195 to 4-NP-196, 4-NP-198 to 4-NP-199, 4-NP-201, 4-NP-204, 4-NP-207, 4-NP-210, 4-NP-213 to 4-NP-214, 4-NP-224 to 4-NP-227, 4-NP-232, 4-NP-235, 4-NP-240 to 4-NP-243, 4-NP-249 to 4-NP-252, 4-NP-256, 4-NP-259, 4-NP-261, 4-NP-264, 4-NP-266 to 4-NP-268, 4-NP-273, 4-NP-275, 4-NP-283 to 4-NP-286, 4-NP-288 to 4-NP-289, 4-NP-292 to 4-NP-296, 4-NP-301, 4-NP-306, 4-NP-311 to 4-NP-314, 4-NP-320, 4-NP-322, 4-NP-323 to 4-NP-329, 4-NP-332, 4-NP-334, 4-NP-344, 4-NP-349 to 4-NP-356, 4-NP-361 to 4-NP-388, 4-NP-392 to 4-NP-393, 4-NP-409 to 4-NP-410, 4-NP-423, 4-NP-425 to 4-NP-427, 4-NP-434, 5-NP-2,5-NP-4, 5-NP-7, 5-NP-9, 5-NP-11 to 5-NP-14, 5-NP-16 to 5-NP-17, 5-NP-19 to 5-NP-20, 6-NP-1, 6-NP-3 to 6-NP-5, showed TNF-α production suppression rates of 50% or higher at 10 μM or lower. These results confirmed that the compound of the present invention potently suppressed the TNF-α produced when LPS was added to mouse blood.

Test Example 4

Measurement of TNF-α Production Suppressing Ability (In Vivo)

Effects of the compound of the present invention on TNF-α produced when LPS was administered to a mouse were measured as follows.

A test compound was orally administered to 6- to 10-week-old female BALE/c mice and 5 μg of LPS (Sigma, U.S.) was intraperitoneally administered 30 minutes later. To prepare a solution for administration, 0.5% w/v Methylcellulose 400 Solution (Wako Pure Chemical Industries, Ltd.) was used as a solvent. At 90 minutes after administration of LPS, blood (50 to 100 μL) was collected from the orbit. The collected blood was centrifuged at 5000 rpm for 5 minutes and the TNF-α concentrations of the obtained plasma fraction were measured using TNF-αELISA Kit (R&D Systems, U.S.). The TNF-α suppression rate in each test compound dose group was obtained assuming the TNF-α concentration in the solvent treatment group as 100% production (suppression rate 0%).

Measurement Results

Among the compounds of the present invention, the representative test compounds, Example compounds 1-N-6, 1-N-19, 2-N-1, 3-N-1, 5-N-4, 2-N-100, and 3-N-202, showed TNF-α production suppression rates of 50% or higher at a dose of 30 mg/kg. These results confirmed that the compound of the present invention potently suppressed the TNF-α produced when LPS was administered to a mouse.

Test Example 5

Effects in Mouse Collagen-Induced Arthritis Model

On Days 0 and 21, 100 mg of chicken cartilage-derived collagen (Nippon Meat Packers, Inc., Japan) in 0.1 mL of complete Freund's adjuvant (Difco Laboratories, Inc., U.S.) was subcutaneously injected to female DBA/1J Jms Slc mice (6- to 8-week-old) (Japan SLC, Japan) to immunize the mice.

Among the compounds of the present invention, a representative test compound (Example compound 1-N-6 or 2-N-100) was orally administered twice daily every day from Day 21 to Day 34 at a dose of 25 or 50 mg/kg (method A) or from Day 21 to Day 29 at a dose of 1, 3, 10, or 30 mg/kg (method B). The solution for administration was prepared by using 0.5% w/v Methylcellulose 400 Solution (Wako Pure Chemical Industries, Ltd.) as a solvent.

After administration of collagen on Day 21, the extent of development of arthritis in the mouse limbs were scored by visually observing each limb periodically according to the clinical scores outlined in Table X-1.

TABLE X-1

| Score | Condition |
|---|---|
| 0 | Normal |
| 1 | Inflammation occurred in 1 or more toe joints |
| 2 | Inflammation occurred in heel or plantar surface |
| 3 | Marked inflammation occurred in ankle, heel, or plantar surface |
| 4 | Ankylosis (motion of hock for flexion and extension significantly decreased) |

The clinical scores for all four limbs were summed up for each mouse and the mean±standard error (SE) of each treatment group was calculated. The results of Example compound 1-N-6 is shown in FIG. 1, and the results of Example compound 2-N-100 are shown in FIG. 2. Evaluation was performed until the following day of the final administration.

Measurement Results

As shown in FIG. 1, Example compound 1-N-6 suppressed the onset of arthritis in the test by method A. At this time, Example compound 1-N-6 did not exhibit toxicity.

These results confirmed that Example compound 1-N-6 had an excellent anti-inflammatory effect.

Furthermore, as shown in FIG. 2, Example compound 2-N-100 suppressed the onset of arthritis in the test by method B. At this time, Example compound 2-N-100 did not exhibit toxicity.

These results confirmed that Example compound 2-N-100 had an excellent anti-inflammatory action.

It was confirmed by performing similar tests that the following Example compounds also had an anti-inflammatory effect.

Example compounds: 1-NP-10, 1-NP-13, 2-N-2, 2-N-94, 3-N-10, 3-N-103, 3-N-202, 3-N-4, 3-NP-114, 3-NP-116, 3-NP-120, 3-NP-122, 3-NP-20, 3-NP-21, 3-NP-23, 3-NP-24, 3-NP-26, 3-NP-37, 3-NP-88, 3-NP-95, 4-NP-109, 4-NP-144, 4-NP-149, 4-NP-31, 4-NP-60, 4-NP-61, 4-NP-83, 4-NP-86

Test Example 6

Effects in Rat Streptococcus Cell Wall (SCW)-Induced Arthritis Model

10 μL of PBS (Invitrogen Corporation, U.S.) solution containing 10 μg of peptidoglycan polysaccharide polymer (PG- PS100P) (MD Biosciences, U.S.) was injected into the joint cavity of the left hindlimb ankle of female LEW/CrlCrlj rats (6- to 8-week-old) (Charles River Laboratories Japan, Inc., Japan) on Day 0 to immunize the rats. Then, 400 μL of PBS solution containing 100 μg of PG-PS100P was added to the caudal vein on Day 14.

Among the compounds of the present invention, the representative test compound, Example compound 3-NP-24, was orally administered once daily every day from Day 14 to Day 16 (dose: 1, 3, or 10 mg/kg). To prepare a solution for administration, 0.5-1; w/v Methylcellulose 400 Solution (Wako Pure Chemical Industries, Ltd.) was used as a solvent.

To evaluate swelling due to arthritis, thickness of the left hindlimb ankle joint of rats was measured every day from Day 14 to Day 17 and the mean±standard error (SE) of the ankle joint thickness in each treatment group was calculated. The results of Example compound 3-NP-24 are shown in FIG. 3.

Measurement Results

As shown in FIG. 3, Example compound 3-NP-24 suppressed swelling and did not exhibit toxicity. These results confirmed that Example compound 3-NP-24 had an excellent anti-inflammatory effect.

It was confirmed by performing similar tests that the following Example compounds also had an anti-inflammatory effect.

Example compounds: 1-NP-10, 1-NP-13, 3-NP-114, 4-NP-61, 4-NP-146, 4-NP-149, 4-NP-152, 4-NP-170, 4-NP-182, 4-NP-199, 4-NP-213, 4-NP-224, 4-NP-242, 4-NP-245, 4-NP-311, 4-NP-313, 4-NP-314, 4-NP-329, 4-NP-363, 4-NP-364, 4-NP-369, 4-NP-372, 4-NP-373, 4-NP-375, 4-NP-376, 4-NP-380

However, Example compounds 4-NP-61, 4-NP-146, 4-NP-149, 4-NP-152, 4-NP-170, 4-NP-182, 4-NP-199, 4-NP-213, 4-NP-224, 4-NP-242, 4-NP-245, 4-NP-311, 4-NP-313, 4-NP-314, 4-NP-329, 4-NP-363, 4-NP-364, 4-NP-369, 4-NP-372, 4-NP-373, 4-NP-375, 4-NP-376, 4-NP-380 were tested by twice daily oral administration.

The present application was filed based on the provisional application for U.S. patent filed on Oct. 2, 2008 (61/102,086) and the content thereof are hereby incorporated by reference into the present application.

INDUSTRIAL APPLICABILITY

The compound of the present invention or a salt thereof has an IKKβ inhibiting activity. The compound of the present invention or a salt thereof is useful for the prophylactic and/or therapeutic treatment of, for example, autoimmune diseases, inflammatory diseases, and the like and can be used in the medical and pharmaceutical industry.

The invention claimed is:

1. A compound represented by the following formula (1) or a salt thereof:

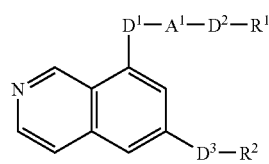

(1)

wherein $D^1$ represents a single bond, —N($R^{11}$)—, —O—, —S—, —S(O)—, or —S(O)$_2$—, wherein $R^{11}$ represents a hydrogen atom or an alkyl group that may be substituted;

$A^1$ represents a single bond, an alkylene that may be substituted, or any of divalent groups selected from the following formulas (1a-1) to (1a-6):

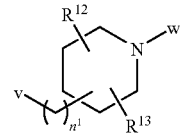

(1a-1)

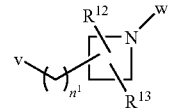

(1a-2)

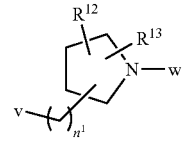

(1a-3)

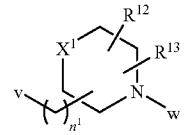

(1a-4)

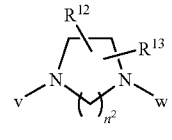

(1a-5)

(1a-6)

wherein $n^1$ is an integer of 0, 1, or 2;

$n^2$ is an integer of 2 or 3;

$n^3$ is an integer of 1 or 2;

$R^{12}$ and $R^{13}$ may be identical to or different from each other and each independently represents a hydrogen atom, a hydroxyl group, or an alkyl group that may be substituted;

$X^1$ represents —N($R^{14}$)—, —O—, or —S—, wherein $R^{14}$ represents a hydrogen atom or an alkyl group that may be substituted;

v represents a bond with $D^1$; and w represents a bond with $D^2$ $D^2$ represents a single bond, an alkylene that may be substituted, —C(O)—, —C(S)—, —S(O)$_2$—, —C(O)—N($R^{15}$), —C(S)—N($R^{15}$)—, or -EC(O)—, wherein E represents an alkylene that may be substituted and $R^{15}$ represents a hydrogen atom or an alkyl group;

$R^1$ represents a hydrogen atom, an alkyl group that may be substituted, an amino group that may be substituted, a saturated heterocyclic group that may be substituted, an aryl group that may be substituted, an aralkyl group that may be substituted, a carbamimidoyl group, or any of groups selected from the following formulas (1b-1) to (1b-4):

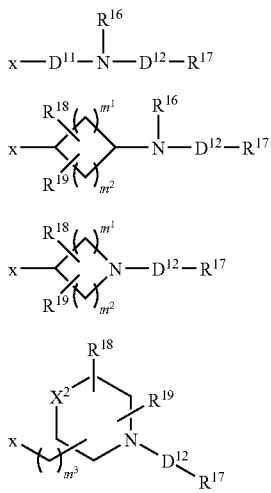

(1b-1)
(1b-2)
(1b-3)
(1b-4)

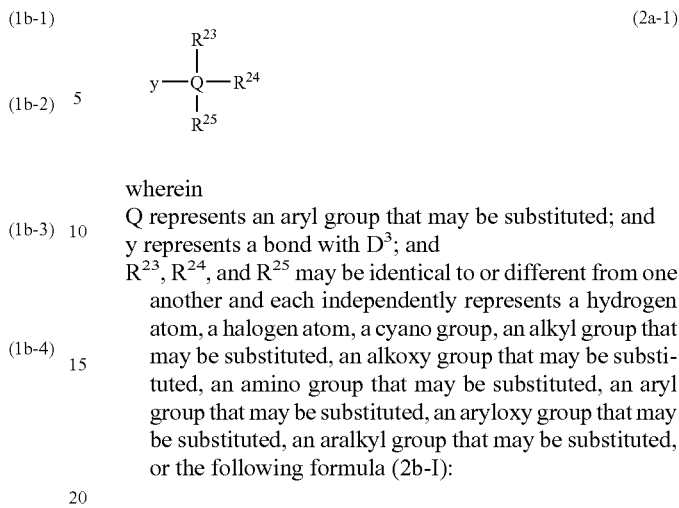

(2a-1)

wherein

Q represents an aryl group that may be substituted; and y represents a bond with $D^3$; and $R^{23}$, $R^{24}$, and $R^{25}$ may be identical to or different from one another and each independently represents a hydrogen atom, a halogen atom, a cyano group, an alkyl group that may be substituted, an alkoxy group that may be substituted, an amino group that may be substituted, an aryl group that may be substituted, an aryloxy group that may be substituted, an aralkyl group that may be substituted, or the following formula (2b-I):

(2b-1)

wherein $D^{21}$ represents a single bond or an alkylene that may be substituted;

$D^{22}$ represents a single bond, an alkylene that may be substituted, —C(O)—, —S(O)$_2$—, or —C(O)—N ($R^{28}$)—;

$R^{26}$, $R^{27}$, and $R^{28}$ may be identical to or different from one another and each independently represents a hydrogen atom or an alkyl group that may be substituted; and z represents a bond with Q;

with the provisos that:

when $D^{22}$ represents a single bond, $R^{27}$ represents a hydrogen atom; and when $D^3$ is —O—, $R^2$ is methyl, $D^1$ is —O—, and $A^1$ and $D^2$ represent a single bond, $R^1$ is not a methyl group.

2. The compound according to claim 1 or a salt thereof, wherein $D^1$ represents a single bond, —N($R^{11}$)—, —O—, or —S—, wherein $R^{11}$ has the same meaning as defined above.

3. The compound according to claim 1 or a salt thereof, wherein $A^1$ represents an alkylene that may be substituted or any of divalent groups selected from the formulas (1a-1) to (1a-5), wherein $n^1$, $n^2$, $X^1$, $R^{12}$, $R^{13}$, $R^{14}$, v, and w have the same meanings as defined above.

4. The compound according to claim 1 or a salt thereof, wherein $A^1$ represents any of divalent groups selected from the formulas (1a-1) to (1a-3) and (1a-5), wherein $n^1$, $n^2$, $R^{12}$, $R^{13}$, v, and w have the same meanings as defined above.

5. The compound according to claim 1 or a salt thereof, wherein $n^1$ is an integer of 0 or 1.

6. The compound according to claim 1 or a salt thereof, wherein $D^2$ represents an alkylene that may be substituted, —C(O)—, or —S(O)$_2$—.

7. The compound according to claim 1 or a salt thereof, wherein $D^2$ represents —C(O)— or —S(O)$_2$—.

8. The compound according to claim 1 or a salt thereof, wherein $R^1$ represents a hydrogen atom, an alkyl group that may be substituted, an aryl group that may be substituted, or an aralkyl group that may be substituted.

9. The compound according to claim 1 or a salt thereof, wherein $R^1$ represents any of divalent groups selected from wherein $m^1$ is an integer of 0, 1, or 2;

$m^2$ is an integer of 1 or 2;

$m^3$ is an integer of 0, 1, or 2;

$X^2$ represents —N($R^{14}$)—, —O—, or —S—, wherein $R^{14}$ represents a hydrogen atom or an alkyl group that may be substituted;

$D^{11}$ represents an alkylene that may be substituted;

$D^{12}$ represents a single bond, an alkylene that may be substituted, —C(O)—, —S(O)$_2$—, or —C(O)—N ($R^{15}$)—, wherein $R^{15}$ represents a hydrogen atom or an alkyl group;

$R^{16}$, $R^{18}$ and $R^{19}$ may be identical to or different from one another and each independently represents a hydrogen atom or an alkyl group that may be substituted;

$R^{17}$ represents a hydrogen atom, an alkyl group that may be substituted, an aryl group that may be substituted, or an aralkyl group that may be substituted; and x represents a bond with $D^2$;

with the proviso that, when $R^{17}$ represents a hydrogen atom, $D^{12}$ represents a single bond;

with the proviso that, when $D^1$ represents a single bond, $A^1$ represents a divalent group represented by the above-mentioned formula (1a-5) or (1a-6);

when $D^1$ represents —N($R^{11}$)—, —O—, —S—, —S(O)—, or —S(O)$_2$, $A^1$ represents a single bond, an alkylene that may be substituted, or any of divalent groups selected from the formulas (1a-1) to (1a-4), wherein, when $A^1$ represents a single bond, $D^2$ represents an alkylene that may be substituted or -E-C(O)—;

when $R^1$ represents an amino group that may be substituted, $D^2$ represents an alkylene that may be substituted or -E-C(O)—; and $D^3$ represents a single bond, —N($R^{21}$)—, —O—, —N($R^{21}$)—C(O)—, or —S—, wherein $R^{21}$ represents a hydrogen atom or an alkyl group that may be substituted; and $R^2$ represents an alkyl group that may be substituted or the following formula (2a-1):

the formulas (1b-1) to (1b-4), wherein $m^1$, $m^2$, $m^3$, $X^2$, $D^{11}$, $D^{12}$, $R^{14}$, $R^{15}$, $R^{16}$, $R^{17}$, $R^{18}$, $R^{19}$, and x have the same meanings as defined above.

10. The compound according to claim 1 or a salt thereof, wherein $D^3$ represents a single bond, —O—, or —N($R^{21}$)—C(O)—, wherein $R^{21}$ have the same meaning as defined above.

11. The compound according to claim 1 or a salt thereof, wherein $D^3$ represents a single bond.

12. The compound according to claim 1 or a salt thereof, wherein $R^2$ represents the formula (2a-1), wherein Q, y, $R^{23}$, $R^{24}$, $R^{25}$, $D^{21}$, $D^{22}$, $R^{26}$, $R^{27}$, $R^{28}$, and z have the same meanings as defined above.

13. The compound according to claim 1 or a salt thereof, wherein Q in the formula (2a-1) represents a monocyclic aromatic group.

14. A compound selected from the following groups or a salt thereof:

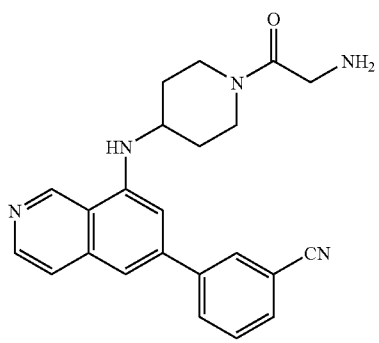

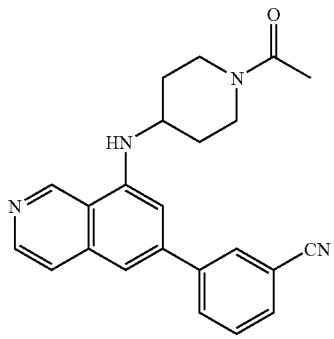

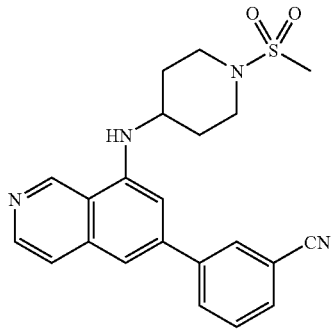

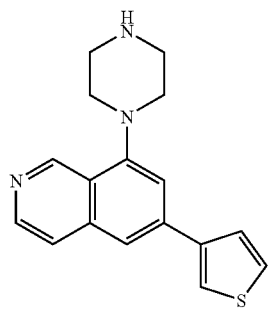

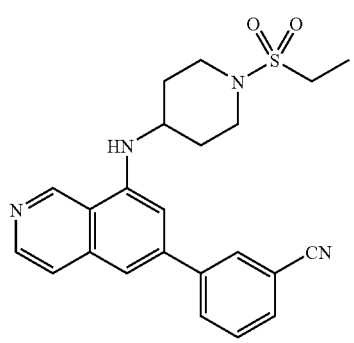

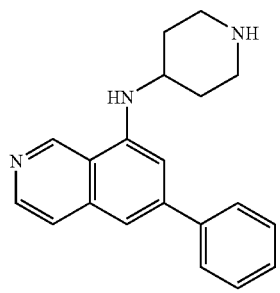

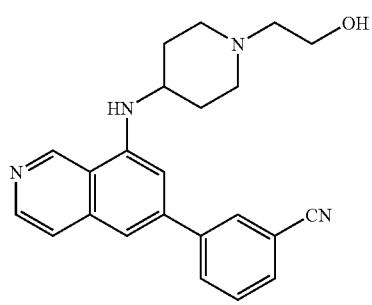

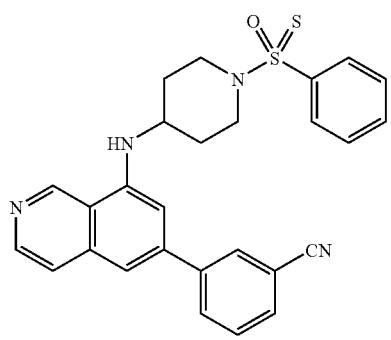

467
-continued
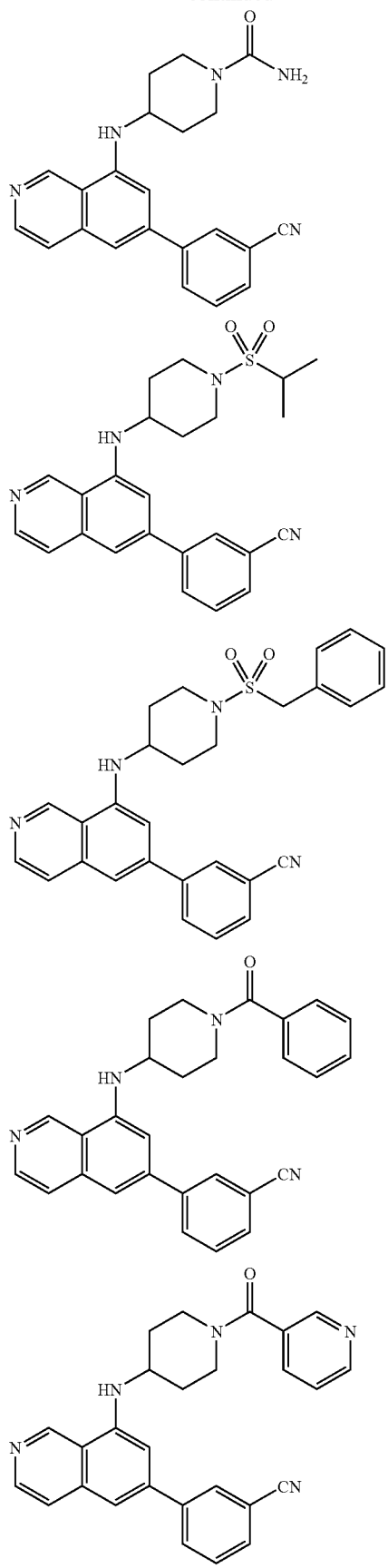
468
-continued
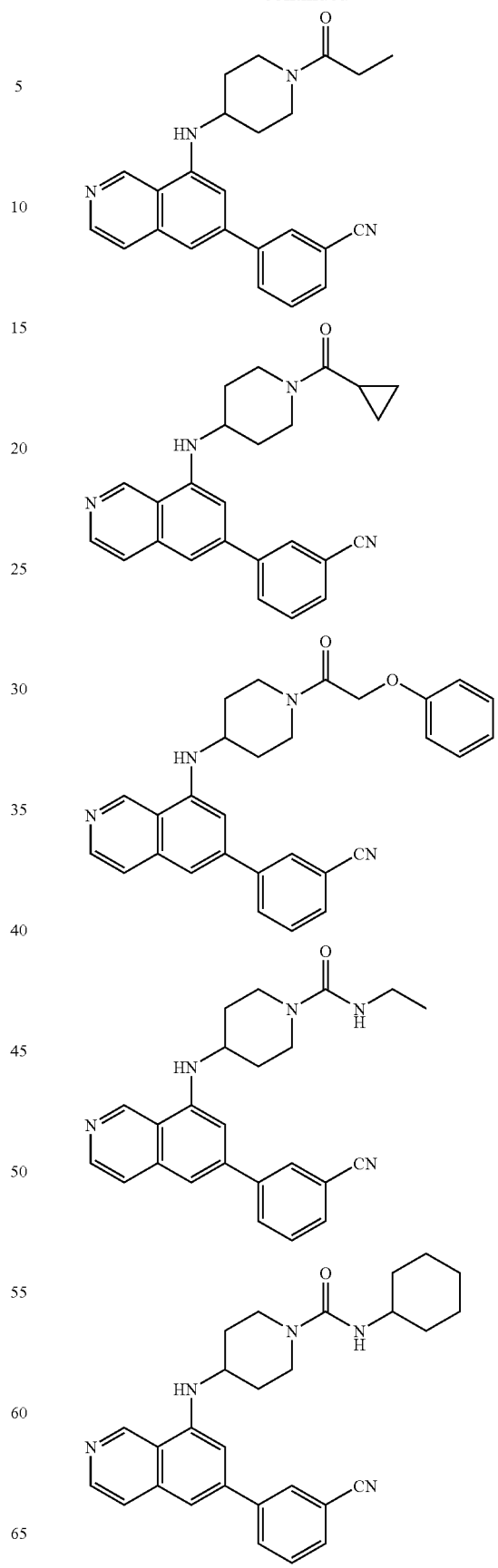

469
-continued
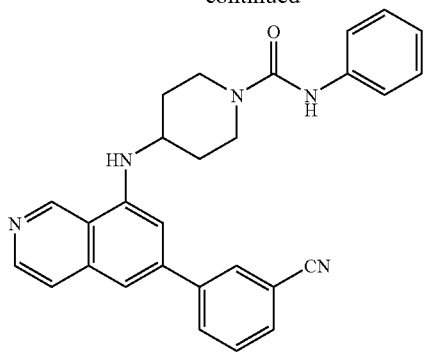
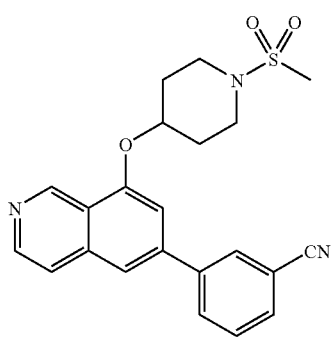
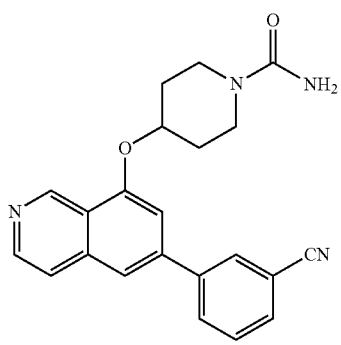
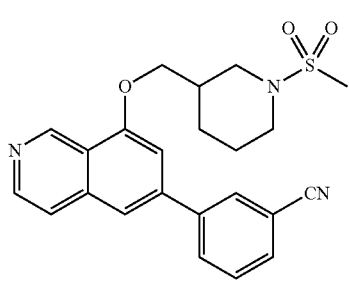
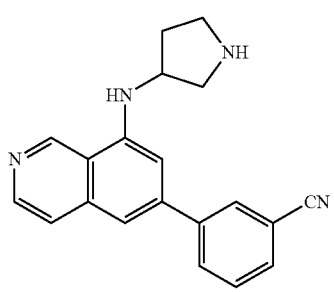
470
-continued
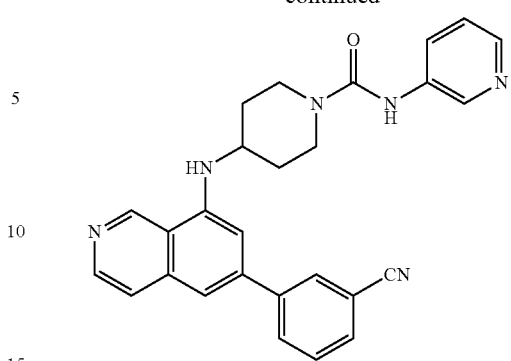
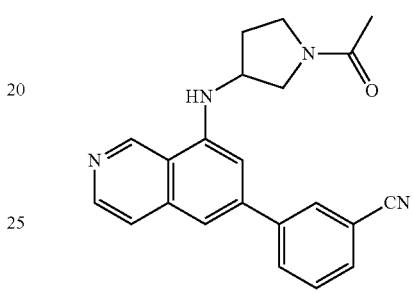
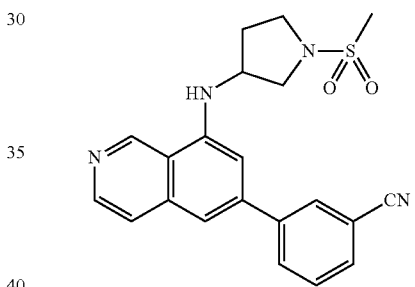
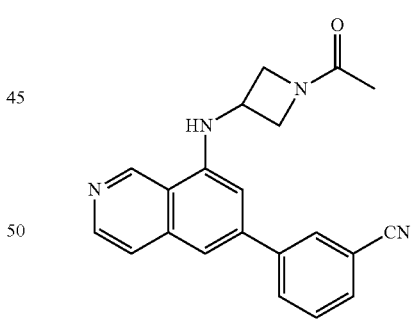
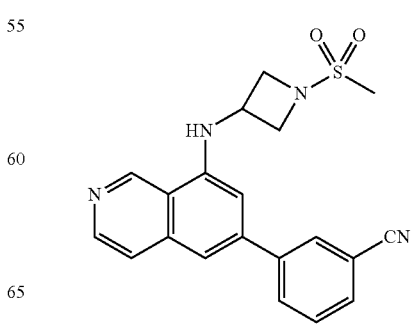

471
-continued
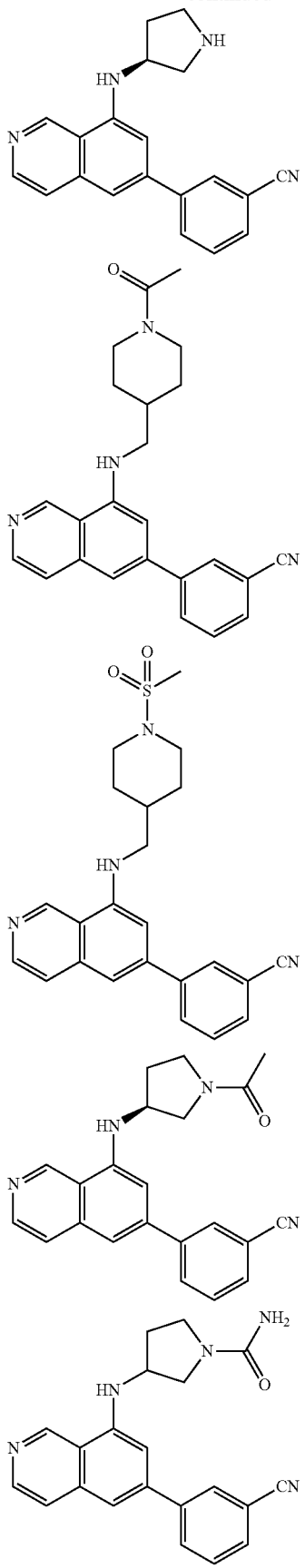
472
-continued
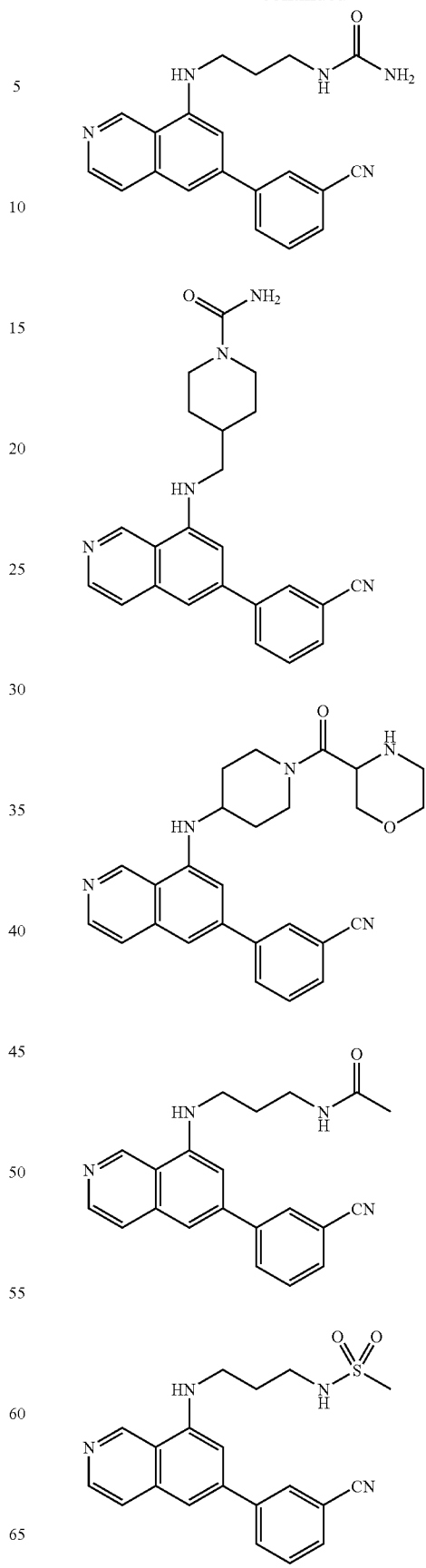

473
-continued
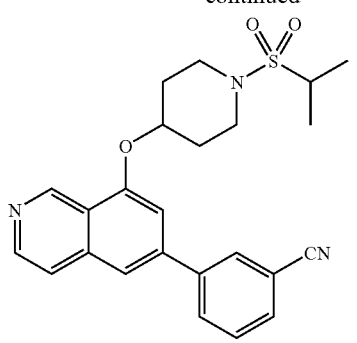
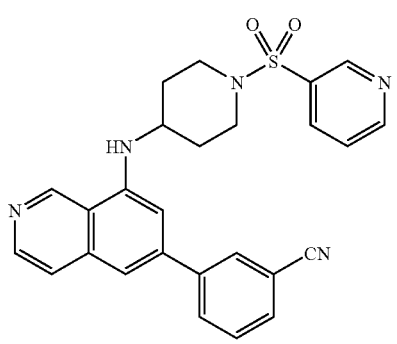
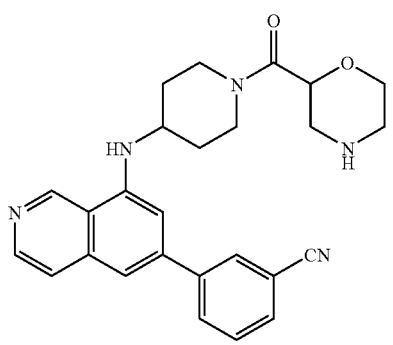
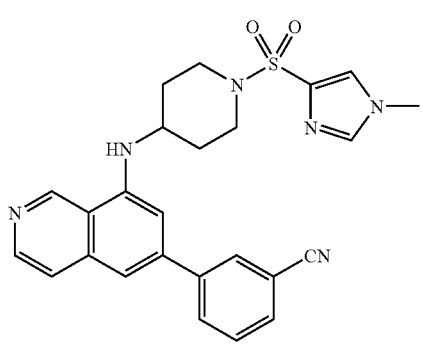
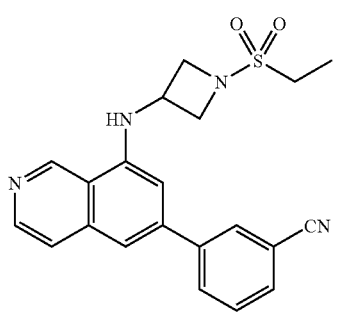
474
-continued
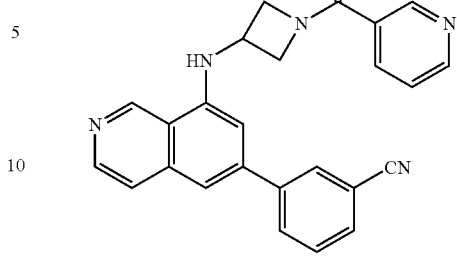
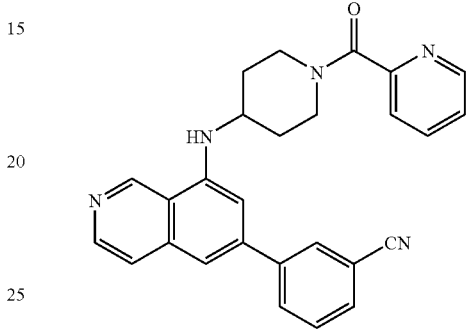
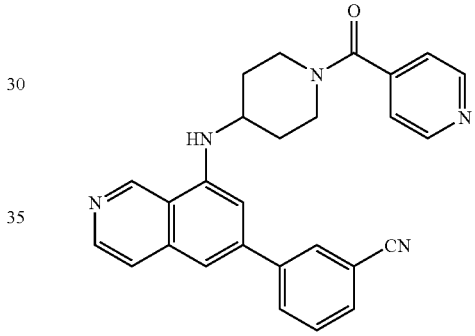
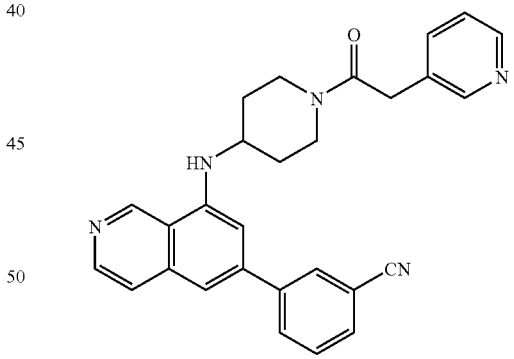
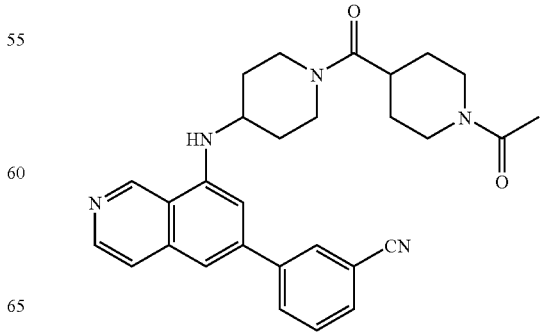

475
-continued
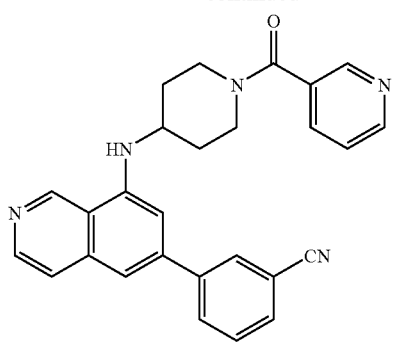
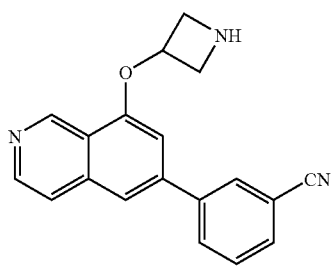
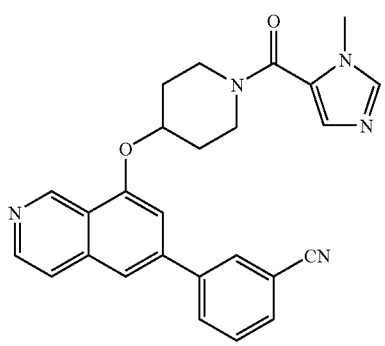
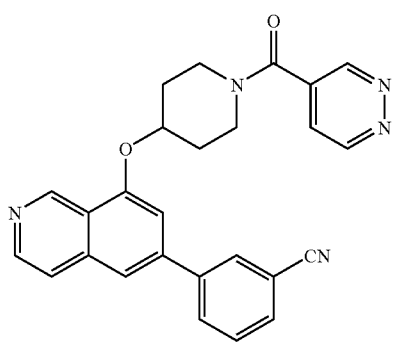
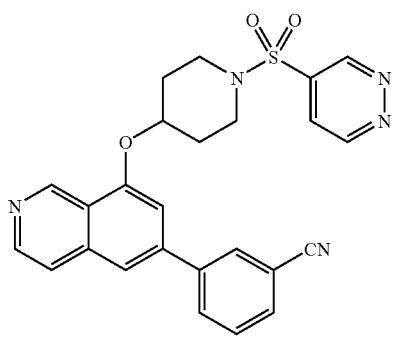
476
-continued
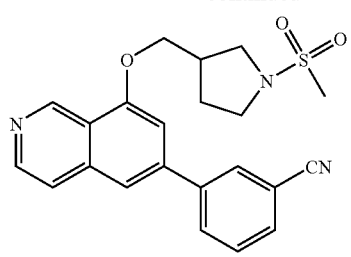
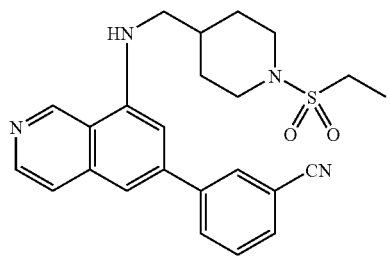
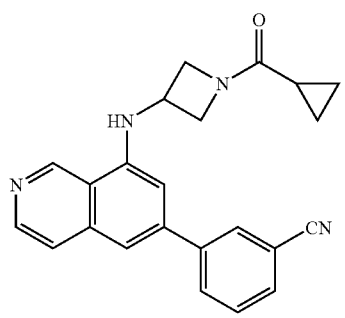
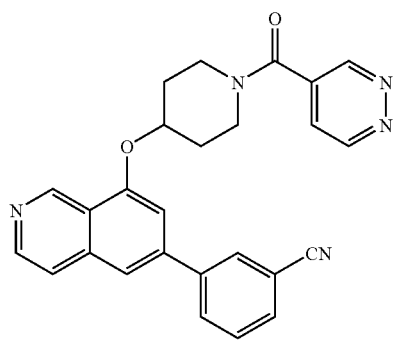
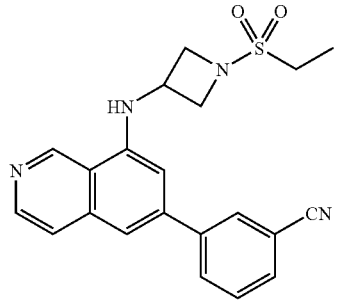

477
-continued
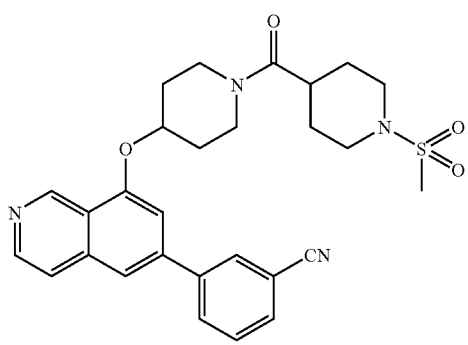
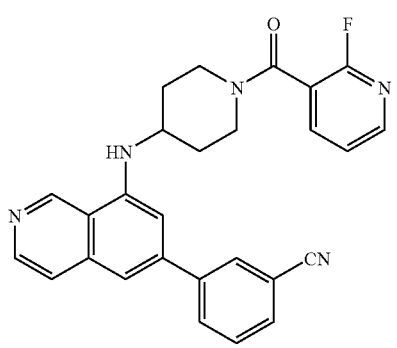
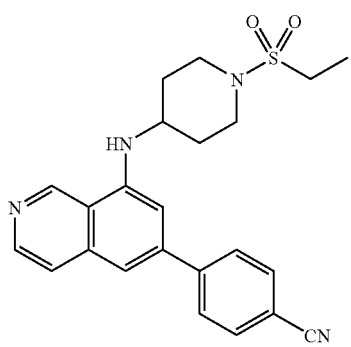
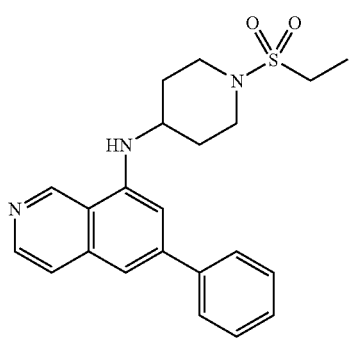
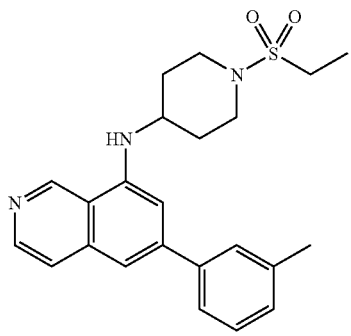
478
-continued
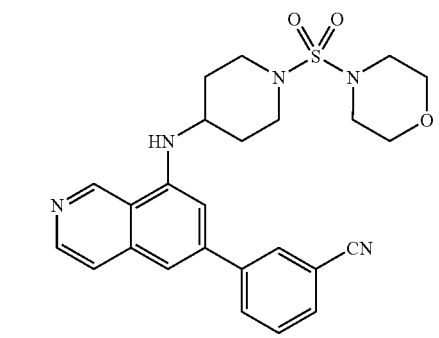
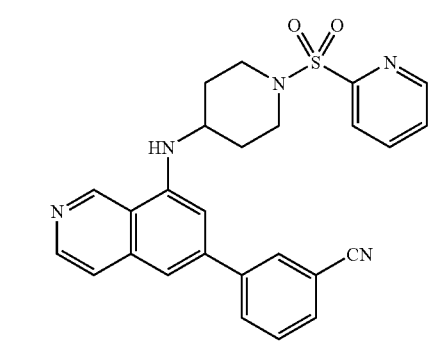
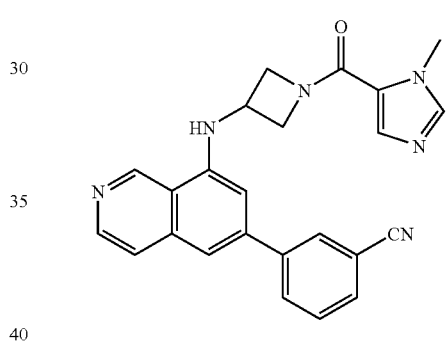
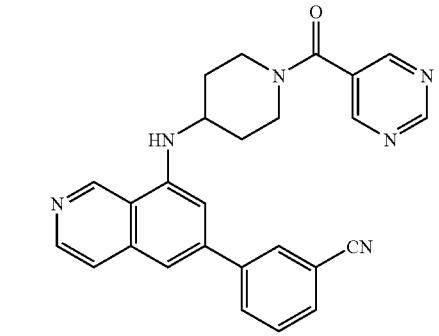
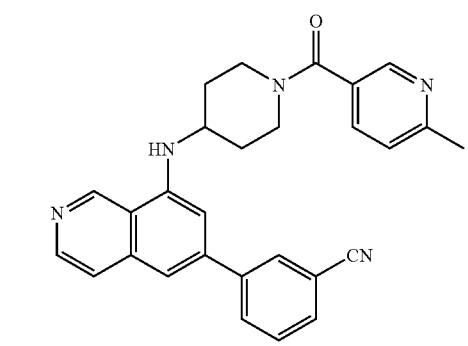

479
-continued
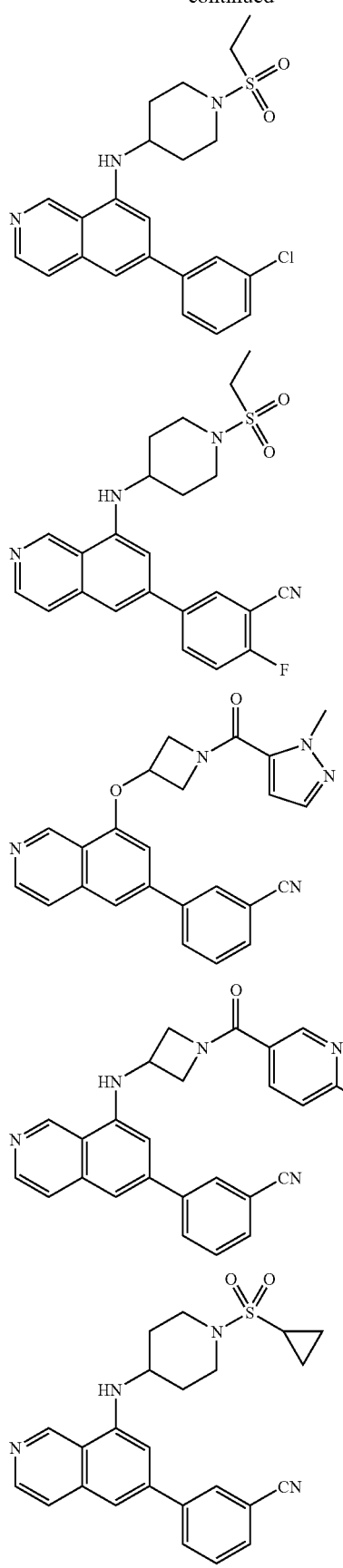
480
-continued
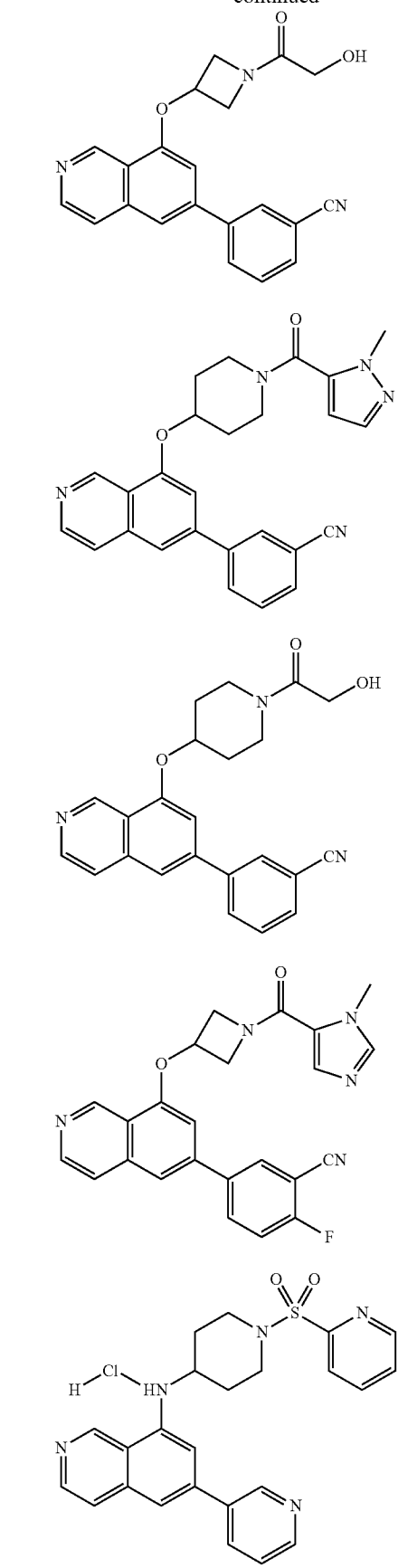

481
-continued
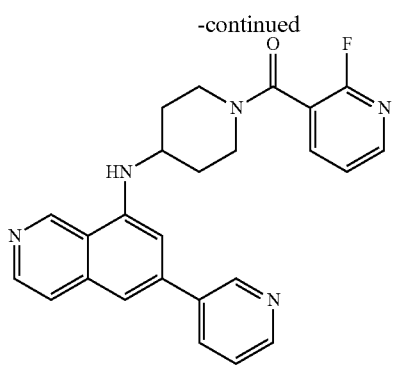
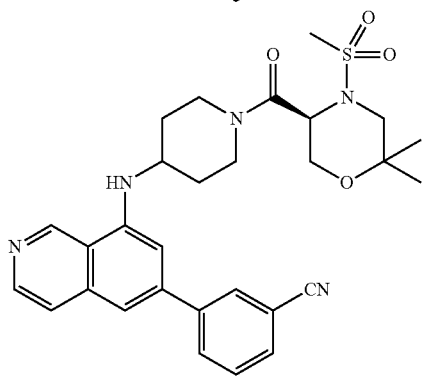
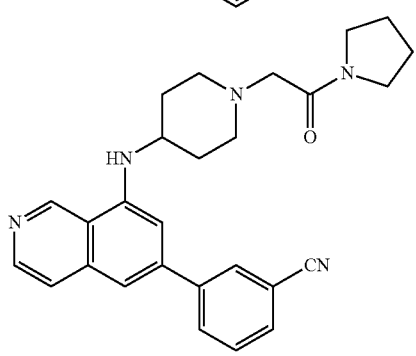
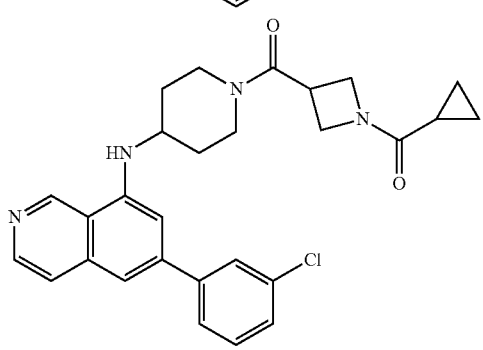
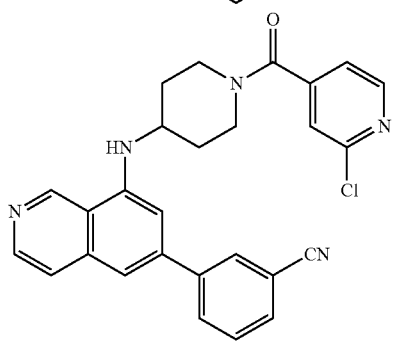
482
-continued
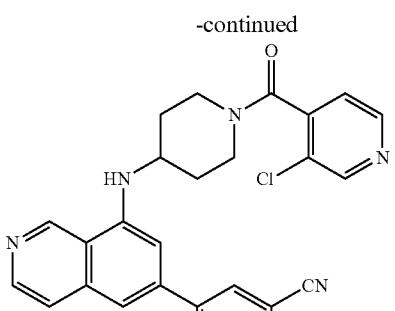
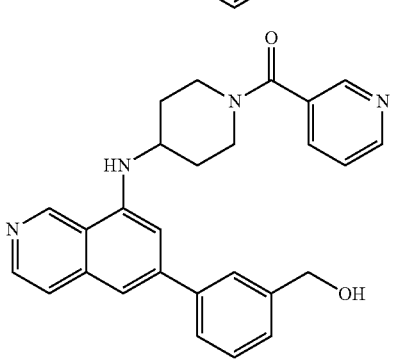
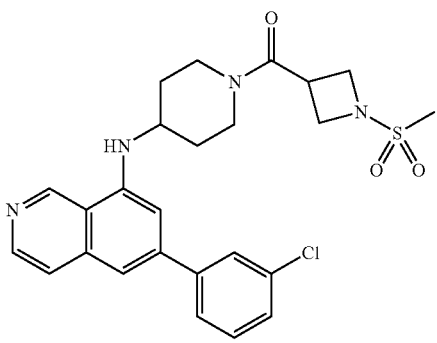
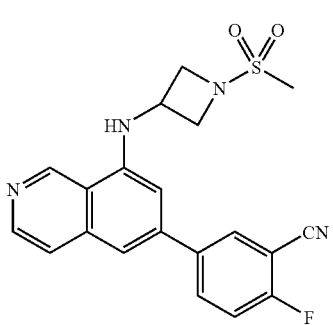
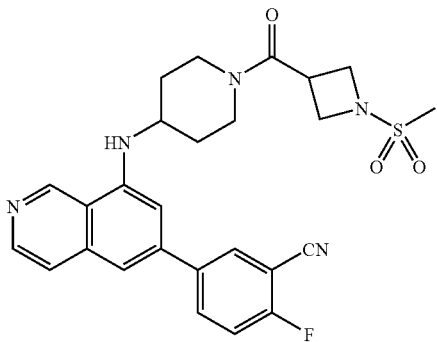

483
-continued
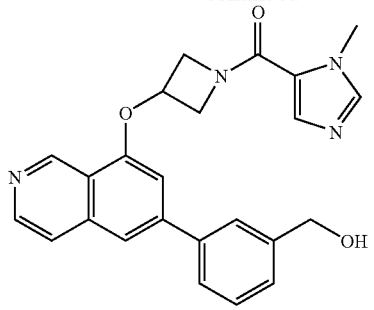
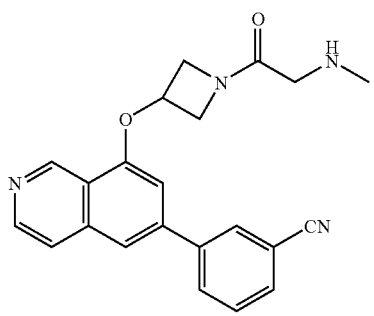
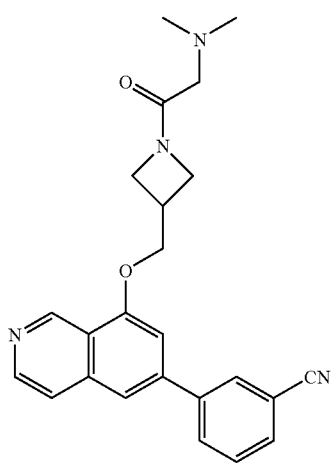
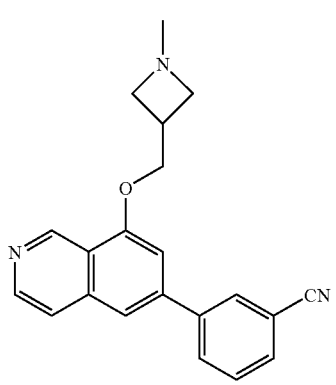
484
-continued
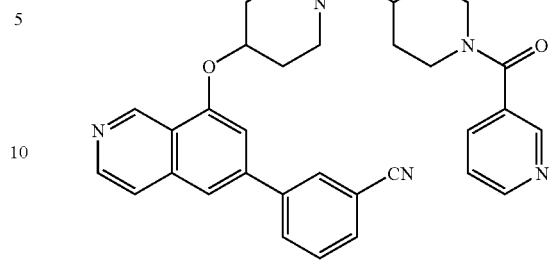
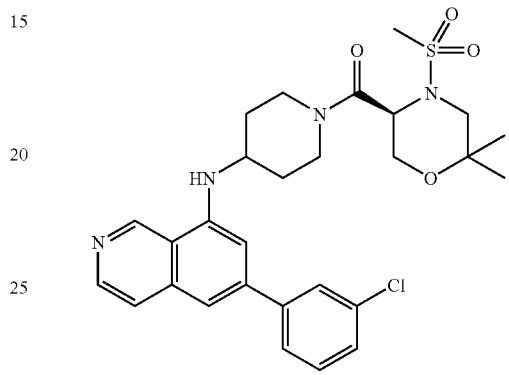
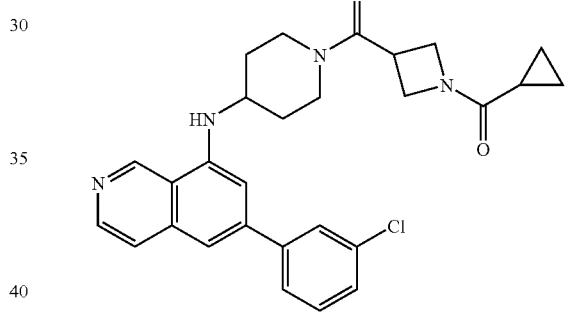
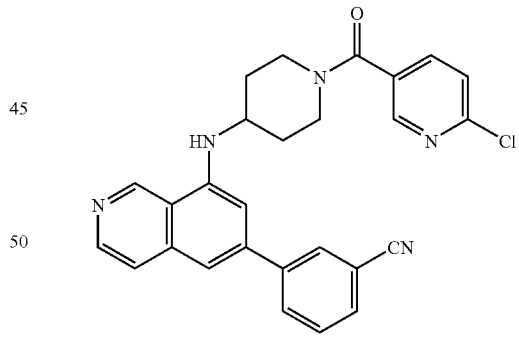
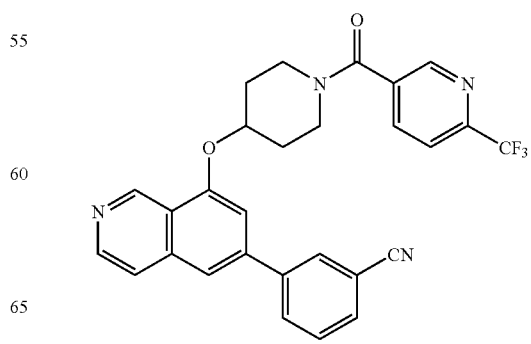

485
-continued
486
-continued
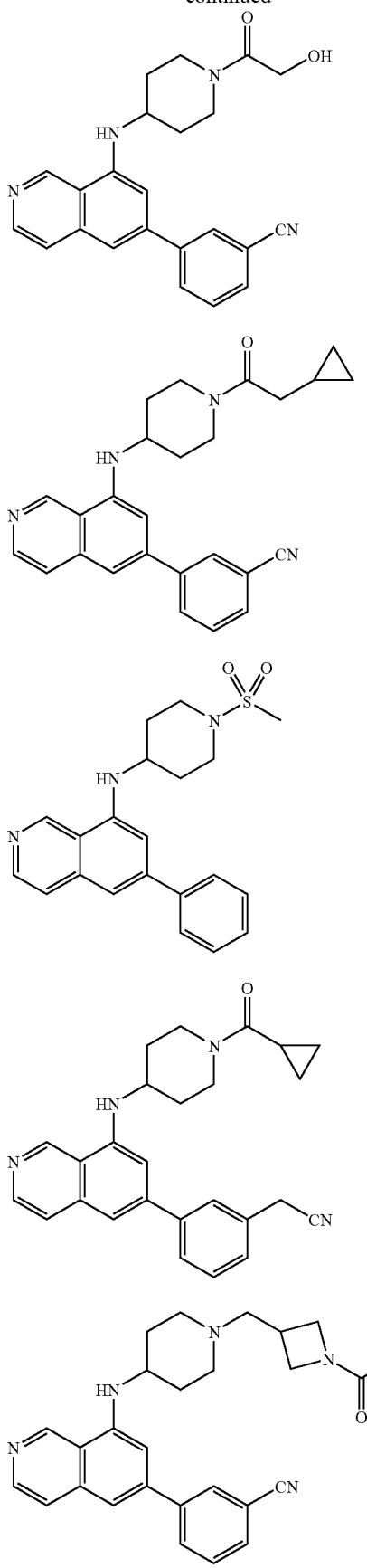
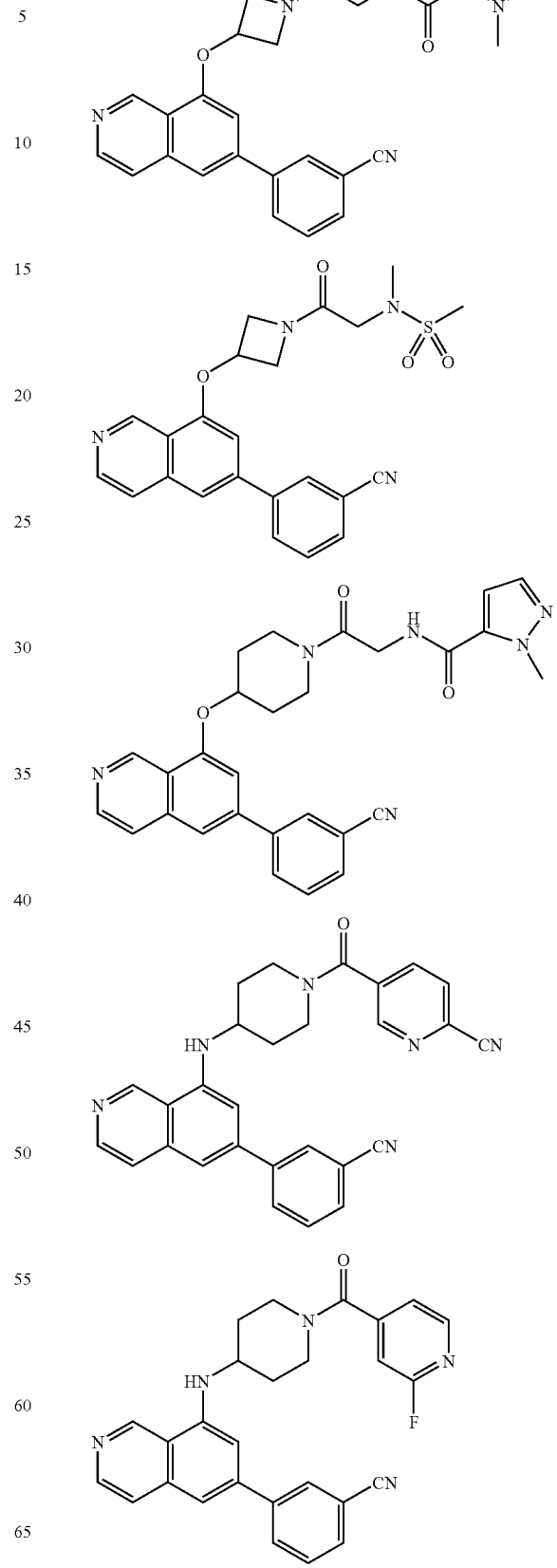

487
-continued
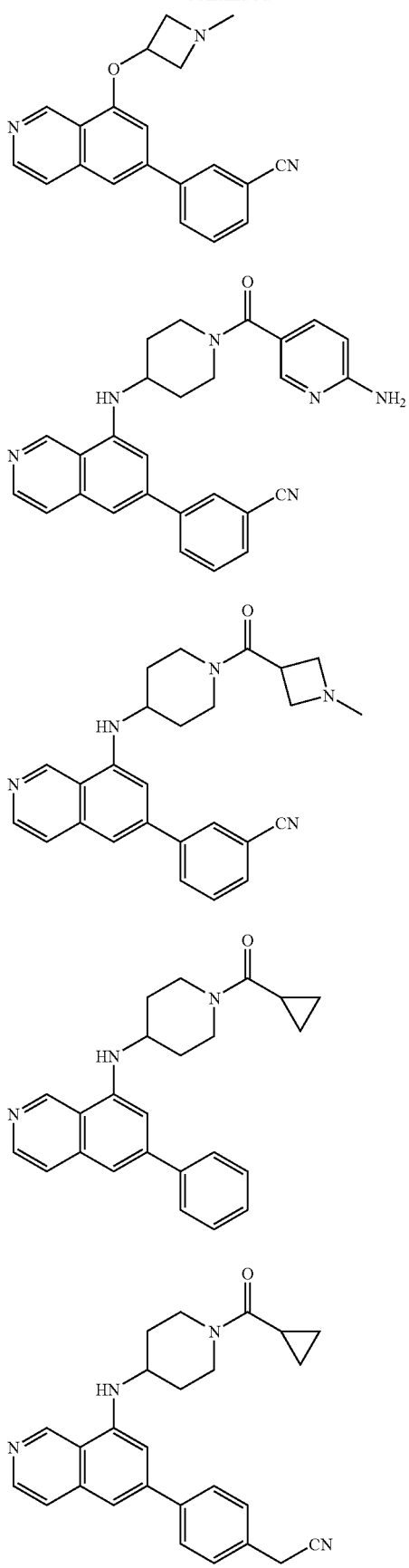
488
-continued
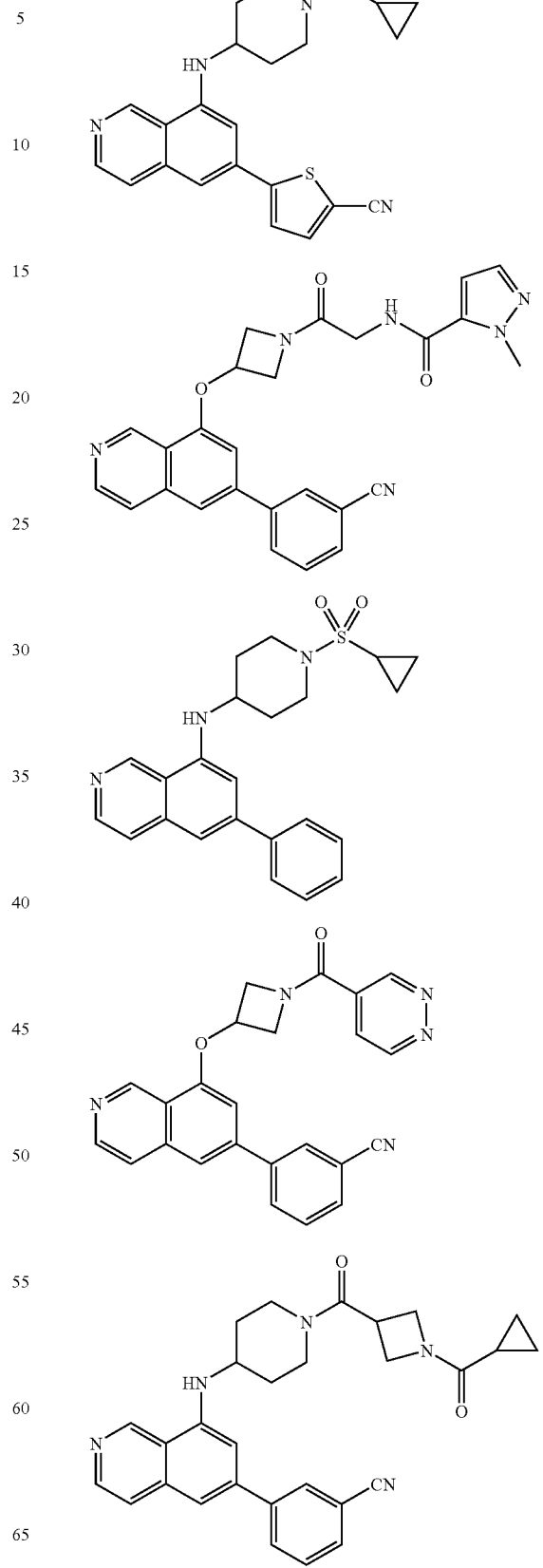

489
-continued
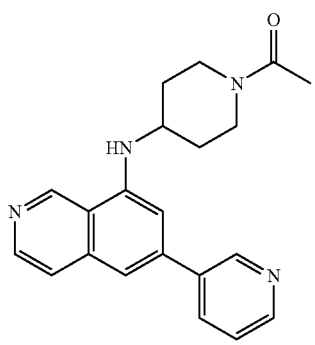
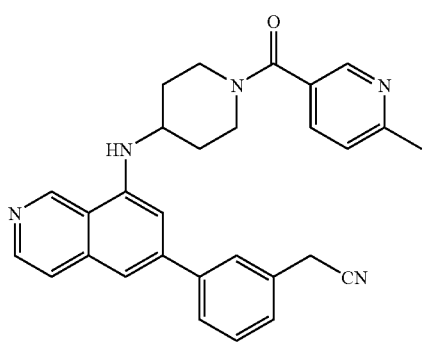
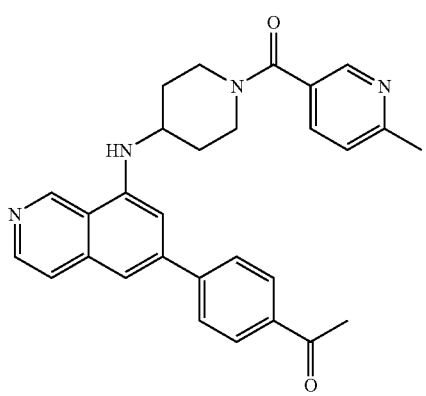
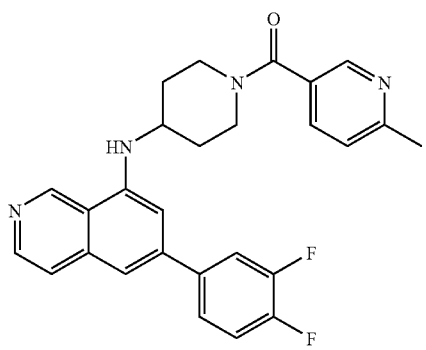
490
-continued
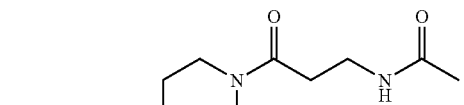
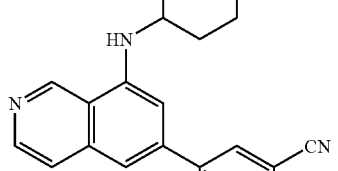
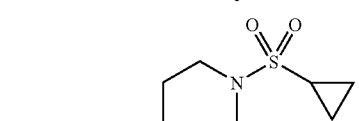
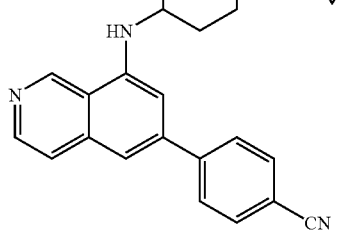
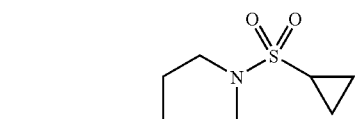
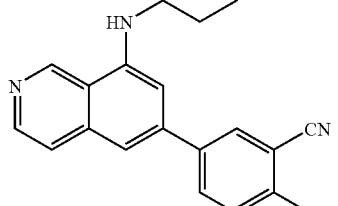
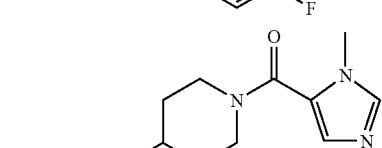
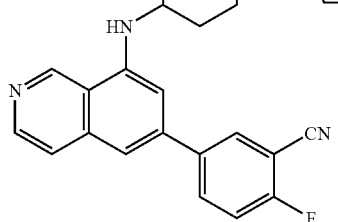
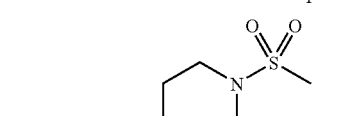
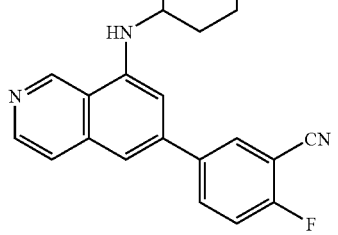

491
-continued
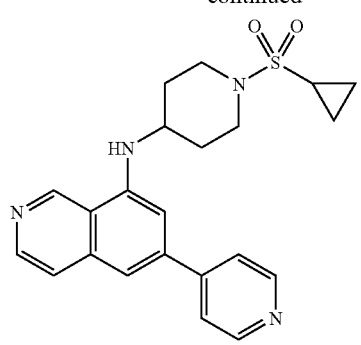
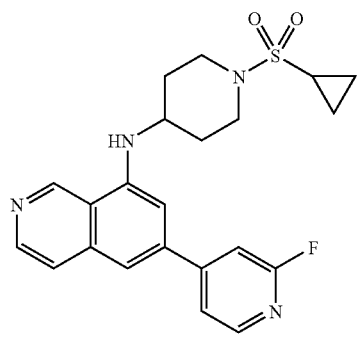
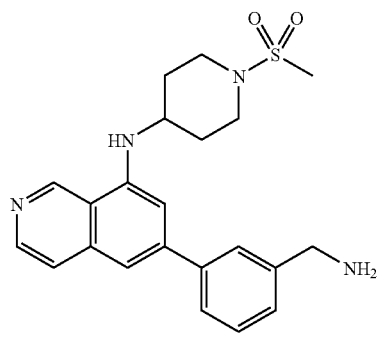
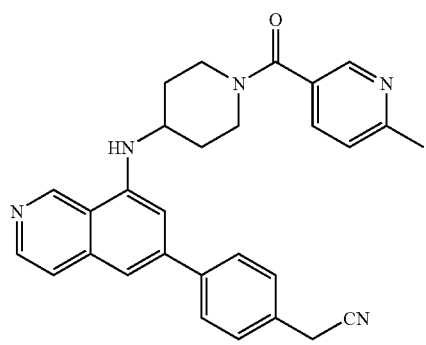
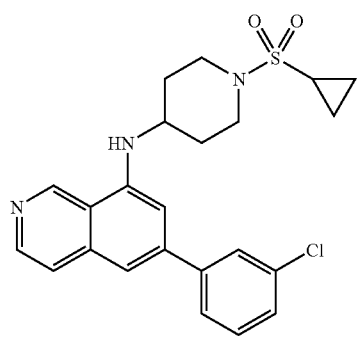
492
-continued
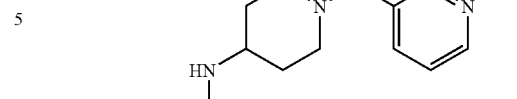
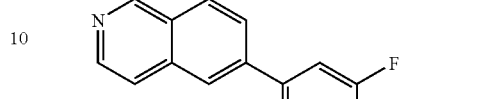
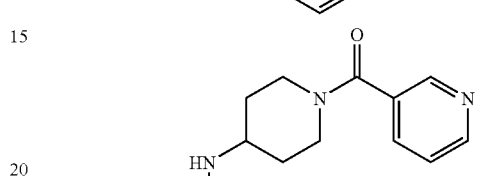
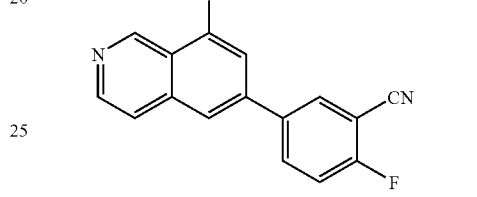
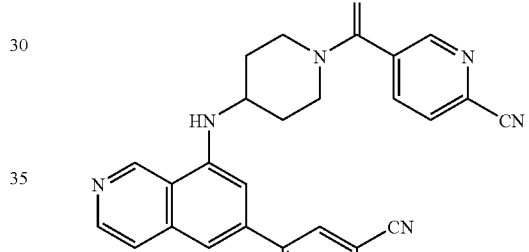
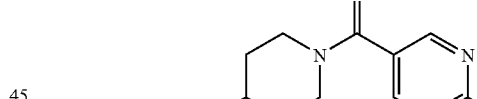
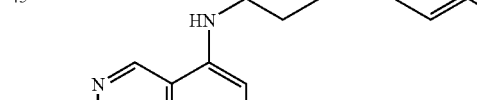
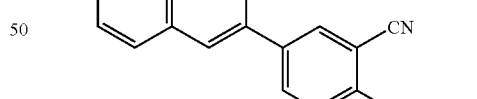
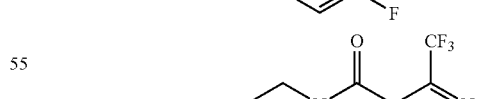
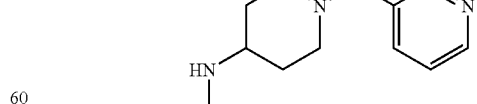
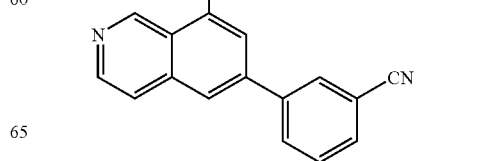

493
-continued
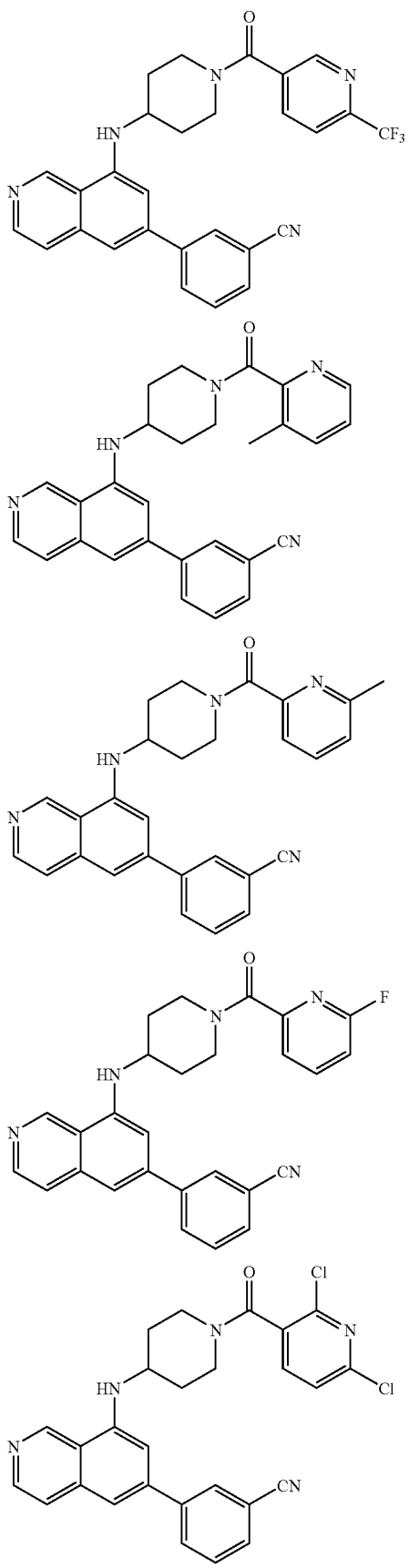
494
-continued
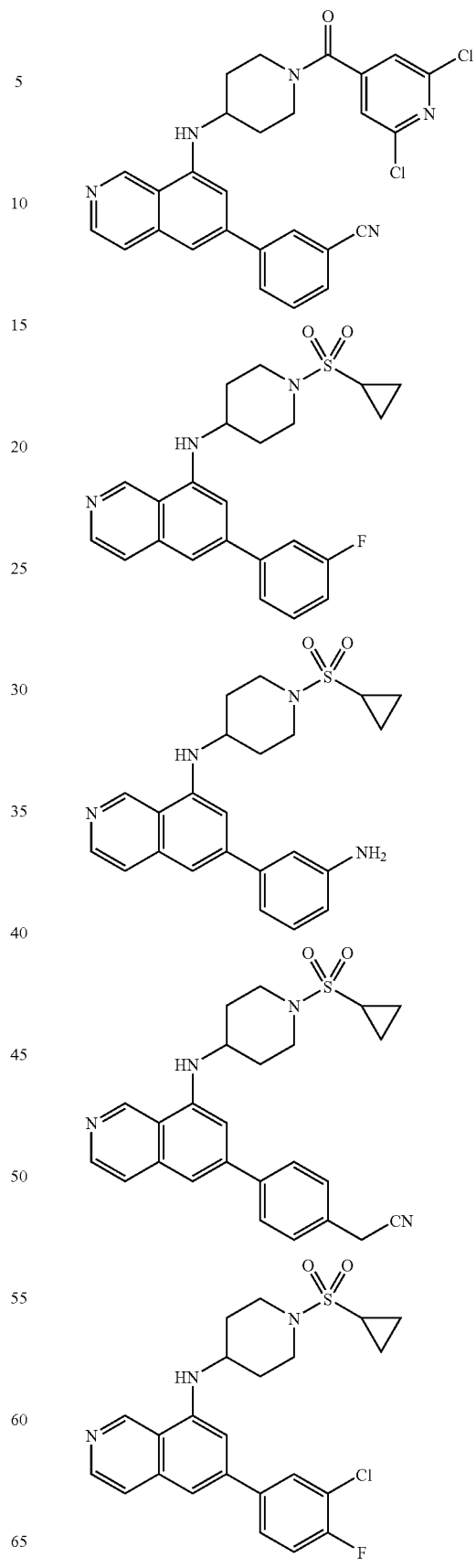

495
-continued
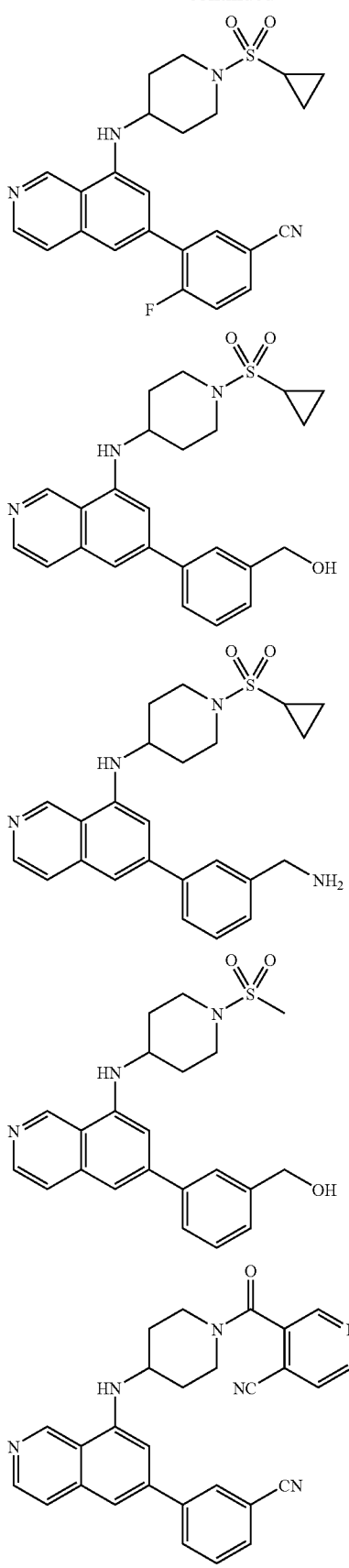
496
-continued
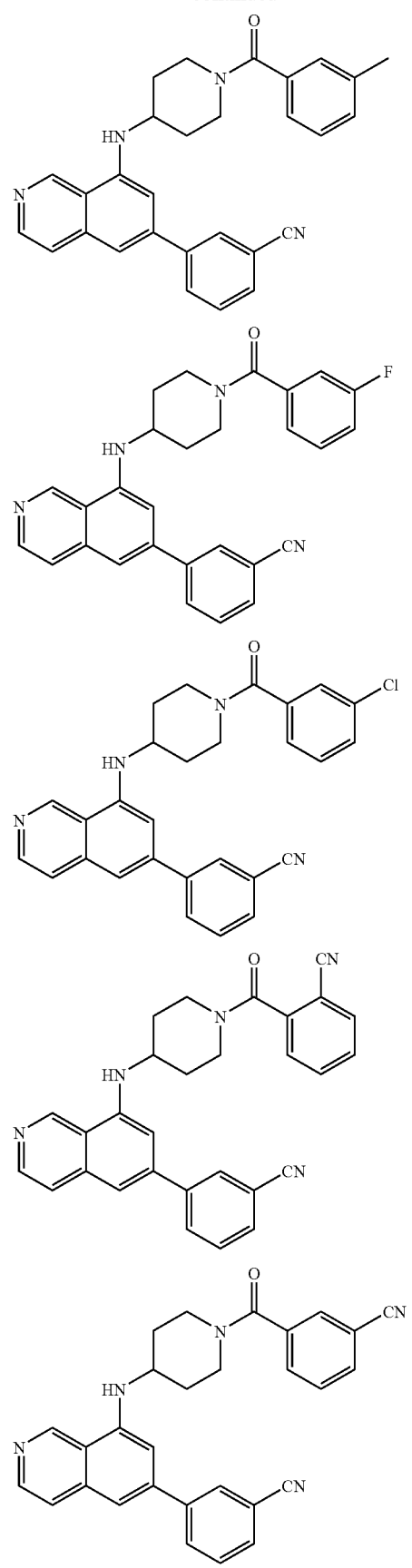

497
-continued
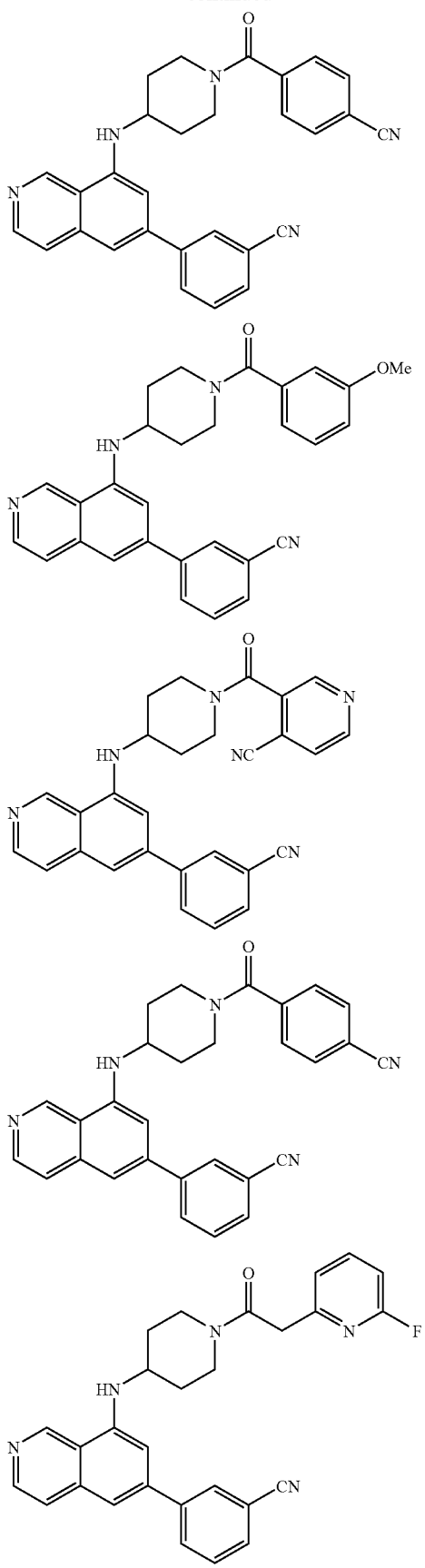
498
-continued
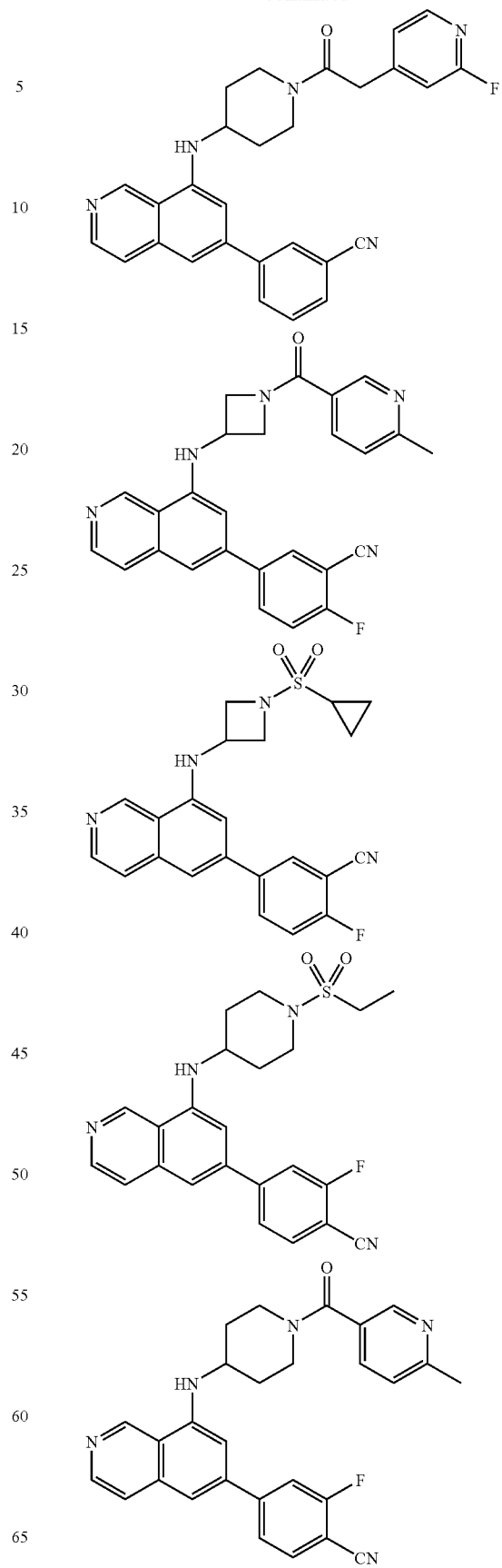

499
-continued
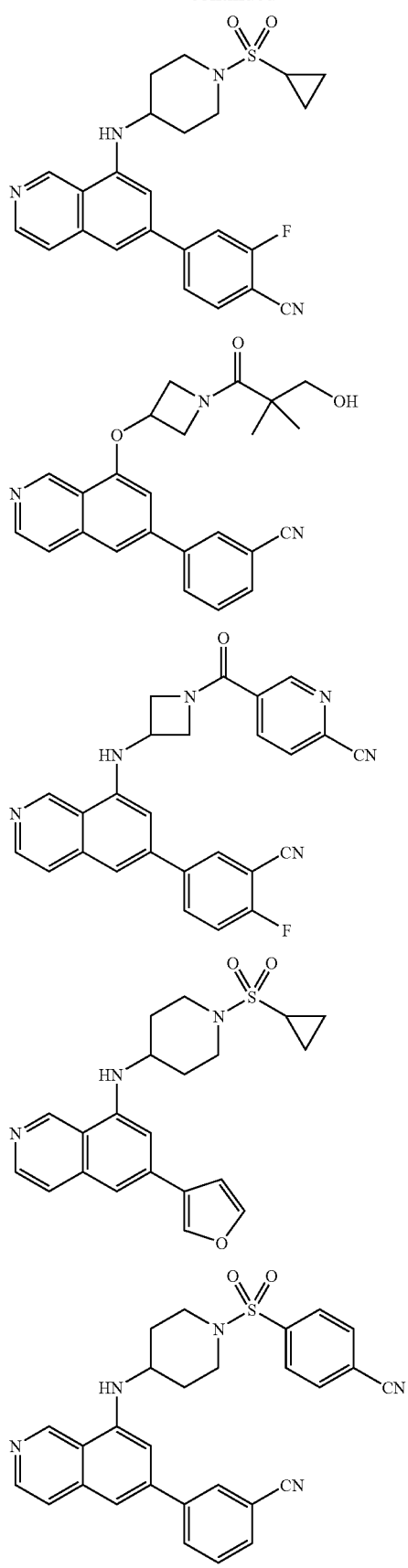
500
-continued
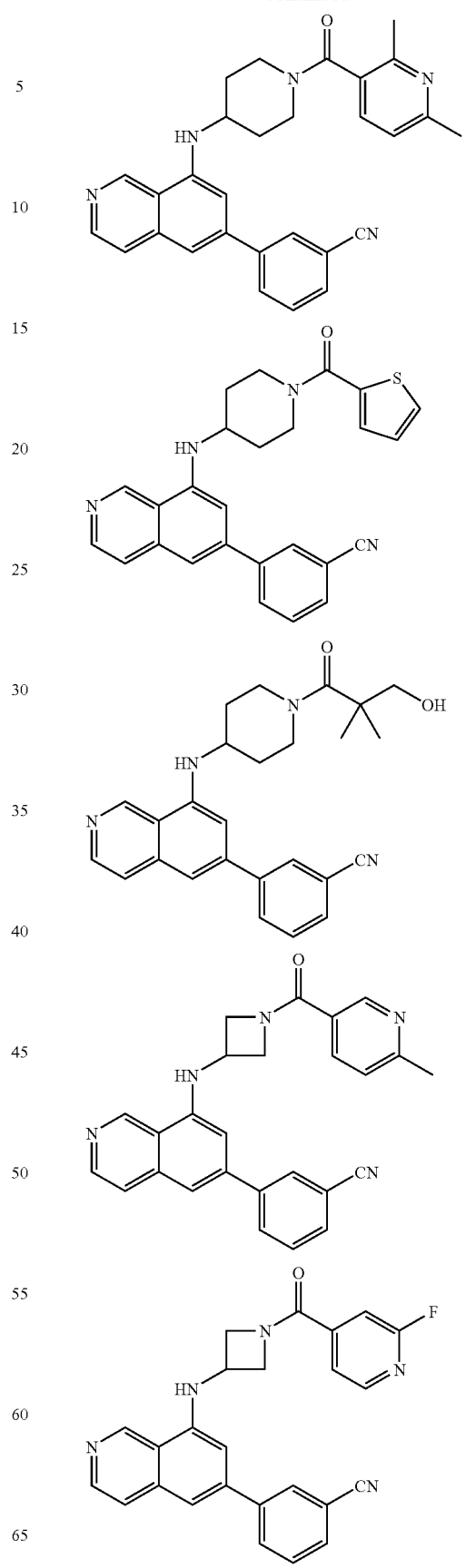

501
-continued
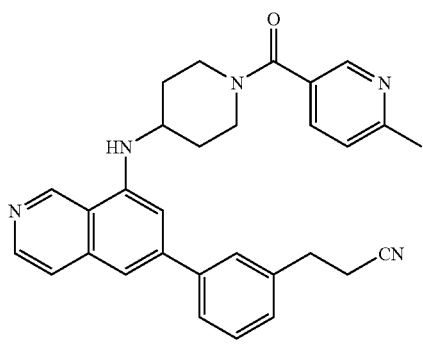
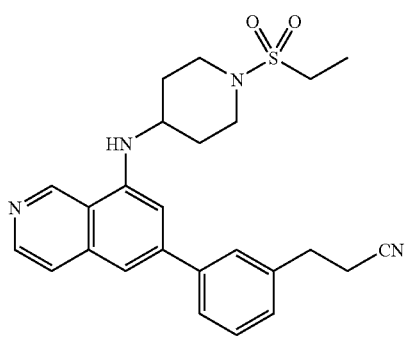
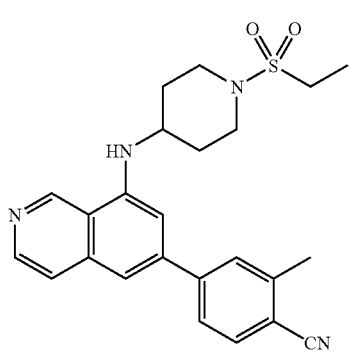
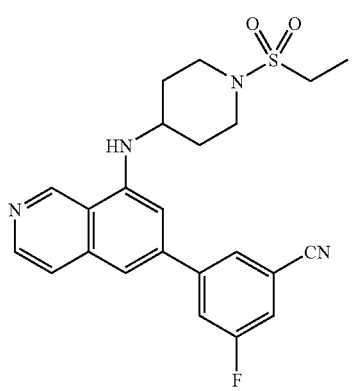
502
-continued
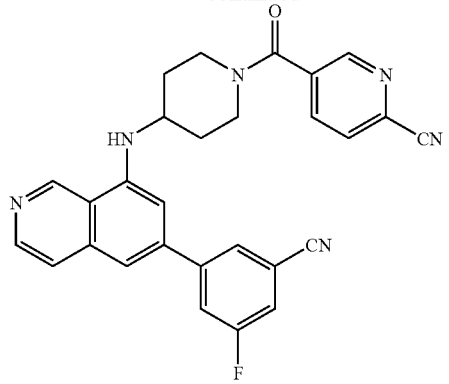
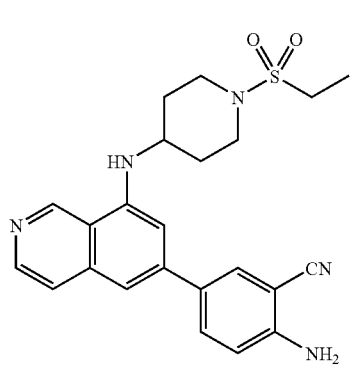
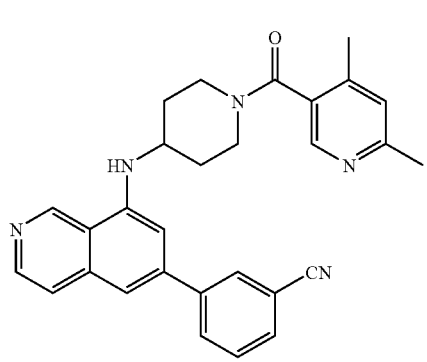
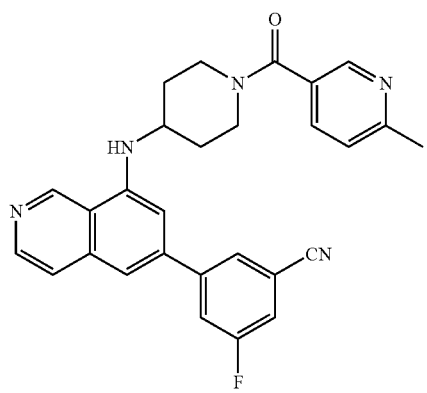

503
-continued
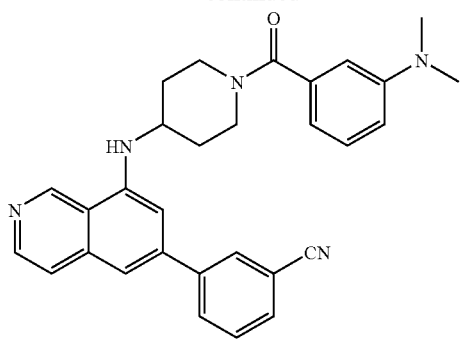
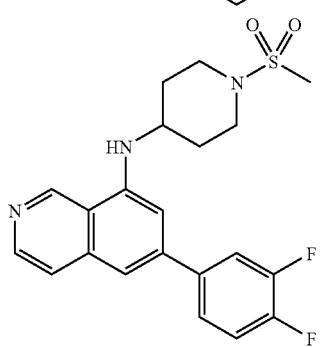
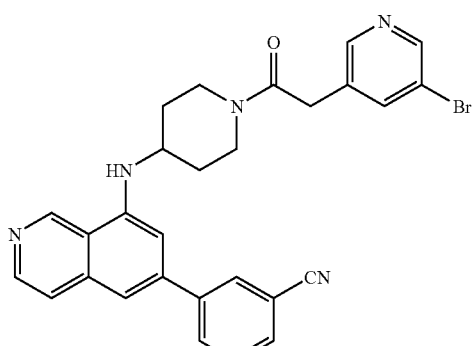
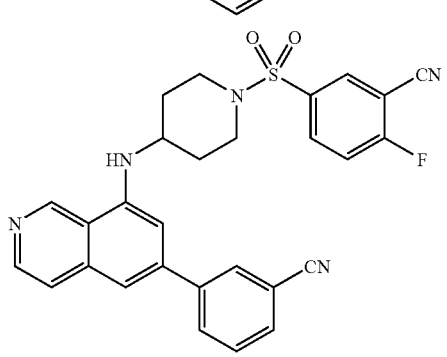
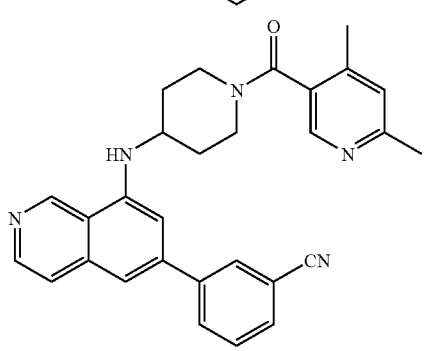
504
-continued
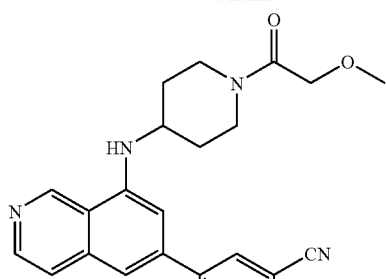
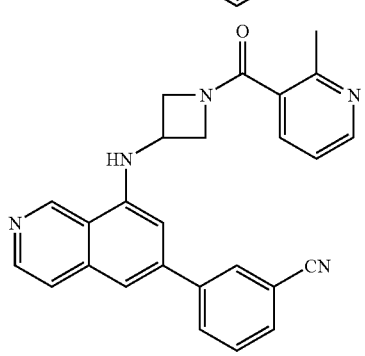
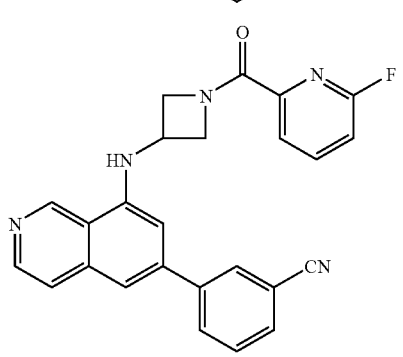
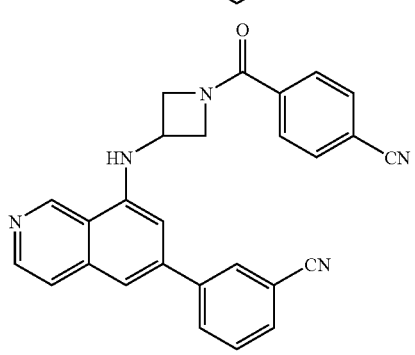
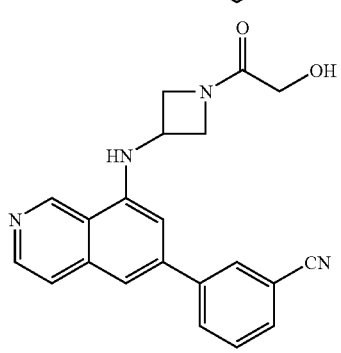

505
-continued
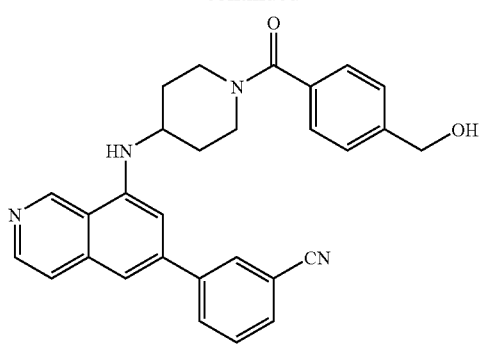
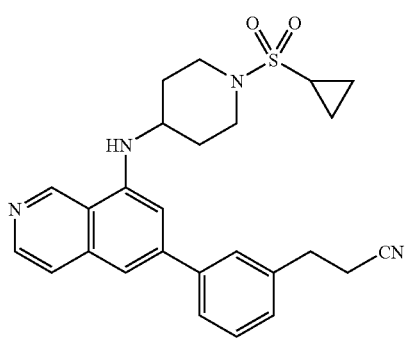
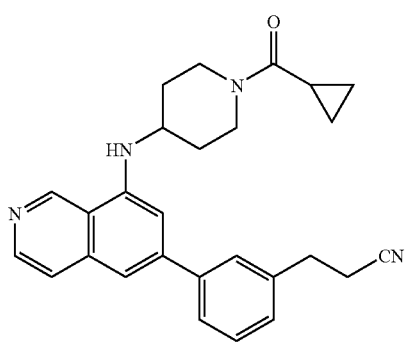
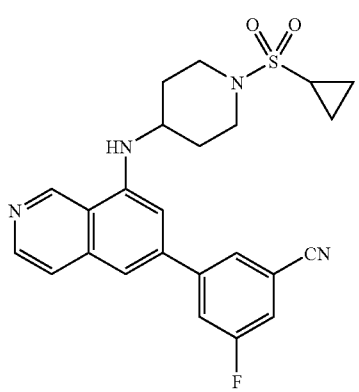
506
-continued
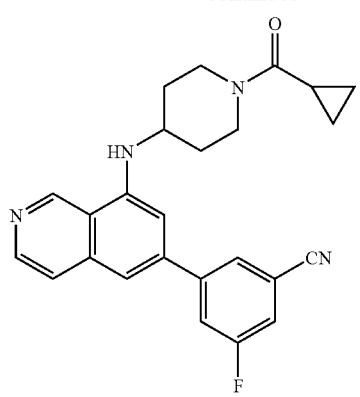
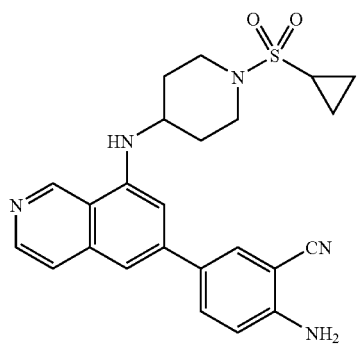
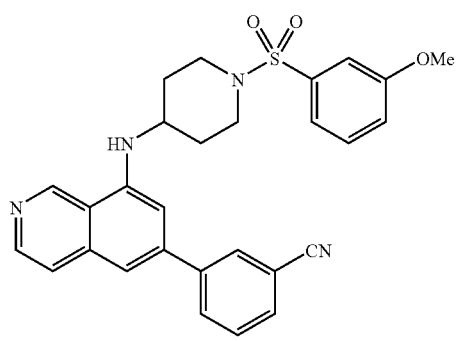
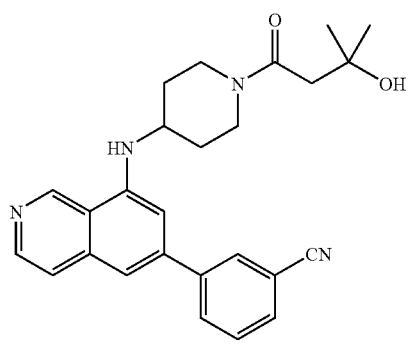

507
-continued
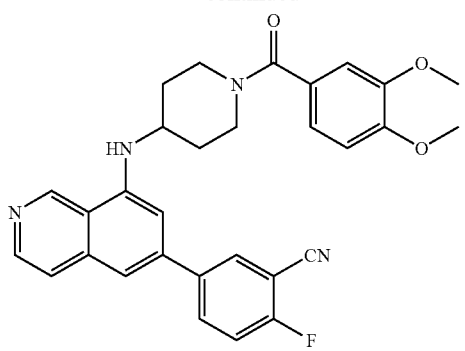
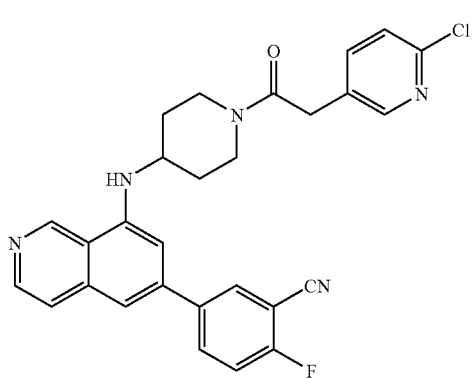
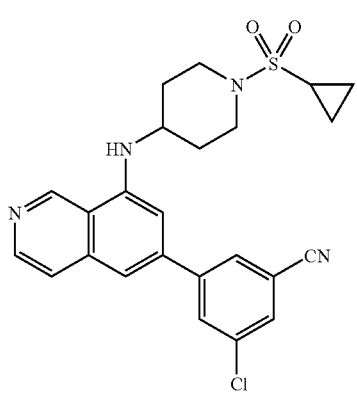
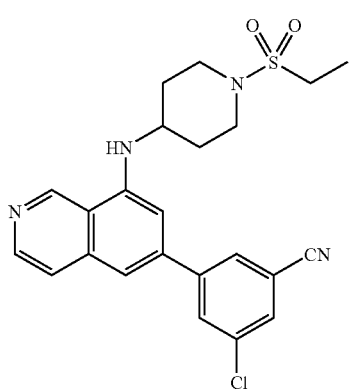
508
-continued
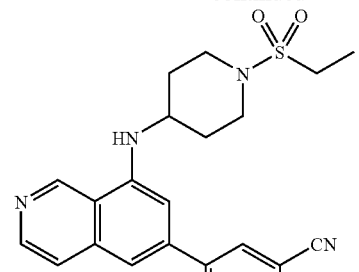
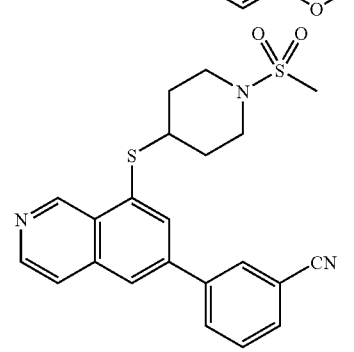
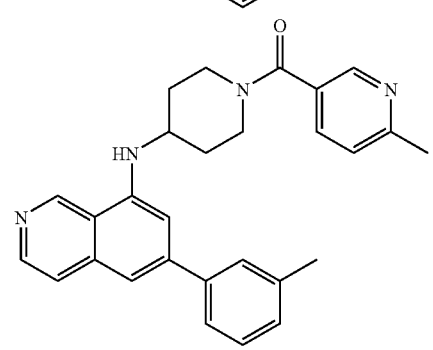
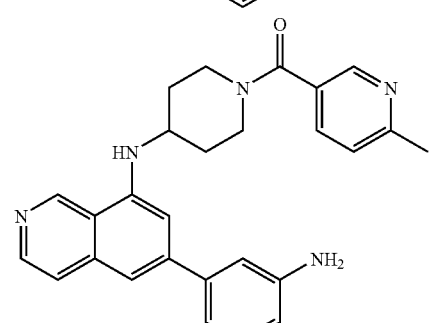
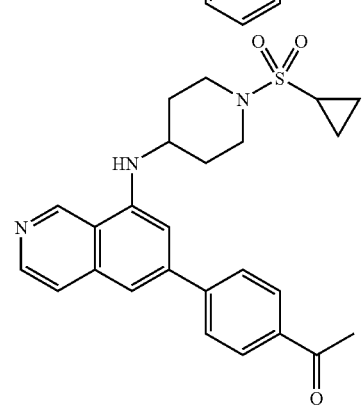

509
-continued
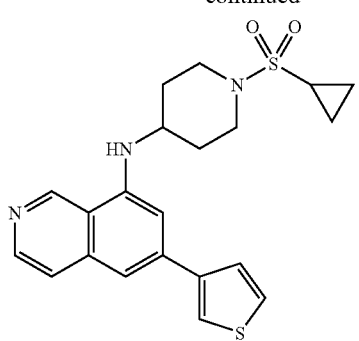
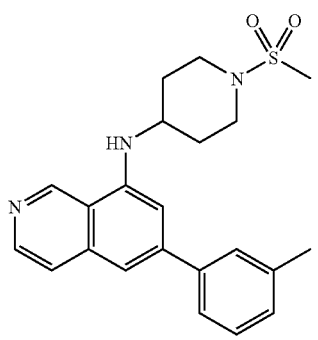
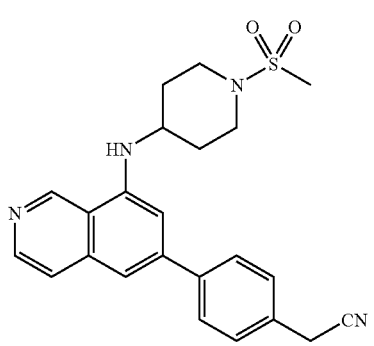
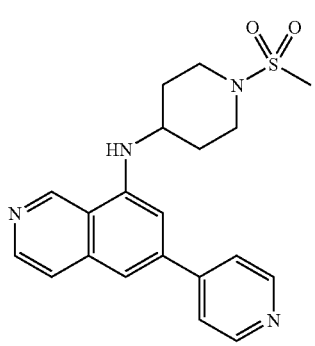
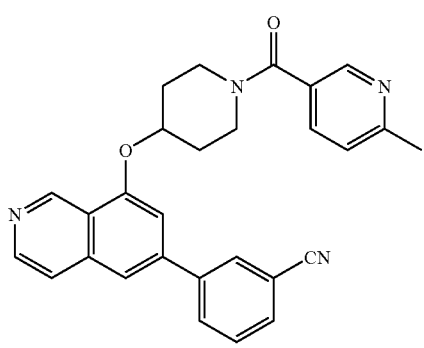
510
-continued
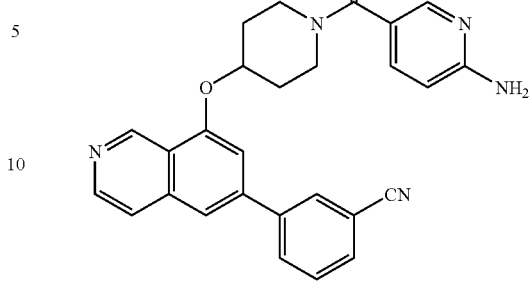
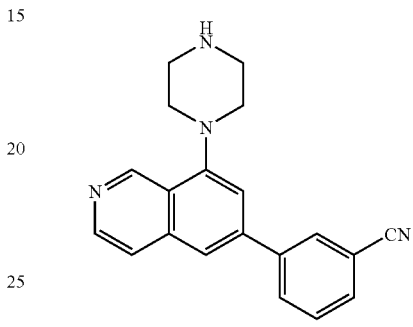
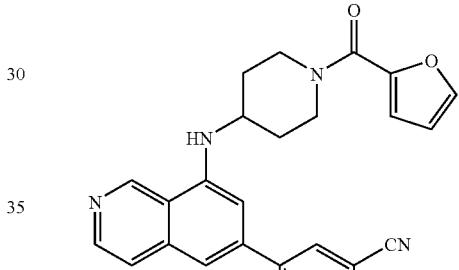
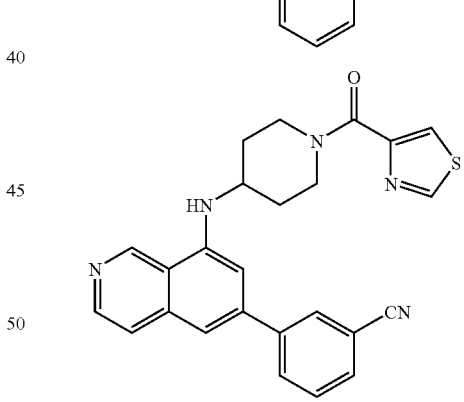
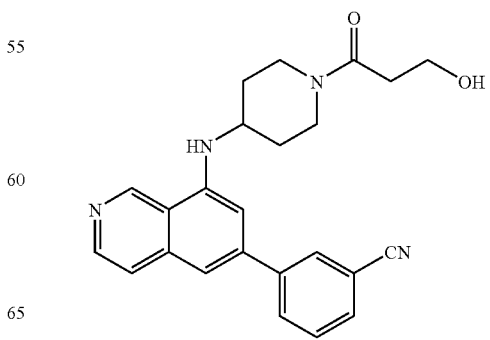

511
-continued
512
-continued
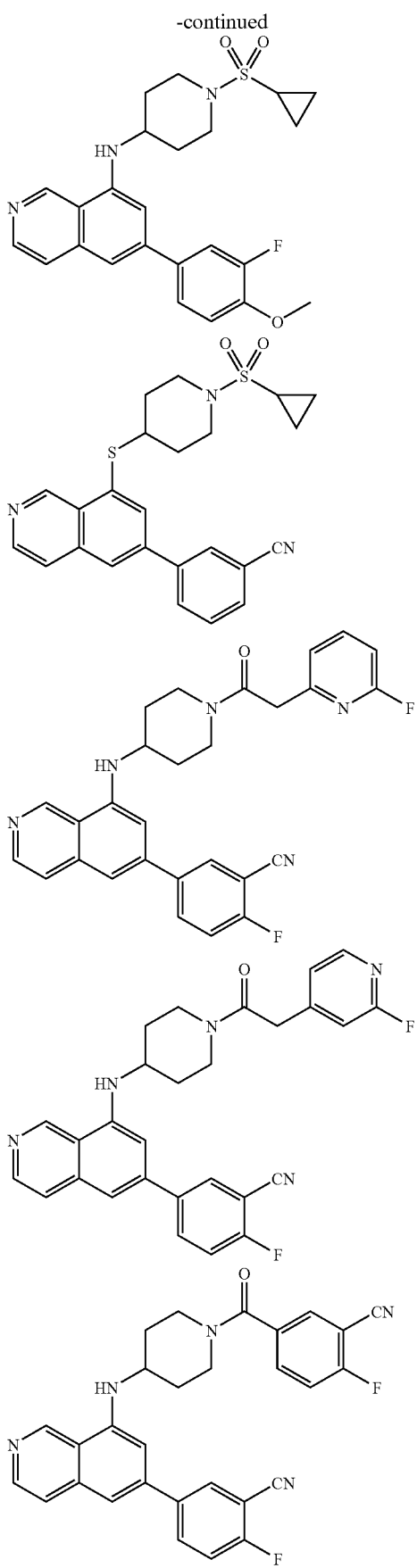

513
-continued
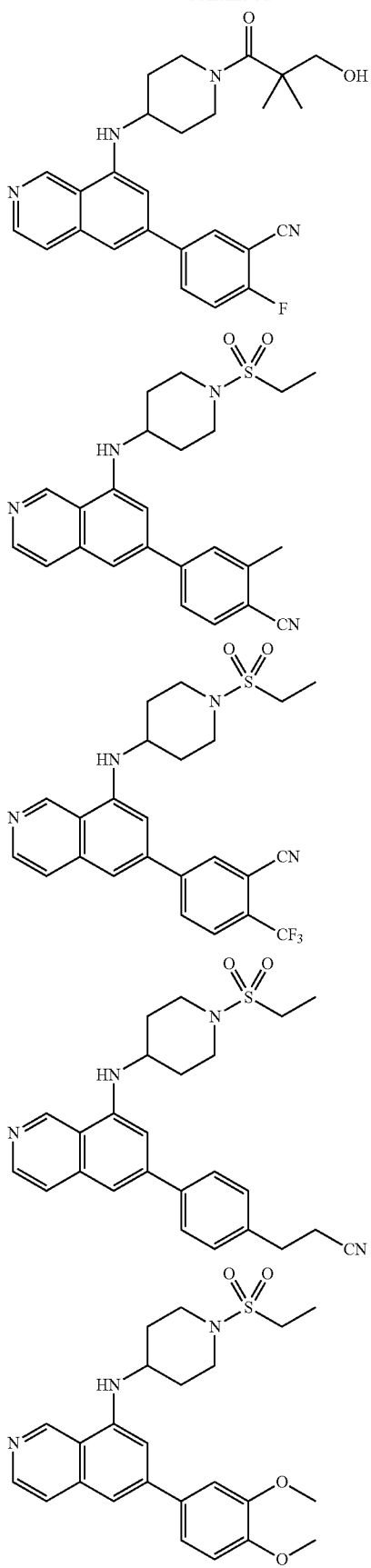
514
-continued
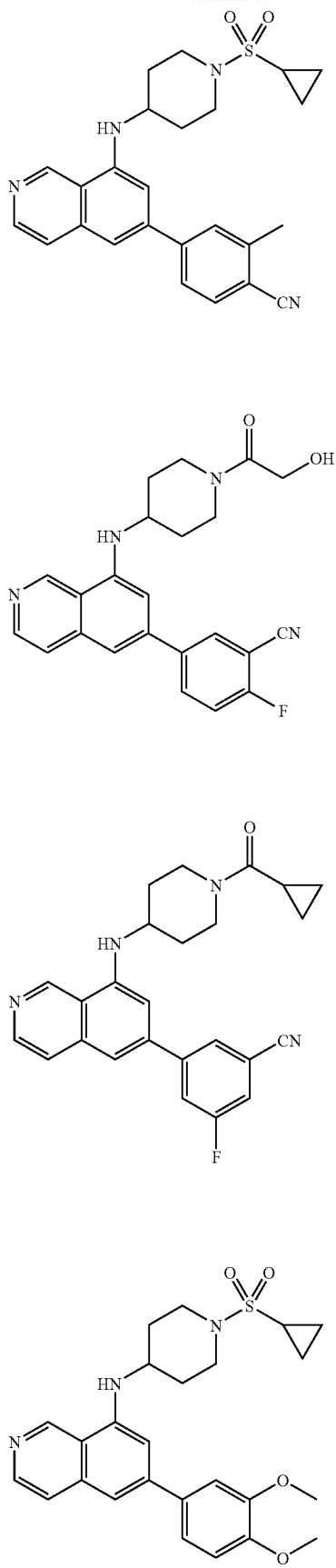

515
-continued
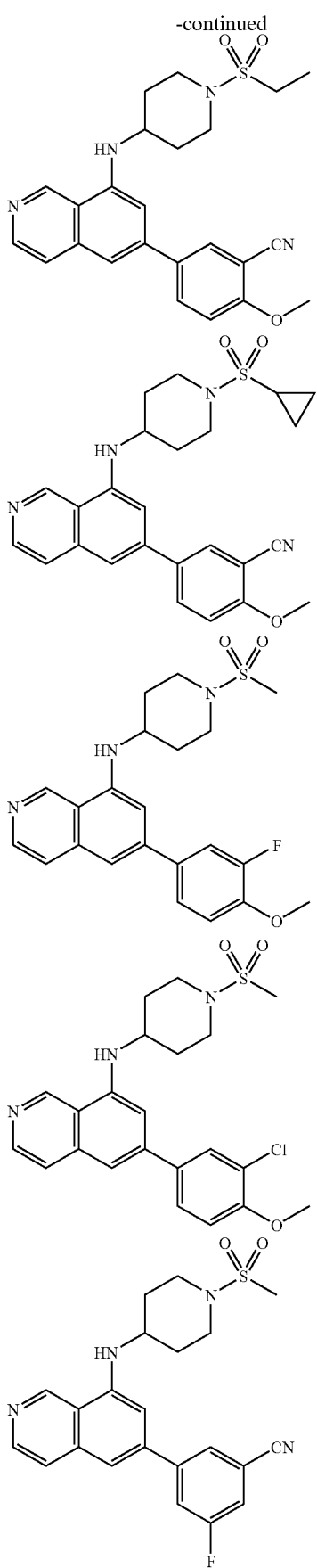
516
-continued
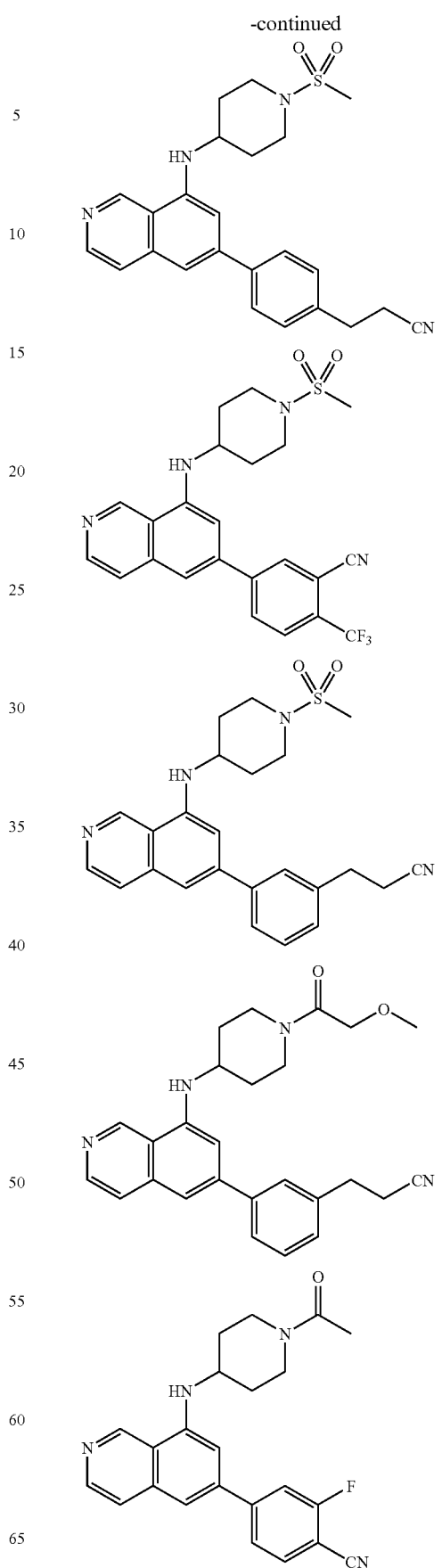

517
-continued
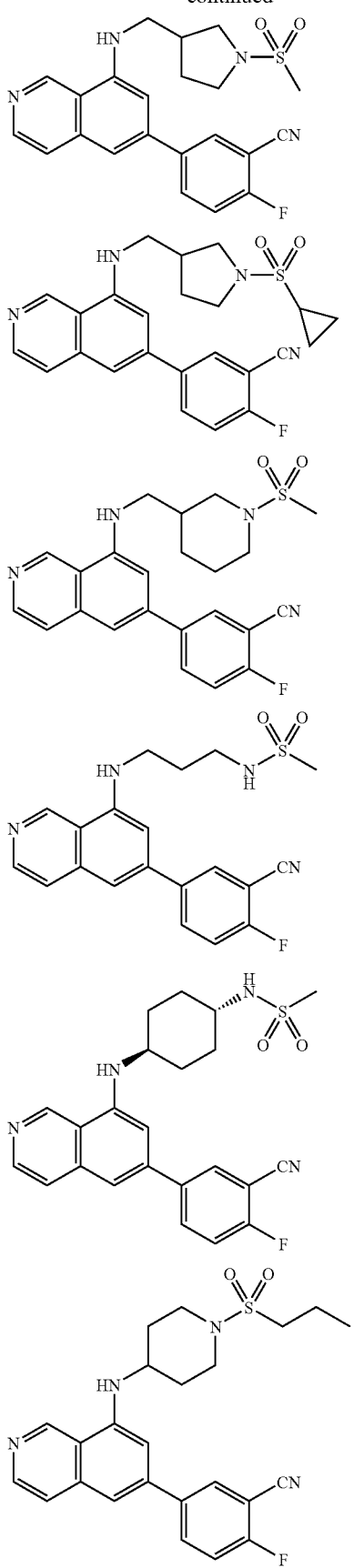
518
-continued
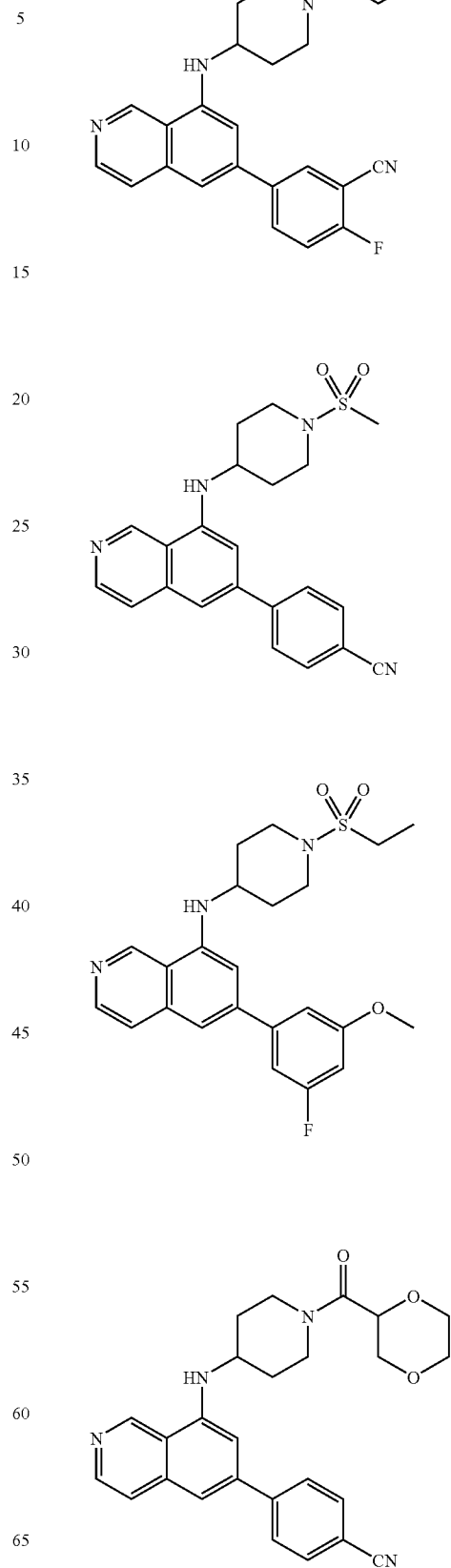

519
-continued
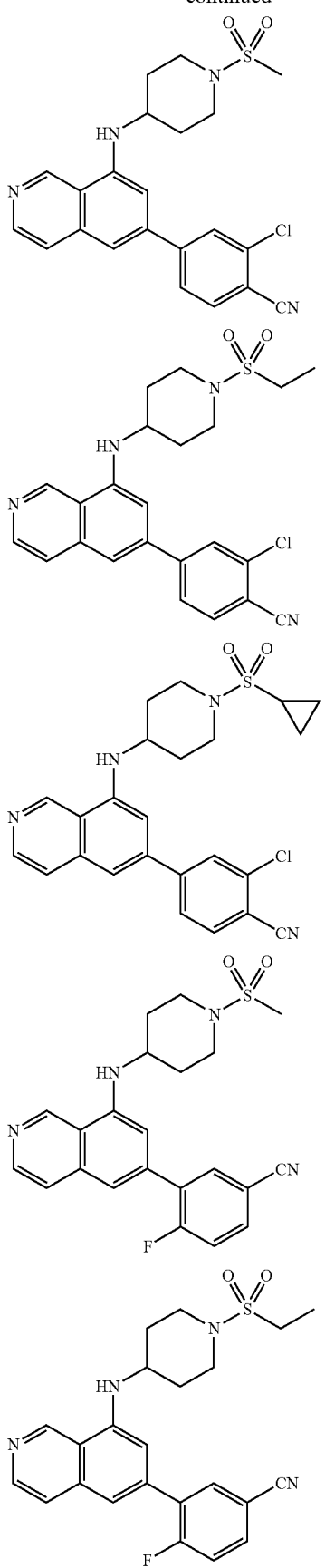
520
-continued
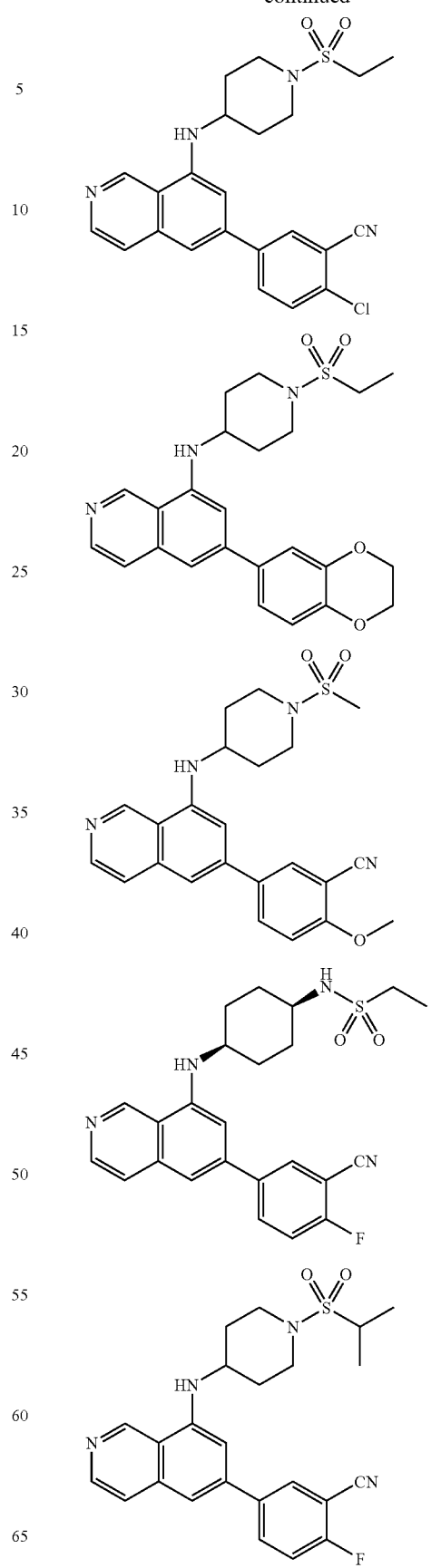

521
-continued
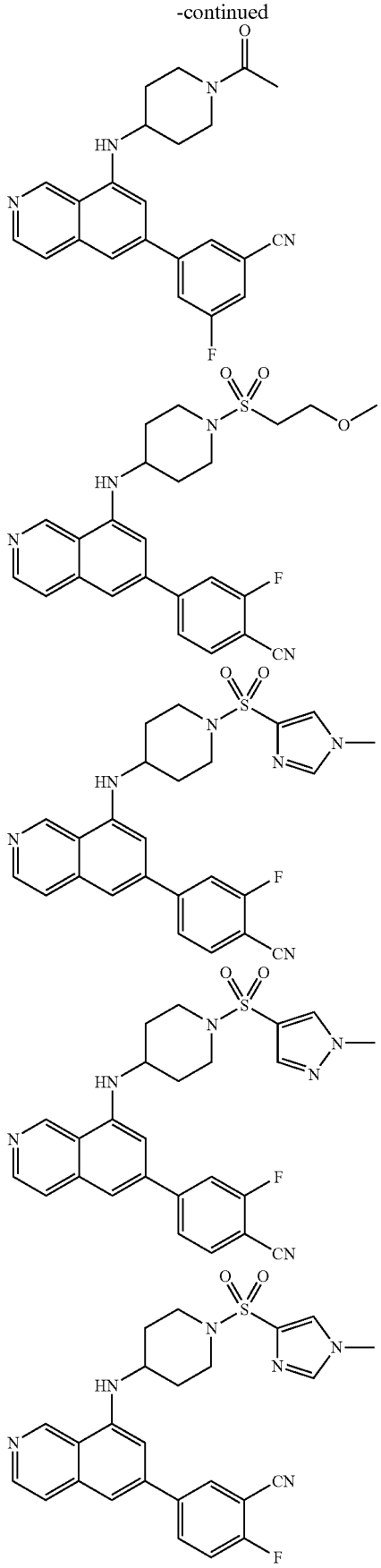
522
-continued
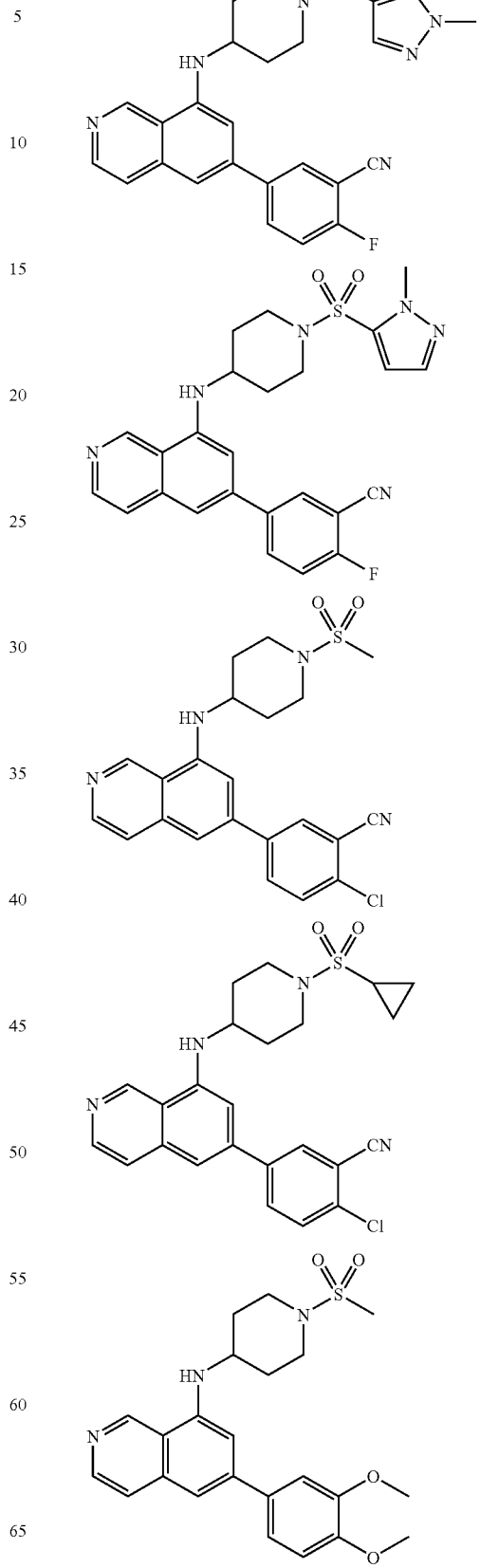

523
-continued
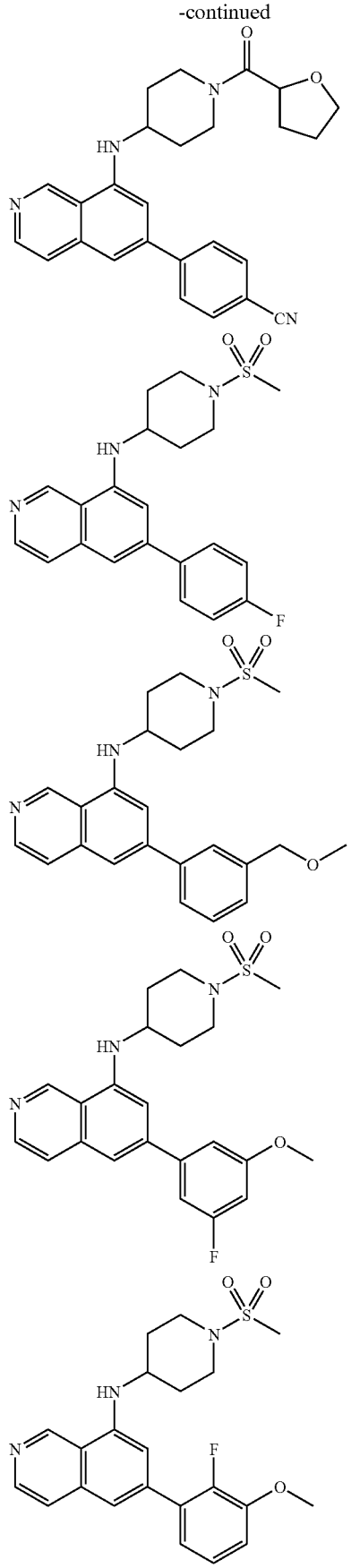
524
-continued
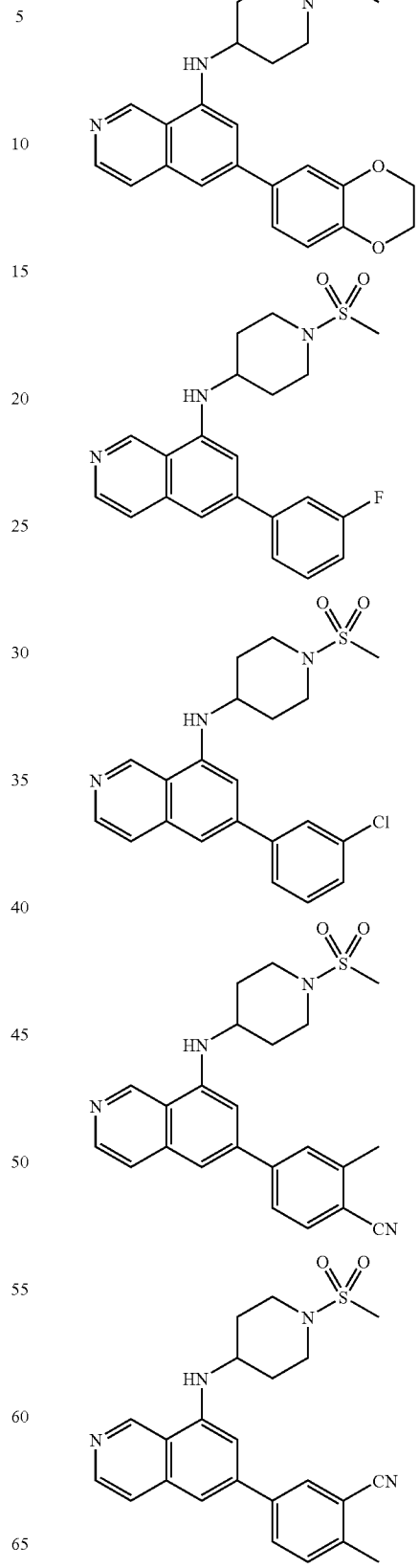

525
-continued
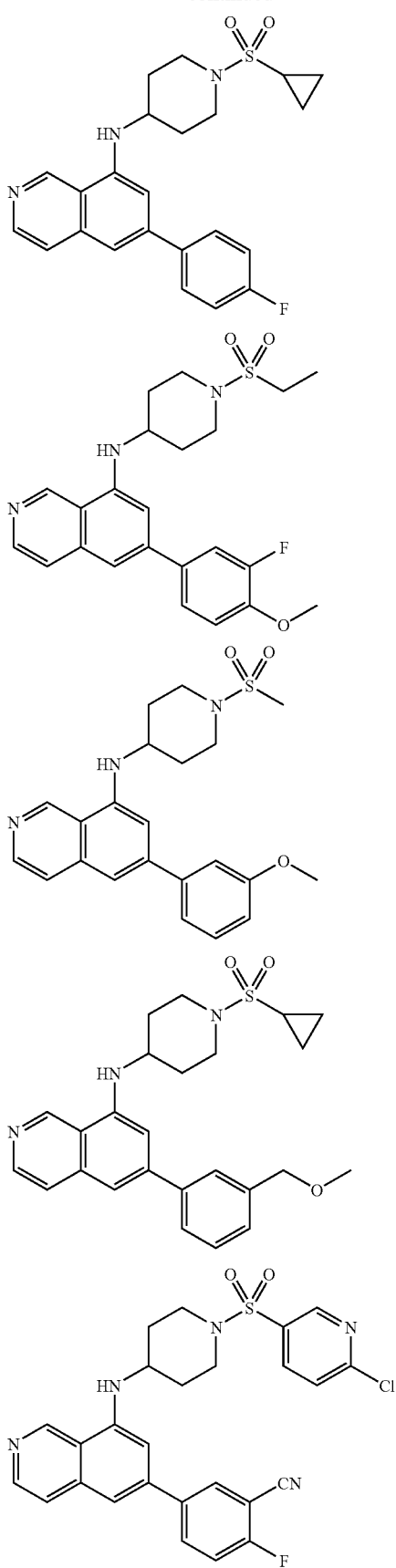
526
-continued
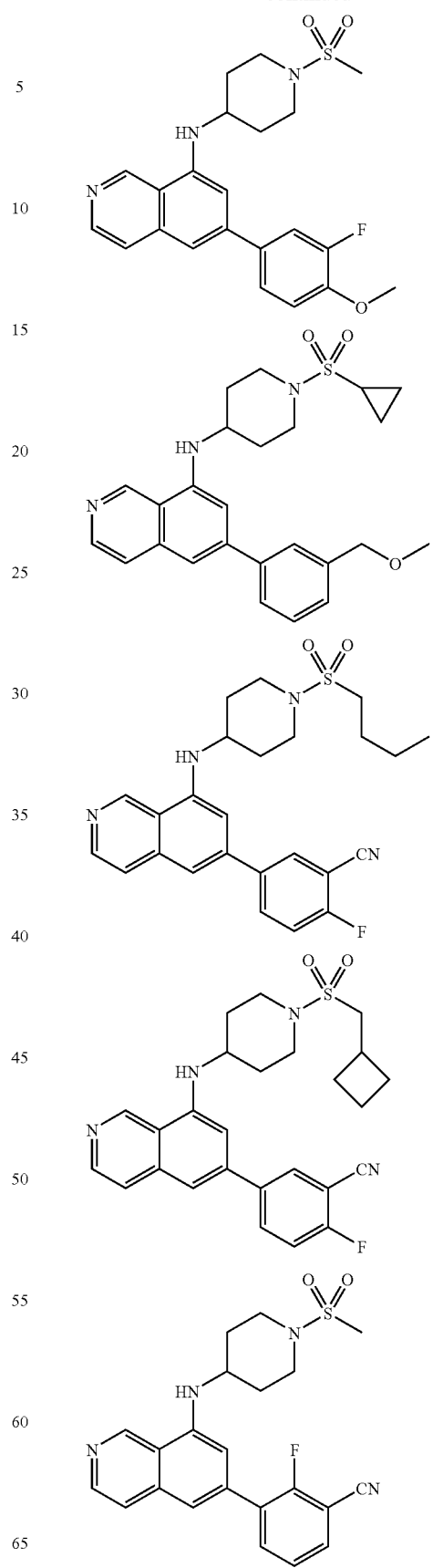

527
-continued
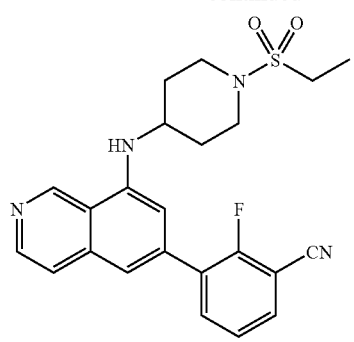
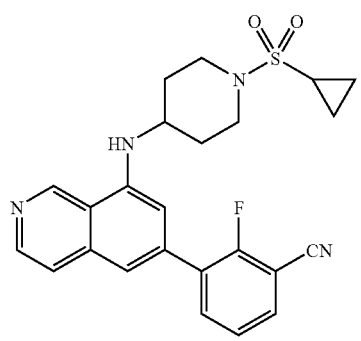
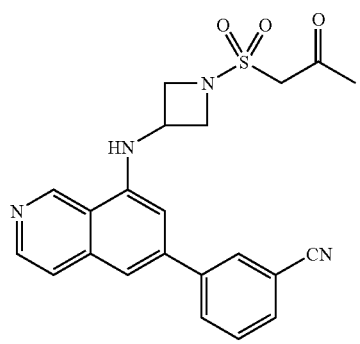
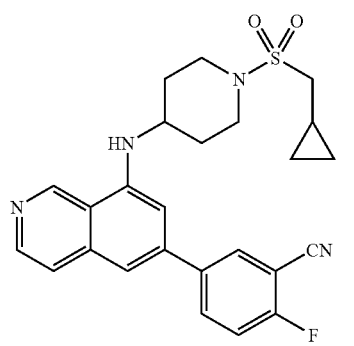
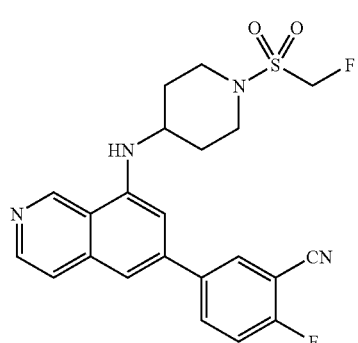
528
-continued
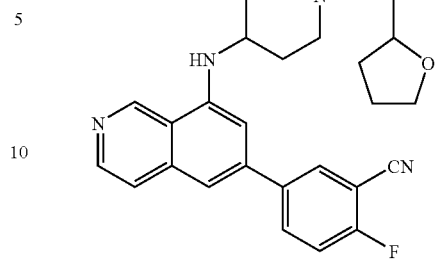
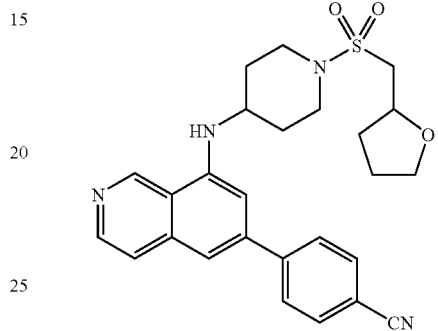
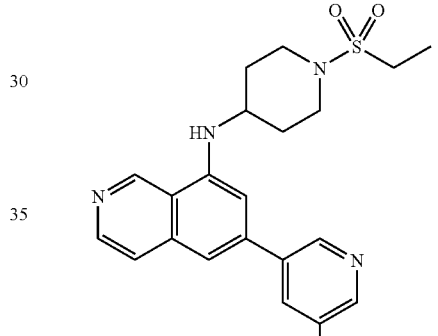
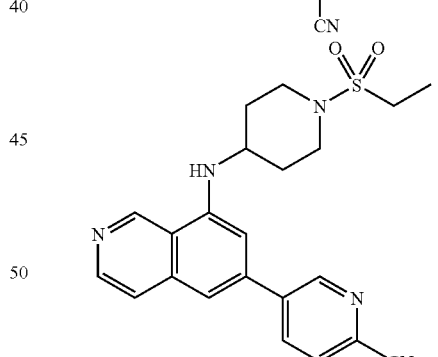
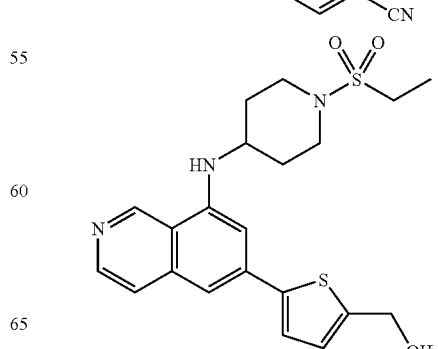

| 529 -continued | 530 -continued |
|---|---|
| 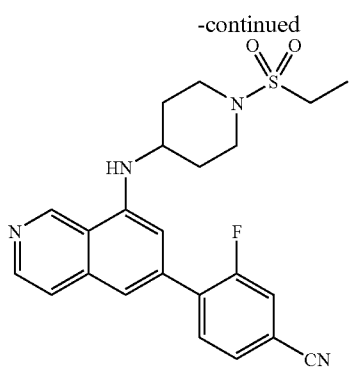 | 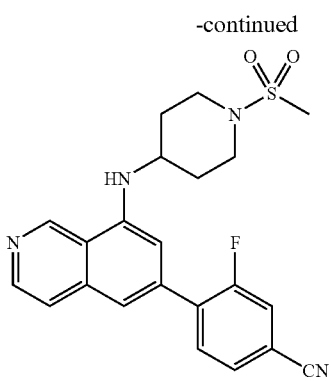 |
| 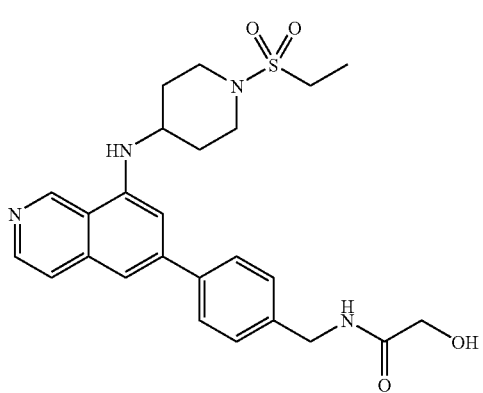 | 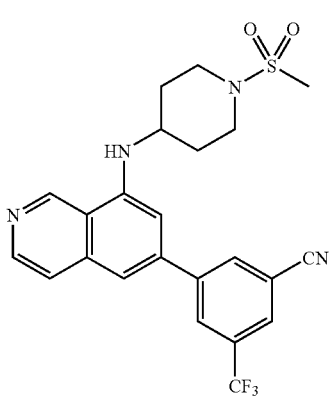 |
| 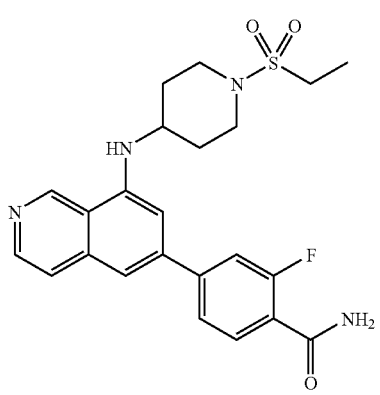 | 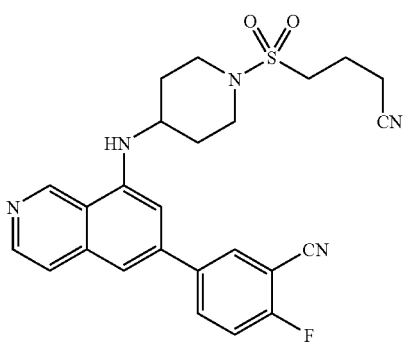 |
| 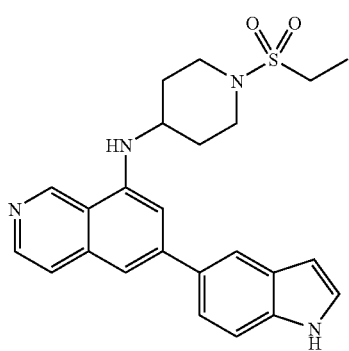 | 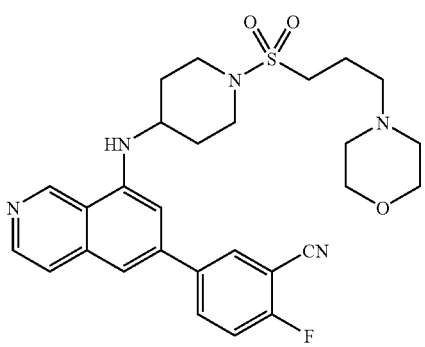 |

| 531 -continued | 532 -continued |
|---|---|
| 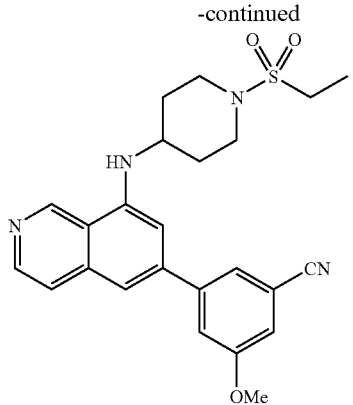 | 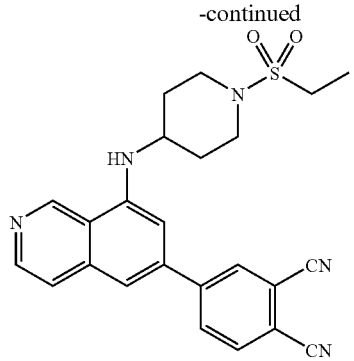 |
| 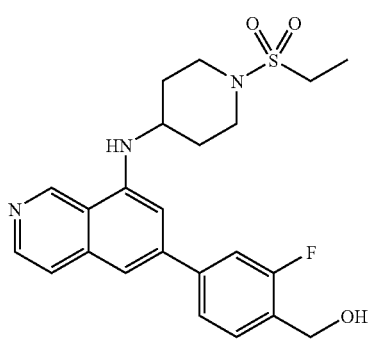 | 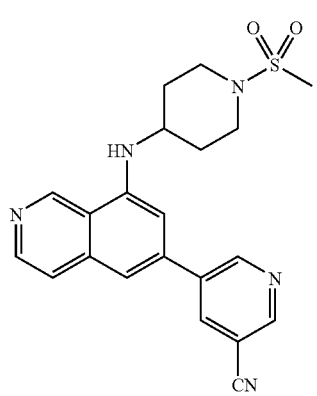 |
| 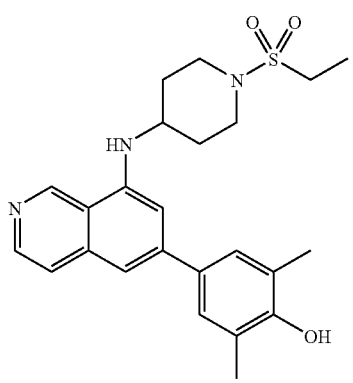 | 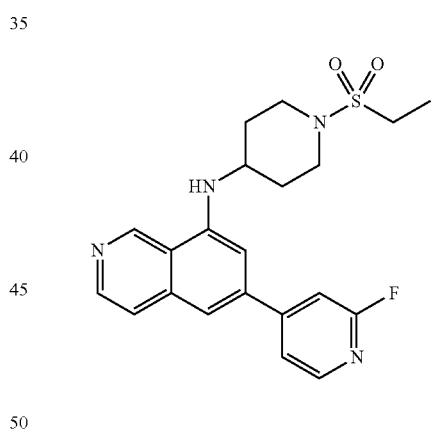 |
| 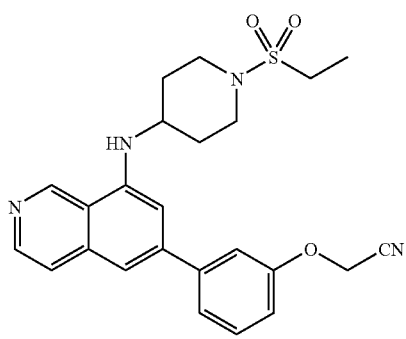 | 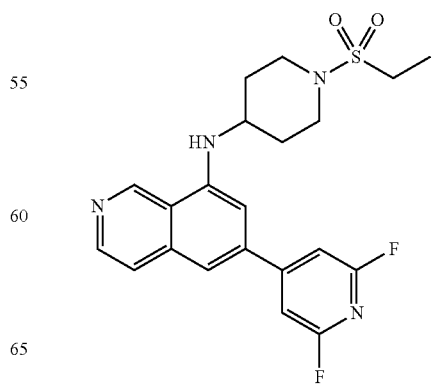 |

533
-continued
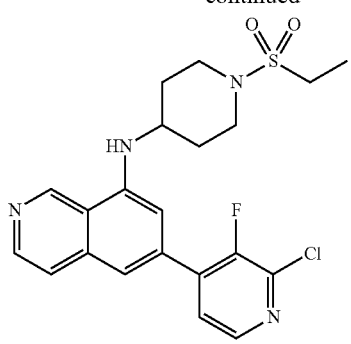
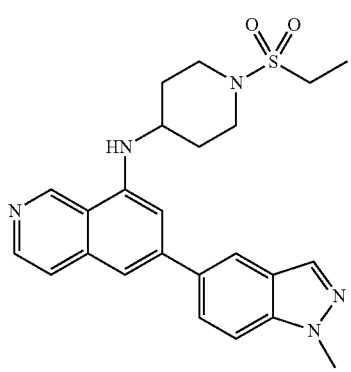
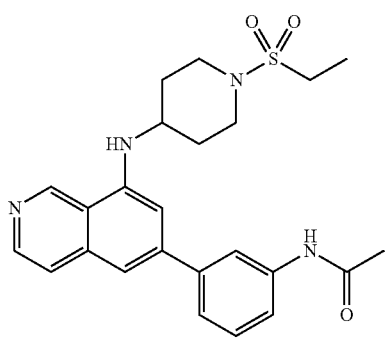
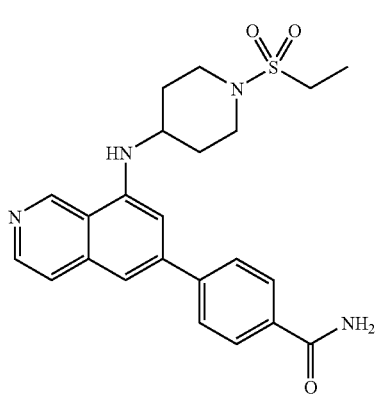
534
-continued
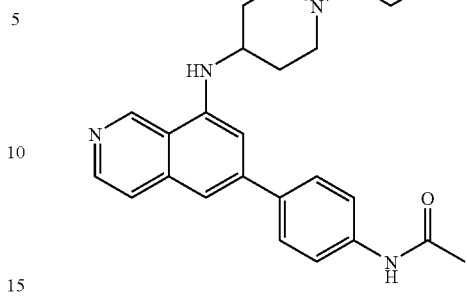
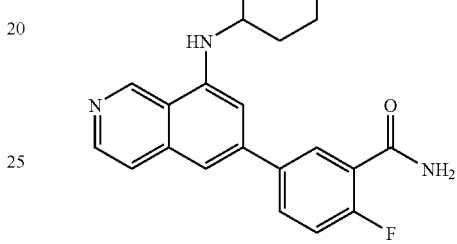
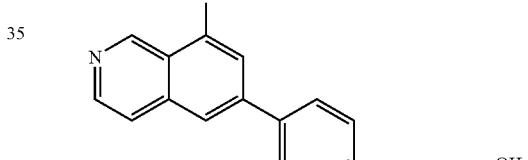
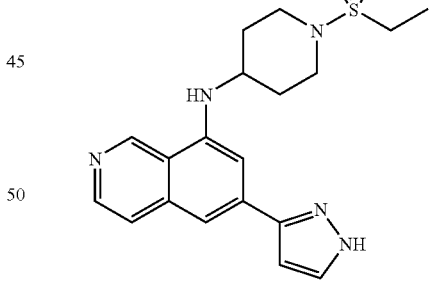
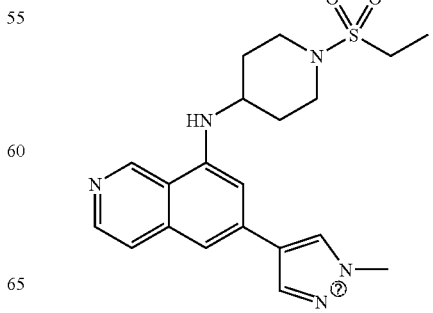

535
-continued
536
-continued
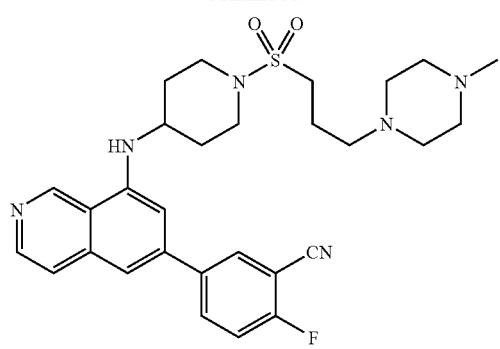
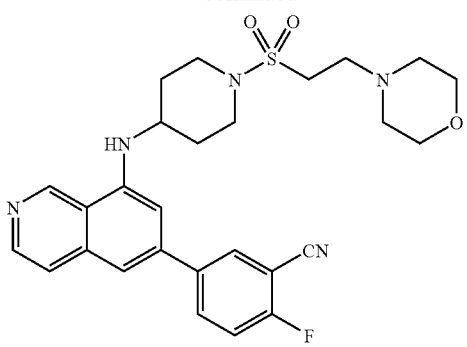
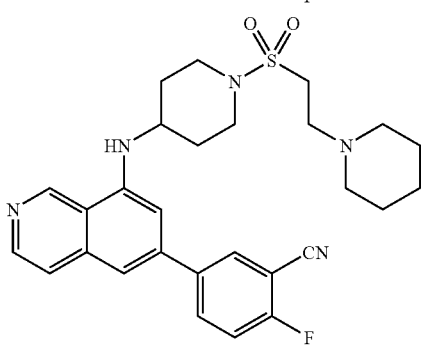
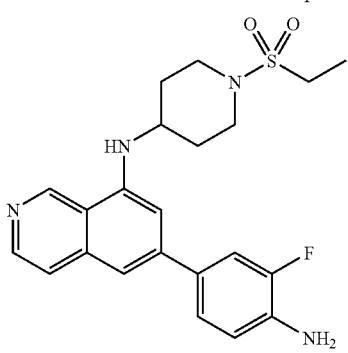
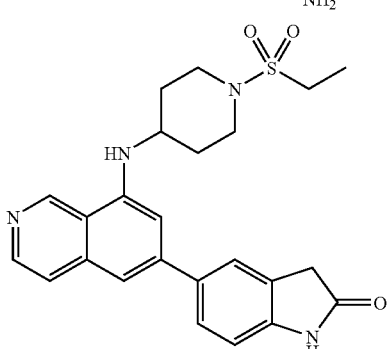
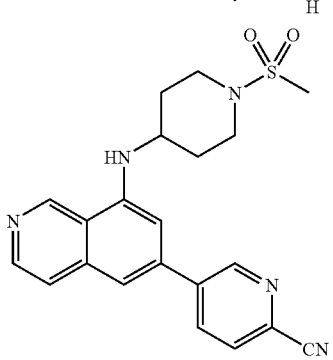

537
-continued
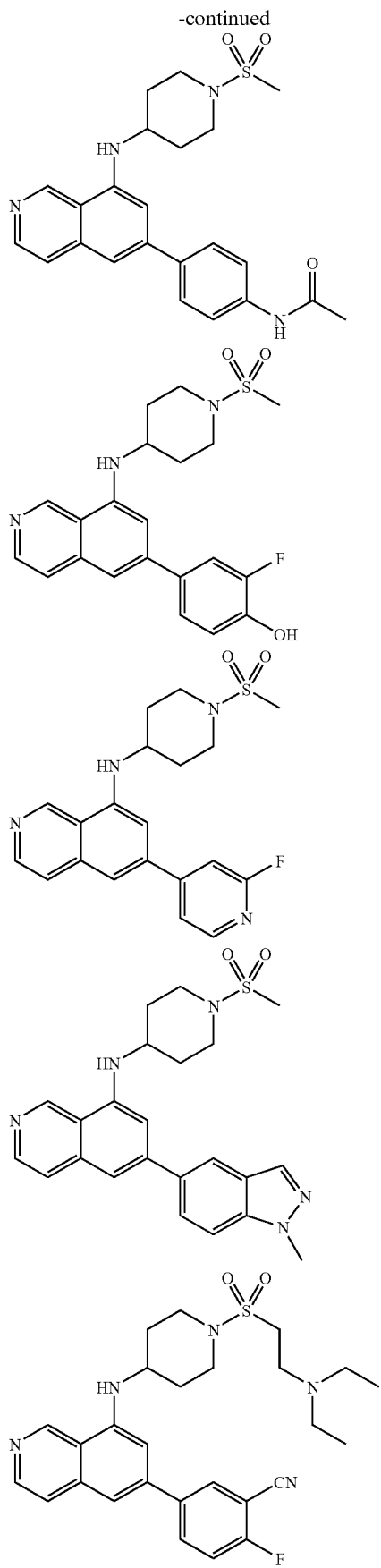
538
-continued
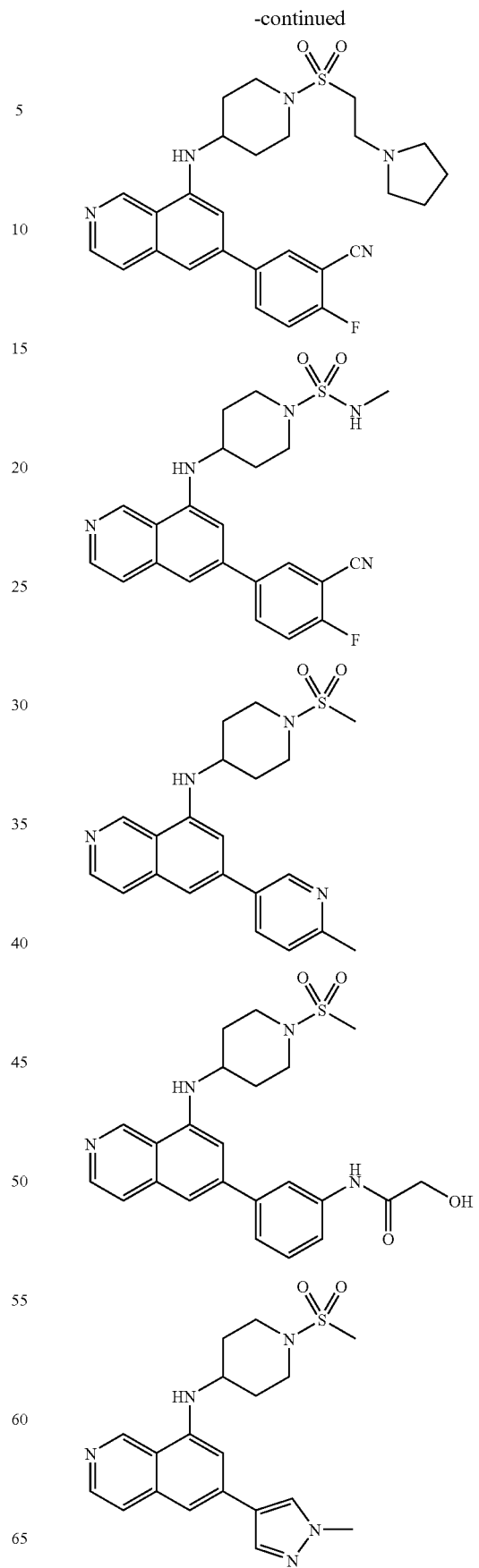

539
-continued
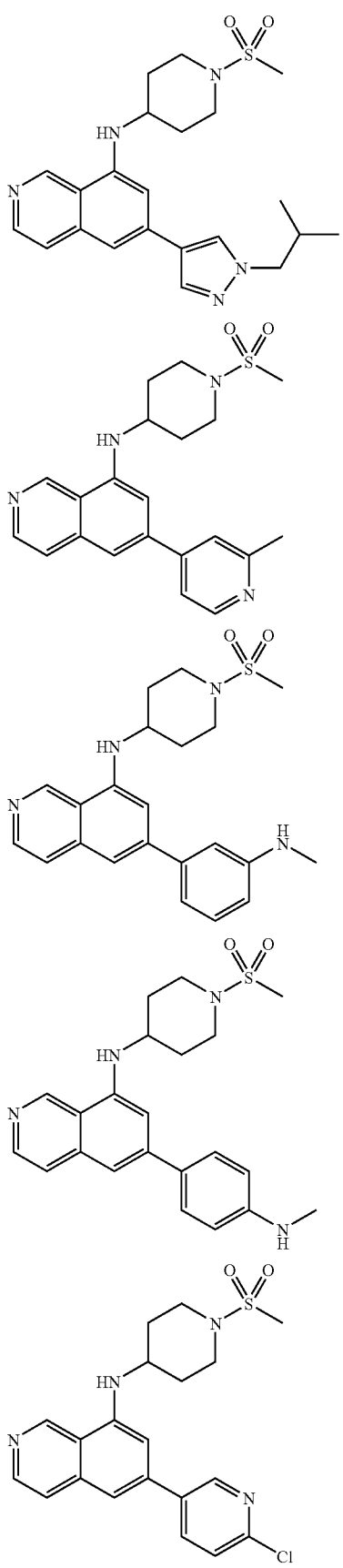
540
-continued
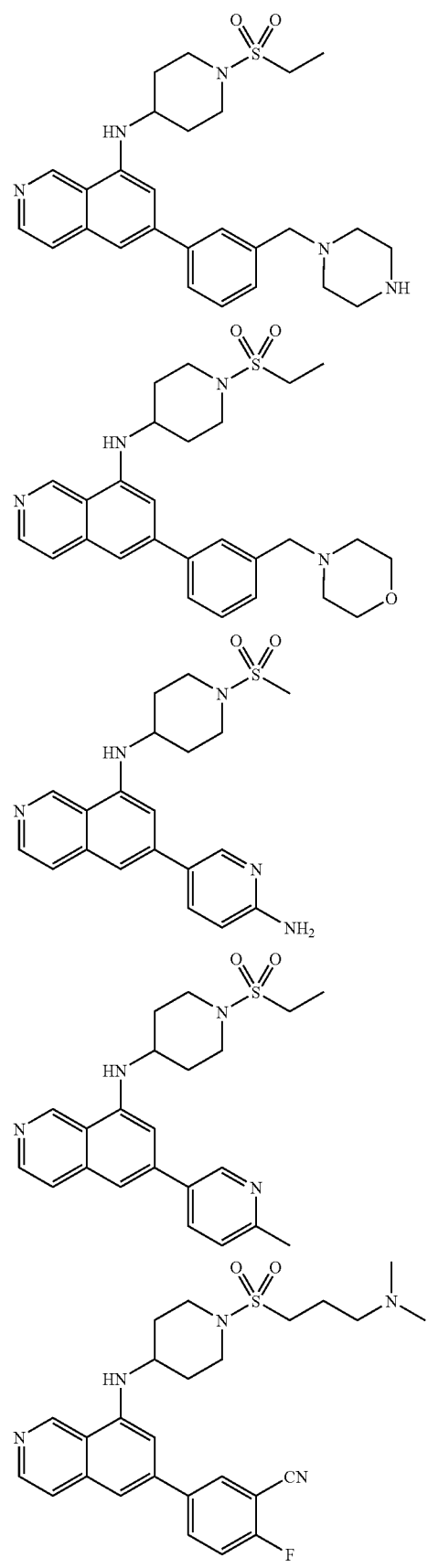

541
-continued
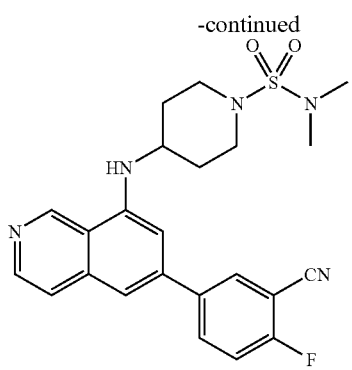
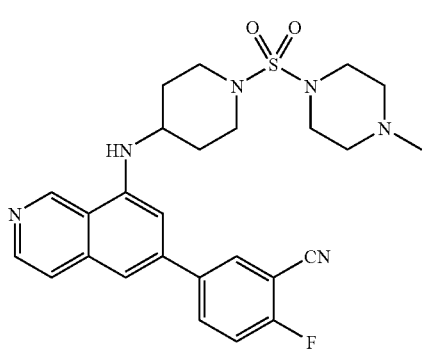
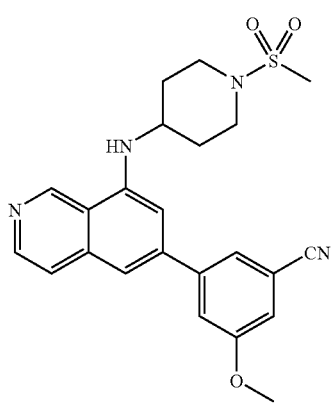
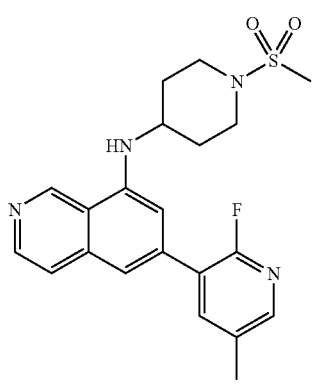
542
-continued
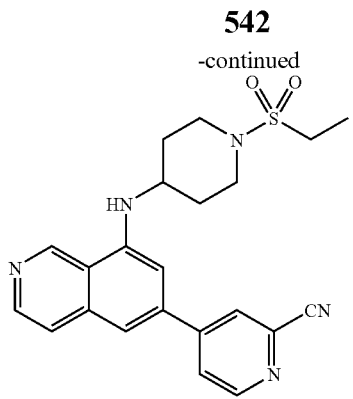
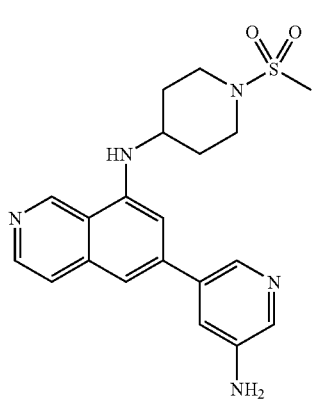
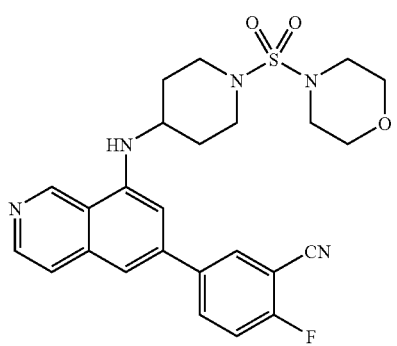
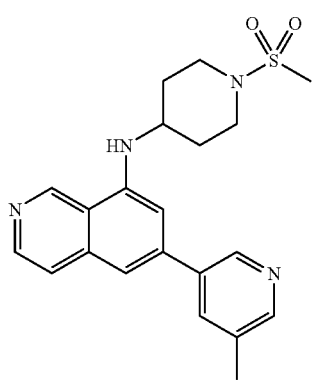

| 543 -continued | 544 -continued |
|---|---|
| 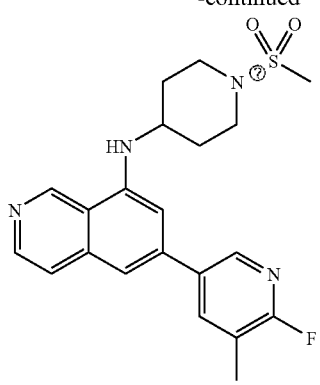 | 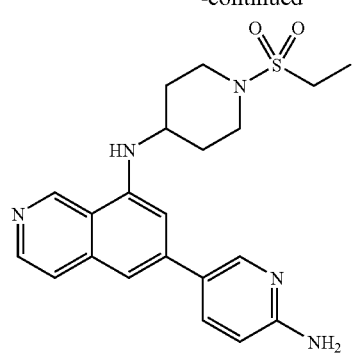 |
| 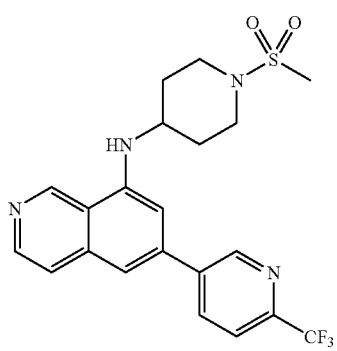 | 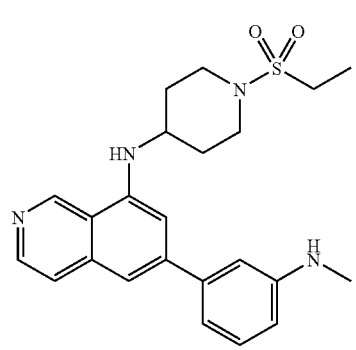 |
| 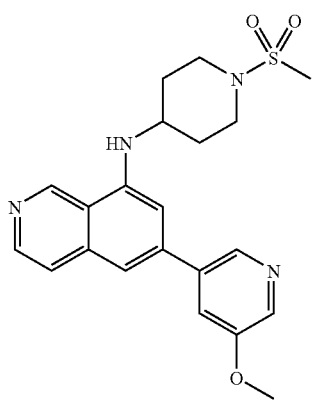 | 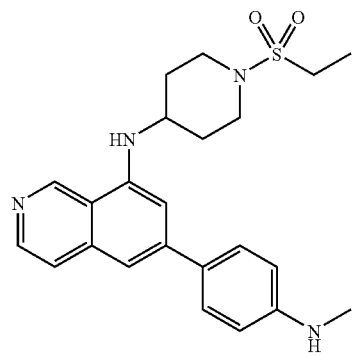 |
| 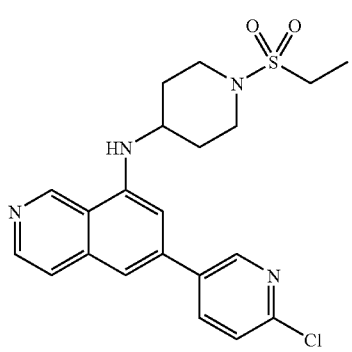 | 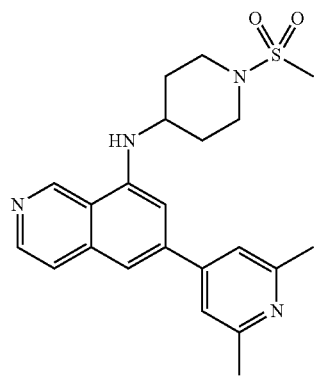 |

545
-continued
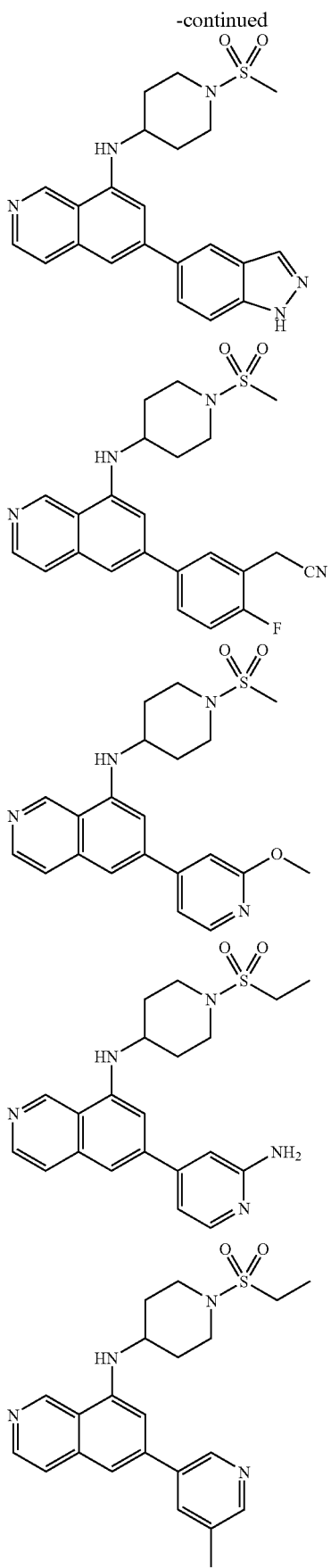
546
-continued
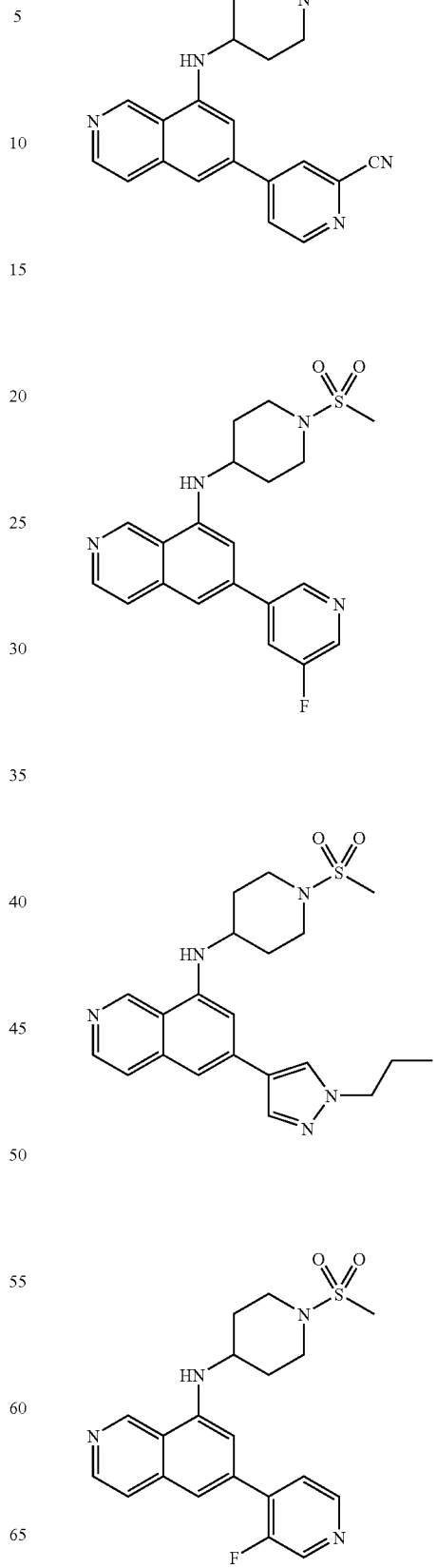

| 547 -continued | 548 -continued |
|---|---|
| 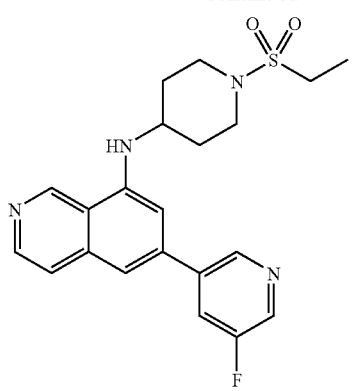 | 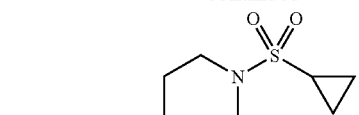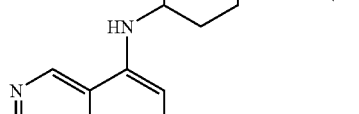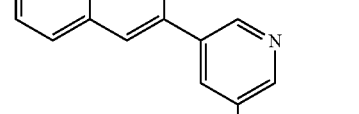 |
| 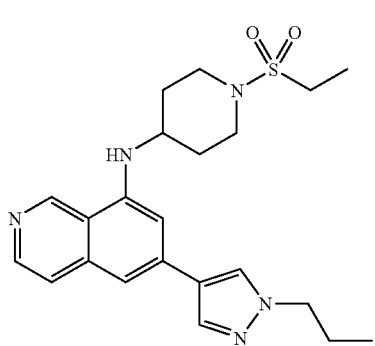 | 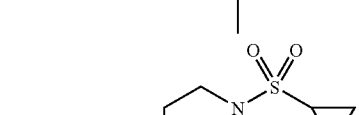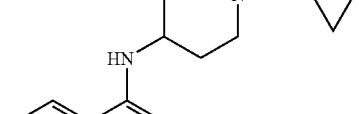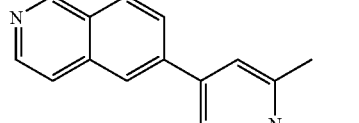 |
| 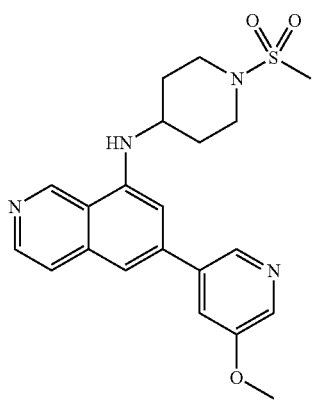 | 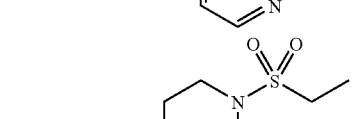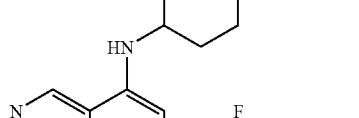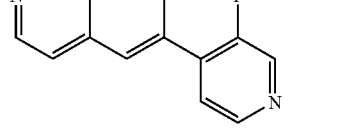 |
| 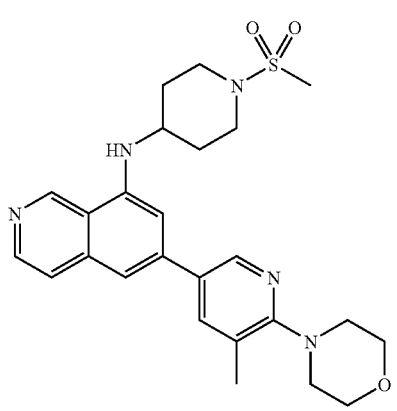 | 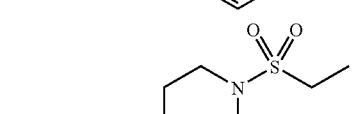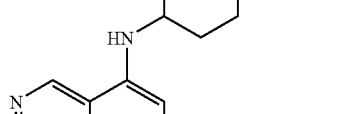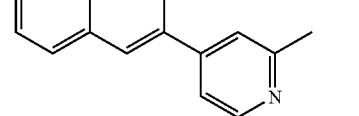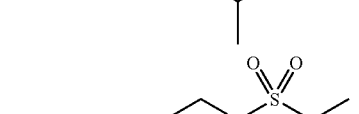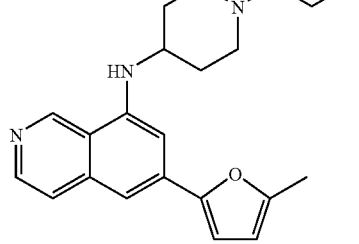 |

549
-continued
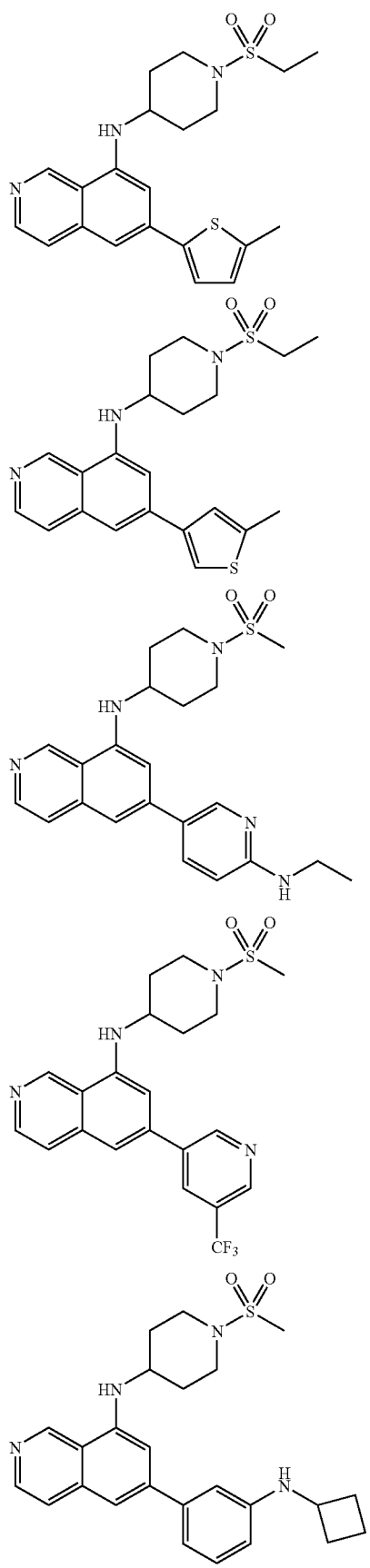
550
-continued
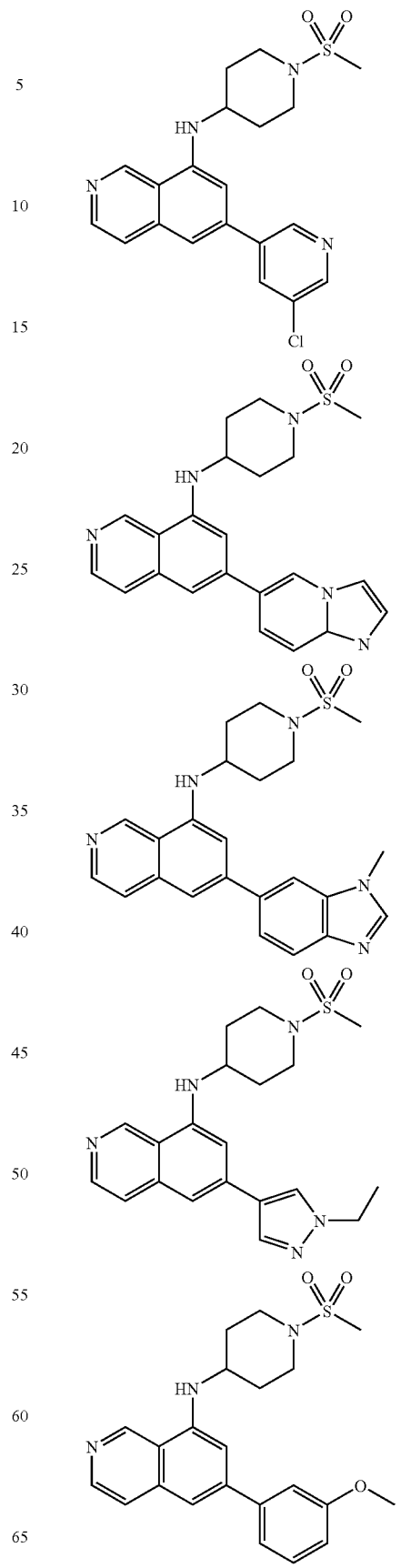

551
-continued
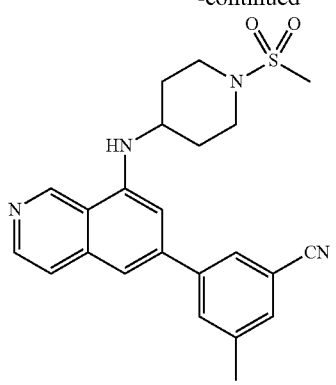
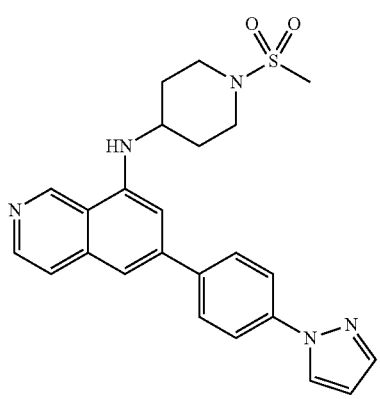
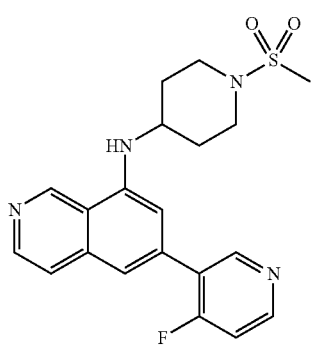
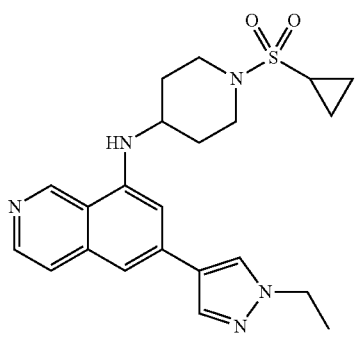
552
-continued
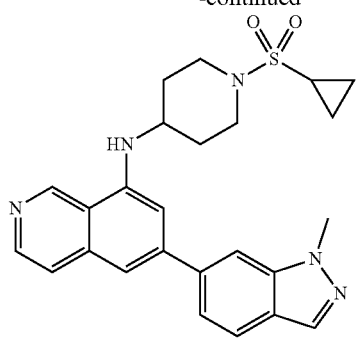
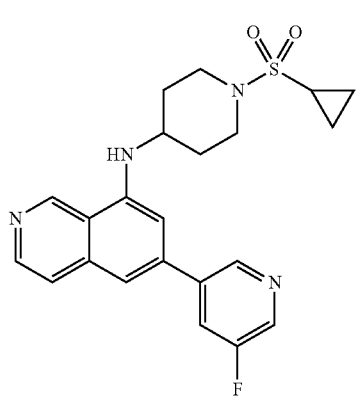
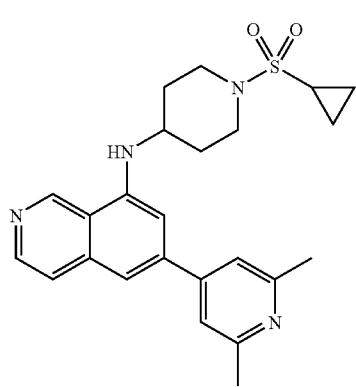
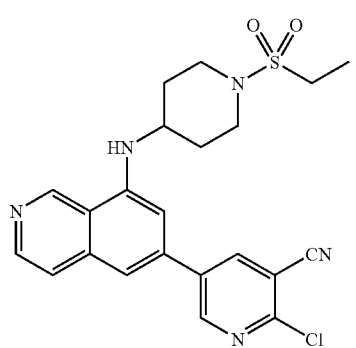

553
-continued
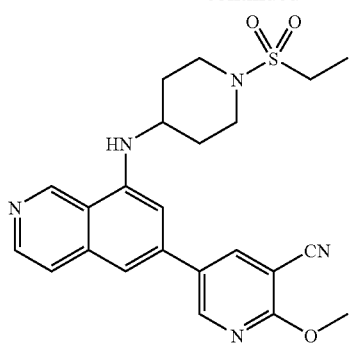
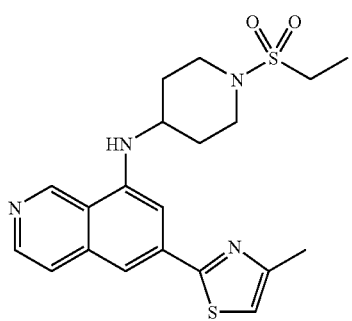
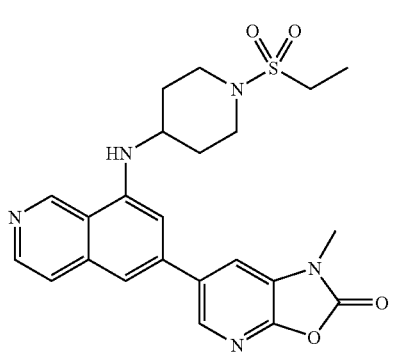
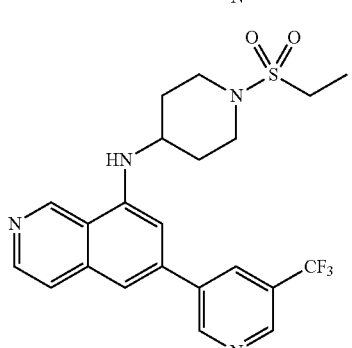
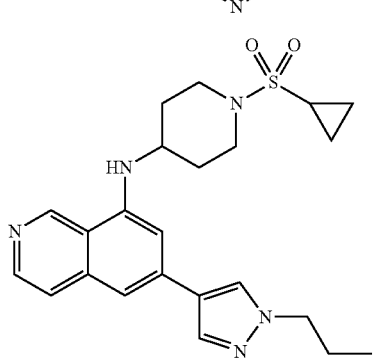
554
-continued
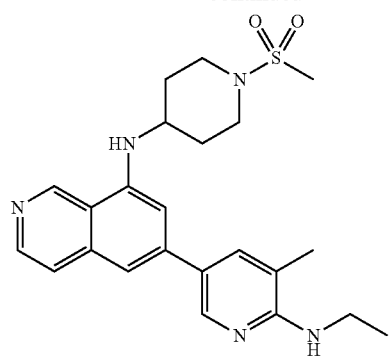
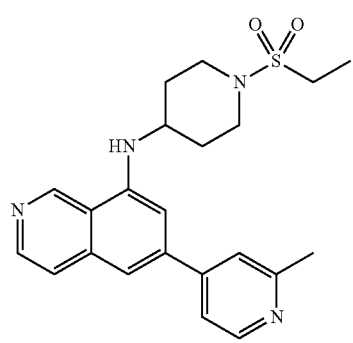
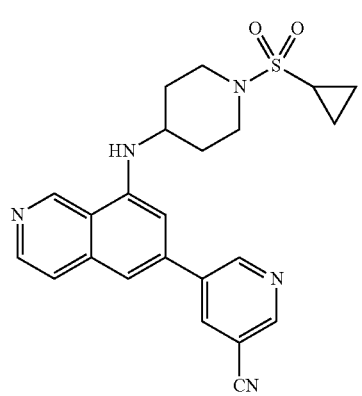
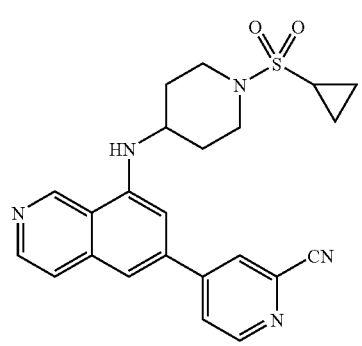

555
-continued
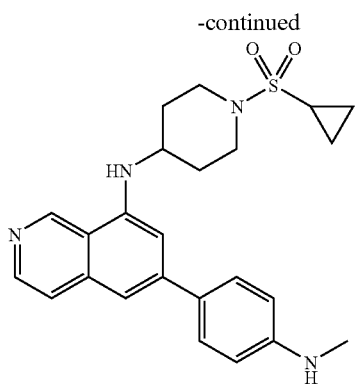
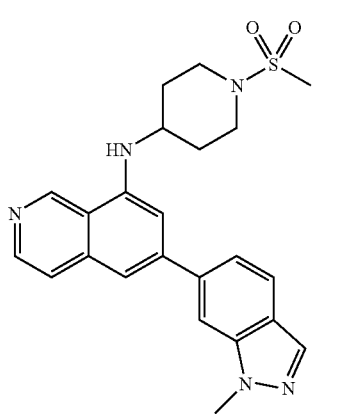
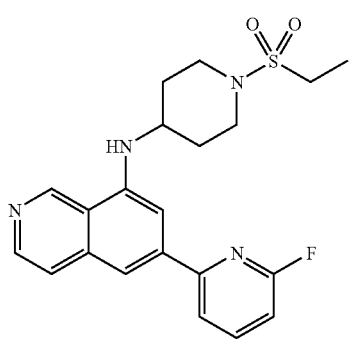
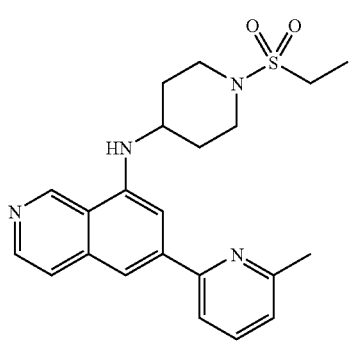
556
-continued
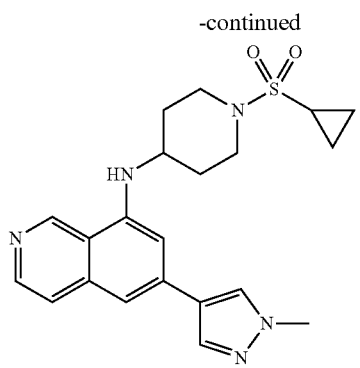
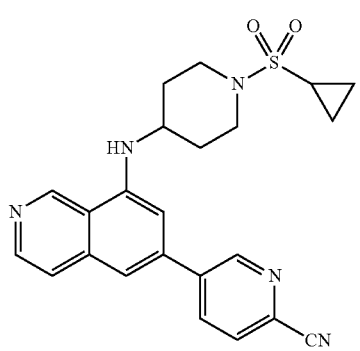
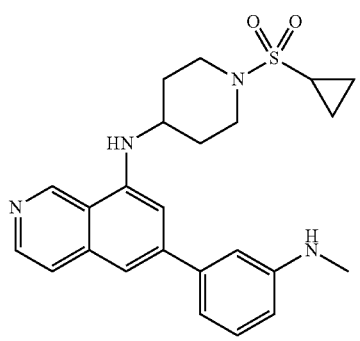
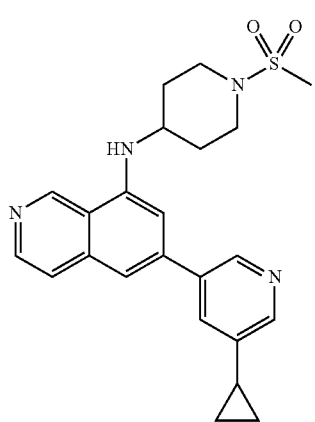

557
-continued
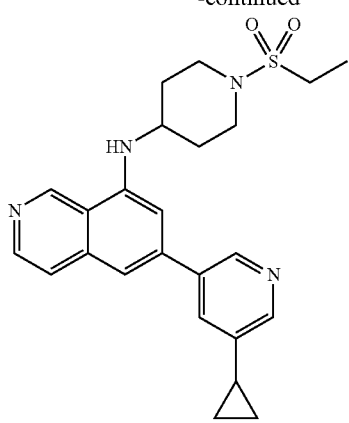
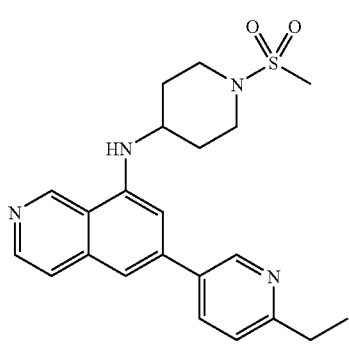
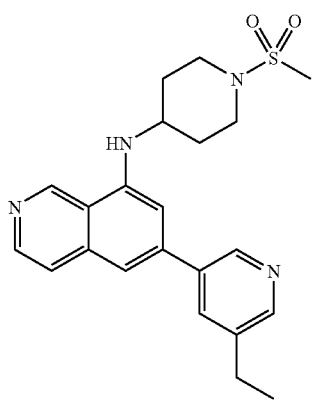
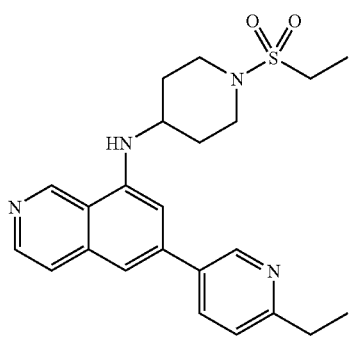
558
-continued
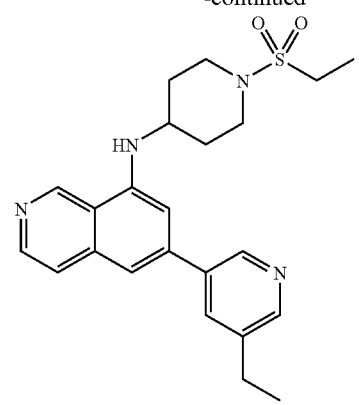
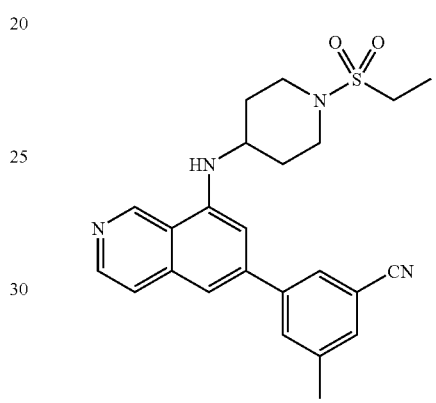
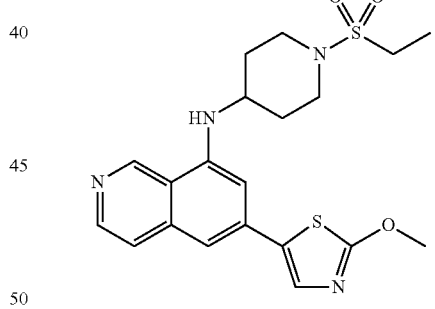
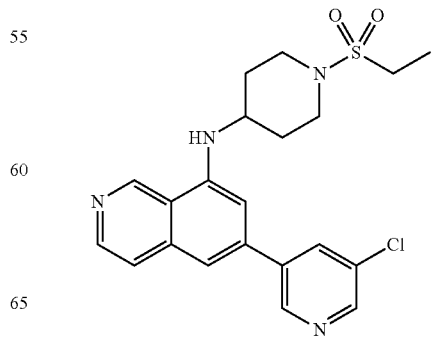

559
-continued
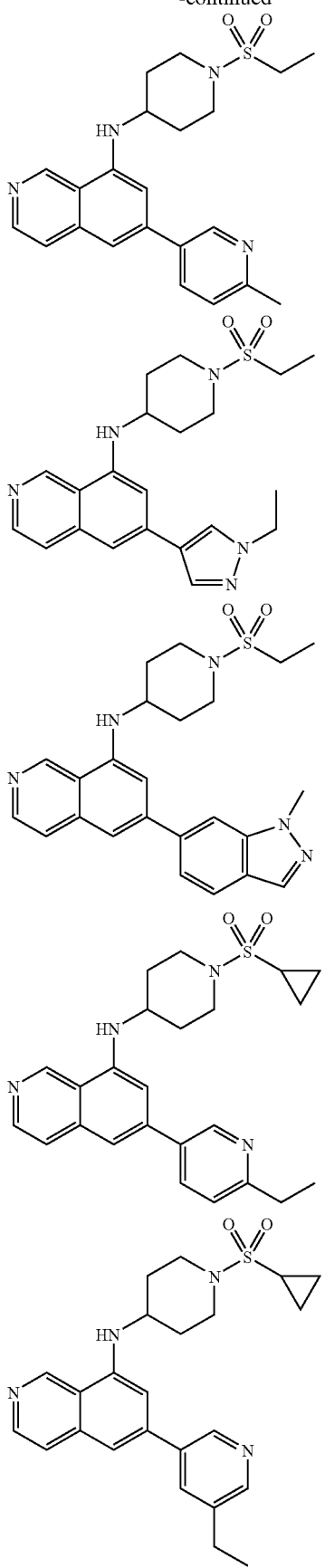
560
-continued
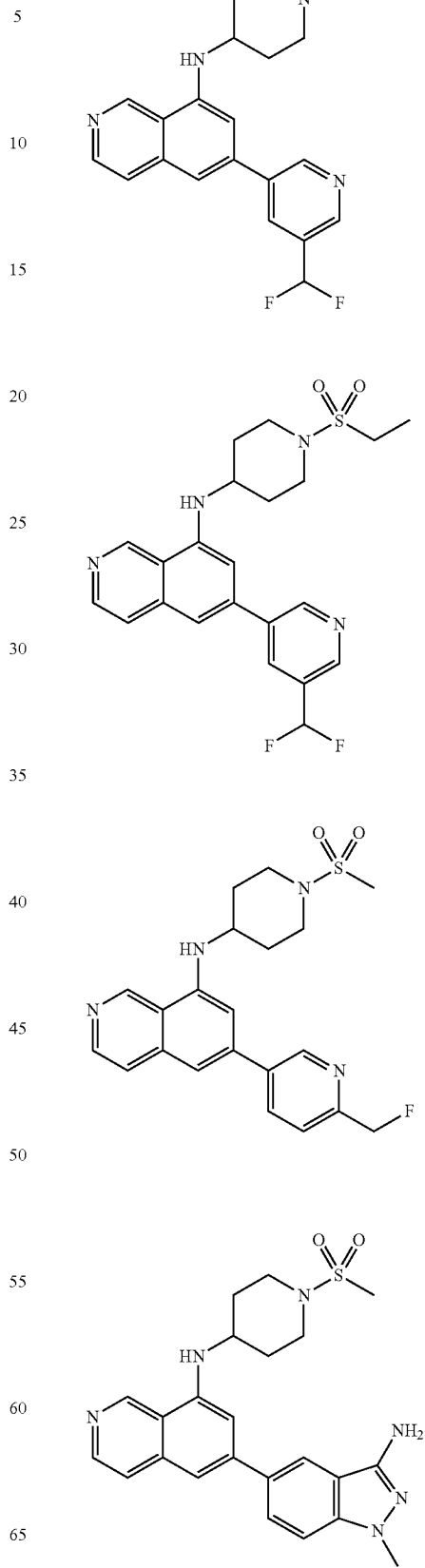

561
-continued
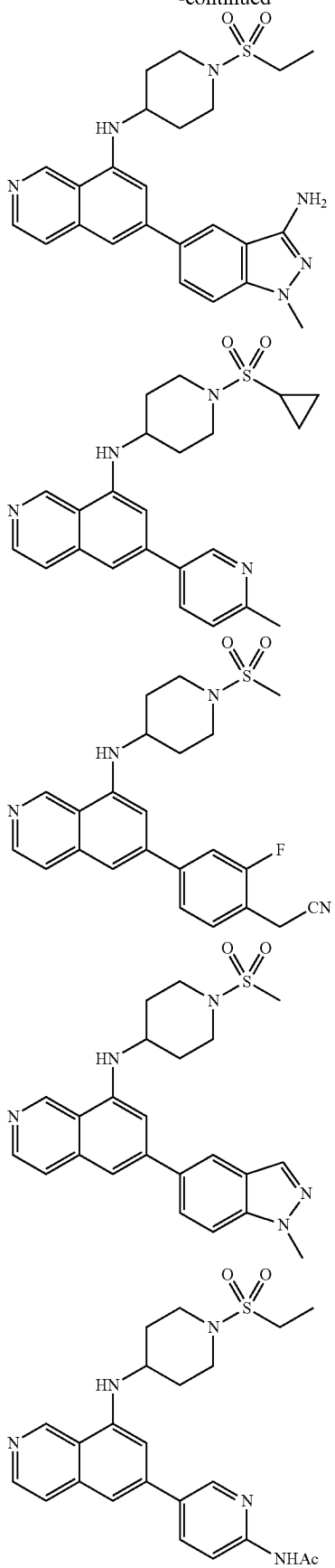
562
-continued
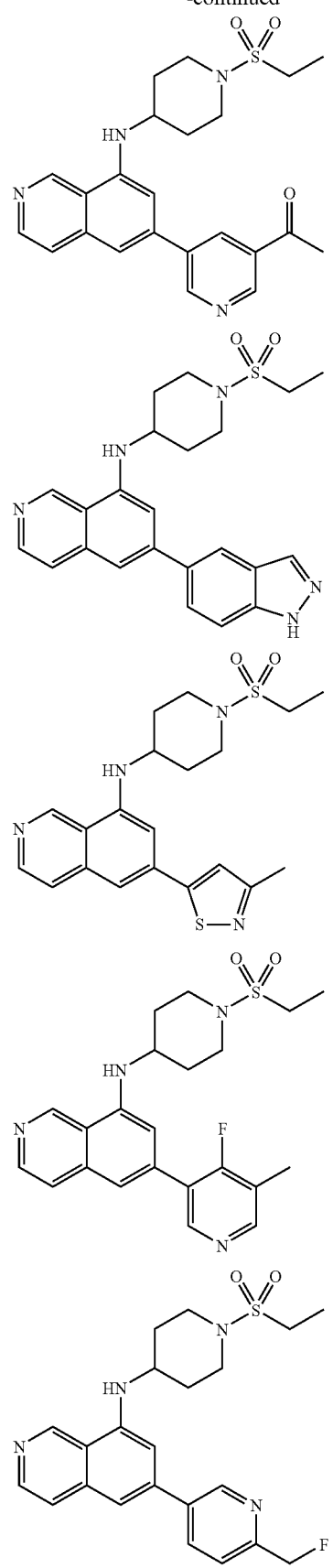

563
-continued
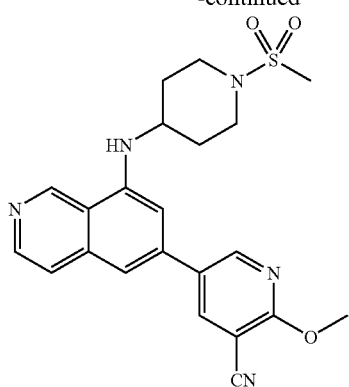
564
-continued
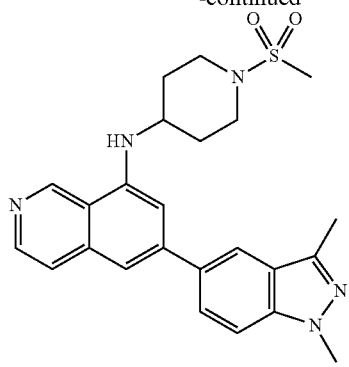
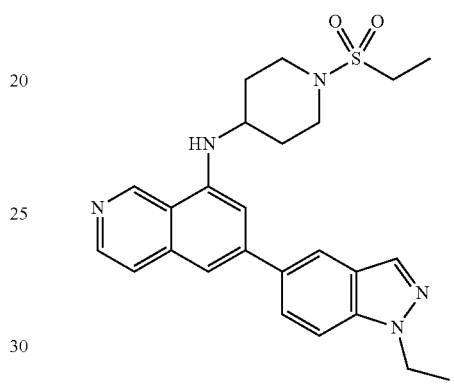
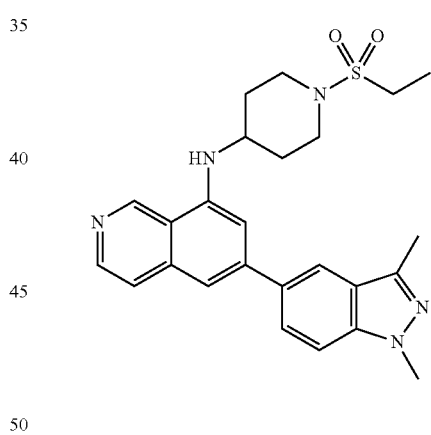
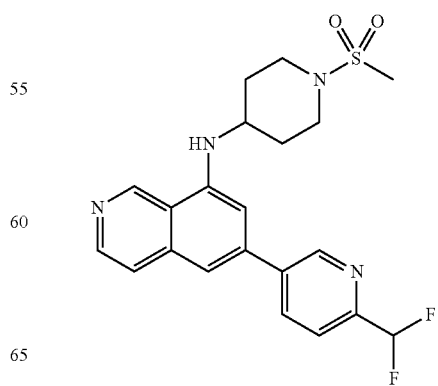

565
-continued
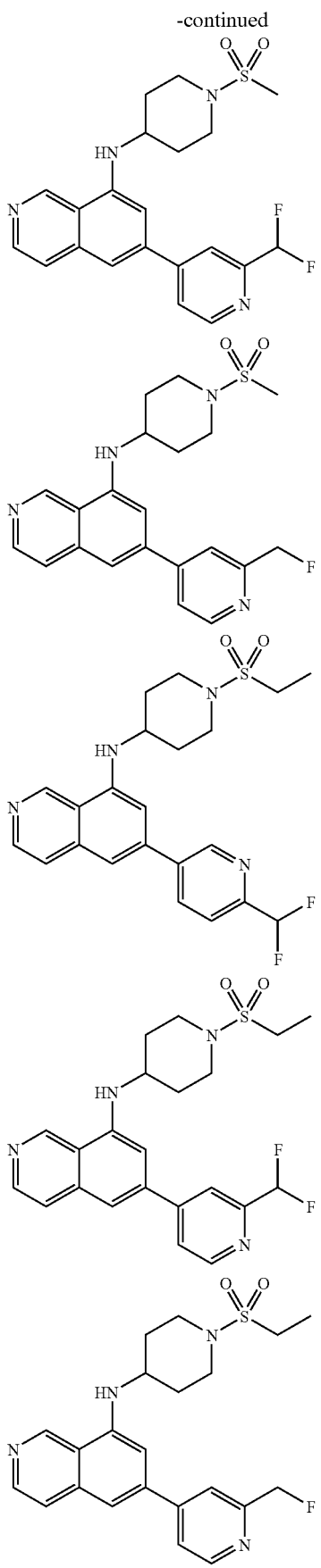
566
-continued
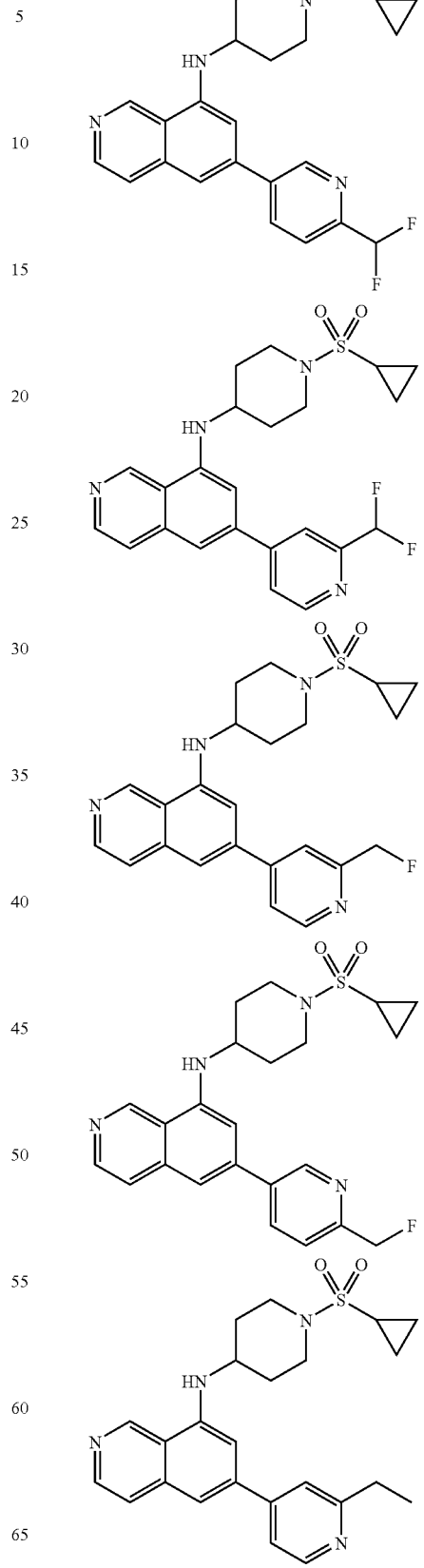

567
-continued
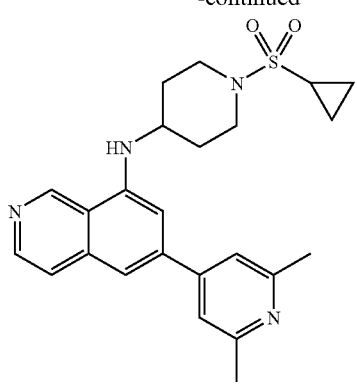
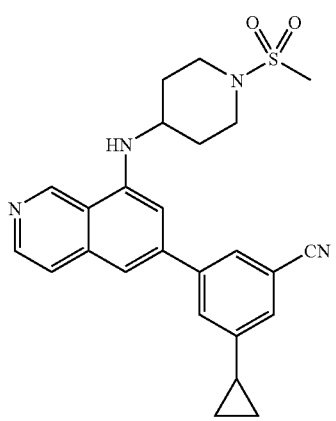
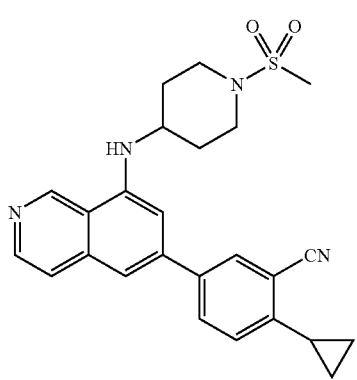
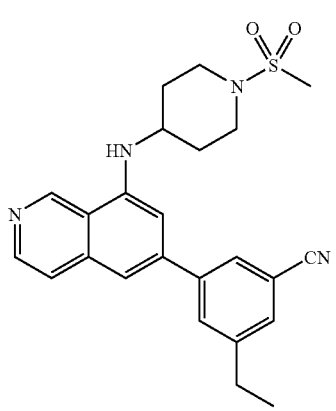
568
-continued
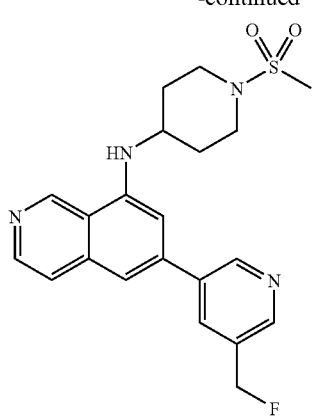
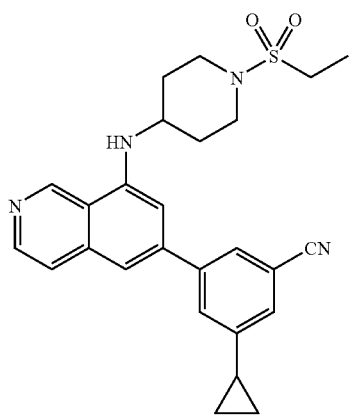
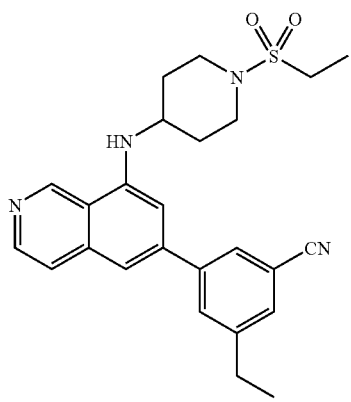
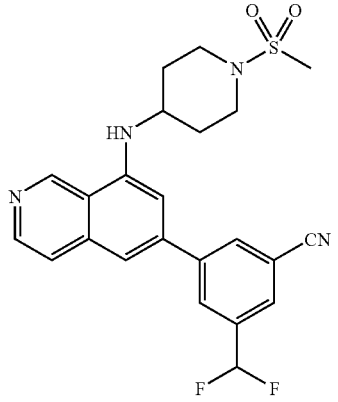

569
-continued
570
-continued
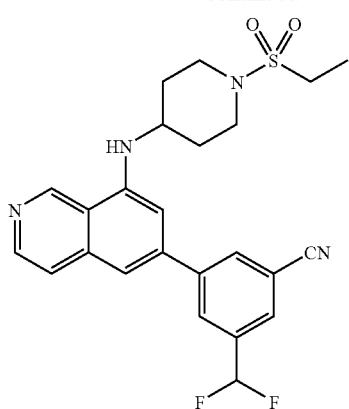
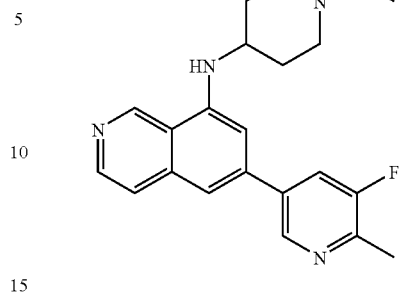
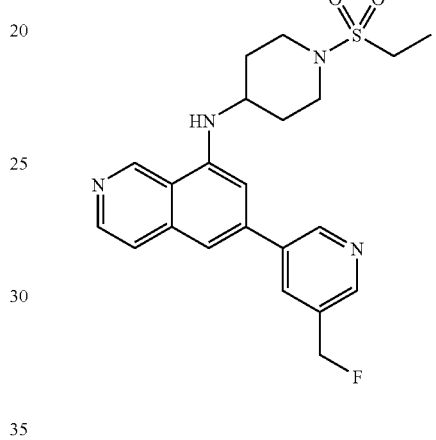
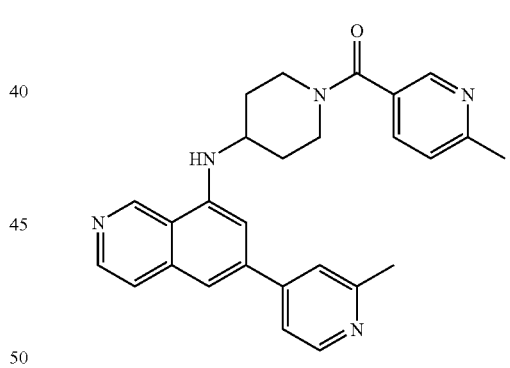
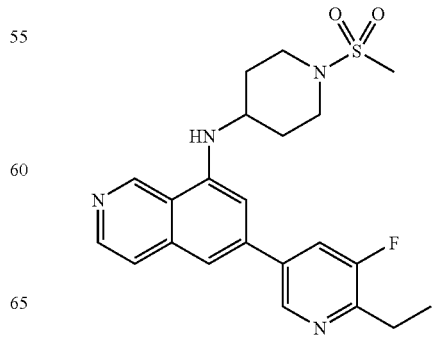

571
-continued
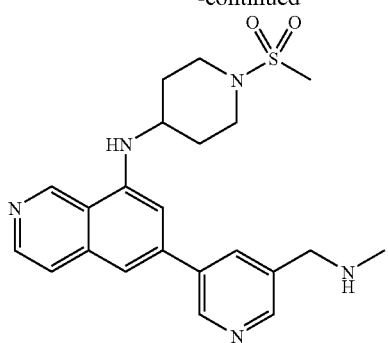
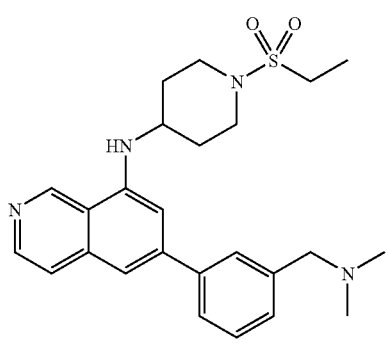
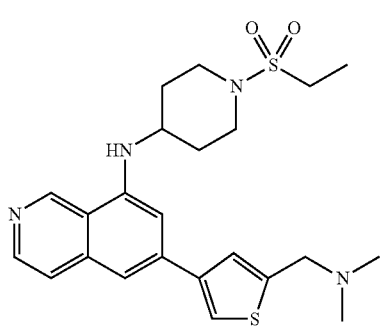
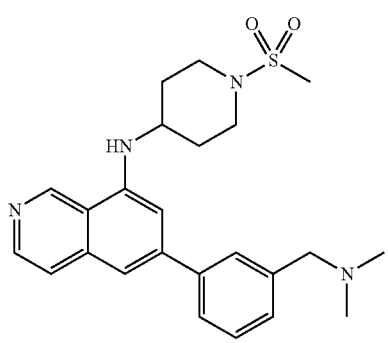
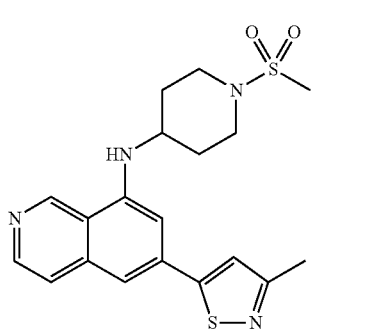
572
-continued
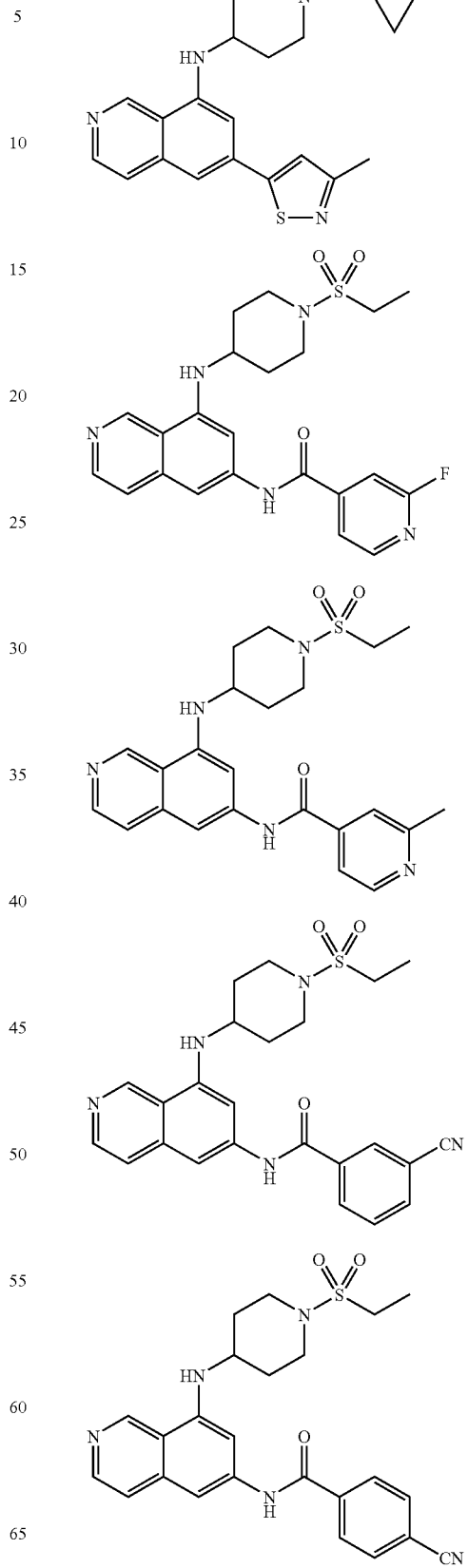

573
-continued
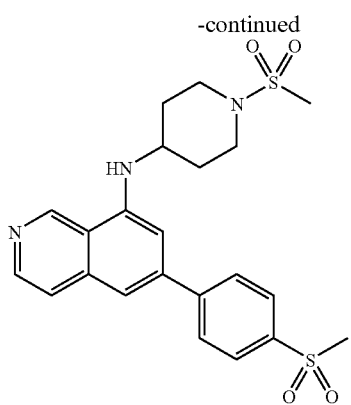
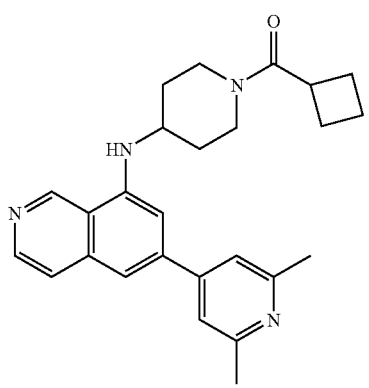
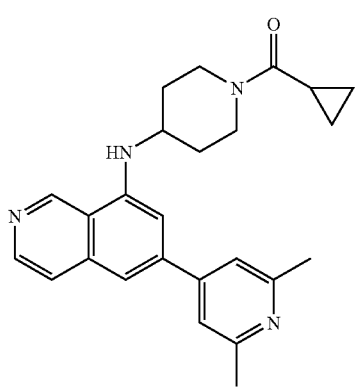
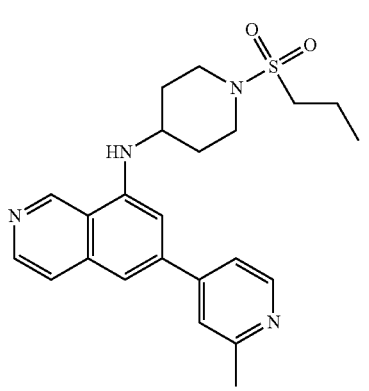
574
-continued
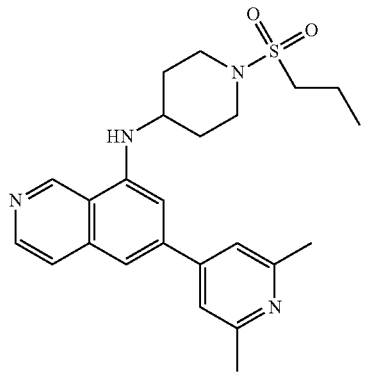
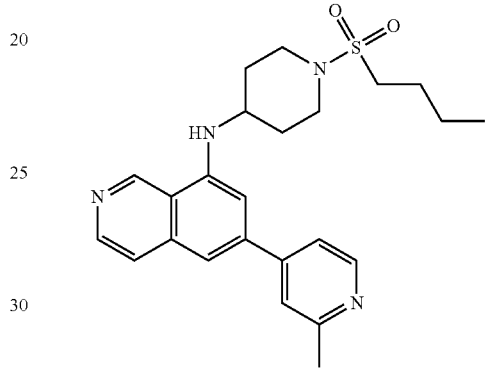
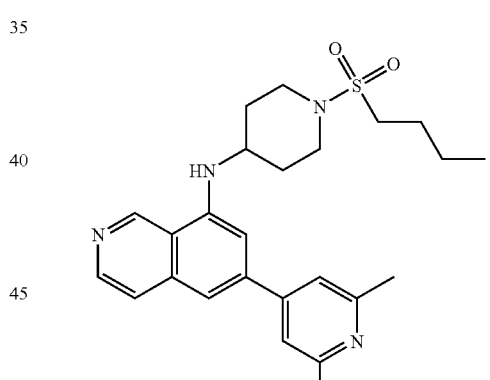
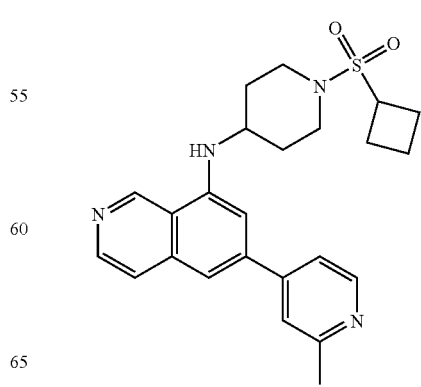

575
-continued
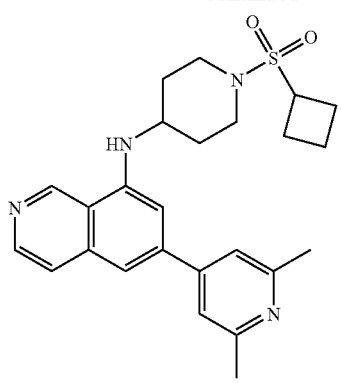
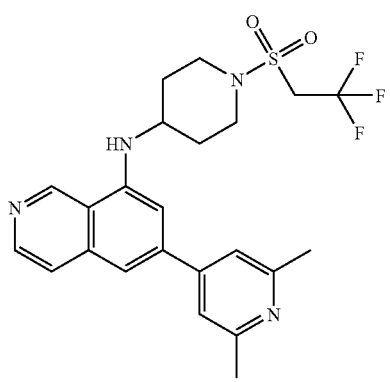
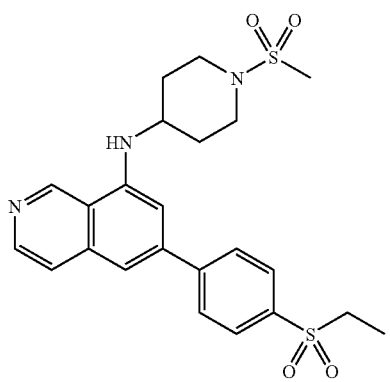
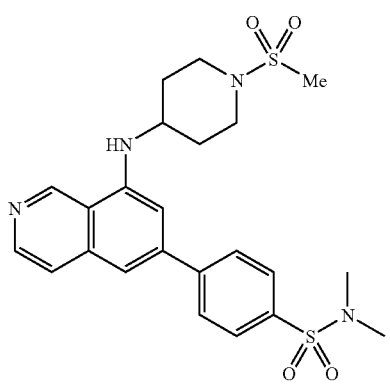
576
-continued
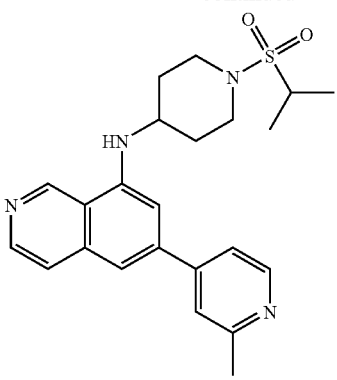
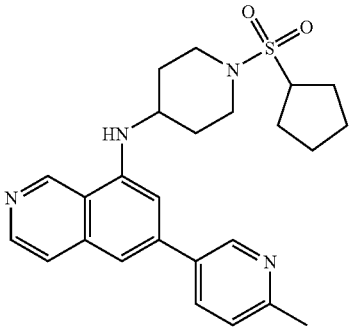
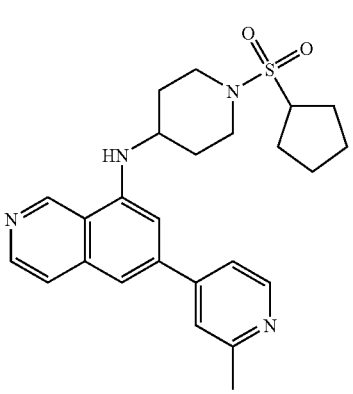

577
-continued
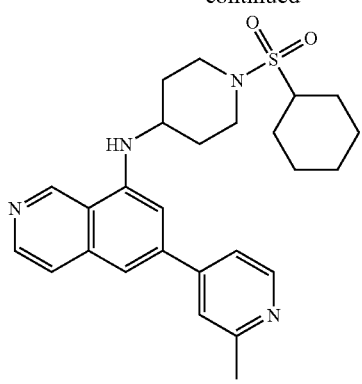
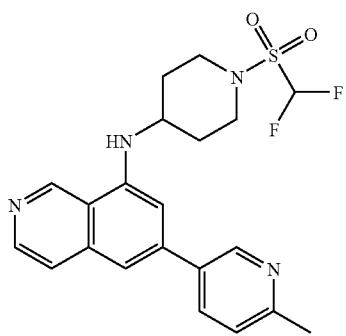
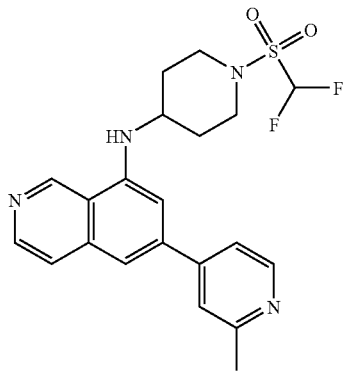
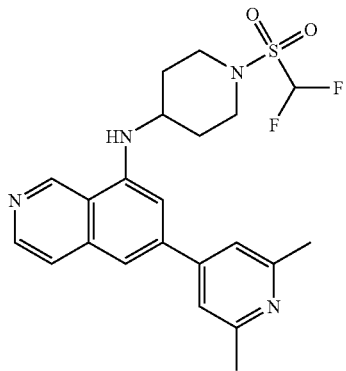
578
-continued
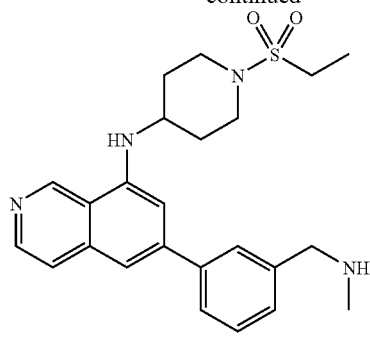
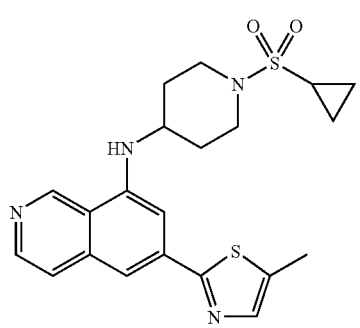
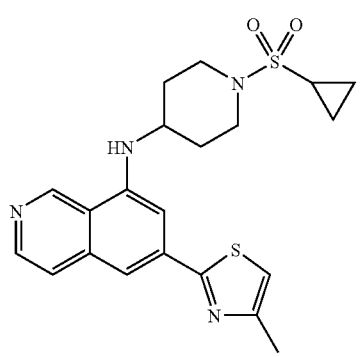
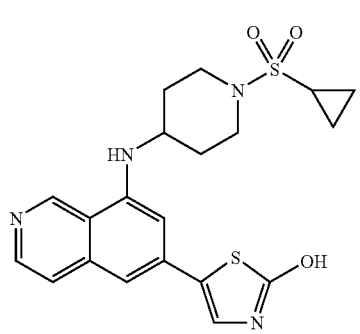
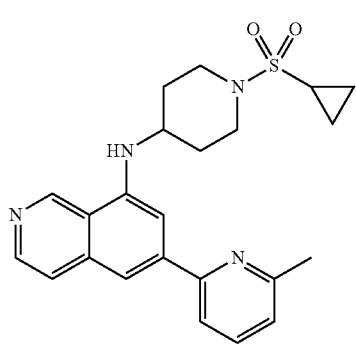

579
-continued
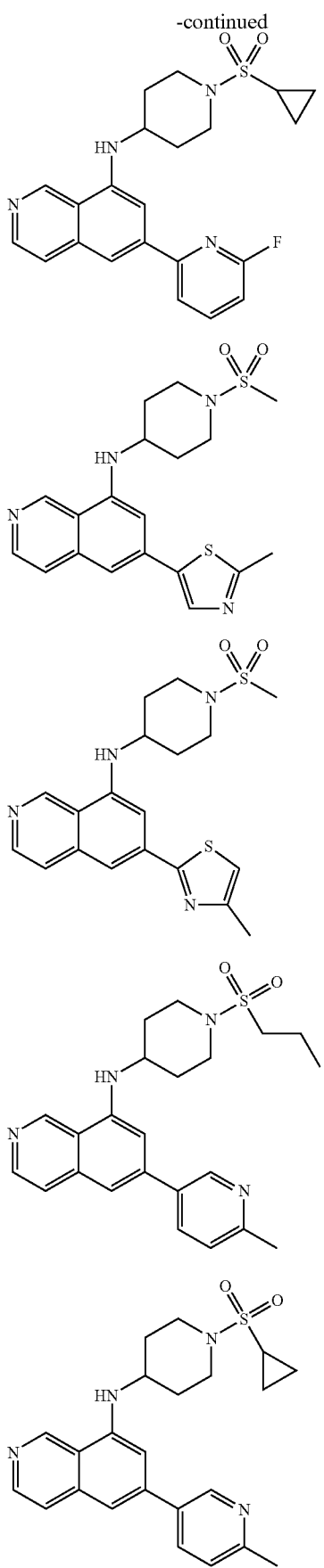
580
-continued
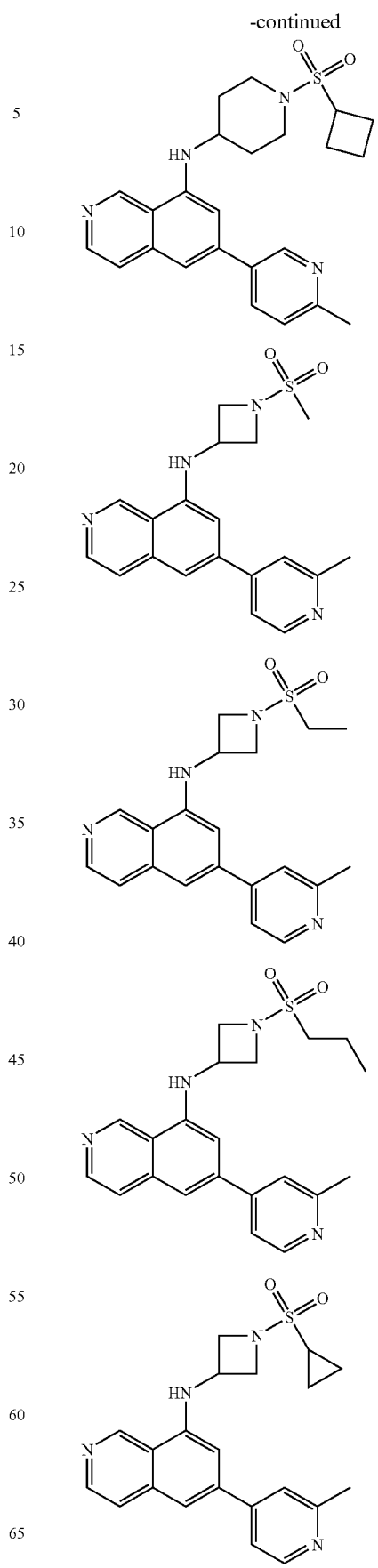

581
-continued
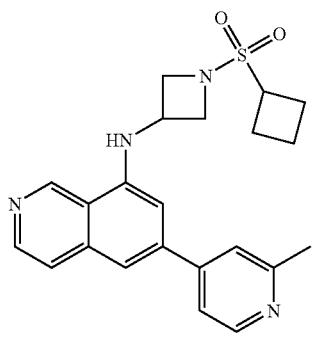
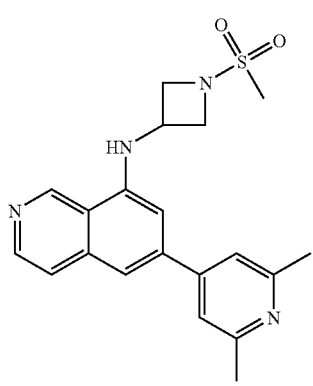
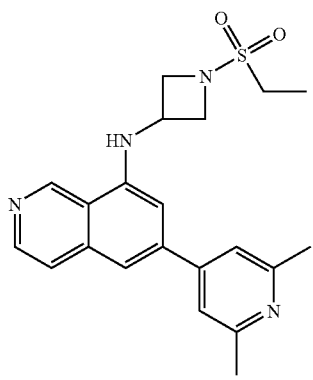
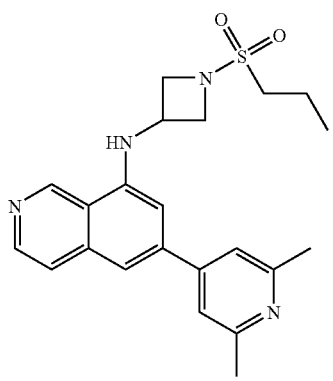
582
-continued
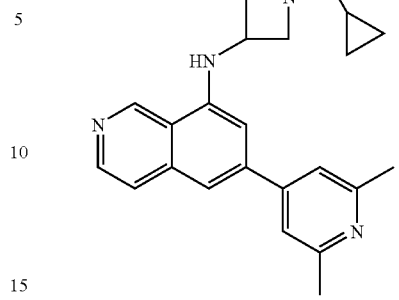
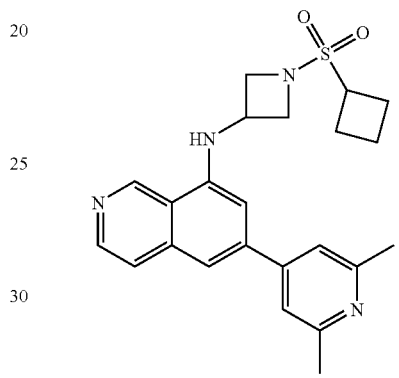
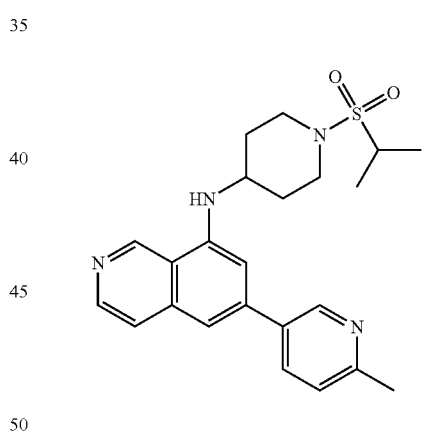
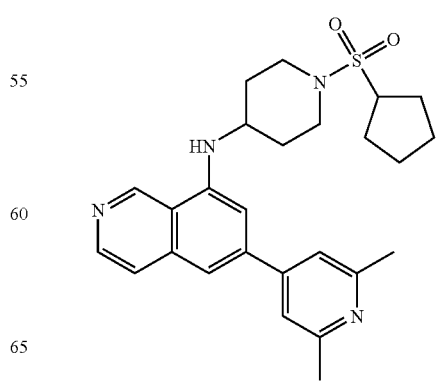

583
-continued
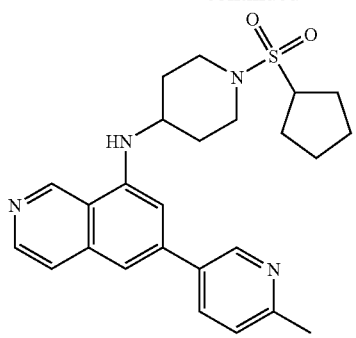
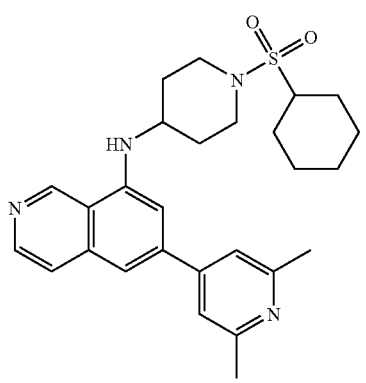
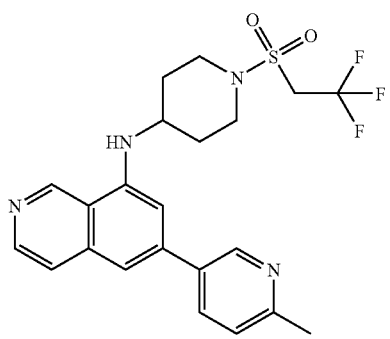
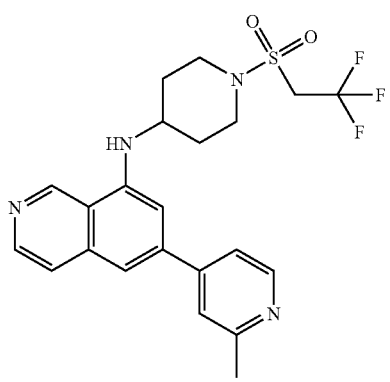
584
-continued
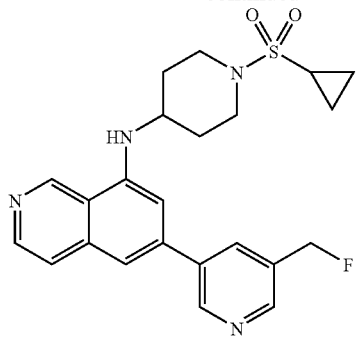
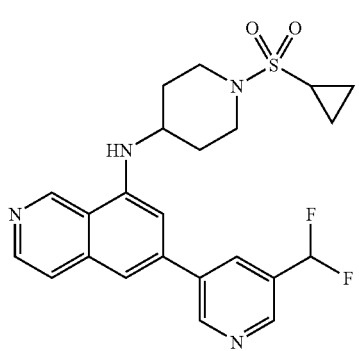
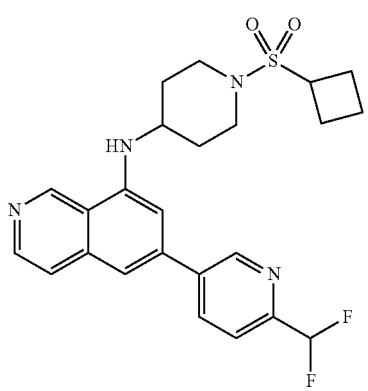
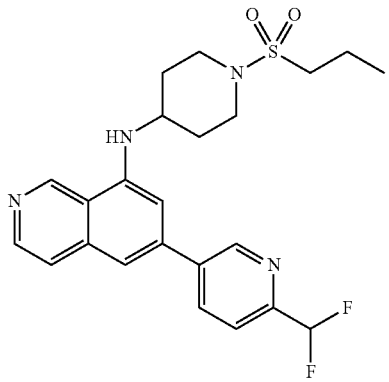
and 585
-continued
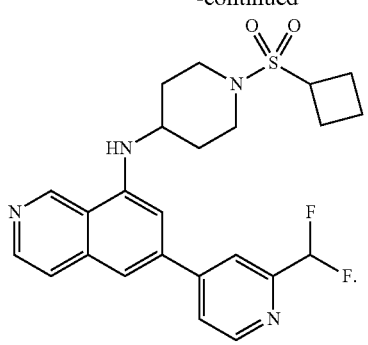
15. A compound selected from the following groups or a salt thereof:
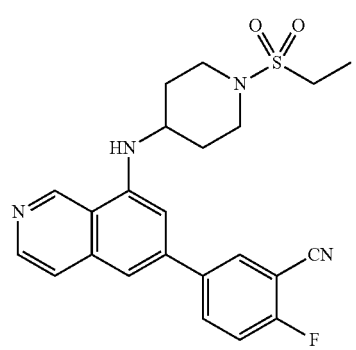
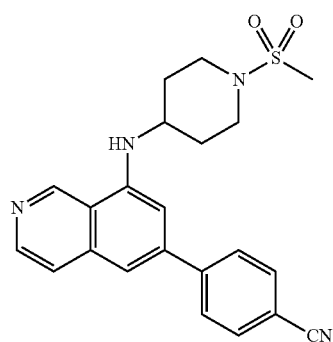
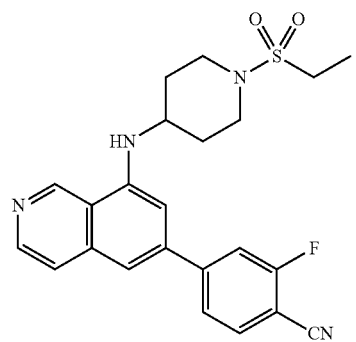
586
-continued
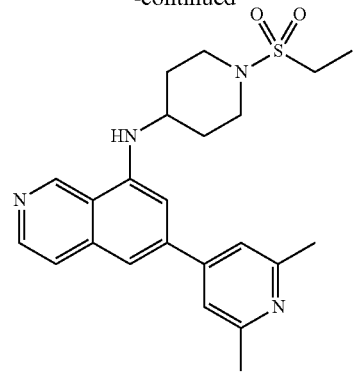
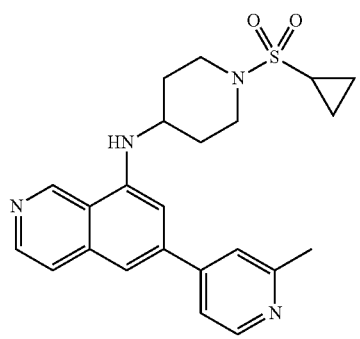
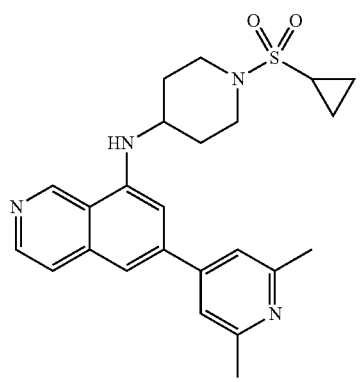
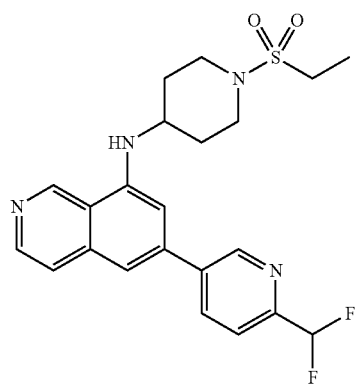

587
-continued
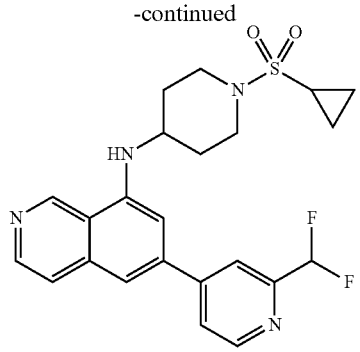
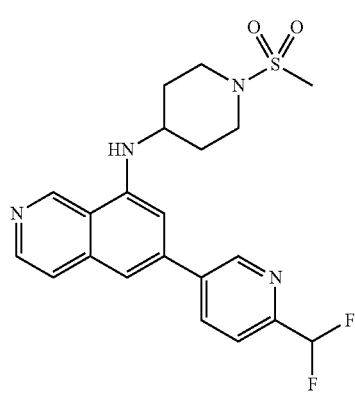
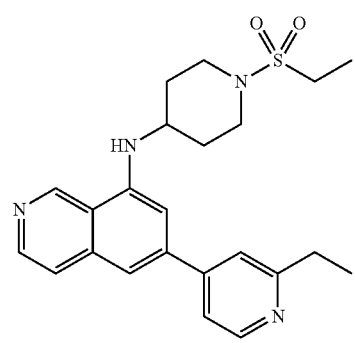
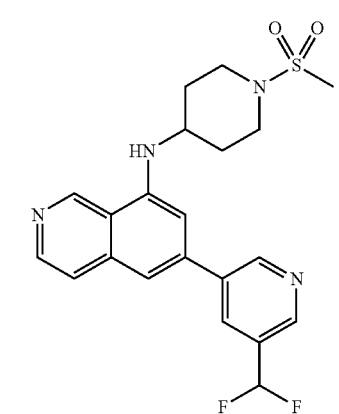
588
-continued
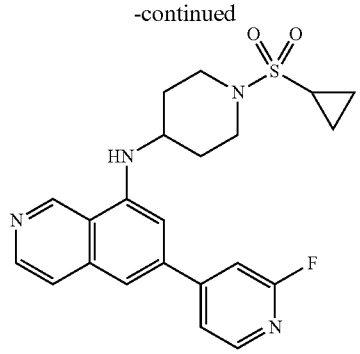
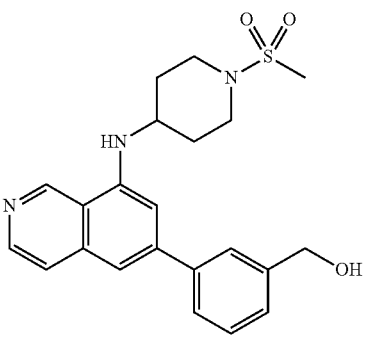
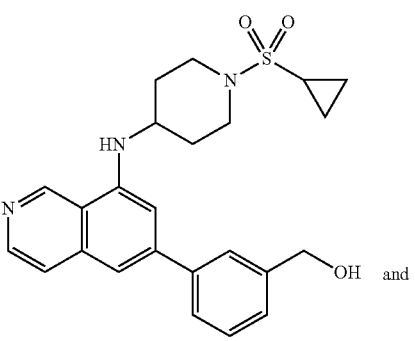
and
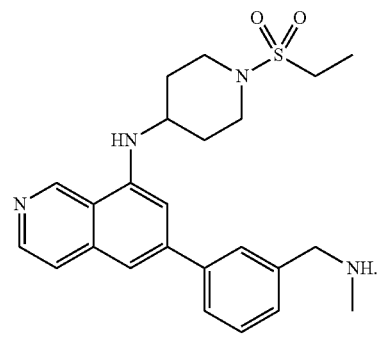

16. The compound or the salt thereof according to claim 15, which is shown below:

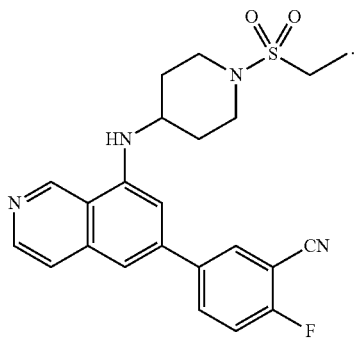

17. The compound or the salt thereof according to claim 15, which is shown below:

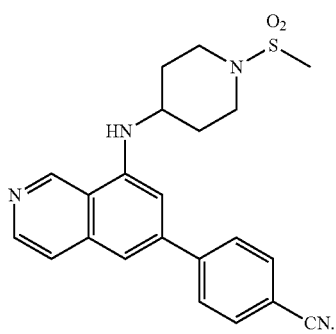

18. The compound or the salt thereof according to claim 15, which is shown below:

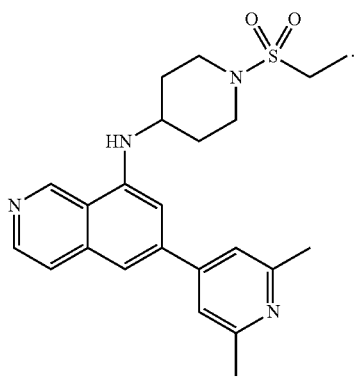

19. The compound or the salt thereof according to claim 15, which is shown below:

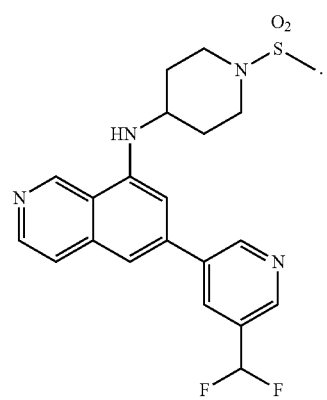

20. The compound or the salt thereof according to claim 15, which is shown below:

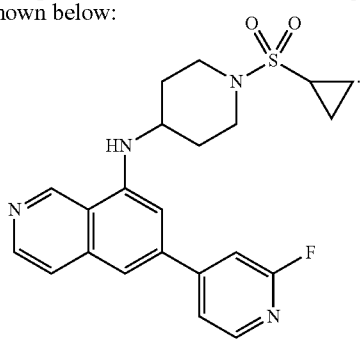

21. The compound or the salt thereof according to claim 15, which is shown below:

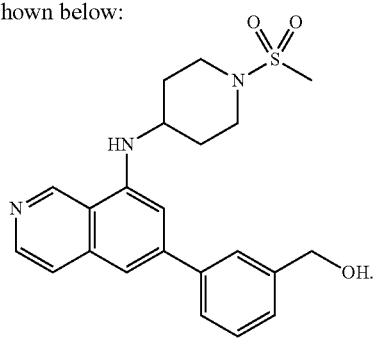

22. The compound or the salt thereof according to claim 15, which is shown below:

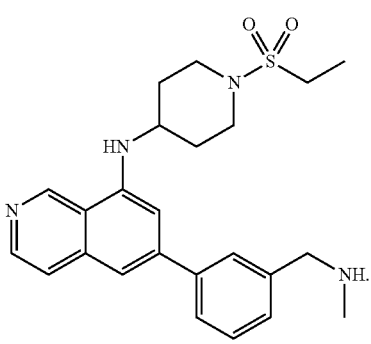

23. The compound according to any one of claims 1-10 or a salt thereof, wherein $D^3$ represents a single bond or —N($R^{21}$)—C(O)—, and wherein $R^{21}$ has the same meaning as defined above.

24. A pharmaceutical composition comprising a compound according to any one of claims 1 to 14 or a pharmaceutically acceptable salt thereof as an active ingredient.

25. The pharmaceutical composition according to claim 24, for preventing and/or treating an NF-κB-associated disease or symptom.

26. The pharmaceutical composition according to claim 24, for preventing and/or treating an IKKβ-associated disease or symptom.

27. The pharmaceutical composition according to claim 24, for preventing and/or treating a TNF-α-associated disease or symptom.

28. The pharmaceutical composition according to claim 24, for preventing and/or treating mammal rheumatoid arthritis.

29. The pharmaceutical composition according to claim 24, for preventing and/or treating a mammal autoimmune disease.

30. The pharmaceutical composition according to claim 24, for preventing and/or treating a mammal inflammatory disease.

31. The pharmaceutical composition according to claim 24, for preventing and/or treating a mammal cardiovascular disease.

32. The pharmaceutical composition according to claim 24, for preventing and/or treating a mammal cancer.

33. The pharmaceutical composition according to claim 24, for preventing and/or treating a disease or symptom associated with acute or chronic inflammatory reaction in mammals.

34. An IKKβ inhibitor, comprising a compound according to any one of claims 1 to 14 or a salt thereof as an active ingredient.

35. A pharmaceutical composition comprising a compound according to any one of claims 15 to 22 or a pharmaceutically acceptable salt thereof as an active ingredient.

36. The pharmaceutical composition according to claim 35, for preventing and/or treating an NF-κB-associated disease or symptom.

37. The pharmaceutical composition according to claim 35, for preventing and/or treating an IKKβ-associated disease or symptom.

38. The pharmaceutical composition according to claim 35, for preventing and/or treating a TNF-α-associated disease or symptom.

39. The pharmaceutical composition according to claim 35, for preventing and/or treating mammal rheumatoid arthritis.

40. The pharmaceutical composition according to claim 35, for preventing and/or treating a mammal autoimmune disease.

41. The pharmaceutical composition according to claim 35, for preventing and/or treating a mammal inflammatory disease.

42. The pharmaceutical composition according to claim 35, for preventing and/or treating a mammal cardiovascular disease.

43. The pharmaceutical composition according to claim 35, for preventing and/or treating a mammal cancer.

44. The pharmaceutical composition according to claim 35, for preventing and/or treating a disease or symptom associated with acute or chronic inflammatory reaction in mammals.

45. An IKKβ inhibitor, comprising a compound according to any one of claims 15 to 22 or a salt thereof as an active ingredient.

46. The pharmaceutical composition according to claim 24, for preventing and/or treating mammal atopic dermatitis.

47. The pharmaceutical composition according to claim 24, for preventing and/or treating mammal inflammatory colitis.

48. The pharmaceutical composition according to claim 24, for preventing and/or treating mammal osteoarthritis.

49. The pharmaceutical composition according to claim 35, for preventing and/or treating mammal atopic dermatitis.

50. The pharmaceutical composition according to claim 35, for preventing and/or treating mammal inflammatory colitis.

51. The pharmaceutical composition according to claim 35, for preventing and/or treating mammal osteoarthritis.

52. A method for treating a disease or symptom associated with acute or chronic inflammatory reaction in mammals comprising administering to a mammal an effective amount of a compound according to any one of claims 1 to 14 or a pharmaceutically acceptable salt thereof.

53. A method for treating a disease or symptom associated with acute or chronic inflammatory reaction in mammals comprising administering to a mammal an effective amount of a compound according to any one of claims 15 to 22 or a pharmaceutically acceptable salt thereof.

* * * * *